(12) United States Patent
Fotin-Mleczek et al.

(10) Patent No.: US 10,988,754 B2
(45) Date of Patent: Apr. 27, 2021

(54) NUCLEIC ACID MOLECULES

(71) Applicant: CureVac AG, Tübingen (DE)

(72) Inventors: Mariola Fotin-Mleczek, Sindelfingen (DE); Katja Fiedler, Bad Urach (DE); Aleksandra Kowalczyk, Stuttgart (DE); Regina Heidenreich, Tübingen (DE)

(73) Assignee: Cure Vac AG, Tübingen (DE)

( * ) Notice: Subject to any disclaimer, the term of this patent is extended or adjusted under 35 U.S.C. 154(b) by 0 days.

(21) Appl. No.: 16/026,729

(22) Filed: Jul. 3, 2018

(65) Prior Publication Data
US 2019/0040378 A1   Feb. 7, 2019

Related U.S. Application Data

(63) Continuation of application No. PCT/EP2017/066676, filed on Jul. 4, 2017.

(51) Int. Cl.
| | | |
|---|---|---|
| *A61K 48/00* | (2006.01) | |
| *A61K 39/00* | (2006.01) | |
| *C12N 9/90* | (2006.01) | |
| *C07K 14/705* | (2006.01) | |
| *A61K 39/39* | (2006.01) | |
| *A61K 39/385* | (2006.01) | |
| *A61K 38/00* | (2006.01) | |

(52) U.S. Cl.
CPC ............. *C12N 9/90* (2013.01); *A61K 39/00* (2013.01); *A61K 39/0011* (2013.01); *A61K 39/385* (2013.01); *A61K 39/39* (2013.01); *C07K 14/70521* (2013.01); *C12Y 503/03012* (2013.01); *A61K 38/00* (2013.01); *A61K 2039/53* (2013.01); *A61K 2039/605* (2013.01); *A61K 2039/6031* (2013.01); *C07K 2319/02* (2013.01); *C07K 2319/03* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,423,023 | B2 * | 9/2008 | Boyle ............... | A61K 39/008 514/44 R |
| 2003/0091590 | A1 | 5/2003 | Pomerantz | |
| 2005/0032730 | A1 | 2/2005 | von der Mülbe et al. | |
| 2005/0059624 | A1 | 3/2005 | Hoerr et al. | |
| 2005/0250723 | A1 | 11/2005 | Hoerr et al. | |
| 2006/0188490 | A1 | 8/2006 | Hoerr et al. | |
| 2007/0048301 | A1 * | 3/2007 | Bodary-Winter ...... | C07K 14/47 424/143.1 |
| 2007/0224208 | A1 * | 9/2007 | Guo ................... | A61K 39/0011 424/184.1 |
| 2008/0025944 | A1 | 1/2008 | Hoerr et al. | |
| 2008/0267873 | A1 | 10/2008 | Hoerr et al. | |
| 2009/0324584 | A1 | 12/2009 | Hoerr et al. | |
| 2010/0048883 | A1 | 2/2010 | Ketterer et al. | |
| 2010/0111993 | A1 * | 5/2010 | Tureci ................. | A61P 35/00 424/192.1 |
| 2010/0189729 | A1 | 7/2010 | Hoerr et al. | |
| 2010/0203076 | A1 | 8/2010 | Fotin-Mleczek et al. | |
| 2010/0291156 | A1 | 11/2010 | Barner et al. | |
| 2010/0305196 | A1 | 12/2010 | Probst et al. | |
| 2011/0053829 | A1 | 3/2011 | Baumhof et al. | |
| 2011/0250225 | A1 | 10/2011 | Fotin-Mleczek et al. | |
| 2012/0021043 | A1 | 1/2012 | Kramps et al. | |
| 2012/0258046 | A1 | 10/2012 | Mutzke | |
| 2013/0129754 | A1 | 5/2013 | Thess et al. | |
| 2013/0142818 | A1 | 6/2013 | Baumhof et al. | |
| 2013/0259879 | A1 | 10/2013 | Baumhof et al. | |
| 2013/0280283 | A1 | 10/2013 | Lorenz et al. | |
| 2013/0282083 | A1 | 10/2013 | Vertikov | |
| 2013/0295043 | A1 | 11/2013 | Kallen et al. | |
| 2013/0336998 | A1 | 12/2013 | Kallen et al. | |
| 2015/0037326 | A1 | 2/2015 | Butler-Ransohoff et al. | |
| 2015/0050302 | A1 | 2/2015 | Thess | |
| 2015/0057340 | A1 | 2/2015 | Thess et al. | |
| 2015/0093413 | A1 | 4/2015 | Thess et al. | |
| 2015/0118183 | A1 | 4/2015 | Baumhof | |
| 2015/0118264 | A1 | 4/2015 | Baumhof et al. | |
| 2015/0165006 | A1 | 6/2015 | Thess et al. | |

(Continued)

FOREIGN PATENT DOCUMENTS

| | | | | |
|---|---|---|---|---|
| WO | WO-9958658 | A2 * | 11/1999 | ............ C07K 14/445 |
| WO | WO 2002/085933 | | 10/2002 | |

(Continued)

OTHER PUBLICATIONS

Weng et al., DNA vaccine elicits an efficient antitumor response by targeting the mutant Kras in a transgenic mouse lung cancer model. Gene Therapy (2014) 21, 888-896 (Year: 2014).*
Huang et al., Enhanced antitumor immunity by fusion of CTLA-4 to a self tumor antigen. Blood. 2000;96: 3663-3670 (Year: 2000).*
Bonifacino et al., "Signals for Sorting of Transmembrane Proteins to Endosomes and Lysosomes," *Annu. Rev. Biochem.*, 72(1):395-447, 2003.
Boyle et al., "Enhanced responses to a DNA vaccine encoding a fusion antigen that is directed to sites of immune induction," *Nature*, 392:408-411, 1998.
Deliyannis et al., "A fusion DNA vaccine that targets antigen-presenting cells increases protection from viral challenge," *Proc. Natl. Acad. Sci. USA*, 97(12):6676-6680, 2000.

(Continued)

*Primary Examiner* — Arthur S Leonard
(74) *Attorney, Agent, or Firm* — Parker Highlander PLLC

(57) ABSTRACT

The present invention provides novel artificial nucleic acid molecules encoding at least one antigenic peptide or protein and at least one additional sequence preferably targeting the antigenic peptides or proteins to cellular compartments of interest. Further, the invention provides (pharmaceutical) compositions or vaccines and kits comprising said nucleic acid molecules. The nucleic acid molecules, (pharmaceutical) compositions or vaccines and kits are useful for treating a variety of diseases such as cancer, infectious diseases, autoimmune diseases, allergies or graft-versus host disease.

21 Claims, 7 Drawing Sheets

Specification includes a Sequence Listing.

(56) References Cited

U.S. PATENT DOCUMENTS

| | | |
|---|---|---|
| 2015/0184195 A1 | 7/2015 | Thess |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake |
| 2016/0304883 A1 | 10/2016 | Grund |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek |
| 2017/0326225 A1 | 11/2017 | Rauch |
| 2018/0044687 A1 | 2/2018 | Thess et al. |
| 2018/0125952 A1 | 5/2018 | Fotin-Mleczek |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237789 A1 | 8/2018 | Schlake |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer |
| 2019/0010485 A1 | 1/2019 | Yazdan Panah et al. |
| 2019/0017100 A1 | 1/2019 | Wochner |
| 2019/0024096 A1 | 1/2019 | Schmid et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0241925 A1* | 8/2019 | Hishiya ............... C07K 14/705 |

FOREIGN PATENT DOCUMENTS

| | | | |
|---|---|---|---|
| WO | WO-2007024708 A2 * | 3/2007 | ........... A61K 38/177 |
| WO | WO 2012/031043 | 3/2012 | |
| WO | WO 2013/033563 | 3/2013 | |
| WO | WO 2014/100385 | 6/2014 | |
| WO | WO 2015/024666 | 2/2015 | |
| WO | WO 2015/082922 | 6/2015 | |
| WO | WO 2015/100219 | 7/2015 | |
| WO | WO 2015/101415 | 7/2015 | |
| WO | WO 2016/170176 | 10/2016 | |
| WO | WO 2017/021546 | 2/2017 | |
| WO | WO 2017/025447 | 2/2017 | |
| WO | WO 2017/064146 | 4/2017 | |
| WO | WO 2017/081110 | 5/2017 | |
| WO | WO 2017/137095 | 8/2017 | |
| WO | WO 2017/140905 | 8/2017 | |
| WO | WO 2017/162297 | 9/2017 | |
| WO | WO 2017/182634 | 10/2017 | |
| WO | WO 2017/186928 | 11/2017 | |
| WO | WO 2017/191258 | 11/2017 | |
| WO | WO 2017/191274 | 11/2017 | |
| WO | WO 2017/203008 | 11/2017 | |
| WO | WO 2017/212006 | 12/2017 | |
| WO | WO 2017/212007 | 12/2017 | |
| WO | WO 2017/212008 | 12/2017 | |
| WO | WO 2017/212009 | 12/2017 | |
| WO | WO 2018/033254 | 2/2018 | |
| WO | WO 2018/078053 | 5/2018 | |

OTHER PUBLICATIONS

Fiedler et al, "mRNA Cancer Vaccines," In: *Current Strategies in Cancer Gene Therapy*, Springer International Publishing AG, pp. 61-85, 2016.

International Search Report and Written Opinion issued in corresponding PCT Application No. PCT/EP2018/068015, dated Oct. 22, 2018.

Kallen et al., "A novel, disruptive vaccination technology: self-adjuvanced RNActive® vaccines," *Human Vaccin. Immunother.*, 9(10):2263-2276, 2013.

Kübler et al., "Self-adjuvanted mRNA vaccination in advanced prostate cancer patients: a first-in-man phase I/IIa study," *J. Immunother. Cancer*, 3(26): , 2015.

Xu et al., "Analysis of the molecular mechanisms of targeted anti-caries DNA plasmid enhancing antibody responses by gene arrays," *J. Gene Med.*, 11(4):354-360, 2009.

* cited by examiner

NUCLEIC ACID MOLECULES

Unlike conventional protein-based vaccines, nucleic acid vaccines are based on nucleic acid molecules-either DNA or RNA-encoding vaccine antigens. DNA vaccines typically consist of antigen-encoding gene(s) inserted into a bacterial plasmid under the control of a eukaryotic promoter, whereas RNA vaccines may usually employ messenger RNAs (mRNA) or other antigen-encoding RNA molecules. Like protein vaccines, nucleic acid vaccines can be delivered through a variety of different routes, including intramuscular, subcutaneous, mucosal, or transdermal delivery. However, unlike protein antigens, the nucleic acid vaccine to be effective must gain entry to the cytoplasm of cells at the injection site in order to induce antigen expression in vivo, thereby enabling antigen presentation on major histocompatability molecules (MHC) and T-cell recognition (Li and Petrovsky Expert Rev Vaccines. 2016; 15(3): 313-329, McNamara et al. J Immunol Res. 2015; 2015: 794528).

DNA vaccines are administered to the host and internalized by host cells, where the antigen-encoding DNA plasmid is transcribed in the nucleus and translated in the cytoplasm by host cellular machinery. Unlike DNA vaccines, antigen-encoding mRNAs only needs to gain entry into the cytoplasm, where translation occurs, in order to transfect a cell. Either way, the resulting proteins are processed into peptides, which are ultimately presented on the surface of host cells in the context of major histocompatibility complex (MHC) molecules. The peptide-MHC complex is recognized by antigen-specific T cells, resulting in a cellular host immune response (McNamara et al. J Immunol Res. 2015; 2015: 794528).

There are two branches of MHC receptor presentation. MHC class I molecules-abundantly expressed in all nucleated cells and also in platelets-bind endogenously produced peptides including viral peptides and tumor antigens in the endoplasmatic reticulum (ER). Specifically, MHC class I molecules present peptides that result from proteolytic cleavage of endogenous proteins. Cleaved peptide fragments bind to an antigen peptide transporter (TAP) of the endoplasmic reticulum (ER), where they undergo further trimming of N-terminal residues and then bind to MHC class I complexes (Murphy K (2011) Janeways Immunobiology. New York: Garland Science).

In contrast, MHC class II molecules are predominantly expressed by professional antigen-presenting cells (APCs) such as macrophages, B cells, and especially dendritic cells (DCs). MHC class II molecules acquire their peptides from endocytosed antigens in endocytic vesicles. Specifically, the class II molecules primarily present peptides of exogenous or plasma membrane proteins that are taken up by APCs during the course of endocytosis. The antigen is processed through a series of endosomal compartments with denaturing environment and a set of proteolytic and denaturing enzymes (Bryant et al. Adv. Immunol. 2002; 80:71-114). As the major proportion of MHC class II epitopes is generated by cleavage and processing of peptides by endosomal and lysosomal proteases, MHC class II epitopes are mainly derived from endocytosed proteins and antigens, which reside in or travel through the endocytic pathway. Proteins without direct access to the endocytic pathway (e.g., antigens naturally located in the cytoplasm, in nonendocytic organelles, or in the nucleus) are in general poorly presented in a MHC class II context.

Antigen/MI-IC complexes are recognized by T-lymphocytes bearing the antigen-specific TORs (T-cell receptors). Antigenic peptides presented in a MHC class I context are recognized by $CD8^+$ cytotoxic T-lymphocytes (CTLs), whereas complexes of antigenic peptides and MHC class II molecules are recognized by $CD4^+$-T helper-cells. While $CD8^+$ CTLs mediate important cell-mediated effector functions including cytotoxic activity directed against cancerous or virus-infected cells, $CD4^+$ T helper cells play a key role in orchestrating CTL effector functions and antibody production. Nucleic acid vaccines have many advantages over traditional peptide/protein vaccines with vaccine design being straightforward, thereby reducing cost and production time. Moreover nucleic acid vaccines allow easy delivery of multiple antigens with one immunization and can induce both humoral and cellular immune responses, which makes tumor/pathogen escape less likely. Additionally, unlike peptide-based vaccines, nucleic acid-based vaccines are not restricted by the patient's HLA type. Furthermore, the in vivo expression of an antigen and endogenous post-translational modification results in native protein structures ensuring appropriate processing and immune presentation. From a safety aspect, cloning or synthesis of nucleic acids rather than having to purify proteins from pathogens avoids the need for use of pathogenic microorganisms in vaccine manufacture, rendering nucleic acid vaccines generally safe and tolerable (Li and Petrovsky Expert Rev Vaccines. 2016; 15(3): 313-329, McNamara et al. J Immunol Res. 2015; 2015: 794528).

Despite their promising characteristics, DNA vaccines were found to elicit less of an immune response than other types of vaccines, including peptide vaccines, cellular vaccines, viral vector vaccines, and RNA vaccines. The relatively poor immunogenicity of DNA vaccines combined with concerns about their potential for oncogenesis via integration into the host genome renders RNA-based vaccines particularly appealing. However, antigens encoded by RNA vaccines are typically translated in the cytoplasm and degraded by proteasomes, resulting predominantly in MHC class I-mediated presentation to $CD8^+$ T cells. In order to foster CTL-mediated immune responses, or even induce antibody production, an additional stimulation of a productive T helper cell response via the MHC class II pathway would be highly desirable (McNamara et al. J Immunol Res. 2015; 2015: 794528).

Different strategies were tested in preclinical models to exploit the therapeutic potential of nucleic acid vaccines, including novel plasmid vectors and codon optimization to enhance antigen expression, new gene transfection systems or electroporation to increase delivery efficiency, protein or live virus vector boosting regimens to maximise immune stimulation, and formulation of nucleic acid vaccines with traditional or molecular adjuvants (Li and Petrovsky Expert Rev Vaccines. 2016; 15(3): 313-329). Several studies have demonstrated that addition of a lysosomal targeting signal to the antigen-encoding sequence can result in a productive T helper cell response. Additionally, tumor antigen mRNAs fused to a signal peptide and an HLA class II sorting can result in HLA class I and II presentation (WO200212281; Marks et al. 1995 J Cell Biol. 1995; 131:351-369; Kreiter et al. 2007 J Immunol. 2008 Jan. 1; 180(1):309-18.). Diebold et al. (Gene Ther. 2001 March; 8(6):487-93) demonstrated that dendritic cells expressing cDNA as transferrin receptor (TfR) or invariant chain fusions were capable of generating MHC class II specific immune responses in addition to MHC class I responses. Kreiter et al. (J Immunol. 2008 Jan. 1; 180(1):309-18) reported that combining an N-terminal leader peptide with an MHC class I trafficking signal (MITD) attached to the C terminus of an RNA-encoded antigen strongly improves the presentation of MHC class I and class II epitopes in human and murine dendritic cells (DCs).

In the two decades since their initial discovery, nucleic acid vaccines technologies have come a long way. However, effective strategies for boosting both CD8$^+$ and CD4$^+$ T cell responses and thereby increasing the therapeutic or prophylactic efficacy of nucleic acid based vaccines are still missing.

Boyle et al. (Nature. 1998 Mar. 26; 392(6674):408-11), Deliyannis et al. (Proc Natl Acad Sci USA. 2000 Jun. 6; 97(12):6676-80) and Xu et al. (J Gene Med. 2009 April; 11(4):354-60) all describe DNA vaccines encoding fusion proteins with extracellular domains of CTLA4. These extracellular domains specifically target the fused antigens to professional antigen-presenting cells expressing the CTLA4 ligand B7.

It is an object of the present invention to comply with the needs in the art and to provide improved therapeutic approaches for the treatment of the diseases specified herein. The object underlying the present invention is solved by the claimed subject matter, inter alia by providing nucleic acids encoding fusion proteins with functional transmembrane domains for improved antigen "loading" of MHC-I and MHC-II in the respective cellular compartments.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

In the present invention, if not otherwise indicated, different features of alternatives and embodiments may be combined with each other.

For the sake of clarity and readability the following definitions are provided. Any technical feature mentioned for these definitions may be read on each and every embodiment of the invention. Additional definitions and explanations may be specifically provided in the context of these embodiments.

Definitions

Artificial nucleic acid molecule: An artificial nucleic acid molecule may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides, which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

DNA: DNA is the usual abbreviation for deoxy-ribo-nucleic acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxy-cytidine-monophosphate monomers which are-by themselves-composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA sequence. DNA may be single stranded or double stranded. In the double stranded form, the nucleotides of the first strand typically hybridize with the nucleotides of the second strand, e.g. by A/T-base-pairing and G/C-base-pairing.

Heterologous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers, which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets, which may be translated into a peptide or protein. An open reading frame preferably contains a start codon, i.e. a combination of three subsequent nucleotides coding usually for the amino acid methionine (ATG), at its 5'-end and a subsequent region, which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated in a longer nucleic acid sequence, for example in a vector or an mRNA. An open reading frame may also be termed "(protein) coding sequence" or, preferably, "coding sequence".

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Polyvalent/multivalent composition: The terms "polyvalent composition" or "multivalent composition" will be recognized and understood by the person of ordinary skill in the art, and are e.g. intended to refer to a composition or a vaccine comprising different antigens or epitopes of different antigens, or comprising different epitopes of the same antigen, or any combination thereof. The terms describe that said vaccine or composition has more than one valence. In the context of the invention, a polyvalent cancer vaccine would comprise at least one artificial nucleic acid molecule e.g.

RNA encoding antigenic peptides or proteins derived from several different antigens or encoding different epitopes from the same antigen, or a combination thereof.

Protein: A protein typically comprises one or more peptides or polypeptides. A protein is typically folded into 3-dimensional form, which may be required for the protein to exert its biological function.

Restriction site: A restriction site, also termed restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA, mRNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino-acid sequence of a particular peptide or protein. Typically, a mature mRNA comprises a 5'-cap, a 5'-UTR, an open reading frame, a 3'-UTR and a poly(A) sequence.

The artificial RNA, preferably the mRNA of the invention may be prepared using any method known in the art, including chemical synthesis such as e.g. solid phase RNA synthesis, as well as in vitro methods, such as RNA in vitro transcription reactions.

RNA in vitro transcription/in vitro transcription: The terms "RNA in vitro transcription" or "in vitro transcription" relate to a process wherein RNA is synthesized in a cell-free system (in vitro). DNA, particularly plasmid DNA (or PCR product), is typically used as template for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase. Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis.

Reagents used in RNA in vitro transcription typically include: a DNA template (linearized plasmid DNA or PCR product) with a promoter sequence that has a high binding affinity for its respective RNA polymerase such as bacteriophage-encoded RNA polymerases (T7, T3, SP6, or Syn5); ribonucleotide triphosphates (NTPs) for the four bases (adenine, cytosine, guanine and uracil); optionally, a cap analogue as defined herein (e.g. m7G(5')ppp(5')G (m7G)); optionally, further modified nucleotides as defined herein; a DNA-dependent RNA polymerase capable of binding to the promoter sequence within the DNA template (e.g. T7, T3, SP6, or Syn5 RNA polymerase); optionally, a ribonuclease (RNase) inhibitor to inactivate any contaminating RNase; optionally, a pyrophosphatase to degrade pyrophosphate, which may inhibit transcription; MgCl2, which supplies Mg2+ ions as a co-factor for the polymerase; a buffer (TRIS or HEPES) to maintain a suitable pH value, which can also contain antioxidants (e.g. DTT), and/or polyamines such as spermidine at optimal concentrations, or a buffer system as disclosed in WO2017/109161.

In the context of nucleic acid vaccine production, it may be required to provide GMP-grade RNA. GMP-grade RNA may be suitably produced using a manufacturing process approved by regulatory authorities. Accordingly, in a particularly preferred embodiment, RNA production is performed under current good manufacturing practice (GMP), implementing various quality control steps on DNA and RNA level, according to WO2016/180430. Accordingly, the RNA of the invention is a GMP-grade RNA, particularly a GMP-grade RNA mRNA.

The obtained RNA products are preferably purified using PureMessenger® (CureVac, Tibingen, Germany; RP-HPLC according to WO2008/077592) and/or tangential flow filtration (as described in WO2016/193206). Where nucleic acid sequences are reported in the context of the present invention, these sequences generally comprise both, the specific RNA or DNA sequence as well as its corresponding DNA or RNA counterpart, respectively. For example, where a DNA sequence is provided, the skilled person knows that the corresponding RNA sequence is obtained by exchange of thymine by uracil residues and vice versa.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity ("% identity), the sequences to be compared are typically considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides or amino acids of a sequence which have the same position in two or more sequences having the same length. Specifically, the "% identity" of two amino acid sequences or two nucleic acid sequences may be determined by aligning the sequences for optimal comparison purposes (e.g., gaps can be introduced in either sequences for best alignment with the other sequence) and comparing the amino acids or nucleotides at corresponding positions. Gaps are usually regarded as non-identical positions, irrespective of their actual position in an alignment. The "best alignment" is typically an alignment of two sequences that results in the highest percent identity. The percent identity is determined by the number of identical nucleotides in the sequences being compared (i.e., % identity=# of identical positions/total # of positions×100). The determination of percent identity between two sequences can be accomplished using a mathematical algorithm known to those of skill in the art.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection:

The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Vector: The term "vector" refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector, which allows the convenient storage of a nucleic acid molecule, for example, of an mRNA molecule. Thus, the vector may comprise a sequence corresponding, e.g., to a desired mRNA sequence or a part thereof, such as a sequence corresponding to the coding sequence and the 3'-UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA polymerase promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector, which is suitable for transferring nucleic acid molecules into cells or organisms, for example, viral vectors. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication.

Vehicle: A vehicle is typically understood to be a material that is suitable for storing, transporting, and/or administering a compound, such as a pharmaceutically active compound. For example, it may be a physiologically acceptable liquid, which is suitable for storing, transporting, and/or administering a pharmaceutically active compound.

The present application is filed together with a sequence listing in electronic format, which is part of the description of the present application (WIPO standard ST.25). The information contained in the electronic format of the sequence listing filed together with this application is incorporated herein by reference in its entirety. Where reference is made herein to a "SEQ ID NO:" the corresponding nucleic acid sequence or amino acid (aa) sequence in the sequence listing having the respective identifier is referred to. For many sequences, the sequence listing also provides additional detailed information, e.g. regarding certain structural features, sequence optimizations, GenBank identifiers, or regarding its coding capacity. In particular, such information is provided under numeric identifier <223> in the WIPO standard ST.25 sequence listing. Accordingly, information provided under said numeric identifier <223> is explicitly included herein in its entirety and has to be understood as integral part of the description of the underlying invention.

The present invention is based, in part, on the surprising finding that antigen fusion to suitable "targeting" sequences derived from a group of signal transduction proteins involved in immune responses advantageously routes these antigens to MHC class I and MHC class II processing compartments. These "targeting" sequences preferably comprise or consist of transmembrane domains. Proteins (e.g. CTLA4) containing the employed "targeting" sequences are expressed on the external side of plasma membranes, and are typically "fast recycling" proteins that are readily and recurrently internalized to enter the endosomal pathways, which preferably intersect MHC class I and in particular also MHC class II pathways. The "targeting" approach of the present invention is therefore different from other prior art approaches in that it preferably targets antigens to desired intracellular pathways, rather than certain cell types.

For effective delivery of antigenic sequences to MHC class I and MHC class II processing compartments, nucleic acid molecules can be engineered to encode antigens/ epitopes that are fused to suitable amino acid sequences derived from fast-recycling proteins residing in the plasma membrane. Targeting can be achieved by using the full-length amino acid sequence of a protein, or preferably its transmembrane (and optionally cytoplasmic) domains, preferably together with a suitable signal peptide. Fusing these sequences to the antigenic peptide or protein of interest preferably facilitates the localization of the antigens/ epitopes to the plasma membrane, and its recycling to cellular compartments where the MHC class I and II processing and loading take place, like the endoplasmic reticulum, endosomes or the lysosome. The unprecedented targeting strategy presented herein exploits the fast-recycling characteristics conferred by amino acid sequences (in particular transmembrane domains) derived from the group of immune-response activating signal transduction (IRST$_{epm}$) proteins residing in the plasma membrane of immune cells. By effectively routing antigenic peptides or proteins to the plasma membrane and effecting their anchorage therein and subsequent recycling to cellular compartments intersecting with the MHC processing and loading pathways via the fused IRST$_{epm}$-derived protein domains, the presentation of encoded antigens/epitopes by MHC class I and MHC class II in recipient cells and therefore the induction of antigen-specific immune responses against the immunogenic epitopes or whole antigens by nucleic acid-based vaccines is preferably increased. The targeting approach presented herein therefore exploits the common pathways of fast-recycling of membrane-bound IRST$_{epm}$-proteins, instead of using state-of-the-art approaches of directing the translated antigenic proteins or peptides directly to endosomal/lysosomal compartments via the fusion of different trafficking sequences.

To that end, the present inventors generated nucleic acid molecules encoding such antigenic fusion proteins and investigated their therapeutic potential in a tumor model. Therefore, antigenic proteins, peptides or epitopes of interest were joined to selected domains or full-length proteins derived from several fast-recycling immune-response activating signal transduction proteins. Typically, nucleic acid constructs were designed by removing the extracellular domain of the protein and replace it by the antigen/epitope. Signal peptides and transmembrane domains can be included to optimize transport to and anchorage on the external site of the plasma membrane. Additionally, suitable linkers were introduced to allow the correct presentation of immunogenic peptides by the MHC class I and class II molecules. T helper cell epitopes may be included to increase the induction of antigen-specific immune responses against the encoded epitopes. The design strategy permitted the targeting of specific epitopes or whole antigens to MHC class I- and class II-enriched cellular compartments.

Surprisingly, the antigenic fusion proteins were capable of effectively inducing antigen-specific T cell responses, and and was shown to efficiently reduce tumor growth in a mouse model.

The novel targeting approach presented herein provides a convenient and effective means to preferably ensure antigen entry into MHC processing pathways. Thereby, said targeting strategy preferably enhances the induction of antigen-specific immune responses against antigenic peptides or proteins or epitopes and opens up new possibilities for the increased therapeutic efficacy of nucleic acid vaccines.

In a first aspect, the present invention relates to an artificial nucleic acid molecule comprising at least one coding region encoding a. at least one antigenic peptide or protein, and b. at least one additional amino acid sequence derived from at least one immune response signal transduction protein located in the external plasma membrane, as defined below.

Preferably, said at least one additional amino acid sequence comprises or consists of at least one transmembrane domain of said protein. Without wishing to be bound by specific theory, it is envisaged that the at least one additional amino acid sequence derived from the at least one immune response signal transduction protein located in the external plasma membrane (also referred to as "IRST$_{epm}$ herein) provides for an improved MHC class I and II presentation efficiency, preferably resulting in simultaneous stimulation and expansion of CD8⁺ and CD4⁺ T cell subsets.

The artificial nucleic acid molecule of the invention-which may preferably be an RNA as described below-thus encodes at least one $IRST_{epm}$ derived amino acid sequence (which is preferably selected based on its capability of routing fused amino acid sequences into desired compartments of MHC processing and loading) and at least one antigenic peptide or protein (which is preferably selected based on the particular disease or condition to be treated or prevented). Both are typically expressed as a fusion protein, which is also referred to as "antigenic fusion protein herein". As described below, the artificial nucleic acid molecules, preferably RNAs, of the invention may encode antigenic polypeptide constructs comprising several (identical or different) $IRST_{epm}$ derived amino acid sequences, several (identical or different) antigenic peptides or proteins, and optionally further (poly-)peptides, proteins or protein domains (such as signal peptides, peptide linkers, and T helper epitopes) in any combination disclosed herein. However, the artificial nucleic acid molecule, preferably RNA, of the invention is envisaged to encode an "antigenic polypeptide construct" comprising at least one antigenic peptide or protein, and at least one $IRST_{epm}$-derived additional amino acid sequence.

Coding Region $IRST_{epm}$-Derived Amino Acid Sequences

The present inventors surprisingly discovered that fusing antigenic peptides or proteins to appropriate targeting sequences derived from immune response-activating signal transduction proteins located in the external plasma membrane ("$IRST_{epm}$") effectively mediates MHC presentation, preferably resulting in increased T cell responses. Without wishing to be bound by specific theory, $IRST_{epm}$-derived amino acid sequences may preferably comprise targeting sequences, which mediate translocation into defined subcellular compartments of MHC processing and loading, resulting in enhanced MHC class I and class II presentation of antigenic peptides and proteins fused thereto. The term "immune-response-activating signal transduction" refers to the cascade of processes by which a signal interacts with a receptor, causing a change in the level or activity of a second messenger or other downstream target, and ultimately leading to activation or perpetuation of an immune response. The term "$IRST_{epm}$ protein" thus refers proteins located in the external plasma membrane, i.e. the leaflet of the plasma membrane that faces away from the cytoplasm, which are involved in such signaling cascades. $IRST_{epm}$ proteins are therefore preferably expressed on the plasma membrane of immune cells, more preferably of antigen-presenting cells (APCs). It will be acknowledged that due to the complexicty of intracellular signaling pathways, the term $IRST_{epm}$ protein may include proteins having dual roles in the regulation of immune responses and have inhibitory and activating effects in different settings. Preferred $IRST_{epm}$ proteins are indicated in Table 1 below. Preferably, "$IRST_{epm}$ proteins" are quickly recycled at the cellular surface.

As explained above, the inventive artificial nucleic acid molecules comprise at least one amino acid sequence "derived from" at least one $IRST_{epm}$ protein as defined herein.

The term "derived from" as used herein generally indicates that a sequence may be isolated from, related to, based on or homologous to a reference sequence. Sequences that are "derived from" a reference sequences thus include sequences that are identical to said reference sequence (i.e. full-length sequences exhibiting 100% sequence identity to said reference sequence), as well as variants, fragments and derivatives of said reference sequences. The definition is applicable to both amino acid sequences and nucleic acid sequences, mutatis mutandis.

Artificial nucleic acid molecules, preferably RNAs, of the invention preferably encode, in their at least one coding region, at least one amino acid sequence derived from an $IRST_{epm}$ protein as described herein, or a fragment, variant or derivative of any of said proteins.

As used herein, the term "(protein/amino acid sequence) variant" in general refers to "sequence variants", i.e. proteins or (poly-)peptides comprising an amino acid sequence that differs in at least one amino acid residue from a reference (or "parent") amino acid sequence of a reference (or "parent") protein or (poly-)peptide.

"Variant" proteins/(poly-)peptides may thus preferably comprise, in their amino acid sequence, at least one amino acid mutation, substitution, insertion or deletion as compared to their respective reference sequence. Substitutions may be selected from conservative or non-conservative substitutions. Protein/(poly-)peptide "variants" may comprise at least one conservative amino acid substitution, wherein amino acids, originating from the same class, are exchanged for one another. In particular, these are amino acids having aliphatic side chains, positively or negatively charged side chains, aromatic groups in the side chains or amino acids, the side chains of which can form hydrogen bridges, e.g. side chains which have a hydroxyl function. By conservative constitution, e.g. an amino acid having a polar side chain may be replaced by another amino acid having a corresponding polar side chain, or, for example, an amino acid characterized by a hydrophobic side chain may be substituted by another amino acid having a corresponding hydrophobic side chain (e.g. serine (threonine) by threonine (serine) or leucine (isoleucine) by isoleucine (leucine)). However, non-conservative amino acid substitutions are also envisaged herein.

Preferably, the term "variant" as used herein includes naturally occurring variants, e.g. preproteins, proproteins, and proteins/(poly-)peptides that have been subjected to post-translational proteolytic processing (this may involve removal of the N-terminal methionine, signal peptide, and/or the conversion of an inactive or non-functional protein to an active or functional one), and naturally occurring mutant proteins/(poly-)peptides. The term "variant" further encompasses engineered variants of proteins/(poly-)peptides, which may be (sequence-)modified to introduce or abolish a certain biological property and/or functionality. The terms "transcript variants" or "splice variants" in the context of proteins/(poly-)peptides refer to variants produced from messenger RNAs that are initially transcribed from the same gene, but are subsequently subjected to alternative (or differential) splicing, where particular exons of a gene may be included within or excluded from the final, processed messenger RNA (mRNA). It will be noted that the term "variant" may essentially be defined by way of a minimum degree of sequence identity (and preferably also a desired biological function/properties) as compared to a reference protein/(poly-)peptides. Thus, fragments or certain derivatives (which also differ in terms of their amino acid sequence from the reference protein/(poly-)peptide) could be classified as "variants" as well. Therefore, a "variant" as defined herein can be derived from, isolated from, related to or based on the reference protein/(poly-)peptide or a fragment or derivative thereof.

The term "(protein/amino acid sequence) variant" as used herein preferably refers to (poly-)peptides having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with an amino acid sequence of the respective naturally occurring (wild-type) protein/(poly-)peptide, or a fragment or derivative thereof.

As used herein, the term "(protein/amino acid sequence) fragment" in general refers to a protein/(poly-)peptide that consists of a continuous subsequence of the full-length amino acid sequence of a reference (or "parent") protein/(poly-)peptide, which is, with regard to its amino acid sequence, N-terminally, C-terminally and/or intrasequentially truncated compared to the amino acid sequence of said reference protein/(poly-)peptide. Such truncation may occur either on the amino acid level or on the nucleic acid level, respectively. In other words, a "fragment" may typically be a shorter portion of a full-length sequence of an amino acid sequence. Accordingly, a fragment, typically, consists of a sequence that is identical to the corresponding stretch within the full-length amino acid sequence. The term includes naturally occurring fragments (such as fragments resulting from naturally occurring in vivo protease activity) as well as engineered fragments.

The term "(protein/amino acid sequence) fragment" as used herein may refer to a protein/(poly-)peptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a reference protein/(poly-)peptide, or a variant or derivative thereof.

A preferred fragment of a sequence in the context of the present invention, consists of a continuous stretch of amino acids corresponding to a continuous stretch of entities in the reference protein/(poly-)peptide, which represents at least 20%, preferably at least 30%, more preferably at least 40%, more preferably at least 50%, even more preferably at least 60%, even more preferably at least 70%, and most preferably at least 80% of the total (i.e. full-length) reference protein/(poly-)peptide, or a variant or derivative thereof, from which the fragment is derived.

A sequence identity indicated with respect to such a fragment preferably refers to the entire amino acid sequence of the reference protein/(poly-)peptide. Preferably, a "fragment" may typically comprise or consist of an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably at least 90% and most preferably of at least 95% or even 97%, with the amino acid sequence of to a reference protein/(poly-)peptide, or a variant or derivative derivative thereof.

As used herein, the term "(protein/amino acid sequence) derivative", is generally to be understood as a protein/(poly-)peptide that has been modified with respect to a reference (or "parent") protein/(poly-)peptide to include a new or additional property or functionality. Derivatives may be modified to comprise desired biological functionalities (e.g. by introducing or removing moieties or domains that confer, enhance, reduce or abolish target binding affinity or specificity or enzymatic activities), manufacturing properties (e.g. by introducing moieties which confer an increased solubility or enhanced excretion, or allow for purification) or pharmacokinetic/pharmacodynamics properties for medical use (e.g. by introducing moieties which confer increased stability, bioavailability, absorption; distribution and/or reduced clearance). Derivatives may be prepared by introducing or removing a moiety or domain that confers a biological property or functionality of interest. Such moieties or domains may be introduced into the amino acid sequence (e.g. at the amino and/or carboxyl terminal residues) post-translationally or at the nucleic acid sequence level using standard genetic engineering techniques (cf. Sambrook J et al., 2012 (4th ed.), Molecular cloning: a laboratory manual. Cold Spring Harbor Laboratory, Cold Spring Harbor, New York). A "derivative" may be derived from (and thus optionally include) the naturally occurring (wild-type) protein/(poly-)peptide amino acid sequence, or a variant or fragment thereof. It will be understood that "(protein/amino acid sequence) derivatives" may differ (e.g. by way of introduction or removal of (poly-)peptide moieties and/or protein domains) in their amino acid sequence from the reference protein/(poly-)peptide that they are derived from, and thus may qualify as "variants" as well. However, whereas "(protein/amino acid sequence) variants" are primarily defined in terms of their sequence identity to a reference amino acid sequence, derivatives are preferably characterized by the presence or absence of a specific biological property or functionality as compared to the reference protein. Nevertheless, "(protein/amino acid sequence) derivatives" may preferably comprise or consist of an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with the amino acid sequence of to a reference protein/(poly-)peptide, or a variant or fragment thereof.

According to preferred embodiments of the invention, the artificial nucleic acid molecule, preferably RNA, of the invention, encodes in its at least one coding region at least one additional amino acid sequence derived from any one of the proteins indicated in Table 1 below, or a (preferably functional) fragment, variant or derivative of any one of said proteins.

Preferably, in the context of the present invention, "functional" fragments, variants or derivatives substantially exhibit the same or comparable biological functionalities as their respective "parent" or "reference" sequence. The definition is applicable to "functional" protein/peptide/amino acid sequence fragments, variants or derivatives as well as "functional" nucleic acid sequence/polynucleotide fragments, variants or derivatives. The desired biological functionality is preferably indicated in the context of the respective sequence. In general, "functional" protein/peptide/amino acid sequence fragments, variants or derivatives may preferably exhibit the same or comparable binding characteristics, targeting characteristics, immune response-inducing characteristics . . . and so an as their "parent" or "reference" sequence. "Functional" nucleic acid sequence/polynucleotide fragments, variants or derivatives may preferably exhibit the same or a comparable capability as to encode and be expressed (i.e. optionally transcribed, and translated) to yield a desired protein/peptide/amino acid sequence as their respective "parent" or "reference" sequence.

"Functional" IRST$_{epm}$ protein fragments, variants and derivatives are preferably capable of directing antigenic proteins or peptides (preferably fused thereto) into MHC class I and preferably MHC class II processing compartments. The use of "functional" IRST$_{epm}$ protein fragments, variants and derivatives therefore preferably enhances CD4$^+$ T helper cell responses, and, accordingly, increased CD8$^+$ CTL and/or antibody-mediated immunity.

TABLE 1

IRST$_{epm}$ proteins

| # | UniProt Identifier | Protein Name | Short Name | SEQ ID NO: wt amino acid sequence | SEQ ID NO: wt nucleic acid sequence | SEQ ID NO: optimized nucleic acid sequence |
|---|---|---|---|---|---|---|
| 1 | P16410 | Cytotoxic T-lymphocyte protein 4 | CTLA4 | SEQ ID NO: 169 | 377 | 585, 793, 1001, 1209, 1417, 1625, 1833, 2041, 2249, 2457, 2665, 2873 |
| 2 | P32248 | C-C chemokine receptor type 7 | CCR7 | SEQ ID NO: 173 | 381 | 589, 797, 1005, 1213, 1421, 1629, 1837, 2045, 2253, 2461, 2669, 2877 |
| 3 | A0A5B9 | T-cell receptor beta-2 chain C region | TRBC2 | SEQ ID NO: 157 | 365 | 573, 781, 989, 1197, 1405, 1613, 1821, 2029, 2237, 2445, 2653, 2861 |
| 4 | B7Z8K6 | T-cell receptor delta TRDC chain C region | | SEQ ID NO: 158 | 366 | 574, 782, 990, 1198, 1406, 1614, 1822, 2030, 2238, 2446, 2654, 2862 |
| 5 | B9A064 | Immunoglobulin lambda-like polypeptide 5 | IGLL5 | SEQ ID NO: 159 | 367 | 575, 783, 991, 1199, 1407, 1615, 1823, 2031, 2239, 2447, 2655, 2863 |
| 6 | O00206 | Toll-like receptor 4 | TLR4 | SEQ ID NO: 160 | 368 | 576, 784, 992, 1200, 1408, 1616, 1824, 2032, 2240, 2448, 2656, 2864 |
| 7 | P01730 | T-cell surface glycoprotein CD4 | CD4 | SEQ ID NO: 161 | 369 | 577, 785, 993, 1201, 1409, 1617, 1825, 2033, 2241, 2449, 2657, 2865 |
| 8 | P01850 | T-cell receptor beta-1 chain C region | TRBC1 | SEQ ID NO: 162 | 370 | 578, 786, 994, 1202, 1410, 1618, 1826, 2034, 2242, 2450, 2658, 2866 |
| 9 | P07766 | T-cell surface glycoprotein CD3 epsilon chain | CD3E | SEQ ID NO: 163 | 371 | 579, 787, 995, 1203, 1411, 1619, 1827, 2035, 2243, 2451, 2659, 2867 |
| 10 | P08575 | Receptor-type tyrosine-protein phosphatase C | PTPRC | SEQ ID NO: 164 | 372 | 580, 788, 996, 1204, 1412, 1620, 1828, 2036, 2244, 2452, 2660, 2868 |

TABLE 1-continued

IRST$_{epm}$ proteins

| # | UniProt Identifier | Protein Name | Short Name | SEQ ID NO: wt amino acid sequence | SEQ ID NO: wt nucleic acid sequence | SEQ ID NO: optimized nucleic acid sequence |
|---|---|---|---|---|---|---|
| 11 | P08637 | Low affinity immunoglobulin gamma Fc region receptor III-A | FCG3A | SEQ ID NO: 165 | 373 | 581, 789, 997, 1205, 1413, 1621, 1829, 2037, 2245, 2453, 2661, 2869 |
| 12 | P10747 | T-cell-specific surface glycoprotein CD28 | CD28 | SEQ ID NO: 166 | 374 | 582, 790, 998, 1206, 1414, 1622, 1830, 2038, 2246, 2454, 2662, 2870 |
| 13 | P11912 | B-cell antigen receptor complex-associated protein alpha chain | CD79A | SEQ ID NO: 167 | 375 | 583, 791, 999, 1207, 1415, 1623, 1831, 2039, 2247, 2455, 2663, 2871 |
| 14 | P15391 | B-lymphocyte antigen CD19 | CD19 | SEQ ID NO: 168 | 376 | 792, 1000, 1208, 1416, 1624, 1832, 2040, 2248, 2456, 2664, 2872, 584 |
| 15 | P16671 | Platelet glycoprotein 4 | CD36 | SEQ ID NO: 170 | 378 | 586, 794, 1002, 1210, 1418, 1626, 1834, 2042, 2250, 2458, 2666, 2874 |
| 16 | P26718 | NKG2-D type II integral membrane protein | NKG2D | SEQ ID NO: 171 | 379 | 587, 795, 1003, 1211, 1419, 1627, 1835, 2043, 2251, 2459, 2667, 2875 |
| 17 | P30273 | High affinity immunoglobulin epsilon receptor subunit gamma | FCERG | SEQ ID NO: 172 | 380 | 588, 796, 1004, 1212, 1420, 1628, 1836, 2044, 2252, 2460, 2668, 2876 |
| 18 | P40259 | B-cell antigen receptor complex-associated protein beta chain, | CD79B | SEQ ID NO: 174 | 382 | 590, 798, 1006, 1214, 1422, 1630, 1838, 2046, 2254, 2462, 2670, 2878 |
| 19 | P42081 | T-lymphocyte activation antigen CD86 | CD86 | SEQ ID NO: 175 | 383 | 591, 799, 1007, 1215, 1423, 1631, 1839, 2047, 2255, 2463, 2671, 2879 |
| 20 | Q15762 | CD226 antigen | CD226 | SEQ ID NO: 176 | 384 | 592, 800, 1008, 1216, 1424, 1632, 1840, 2048, 2256, 2464, 2672, 2880 |
| 21 | Q685J3 | Mucin-17 | MUC17 | SEQ ID NO: 177 | 385 | 593, 801, 1009, 1217, 1425, 1633, 1841, 2049, 2257, 2465, 2673, 2881 |
| 22 | Q9NNX6 | CD209 | CD209 antigen | SEQ ID NO: 178 | 386 | 594, 802, 1010, 1218, 1426, 1634, 1842, 2050, 2258, 2466, 2674, 2882 |

TABLE 1-continued

IRST$_{epm}$ proteins

| # | UniProt Identifier | Protein Name | Short Name | SEQ ID NO: wt amino acid sequence | SEQ ID NO: wt nucleic acid sequence | SEQ ID NO: optimized nucleic acid sequence |
|---|---|---|---|---|---|---|
| 23 | Q9NR97 | TLR8 | Toll-like receptor 8 | SEQ ID NO: 179 | 387 | 803, 1011, 1219, 1427, 1635, 1843, 2051, 2259, 2467, 2675, 2883, 595 |

According to preferred embodiments, the artificial nucleic acid molecule, preferably RNA, according to the invention may encode in its at least one encoding region at least one IRST$_{epm}$-derived additional amino acid sequence comprising or consisting of an amino acid sequence according to any one of SEQ ID NOs: 157-179, or a (preferably functional) fragment, variant or derivative of any one of said sequences, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

Accordingly, the coding region of the artificial nucleic acid molecule, preferably RNA, according to the invention may preferably comprise a nucleic acid sequence according to any one of SEQ ID NOs: 365-387, or a (preferably functional) fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

The term "(nucleic acid sequence/polynucleotide/gene) variant" refers to nucleic acid sequence variants, i.e. nucleic acid sequences or genes comprising a nucleic acid sequence that differs in at least one nucleic acid from a reference (or "parent") nucleic acid sequence of a reference (or "parent") nucleic acid or gene. Variant nucleic acids or genes may thus preferably comprise, in their nucleic acid sequence, at least one mutation, substitution, insertion or deletion as compared to their respective reference sequence. Preferably, the term "variant" as used herein includes naturally occurring variants, and engineered variants of nucleic acid sequences or genes. Therefore, a "variant" as defined herein can be derived from, isolated from, related to, based on or homologous to the reference nucleic acid sequence. "Variants" may preferably have a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, to a nucleic acid sequence of the respective naturally occurring (wild-type) nucleic acid sequence or gene, or a homolog, fragment or derivative thereof.

The term "(nucleic acid sequence/polynucleotide/gene) fragment" refers to a continuous subsequence of the full-length reference (or "parent") nucleic acid sequence or gene. In other words, a "fragment" may typically be a shorter portion of a full-length nucleic acid sequence or gene. Accordingly, a fragment, typically, consists of a sequence that is identical to the corresponding stretch within the full-length nucleic acid sequence or gene. The term includes naturally occurring fragments as well as engineered fragments. A preferred fragment of a sequence in the context of the present invention, consists of a continuous stretch of nucleic acids corresponding to a continuous stretch of entities in the nucleic acid or gene the fragment is derived from, which represents at least 20%, preferably at least 30%, more preferably at least 40%, more preferably at least 50%, even more preferably at least 60%, even more preferably at least 70%, and most preferably at least 80% of the total (i.e. full-length) nucleic acid sequence or gene from which the fragment is derived.

A sequence identity indicated with respect to such a fragment preferably refers to the entire nucleic acid sequence or gene. Preferably, a "fragment" may comprise a nucleic acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, to a reference nucleic acid sequence or gene that it is derived from.

The term "(nucleic acid sequence/polynucleotide/gene) derivative", is generally to be understood as a nucleic acid sequence/polynucleotide/gene that has been modified with respect to a reference (or "parent") nucleic acid sequence/polynucleotide/gene to include a new or additional property or functionality. Derivatives may be modified to comprise desired biological functionalities (e.g. resistance to enzymatic degradation, translation efficacy), manufacturing properties, or pharmacokinetic/pharmacodynamics properties for medical use (e.g. by introducing moieties which confer increased stability, bioavailability, absorption; distribution and/or reduced clearance). Derivatives may be prepared by introducing or removing a nucleic acid sequence or additional moiety that confers a biological property or functionality of interest. Such nucleic acid sequences or additional moieties may be introduced using standard genetic engineering techniques (cf. Sambrook J et al., 2012 (4th ed.), Molecular cloning: a laboratory manual. Cold Spring Harbor Laboratory, Cold Spring Harbor, New York).

A "derivative" may be derived from (and thus optionally include) the naturally occurring (wild-type) nucleic acid sequence/polynucleotide/gene, or a variant or fragment thereof. It will be understood that "(nucleic acid sequence/ polynucleotide/gene) derivatives" may differ (e.g. by way of introduction or removal of (poly-)nucleotides) in their nucleotide sequence from the reference nucleic acid sequence/polynucleotide/gene that they are derived from, and thus may qualify as "variants" as well. However, whereas "(nucleic acid sequence/polynucleotide/gene) variants" are primarily defined in terms of their % sequence identity to a reference nucleotide sequence, "derivatives" are preferably characterized by the presence or absence of a specific biological property or functionality as compared to the reference nucleic acid sequence/polynucleotide/gene. Nevertheless, "(nucleic acid sequence/polynucleotide/gene) derivatives" may preferably comprise or consist of an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with the nucleic acid sequence of a reference nucleic acid sequence/polynucleotide/gene, or a variant or fragment thereof.

In the context of the present invention, "(nucleic acid sequence/polynucleotide) derivatives" may particularly include nucleic acid sequence/polynucleotide sequences which have been modified or stabilized as compared to the "parent" or "reference" nucleic acid sequences that they are derived from. It will however be understood that such modified/stabilized nucleic acid sequences/polynucleotides may be defined as "variants" as well.

A "functional" fragment, variant or derivative of said nucleic acid sequences preferably encodes (and thus allows expression of) an $IRST_{epm}$-derived additional amino acid sequence as defined herein.

According to preferred embodiments, the coding region of the artificial nucleic acid molecule, preferably RNA, according to the invention may preferably comprise a nucleic acid sequence according to any one of SEQ ID NOs: 365-387, 573-595, 781-803, 989-1011, 1197-1219, 1613-1635, 1821-1843, 2029-2051, 2237-2259, 2445-2467, 2653-2675, 2861-2883 or a (preferably functional) fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

It will be understood that the artificial nucleic acid molecule, preferably RNA, according to the invention may encode at least one, or a plurality of at least two (identical or different) $IRST_{epm}$-derived amino acid sequences (cf. "Monocistronic, bi- and multicistronic RNAs").

In general, "identical" sequences (or molecules characterized by said sequences, such as (poly-)peptides or nucleic acid molecules) share 100% sequence identity, whereas "different" sequences (or molecules characterized by said sequences, such as (poly-)peptides or nucleic acid molecules) share a sequence identity of less than 100%, such as 99% or less, 90% or less, 80% or less, 70% or less, 60% or less, 50% or less, 40% or less, 30% or less, 20% or less, 10% or less, 5% or less, or 2% or less.

A particularly preferred $IRST_{epm}$ protein may be CTLA4. The additional amino acid sequence(s) encoded by the at least one coding region of the inventive artificial nucleic acid molecule, preferably RNA, of the invention may be derived from CTLA4.

Accordingly, in preferred embodiments, the artificial nucleic acid molecule, preferably RNA, of the invention may encode in its at least one coding region a CTLA4-derived additional amino acid sequence comprising or consisting of an amino acid sequence according to SEQ ID NO: 169, or a (preferably functional) fragment, variant or derivative thereof, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to SEQ ID NO: 169.

Preferably, the artificial nucleic acid molecule, preferably RNA, of the invention may thus comprise in its at least one coding region a nucleic acid sequence comprising or consisting of a nucleic acid sequence according to any one of SEQ ID Nos: 377, 585, 793, 1001, 1209, 1417, 1625, 1833, 2041, 2249, 2457, 2665 or 2873, or a (preferably functional) fragment, variant or derivative of any one of said sequences, preferably preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

Transmembrane domain (TMD)

According to preferred embodiments, the at least one $IRST_{epm}$-derived additional amino acid sequence encoded in the at least one coding region of the artificial nucleic acid molecule, preferably RNA, according to the invention, may comprise or consist of an $IRST_{epm}$-derived transmembrane domain. Accordingly, in the artificial nucleic acid molecule, preferably RNA, of the invention, said at least one additional $IRST_{epm}$-derived amino acid sequence may preferably comprise or consist of b. at least one transmembrane domain.

"Transmembrane domains" are membrane-spanning, typically short (less than 50 amino acid) helical or beta-stranded domain protein domains. Transmembrane domains may be determined by experimentally, e.g. by X-ray diffraction, or may be predicted based on sequence similarities or using known prediction tools, such as MHMM, Memsat, Phobius and the hydrophobic moment plot method. Without wishing to be bound by specific theory, it is envisaged that "fast-recycling" $IRST_{epm}$-derived transmembrane domains are advantageously capable of anchoring fused antigenic peptides or proteins to the plasma membrane, where they are recycled and guided to the cellular compartments of MHC I and in particular MHC II processing.

According to preferred embodiments of the invention, the artificial nucleic acid molecule, preferably RNA, of the invention, encodes in its at least one coding region at least one transmembrane domain as indicated in Table 2 below, or a (preferably functional) fragment, variant or derivative of any of said transmembrane domains.

TABLE 2

| | | | | TM domain amino acid position | SEQ ID NO: wt amino acid sequence | SEQ ID NO: wt nucleic acid sequence | SEQ ID NO: optimized nucleic acid sequence |
|---|---|---|---|---|---|---|---|
| # | UniProt Identifier | Short name | Protein names | | | | |

IRST_spm-derived transmembrane domains

| # | UniProt Identifier | Short name | Protein names | TM domain amino acid position | SEQ ID NO: wt amino acid sequence | SEQ ID NO: wt nucleic acid sequence | SEQ ID NO: optimized nucleic acid sequence |
|---|---|---|---|---|---|---|---|
| 24 | P16671 | CD36 | Platelet glycoprotein 4 (Fatty acid translocase) (FAT) (Glycoprotein IIIb) (GPIIIB) (Leukocyte differentiation antigen CD36) (PAS IV) (PAS-4) (Platelet collagen receptor) (Platelet glycoprotein IV) (GPIV) (Thrombospondin receptor) (CD antigen CD36) | 8-29 | SEQ ID NO: 180 | SEQ ID NO: 388 | 596, 804, 1012, 1220, 1428, 1636, 1844, 2052, 2260, 2468, 2676, 2884 |
| 25 | P16671 | CD36 | See #24 | 440-461 | SEQ ID NO: 182 | SEQ ID NO: 390 | 598, 806, 1014, 1222, 1430, 1638, 1846, 2054, 2262, 2470, 2678, 2886 |
| 26 | P32248 | CCR7 | C-C chemokine receptor type 7 (C-C CKR-7) (CC-CKR-7) (CCR-7) (BLR2) (CDw197) (Epstein-Barr virus-induced G-protein coupled receptor 1) (EBI1) (EBV-induced G-protein coupled receptor 1) (MIP-3 beta receptor) (CD antigen CD197) | 60-86 | SEQ ID NO: 181 | SEQ ID NO: 389 | 597, 805, 1013, 1221, 1429, 1637, 1845, 2053, 2261, 2469, 2677, 2885 |
| 27 | P32248 | CCR7 | See #26 | 96-116 | SEQ ID NO: 183 | SEQ ID NO: 391 | 599, 807, 1015, 1223, 1431, 1639, 1847, 2055, 2263, 2471, 2679, 2887 |
| 28 | P32248 | CCR7 | See #26 | 131-152 | SEQ ID NO: 184 | SEQ ID NO: 392 | 600, 808, 1016, 1224, 1432, 1640, 1848, 2056, 2264, 2472, 2680, 2888 |
| 29 | P32248 | CCR7 | See #26 | 171-191 | SEQ ID NO: 185 | SEQ ID NO: 393 | 601, 809, 1017, 1225, 1433, 1641, 1849, 2057, 2265, 2473, 2681, 2889 |
| 30 | P32248 | CCR7 | See #26 | 220-247 | SEQ ID NO: 186 | SEQ ID NO: 394 | 602, 810, 1018, 1226, 1434, 1642, 1850, 2058, 2266, 2474, 2682, 2890 |
| 31 | P32248 | CCR7 | See #26 | 264-289 | SEQ ID NO: 187 | SEQ ID NO: 395 | 603, 811, 1019, 1227, 1435, 1643, 1851, 2059, 2267, 2475, 2683, 2891 |
| 32 | P32248 | CCR7 | See #26 | 314-331 | SEQ ID NO: 188 | SEQ ID NO: 396 | 604, 812, 1020, 1228, 1436, 1644, 1852, 2060, 2268, 2476, 2684, 2892 |
| 33 | A0A5B9 | TRBC2 | T-cell receptor beta-2 chain C region | 146-168 | SEQ ID NO: 189 | SEQ ID NO: 397 | 605, 813, 1021, 1229, 1437, 1645, 1853, 2061, 2269, 2477, 2685, 2893 |
| 34 | B7Z8K6 | TRDC | T-cell receptor delta chain C region | 131-153 | SEQ ID NO: 190 | SEQ ID NO: 398 | 606, 814, 1022, 1230, 1438, 1646, 1854, 2062, 2270, 2478, 2686, 2894 |
| 35 | O00206 | TLR4 | Toll-like receptor 4 (hToll) (CD antigen CD284) | 632-652 | SEQ ID NO: 191 | SEQ ID NO: 399 | 607, 815, 1023, 1231, 1439, 1647, 1855, 2063, 2271, 2479, 2687, 2895 |
| 36 | P01730 | CD4 | T-cell surface glycoprotein CD4 (T-cell surface antigen T4/Leu-3) (CD antigen CD4) | 397-418 | SEQ ID NO: 192 | SEQ ID NO: 400 | 608, 816, 1024, 1232, 1440, 1648, 1856, 2064, 2272, 2480, 2688, 2896 |
| 37 | P01850 | TRBC1 | T-cell receptor beta-1 chain C region | 152-172 | SEQ ID NO: 193 | SEQ ID NO: 401 | 609, 817, 1025, 1233, 1441, 1649, 1857, 2065, 2273, 2481, 2689, 2897 |

TABLE 2-continued

IRST$_{apm}$-derived transmembrane domains

| # | UniProt Identifier | Short name | Protein names | TM domain amino acid position | SEQ ID NO: wt amino acid sequence | SEQ ID NO: wt nucleic acid sequence | SEQ ID NO: optimized nucleic acid sequence |
|---|---|---|---|---|---|---|---|
| 38 | P07766 | CD3E | T-cell surface glycoprotein CD3 epsilon chain (T-cell surface antigen T3/Leu-4 epsilon chain) (CD antigen CD3e) | 127-152 | SEQ ID NO: 194 | SEQ ID NO: 402 | 610, 818, 1026, 1234, 1442, 1650, 1858, 2066, 2274, 2482, 2690, 2898 |
| 39 | P08575 | PTPRC | Receptor-type tyrosine-protein phosphatase C (EC 3.1.3.48) (Leukocyte common antigen) (L-CA) (T200) (CD antigen CD45) | 576-597 | SEQ ID NO: 195 | SEQ ID NO: 403 | 611, 819, 1027, 1235, 1443, 1651, 1859, 2067, 2275, 2483, 2691, 2899 |
| 40 | P08637 | FCG3A | Low affinity immunoglobulin gamma Fc region receptor III-A (CD16a antigen) (Fc-gamma RIII-alpha) (Fc-gamma RIII) (Fc-gamma RIIIa) (FcRIII) (FcRIIIa) (FcR-10) (IgG Fc receptor III-2) (CD antigen CD16a) | 209-229 | SEQ ID NO: 404 196 | | 612, 820, 1028, 1236, 1444, 1652, 1860, 2068, 2276, 2484, 2692, 2900 |
| 41 | P10747 | CD28 | T-cell-specific surface glycoprotein CD28 (TP44) (CD antigen CD28) | 153-179 | SEQ ID NO: 197 | SEQ ID NO: 405 | 613, 821, 1029, 1237, 1445, 1653, 1861, 2069, 2277, 2485, 2693, 2901 |
| 42 | P11912 | CD79A | B-cell antigen receptor complex-associated protein alpha chain (Ig-alpha) (MB-1 membrane glycoprotein) (Membrane-bound immunoglobulin-associated protein) (Surface IgM-associated protein) (CD antigen CD79a) | 144-165 | SEQ ID NO: 198 | SEQ ID NO: 406 | 614, 822, 1030, 1238, 1446, 1654, 1862, 2070, 2278, 2486, 2694, 2902 |
| 43 | P15391 | CD19 | B-lymphocyte antigen CD19 (B-lymphocyte surface antigen B4) (Differentiation antigen CD19) (T-cell surface antigen Leu-12) (CD antigen CD19) | 292-313 | SEQ ID NO: 199 | SEQ ID NO: 407 | 615, 823, 1031, 1239, 1447, 1655, 1863, 2071, 2279, 2487, 2695, 2903 |
| 44 | P16410 | CTLA4 | Cytotoxic T-lymphocyte protein 4 (Cytotoxic T-lymphocyte-associated antigen 4) (CTLA-4) (CD antigen CD152) | 162-182 | SEQ ID NO: 200 | SEQ ID NO: 408 | 616, 824, 1032, 1240, 1448, 1656, 1864, 2072, 2280, 2488, 2696, 2904 |
| 45 | P26718 | NKG2D | NKG2-D type II integral membrane protein (Killer cell lectin-like receptor subfamily K member 1) (NK cell receptor D) (NKG2-D-activating NK receptor) (CD antigen CD314) | 52-72 | SEQ ID NO: 201 | SEQ ID NO: 409 | 617, 825, 1033, 1241, 1449, 1657, 1865, 2073, 2281, 2489, 2697, 2905 |
| 46 | P30273 | FCERG | High affinity immunoglobulin epsilon receptor subunit gamma (Fc receptor gamma-chain) (FcRgamma) (Fc-epsilon RI-gamma) (IgE Fc receptor subunit gamma) (FceRI gamma) | 24-44 | SEQ ID NO: 202 | SEQ ID NO: 410 | 618, 826, 1034, 1242, 1450, 1658, 1866, 2074, 2282, 2490, 2698, 2906 |
| 47 | P40259 | CD79B | B-cell antigen receptor complex-associated protein beta chain (B-cell-specific glycoprotein B29) (Ig-beta) (Immunoglobulin-associated B29 protein) (CD antigen CD79b) | 160-180 | SEQ ID NO: 203 | SEQ ID NO: 411 | 619, 827, 1035, 1243, 1451, 1659, 1867, 2075, 2283, 2491, 2699, 2907 |

TABLE 2-continued

IRST$_{epm}$-derived transmembrane domains

| # | UniProt Identifier | Short name | Protein names | TM domain amino acid position | SEQ ID NO: wt amino acid sequence | SEQ ID NO: wt nucleic acid sequence | SEQ ID NO: optimized nucleic acid sequence |
|---|---|---|---|---|---|---|---|
| 48 | P42081 | CD86 | T-lymphocyte activation antigen CD86 (Activation B7-2 antigen) (B70) (BU63) (CTLA-4 counter-receptor B7.2) (FUN-1) (CD antigen CD86) | 248-268 | SEQ ID NO: 204 | SEQ ID NO: 412 | 620, 828, 1036, 1244, 1452, 1660, 1868, 2076, 2284, 2492, 2700, 2908 |
| 49 | Q15762 | CD226 | CD226 antigen (DNAX accessory molecule 1) (DNAM-1) (CD antigen CD226) | 255-275 | SEQ ID NO: 205 | SEQ ID NO: 413 | 621, 829, 1037, 1245, 1453, 1661, 1869, 2077, 2285, 2493, 2701, 2909 |
| 50 | Q685J3 | MUC17 | Mucin-17 (MUC-17) (Small intestinal mucin-3) (MUC-3) | 4394-4414 | SEQ ID NO: 206 | SEQ ID NO: 414 | 622, 830, 1038, 1246, 1454, 1662, 1870, 2078, 2286, 2494, 2702, 2910 |
| 51 | Q9NNX6 | CD209 | CD209 antigen (C-type lectin domain family 4 member L) (Dendritic cell-specific ICAM-3-grabbing non-integrin 1) (DC-SIGN) (DC-SIGN1) (CD antigen CD209) | 38-58 | SEQ ID NO: 207 | SEQ ID NO: 415 | 623, 831, 1039, 1247, 1455, 1663, 1871, 2079, 2287, 2495, 2703, 2911 |
| 52 | Q9NR97 | TLR8 | Toll-like receptor 8 (CD antigen CD288) | 828-848 | SEQ ID NO: 208 | SEQ ID NO: 416 | 624, 832, 1040, 1248, 1456, 1664, 1872, 2080, 2288, 2496, 2704, 2912 |

According to preferred embodiments, the artificial nucleic acid molecule according to the invention may encode in its at least one encoding region at least one IRST$_{epm}$-derived transmembrane domain comprising or consisting of an amino acid sequence according to any one of SEQ ID NOs: 180-208, or a (preferably functional) fragment, variant or derivative of any one of said sequences, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

Accordingly, the artificial nucleic acid molecule, preferably RNA, of the invention may preferably comprise in its at least one coding region a nucleic acid sequence according to any one of SEQ ID NOs: 388-416, 596-624, 804-832, 1012-1040, 1220-1248, 1428-1456, 1636-1664, 1844-1872, 2052-2080, 2260-2288, 2468-2496, 2676-2704, 2884-2912, or a (preferably functional) fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

More preferably, the artificial nucleic acid molecule, preferably RNA, of the invention may encode in its at least one coding region a CTLA4-derived transmembrane domain comprising or consisting of an amino acid sequence according to SEQ ID NO: 200, or a (preferably functional) fragment, variant or derivative thereof, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to SEQ ID NO: 200.

Preferably, the artificial nucleic acid molecule, preferably RNA, of the invention may thus comprise in its at least one coding region a nucleic acid sequence comprising or consisting of a nucleic acid sequence according to any one of SEQ ID NOs: 408, 616, 824, 1032, 1240, 1448, 1656, 1864, 2072, 2280, 2488, 2696 or 2904, or a (preferably functional) fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

Cytoplasmic Domain (CD)

According to preferred embodiments, the at least one IRST$_{epm}$-derived additional amino acid sequence encoded in the at least one coding region of the artificial nucleic acid molecule, preferably RNA, according to the invention, may optionally (further) comprise or consist of an IRST$_{epm}$-derived cytoplasmic domain. Accordingly, in the artificial nucleic acid molecule, preferably RNA, of the invention, said at least one additional IRST$_{epm}$-derived amino acid sequence may preferably (further) comprise or consist of c. at least one cytoplasmic domain.

"Cytoplasmic domains" are intracellular domains that typically interact with the interior of the cell. Without wishing to be bound by specific theory, it is envisaged that IRST$_{epm}$-derived cytoplasmic domains may confer further advantageous targeting characteristics to the encoded antigenic peptides or proteins to MHC I and in particular MHC II processing compartments.

Preferably, the IRST$_{epm}$-derived cytoplasmic domain may be present in addition to the IRST$_{epm}$-derived transmembrane domain. The cytoplasmic domain and the transmembrane domain may be derived from identical or different IRST$_{epm}$ proteins. According to some preferred embodiments, the cytoplasmic domain and transmembrane domain are present in one continuous additional IRST$_{epm}$-derived amino acid sequence.

Transmembrane Domain+Cytoplasmic Domain (CD)

According to preferred embodiments, the at least one IRST$_{epm}$-derived additional amino acid sequence encoded in the at least one coding region of the artificial nucleic acid molecule, preferably RNA, according to the invention, may comprise or consist of an IRST$_{epm}$-derived transmembrane domain and an IRST$_{epm}$-derived cytoplasmic domain. Accordingly, in the artificial nucleic acid molecule, preferably RNA, of the invention, said at least one additional IRST$_{epm}$-derived amino acid sequence may preferably comprise or consist of b. at least one transmembrane domain and c. at least one cytoplasmic domain.

TABLE 3

IRST$_{epm}$-derived proteins comprising a transmembrane domain and a cytoplasmatic domain

| # | UniProt Identifier | Short name | TM + Cys domain amino acid position | SEQ ID NO: (AA) | Gene names | SEQ ID NO: wt nucleic acid | SEQ ID NO: optimized nucleic acid |
|---|---|---|---|---|---|---|---|
| 53 | P16671 | CD36 | 440-472 | SEQ ID NO: 76645 | CD36 GP3B GP4 | 76668 | 76691, 76714, 76737, 76760, 76783, 76806, 76829, 76852, 76875, 76898, 76921, 76944 |
| 54 | P32248 | CCR7 | 153-191 | SEQ ID NO: 76646 | CCR7 CMKBR7 EBI1 EVI1 | 76669 | 76692, 76715, 76738, 76761, 76784, 76807, 76830, 76853, 76876, 76899, 76922, 76945 |
| 55 | P32248 | CCR7 | 248-289 | SEQ ID NO: 76647 | CCR7 CMKBR7 EBI1 EVI1 | 76670 | 76693, 76716, 76739, 76762, 76785, 76808, 76831, 76854, 76877, 76900, 76923, 76946 |
| 56 | A0A5B9 | TRBC2 | 145-178 | SEQ ID NO: 76625 | TRBC2 TCRBC2 | 76648 | 76671, 76694, 76717, 76740, 76763, 76786, 76809, 76832, 76855, 76878, 76901, 76924 |
| 57 | B7Z8K6 | TRDC | 131-154 | SEQ ID NO: 76626 | TRDC | 76649 | 76672, 76695, 76718, 76741, 76764, 76787, 76810, 76833, 76856, 76879, 76902, 76925 |
| 58 | O00206 | TLR4 | 632-839 | SEQ ID NO: 76627 | TLR4 | 76650 | 76673, 76696, 76719, 76742, 76765, 76788, 76811, 76834, 76857, 76880, 76903, 76926 |
| 59 | P01730 | CD4 | 397-458 | SEQ ID NO: 76628 | CD4 | 76651 | 76674, 76697, 76720, 76743, 76766, 76789, 76812, 76835, 76858, 76881, 76904, 76927 |
| 60 | P01850 | TRBC1 | 152-178 | SEQ ID NO: 76629 | TRBC1 | 76652 | 76675, 76698, 76721, 76744, 76767, 76790, 76813, 76836, 76859, 76882, 76905, 76928 |

TABLE 3-continued

IRST_opm_-derived proteins comprising a transmembrane domain and a cytoplasmatic domain

| # | UniProt Identifier | Short name | TM + Cys domain amino acid position | SEQ ID NO: (AA) | Gene names | SEQ ID NO: wt nucleic acid | SEQ ID NO: optimized nucleic acid |
|---|---|---|---|---|---|---|---|
| 61 | P07766 | CD3E | 27-207 | SEQ ID NO: 76630 | CD3E T3E | 76653 | 76676, 76699, 76722, 76745, 76768, 76791, 76814, 76837, 76860, 76883, 76906, 76929 |
| 62 | P08575 | PTPRC | 576-1304 | SEQ ID NO: 76631 | PTPRC CD45 | 76654 | 76677, 76700, 76723, 76746, 76769, 76792, 76815, 76838, 76861, 76884, 76907, 76930 |
| 63 | P08637 | FCG3A | 209-254 | SEQ ID NO: 76632 | FCGR3A CD16A FCG3 FCGR3 IGFR3 | 76655 | 76678, 76701, 76724, 76747, 76770, 76793, 76816, 76839, 76862, 76885, 76908, 76931 |
| 64 | P10747 | CD28 | 153-179 | SEQ ID NO: 76633 | CD28 | 76656 | 76679, 76702, 76725, 76748, 76771, 76794, 76817, 76840, 76863, 76886, 76909, 76932 |
| 65 | P11912 | CD79A | 144-226 | SEQ ID NO: 76634 | CD79A IGA MB1 | 76657 | 76680, 76703, 76726, 76749, 76772, 76795, 76818, 76841, 76864, 76887, 76910, 76933 |
| 66 | P15391 | CD19 | 292-556 | SEQ ID NO: 76635 | CD19 | 76658 | 76681, 76704, 76727, 76750, 76773, 76796, 76819, 76842, 76865, 76888, 76911, 76934 |
| 67 | P16410 | CTLA4 | 162-223 | SEQ ID NO: 76636 | CTLA4 CD152 | 76659 | 76682, 76705, 76728, 76751, 76774, 76797, 76820, 76843, 76866, 76889, 76912, 76935, 76947, 77004-77017, 77066 |
| 68 | P26718 | NKG2D | 1-72 | SEQ ID NO: 76637 | KLRK1 D12S2489E NKG2D | 76660 | 76683, 76706, 76729, 76752, 76775, 76798, 76821, 76844, 76867, 76890, 76913, 76936 |
| 69 | P30273 | FCERG | 24-86 | SEQ ID NO: 76638 | FCER1G | 76661 | 76684, 76707, 76730, 76753, 76776, 76799, 76822, 76845, 76868, 76891, 76914, 76937 |
| 70 | P40259 | CD79B | 160-229 | SEQ ID NO: 76639 | CD79B B29 IGB | 76662 | 76685, 76708, 76731, 76754, 76777, 76800, 76823, 76846, 76869, 76892, 76915, 76938 |
| 71 | P42081 | CD86 | 248-329 | SEQ ID NO: 76640 | CD86 CD28LG2 | 76663 | 76686, 76709, 76732, 76755, 76778, 76801, 76824, 76847, 76870, 76893, 76916, 76939 |
| 72 | Q15762 | CD226 | 255-336 | SEQ ID NO: 76641 | CD226 DNAM1 | 76664 | 76687, 76710, 76733, 76756, 76779, 76802, |

TABLE 3-continued

IRST$_{epm}$-derived proteins comprising a transmembrane domain and a cytoplasmatic domain

| # | UniProt Identifier | Short name | TM + Cys domain amino acid position | SEQ ID NO: (AA) | Gene names | SEQ ID NO: wt nucleic acid | SEQ ID NO: optimized nucleic acid |
|---|---|---|---|---|---|---|---|
| 73 | Q685J3 | MUC17 | 4393-4493 | SEQ ID NO: 76642 | MUC17 MUC3 | 76665 | 76825, 76848, 76871, 76894, 76917, 76940 76688, 76711, 76734, 76757, 76780, 76803, 76826, 76849, 76872, 76895, 76918, 76941 |
| 74 | Q9NNX6 | CD209 | 1-58 | SEQ ID NO: 76643 | CD209 CLEC4L | 76666 | 76689, 76712, 76735, 76758, 76781, 76804, 76827, 76850, 76873, 76896, 76919, 76942 |
| 75 | Q9NR97 | TLR8 | 828-1041 | SEQ ID NO: 76644 | TLR8 UNQ249/PRO286 | 76667 | 76690, 76713, 76736, 76759, 76782, 76805, 76828, 76851, 76874, 76897, 76920, 76943 |

According to preferred embodiments, the artificial nucleic acid molecule according to the invention may encode in its at least one coding region at least one IRST$_{epm}$-derived transmembrane domain and at least one cytoplasmic domain comprising or consisting of an amino acid sequence according to any one of SEQ ID NOs: 76625-76647, or a (preferably functional) fragment, variant or derivative of any one of said sequences, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

Accordingly, the artificial nucleic acid molecule, preferably RNA, of the invention may preferably comprise in its at least one coding region a nucleic acid sequence according to any one of SEQ ID NOs: 76648-76670, 76694-76716, 76717-76739, 76671-76693, 77004-770017, 76763-76785, 76786-76808, 76809-76831, 76832-76854, 76855-76877, 76878-76900, 76901-76923, 76924-76946, 76947, 76740-76762, 77066, or a (preferably functional) fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

More preferably, the artificial nucleic acid molecule, preferably RNA, of the invention may encode in its at least one coding region a CTLA4-derived transmembrane domain and cytoplasmic domain comprising or consisting of an amino acid sequence according to SEQ ID NO: 76636, or a (preferably functional) fragment, variant or derivative thereof, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to SEQ ID NO: 76636.

Preferably, the artificial nucleic acid molecule, preferably RNA, of the invention may thus comprise in its at least one coding region a nucleic acid sequence comprising or consisting of a nucleic acid sequence according to any one of SEQ ID NOs: 76659, 76705, 76728, 76682, 77004-77017, 76774, 76797, 76820, 76843, 76866, 76912, 76889, 76935, 76947, 76751, 77066 or a (preferably functional) fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

The nucleic acid sequence of the RNA of the invention may be adapted in a manner to allow differentiation of different RNA species in a composition comprising more than one RNA species. Preferably, the nucleic acid sequence of the RNA is adapted without introducing changes in the amino acid sequence encoded by the respective RNA. Preferably, the nucleic acid sequence of the RNA is adapted in a stretch of 10-200 nucleotides to allow differentiation of different RNA species via PCR based analytical methods. Said adapted sequence stretch(es) may be positioned in an untranslated region (UTR), in the coding sequence of a signal peptide, in the coding sequence of the epitope, in a linker region, in the coding sequence of a helper epitope, in the CTLA4 transmembrane region, in the CTLA4 cytoplasmatic region, in the CTLA4 transmembrane and cytoplasmatic region. Preferably, adapted sequence stretches allowing differentiation of different RNA species in a composition are introduced in the CTLA4 transmembrane and cytoplasmatic region. As a non-limiting example, a composition comprising two different RNA species, wherein the adapted sequence stretches allowing for differentiation is in the CTLA4 transmembrane and cytoplasmatic region (for example SEQ ID NO: 77004 and SEQ ID NO: 77005). As a further non-limiting example, a composition comprising three different RNA species, wherein the adapted sequence stretches allowing for differentiation is in the CTLA4 transmembrane and cytoplasmatic region (for example SEQ ID NO: 77004, SEQ ID NO: 77005 and SEQ ID NO: 77006). As a further non-limiting example, a composition comprising thirteen different RNA species, wherein the adapted sequence stretches allowing for differentiation is in the CTLA4 transmembrane and cytoplasmatic region (for example SEQ ID NO: 77004-SEQ ID NO: 77017).

Antigenic Peptide or Protein (AN)

The artificial nuclei acid molecule, preferably RNA, according to the invention encodes, in its at least one coding region, a. at least one antigenic peptide or protein. According to preferred embodiments, the nucleic acid sequence encoding said at least one antigenic peptide or protein may be fused (in frame) to a nucleic acid sequence encoding the at least one $IRST_{epm}$-derived amino acid sequence. Therefore, expression of the artificial nucleic acid molecule, preferably RNA, of the invention may preferably result in a fusion protein comprising the at least one antigenic protein or peptide joined to (optionally via appropriate linkers) the at least one $IRST_{epm}$-derived additional amino acid sequence. Said additional amino acid sequence preferably directs the antigenic peptide or protein to MHC class I and more preferably MHC class II processing compartments, resulting in enhanced MHC class I and/or preferably MHC class II presentation. Generally, the present invention envisages the combination of any of the antigenic peptides or proteins described herein with any of the $IRST_{epm}$-derived additional amino acid sequences, any of the linkers, and any of the signal peptides described herein, in any suitable order, in the antigenic fusion proteins encoded by the artificial nucleic acid molecules, preferably RNAs, of the invention.

The term "antigenic peptide or protein" generally refers to any peptide or protein capable, under appropriate conditions, of interacting with/being recognized by components of the immune system (such as antibodies or immune cells). The "antigenic peptide or protein" preferably interacts with/is recognized by the components of the immune system via its "epitope(s)" or "antigenic determinant(s)". Thus, the term "antigenic peptide or protein" refers to a (poly-)peptide comprising, consisting of or being capable of providing at least one (functional) epitope. It is particularly envisaged that the artificial nucleic acid molecules, preferably RNAs, of the invention encode full-length antigenic peptides or proteins, or preferably fragmenst thereof. Said fragment may comprise or consist of (functional) epitopes of said antigenic peptides or proteins. Preferably, said fragments or epitopes are expressed in the host cell, directed to MHC class I and preferably MHC class II processing compartments, and recognized by components of the immune system.

The term "components of the immune system" preferably refers to immune cells, immune cell receptors and antibodies of the adaptive immune system. "Antigenic peptides or proteins" are preferably capable of being processed by the intracellular machinery to be presented to immune cells on an MHC molecule, preferably resulting in an antigen-specific immune response (e.g. cell-mediated immunity or formation of antibodies). "Antigenic peptides or proteins" may be the product of translation of an artificial nucleic acid molecule, preferably RNA, of the invention.

The term "epitope" or "antigenic determinant" refers to a part or fragment of an antigenic peptide or protein that is recognized by the immune system. Said fragment may typically comprise from about 5 to about 20 or even more amino acids. Epitopes may be "conformational" (or "discontinuous"), i.e. composed of discontinuous sequences of the amino acids of the antigenic peptide or protein that they are derived from, but brought together in the three-dimensional structure of e.g. a MHC-complex, or "linear", i.e. consist of a continuous sequence of amino acids of the antigenic peptides or proteins that they are derived from. The term "epitope" generally encompasses "T cell epitopes" (recognized by T cells via their T cell receptor) and "B cell epitopes" (recognized by B cells via their B cell receptor). "B cell epitopes" are typically located on the outer surface of (native) protein or peptide antigens as defined herein, and may preferably comprise or consist of between 5 to 15 amino acids, more preferably between 5 to 12 amino acids, even more preferably between 6 to 9 amino acids. "T cell epitopes" are typically recognized by T cells in a MHC-I or MHC-II bound form, i.e. as a complex formed by an antigenic protein or peptide fragment comprising the epitope, and a MHC-I or MHC-II surface molecule. "T cell epitopes" may typically have a length of about 6 to about 20 or even more amino acids, T cell epitopes presented by MHC class I molecules may preferably have a length of about 8 to about 10 amino acids, e.g. 8, 9, or 10, (or even 11, or 12 amino acids). T cell epitopes presented by MHC class II molecules may preferably have a length of about 13 or more amino acids, e.g. 13, 14, 15, 16, 17, 18, 19, 20, 21, 22, 23, 24, 25, 26, 27, 28, 29, 30 or even more amino acids. In the context of the present invention, the term "epitope" may in particular refer to T cell epitopes.

When referring to an artificial nucleic acid molecule, preferably RNA, encoding "at least one antigenic peptide or protein" herein, it is envisaged that said artificial nucleic acid molecule may encode one or more full-length (wild-type/variant/derivative) antigenic peptide(s) or protein(s), or one or more fragment(s), in particular a (functional) epitope (s), of said (wild-type/variant/derivative) antigenic peptide or protein. Said full-length (wild-type/variant/derivative) antigenic peptide(s) or protein(s), or its fragment(s), preferably comprises, consists of or provides at least one (functional) epitope, i.e. said (wild-type/variant/derivative) antigenic peptide(s) or protein(s) or its fragment(s) preferably either comprise(s) or consist(s) of a native epitope (preferably recognized by B cells) or is capable of being processed and presented by an MHC-I or MHC-II molecule to provide a MHC-bound epitope (preferably recognized by T cells). A "functional" epitope refers to an epitope capable of inducing a desired adaptive immune response in a subject.

The at least one antigenic peptide or protein encoded by the artificial nucleic acid molecule, preferably RNA, of the invention may be N-terminally, C-terminally or intrasequentially fused to or comprised by the at least one $IRST_{epm}$-derived amino acid sequence, optionally via appropriate peptide linkers (providing an "antigenic fusion protein" as defined herein). Thus, it is inter alia envisaged herein that the artificial nucleic acid molecule, preferably RNA, of the invention encodes an $IRST_{epm}$-derived amino acid sequence as defined herein, which comprises an antigenic peptide or protein, or yields a functional epitope, as defined herein.

The choice of appropriate antigenic peptides or proteins generally depends on the condition or disease to be treated or prevented. In general, the artificial nucleic acid molecule, preferably RNA, may encode any antigenic peptide or protein (or any desired combination of antigenic peptides or proteins) in its at least one coding region. It is also envisaged herein to provide artificial nucleic acid molecules, preferably RNAs, encoding a plurality of any combination of at least 2, 3, 4, 5, 6, 7, 8, 9 or 10 or more (identical or different) antigenic peptides or proteins, preferably as defined herein (see e.g. polyvalent vaccines).

Preferred antigenic peptides and proteins are specified below.

Antigenic Peptides or Proteins Derived from Tumor Antigens

According to preferred embodiments, the artificial nucleic acid molecule, preferably RNA, according to the invention encodes, in its at least one coding region, at least one antigenic peptide or protein derived from a tumor antigen.

The term "tumor antigen" refers to antigens derived from or associated with a (preferably malignant) tumor or a cancer disease. As used herein, the terms "cancer" and "tumor" are used interchangeably to refer to a neoplasm characterized by the uncontrolled and usually rapid proliferation of cells that tend to invade surrounding tissue and to metastasize to distant body sites. The term encompasses benign and malignant neoplasms. Malignancy in cancers is typically characterized by anaplasia, invasiveness, and metastasis; whereas benign malignancies typically have none of those properties. The terms "cancer" and "tumor" in particular refer to neoplasms characterized by tumor growth, but also to cancers of blood and lymphatic system. A "tumor antigen" is typically derived from a tumor/cancer cell, preferably a mammalian tumor/cancer cell, and may be located in or on the surface of a tumor cell derived from a mammalian, preferably from a human, tumor, such as a systemic or a solid tumor. "Tumor antigens" generally include tumor-specific antigens (TSAs) and tumor-associated-antigens (TAAs). TSAs may only be presented by tumor cells and not by normal "healthy" cells. They typically result from a tumor specific mutation. TAAs, which are more common, are usually presented by both tumor and healthy cells. These antigens are recognized and the antigen-presenting cell can be destroyed by cytotoxic T cells. Additionally, tumor antigens can also occur on the surface of the tumor in the form of, e.g., a mutated receptor. In this case, they can be recognized by antibodies.

Preferably, the at least one antigenic peptide or protein encoded by the at least one coding region of the artificial nucleic acid molecule, preferably RNA, of the invention, may be derived from Melanoma antigen recognized by T-cells 1, Eukaryotic translation initiation factor 4 gamma 1, Histone H1.2, Cyclin-dependent kinase 4, 40S ribosomal protein S21, DNA replication licensing factor MCM4, Actin, gamma-enteric smooth muscle, Melanocyte protein PMEL, Phospholipid transfer protein, Vimentin, Eukaryotic translation initiation factor 3 subunit D, Melanoma-associated antigen 1, Fructose-bisphosphate aldolase A, Guanine nucleotide-binding protein G(I)/G(S)/G(T) subunit beta-2, ER membrane protein complex subunit 7, Actin, cytoplasmic 1, High mobility group protein B1, Coiled-coil-helix-coiled-coil-helix domain-containing protein 2, HLA class II histocompatibility antigen, DP beta 1 chain, 60S ribosomal protein L13, Thymosin beta-10, Guanine nucleotide-binding protein G(s) subunit alpha isoforms short, Guanine nucleotide-binding protein subunit beta-2-like 1, Bax inhibitor 1, Wilms tumor protein, Gamma-secretase C-terminal fragment 59, Thymidylate synthase, 60S ribosomal protein L10, Lys-63-specific deubiquitinase BRCC36, Myelin basic protein, HLA class I histocompatibility antigen, A-2 alpha chain, Ragulator complex protein LAMTOR5, 40S ribosomal protein S25, POTE ankyrin domain family member F, Mortality factor 4-like protein 1, Melanoma-associated antigen 3, Heme oxygenase 1, G2/mitotic-specific cyclin-B1, Proteasome subunit alpha type-5, Protein THEMIS2, Fatty acid synthase, Mammaglobin-A, Actin-related protein 2, 60S ribosomal protein L28, 60S acidic ribosomal protein P0, Cellular tumor antigen p53, Proteasome subunit beta type-3, DNA (cytosine-5)-methyltransferase 1, Catenin beta-1, Myosin-9, Reticulocalbin-2, Heterogeneous nuclear ribonucleoprotein A1, 60S ribosomal protein L8, Ribonucleoside-diphosphate reductase subunit M2, Melanoma-associated antigen B2, Protein SSX2, Proliferating cell nuclear antigen, Receptor tyrosine-protein kinase erbB-2, Heat shock protein HSP 90-beta, Ornithine decarboxylase, Ubiquitin-conjugating enzyme E2 E3, 60S ribosomal protein L19, Small nuclear ribonucleoprotein-associated proteins B and B', Elongation factor 2, Putative small nuclear ribonucleoprotein G-like protein 15, Serine-tRNA ligase, cytoplasmic, Beta-2-microglobulin, ADP/ATP translocase 2, Acyl-CoA desaturase, Ubiquitin-60S ribosomal protein L40, Prelamin-A/C, Heat shock cognate 71 kDa protein, Melanoma-associated antigen 2, Beta-adrenergic receptor kinase 1, Farnesyl pyrophosphate synthase, 40S ribosomal protein S8, Glutamate carboxypeptidase 2, Serine/threonine-protein phosphatase PP1-beta catalytic subunit, ATP-binding cassette sub-family F member 2, Gamma-interferon-inducible lysosomal thiol reductase, Stress-70 protein, mitochondrial, Mucin-1, Rac GTPase-activating protein 1, HLA class I histocompatibility antigen, B-39 alpha chain, 40S ribosomal protein S16, Tyrosinase, HLA class I histocompatibility antigen, alpha chain E, Bifunctional purine biosynthesis protein PURH, Transferrin receptor protein 1, ELAV-like protein 1, U1 small nuclear ribonucleoprotein A, Heat shock 70 kDa protein 1-like, HLA class II histocompatibility antigen, DR alpha chain, T-complex protein 1 subunit alpha, Carcinoembryonic antigen-related cell adhesion molecule 5, Histone H2AX, Lamin-B1, 60S acidic ribosomal protein P2, Actin, cytoplasmic 2, B-lymphocyte antigen CD20, Actin, aortic smooth muscle, Probable global transcription activator SNF2L2, Myotubularin-related protein 5, Proteasome subunit beta type-1, 60S ribosomal protein L7a, Histone H3.3, 60S ribosomal protein L24, 40S ribosomal protein S3, HLA class I histocompatibility antigen, Cw-7 alpha chain, HLA class I histocompatibility antigen, B-15 alpha chain, Serine/threonine-protein kinase Sgk1, Serine/threonine-protein phosphatase PP1-alpha catalytic subunit, Heterogeneous nuclear ribonucleoprotein K, L-dopachrome tautomerase, Protein flightless-1 homolog, Dual specificity protein phosphatase 5, TSC22 domain family protein 3, Cancer/testis antigen 1, Serine/threonine-protein phosphatase 2A 65 kDa regulatory subunit A alpha isoform, Protein transport protein Sec23B, Protein transport protein Sec23A, CD59 glycoprotein, Collagen alpha-5(IV) chain, AT-rich interactive domain-containing protein 3A, Polypyrimidine tract-binding protein 1, Spermine synthase, Glutamine-fructose-6-phosphate aminotransferase [isomerizing] 1, Eukaryotic translation initiation factor 3 subunit L, Protein BTG2, DNA-directed RNA polymerase II subunit RPB1, Myeloblastin, HLA class I histocompatibility antigen, Cw-3 alpha chain, Importin subunit alpha-5, rRNA 2'-O-methyltransferase fibrillarin, Cyclin-A2, Probable ATP-dependent RNA helicase DDX5, Cytochrome c oxidase subunit 2, IST1 homolog, 60S ribosomal protein L35, Triosephosphate isomerase, Sorting nexin-5, Melanoma-associated antigen 4, Ubiquilin-4, HLA class I histocompatibility antigen, Cw-2 alpha chain, Interferon-induced transmembrane protein 1, Amyloid beta A4 protein, Heat shock 70 kDa protein 1B, HLA class I histocompatibility antigen, A-1 alpha chain, G antigen 12H, Transaldolase, Putative pre-mRNA-splicing factor ATP-dependent RNA helicase DHX16, 14-3-3 protein gamma, Serine/threonine-protein kinase SMG1, Cyclin-L1, Glyceraldehyde-3-phosphate dehydrogenase, Elongation of very long chain fatty acids protein 1, Microtubule-associated protein RP/EB family member 2, T-complex protein 1 subunit epsilon, Sphingolipid delta(4)-desaturase DES1, Elongation of very long chain fatty acids protein 5, ORM1-like protein 2, Baculoviral IAP repeat-containing protein 7, E3 ubiquitin-protein ligase TRIM68, Putative HTLV-1-related endogenous sequence, Myelin proteolipid protein, SAM and SH3 domain-containing protein 1, E3 ubiquitin-protein ligase SIAH1, Muscleblind-like protein 2, Annexin A1, Nuclear ubiquitous casein and cyclin-dependent kinase substrate 1, Pleiotropic regulator 1, NADH dehydrogenase [ubiquinone] 1 alpha subcomplex subunit 3, CD99 antigen, Guanine nucleotide-binding protein G(o) subunit alpha, Calsyntenin-1, GPI transamidase component PIG-T, Perilipin-3, WD40 repeat-containing protein SMU1, Protein S100-B, Annexin A11, Histone H2B type 2-F, Calmodulin, Phosphoinositide-3-kinase-interacting protein 1, THO complex subunit 4, Neuroblast differentiation-associated protein AHNAK, Phosphoserine aminotransferase, Histone deacetylase 7, Gelsolin, Tight junction protein ZO-1, NADH dehydrogenase [ubiquinone] iron-sulfur protein 7, mitochondrial, LIM domain transcription factor LMO4, Spectrin beta chain, non-erythrocytic 1, NADH dehydrogenase [ubiquinone] 1 subunit C2, Testican-2, Alpha-adducin, V-type proton ATPase subunit F, 40S ribosomal protein SA, Bcl-2-associated transcription factor 1, ATP synthase-coupling factor 6, mitochondrial, Phosphatidylethanolamine-binding protein 1, 40S ribosomal protein S29, Septin-2, Methyl-CpG-binding domain protein 3, Transformation/transcription domain-associated protein, Transcription factor HES-1, Paralemmin-2, Sodium/potassium-transporting ATPase subunit alpha-3, Stathmin, Heterogeneous nuclear ribonucleoprotein L-like, Nodal modulator 3, Interferon-induced GTP-binding protein Mx2, Neuronal membrane glycoprotein M6-b, Contactin-1, Cytosolic non-specific dipeptidase, Noelin-2, Serine/threonine-protein kinase DCLK1, U2 small nuclear ribonucleoprotein B, Nuclear autoantigenic sperm protein, 60S ribosomal protein L5, Endoplasmic reticulum-Golgi intermediate compartment protein 1, Programmed cell death protein 4, Endoplasmin, Eukaryotic translation initiation factor 3 subunit F, Cofilin-1, Pyruvate kinase PKM, Dolichyl-diphosphooligosaccharide-protein glycosyltransferase subunit STT3A, 5'(3')-deoxyribonucleotidase, cytosolic type, CKLF-like MARVEL transmembrane domain-containing protein 6, Cleavage and polyadenylation specificity factor subunit 1, Neutral amino acid transporter B(0), Protein PRRC1, Probable ATP-dependent RNA helicase DDX49, Nuclear pore complex protein Nup160, ATP synthase subunit beta, mitochondrial, Signal peptidase complex subunit 2, Protein kinase C iota type, Histone acetyltransferase p300, Histone H2A type 1-A, Small nuclear ribonucleoprotein G, Nucleosome assembly protein 1-like 1, 40S ribosomal protein S11, Structural maintenance of chromosomes protein 3, Centrin-2, GTP-binding nuclear protein Ran, 40S ribosomal protein S3a, ATP-dependent RNA helicase A, T-complex protein 1 subunit eta, Proteasome-associated protein ECM29 homolog, GPN-loop GTPase 1, 60S ribosomal protein L10a, Heterogeneous nuclear ribonucleoproteins C1/C2, Hydroxymethylglutaryl-CoA synthase, cytoplasmic, Sterol O-acyltransferase 1, Tuberin, Eukaryotic translation elongation factor 1 epsilon-1, Phosphoinositide 3-kinase regulatory subunit 4, Annexin A2, U2 small nuclear ribonucleoprotein A', Serine/threonine-protein kinase SIK1, Nucleolin, L-lactate dehydrogenase B chain, L-lactate dehydrogenase A chain, Aladin, Microtubule-associated protein 4, Peroxiredoxin-5, mitochondrial, HLA class I histocompatibility antigen, B-7 alpha chain, Carbamoyl-phosphate synthase [ammonia], mitochondrial, Coiled-coil domain-containing protein 12, Kinectin, Keratin, type I cytoskeletal 18, 40S ribosomal protein S5, Nucleosome assembly protein 1-like 4, U4/U6 small nuclear ribonucleoprotein Prp31, ELAV-like protein 3, Minor histocompatibility protein HA-1, Low affinity immunoglobulin epsilon Fc receptor, 26S proteasome non-ATPase regulatory subunit 2, ATP-dependent RNA helicase DDX3X, Putative homeodomain transcription factor 2, Transcription factor BTF3, Ribosome biogenesis protein BRX1 homolog, HLA class I histocompatibility antigen, B-8 alpha chain, Dynamin-2, ELAV-like protein 4, ATP-dependent RNA helicase DDX3Y, Histone demethylase UTY, Pumilio homolog 3, Histone H4, Histone H3.2, Protein S100-A9, Macrophage migration inhibitory factor, Hemoglobin subunit alpha, 40S ribosomal protein S17, Collagen alpha-1(I) chain, Collagen alpha-2(I) chain, T-complex protein 1 subunit theta, Cullin-1, DNA replication licensing factor MCM7, BolA-like protein 2, DNA topoisomerase 2-beta, Proteasome subunit alpha type-4, Bifunctional glutamate/proline-tRNA ligase, Sodium/potassium-transporting ATPase subunit alpha-1, MICOS complex subunit MIC60, Peptidyl-prolyl cis-trans isomerase A, NADH dehydrogenase [ubiquinone] 1 beta subcomplex subunit 7, Zinc finger MYM-type protein 2, Transforming protein RhoA, Putative endoplasmin-like protein, Plasminogen activator inhibitor 1 RNA-binding protein, Uncharacterized protein C20orf24, Importin subunit beta-1, Melanoma-associated antigen D2, Protein Spindly, Coatomer subunit epsilon, Targeting protein for Xklp2, H/ACA ribonucleoprotein complex subunit 4, H/ACA ribonucleoprotein complex subunit 3, Cerebellar degeneration-related protein 2, Exocyst complex component 2, 1-phosphatidylinositol 3-phosphate 5-kinase, Proteasome activator complex subunit 3, Nuclear pore complex protein Nup205, Neurogenic locus notch homolog protein 1, Lysosomal protective protein, Serine/threonine-protein kinase 38-like, Alpha-1B-glycoprotein, Neuropilin-2, Calreticulin, Filamin-A, Syntenin-1, Cathepsin D, HLA class I histocompatibility antigen, B-51 alpha chain, Profilin-1, Lymphocyte-specific protein 1, Synemin, Insulin receptor substrate 2, ETS translocation variant 5, E3 ubiquitin-protein ligase Mdm2, U1 small nuclear ribonucleoprotein 70 kDa, Coatomer subunit gamma-1, T-complex protein 1 subunit gamma, DCN1-like protein 1, U3 small nucleolar ribonucleoprotein protein IMP3, Phosphoglycerate kinase 1, Diphthamide biosynthesis protein 1, Methionine aminopeptidase 2, Dipeptidyl peptidase 9, Chloride intracellular channel protein 4, 3-hydroxy-3-methylglutaryl-coenzyme A reductase, Acyl-protein thioesterase 2, 26S proteasome non-ATPase regulatory subunit 14, Golgi-specific brefeldin A-resistance guanine nucleotide exchange factor 1, E3 ubiquitin-protein ligase BRE1A, Abl interactor 2, Nuclear pore complex protein Nup88, Thioredoxin-like protein 4A, Transmembrane emp24 domain-containing protein 2, Glycogen phosphorylase, muscle form, Junction plakoglobin, Dolichyl-diphosphooligosaccharide-protein glycosyltransferase subunit 2, Putative eukaryotic translation initiation factor 2 subunit 3-like protein, Serine/threonine-protein kinase/endoribonuclease IRE1, Interferon-induced GTP-binding protein Mx1, Mitotic spindle-associated MMXD complex subunit MIP18, Sulfiredoxin-1, Nucleolar GTP-binding protein 1, 10 kDa heat shock protein, mitochondrial, Anoctamin-6, Nucleolar pre-ribosomal-associated protein 1, RNA-binding protein 34, S-adenosylmethionine synthase isoform type-2, Transmembrane protein 209, HLA class I histocompatibility antigen, B-13 alpha chain, Ubiquitin carboxyl-terminal hydrolase 11, Ataxin-10, Vacuolar protein sorting-associated protein 13B, Suppressor of SWI41 homolog, Golgin subfamily A member 7, Stomatin-like protein 2, mitochondrial, Nuclear pore complex protein Nup107, N-alpha-acetyltransferase 10, Cytochrome c oxidase subunit 6B1, General transcription factor II-1 repeat domain-containing protein 2B, Heterogeneous nuclear ribonucleoprotein A0, Condensin complex subunit 3, Regulation of nuclear pre-mRNA domain-containing protein 1A, Helicase SRCAP, Spartin, Uncharacterized protein ZMYM6NB, CLIP-associating protein 1, Alpha-actinin-4, Nucleolar protein 58, Serine/threonine-protein kinase Kist, Transcription factor Sp2, Apolipoprotein L1, Tankyrase-2, Uncharacterized protein C19orf43, Heat shock protein HSP 90-alpha, X-ray repair cross-complementing protein 5, Nucleolar protein 7, U5 small nuclear ribonucleoprotein 200 kDa helicase, 15 kDa selenoprotein, Ribosomal RNA processing protein 1 homolog B, 116 kDa U5 small nuclear ribonucleoprotein component, Paraneoplastic antigen Ma1, Retinoic acid-induced protein 1, ADP-ribosylation factor GTPase-activating protein 2, Nucleolar protein 56, RNA-binding protein 14, Eukaryotic initiation factor 4A-1, Septin-7, Protein polybromo-1, Annexin A4, Centromere protein F, 60S ribosomal protein L22-like 1, Histone H2B type 1-A, ADP-dependent glucokinase, Heterogeneous nuclear ribonucleoprotein U, High affinity cAMP-specific 3',5'-cyclic phosphodiesterase 7A, E3 ubiquitin-protein ligase UBR2, m7GpppX diphosphatase, Microtubule-actin cross-linking factor 1, isoforms 1/2/3/5, YTH domain-containing protein 1, Eukaryotic translation initiation factor 5A-1, Activating transcription factor 7-interacting protein 1, Transmembrane protein 258, U3 small nucleolar RNA-associated protein 6 homolog, Nucleolar RNA helicase 2, DNA-directed RNA polymerase II subunit RPB7, RRP12-like protein, 26S protease regulatory subunit 6B, 26S protease regulatory subunit 7, 26S protease regulatory subunit 4, Nucleolar protein 11, Prothymosin alpha, Vezatin, Protein AF-10, Negative elongation factor C/D, Transcription factor E2F1, RNA-binding protein 6, Eukaryotic translation initiation factor 4 gamma 3, Next to BRCA1 gene 1 protein, Mitochondrial import receptor subunit TOM7 homolog, Heterogeneous nuclear ribonucleoprotein U-like protein 1, Poly [ADP-ribose] polymerase 1, Eukaryotic translation initiation factor 3 subunit C, Condensin-2 complex subunit G2, Signal transducer and activator of transcription 1-alpha/beta, Signal transducer and activator of transcription 3, Ataxin-2-like protein, G patch domain-containing protein 4, Golgi resident protein GCP60, AP-1 complex subunit sigma-3, Cleavage stimulation factor subunit 3, ATP-dependent RNA helicase DDX24, Mediator of RNA polymerase II transcription subunit 23, Sorting and assembly machinery component 50 homolog, Protein LAP2, Spectrin beta chain, erythrocytic, E3 ubiquitin-protein ligase RBBP6, 40S ribosomal protein S18, Keratinocyte-associated protein 2, Dolichyl-diphosphooligosaccharide-protein glycosyltransferase subunit DAD1, Minor histocompatibility antigen H13, Catenin alpha-2, TBC1 domain family member 31, Poly [ADP-ribose] polymerase 4, Basic leucine zipper and W2 domain-containing protein 1, Neutral alpha-glucosidase AB, RuvB-like 2, Protein MCM10 homolog, Plexin-C1, DNA repair protein XRCC1, Protein AATF, Short transient receptor potential channel 4-associated protein, Cell cycle progression protein 1, Dihydrofolate reductase, mitochondrial, Splicing factor 3A subunit 3, RNMT-activating mini protein, Coatomer subunit delta, Coatomer subunit alpha, Mothers against decapentaplegic homolog 9, Ubiquitin-like protein FUBI, Lysine-tRNA ligase, Cytochrome c oxidase subunit 6A1, mitochondrial, Polycomb protein SUZ12, SNARE-associated protein Snapin, Signal recognition particle 54 kDa protein, Probable JmjC domain-containing histone demethylation protein 2C, Putative ATP-dependent RNA helicase DDX11-like protein 8, General transcription factor 3C polypeptide 1, Tonsoku-like protein, Nuclear pore complex protein Nup214, ATP-dependent 6-phosphofructokinase, platelet type, Alpha-endosulfine, 60S ribosomal protein L26, DNA mismatch repair protein Msh2, Chromodomain-helicase-DNA-binding protein 8, Cell division cycle protein 27 homolog, Transmembrane protein 43, Clathrin heavy chain 1, Disintegrin and metalloproteinase domain-containing protein 10, Protein CASP, Gem-associated protein 5, Ribosomal biogenesis protein LAS1L, WD repeat-containing protein 34, DnaJ homolog subfamily B member 4, Tyrosine-protein kinase Fyn, Activating signal cointegrator 1, Putative mitochondrial import inner membrane translocase subunit Tim23B, Peroxisomal acyl-coenzyme A oxidase 1, HLA class II histocompatibility antigen, DO alpha chain, Poly [ADP-ribose] polymerase 14, Mediator of RNA polymerase II transcription subunit 18, 60S ribosomal protein L7, Zinc finger protein 548, Protein FAM32A, Heat shock protein HSP 90-alpha A2, Myc-associated zinc finger protein, Heterogeneous nuclear ribonucleoproteins A2/B1, V-type proton ATPase 116 kDa subunit a isoform 4, Zinc finger protein 770, Protein SSXT, Zinc finger and BTB domain-containing protein 43, Signal transducing adapter molecule 2, Cirhin, DTW domain-containing protein 1, Bone morphogenetic protein receptor type-2, Dedicator of cytokinesis protein 7, SUMO-activating enzyme subunit 1, Superkiller viralicidic activity 2-like 2, 60S ribosomal protein L15, Transcription elongation factor SPT6, 60S ribosomal protein L18a, Catalase, Tuftelin-interacting protein 11, Hepatoma-derived growth factor-related protein 2, Putative annexin A2-like protein, Protein transport protein Sec16A, Transcription elongation factor SPT5, Splicing factor 3B subunit 4, Serine/threonine-protein kinase 17B, Pre-mRNA-splicing factor CWC22 homolog, Serine/threonine-protein kinase mTOR, E3 ubiquitin-protein ligase RNF213, RNA polymerase I-specific transcription initiation factor RRN3, Nuclear receptor corepressor 2, HLA class II histocompatibility antigen, DQ alpha 1 chain, Nuclear pore membrane glycoprotein 210, NADH dehydrogenase [ubiquinone] 1 beta subcomplex subunit 10, Lysine-specific histone demethylase 1A, Thioredoxin-interacting protein, 60S ribosomal protein L27, Putative elongation factor 1-alpha-like 3, Long-chain-fatty-acid-CoA ligase 4, Signal recognition particle receptor subunit alpha, Embryonic stem cell-specific 5-hydroxymethylcytosine-binding protein, DNA-directed RNA polymerases I, II, and III subunit RPABC5, Dystonin, 60S ribosomal protein L23a, ATP-citrate synthase, Protein quaking, Homocysteine-responsive endoplasmic reticulum-resident ubiquitin-like domain member 1 protein, Transducin-like enhancer protein 2, Gamma-interferon-inducible protein 16, Cytoplasmic dynein 1 heavy chain 1, Staphylococcal nuclease domain-containing protein 1, Thioredoxin, Ribonucleoside-diphosphate reductase large subunit, Lamin-B receptor, Asparagine synthetase [glutamine-hydrolyzing], Heterogeneous nuclear ribonucleoprotein L, Caprin-1, DNA-dependent protein kinase catalytic subunit, RAC-beta serine/threonine-protein kinase, Replication factor C subunit 1, Pre-mRNA-processing factor 40 homolog A, Helicase-like transcription factor, Pre-mRNA-splicing factor RBM22, Kinesin-like protein KIF18A, Vacuolar protein sorting-associated protein 13A, Raftlin, Coiled-coil domain-containing protein 94, Signal-induced proliferation-associated 1-like protein 2, Pre-mRNA-processing-splicing factor 8, Serine/arginine-rich splicing factor 3, T-complex protein 1 subunit zeta-2, Periphilin-1, Metastasis-associated protein MTA2, Spatacsin, Heterogeneous nuclear ribonucleoprotein A/B, Protein RRP5 homolog, 60 kDa heat shock protein, mitochondrial, Protein transport protein Sec61 subunit beta, 40S ribosomal protein S19, Protein DEK, Cyclin-dependent kinases regulatory subunit 2, Protein disulfide-isomerase A3, Heterogeneous nuclear ribonucleoprotein R, Lamina-associated polypeptide 2, isoform alpha, ATP synthase F(0) complex subunit C1, mitochondrial, Cytospin-A, Zinc finger protein 557, Zinc finger protein 669, WD repeat-containing protein 6, Signal transducer and activator of transcription 6, Antigen peptide transporter 1, Retinoic acid receptor RXR-gamma, Eukaryotic translation initiation factor 2-alpha kinase 1, CDK5 regulatory subunit-associated protein 2, Trifunctional purine biosynthetic protein adenosine-3, R3H domain-containing protein 4, WD repeat-containing protein 27, UAP56-interacting factor, Histone acetyltransferase KAT8, Probable tRNA N6-adenosine threonylcarbamoyltransferase, Deoxynucleotidyltransferase terminal-interacting protein 2, Serpin B8, ATP synthase subunit alpha, mitochondrial, 1,4-alpha-glucan-branching enzyme, Phosphatidylinositol 4,5-bisphosphate 3-kinase catalytic subunit alpha isoform, Probable threonine-tRNA ligase 2, cytoplasmic, Coiled-coil domain-containing protein 127, Glucosylceramidase, ATPase family AAA domain-containing protein 5, Casein kinase II subunit alpha, Gamma-tubulin complex component 2, Integrator complex subunit 11, Pogo transposable element with KRAB domain, Nuclear factor erythroid 2-related factor 2, Serpin B9, Folliculin-interacting protein 2, Exportin-5, Protein transport protein Sec61 subunit gamma, Brefeldin A-inhibited guanine nucleotide-exchange protein 1, Charged multivesicular body protein 5, Calpain small subunit 1, PR domain zinc finger protein 15, DnaJ homolog subfamily C member 11, Ubiquitin-conjugating enzyme E2 variant 3, Spermatid perinuclear RNA-binding protein, Cytosolic carboxypeptidase 1, DNA repair protein RAD51 homolog 1, Eukaryotic translation initiation factor 3 subunit C-like protein, Methionine aminopeptidase 1, Tyrosine-protein phosphatase non-receptor type 11, Protein UXT, Nardilysin, Mediator of RNA polymerase II transcription subunit 13, Absent in melanoma 1 protein, Ubiquitin carboxyl-terminal hydrolase 22, ADP-sugar pyrophosphatase, Ras GTPase-activating protein-binding protein 1, Nuclear pore complex protein Nup155, Zinc finger protein 550, Zinc finger protein 674, Nucleoporin NUP188 homolog, Signal recognition particle subunit SRP72, Oxysterol-binding protein-related protein 8, Probable cation-transporting ATPase 13A3, Band 4.1-like protein 2, 26S proteasome non-ATPase regulatory subunit 13, Cytochrome b-c1 complex subunit 9, Mitotic checkpoint protein BUB3, Exocyst complex component 4, Patatin-like phospholipase domain-containing protein 2, Tubulin beta-4A chain, ATP-binding cassette sub-family F member 3, Pre-mRNA-splicing factor ATP-dependent RNA helicase DHX15, Actin-related protein 2/3 complex subunit 2, Protein FAM60A, Chromobox protein homolog 6, Splicing factor 3B subunit 1, FAS-associated factor 2, 26S proteasome non-ATPase regulatory subunit 3, Histone deacetylase 9, F-box only protein 5, ATP-binding cassette sub-family D member 1, V-type proton ATPase subunit d 1, Enhancer of rudimentary homolog, ATP synthase subunit epsilon-like protein, mitochondrial, Polyadenylate-binding protein 1, Protein OS-9, Interferon-induced, double-stranded RNA-activated protein kinase, Alpha-taxilin, Tetratricopeptide repeat protein 9C, Transmembrane emp24 domain-containing protein 4, Non-receptor tyrosine-protein kinase TYK2, E3 ubiquitin-protein ligase AMFR, Proteasome subunit alpha type-2, Nucleolysin TIA-1 isoform p40, Nucleolysin TIAR, Kinesin-like protein KIF20A, Non-specific lipid-transfer protein, Ectonucleoside triphosphate diphosphohydrolase 1, FACT complex subunit SSRP1, Double-stranded RNA-binding protein Staufen homolog 1, Serine/threonine-protein phosphatase 6 regulatory subunit 3, SUMO-specific isopeptidase USPL1, 5'-nucleotidase domain-containing protein 1, Serine/arginine-rich splicing factor 6, Serine/threonine-protein kinase 17A, A-kinase anchor protein 2, Zinc finger protein Rlf, Histone-lysine N-methyltransferase SETD2, Nesprin-2, Uncharacterized protein C14orf119, Cyclin-G-associated kinase, Peroxisomal membrane protein 2, Nucleoporin GLE1, Nuclear pore complex protein Nup93, 60S ribosomal export protein NMD3, 14 kDa phosphohistidine phosphatase, MK167 FHA domain-interacting nucleolar phosphoprotein, Kinesin-associated protein 3, U4/U6 small nuclear ribonucleoprotein Prp4, Transmembrane emp24 domain-containing protein 3, E3 ubiquitin-protein ligase MARCH7, Midasin, Arf-GAP with coiled-coil, ANK repeat and PH domain-containing protein 2, Zinc finger protein 330, Protein FAM208B, Heat shock 70 kDa protein 14, COP9 signalosome complex subunit 6, Axin-1, Proteasome subunit beta type-8, Dedicator of cytokinesis protein 11, Mitochondrial Rho GTPase 2, Cysteine-rich PDZ-binding protein, Exosome complex exonuclease RRP44, Collagen type IV alpha-3-binding protein, Vigilin, WD repeat-containing protein 1, Cytoplasmic FMR1-interacting protein 1, Eukaryotic translation initiation factor 3 subunit I, Epidermal growth factor receptor substrate 15, E3 ubiquitin-protein ligase Topors, Tubulin beta chain, Cohesin subunit SA-2, Phosphatidylinositol 3,4,5-trisphosphate-dependent Rac exchanger 1 protein, Phospholipid-transporting ATPase IG, Vacuolar protein sorting-associated protein 26A, Syntaxin-binding protein 3, Centrosomal protein CEP57L1, Pleckstrin homology domain-containing family B member 2, Zinc finger protein 706, SWI/SNF-related matrix-associated actin-dependent regulator of chromatin subfamily D member 2, V-type proton ATPase subunit E 2, 40S ribosomal protein S13, Cation-independent mannose-6-phosphate receptor, Nucleoporin Nup37, RNA polymerase II elongation factor ELL, Heterogeneous nuclear ribonucleoprotein F, Tetratricopeptide repeat protein 13, Tapasin, Condensin-2 complex subunit D3, Endoplasmic reticulum-Golgi intermediate compartment protein 3, Threonine-tRNA ligase, cytoplasmic, Choline/ethanolaminephosphotransferase 1, 28S ribosomal protein S17, mitochondrial, Protein Niban, Ubiquitin carboxyl-terminal hydrolase 7, E3 ubiquitin-protein ligase RNF19A, Interleukin enhancer-binding factor 2, Transitional endoplasmic reticulum ATPase, Nuclear factor NF-kappa-B p100 subunit, Phospholipase D2, Acidic fibroblast growth factor intracellular-binding protein, Alanine-tRNA ligase, cytoplasmic, Histone-lysine N-methyltransferase 2C, Attractin, Histone-lysine N-methyltransferase, H3 lysine-79 specific, Dynamin-1-like protein, Pyridine nucleotide-disulfide oxidoreductase domain-containing protein 1, Chromodomain-helicase-DNA-binding protein 7, Polypyrimidine tract-binding protein 3, HLA class I histocompatibility antigen, B-52 alpha chain, Cell division cycle-associated 7-like protein, Mediator of RNA polymerase II transcription subunit 10, Hypoxia-inducible factor 1-alpha, Metastasis-associated protein MTA3, Oxysterol-binding protein-related protein 3, tRNA (adenine(58)-N(1))-methyltransferase non-catalytic subunit TRM6, Nucleolar complex protein 4 homolog, Geminin, Chromodomain-helicase-DNA-binding protein 1-like, Up-regulated during skeletal muscle growth protein 5, Integrator complex subunit 3, Mitogen-activated protein kinase 6, RNA binding motif protein, X-linked-like-1, Serine/threonine-protein kinase PLK1, Glycoprotein endo-alpha-1,2-mannosidase-like protein, Cold-inducible RNA-binding protein, DNA mismatch repair protein Msh6, Serine hydroxymethyltransferase, cytosolic, Store-operated calcium entry-associated regulatory factor, FACT complex subunit SPT16, Histone-lysine N-methyltransferase EZH1, Trafficking protein particle complex subunit 4, DnaJ homolog subfamily C member 3, Meckelin, Serine/threonine-protein kinase pim-2, RNA-binding protein 7, Glutathione S-transferase Mu 2, Protein patched homolog 1, ARF GTPase-activating protein GIT2, Thioredoxin-related transmembrane protein 2, Zinc finger CCCH domain-containing protein 18, Probable ATP-dependent RNA helicase DDX47, Eukaryotic translation initiation factor 2 subunit 3, AP-1 complex subunit beta-1, Septin-6, DNA topoisomerase 2-alpha, Coilin, ATPase family AAA domain-containing protein 2, Choline-phosphate cytidylyltransferase A, Serine/threonine-protein kinase pim-1, Death-associated protein kinase 2, Transcription termination factor 2, C-1-tetrahydrofolate synthase, cytoplasmic, Major histocompatibility complex class I-related gene protein, Delta(24)-sterol reductase, Protein SET, Constitutive coactivator of PPAR-gamma-like protein 1, DNA replication complex GINS protein PSF1, AP-1 complex subunit mu-2, Dolichol-phosphate mannosyltransferase subunit 1, Heterogeneous nuclear ribonucleoprotein M, Plastin-3, THO complex subunit 2, 60S ribosomal protein L4, Hexokinase-2, Ribosome-binding protein 1, Proteasome subunit beta type-5, Anaphase-promoting complex subunit 2, Protein-tyrosine kinase 2-beta, NEDD8 ultimate buster 1, Baculoviral IAP repeat-containing protein 6, E3 ubiquitin-protein ligase CBL-B, Basigin, Phosphatidylinositol 4-kinase type 2-beta, Histone-binding protein RBBP7, High mobility group protein B3, Lymphocyte antigen 75, Putative RRN3-like protein RRN3P1, Chloride intracellular channel protein 1, Transmembrane emp24 domain-containing protein 7, Myosin light polypeptide 6, Proteasome inhibitor PI31 subunit, Kinesin-like protein KIF20B, rRNA-processing protein FCF1 homolog, Cyclin-dependent kinase 6, Filamin A, Replication protein A 32 kDa subunit, ATP-dependent RNA helicase DHX8, Cysteine and glycine-rich protein 1, ER membrane protein complex subunit 2, Cleavage stimulation factor subunit 1, Exportin-2, Protein KIAA0100, Cyclin-dependent kinase inhibitor 3, Eukaryotic translation initiation factor 3 subunit M, Sigma non-opioid intracellular receptor 1, DNA repair protein RAD50, Nuclear pore complex protein Nup153, Protein SCO1 homolog, mitochondrial, F-box/LRR-repeat protein 3, von Willebrand factor, DNA nucleotidylexotransferase, Endothelial differentiation-related factor 1, Serine/arginine-rich splicing factor 9, Probable E3 ubiquitin-protein ligase makorin-2, Antigen KI-67, Mediator of RNA polymerase II transcription subunit 17, Non-canonical poly(A) RNA polymerase PAPD5, Interleukin-9 receptor, Trafficking protein particle complex subunit 5, Magnesium transporter protein 1, Transforming acidic coiled-coil-containing protein 3, Membrane-associated tyrosine- and threonine-specific cdc2-inhibitory kinase, Ig kappa chain C region, Multifunctional protein ADE2, TPT1-like protein, AP-5 complex subunit zeta-1, Protein transport protein Sec31A, DnaJ homolog subfamily C member 7, WD repeat-containing protein 82, Disco-interacting protein 2 homolog A, DNA replication licensing factor MCM5, Disks large homolog 1, Ubiquitin-conjugating enzyme E2 J1, Nucleolar transcription factor 1, Citrate synthase, mitochondrial, GMP reductase 2, Single Ig IL-1-related receptor, Sulfhydryl oxidase 1, Cyclin-D1-binding protein 1, HLA class II histocompatibility antigen, DRB1-15 beta chain, Pre-mRNA-splicing factor ISY1 homolog, CUGBP Elav-like family member 1, Gamma-secretase subunit PEN-2, Tyrosine-protein kinase BAZ1B, Influenza virus NS1A-binding protein, Target of rapamycin complex subunit LST8, Splicing factor 3B subunit 2, Importin subunit alpha-1, Cullin-4A, Carbonic anhydrase 9, BTB/POZ domain-containing adapter for CUL3-mediated RhoA degradation protein 3, Melanoma-associated antigen 10, 26S proteasome non-ATPase regulatory subunit 6, 40S ribosomal protein S26, Long-chain-fatty-acid-CoA ligase 3, N6-adenosine-methyltransferase subunit METTL14, Ubiquitin-conjugating enzyme E2 H, Adenylosuccinate synthetase isozyme 2, Serine/threonine-protein phosphatase 2A 56 kDa regulatory subunit epsilon isoform, Actin-binding protein IPP, Mitogen-activated protein kinase 4, Tyrosine-protein phosphatase non-receptor type 23, Mitochondrial carrier homolog 1, Microspherule protein 1, Splicing factor 3B subunit 3, Casein kinase I isoform delta, Protein kish-A, Seipin, CMP-N-acetylneuraminate-beta-galactosamide-alpha-2,3-sialyltransferase 2, Cleft lip and palate transmembrane protein 1, Proteasome subunit beta type-6, RNA-binding protein 42, Alpha-enolase, Unconventional myosin-Ic, THO complex subunit 5 homolog, Solute carrier family 35 member B1, Sarcoplasmic/endoplasmic reticulum calcium ATPase 1, ATP-dependent RNA helicase DDX50, Splicing factor, proline- and glutamine-rich, DDB1- and CUL4-associated factor 11, EH domain-containing protein 1, COP9 signalosome complex subunit 7a, Cullin-2, Glutathione S-transferase A4, WD repeat-containing protein 19, Serine palmitoyltransferase 2, Apoptosis-associated speck-like protein containing a CARD, DNA damage-inducible transcript 3 protein, Erlin-2, DNA polymerase alpha subunit B, Thyroid adenoma-associated protein, AP-3 complex subunit delta-1, Extended synaptotagmin-2, Transportin-1, NudC domain-containing protein 3, Ubiquitin carboxyl-terminal hydrolase 35, Proline and serine-rich protein 1, Hsp90 co-chaperone Cdc37, Ubiquitin-conjugating enzyme E2 S, Talin-1, Kinetochore protein NDC80 homolog, Integrator complex subunit 4, BRISC complex subunit Abro1, Enhancer of filamentation 1, SET and MYND domain-containing protein 4, Leucine-rich PPR motif-containing protein, mitochondrial, HAUS augmin-like complex subunit 1, T-complex protein 1 subunit zeta, FERM, RhoGEF and pleckstrin domain-containing protein 2, Mannose-1-phosphate guanyltransferase alpha, Structural maintenance of chromosomes flexible hinge domain-containing protein 1, A-kinase anchor protein 11, tRNA-splicing ligase RtcB homolog, Sister chromatid cohesion protein PDS5 homolog A, Autophagy-related protein 101, ATP-binding cassette sub-family F member 1, Ankyrin repeat and KH domain-containing protein 1, Phosphopantothenoylcysteine decarboxylase, Bifunctional methylenetetrahydrofolate dehydrogenase/cyclohydrolase, mitochondrial, Leucine-rich repeat flightless-interacting protein 2, ADP-ribosylation factor GTPase-activating protein 3, Plexin-B2, Ankyrin repeat and LEM domain-containing protein 2, Signal transducer and activator of transcription 5B, DNA-directed RNA polymerase I subunit RPA2, Son of sevenless homolog 1, Formin-like protein 1, Cytoskeleton-associated protein 5, DNA dC→dU-editing enzyme APOBEC-3F, General transcription factor 3C polypeptide 2, DCC-interacting protein 13-alpha, Nucleoside diphosphate kinase 3, Dipeptidyl peptidase 8, Myotubularin, Ubiquitin fusion degradation protein 1 homolog, Epidermal growth factor receptor substrate 15-like 1, Serine/threonine-protein kinase N1, Sphingomyelin phosphodiesterase 4, Probable dolichyl pyrophosphate Glc1Man9GlcNAc2 alpha-1,3-glucosyltransferase, Gamma-tubulin complex component 5, Bromodomain adjacent to zinc finger domain protein 2A, Serine/threonine-protein phosphatase 4 regulatory subunit 3A, Protein yippee-like 5, Protein TASOR, Protein FAM177A1, 60S ribosomal protein L34, TBCC domain-containing protein 1, T-complex protein 1 subunit beta, Plectin, GDP-mannose 4,6 dehydratase, Protein arginine N-methyltransferase 3, Unconventional myosin-If, TBC1 domain family member 9B, Poly [ADP-ribose] polymerase 10, Transport and Golgi organization protein 6 homolog, Protein transport protein Sec24A, GMP synthase [glutamine-hydrolyzing], Nuclear pore complex protein Nup133, SHC SH2 domain-binding protein 1, 3-hydroxyacyl-CoA dehydrogenase type-2, Translation initiation factor eIF-2B subunit delta, Ubiquitin-associated protein 2-like, DNA dC→dU-editing enzyme APOBEC-3B, Proteasome activator complex subunit 4, cAMP-dependent protein kinase type I-alpha regulatory subunit, 6-phosphofructo-2-kinase/fructose-2,6-bisphosphatase 4, Calcium and integrin-binding protein 1, Zinc transporter ZIP6, DDB1- and CUL4-associated factor 15, Alpha-ketoglutarate-dependent dioxygenase FTO, Serine/threonine-protein phosphatase 6 catalytic subunit, U4/U6 small nuclear ribonucleoprotein Prp3, Putative helicase MOV-10, Ubiquitin carboxyl-terminal hydrolase 10, CAD protein, Importin-4, Filamin-B, Probable helicase with zinc finger domain, Rho GTPase-activating protein 12, Proline-rich protein 12, WD repeat-containing protein 70, Hexokinase-1, Nischarin, Protein SPT2 homolog, Bardet-Biedl syndrome 1 protein, Ubiquitin-like domain-containing CTD phosphatase 1, Programmed cell death protein 5, Na(+)/H(+) exchange regulatory cofactor NHE-RF1, Hom s 1, Tumor necrosis factor receptor superfamily member 10B, Glucocorticoid modulatory element-binding protein 1, Hydroxyacyl-coenzyme A dehydrogenase, mitochondrial, Myocyte-specific enhancer factor 2A, Zinc finger protein 106, Rho GTPase-activating protein 35, Probable RNA-binding protein 23, Anamorsin, Anaphase-promoting complex subunit 1, Intraflagellar transport protein 172 homolog, Protein PRRC2B, TRPM8 channel-associated factor 1, DNA damage-binding protein 1, ORM1-like protein 3, WD repeat-containing protein 18, Chitinase domain-containing protein 1, Protein VPRBP, E3 ubiquitin-protein ligase TRIM22, Tetratricopeptide repeat protein 17, Ninein, Golgin subfamily A member 4, Multiple C2 and transmembrane domain-containing protein 1, Nucleoside diphosphate-linked moiety X motif 19, Probable helicase senataxin, Folliculin-interacting protein 1, Ras GTPase-activating-like protein IQGAP1, 26S proteasome non-ATPase regulatory subunit 1, F-box only protein 8, Melanoma inhibitory activity protein 3, IQ domain-containing protein D, Dihydroxyacetone phosphate acyltransferase, Protein DBF4 homolog A, F-box only protein 25, Hermansky-Pudlak syndrome 5 protein, Guanine nucleotide-binding protein subunit beta-5, Cytosolic phospholipase A2, 60S acidic ribosomal protein P1, ATP-binding cassette sub-family B member 7, mitochondrial, Dual specificity mitogen-activated protein kinase kinase 7, Lon protease homolog 2, peroxisomal, Protein virilizer homolog, Histone-lysine N-methyltransferase SETD1A, Endosomal/lysomomal potassium channel TMEM175, Serine/threonine-protein kinase TAO2, Cell division control protein 6 homolog, AT-rich interactive domain-containing protein 4B, Transcription activator BRG1, Ankyrin repeat and SOCS box protein 3, Ribonucleases P/MRP protein subunit POP1, Translin-associated protein X, Phosphotriesterase-related protein, Methionine adenosyltransferase 2 subunit beta, Chromosome transmission fidelity protein 8 homolog, Catenin alpha-1, Splicing factor 3A subunit 1, Aurora kinase B, Vam6/Vps39-like protein, Kelch-like protein 13, Interleukin-6 receptor subunit beta, Ankyrin repeat domain-containing protein 17, Protein IWS1 homolog, G2/M phase-specific E3 ubiquitin-protein ligase, Adenomatous polyposis coli protein, Flotillin-2, Calpastatin, Cyclin-dependent kinase 9, E3 ubiquitin-protein ligase listerin, Guanosine-3',5'-bis(diphosphate) 3'-pyrophosphohydrolase MESH1, Protein PRR14L, MAP kinase-activated protein kinase 5, Nck-associated protein 1, Nuclear pore glycoprotein p62, DNA excision repair protein ERCC-6-like, Kelch repeat and BTB domain-containing protein 4, N-acetylneuraminate lyase, DENN domain-containing protein 4C, Fatty acyl-CoA reductase 2, 28S ribosomal protein S33, mitochondrial, RNA-binding protein 4B, Zinc finger protein 143, cAMP-responsive element modulator, WD repeat-containing protein 43, CTD small phosphatase-like protein 2, Ras-related GTP-binding protein C, DNA repair and recombination protein RAD54B, HIV Tat-specific factor 1, Negative elongation factor A, Rho-associated protein kinase 1, E3 ISG15-protein ligase HERC5, Renal cancer differentiation gene 1 protein, E3 ubiquitin-protein ligase UBR4, Prolyl 4-hydroxylase subunit alpha-1, Archaemetzincin-2, EH domain-binding protein 1, Hyaluronan mediated motility receptor, Conserved oligomeric Golgi complex subunit 5, Ribosomal L1 domain-containing protein 1, Regulator of G-protein signaling 10, Protein Jade-2, DNA-directed RNA polymerase II subunit RPB3, Electron transfer flavoprotein subunit beta, Protein Mis18-alpha, Phosphatidylinositol 4-kinase beta, Cytochrome P450 20A1, Ectopic P granules protein 5 homolog, CCAAT/enhancer-binding protein zeta, MORF4 family-associated protein 1-like 1, Proteasome subunit beta type-2, cAMP-dependent protein kinase type I-beta regulatory subunit, Rap1 GTPase-GDP dissociation stimulator 1, Probable E3 ubiquitin-protein ligase HERC4, Protein SON, Proteasome activator complex subunit 2, CCR4-NOT transcription complex subunit 1, DNA fragmentation factor subunit beta, CREB-binding protein, SCAN domain-containing protein 1, Cyclin-dependent kinase inhibitor 1C, ERI1 exoribonuclease 3, Cyclin-1, Tight junction protein ZO-2, DNA-directed RNA polymerase II subunit RPB11-b1, Conserved oligomeric Golgi complex subunit 4, Cipl-interacting zinc finger protein, Neuferricin, Cyclin-dependent kinase 1, RCC1 and BTB domain-containing protein 1, Eukaryotic translation initiation factor 3 subunit H, Zinc finger SWIM domain-containing protein 1, DNA-directed RNA polymerase II subunit RPB4, Rho guanine nucleotide exchange factor 2, E3 ubiquitin-protein ligase TRIM37, DEP domain-containing protein 1A, Small nuclear ribonucleoprotein Sm D1, Lipopolysaccharide-responsive and beige-like anchor protein, Electron transfer flavoprotein subunit alpha, mitochondrial, Solute carrier family 43 member 3, Integrin alpha-4, Uridine-cytidine kinase-like 1, KH domain-containing, RNA-binding, signal transduction-associated protein 1, Rho guanine nucleotide exchange factor 18, Steroid receptor RNA activator 1, Cytochrome c oxidase subunit 7C, mitochondrial, Flotillin-1, Breast cancer type 1 susceptibility protein, Ral GTPase-activating protein subunit beta, F-box only protein 22, Glycerol-3-phosphate dehydrogenase, mitochondrial, Propionyl-CoA carboxylase beta chain, mitochondrial, Utrophin, Testis-expressed sequence 10 protein, SEC14-like protein 1, Ethylmalonyl-CoA decarboxylase, HEAT repeat-containing protein 2, 60S ribosomal protein L6, Mitochondrial dynamics protein MID51, Zinc finger protein 131, Vacuolar protein sorting-associated protein 53 homolog, Putative sodium-coupled neutral amino acid transporter 10, KN motif and ankyrin repeat domain-containing protein 2, Pyridoxal-dependent decarboxylase domain-containing protein 1, Pinin, V-type proton ATPase subunit H, Ubiquitin-conjugating enzyme E2 B, Inhibitor of nuclear factor kappa-B kinase-interacting protein, Double-strand-break repair protein rad21 homolog, PRA1 family protein 3, DEP domain-containing protein 1 B, ATP-binding cassette sub-family B member 10, mitochondrial, SHC-transforming protein 1, Serine/threonine-protein phosphatase PP1-gamma catalytic subunit, Eukaryotic translation initiation factor 2 subunit 1, Anaphase-promoting complex subunit 7, TATA-binding protein-associated factor 172, 2'-5'-oligoadenylate synthase 3, LisH domain-containing protein ARMC9, Ankyrin repeat and SOCS box protein 6, DNA polymerase epsilon catalytic subunit A, Sestrin-1, V-type proton ATPase catalytic subunit A, Trinucleotide repeat-containing gene 6A protein, TNFAIP3-interacting protein 2, Phosphatidylinositol 3-kinase regulatory subunit gamma, TELO2-interacting protein 1 homolog, Leucine-rich repeat and coiled-coil domain-containing protein 1, Transmembrane emp24 domain-containing protein 9, F-box/LRR-repeat protein 5, Programmed cell death 6-interacting protein, Ribosome production factor 1, Exostosin-2, Bloom syndrome protein, U1 small nuclear ribonucleoprotein C, Transcription factor RFX3, Ubiquitin carboxyl-terminal hydrolase 34, Polymerase I and transcript release factor, Mediator of RNA polymerase II transcription subunit 12, Heterogeneous nuclear ribonucleoprotein C-like 1, Serine/threonine-protein kinase ATR, Neurochondrin, Adrenocortical dysplasia protein homolog, Ran GTPase-activating protein 1, Arfaptin-2, Pericentrin, Hermansky-Pudlak syndrome 4 protein, Choline/ethanolamine kinase, WD repeat-containing protein 3, Peroxisomal membrane protein 4, Dynactin subunit 1, AP-3 complex subunit mu-1, Alsin, RNA-binding protein 28, Zinc finger MYM-type protein 3, RNA polymerase II-associated protein 1, General transcription factor 3C polypeptide 5, EH domain-containing protein 4, Huntingtin, Set1/Ash2 histone methyltransferase complex subunit ASH2, Non-POU domain-containing octamer-binding protein, Ancient ubiquitous protein 1, Coiled-coil domain-containing protein 93, Probable ATP-dependent RNA helicase DDX27, Nuclear respiratory factor 1, Fanconi anemia group D2 protein, E3 ubiquitin-protein ligase UHRF1, Cyclic AMP-dependent transcription factor ATF-1, HEAT repeat-containing protein 5B, NmrA-like family domain-containing protein 1, Tetratricopeptide repeat protein 21 B, Inositol 1,4,5-trisphosphate receptor type 1, Perilipin-2, V-type proton ATPase subunit C 1, Protein NOXP20, Short transient receptor potential channel 1, Mitochondrial import receptor subunit TOM22 homolog, AP-3 complex subunit mu-2, Malate dehydrogenase, mitochondrial, Quinone oxidoreductase, Dual specificity protein phosphatase 14, Cell division cycle and apoptosis regulator protein 1, Protein PAT1 homolog 2, Tropomyosin alpha-4 chain, 40S ribosomal protein S15a, Prefoldin subunit 4, Neurobeachin-like protein 2, E3 ubiquitin-protein ligase RNF130, Calmodulin-regulated spectrin-associated protein 1, HEAT repeat-containing protein 3, Carbohydrate sulfotransferase 14, Isochorismatase domain-containing protein 1, Rab GTPase-activating protein 1-like, Centrosomal protein of 76 kDa, Exportin-1, von Willebrand factor A domain-containing protein 8, Ras-related protein Rab-5A, MAU2 chromatid cohesion factor homolog, Kelch-like protein 24, Protein FAM171B, Protein yippee-like 1, Inhibitor of nuclear factor kappa-B kinase subunit alpha, Probable ATP-dependent RNA helicase DDX56, Uncharacterized protein C18orf8, Protein LLP homolog, AP-2 complex subunit sigma, Maestro heat-like repeat-containing protein family member 1, Nucleolar protein 9, High mobility group protein 20A, HLA class II histocompatibility antigen, DR beta 3 chain, Importin-9, Protein asunder homolog, Ribonuclease UK114, Zinc finger BED domain-containing protein 1, Tyrosine-protein kinase JAK1, Putative RNA-binding protein 15, AKT-interacting protein, Werner syndrome ATP-dependent helicase, Protein downstream neighbor of Son, Protein artemis, Adenosylhomocysteinase 2, Ligand-dependent nuclear receptor-interacting factor 1, Kelch-like protein 8, Adenosylhomocysteinase, DNA-directed RNA polymerases I, II, and III subunit RPABC3, Transcription factor 25, Nuclear migration protein nudC, COP9 signalosome complex subunit 1, Nucleoprotein TPR, Neutral alpha-glucosidase C, UPF0585 protein C16orf13, BTB/POZ domain-containing protein KCTD3, DBF4-type zinc finger-containing protein 2, NADH dehydrogenase [ubiquinone] iron-sulfur protein 8, mitochondrial, Protein unc-50 homolog, Vacuole membrane protein 1, SUMO-activating enzyme subunit 2, Mitotic checkpoint serine/threonine-protein kinase BUB1 beta, EKC/KEOPS complex subunit TPRKB, PRKC apoptosis WT1 regulator protein, Probable methyltransferase TARBP1, E3 ubiquitin-protein ligase HUWE1, 26S proteasome non-ATPase regulatory subunit 8, Leucine-tRNA ligase, cytoplasmic, Striatin-interacting protein 2, Zinc finger protein Pegasus, A-kinase anchor protein 10, mitochondrial, RNA polymerase II subunit A C-terminal domain phosphatase, DNA repair protein complementing XP-G cells, Protein phosphatase 1 G, Interleukin-1 receptor-associated kinase-like 2, Dual specificity protein kinase CLK2, Sterol regulatory element-binding protein 2, Actin-related protein 2/3 complex subunit 4, Replication factor C subunit 5, Histone deacetylase 3, 40S ribosomal protein S10, Protein unc-93 homolog B1, Sodium- and chloride-dependent taurine transporter, Cullin-7, Kinetochore-associated protein 1, Histone deacetylase 1, Syntaxin-binding protein 5, Speriolin-like protein, Erythroid differentiation-related factor 1, Ubiquitin-conjugating enzyme E2 J2, E3 ubiquitin-protein ligase Hakai, Annexin A5, cAMP-dependent protein kinase catalytic subunit alpha, Cytochrome c, COMM domain-containing protein 2, Akirin-1, ORM1-like protein 1, Sodium channel and clathrin linker 1, Tetratricopeptide repeat protein 14, Structural maintenance of chromosomes protein 4, BCL-6 corepressor, NEDD8-activating enzyme E1 regulatory subunit, RANBP2-like and GRIP domain-containing protein 2, Mediator of RNA polymerase II transcription subunit 19, Afadin, Tubulin beta-2A chain, N-alpha-acetyltransferase 50, Origin recognition complex subunit 1, Syntaxin-binding protein 2, Abl interactor 1, FERM domain-containing protein 4A, 60S ribosome subunit biogenesis protein NIP7 homolog, Dolichol-phosphate mannosyltransferase subunit 3, Protein enabled homolog, F-actin-capping protein subunit beta, Centromere protein W, Histone H1.1, Crooked neck-like protein 1, Exportin-T, Chondroitin sulfate glucuronyltransferase, 78 kDa glucose-regulated protein, X-ray repair cross-complementing protein 6, WD and tetratricopeptide repeats protein 1, DNA replication licensing factor MCM3, Retinoblastoma-like protein 1, Alpha-2-macroglobulin receptor-associated protein, Immunoglobulin-binding protein 1, Myeloid leukemia factor 2, Histone-lysine N-methyltransferase NSD3, Secernin-1, DNA dC→dU-editing enzyme APOBEC-3D, Syntaxin-18, WD repeat-containing protein 91, Tubulin-specific chaperone A, MAP3K12-binding inhibitory protein 1, Spectrin alpha chain, non-erythrocytic 1, Transcriptional regulator ATRX, Nuclear receptor corepressor 1, Protein kinase C delta type, ATP-dependent RNA helicase DDX42, E3 ubiquitin-protein ligase TTC3, RAB6A-GEF complex partner protein 1, B-cell receptor-associated protein 31, Poly(A)-specific ribonuclease PARN, Translation initiation factor eIF-2B subunit epsilon, RNA-binding protein 8A, Pre-mRNA-processing factor 6, Cleavage and polyadenylation specificity factor subunit 7, 39S ribosomal protein L20, mitochondrial, Melanoma-associated antigen F1, Lysine-specific demethylase 2B, Translation factor GUF1, mitochondrial, V-type proton ATPase subunit E 1, 60S ribosomal protein L9, Actin-related protein 2/3 complex subunit 5, Prefoldin subunit 6, Serine hydroxymethyltransferase, mitochondrial, Interferon alpha-inducible protein 6, Engulfment and cell motility protein 2, Transcription initiation factor IIE subunit beta, F-box only protein 21, Cytochrome c oxidase subunit 7A-related protein, mitochondrial, Mitochondrial ubiquitin ligase activator of NFKB 1, NAD(P)H dehydrogenase [quinone] 1, Lysine-specific demethylase 5D, Major facilitator superfamily domain-containing protein 12, Casein kinase II subunit beta, Sec1 family domain-containing protein 1, Receptor expression-enhancing protein 3, Kinetochore protein Nuf2, E3 ubiquitin-protein ligase makorin-1, Probable ATP-dependent RNA helicase DHX37, Exosome complex component RRP41, Angio-associated migratory cell protein, Trans-3-hydroxy-L-proline dehydratase, Helicase with zinc finger domain 2, Fanconi anemia group I protein, Pescadillo homolog, Nucleolar and spindle-associated protein 1, Retinoblastoma-associated protein, DNA repair protein XRCC2, Derlin-1, DNA (cytosine-5)-methyltransferase 3A, Putative rhophilin-2-like protein RHPN2P1, TRAF2 and NCK-interacting protein kinase, Nucleoside diphosphate kinase 6, Methylsterol monooxygenase 1, Protein HIRA, Probable phospholipid-transporting ATPase IF, Integrator complex subunit 12, Signal peptidase complex catalytic subunit SEC11C, Sororin, Histone H2B type 1-K, Integrator complex subunit 8, Toll-interacting protein, Amyloid protein-binding protein 2, 182 kDa tankyrase-1-binding protein, Cytoplasmic FMR1-interacting protein 2, Heat shock protein 105 kDa, Chromodomain-helicase-DNA-binding protein 2, 26S protease regulatory subunit 10B, Zinc finger MYND domain-containing protein 11, General transcription factor IIH subunit 5, Ubiquitin carboxyl-terminal hydrolase 19, Serrate RNA effector molecule homolog, Ras GTPase-activating protein-binding protein 2, Heat shock 70 kDa protein 4, Coatomer subunit beta, NADH dehydrogenase [ubiquinone] 1 alpha subcomplex subunit 13, DDB1- and CUL4-associated factor 10, Negative elongation factor E, Coiled-coil domain-containing protein 66, E3 ubiquitin-protein ligase MGRN1, WD repeat-containing protein 36, Unconventional myosin-Ie, PH domain leucine-rich repeat-containing protein phosphatase 1, Paxillin, Kinesin-like protein KIF21A, 2',3'-cyclic-nucleotide 3'-phosphodiesterase, Protein FAM192A, Proteasome subunit beta type-4, Sorting nexin-14, Krueppel-like factor 6, Tropomodulin-3, Nuclear receptor-binding protein, Nitrogen permease regulator 2-like protein, OTU domain-containing protein 5, Histone-binding protein RBBP4, Sorting nexin-24, Poly(rC)-binding protein 2, Vacuolar fusion protein CCZ1 homolog, ATP-dependent RNA helicase DDX19B, Elongation factor 1-gamma, Adenylate cyclase type 3, MICOS complex subunit MIC19, Ferritin light chain, Glutaredoxin-3, Pre-B-cell leukemia transcription factor 3, AP-2 complex subunit alpha-1, 40S ribosomal protein S24, Enhancer of mRNA-decapping protein 3, Neuroblastoma-amplified sequence, Protein phosphatase 1 regulatory subunit 7, Exosome component 10, Cyclin-dependent kinase 14, Translocation protein SEC62, Constitutive coactivator of peroxisome proliferator-activated receptor gamma, Protein SCAF11, Rho GTPase-activating protein 21, Arfaptin-1, AP-2 complex subunit mu, Ubiquitin carboxyl-terminal hydrolase 36, Glutathione S-transferase kappa 1, Kelch repeat and BTB domain-containing protein 7, Calcium homeostasis endoplasmic reticulum protein, RNA polymerase II-associated protein 3, Zinc finger E-box-binding homeobox 1, Dynein light chain 1, cytoplasmic, 39S ribosomal protein L2, mitochondrial, Fidgetin-like protein 1, WD repeat-containing protein 46, Exosome complex component RRP40, Ubiquinol-cytochrome-c reductase complex assembly factor 1, Antizyme inhibitor 1, Transketolase, Carbohydrate sulfotransferase 10, LanC-like protein 1, Histone H2A.V, E3 ubiquitin-protein ligase TRIP12, Unconventional myosin-VI, Integrin-linked protein kinase, Serine/threonine-protein kinase WNK1, Centromere protein M, Ankyrin repeat family A protein 2, Little elongation complex subunit 1, Deoxynucleoside triphosphate triphosphohydrolase SAMHD1, Lanosterol 14-alpha demethylase, NADH dehydrogenase [ubiquinone] 1 beta subcomplex subunit 4, TFIIH basal transcription factor complex helicase XPD subunit, Thymidine kinase, cytosolic, Peroxiredoxin-6, LYR motif-containing protein 1, SWI/SNF complex subunit SMARCC2, Lysine-specific histone demethylase 1B, Induced myeloid leukemia cell differentiation protein Mcl-1, V-type proton ATPase 16 kDa proteolipid subunit, HLA class II histocompatibility antigen, DP alpha 1 chain, ATP synthase subunit g, mitochondrial, Interferon regulatory factor 9, Cleavage and polyadenylation specificity factor subunit 2, Sentrin-specific protease 6, Zinc finger CCCH domain-containing protein 4, Squalene monooxygenase, RNA cytidine acetyltransferase, Ribonuclease inhibitor, UDP-glucose:glycoprotein glucosyltransferase 2, Bifunctional apoptosis regulator, SWI/SNF-related matrix-associated actin-dependent regulator of chromatin subfamily E member 1, Zinc finger protein 302, Phosphatidylinositol 4-phosphate 5-kinase type-1 alpha, Transmembrane emp24 domain-containing protein 10, Phosphatidylinositol-binding clathrin assembly protein, DnaJ homolog subfamily B member 14, Ezrin, Moesin, Transcription elongation factor B polypeptide 2, Small kinetochore-associated protein, RANBP2-like and GRIP domain-containing protein 1, Mitochondrial fission 1 protein, Spliceosome RNA helicase DDX39B, Activating signal cointegrator 1 complex subunit 2, Fibroblast growth factor receptor 1, 60S ribosomal protein L7-like 1, Tyrosine-protein kinase JAK2, Replication factor C subunit 2, SAGA-associated factor 29, B-cell linker protein, SWI/SNF-related matrix-associated actin-dependent regulator of chromatin subfamily A member 5, Myc proto-oncogene protein, Translationally-controlled tumor protein, Baculoviral IAP repeat-containing protein 2, Serine/threoni ne-protein kinase Chk1, 40S ribosomal protein S9, Galactosylgalactosylxylosylprotein 3-beta-glucuronosyltransferase 3, BRISC and BRCA1-A complex member 1, SWI/SNF-related matrix-associated actin-dependent regulator of chromatin subfamily D member 3, Tyrosine-tRNA ligase, cytoplasmic, Target of rapamycin complex 2 subunit MAPKAP1, Activator of 90 kDa heat shock protein ATPase homolog 1, Class E basic helix-loop-helix protein 40, 60S ribosomal protein L27a, Cilia- and flagella-associated protein 20, Polyribonucleotide 5'-hydroxyl-kinase Clpl, Elongator complex protein 3, Nodal modulator 2, Low density lipoprotein receptor adapter protein 1, Protein FAM136A, Selenoprotein T, cAMP-dependent protein kinase catalytic subunit beta, Small EDRK-rich factor 2, A-kinase anchor protein 13, Renin receptor, Chromosome alignment-maintaining phosphoprotein 1, Mediator of RNA polymerase II transcription subunit 27, Zinc finger and BTB domain-containing protein 40, Protein FAM3C, Pseudouridylate synthase 7 homolog, Cyclin-dependent kinase 11A, Cyclin-dependent kinase 11B, Zinc finger FYVE domain-containing protein 16, Cyclic AMP-dependent transcription factor ATF-6 beta, Bridging integrator 3, 26S proteasome non-ATPase regulatory subunit 11, RNA-binding protein 43, Serine/threonine-protein kinase Chk2, 60S ribosomal protein L13a, G2/mitotic-specific cyclin-B2, Tryptophan-tRNA ligase, mitochondrial, B-lymphocyte antigen CD19, Astrotactin-2, Rab GDP dissociation inhibitor beta, Unconventional myosin-Id, Nipped-B-like protein, E3 ubiquitin-protein ligase RAD18, Motile sperm domain-containing protein 2, Microtubule-associated protein RP/EB family member 1, DNA replication licensing factor MCM2, Methionine synthase reductase, Leucine-rich repeat-containing protein 58, Proteasome assembly chaperone 2, Neuroguidin, 40S ribosomal protein S7, PRELI domain containing protein 3B, Cyclin-T1, Dolichyl-diphosphooligosaccharide-protein glycosyltransferase 48 kDa subunit, Large proline-rich protein BAG6, Myosin-7B, DnaJ homolog subfamily B member 5, Nuclear factor interleukin-3-regulated protein, Ras-related protein Rab-7a, Fizzy-related protein homolog, CUGBP Elav-like family member 2, Serine/threonine-protein kinase PAK 2, Serine/threonine/tyrosine-interacting-like protein 1, Monocarboxylate transporter 7, Oxysterol-binding protein-related protein 9, DnaJ homolog subfamily A member 1, Copine-8, Forkhead box protein K2, RNA polymerase II subunit A C-terminal domain phosphatase SSU72, Alpha-galactosidase A, Mis18-binding protein 1, Desmin, DNA-(apurinic or apyrimidinic site) lyase, tRNA (cytosine(34)-C(5))-methyltransferase, Condensin-2 complex subunit H2, Protein C10, TRAF3-interacting JNK-activating modulator, Eukaryotic translation initiation factor 3 subunit E, TCF3 fusion partner, Inorganic pyrophosphatase, LBH domain-containing protein 1, NADH dehydrogenase [ubiquinone] 1 beta subcomplex subunit 11, mitochondrial, Ubiquilin-2, Gamma-taxilin, Di-N-acetylchitobiase, Sorting nexin-17, Ras-related GTP-binding protein A, Tropomyosin alpha-3 chain, Tetratricopeptide repeat protein 39C, Aurora kinase A, Histone H2B type 2-E, Sorbitol dehydrogenase, Serine/threonine-protein kinase Nek6, U3 small nucleolar ribonucleoprotein protein MPP10, 60S ribosomal protein L31, Importin-8, Replication factor C subunit 4, Putative Polycomb group protein ASXL1, Protein PML, DNA-directed RNA polymerases I, II, and Ill subunit RPABC2, Translational activator GCN1, Zinc finger protein 195, Fragile X mental retardation syndrome-related protein 1, Dual specificity tyrosine-phosphorylation-regulated kinase 1A, Integrator complex subunit 1, RNA pseudouridylate synthase domain-containing protein 4, Phosducin-like protein 3, Golgi phosphoprotein 3, Guanine nucleotide-binding protein G(I)/G(S)/G(O) subunit gamma-5, Cartilage-associated protein, Ubiquitin-associated domain-containing protein 2, Heterogeneous nuclear ribonucleoprotein Q, Semaphorin-7A, Pentatricopeptide repeat domain-containing protein 3, mitochondrial, Egl nine homolog 2, Parkinson disease 7 domain-containing protein 1, Nuclear pore complex protein Nup98-Nup96, Glycogen synthase kinase-3 beta, BTB/POZ domain-containing protein KCTD20, Tubulin gamma-1 chain, LYR motif-containing protein 2, NF-kappa-B inhibitor beta, Kinesin-like protein KIF18B, Histone deacetylase 5, HCLS1-associated protein X-1, 40S ribosomal protein S4, X isoform, E3 ubiquitin-protein ligase MARCH6, Kelch-like protein 20, Terminal uridylyltransferase 4, TNF receptor-associated factor 1, DnaJ homolog subfamily B member 12, E3 ubiquitin-protein ligase UBR5, DNA methyltransferase 1-associated protein 1, Zinc finger MIZ domain-containing protein 1, Apoptosis inhibitor 5, 39S ribosomal protein L55, mitochondrial, Phosphate carrier protein, mitochondrial, Formin-binding protein 1, F-box only protein 33, Protein-lysine N-methyltransferase EEF2KMT, Growth factor receptor-bound protein 2, 60S ribosomal protein L23, Neuroepithelial cell-transforming gene 1 protein, Isoleucine-tRNA ligase, cytoplasmic, Uncharacterized protein KIAA1551, 60S ribosomal protein L30, Protein BRICK1, Protein PRRC2C, Cytoskeleton-associated protein 2-like, Cyclin-dependent kinase 12, Cold shock domain-containing protein E1, Eukaryotic translation initiation factor 4H, Cell division cycle 5-like protein, Biogenesis of lysosome-related organelles complex 1 subunit 1, Beta-catenin-like protein 1, 60S ribosomal protein L37a, Peroxisomal multifunctional enzyme type 2, Ubiquitin-40S ribosomal protein S27a, RAD50-interacting protein 1, Dynamin-binding protein, Diphosphoinositol polyphosphate phosphohydrolase 1, Diphosphoinositol polyphosphate phosphohydrolase 2, Coatomer subunit beta', Plakophilin-4, tRNA pseudouridine synthase-like 1, Protein ERGIC-53, F-box only protein 3, ATP synthase mitochondrial F1 complex assembly factor 1, tRNA (guanine(26)-N(2))-dimethyltransferase, Poly [ADP-ribose] polymerase 3, Drebrin-like protein, YEATS domain-containing protein 4, Sorting nexin-3, Copper transport protein ATOX1, U3 small nucleolar RNA-associated protein 14 homolog A, Acetolactate synthase-like protein, Inosine-5'-monophosphate dehydrogenase 2, Transmembrane protein 107, Mitochondrial import receptor subunit TOM5 homolog, Ribosome biogenesis protein WDR12, WD repeat-containing protein 74, Centrosomal protein of 104 kDa, Probable E3 ubiquitin-protein ligase TRIM8, UPF0769 protein C21orf59, E3 ubiquitin-protein ligase Itchy homolog, Ubiquilin-1, Ferritin heavy chain, Single-stranded DNA-binding protein 2, PERQ amino acid-rich with GYF domain-containing protein 2, Transcriptional adapter 1, Zinc finger protein 296, UV-stimulated scaffold protein A, WD repeat-containing protein 63, Programmed cell death protein 6, WD repeat-containing protein 62, Beta-parvin, DnaJ homolog subfamily A member 2, Protein sel-1 homolog 1, HLA class II histocompatibility antigen, DRB1-11 beta chain, Retinoic acid receptor alpha, Vacuolar protein sorting-associated protein 51 homolog, Misshapen-like kinase 1, Arginine-glutamic acid dipeptide repeats protein, Manganese-transporting ATPase 13A1, Myotubularin-related protein 10, Double-stranded RNA-specific adenosine deaminase, Adenylate cyclase type 6, Cytochrome c oxidase subunit 6C, N-alpha-acetyltransferase 30, COP9 signalosome complex subunit 2, Cell division cycle-associated protein 2, Zinc finger protein 697, Protection of telomeres protein 1, Uridine diphosphate glucose pyrophosphatase, Ubiquitin carboxyl-terminal hydrolase 48, RNA-binding protein EWS, Immediate early response gene 5 protein, PCI domain-containing protein 2, MAP7 domain-containing protein 1, 60S ribosomal protein L18, WD repeat and coiled-coil-containing protein C2orf44, Kanadaptin, Double-stranded RNA-binding protein Staufen homolog 2, F-box only protein 11, E3 ubiquitin-protein ligase CHFR, Heterogeneous nuclear ribonucleoprotein U-like protein 2, Cathepsin Z, MOB kinase activator 1A, Lysine-specific demethylase 5C, Lysine-specific demethylase 5A, Probable cation-transporting ATPase 13A4, Sentrin-specific protease 5, SRR1-like protein, Epidermal growth factor receptor kinase substrate 8, Cytoplasmic dynein 1 light intermediate chain 1, Zinc finger protein 619, Fatty acyl-CoA reductase 1, NHP2-like protein 1, RNA-binding protein 27, RNA-binding protein 26, Geranylgeranyl pyrophosphate synthase, Myosin phosphatase Rho-interacting protein, Protein kinase C delta-binding protein, Histidine triad nucleotide-binding protein 1, Interferon-related developmental regulator 1, GPI mannosyltransferase 3, Ubiquitin-like protein 7, Exportin-6, Male-specific lethal 3 homolog, Flap endonuclease 1, Elongation factor 1-alpha 1, COP9 signalosome complex subunit 3, HIG1 domain family member 2A, mitochondrial, 3-phosphoinositide-dependent protein kinase 1, Sodium-coupled neutral amino acid transporter 2, Intraflagellar transport protein 81 homolog, Cleavage and polyadenylation specificity factor subunit 3, Centrosomal protein of 57 kDa, Interferon-stimulated gene 20 kDa protein, DNA-directed RNA polymerase II subunit RPB2, Protein kintoun, Leucine-rich repeat-containing protein 20, Probable 18S rRNA (guanine-N(7))-methyltransferase, Heterogeneous nuclear ribonucleoprotein A3, Transmembrane protein 263, Glutathione S-transferase P, Adenylosuccinate lyase, ER membrane protein complex subunit 1, JmjC domain-containing protein 8, AN1-type zinc finger protein 5, Cullin-3, MICOS complex subunit MIC27, Selenoprotein H, Centromere protein H, Beta-hexosaminidase subunit alpha, Zinc phosphodiesterase ELAC protein 2, BRCA1-A complex subunit BRE, SRSF protein kinase 1, Insulin-like growth factor 2 mRNA-binding protein 2, Coiled-coil domain-containing protein 85B, Centrosomal protein of 55 kDa, COMM domain-containing protein 4, 14-3-3 protein theta, Armadillo repeat-containing X-linked protein 3, Uncharacterized protein C6orf226, DNA-directed RNA polymerase I subunit RPA1, Syntaxin-binding protein 1, Small nuclear ribonucleoprotein Sm D2, T-complex protein 1 subunit delta, Nucleophosmin, Serine/arginine repetitive matrix protein 2, PC4 and SFRS1-interacting protein, Nardilysin (N-arginine dibasic convertase), isoform CRA_d, Ragulator complex protein LAMTOR4, Golgin subfamily B member 1, E3 SUMO-protein ligase PIAS3, Prohibitin, Maspardin, Chromodomain-helicase-DNA-binding protein 6, V-type proton ATPase subunit D, Taperin, Coronin-1C, Importin subunit alpha-4, Pre-mRNA-processing factor 19, Single-stranded DNA-binding protein, mitochondrial, Vacuolar protein sorting-associated protein 33A, STAGA complex 65 subunit gamma, F-box only protein 38, Protein C-ets-1, DNA repair endonuclease XPF, Clathrin light chain A, Inhibitor of growth protein 4, Protein zer-1 homolog, Apolipoprotein L2, Serine/Arginine-related protein 53, Transcription initiation factor IIB, Ras suppressor protein 1, V-type proton ATPase 116 kDa subunit a isoform 1, Scavenger receptor class B member 1, Importin-11, Periodic tryptophan protein 1 homolog, Sequestosome-1, DNA replication licensing factor MCM6, Lupus La protein, 40S ribosomal protein S2, DNA-directed RNA polymerases I, II, and III subunit RPABC4, Dual specificity protein kinase CLK3, Mitochondrial import inner membrane translocase subunit TIM50, Cyclin-dependent kinase 7, Interleukin enhancer-binding factor 3, Poly(U)-binding-splicing factor PUF60, Fc receptor-like A, Heterogeneous nuclear ribonucleoprotein H, Nucleolar complex protein 2 homolog, DNA topoisomerase 1, Eukaryotic initiation factor 4A-II, Inner centromere protein, ZW10 interactor, Epsilon-sarcoglycan, Protein disulfide-isomerase A6, Transcription factor E2F7, GDP-L-fucose synthase, Runt-related transcription factor 3, Chromodomain-helicase-DNA-binding protein 4, SRA stem-loop-interacting RNA-binding protein, mitochondrial, Poly [ADP-ribose] polymerase 9, Zinc finger protein 451, Coatomer subunit zeta-1, Eukaryotic translation initiation factor 4B, Death-associated protein kinase 3, Leucine-rich repeat-containing protein 47, Guanylate-binding protein 1, Actin-related protein 2/3 complex subunit 1B, Proteasome maturation protein, Probable ATP-dependent RNA helicase DDX41, General vesicular transport factor p115, SH2 domain-containing protein 3C, Polyadenylate-binding protein-interacting protein 1, Histone H3.1, Probable ATP-dependent RNA helicase DDX6, Poly(rC)-binding protein 1, Steroid hormone receptor ERR1, Cytoskeleton-associated protein 4, Integrin beta-7, Eukaryotic translation initiation factor 3 subunit A, F-box only protein 7, GPN-loop GTPase 2, Melanoma-associated antigen 12, Basic leucine zipper and W2 domain-containing protein 2, Stomatin-like protein 3, Condensin complex subunit 1, Septin-11, Glutamine-dependent NAD(+) synthetase, Mitogen-activated protein kinase kinase kinase 5, Ubiquitin-like modifier-activating enzyme 1, Disco-interacting protein 2 homolog B, HLA class I histocompatibility antigen, A-24 alpha chain, Integrator complex subunit 2, UPF0428 protein CXorf56, MMS19 nucleotide excision repair protein homolog, AF4/FMR2 family member 4, Ras-related C3 botulinum toxin substrate 1, Bone morphogenetic protein receptor type-1B, Multiple epidermal growth factor-like domains protein 8, Keratin, type II cytoskeletal 1, Tumor suppressor candidate 3, Rho GTPase-activating protein 24, Nuclear nucleic acid-binding protein C1 D, Pecanex-like protein 1, Melanoma antigen preferentially expressed in tumors, RNA exonuclease 4, YTH domain-containing family protein 2, Probable bifunctional methylenetetrahydrofolate dehydrogenase/cyclohydrolase 2, HLA class I histocompatibility antigen, A-29 alpha chain, Ubiquitin-like protein ISG15, N-acetyltransferase 8, Protein prune homolog 2, Phosphatidylinositol 4,5-bisphosphate 3-kinase catalytic subunit delta isoform, Glutathione peroxidase 1, Dermokine, PRELI domain-containing protein 1, mitochondrial, Putative WAS protein family homolog 3, Mitochondrial import inner membrane translocase subunit Tim23, SLAM family member 6, Probable ubiquitin carboxyl-terminal hydrolase FAF-Y, Annexin A3, Microtubule-associated protein 1B, Glyoxylate reductase/hydroxypyruvate reductase, 40S ribosomal protein S4, Y isoform 1, Probable ATP-dependent RNA helicase DDX4, EH domain-containing protein 2, Ubiquitin carboxyl-terminal hydrolase 45, Trinucleotide repeat-containing gene 18 protein, Aldo-keto reductase family 1 member C1, Protein phosphatase 1 regulatory subunit 35, Frizzled-2, E3 ubiquitin-protein ligase HECTD1, V-type proton ATPase subunit S1, Peroxisomal membrane protein PEX16, Pro-interleukin-16, Amidophosphoribosyltransferase, Hsc70-interacting protein, YEATS domain-containing protein 2, Protein arginine N-methyltransferase 1, Cyclic AMP-responsive element-binding protein 3-like protein 2, Solute carrier family 25 member 46, General transcription factor II-I, 40S ribosomal protein S30, 2'-5'-oligoadenylate synthase 1, NADH dehydrogenase [ubiquinone] 1 alpha subcomplex subunit 1, Reticulocalbin-1, S-adenosylmethionine synthase isoform type-1, Membralin, Dynamin-like 120 kDa protein, mitochondrial, Growth hormone-inducible transmembrane protein, Heat shock-related 70 kDa protein 2, Eukaryotic translation initiation factor 3 subunit B, Ras-specific guanine nucleotide-releasing factor 1, Voltage-dependent anion-selective channel protein 2, Protein unc-13 homolog D, Golgi apparatus protein 1, Eukaryotic translation initiation factor 6, Probable ribonuclease ZC3H12D, Ragulator complex protein LAMTOR1, Ribonucleoside-diphosphate reductase subunit M2 B, Zinc finger protein 638, B- and T-lymphocyte attenuator, CD44 antigen, Cordon-bleu protein-like 1, C—C chemokine receptor type 7, Ragulator complex protein LAMTOR3, IgG receptor FcRn large subunit p51, Serine/threonine-protein kinase LATS1, E3 ubiquitin-protein ligase CHIP, T-cell activation Rho GTPase-activating protein, Platelet endothelial cell adhesion molecule, TBC1 domain family member 22A, Endoplasmic reticulum resident protein 44, Lipolysis-stimulated lipoprotein receptor, Glucose-6-phosphate isomerase, Cystatin-C, Ras-related protein Rab-11A, Cadherin EGF LAG seven-pass G-type receptor 1, Tumor protein p53-inducible protein 11, Short-chain dehydrogenase/reductase 3, Probable ribosome biogenesis protein RLP24, Ceruloplasmin, Ceramide glucosyltransferase, Dystrophin, Uncharacterized protein CXorf21, MyoD family inhibitor domain-containing protein, Obscurin-like protein 1, Beta-1,4-galactosyltransferase 1, Plasma membrane calcium-transporting ATPase 1, Vesicle-associated membrane protein 3, Protein CDV3 homolog, Peroxiredoxin-1, Methyltransferase-like protein 7A, HLA class II histocompatibility antigen, DO beta chain, Receptor-type tyrosine-protein phosphatase alpha, ATP-binding cassette sub-family A member 6, 14-3-3 protein beta/alpha, Glycosyltransferase 8 domain-containing protein 1, Serine incorporator 3, NACHT, LRR and PYD domains-containing protein 2, Baculoviral IAP repeat-containing protein 5, Alpha-mannosidase 2, DnaJ homolog subfamily C member 5, Fas apoptotic inhibitory molecule 3, HLA class II histocompatibility antigen, DM alpha chain, Heterogeneous nuclear ribonucleoprotein A1-like 2, Transcription regulator protein BACH2, Zinc finger protein 107, Probable ATP-dependent RNA helicase DDX46, Kynureninase, Interleukin-4 receptor subunit alpha, Polypeptide N-acetylgalactosaminyltransferase 1, Fibromodulin, Pericentriolar material 1 protein, 60S ribosomal protein L3, Glycosylphosphatidylinositol anchor attachment 1 protein, AT-rich interactive domain-containing protein 5B, Carbohydrate sulfotransferase 2, Kelch-like ECH-associated protein 1, DmX-like protein 1, 14-3-3 protein zeta/delta, Plexin-B3, Elongation factor Tu, mitochondrial, Protocadherin-9, Monoglyceride lipase, Afadin- and alpha-actinin-binding protein, Platelet glycoprotein 4, Transmembrane protein C16orf54, Cullin-associated NEDD8-dissociated protein 1, Proline and serine-rich protein 2, Pro-cathepsin H, RUN and FYVE domain-containing protein 1, Neurofibromin, Leukosialin, Arrestin domain-containing protein 4, TP53-target gene 5 protein, Vitamin D-binding protein, Tumor necrosis factor receptor superfamily member 13C, Phosphate-regulating neutral endopeptidase, Interleukin-1 beta, Interleukin-17 receptor A, Putative heat shock 70 kDa protein 7, Cytochrome b ascorbate-dependent protein 3, Vesicle-associated membrane protein 1, Ras GTPase-activating protein nGAP, BRCA2 and CDKN1A-interacting protein, Rab GTPase-activating protein 1, Melanoma-associated antigen C2, C—C motif chemokine 3, Ig gamma-1 chain C region, Serum albumin, Basement membrane-specific heparan sulfate proteoglycan core protein, Protein phosphatase 1M, Guanine nucleotide-binding protein G(I)/G(S)/G(T) subunit beta-1, HLA class I histocompatibility antigen, A-23 alpha chain, Zinc finger protein ZPR1, Cytochrome c oxidase assembly factor 3 homolog, mitochondrial, Arf-GAP with Rho-GAP domain, ANK repeat and PH domain-containing protein 1, Keratin, type I cytoskeletal 9, Anion exchange protein 2, Tumor susceptibility gene 101 protein, A-kinase anchor protein 1, mitochondrial, 4-hydroxyphenylpyruvate dioxygenase-like protein, Nucleosome-remodeling factor subunit BPTF, Centrin-3, Uridine-cytidine kinase 2, Isovaleryl-CoA dehydrogenase, mitochondrial, Alkyldihydroxyacetonephosphate synthase, peroxisomal, Polyadenylate-binding protein 4, Polyadenylate-binding protein 3, Bromodomain adjacent to zinc finger domain protein 2B, Protein unc-45 homolog A, Iron-sulfur cluster assembly 2 homolog, mitochondrial, ATP-dependent RNA helicase DHX36, Multidrug resistance protein 1, WD repeat-containing protein 11, Serine-rich coiled-coil domain-containing protein 2, Protein KRI1 homolog, Centrosomal protein of 192 kDa, Zinc finger protein 829, Protein kinase C-binding protein 1, AT-rich interactive domain-containing protein 1A, Msx2-interacting protein, Long-chain-fatty-acid-CoA ligase 1, Intercellular adhesion molecule 3, Treacle protein, Cytochrome c oxidase subunit 7A2, mitochondrial, HLA class I histocompatibility antigen, Cw-5 alpha chain, HLA class I histocompatibility antigen, B-55 alpha chain, Dihydropyrimidinase-related protein 2, Deoxyuridine 5'-triphosphate nucleotidohydrolase, mitochondrial, Translocon-associated protein subunit alpha, Endoplasmic reticulum resident protein 29, Lysosomal alpha-glucosidase, Armadillo repeat-containing protein 8, Pre-rRNA-processing protein TSR1 homolog, Protein FAM98B, 40S ribosomal protein S28, Rab GDP dissociation inhibitor alpha, Lysosome-associated membrane glycoprotein 2, Menin, Uncharacterized protein C1orf131, Protein MON2 homolog, Major facilitator superfamily domain-containing protein 10, Protein CNPPD1, E3 ubiquitin-protein ligase MYCBP2, NEDD4 family-interacting protein 1, Inositol hexakisphosphate kinase 2, Translocon-associated protein subunit delta, Cleavage and polyadenylation specificity factor subunit 5, Zinc finger protein 281, Calpain-1 catalytic subunit, Copine-1, Ornithine decarboxylase antizyme 1, ER degradation-enhancing alpha-mannosidase-like protein 1, Nuclear envelope integral membrane protein 1, ER membrane protein complex subunit 4, 60S ribosomal protein L17, Charged multivesicular body protein 2a, Pre-mRNA cleavage complex 2 protein Pcf11, Myosin-7, NADH dehydrogenase [ubiquinone] 1 beta subcomplex subunit 5, mitochondrial, Protein diaphanous homolog 3, Cytochrome b-c1 complex subunit 8, Intron-binding protein aquarius, Serine/threonine-protein kinase 38, 39S ribosomal protein L43, mitochondrial, Protein diaphanous homolog 1, 60S ribosomal protein L37, Vacuolar protein sorting-associated protein 4A, COMM domain-containing protein 3, POTE ankyrin domain family member E, TAR DNA-binding protein 43, Hemoglobin subunit delta, Ubiquitin-conjugating enzyme E2 D2, CDK5 regulatory subunit-associated protein 1, Nuclear export mediator factor NEMF, Late secretory pathway protein AVL9 homolog, Elongation factor 1-beta, Poly(A) RNA polymerase GLD2, Little elongation complex subunit 2, Modulator of apoptosis 1, Zinc finger protein 24, G1/S-specific cyclin-E2, Signal peptidase complex subunit 1, Lon protease homolog, mitochondrial, Deoxynucleotidyltransferase terminal-interacting protein 1, Retinoblastoma-like protein 2, Cullin-4B, DDB1- and CUL4-associated factor 8, Zyxin, Protein SDA1 homolog, Muscleblind-like protein 3, U6 snRNA-associated Sm-like protein LSm7, RuvB-like 1, Calcium-binding protein 39-like, Small subunit processome component 20 homolog, Mitochondrial-processing peptidase subunit alpha, DNA ligase 1, Gamma-aminobutyric acid receptor-associated protein-like 1, Translocating chain-associated membrane protein 1, NADH dehydrogenase [ubiquinone] iron-sulfur protein 5, Heme oxygenase 2, WD repeat-containing protein 35, NADH dehydrogenase [ubiquinone] 1 alpha subcomplex subunit 12, Nuclear factor erythroid 2-related factor 3, Rho GTPase-activating protein 1, Tubulin alpha-1C chain, Sorting nexin-4, CWF19-like protein 1, Methionine-tRNA ligase, cytoplasmic, Nuclease-sensitive element-binding protein 1, pre-mRNA 3' end processing protein WDR33, Fatty acid desaturase 2, Surfeit locus protein 4, Protein BIVM-ERCC5, Interferon-induced helicase C domain-containing protein 1, Suppressor of fused homolog, Astrocytic phosphoprotein PEA-15, Protein ELYS, Solute carrier family 23 member 2, Splicing factor 3B subunit 5, Lymphokine-activated killer T-cell-originated protein kinase, Signal transducer and activator of transcription 2, Zinc finger protein 280C, Peroxisomal acyl-coenzyme A oxidase 3, Oxidative stress-induced growth inhibitor 2, Iron-responsive element-binding protein 2, StAR-related lipid transfer protein 7, mitochondrial, F-actin-capping protein subunit alpha-2, Mitochondrial folate transporter/carrier, Protein-lysine N-methyltransferase METTL10, Cytochrome c oxidase subunit 4 isoform 1, mitochondrial, Guanine nucleotide-binding protein-like 3-like protein, Rho-related BTB domain-containing protein 1, Pre-mRNA-splicing factor SPF27, Serine/arginine-rich splicing factor 1, Ribosome biogenesis protein BMS1 homolog, BRCA1-associated protein, Lipopolysaccharide-induced tumor necrosis factor-alpha factor, TraB domain-containing protein, Phosphatidylinositol 4-kinase alpha, Microsomal glutathione S-transferase 3, Prolyl endopeptidase, Vacuolar protein sorting-associated protein 41 homolog, GTPase-activating protein and VPS9 domain-containing protein 1, 26S proteasome non-ATPase regulatory subunit 4, Protein SDE2 homolog, ADP-ribosylation factor 5, Regulation of nuclear pre-mRNA domain-containing protein 2, ADP/ATP translocase 3, 60S ribosomal protein L36, Myotrophin, Protein PRRC2A, NSFL1 cofactor p47, Interferon regulatory factor 2-binding protein 1, Serine/threonine-protein kinase 4, S-formylglutathione hydrolase, E3 ubiquitin/ISG15 ligase TRIM25, Omega-amidase NIT2, COP9 signalosome complex subunit 8, Asparagine-tRNA ligase, cytoplasmic, Glucose-6-phosphate 1-dehydrogenase, Transgelin-2, Malignant T-cell-amplified sequence 1, Synaptic vesicle membrane protein VAT-1 homolog, Calnexin, Parafibromin, Transcription factor 12, Extended synaptotagmin-1, Spectrin beta chain, non-erythrocytic 4, COX assembly mitochondrial protein 2 homolog, Lymphocyte cytosolic protein 2, DNA polymerase epsilon subunit 3, Sorting nexin-1, BAG family molecular chaperone regulator 3, Beta-enolase, RNA-binding protein 4, Destrin, Eukaryotic translation initiation factor 1A, Y-chromosomal, 5'-3' exoribonuclease 2, Nucleoporin SEH1, Reticulon-4, 26S protease regulatory subunit 6A, Heat shock 70 kDa protein 4L, Cytoskeleton-associated protein 2, Coiled-coil domain-containing protein 124, Serine-threonine kinase receptor-associated protein, 26S proteasome non-ATPase regulatory subunit 12, Ataxin-3, Polyglutamine-binding protein 1, Transcriptional repressor p66-alpha, Paired amphipathic helix protein Sin3a, Ribose-5-phosphate isomerase, Transmembrane and coiled-coil domain-containing protein 1, Dynein light chain roadblock-type 1, Rho guanine nucleotide exchange factor 1, Isocitrate dehydrogenase [NADP] cytoplasmic, Trifunctional enzyme subunit alpha, mitochondrial, Cleavage stimulation factor subunit 2, Telomeric repeat-binding factor 2-interacting protein 1, RNA-binding protein FUS, Far upstream element-binding protein 3, TATA-binding protein-associated factor 2N, Prosaposin, Myb-binding protein 1A, Barrier-to-autointegration factor, Signal recognition particle subunit SRP68, Protein FAM219A, Tripeptidyl-peptidase 1, HLA class I histocompatibility antigen, B-38 alpha chain, Proteasome subunit beta type-7, Neudesin, Tubulin beta-6 chain, Actin-related protein 2/3 complex subunit 3, Solute carrier family 35 member F5, Myoferlin, HLA class I histocompatibility antigen, B-44 alpha chain, Fructose-bisphosphate aldolase B, Neutral cholesterol ester hydrolase 1, FERM domain-containing protein 6, Cyclic AMP-dependent transcription factor ATF-4, Transcription factor AP-1, Growth arrest and DNA damage-inducible protein GADD45 alpha, Probable C-mannosyltransferase DPY19L4, Integrin alpha-3, Protein transport protein Sec61 subunit alpha isoform 2, Rho GTPase-activating protein 7, Exosome complex component RRP42, WD repeat-containing protein 48, Protein LDOC1, BTB/POZ domain-containing protein KCTD4, DNA-binding protein SATB2, Tribbles homolog 3, Small nuclear ribonucleoprotein E, SH3 domain-binding glutamic acid-rich-like protein 3, HLA class II histocompatibility antigen, DRB1-4 beta chain, HLA class I histocompatibility antigen, Cw-4 alpha chain, Fatty acid-binding protein, liver, Polymeric immunoglobulin receptor, DAZ-associated protein 2, Lck-interacting transmembrane adapter 1, Cysteine-rich protein 2-binding protein, Bifunctional 3'-phosphoadenosine 5'-phosphosulfate synthase 2, Bifunctional 3'-phosphoadenosine 5'-phosphosulfate synthase 1, Phosphatidylinositol 5-phosphate 4-kinase type-2 alpha, Calsyntenin-3, Ras-related protein Rab-20, Structure-specific endonuclease subunit SLX4, Myosin regulatory light polypeptide 9, Centrosome-associated protein 350, StAR-related lipid transfer protein 5, WASH complex subunit 7, Lysocardiolipin acyltransferase 1, Puromycin-sensitive aminopeptidase-like protein, Myocyte-specific enhancer factor 2D, Ribosomal RNA processing protein 36 homolog, G1/S-specific cyclin-D3, Dipeptidyl peptidase 1, Histone acetyltransferase KAT6A, Putative ATP-dependent RNA helicase DHX57, Histone-arginine methyltransferase CARM 1, Myosin regulatory light chain 12A, Cytochrome c oxidase subunit NDUFA4, Ras-related protein Rab-5B, Dermcidin, RING finger and transmembrane domain-containing protein 2, Inositol 1,4,5-trisphosphate receptor type 3, E3 ubiquitin-protein ligase TRIM56, DNA repair protein complementing XP-C cells, HLA class I histocompatibility antigen, B-35 alpha chain, Ubiquitin-conjugating enzyme E2 C, Bardet-Biedl syndrome 2 protein, Protein S100-A8, Zinc finger protein 608, BTB/POZ domain-containing protein KCTD1, RNA-binding protein with serine-rich domain 1, Laminin subunit beta-3, UDP-N-acetylglucosamine-dolichyl-phosphate N-acetylglucosaminephosphotransferase, DAZ-associated protein 1, Ribosomal protein S6 kinase alpha-1, Type II inositol 3,4-bisphosphate 4-phosphatase, Zinc finger CCHC domain-containing protein 14, Prefoldin subunit 5, Protein prenyltransferase alpha subunit repeat-containing protein 1, Peroxisomal membrane protein PEX14, Protein FAM134C, Dolichol kinase, Eukaryotic peptide chain release factor subunit 1, Cyclin-H, Phosphorylated CTD-interacting factor 1, Golgi-associated PDZ and coiled-coil motif-containing protein, Protein farnesyltransferase/geranylgeranyltransferase type-1 subunit alpha, SPRY domain-containing protein 3, Platelet-activating factor acetylhydrolase IB subunit alpha, Elongation factor Tu GTP-binding domain-containing protein 1, Protein RMD5 homolog B, Probable E3 ubiquitin-protein ligase HECTD4, KIF1-binding protein, CDNA FLJ25829 fis, clone TST08126, Heat shock protein beta-1, Serpin B12, S1 RNA-binding domain-containing protein 1, Agrin, Abhydrolase domain-containing protein 2, Muskelin, DNA polymerase delta catalytic subunit, Zinc finger protein 419, Angiomotin, Protein Smaug homolog 2, N-acetylgalactosamine-6-sulfatase, Probable C-mannosyltransferase DPY19L3, Src substrate cortactin, Signal peptidase complex catalytic subunit SEC11A, Matrin-3, NFX1- type zinc finger-containing protein 1, UPF0505 protein C16orf62, DNA damage-regulated autophagy modulator protein 2, Semaphorin-4C, Niemann-Pick C1 protein, Transmembrane 9 superfamily member 2, Cyclin-dependent kinase 19, Probable glutamate-tRNA ligase, mitochondrial, Chondroitin sulfate proteoglycan 4, Peroxisomal carnitine O-octanoyltransferase, WD repeat-containing protein 44, Cytochrome c oxidase subunit 1, Regulator of microtubule dynamics protein 1, GPI transamidase component PIG-S, Ubiquitin-protein ligase E3C, Transcription elongation regulator 1, Sorting nexin-9, N-acetylglucosamine-6-sulfatase, Thymosin beta-4, Integral membrane protein GPR155, Intraflagellar transport protein 122 homolog, Calponin-3, Inactive hydroxysteroid dehydrogenase-like protein 1, Calcyclin-binding protein, F-box only protein 31, MORN repeat-containing protein 1, Leukocyte receptor cluster member 8, Serine/threonine-protein kinase NLK, Histone acetyltransferase KAT6B, Protein FAM26F, MORN repeat-containing protein 2, Probable ATP-dependent RNA helicase YTHDC2, Leucine-rich repeat-containing protein 1, Sphingomyelin phosphodiesterase 2, Myosin regulatory light chain 12B, Sorting nexin-6, Peptidyl-prolyl cis-trans isomerase-like 2, Nucleolar GTP-binding protein 2, Serine/threonine-protein kinase MRCK alpha, 2-oxoisovalerate dehydrogenase subunit alpha, mitochondrial, Structural maintenance of chromosomes protein 1A, Ubiquitin-like modifier-activating enzyme 6, SAFB-like transcription modulator, Putative heat shock protein HSP 90-beta 2, Ubiquitin-like protein 3, Kelch repeat and BTB domain-containing protein 6, WD repeat-containing protein 81, DDB1- and CUL4-associated factor 13, T-complex protein 11-like protein 1, Aspartate-tRNA ligase, cytoplasmic, MAP kinase-activated protein kinase 2, Thyroid receptor-interacting protein 11, Clusterin-associated protein 1, Ubiquitin carboxyl-terminal hydrolase 32, Low-density lipoprotein receptor class A domain-containing protein 3, Homeodomain-interacting protein kinase 2, Zinc finger protein 318, E3 ubiquitin-protein ligase BRE1B, O-acetyl-ADP-ribose deacetylase 1, Coiled-coil domain-containing protein 141, Endoribonuclease Dicer, EVI5-like protein, MAP kinase-interacting serine/threonine-protein kinase 2, Nicotinamide phosphoribosyltransferase, Fibronectin type III domain-containing protein 3B, Alpha-catulin, TOX high mobility group box family member 4, Nuclear factor of activated T-cells 5, Elongator complex protein 5, Protein FAM13A, Transcription factor E2F3, Tubulin-specific chaperone cofactor E-like protein, Phospholipid scramblase 4, Complex I intermediate-associated protein 30, mitochondrial, Replication protein A 70 kDa DNA-binding subunit, Adenylyl cyclase-associated protein 1, Protein arginine N-methyltransferase 7, LIM domain kinase 2, NADPH-cytochrome P450 reductase, Peptidyl-prolyl cis-trans isomerase D, Ankyrin repeat and IBR domain-containing protein 1, Small G protein signaling modulator 2, Protein-glutamate O-methyltransferase, Zinc transporter 5, Peptidyl-prolyl cis-trans isomerase FKBP8, Eyes absent homolog 3, Nicotinamide riboside kinase 1, PCNA-interacting partner, Beta-mannosidase, Probable ATP-dependent RNA helicase DDX17, Synergin gamma, Kremen protein 2, Guanine nucleotide exchange factor VAV3, DNA polymerase zeta catalytic subunit, Histone acetyltransferase type B catalytic subunit, Interferon regulatory factor 2-binding protein-like, Protein YIF1B, Ubiquitin carboxyl-terminal hydrolase 8, Group XV phospholipase A2, Probable C-mannosyltransferase DPY19L1, Probable E3 ubiquitin-protein ligase HERC1, Iduronate 2-sulfatase, Type 2 lactosamine alpha-2,3-sialyltransferase, Protein FAM65B, Protein RCC2, DNA ligase 3, FAS-associated factor 1, Geranylgeranyl transferase type-2 subunit alpha, CLIP-associating protein 2, Zinc finger protein 746, G patch domain and KOW motifs-containing protein, Retinoid-inducible serine carboxypeptidase, Kelch-like protein 15, Trafficking protein particle complex subunit 3, Xaa-Pro aminopeptidase 1, PMS1 protein homolog 1, SEC23-interacting protein, Syndetin, CDK5 regulatory subunit-associated protein 3, Endophilin-B1, GON-4-like protein, MHC class I polypeptide-related sequence A, Zinc finger protein with KRAB and SCAN domains 5, Zinc finger CW-type PWWP domain protein 1, Conserved oligomeric Golgi complex subunit 6, Unconventional myosin-Va, N6-adenosine-methyltransferase 70 kDa subunit, Arylamine N-acetyltransferase 1, CD82 antigen, Lathosterol oxidase, Synembryn-B, Mitochondrial enolase superfamily member 1, Serine/threonine-protein kinase N2, Hermansky-Pudlak syndrome 1 protein, Protein 4.1, Lysine-specific demethylase 2A, TP53-regulating kinase, Tubulin beta-4B chain, Integrin alpha-V, Protein disulfide-isomerase A5, Oligoribonuclease, mitochondrial, Protein furry homolog-like, N-alpha-acetyltransferase 16, NatA auxiliary subunit, Trophinin, Vacuolar protein sorting-associated protein 13C, F-box/LRR-repeat protein 14, F-box/LRR-repeat protein 17, Transmembrane protein 218, Protein unc-13 homolog B, RNA-binding protein Raly, Interferon-induced protein with tetratricopeptide repeats 1, Mitochondrial import receptor subunit TOM70, RNA polymerase II-associated factor 1 homolog, Cytokine receptor-like factor 3, Cytosol aminopeptidase, Protein zyg-11 homolog B, N-acetylglucosamine-1-phosphotransferase subunits alpha/beta, Protein transport protein Sec61 subunit alpha isoform 1, Mitogen-activated protein kinase kinase kinase 7, Intraflagellar transport protein 43 homolog, Zinc finger protein 627, Zinc finger protein 614, Zinc finger protein 324B, S100P-binding protein, Early endosome antigen 1, Phospholipid scramblase 1, Sialidase-1, Inhibitor of nuclear factor kappa-B kinase subunit beta, Deoxyribose-phosphate aldolase, Rho-related BTB domain-containing protein 3, Ribosomal protein S6 kinase delta-1, Nucleoporin NDC1, Importin-7, Cyclin-dependent kinase 2-associated protein 1, PAS domain-containing serine/threonine-protein kinase, Vacuolar protein sorting-associated protein 18 homolog, Transmembrane and TPR repeat-containing protein 3, Alpha/beta hydrolase domain-containing protein 17B, Immediate early response gene 5-like protein, Casein kinase II subunit alpha', DNA excision repair protein ERCC-6-like 2, 3'(2'),5'-bisphosphate nucleotidase 1, MAP kinase-activating death domain protein, Dynactin subunit 2, Mucosa-associated lymphoid tissue lymphoma translocation protein 1, Putative deoxyribonuclease TATDN1, Interferon regulatory factor 3, Tubulin polyglutamylase complex subunit 2, Regulator of microtubule dynamics protein 3, Probable histidine-tRNA ligase, mitochondrial, 39S ribosomal protein L52, mitochondrial, Tectonin beta-propeller repeat-containing protein 2, 7SK snRNA methylphosphate capping enzyme, Proline-rich nuclear receptor coactivator 1, Ubiquinone biosynthesis protein COQ9, mitochondrial, Clustered mitochondria protein homolog, Dexamethasone-induced protein, Semaphorin-4F, Fatty acid-binding protein, epidermal, Acylamino-acid-releasing enzyme, Zinc finger MYM-type protein 4, YTH domain-containing family protein 3, A-kinase anchor protein 6, Lambda-crystallin homolog, Telomerase protein component 1, DNA helicase B, Presenilin-1, Zinc finger protein 428, NF-kappa-B-repressing factor, Probable ATP-dependent RNA helicase DHX35, Prolyl 3-hydroxylase OGFOD1, N-alpha-acetyltransferase 20, E3 ubiquitin-protein ligase RNF135, Thrombospondin-3, NADH-ubiquinone oxidoreductase chain 5, 52 kDa repressor of the inhibitor of the protein kinase, Homeodomain-interacting protein kinase 1, Serine/threonine-protein kinase R103, YY1-associated protein 1, Myosin-14, LIM domain and actin-binding protein 1, Zinc finger protein 462, Protein YIPF5, Putative SMEK homolog 3, Charged multivesicular body protein 4b, Microphthalmia-associated transcription factor, Unhealthy ribosome biogenesis protein 2 homolog, Probable 28S rRNA (cytosine-C(5))-methyltransferase, Vesicle-associated membrane protein 7, Leucyl-cystinyl aminopeptidase, Mitogen-activated protein kinase kinase kinase kinase 2, GRAM domain-containing protein 4, Nuclear factor erythroid 2-related factor 1, Uncharacterized protein KIAA2013, Lysophospholipid acyltransferase LPCAT4, Actin-related protein 6, Hepatocyte growth factor-regulated tyrosine kinase substrate, Zinc finger protein 74, Phosphofurin acidic cluster sorting protein 1, PH domain leucine-rich repeat-containing protein phosphatase 2, HMG box-containing protein 1, Aryl hydrocarbon receptor, LIM and SH3 domain protein 1, E3 ubiquitin-protein ligase synoviolin, Vacuolar protein sorting-associated protein 13D, Ubiquitin carboxyl-terminal hydrolase 25, RNA polymerase-associated protein CTR9 homolog, Charged multivesicular body protein 7, RAB6A-GEF complex partner protein 2, UDP-glucose:glycoprotein glucosyltransferase 1, DNA-directed RNA polymerase II subunit RPB9, Nitric oxide synthase, endothelial, Peptidyl-prolyl cis-trans isomerase FKBP3, Ubiquitin carboxyl-terminal hydrolase 15, WASH complex subunit strumpellin, Selenocysteine insertion sequence-binding protein 2-like, Nuclear cap-binding protein subunit 2, Methyltransferase-like protein 22, F-box only protein 9, DmX-like protein 2, Ectonucleotide pyrophosphatase/phosphodiesterase family member 2, Creatine kinase B-type, Protein FAM91A1, Paired box protein Pax-3, Integrin beta-3, Protein SEC13 homolog, Histone-lysine N-methyltransferase SETDB2, Scm-like with four MBT domains protein 1, Forkhead box protein M1, Protein kinase C and casein kinase substrate in neurons protein 2, Clathrin interactor 1, Protein FAM189B, Nuclear receptor-interacting protein 1, Centriole, cilia and spindle-associated protein, Ubiquitin carboxyl-terminal hydrolase 38, Recombining binding protein suppressor of hairless, Holliday junction recognition protein, Integrin alpha-5, Immunoglobulin superfamily member 8, Signal-induced proliferation-associated 1-like protein 1, Eukaryotic translation initiation factor 2A, Mitochondrial import inner membrane translocase subunit Tim17-A, Protein strawberry notch homolog 1, Splicing factor 3B subunit 6, Glutamine-tRNA ligase, BRCA2-interacting transcriptional repressor EMSY, E3 SUMO-protein ligase NSE2, Retinal dehydrogenase 1, Alpha-N-acetylglucosaminidase, E3 SUMO-protein ligase RanBP2, Endoplasmic reticulum metallopeptidase 1, Leucine-rich repeat flightless-interacting protein 1, Uncharacterized protein C15orf41, High affinity cAMP-specific and IBMX-insensitive 3',5'-cyclic phosphodiesterase 8A, Sodium/potassium-transporting ATPase subunit alpha-2, Neuroplastin, Leukotriene A-4 hydrolase, DNA-directed RNA polymerases I and III subunit RPAC1, Mitotic spindle assembly checkpoint protein MAD2A, Exosome complex component RRP4, SET domain-containing protein 4, Transmembrane protein 70, mitochondrial, Mitotic spindle assembly checkpoint protein MAD1, Akirin-2, BCL2/adenovirus E1B 19 kDa protein-interacting protein 2, U3 small nucleolar RNA-associated protein 15 homolog, Fascin, Proteasome subunit alpha type-7, 14-3-3 protein epsilon, Spindlin-3, LETM1 and EF-hand domain-containing protein 1, mitochondrial, Nucleolar protein 14, Ubiquitin-conjugating enzyme E2 Z, Elongator complex protein 1, DNA repair protein XRCC4, Importin-5, Splicing factor 1, Phosphatidylinositol 4-phosphate 3-kinase C2 domain-containing subunit beta, Acetyl-coenzyme A transporter 1, Zinc finger protein 275, E3 ubiquitin-protein ligase HACE1, AT-rich interactive domain-containing protein 2, Tetraspanin-33, Peroxisome assembly factor 2, Oral-facial-digital syndrome 1 protein, Nuclear factor of activated T-cells, cytoplasmic 1, TBC1 domain family member 8, Protein MEF2BNB, Complex I assembly factor TMEM126B, mitochondrial, DNA polymerase delta subunit 3, Gamma-secretase subunit APH-1A, Bcl-2-modifying factor, Epididymis-specific alpha-mannosidase, Ras association domain-containing protein 3, Uncharacterized protein C15orf61, Spindlin-1, Cholinesterase, Acetyl-CoA carboxylase 1, Transmembrane protein 87A, Lysyl oxidase homolog 3, SWI/SNF-related matrix-associated actin-dependent regulator of chromatin subfamily E member 1-related, Prostamide/prostaglandin F synthase, E3 ubiquitin-protein ligase TRIM4, MAGUK p55 subfamily member 2, Far upstream element-binding protein 1, Dimethylaniline monooxygenase [N-oxide-forming] 4, Dihydropyrimidine dehydrogenase [NADP(+)], Spermatogenesis-associated protein 20, AN1-type zinc finger protein 6, YTH domain-containing family protein 1, SUN domain-containing protein 2, 45 kDa calcium-binding protein, Integrator complex subunit 6, Protein Lines homolog 1, Proline-rich protein 7, Zinc finger MIZ domain-containing protein 2, RNA-binding protein 5, Serine/arginine-rich splicing factor 10, Tetraspanin-4, Ribosomal RNA small subunit methyltransferase NEP1, Presenilin-2, Prolyl 3-hydroxylase 2, Mitogen-activated protein kinase kinase kinase 1, Coiled-coil domain-containing protein 121, Osteoclast-stimulating factor 1, 39S ribosomal protein L35, mitochondrial, UDP-N-acetylhexosamine pyrophosphorylase-like protein 1, RNA-binding protein 39, Thioredoxin-like protein AAED1, Eukaryotic translation initiation factor 3 subunit K, Protein timeless homolog, Zinc finger and BTB domain-containing protein 6, ATP-binding cassette sub-family A member 3, Vinculin, Microtubule-associated protein 1A, C-Jun-amino-terminal kinase-interacting protein 2, Plakophilin-2, 39S ribosomal protein L34, mitochondrial, Ras-related protein Rab-27A, Serine/threonine-protein kinase tousled-like 1, Protein S100-A4, Centriolin, Transcriptional repressor CTCF, Golgin subfamily A member 3, Death-inducer obliterator 1, Glycogen debranching enzyme, Transmembrane protein 181, A-kinase anchor protein 9, E3 ubiquitin-protein ligase MYLIP, Guanine nucleotide-binding protein G(i) subunit alpha-2, Peptidyl-prolyl cis-trans isomerase FKBP4, Metaxin-1, Uncharacterized protein KIAA1143, Disabled homolog 2, Serine/threonine-protein kinase tousled-like 2, Squamous cell carcinoma antigen recognized by T-cells 3, Natural resistance-associated macrophage protein 2, S-adenosyl-L-methionine-dependent tRNA 4-demethylwyosine synthase, Puromycin-sensitive aminopeptidase, Protocadherin gamma-A11, Eukaryotic peptide chain release factor GTP-binding subunit ERF3A, Protocadherin Fat 1, H(+)/Cl(−) exchange transporter 7, Zinc finger protein 407, Desmoplakin, Kelch-like protein 7, H(+)/Cl(−) exchange transporter 3, Protein phosphatase 1 regulatory subunit 3C, Interleukin-17 receptor C, Solute carrier family 22 member 18, Sodium/potassium-transporting ATPase subunit beta-1, ATP-binding cassette sub-family B member 8, mitochondrial, Sorbin and SH3 domain-containing protein 2, Histidine-tRNA ligase, cytoplasmic, Probable cation-transporting ATPase 13A2, Unconventional myosin-Ib, MAP/microtubule affinity-regulating kinase 3, NADH dehydrogenase [ubiquinone] flavoprotein 2, mitochondrial, Ceramide synthase 5, Transcription intermediary factor 1-beta, Arginine-tRNA ligase, cytoplasmic, Neurosecretory protein VGF, U8 snoRNA-decapping enzyme, Epididymal secretory protein E1, Phenylalanine-tRNA ligase alpha subunit, Zinc finger protein 536, Vascular endothelial growth factor A, Decapping and exoribonuclease protein, Glia-derived nexin, PITH domain-containing protein 1, Gamma-aminobutyric acid receptor subunit beta-3, Lysine-specific demethylase 3B, Protein diaphanous homolog 2, Nuclear protein localization protein 4 homolog, Aldehyde dehydrogenase family 1 member A3, Ubiquitin-like protein 5, Zinc finger BED domain-containing protein 5, Rho GTPase-activating protein 5, Tyrosine-protein phosphatase non-receptor type 1, ATP-dependent RNA helicase DDX18, Structural maintenance of chromosomes protein 2, Dihydropyrimidinase-related protein 1, Mitochondrial import receptor subunit TOM20 homolog, ADP-ribosylation factor 3, WD repeat-containing protein 26, Mitogen-activated protein kinase kinase kinase 3, Zinc finger protein 579, Uridine phosphorylase 1, MORF4 family-associated protein 1, Exocyst complex component 1, Keratin, type I cytoskeletal 10, Rho GTPase-activating protein 18, Mitotic checkpoint serine/threonine-protein kinase BUB1, Transmembrane protein 131, Ceramide synthase 6, MICOS complex subunit MIC25, E3 ubiquitin-protein ligase RNF114, JNK1/MAPK8-associated membrane protein, Coiled-coil domain-containing protein 14, Brefeldin A-inhibited guanine nucleotide-exchange protein 2, Exosome complex component MTR3, PR domain zinc finger protein 4, Protein CutA, Trafficking protein particle complex subunit 2-like protein, TGF-beta-activated kinase 1 and MAP3K7-binding protein 1, Cyclin-dependent kinase 2-associated protein 2, Wings apart-like protein homolog, Pre-mRNA-splicing factor ATP-dependent RNA helicase PRP16, Two pore calcium channel protein 1, DNA/RNA-binding protein KIN17, Ribonucleoprotein PTB-binding 1, Sterol regulatory element-binding protein 1, NADH dehydrogenase [ubiquinone] 1 alpha subcomplex assembly factor 4, Proline-rich nuclear receptor coactivator 2, Zinc finger protein 526, Protein Wiz, PHD finger protein 23, Carboxymethylenebutenolidase homolog, Protein phosphatase 1 regulatory subunit 15B, Putative PIP5K1A and PSMD4-like protein, Acyl-protein thioesterase 1, Alpha-1,2-mannosyltransferase ALG9, Ankyrin repeat domain-containing protein 10, Vesicle transport protein SEC20, Triple functional domain protein, Inositol hexakisphosphate and diphosphoinositol-pentakisphosphate kinase 1, Probable ATP-dependent RNA helicase DDX10, Zinc finger protein 292, Leucine-rich repeat and calponin homology domain-containing protein 3, Calcium-binding protein 39, Small integral membrane protein 15, Protein phosphatase 1A, ATP-dependent RNA helicase DHX29, Structural maintenance of chromosomes protein 6, Caldesmon, REST corepressor 1, Calmodulin-like protein 4, F-box/WD repeat-containing protein 5, Zinc finger RNA-binding protein, L-aminoadipate-semialdehyde dehydrogenase-phosphopantetheinyl transferase, Hom s 5, Harmonin, tRNA selenocysteine 1-associated protein 1, Vacuolar protein sorting-associated protein 35, Argininosuccinate synthase, RNA-binding protein 3, 40S ribosomal protein S6, Myosin-11, Carbonic anhydrase 12, Myosin-10, Carboxy-terminal domain RNA polymerase II polypeptide A small phosphatase 2, Electrogenic sodium bicarbonate cotransporter 1, Epidermal growth factor receptor, 39S ribosomal protein L49, mitochondrial, ELKS/Rab6-interacting/CAST family member 1, Statherin, ATP-dependent RNA helicase DDX1, 6-phosphofructo-2-kinase/fructose-2,6-bisphosphatase 3, Formin-like protein 3, Elongator complex protein 2, Prostaglandin G/H synthase 1, ATP-dependent DNA helicase Q5, Nucleolar protein 10, Thioredoxin-like protein 1, ETS translocation variant 3, Actin, alpha skeletal muscle, KAT8 regulatory NSL complex subunit 3, Neutral and basic amino acid transport protein rBAT, Myotubularin-related protein 2, Glutathione S-transferase Mu 4, ADP-ribosylation factor-like protein 2-binding protein, A-kinase-interacting protein 1, Sorting nexin-7, Serine-protein kinase ATM, Poly [ADP-ribose] polymerase, Piezo-type mechanosensitive ion channel component 1, Multidrug resistance-associated protein 1, Glutathione-specific gamma-glutamylcyclotransferase 1, Macrophage metalloelastase, SURP and G-patch domain-containing protein 1, Factor VIII intron 22 protein, Sacsin, Epithelial discoidin domain-containing receptor 1, Pseudouridylate synthase 7 homolog-like protein, La-related protein 1, Adenylate kinase 2, mitochondrial, ATR-interacting protein, Transmembrane protein 41B, Protein SZT2, Transient receptor potential cation channel subfamily V member 2, Phosphatidylcholine translocator ABCB4, Ras GTPase-activating-like protein IQGAP2, F-box DNA helicase 1, Fas apoptotic inhibitory molecule 1, Interferon regulatory factor 2-binding protein 2, Inactive serine/threonine-protein kinase VRK3, Complement C1q tumor necrosis factor-related protein 3, Coiled-coil domain-containing protein 106, LIM and senescent cell antigen-like-containing domain protein 1, Fibrinogen alpha chain, Cytospin-B, DNA-directed RNA polymerase III subunit RPC7, Regulator of nonsense transcripts 1, Keratin, type II cytoskeletal 2 epidermal, Gem-associated protein 4, Histone-lysine N-methyltransferase ASH1 L, MORC family CW-type zinc finger protein 4, C-terminal-binding protein 2, Basic salivary proline-rich protein 2, Salivary acidic proline-rich phosphoprotein 1/2, Histone chaperone ASF1A, Beclin-1, Putative methyltransferase-like protein 15P1, Putative peripheral benzodiazepine receptor-related protein, Protein FAM216A, AP-2 complex subunit beta, PHD and RING finger domain-containing protein 1, E3 ubiquitin-protein ligase TRAF7, Voltage-dependent anion-selective channel protein 3, F-box/WD repeat-containing protein 11, Protein O-GlcNAcase, Tubulin-folding cofactor B, Activating signal cointegrator 1 complex subunit 1, Polypyrimidine tract-binding protein 2, Mitochondrial genome maintenance exonuclease 1, NEDD4-binding protein 2-like 1, Zinc finger and BTB domain-containing protein 38, Protein sel-1 homolog 3, Repressor of RNA polymerase III transcription MAF1 homolog, Versican core protein, Histone-lysine N-methyltransferase 2E, Endothelial PAS domain-containing protein 1, Histone-lysine N-methyltransferase NSD2, Amyloid-like protein 2, Transcription initiation factor TFIID subunit 4, Cysteine and histidine-rich protein 1, Formin-like protein 2, KRR1 small subunit processome component homolog, V-type proton ATPase 116 kDa subunit a isoform 3, Dymeclin, Histone deacetylase 4, Solute carrier family 2, facilitated glucose transporter member 1, Tripeptidyl-peptidase 2, Probable UDP-sugar transporter protein SLC35A5, Probable ATP-dependent RNA helicase DDX60-like, Cystatin-A, Splicing factor U2AF 65 kDa subunit, Membrane-bound transcription factor site-1 protease, UBX domain-containing protein 4, Kinesin-like protein KIF11, FAST kinase domain-containing protein 2, LEM domain-containing protein 2, Galectin-3, Solute carrier family 12 member 6, BCL2/adenovirus E1B 19 kDa protein-interacting protein 3, Serine/threonine-protein phosphatase 2A 56 kDa regulatory subunit gamma isoform, Bardet-Biedl syndrome 4 protein, Progestin and adipoQ receptor family member 4, 40S ribosomal protein S23, Peroxisomal membrane protein PMP34, Polycystic kidney disease and receptor for egg jelly-related protein, Protein Red, Protein KHNYN, 40S ribosomal protein S15, Putative methyltransferase NSUN6, Sin3 histone deacetylase corepressor complex component SDS3, Protein S100-A10, Melanoma-associated antigen D4, Calcium/calmodulin-dependent protein kinase type IV, E3 ubiquitin-protein ligase RNF19B, Girdin, Testin, SWI/SNF-related matrix-associated actin-dependent regulator of chromatin subfamily B member 1, Calcium uptake protein 2, mitochondrial, Tetratricopeptide repeat protein 25, Inhibitor of growth protein 5, Son of sevenless homolog 2, Trans-Golgi network integral membrane protein 2, Insulin-like growth factor 2 mRNA-binding protein 3, Transcription factor SOX-8, Serine/threonine-protein kinase DCLK2, Golgin subfamily A member 5, TBC1 domain family member 13, HLA class II histocompatibility antigen, DR beta 5 chain, E3 SUMO-protein ligase CBX4, PWWP domain-containing protein MUM1, Interferon-induced transmembrane protein 2, DNA polymerase kappa, Methionine synthase, SWI/SNF-related matrix-associated actin-dependent regulator of chromatin subfamily A containing DEAD/H box 1, Translocation protein SEC63 homolog, Chromodomain Y-like protein, Procollagen-lysine,2-oxoglutarate 5-dioxygenase 2, F-box only protein 28, Tripartite motif-containing protein 34, Tubulin-tyrosine ligase, DNA topoisomerase 3-beta-1, Hermansky-Pudlak syndrome 3 protein, G/T mismatch-specific thymine DNA glycosylase, Transducin beta-like protein 3, Negative regulator of reactive oxygen species, BAG family molecular chaperone regulator 2, Ganglioside GM2 activator, RNA-binding protein 12B, Beta-galactoside alpha-2,6-sialyltransferase 1, Dynactin subunit 5, N-terminal Xaa-Pro-Lys N-methyltransferase 1, Ran-binding protein 9, E3 ubiquitin-protein ligase RNF216, SET domain-containing protein 5, F-box/WD repeat-containing protein 7, TRIO and F-actin-binding protein, Pleckstrin homology domain-containing family A member 2, Beta-actin-like protein 2, Stimulator of interferon genes protein, Putative V-set and immunoglobulin domain-containing-like protein IGHV4OR15-8, Ig kappa chain V-I region HK102, Arachidonate 5-lipoxygenase, U2 snRNP-associated SURP motif-containing protein, HLA class I histocompatibility antigen, A-3 alpha chain, Nuclear pore complex protein Nup50, Trinucleotide repeat-containing gene 6B protein, Four and a half LIM domains protein 2, Protein disulfide-isomerase, Radial spoke head protein 3 homolog, Collagen alpha-3(VI) chain, Synaptobrevin homolog YKT6, Myotubularin-related protein 6, Polypeptide N-acetylgalactosaminyltransferase 2, Cytochrome c oxidase subunit 5B, mitochondrial, Dol-P-Man:Man(7)GlcNAc(2)-PP-Dol alpha-1,6-mannosyltransferase, Serglycin, UDP-glucuronic acid decarboxylase 1, Integrin beta-2, Forkhead-associated domain-containing protein 1, Zinc finger protein 36, C3H1 type-like 2, Chloride intracellular channel protein 6, Rab3 GTPase-activating protein non-catalytic subunit, Guanylate-binding protein 4, Cell division control protein 42 homolog, 40S ribosomal protein S27-like, Septin-9, Macrosialin, Serine/threonine-protein kinase RIO1, Transcription elongation factor A protein 1, Transmembrane protein 14A, Protein nepro homolog, Torsin-4A, Protein CEBPZOS, HLA class I histocompatibility antigen, B-57 alpha chain, Ras-related protein M-Ras, DNA polymerase delta subunit 2, Zinc finger protein 343, ADP-ribosylation factor 6, Discoidin, CUB and LCCL domain-containing protein 2, Deoxyhypusine synthase, Lysophospholipid acyltransferase 5, Nuclear cap-binding protein subunit 1, 40S ribosomal protein S27, Serpin H1, Tetratricopeptide repeat protein 30A, A-kinase anchor protein 8-like, Actin-related protein 3, Inositol-tetrakisphosphate 1-kinase, STE20-related kinase adapter protein alpha, Grancalcin, Transcriptional repressor p66-beta, Cytochrome b-245 heavy chain, Lanosterol synthase, Protein phosphatase 1 regulatory subunit 12A, Protein FAM168A, HLA class II histocompatibility antigen, DRB1-16 beta chain, Rotatin, Histone H2A type 1-B/E, SH3 domain-binding glutamic acid-rich-like protein, WD repeat domain phosphoinositide-interacting protein 3, Lysine-specific demethylase 6B, Poly [ADP-ribose] polymerase 8, Intraflagellar transport protein 25 homolog, Histone-lysine N-methyltransferase setd3, Rho guanine nucleotide exchange factor 12, Cell division cycle protein 16 homolog, ATP-dependent zinc metalloprotease YME1L1, Ubiquitin thioesterase OTUB1, Homeobox-containing protein 1, Protein FAM162A, Group XIIB secretory phospholipase A2-like protein, SH3 domain-binding protein 2, 14-3-3 protein eta, CTTNBP2 N-terminal-like protein, Claspin, ADP-ribosylation factor 4, Geranylgeranyl transferase type-1 subunit beta, Galectin-2, CAAX prenyl protease 1 homolog, Phospholipase D1, DNA-directed RNA polymerase III subunit RPC4, Serine/threonine-protein kinase MARK2, FGFR1 oncogene partner 2, 4F2 cell-surface antigen heavy chain, Bromodomain-containing protein 8, Mitochondrial coenzyme A transporter SLC25A42, Terminal uridylyltransferase 7, Hyccin, Serine/threonine-protein phosphatase 2B catalytic subunit beta isoform, Transcription factor SOX-9, F-box/LRR-repeat protein 6, Adiponectin receptor protein 1, Ribosomal protein S6 kinase beta-1, Zinc finger protein 655, Probable aminopeptidase NPEPL1, Dolichyl-diphosphooligosaccharide-protein glycosyltransferase subunit 1, Nuclear transcription factor Y subunit gamma, COUP transcription factor 2, Chromodomain-helicase-DNA-binding protein 1, Glycogen phosphorylase, brain form, Disintegrin and metalloproteinase domain-containing protein 23, Insulin-like growth factor I, Sentrin-specific protease 2, Actin, alpha cardiac muscle 1, Apoptosis-inducing factor 1, mitochondrial, Denticleless protein homolog, Sarcoplasmic/endoplasmic reticulum calcium ATPase 2, Chromodomain-helicase-DNA-binding protein 3, Histone-lysine N-methyltransferase EHMT1, Mediator of RNA polymerase II transcription subunit 6, Chromatin complexes subunit BAP18, Anaphase-promoting complex subunit 16, Exocyst complex component 6, Dehydrodolichyl diphosphate syntase complex subunit NUS1, Tetratricopeptide repeat protein 27, DNA-directed RNA polymerase II subunit RPB11-b2, Tensin-1, Keratin, type I cytoskeletal 19, UPF0568 protein C14orfi 66, Disheveled-associated activator of morphogenesis 1, Thiopurine S-methyltransferase, Tuftelin, Autophagy-related protein 9A, Serine/threonine-protein phosphatase 6 regulatory ankyrin repeat subunit C, Leucine-rich repeat-containing protein 41, Transmembrane protein 50A, snRNA-activating protein complex subunit 4, Galectin-8, WAS/WASL-interacting protein family member 1, ATP synthase F(0) complex subunit C2, mitochondrial, MIT domain-containing protein 1, 28S ribosomal protein S24, mitochondrial, Glycine-tRNA ligase, Ubiquitin-protein ligase E3A, Bifunctional polynucleotide phosphatase/kinase, Serine/threonine-protein kinase PLK2, Ubiquitin carboxyl-terminal hydrolase 16, Cholesteryl ester transfer protein, Rho GDP-dissociation inhibitor 1, F-box/LRR-repeat protein 19, Interleukin-12 subunit alpha, Tumor necrosis factor receptor superfamily member 19, 2'-deoxynucleoside 5'-phosphate N-hydrolase 1, Protein phosphatase 1 regulatory subunit 15A, Transmembrane protein 140, DNA damage-inducible transcript 4 protein, Tetratricopeptide repeat protein 28, Beta-2-syntrophin, Jouberin, Ribose-phosphate pyrophosphokinase 1, Inactive tyrosine-protein kinase 7, Protein LYRIC, HLA class I histocompatibility antigen, alpha chain G, Transcriptional adapter 2-alpha, Myeloid cell nuclear differentiation antigen, Integrin beta-1, Solute carrier family 25 member 43, UDP-N-acetylglucosamine transporter, Zinc finger protein 573, Ubiquitin-conjugating enzyme E2 E1, All-trans-retinol 13,14-reductase, Laminin subunit gamma-1, Bromodomain and WD repeat-containing protein 1, ATP-dependent RNA helicase DDX51, Cytosolic purine 5'-nucleotidase, Sterol regulatory element-binding protein cleavage-activating protein, Tankyrase-1, Zinc finger protein 609, M-phase inducer phosphatase 2, Uncharacterized protein C8orf59, Intraflagellar transport protein 27 homolog, RNA-binding motif, single-stranded-interacting protein 2, S-phase kinase-associated protein 1, Mitochondrial fission process protein 1, Protein SHQ1 homolog, Carboxypeptidase Q, Serine/threonine-protein kinase 10, Cardiolipin synthase (CMP-forming), Splicing regulatory glutamine/lysine-rich protein 1, ATP-binding cassette sub-family A member 7, AT-rich interactive domain-containing protein 1B, Sodium/potassium-transporting ATPase subunit beta-3, RING finger protein 214, UDP-glucuronosyltransferase 1-10, Developmentally-regulated GTP-binding protein 2, Transcription factor Maf, Serine/threonine-protein kinase 35, GRIP and coiled-coil domain-containing protein 2, Transcription factor IIIB 90 kDa subunit, TAF6-like RNA polymerase II p300/CBP-associated factor-associated factor 65 kDa subunit 6L, Serine/threonine-protein phosphatase 6 regulatory ankyrin repeat subunit B, Ankyrin repeat domain-containing protein 27, Zinc finger protein 148, Glutamate-rich WD repeat-containing protein 1, TBC domain-containing protein kinase-like protein, Enhancer of mRNA-decapping protein 4, Quinone oxidoreductase-like protein 1, Transcription initiation factor TFIID subunit 2, Beta-hexosaminidase subunit beta, Transmembrane protein 234, 28S ribosomal protein S29, mitochondrial, CAS1 domain-containing protein 1, Ubiquitin carboxyl-terminal hydrolase 4, Biogenesis of lysosome-related organelles complex 1 subunit 3, Ankyrin repeat domain-containing protein 11, Zinc fingers and homeoboxes protein 2, Hepatoma-derived growth factor, Cancer/testis antigen 2, Histone deacetylase 6, Conserved oligomeric Golgi complex subunit 7, Striatin-4, Tricarboxylate transport protein, mitochondrial, General transcription factor IIF subunit 2, RNA demethylase ALKBH5, Phosphatidylinositide phosphatase SAC2, tRNA-splicing endonuclease subunit Sen34, WAS/WASL-interacting protein family member 2, Protocadherin gamma-C3, Round spermatid basic protein 1-like protein, Alpha-mannosidase 2C1, Transcription factor p65, Serine protease 23, Splicing factor, arginine/serine-rich 15, Neuropathy target esterase, Tubulin epsilon chain, MICOS complex subunit MIC13, Endonuclease domain-containing 1 protein, Sodium-dependent phosphate transport protein 4, Deubiquitinating protein VCIP135, Kinase D-interacting substrate of 220 kDa, Multivesicular body subunit 12A, Heterogeneous nuclear ribonucleoprotein D-like, Gamma-adducin, Nucleotide exchange factor SIL1, Protein FAM76B, Nuclear mitotic apparatus protein 1, Isoaspartyl peptidase/L-asparaginase, Chromobox protein homolog 2, Cilia- and flagella-associated protein 97, Heme-binding protein 1, SCY1-like protein 2, E3 ubiquitin-protein ligase RNF123, Transcription termination factor 1, COP9 signalosome complex subunit 4, UDP-N-acetylglucosamine-peptide N-acetylglucosaminyltransferase 110 kDa subunit, Conserved oligomeric Golgi complex subunit 2, Rho-associated protein kinase 2, Uncharacterized protein Clorf43, Protein FAM179B, Cyclic AMP-responsive element-binding protein 1, Endothelin-converting enzyme 1, Torsin-1A-interacting protein 1, ATP-binding cassette sub-family E member 1, 5'-3' exoribonuclease 1, MAX gene-associated protein, Protein MAK16 homolog, Arf-GAP with Rho-GAP domain, ANK repeat and PH domain-containing protein 3, Lysine-specific demethylase 5B, Signal recognition particle 9 kDa protein, DnaJ homolog subfamily C member 16, CSC1-like protein 1, 39S ribosomal protein L38, mitochondrial, Golgin subfamily A member 2, N-alpha-acetyltransferase 25, NatB auxiliary subunit, ADP-ribosylation factor-like protein 2, Protein Asterix, Dapper homolog 1, Transmembrane protein 64, Transcription factor EB, Magnesium transporter NIPA2, DnaJ homolog subfamily C member 8, Membrane-bound transcription factor site-2 protease, Coiled-coil domain-containing protein 134, Kynurenine 3-monooxygenase, Peptidyl-prolyl cis-trans isomerase F, mitochondrial, GH3 domain-containing protein, AF4/FMR2 family member 1, Trafficking protein particle complex subunit 9, Calcineurin B homologous protein 1, Poly(ADP-ribose) glycohydrolase ARH3, TERF1-interacting nuclear factor 2, Prefoldin subunit 2, Pumilio homolog 1, Arf-GAP with SH3 domain, ANK repeat and PH domain-containing protein 2, Protein CMSS1, Beta-lactamase-like protein 2, ERO1-like protein alpha, Protein SLX41P, Vacuolar protein sorting-associated protein 8 homolog, RING finger protein 145, Type II inositol 1,4,5-trisphosphate 5-phosphatase, Transmembrane anterior posterior transformation protein 1 homolog, Glutamyl-tRNA(Gln) amidotransferase subunit A, mitochondrial, G1/S-specific cyclin-D2, Transcription termination factor 1, mitochondrial, Sterol 26-hydroxylase, mitochondrial, Alpha/beta hydrolase domain-containing protein 17C, PHD finger protein 10, SNF-related serine/threonine-protein kinase, Transcription initiation factor TFIID subunit 1-like, Shootin-1, Glucocorticoid receptor, Histone H2A deubiquitinase MYSM1, CD9 antigen, Calcium signal-modulating cyclophilin ligand, NADH dehydrogenase [ubiquinone] 1 beta subcomplex subunit 6, Tyrosyl-DNA phosphodiesterase 2, 60 kDa SS-A/Ro ribonucleoprotein, Insulin-degrading enzyme, Cytosolic 5'-nucleotidase 3A, Mediator of RNA polymerase II transcription subunit 26, Ribosomal protein S6 kinase alpha-3, DNA polymerase eta, Glycylpeptide N-tetradecanoyltransferase 1, DNA-directed RNA polymerases I, II, and Ill subunit RPABC1, Volume-regulated anion channel subunit LRRC8D, Peptide-N(4)-(N-acetyl-beta-glucosaminyl)asparagine amidase, GA-binding protein subunit beta-1, Inverted formin-2, Oxysterol-binding protein, Phospholipid hydroperoxide glutathione peroxidase, mitochondrial, Chromatin assembly factor 1 subunit B, Putative heat shock protein HSP 90-alpha A5, Phosphatidylinositol 4,5-bisphosphate 3-kinase catalytic subunit gamma isoform, Rho GTPase-activating protein 4, WD repeat-containing protein 47, Probable ubiquitin carboxyl-terminal hydrolase FAF-X, Endoplasmic reticulum aminopeptidase 1, HEAT repeat-containing protein 1, cAMP-specific 3',5'-cyclic phosphodiesterase 4B, Serine/threonine-protein kinase 11-interacting protein, Atlastin-3, Glycerol-3-phosphate acyltransferase 4, Bifunctional coenzyme A synthase, Arginyl aminopeptidase-like 1, Acidic leucine-rich nuclear phosphoprotein 32 family member A, Mannosyl-oligosaccharide glucosidase, rRNA methyltransferase 1, mitochondrial, tRNA-splicing endonuclease subunit Sen15, Ecto-NOX disulfide-thiol exchanger 1, Zinc finger protein 662, Glutamine-fructose-6-phosphate aminotransferase [isomerizing] 2, Transcription intermediary factor 1-alpha, Nicotinate phosphoribosyltransferase, 5-aminolevulinate synthase, nonspecific, mitochondrial, Actin-binding protein anillin, Putative deoxyribonuclease TATDN3, WD repeat-containing protein 61, Protein SCAF8, MKL/myocardin-like protein 2, TRPM8 channel-associated factor 2, Rapamycin-insensitive companion of mTOR, Nuclear receptor subfamily 2 group C member 2, Lysophospholipid acyltransferase 7, Complex I assembly factor TIMMDC1, mitochondrial, KATNB1-like protein 1, Putative ATP-dependent RNA helicase DHX30, RNA-binding protein 12, Transmembrane protein 214, PHD finger protein 3, COP9 signalosome complex subunit 5, Neutral amino acid transporter A, AP-5 complex subunit beta-1, PX domain-containing protein kinase-like protein, Putative inactive carbonic anhydrase 5B-like protein, Small integral membrane protein 4, DNA cross-link repair 1A protein, Mothers against decapentaplegic homolog 2, TIP41-like protein, Retinol dehydrogenase 10, Hippocampus abundant transcript-like protein 1, N-acetyltransferase 9, MOB kinase activator 3A, Transcriptional repressor protein YY1, Kelch-like protein 6, Squalene synthase, N-alpha-acetyltransferase 38, NatC auxiliary subunit, Dedicator of cytokinesis protein 2, E3 ubiquitin-protein ligase TRIM11, tRNA-specific adenosine deaminase 1, Transmembrane protein 248, E3 ubiquitin-protein ligase RNF167, Uncharacterized protein C20orf196, Polycomb protein EED, Exosome complex component RRP46, Kelch-like protein 11, POTE ankyrin domain family member I, Activity-dependent neuroprotector homeobox protein, DNA-binding protein inhibitor ID-4, Secernin-2, ETS-related transcription factor Elf-1, TCDD-inducible poly [ADP-ribose] polymerase, Proliferation-associated protein 2G4, NudC domain-containing protein 1, ATPase family AAA domain-containing protein 2B, Zinc fingers and homeoboxes protein 3, Methylmalonyl-CoA mutase, mitochondrial, Protein RRNAD1, Phospholipase A-2-activating protein, Glycerol-3-phosphate acyltransferase 3, Protein FAM122B, Uncharacterized protein KIAA1109, Phenylalanine-tRNA ligase, mitochondrial, Serine/threonine-protein phosphatase 2B catalytic subunit alpha isoform, Thioredoxin domain-containing protein 11, Bladder cancer-associated protein, Membrane cofactor protein, Nuclear factor of activated T-cells, cytoplasmic 2, Smith-Magenis syndrome chromosomal region candidate gene 8 protein, Krueppel-like factor 3, CDK5 and ABL1 enzyme substrate 1, 40S ribosomal protein S14, Phosphatidylinositol 4-phosphate 5-kinase type-1 beta, Cyclin-dependent kinase 16, SAP domain-containing ribonucleoprotein, Protein NDRG1, WAS protein family homolog 1, Interferon regulatory factor 4, DNA-directed DNA/RNA polymerase mu, Actin-like protein 6A, Dedicator of cytokinesis protein 4, Protein furry homolog, Telomere-associated protein RIF1, Ras association domain-containing protein 1, Cytochrome P450 2J2, Protein scribble homolog, Proheparin-binding EGF-like growth factor, Cytosolic acyl coenzyme A thioester hydrolase, Cohesin subunit SA-1, Myomegalin, Twinfilin-1, Stromal interaction molecule 1, Probable U3 small nucleolar RNA-associated protein 11, Centromere-associated protein E, Zinc finger C3H1 domain-containing protein, EF-hand domain-containing protein D1, Keratin, type II cytoskeletal 8, Retrotransposon-derived protein PEG10, Cyclin-dependent kinase 2, UBX domain-containing protein 11, Pecanex-like protein 3, Rho guanine nucleotide exchange factor 3, ADP-ribosylation factor-like protein 4C, Ribosome biogenesis protein BOP1, KDEL motif-containing protein 2, Structural maintenance of chromosomes protein 5, La-related protein 4B, Acid ceramidase, Proteasome assembly chaperone 1, Radixin, Retinoblastoma-binding protein 5, Forkhead box protein N2, rRNA-processing protein UTP23 homolog, Src kinase-associated phosphoprotein 2, Volume-regulated anion channel subunit LRRC8C, Acyl-CoA dehydrogenase family member 9, mitochondrial, Beta-synuclein, Short coiled-coil protein, Collagen alpha-2(VI) chain, Ubinuclein-2, Plasmalemma vesicle-associated protein, Mitofusin-2, Small integral membrane protein 20, Stromal interaction molecule 2, Threonylcarbamoyladenosine tRNA methylthiotransferase, Alpha-soluble NSF attachment protein, Putative E3 ubiquitin-protein ligase UBR7, BRCA1-associated ATM activator 1, Group XIIA secretory phospholipase A2, Transcription factor 20, Potassium channel subfamily K member 4, Casein kinase I isoform alpha, Bombesin receptor-activated protein C6orf89, Peripheral plasma membrane protein CASK, Proline-rich protein PRCC, Serine/threonine-protein kinase SIK2, Host cell factor 1, Transducin-like enhancer protein 4, Biogenesis of lysosome-related organelles complex 1 subunit 6, Queuine tRNA-ribosyltransferase subunit QTRTD1, RNA-binding protein 33, Leucine-rich repeat-containing protein 59, Transcription factor Sp3, Eukaryotic initiation factor 4A-III, E3 ubiquitin-protein ligase RNF181, Mediator of RNA polymerase II transcription subunit 7, Transcription elongation factor SPT4, Homeobox protein TGIF2, Carnitine O-palmitoyltransferase 1, liver isoform, cGMP-inhibited 3',5'-cyclic phosphodiesterase B, Polymerase delta-interacting protein 3, Runt-related transcription factor 2, THUMP domain-containing protein 3, Serpin B6, Interleukin-32, Sodium-coupled neutral amino acid transporter 1, Nucleoside diphosphate kinase A, Cytochrome b, Putative uncharacterized protein ZNF436-AS1, Beta-1-syntrophin, Mitotic-spindle organizing protein 2A, Calcium/calmodulin-dependent protein kinase II inhibitor 1, Necdin, FERM domain-containing protein 8, Serine/threonine-protein phosphatase 2A catalytic subunit beta isoform, Transcription factor 4, SHC-transforming protein 4, Dedicator of cytokinesis protein 8, Ankyrin repeat domain-containing protein 54, Transcription factor jun-B, Periodic tryptophan protein 2 homolog, RUS1 family protein C16orf58, Pterin-4-alpha-carbinolamine dehydratase, Tyrosine-protein phosphatase non-receptor type 13, Chloride intracellular channel protein 5, PHD finger protein 20-like protein 1, 55 kDa erythrocyte membrane protein, Tetratricopeptide repeat protein 4, Roundabout homolog 1, Putative methyltransferase NSUN3, Toll-like receptor 9, E3 ubiquitin-protein ligase DTX3L, Arf-GAP with SH3 domain, ANK repeat and PH domain-containing protein 1, GRB2-related adapter protein, Fructosamine-3-kinase, TATA element modulatory factor, Nuclear autoantigen Sp-100, Solute carrier family 41 member 3, Putative Polycomb group protein ASXL2, Protein ZGRF1, Transmembrane emp24 domain-containing protein 5, E3 ubiquitin-protein ligase RNF31, B-cell receptor-associated protein 29, mRNA cap guanine-N7 methyltransferase, Uromodulin, Signal transducer CD24, Integrin alpha-6, NF-kappa-B essential modulator, Kinesin-like protein KIFC1, Translation machinery-associated protein 16, Valine-tRNA ligase, COMM domain-containing protein 9, 28S ribosomal protein S21, mitochondrial, Kalirin, Prostaglandin F2 receptor negative regulator, BTB/POZ domain-containing protein 2, Dol-P-Man:Man(5)GlcNAc(2)-PP-Dol alpha-1,3-mannosyltransferase, tRNA-dihydrouridine(20) synthase [NAD(P)+]-like, Surfeit locus protein 6, Rho GTPase-activating protein 19, Eukaryotic translation initiation factor 4E, C—X—C motif chemokine 14, Engulfment and cell motility protein 1, Collagen alpha-1(XVIII) chain, Isochorismatase domain-containing protein 2, Coatomer subunit gamma-2, DNA-directed RNA polymerase III subunit RPC1, Kazrin, Synaptojanin-2-binding protein, Centrosomal protein of 85 kDa, Transmembrane protein 69, Lariat debranching enzyme, Receptor activity-modifying protein 2, F-box only protein 32, Transcription cofactor vestigial-like protein 4, SH3 domain-binding protein 1, Epsin-2, Mitogen-activated protein kinase 3, Ragulator complex protein LAMTOR2, Mitogen-activated protein kinase 9, Adipocyte plasma membrane-associated protein, [Pyruvate dehydrogenase [acetyl-transferring]]-phosphatase 1, mitochondrial, 28S ribosomal protein S12, mitochondrial, WD repeat and FYVE domain-containing protein 1, Protein disulfide-isomerase A4, Protein DEPP, Antigen peptide transporter 2, CDC42 small effector protein 1, Cyclin-dependent kinase 13, MICOS complex subunit MIC10, Nicastrin, Protein FAM73A, Complement C1q subcomponent subunit C, 28S ribosomal protein S7, mitochondrial, Serine/threonine-protein kinase TAO1, Ras GTPase-activating protein 3, Protein LDOC1L, Cytosolic 10-formyltetrahydrofolate dehydrogenase, Smoothelin, WW domain-binding protein 5, Phosphatidylinositide phosphatase SAC1, 39S ribosomal protein L3, mitochondrial, Inositol-trisphosphate 3-kinase B, Erythrocyte band 7 integral membrane protein, Solute carrier family 35 member E1, Probable 28S rRNA (cytosine(4447)-C(5))-methyltransferase, Y-box-binding protein 3, Proline-, glutamic acid- and leucine-rich protein 1, HCLS1-binding protein 3, Ubiquitin carboxyl-terminal hydrolase 37, Protein-L-isoaspartate(D-aspartate)O-methyltransferase, Transcriptional activator Myb, Abnormal spindle-like microcephaly-associated protein, Exportin-4, GMP reductase 1, Sperm-associated antigen 7, Tyrosine-protein kinase Fer, Coronin-1B, Acidic leucine-rich nuclear phosphoprotein 32 family member B, Schlafen family member 5, Macrophage erythroblast attacher, Histone acetyltransferase KAT2A, Mitotic spindle assembly checkpoint protein MAD2B, RecQ-mediated genome instability protein 1, Up-regulator of cell proliferation, Nucleoside diphosphate kinase, C-myc promoter-binding protein, Molybdate-anion transporter, Integrator complex subunit 5, Centrosomal protein of 170 kDa, Protein CASC5, Ephrin-A4, Tumor suppressor p53-binding protein 1, Proteasomal ATPase-associated factor 1, Gephyrin, Helicase SKI2W, Pleckstrin homology domain-containing family G member 2, Serine/threonine-protein kinase receptor R3, AP-5 complex subunit mu-1, Nuclear receptor subfamily 1 group D member 1, DnaJ homolog subfamily B member 2, Merlin, Ashwin, Transmembrane protein 176A, Synaptotagmin-like protein 2, Serine/threonine-protein kinase R102, AP-3 complex subunit beta-1, Forkhead box protein O1, Protein STON1-GTF2A1 L, Lysine-specific demethylase 7A, Inactive phospholipase C-like protein 2, Transcription factor MafG, Protein TBRG4, Nesprin-1, Type I inositol 1,4,5-trisphosphate 5-phosphatase, Disks large homolog 3, Long-chain-fatty-acid-CoA ligase 5, Trafficking protein particle complex subunit 1, Bromodomain testis-specific protein, Heterochromatin protein 1-binding protein 3, Histone H1.3, Malectin, Glyoxalase domain-containing protein 4, SRSF protein kinase 2, Twinfilin-2, ATPase WRNIP1, Transgelin, Echinoderm microtubule-associated protein-like 3, Histone deacetylase complex subunit SAP18, RE1-silencing transcription factor, Protein tyrosine phosphatase type IVA 1, Phospholipase D3, Microfibrillar-associated protein 1, Putative protein arginine N-methyltransferase 9, Protein NYNRIN, NADH-cytochrome b5 reductase 1, Centrosomal protein POC5, Protrudin, Transcription initiation factor TFIID subunit 8, Motile sperm domain-containing protein 1, Splicing factor, arginine/serine-rich 19, BTB/POZ domain-containing adapter for CUL3-mediated RhoA degradation protein 2, Sentrin-specific protease 3, Interferon regulatory factor 1, 40S ribosomal protein S4, Y isoform 2, Transmembrane protein 147, Transcriptional regulator Kaiso, HCG2043421, isoform CRA_c, WD repeat-containing protein 78, 1,2-dihydroxy-3-keto-5-methylthiopentene dioxygenase, Aldehyde dehydrogenase family 16 member A1, Protein phosphatase 1 D, Caspase-1, CMP-N-acetylneuraminate-beta-galactosamide-alpha-2,3-sialyltransferase 1, Putative 40S ribosomal protein S10-like, Protein DENND6A, N-glycosylase/DNA lyase, Kelch-like protein 5, RNA-binding protein 40, Major prion protein, Fibroblast growth factor receptor substrate 2, Fragile X mental retardation protein 1, Signal recognition particle 14 kDa protein, Sarcolemmal membrane-associated protein, 5-formyltetrahydrofolate cyclo-ligase, 2',5'-phosphodiesterase 12, Receptor-type tyrosine-protein phosphatase U, Translocon-associated protein subunit gamma, Guanine nucleotide-binding protein-like 3, Ran-binding protein 6, Transcription factor Sp4, Histone deacetylase complex subunit SAP130, Adapter protein CIKS, PDZ and LIM domain protein 5, Ankyrin repeat domain-containing protein 40, Uroporphyrinogen decarboxylase, DNA repair protein RAD51 homolog 3, CGG triplet repeat-binding protein 1, Ubiquitin carboxyl-terminal hydrolase BAP1, ATP-dependent DNA helicase Q1, Sorting nexin-8, Syntaxin-binding protein 6, Protein syndesmos, Mitogen-activated protein kinase kinase kinase 6, Gametogenetin-binding protein 2, ATP-dependent 6-phosphofructokinase, muscle type, ADP-ribosylation factor-like protein 6-interacting protein 1, Protein dpy-30 homolog, Ras-like protein family member 11A, Core histone macro-H2A.1, Vacuolar protein sorting-associated protein 16 homolog, ER lumen protein-retaining receptor 2, Ubiquitin-conjugating enzyme E2 L3, Phosphatidate cytidylyltransferase 1, Putative oxidoreductase GLYR1, 39S ribosomal protein L37, mitochondrial, HLA class II histocompatibility antigen, DQ beta 1 chain, Mitogen-activated protein kinase 14, Mitogen-activated protein kinase 7, Endoplasmic reticulum lectin 1, Rho GTPase-activating protein 17, EP300-interacting inhibitor of differentiation 1, Codanin-1, Tetratricopeptide repeat protein 19, mitochondrial, High affinity cationic amino acid transporter 1, Protein strawberry notch homolog 2, Rabankyrin-5, HEAT repeat-containing protein 6, Mitochondrial antiviral-signaling protein, Liprin-alpha-1, Chromodomain-helicase-DNA-binding protein 9, Ras-specific guanine nucleotide-releasing factor RalGPS2, Transmembrane 9 superfamily member 1, Dipeptidyl peptidase 2, Lysophosphatidylcholine acyltransferase 1, E1A-binding protein p400, DNA fragmentation factor subunit alpha, DNA mismatch repair protein Mlhi, Receptor-interacting serine/threonine-protein kinase 4, Alpha-tubulin N-acetyltransferase 1, HLA class I histocompatibility antigen, B-40 alpha chain, RILP-like protein 1, Aminopeptidase B, Protein fem-1 homolog A, DNA polymerase alpha catalytic subunit, Protein DGCR6L, Histone deacetylase 10, DENN domain-containing protein 4B, Transmembrane protein 102, Cell differentiation protein RCD1 homolog, GSK3-beta interaction protein, Multiple inositol polyphosphate phosphatase 1, THAP domain-containing protein 11, Synaptosomal-associated protein 29, Inversin, Small integral membrane protein 10, Kinesin light chain 1, tRNA-splicing endonuclease subunit Sen2, Putative phospholipase B-like 2, AP-1 complex subunit gamma-1, E3 ubiquitin-protein ligase RFWD2, Integrin alpha-X, Chitobiosyldiphosphodolichol beta-mannosyltransferase, Tripartite motif-containing protein 44, Histone H1.4, Liprin-beta-1, Zinc finger HIT domain-containing protein 2, RELT-like protein 1, Rhotekin, Long-chain fatty acid transport protein 1, Coiled-coil domain-containing protein 50, Pumilio homolog 2, Alpha-actinin-1, Vacuolar protein sorting-associated protein 54, Erlin-1, Ubiquitin carboxyl-terminal hydrolase 28, Echinoderm microtubule-associated protein-like 5, GRB2-associated-binding protein 1, Protein BANP, DNA excision repair protein ERCC-1, Zinc finger and BTB domain-containing protein 17, Autophagy-related protein 16-1, Segment polarity protein dishevelled homolog DVL-2, GRIP1-associated protein 1, Circadian clock protein PASD1, Cyclin-J-like protein, Tristetraprolin, Ral GTPase-activating protein subunit alpha-1, DENN domain-containing protein 5B, Caspase recruitment domain-containing protein 19, Eukaryotic translation initiation factor 4 gamma 2, Phospholipase DDHD1, Major facilitator superfamily domain-containing protein 1, Beta-glucuronidase, Putative protein PLEKHA9, Probable ATP-dependent RNA helicase DDX59, Putative histone H2B type 2-D, Osteopetrosis-associated transmembrane protein 1, Structure-specific endonuclease subunit SLX1, Nicalin, E3 ubiquitin-protein ligase XIAP, Rhomboid domain-containing protein 2, Telomere length regulation protein TEL2 homolog, Leucine-rich repeat serine/threonine-protein kinase 2, U3 small nucleolar RNA-associated protein 18 homolog, CAP-Gly domain-containing linker protein 1, Autophagy-related protein 13, WD repeat and FYVE domain-containing protein 3, Transcription initiation factor TFIID subunit 4B, Phosphatidylinositol N-acetylglucosaminyltransferase subunit H, Adiponectin receptor protein 2, Protein GPR107, Tumor protein p53-inducible protein 13, Apoptosis-stimulating of p53 protein 2, Kelch domain-containing protein 3, Leucine-rich repeat and calponin homology domain-containing protein 1, Vascular endothelial growth factor receptor 1, Transcription factor E2-alpha, Pre-mRNA-processing factor 17, Leupaxin, Transmembrane protein 2, Huntingtin-interacting protein 1, NIPA-like protein 3, Glucosamine-6-phosphate isomerase 2, U6 snRNA-associated Sm-like protein LSm8, Copper chaperone for superoxide dismutase, Major facilitator superfamily domain-containing protein 8, Integrator complex subunit 7, Cytoplasmic dynein 1 light intermediate chain 2, Protein angel homolog 1, Protein cramped-like, Transmembrane protein 261, Apoptosis-resistant E3 ubiquitin protein ligase 1, Endonuclease G, mitochondrial, Something about silencing protein 10, Calpain-7, Probable ATP-dependent RNA helicase DDX60, KAT8 regulatory NSL complex subunit 1, Protein NPAT, Rab3 GTPase-activating protein catalytic subunit, Transmembrane protein 223, tRNA wybutosine-synthesizing protein 2 homolog, T-complex protein 11-like protein 2, TATA box-binding protein-associated factor RNA polymerase I subunit B, Rab-like protein 2A, Inactive ubiquitin carboxyl-terminal hydrolase 54, Inner nuclear membrane protein Man1, Ribosomal protein S6 kinase alpha-4, Ligand of Numb protein X 2, DDB1- and CUL4-associated factor 16, HCG2044777, TELO2-interacting protein 2, Bromodomain-containing protein 9, Zinc finger protein 644, Dual specificity protein phosphatase 10, Taxi-binding protein 1, THAP domain-containing protein 4, DNA topoisomerase I, mitochondrial, NFATC2-interacting protein, ATPase family AAA domain-containing protein 1, Protein Hook homolog 1, Polypeptide N-acetylgalactosaminyltransferase 18, Kinesin-like protein KIF1C, Trafficking protein particle complex subunit 11, Cytochrome P450 4V2, NADH dehydrogenase [ubiquinone] iron-sulfur protein 2, mitochondrial, cAMP-dependent protein kinase type II-alpha regulatory subunit, Transmembrane protein 245, Acetyl-CoA acetyltransferase, mitochondrial, AP-1 complex subunit sigma-1A, mRNA export factor, Ski oncogene, Breast cancer type 2 susceptibility protein, E3 UFM1-protein ligase 1, Ribonuclease H2 subunit B, Beta-secretase 2, Growth arrest-specific protein 7, Lethal(2) giant larvae protein homolog 2, Activating signal cointegrator 1 complex subunit 3, Zinc finger protein 532, DNA-directed RNA polymerase II subunit RPB11-a, Ubiquitin/ISG15-conjugating enzyme E2 L6, Kelch-like protein 12, tRNA-dihydrouridine(47) synthase [NAD(P)(+)]-like, Activating molecule in BECN1-regulated autophagy protein 1, Angiomotin-like protein 1, Pleckstrin homology domain-containing family A member 4, Liprin-alpha-3, Fasciculation and elongation protein zeta-2, 5'-nucleotidase domain-containing protein 3, Growth arrest-specific protein 8, SLIT-ROBO Rho GTPase-activating protein 2, DNA dC→dU-editing enzyme APOBEC-3A, N-acetylgalactosamine kinase, U6 snRNA-associated Sm-like protein LSm4, Keratinocyte-associated transmembrane protein 2, E3 ubiquitin-protein ligase UBR1, Riboflavin kinase, TFIIH basal transcription factor complex helicase XPB subunit, GPN-loop GTPase 3, Nitrogen permease regulator 3-like protein, SH3KBP1-binding protein 1, Serine/threonine-protein phosphatase 4 regulatory subunit 3B, Unconventional myosin-XVIIIlla, Ras GTPase-activating-like protein IQGAP3, Protein TRIM6-TRIM34, Calponin-2, Developmentally-regulated GTP-binding protein 1, Transcription initiation factor TFIID subunit 1, Zinc finger BED domain-containing protein 4, Ubiquitin-like modifier-activating enzyme 7, Protein C12orf4, Prefoldin subunit 1, Phosphatidate phosphatase LPIN1, N-acetyllactosaminide beta-1,3-N-acetylglucosaminyltransferase 2, Mitochondrial fission regulator 1, Palladin, Forkhead box protein J3, Tyrosine-protein phosphatase non-receptor type 12, Phospholipase A1 member A, Eyes absent homolog 2, Dual specificity protein phosphatase 6, COMM domain-containing protein 8, Nuclear factor NF-kappa-B p105 subunit, Ketosamine-3-kinase, E3 ubiquitin-protein ligase RLIM, Cyclin-L2, WD repeat domain phosphoinositide-interacting protein 4, DDB1- and CUL4-associated factor 4-like protein 1, Partitioning defective 3 homolog, 3-ketodihydrosphingosine reductase, Upstream-binding protein 1, Xyloside xylosyltransferase 1, Suppressor APC domain-containing protein 2, Translocon-associated protein subunit beta, Vacuolar protein sorting-associated protein 33B, Probable inactive glycosyltransferase 25 family member 3, HMG domain-containing protein 4, Protein orai-3, Copine-3, Myeloid-derived growth factor, BTB/POZ domain-containing adapter for CUL3-mediated RhoA degradation protein 1, Calcium-independent phospholipase A2-gamma, Sperm-specific antigen 2, Glycerol-3-phosphate acyltransferase 1, mitochondrial, Replication initiator 1, Uncharacterized protein C15orf39, Uncharacterized protein C5orf34, FAD synthase, Inhibitor of Bruton tyrosine kinase, Cell growth-regulating nucleolar protein, EF-hand domain-containing protein 1, Centrosome-associated protein CEP250, SH3 domain and tetratricopeptide repeat-containing protein 1, Kelch-like protein 21, Cullin-9, Optineurin, Kelch domain-containing protein 10, Cation channel sperm-associated protein 2, Solute carrier family 35 member C2, Carboxypeptidase D, Peroxisomal biogenesis factor 3, Kinesin-like protein KIF3A, Lysosomal-trafficking regulator, Uncharacterized aarF domain-containing protein kinase 2, Transportin-3, Mediator of RNA polymerase II transcription subunit 24, CAP-Gly domain-containing linker protein 2, Solute carrier family 35 member E4, Sestrin-3, Bromodomain adjacent to zinc finger domain protein 1A, Dehydrogenase/reductase SDR family member 1, Cyclin-dependent-like kinase 5, Heat shock factor protein 2, Serine/threonine-protein kinase TBK1, Ubiquitin conjugation factor E4 B, Band 4.1-like protein 3, ADNP homeobox protein 2, Ubiquitin carboxyl-terminal hydrolase 6, Mediator of DNA damage checkpoint protein 1, Mitochondrial fission factor, PDZ domain-containing protein GIPC1, Serine incorporator 1, Nectin-2, Phosphopantothenate-cysteine ligase, Paraspeckle component 1, Tumor necrosis factor receptor superfamily member 6, Vacuolar protein sorting-associated protein 29, EMILIN-2, Ubiquitin carboxyl-terminal hydrolase 33, Mediator of RNA polymerase II transcription subunit 14, Histone-lysine N-methyltransferase 2B, Coronin, Signal-induced proliferation-associated protein 1, 2-hydroxyacyl-CoA lyase 1, Kelch-like protein 22, Vacuolar protein sorting-associated protein 11 homolog, 1-phosphatidylinositol 4,5-bisphosphate phosphodiesterase gamma-1, Acylglycerol kinase, mitochondrial, Transmembrane protein 9B, Insulin-like growth factor 2 mRNA-binding protein 1, Tartrate-resistant acid phosphatase type 5, Kelch-like protein 18, Glycogen phosphorylase, liver form, Protein Mis18-beta, Guanine nucleotide-binding protein G(i) subunit alpha-1, Disheveled-associated activator of morphogenesis 2, Protein VAC14 homolog, Ubiquitin-like protein 4A, Vesicle-trafficking protein SEC22b, Zinc finger CCCH-type antiviral protein 1, Phosphatidylinositol N-acetylglucosaminyltransferase subunit A, Coiled-coil domain-containing protein 84, Vesicle-associated membrane protein 4, UPF0606 protein KIAA1549L, Phosphatidylglycerophosphatase and protein-tyrosine phosphatase 1, Uncharacterized protein C11orf24, 60S ribosomal protein L32, EF-hand calcium-binding domain-containing protein 7, Glucose-fructose oxidoreductase domain-containing protein 2, Nucleolar protein 6, NAD kinase, Methyltransferase-like protein 9, GTP-binding protein 2, Protocadherin beta-6, Myotubularin-related protein 4, Serine palmitoyltransferase small subunit A, G patch domain-containing protein 11, GRB2-associated-binding protein 2, Copper-transporting ATPase 1, Coiled-coil and C2 domain-containing protein 2A, Helicase ARIP4, Uncharacterized protein C20orf144, Gamma-soluble NSF attachment protein, Lysine-specific demethylase 6A, Protein S100-A6, Collagen alpha-2(VIII) chain, Ephrin type-B receptor 1, Fer-1-like protein 5, Molybdenum cofactor sulfurase, Cysteine-rich protein 2, Interferon-induced protein with tetratricopeptide repeats 2, Fas-binding factor 1, IQ motif and SEC7 domain-containing protein 2, Beta-secretase 1, GDNF family receptor alpha-1, H/ACA ribonucleoprotein complex subunit 2, Rho guanine nucleotide exchange factor 17, Uncharacterized protein C2orf15, Nesprin-3, Ankyrin repeat domain-containing protein 35, Probable ATP-dependent RNA helicase DDX53, DNA-binding protein RFX6, BTB/POZ domain-containing protein KCTD7, Fanconi anemia group M protein, Collagen alpha-4(IV) chain, Complement C4-A, Collagen alpha-1(XIX) chain, Neuronal tyrosine-phosphorylated phosphoinositide-3-kinase adapter 2, Kinesin-like protein KIF27, Meprin A subunit beta, F-box/LRR-repeat protein 4, PHD finger protein 14, Arylsulfatase E, NACHT, LRR and PYD domains-containing protein 9, Kelch-like protein 2, Protein RER1, L-lactate dehydrogenase A-like 6B, Diacylglycerol O-acyltransferase 2, PWWP domain-containing protein 2B, DNA mismatch repair protein MIh3, Cathepsin K, Synaptojanin-1, Zinc finger MYND domain-containing protein 15, Histone H2A type 2-A, D-dopachrome decarboxylase, FAST kinase domain-containing protein 1, F-box only protein 41, Threonine synthase-like 1, Beta-1,4-galactosyltransferase 7, Usherin, Nucleoside diphosphate kinase B, Endoplasmic reticulum aminopeptidase 2, Wiskott-Aldrich syndrome protein, Cartilage intermediate layer protein 1, Probable phosphoglycerate mutase 4, Tumor protein D52, Histidine protein methyltransferase 1 homolog, Glutaredoxin-2, mitochondrial, Polycystin-1, Cilia- and flagella-associated protein 52, Oxysterol-binding protein 2, UV excision repair protein RAD23 homolog B, Protein boule-like, Beta-1,3-galactosyltransferase 6, Sodium-coupled monocarboxylate transporter 2, Rabenosyn-5, Leucine-rich repeat-containing protein 28, NUAK family SNF1-like kinase 2, Laminin subunit alpha-4, Otoferlin, Procollagen-lysine,2-oxoglutarate 5-dioxygenase 1, Galectin-1, Ovochymase-1, Envoplakin, Neuron navigator 2, VIP peptides, Activin receptor type-2A, Serine/threonine-protein phosphatase with EF-hands 1, Kin of IRRE-like protein 3, Ankyrin repeat domain-containing protein 26, Microsomal glutathione S-transferase 1, Gamma-enolase, Matrix-remodeling-associated protein 5, HMG domain-containing protein 3, Selenide, water dikinase 2, Transmembrane glycoprotein NMB, Cytochrome b-245 light chain, Transcription factor 7-like 2, Tumor protein p63-regulated gene 1-like protein, Transmembrane protein 141, Protein FAM188B, Protein TANC1, 5-oxoprolinase, Tryptophan-tRNA ligase, cytoplasmic, Leishmanolysin-like peptidase, Kinesin-like protein KIF7, 40S ribosomal protein S12, Anthrax toxin receptor 1, Actin-related protein 2/3 complex subunit 1A, Nicotinate-nucleotide pyrophosphorylase [carboxylating], Caskin-2, Protein Wnt-5a, Dehydrogenase/reductase SDR family member 4, Fatty acid desaturase 1, RalBP1-associated Eps domain-containing protein 1, Cadherin-5, Mitogen-activated protein kinase kinase kinase MLT, Transcription initiation protein SPT3 homolog, HEAT repeat-containing protein 5A, Solute carrier family 26 member 6, CD109 antigen, Stress-induced-phosphoprotein 1, Nuclear receptor coactivator 7, Liprin-alpha-4, Mesoderm induction early response protein 1, Kynurenine-oxoglutarate transaminase 3, Leucine-zipper-like transcriptional regulator 1, Ubiquitin-like-conjugating enzyme ATG3, Protein shisa-5, Cell adhesion molecule-related/down-regulated by oncogenes, Breast cancer anti-estrogen resistance protein 3, Phosphoacetylglucosamine mutase, Ras-related protein Rab-14, Glutamate receptor ionotropic, kainate 2, DNA-directed RNA polymerase III subunit RPC3, Enhancer of polycomb homolog 1, Nuclear protein 1, Melanoma-associated antigen 11, Inositol polyphosphate multikinase, Sorting nexin-18, Poly [ADP-ribose]polymerase 12, Ubiquitin-conjugating enzyme E2 K, Leucine-rich repeats and immunoglobulin-like domains protein 2, Trifunctional enzyme subunit beta, mitochondrial, Cytoplasmic dynein 2 heavy chain 1, Thimet oligopeptidase, Regulatory-associated protein of mTOR, Protein FAM83H, DDB1- and CUL4-associated factor 12, Creatine kinase M-type, Nestin, ADP-ribosylation factor-binding protein GGA1, DDRGK domain-containing protein 1, Laminin subunit alpha-1, Upstream stimulatory factor 1, Reticulocalbin-3, Low-density lipoprotein receptor-related protein 4, PR domain zinc finger protein 10, Glutathione S-transferase Mu 3, Ribosomal protein S6 kinase alpha-5, Protein CLEC16A, Zinc transporter SLC39A7, Armadillo repeat containing 8, isoform CRA_g, Uncharacterized protein KIAA0355, Caseinolytic peptidase B protein homolog, Hypoxanthine-guanine phosphoribosyltransferase, Receptor-type tyrosine-protein phosphatase F, Rhophilin-2, E3 ubiquitin-protein ligase Arkadia, Dedicator of cytokinesis protein 5, Dynein heavy chain 14, axonemal, U5 small nuclear ribonucleoprotein 40 kDa protein, Progesterone-induced-blocking factor 1, Vesicle-associated membrane protein-associated protein A, Switch-associated protein 70, Prolow-density lipoprotein receptor-related protein 1, Noelin, D-3-phosphoglycerate dehydrogenase, Serine/threonine-protein kinase 24, Serine protease HTRA1, 39S ribosomal protein L12, mitochondrial, Peptidyl-prolyl cis-trans isomerase FKBP9, E3 ubiquitin-protein ligase TRIM21, Wee1-like protein kinase, Hydroxyacylglutathione hydrolase, mitochondrial, Solute carrier family 12 member 4, 1-phosphatidylinositol 4,5-bisphosphate phosphodiesterase gamma-2, USP6 N-terminal-like protein, Collagen alpha-1(XV) chain, Nuclear fragile X mental retardation-interacting protein 2, Protein unc- 119 homolog B, Exocyst complex component 6B, Aminoacylase-1, Kelch domain-containing protein 7B, pre-rRNA processing protein FTSJ3, Ryanodine receptor 1, Nucleobindin-1, Striatin-3, Serine/threonine-protein kinase ULK4, GTP-binding protein Rheb, Probable E3 ubiquitin-protein ligase HERC3, Dedicator of cytokinesis protein 1, Proline-rich protein 11, Sister chromatid cohesion protein PDS5 homolog B, Breast cancer anti-estrogen resistance protein 1, Vitamin K-dependent protein S, POZ-, AT hook-, and zinc finger-containing protein 1, Probable global transcription activator SNF2L1, Hepatocyte growth factor receptor, Leucine-rich repeat-containing protein 42, AMP deaminase 2, Protein phosphatase Slingshot homolog 3, Serine/threonine-protein kinase PLK3, BTB/POZ domain-containing protein 3, General transcription factor IIF subunit 1, Protein SOGA1, Serine/threonine-protein phosphatase 4 catalytic subunit, Zinc finger protein 3, Neurolysin, mitochondrial, T-box transcription factor TBX3, Bardet-Biedl syndrome 10 protein, Inositol-trisphosphate 3-kinase C, Serine/threonine-protein phosphatase 5, Phospholipase DDHD2, Zinc finger protein 530, Phospholysine phosphohistidine inorganic pyrophosphate phosphatase, SPRY domain-containing SOCS box protein 1, Supervillin, UDP-N-acetylglucosamine/UDP-glucose/GDP-mannose transporter, Complement decay-accelerating factor, LIM and calponin homology domains-containing protein 1, Lysosomal Pro-X carboxypeptidase, Putative RNA polymerase II subunit B1 CTD phosphatase RPAP2, Heat shock 70 kDa protein 13, Alpha/beta hydrolase domain-containing protein 14B, Unconventional myosin-X, Mimitin, mitochondrial, Protein TALPID3, Centrosomal protein of 63 kDa, Very-long-chain (3R)-3-hydroxyacyl-CoA dehydratase 3, HAUS augmin-like complex subunit 6, Neural cell adhesion molecule L1, Oxysterol-binding protein-related protein 1, Caspase recruitment domain-containing protein 8, Ras-related protein Rap-2c, Sorting nexin-30, Serine/threonine-protein kinase D3, Progressive ankylosis protein homolog, Bleomycin hydrolase, Trafficking protein particle complex subunit 2, Pyruvate carboxylase, mitochondrial, Peroxisome proliferator-activated receptor gamma coactivator 1-alpha, Cadherin EGF LAG seven-pass G-type receptor 2, Dedicator of cytokinesis protein 9, C-Jun-amino-terminal kinase-interacting protein 4, E3 ubiquitin-protein ligase SHPRH, Alpha-mannosidase 2x, H/ACA ribonucleoprotein complex subunit 1, Zinc finger protein 503, Tubulin polyglutamylase TTLL4, Oxysterol-binding protein-related protein 10, Origin recognition complex subunit 5, Serine/threonine-protein kinase PLK4, Disks large homolog 5, H/ACA ribonucleoprotein complex non-core subunit NAF1, Prolyl 3-hydroxylase 1, Protein FAM46B, Nuclear factor 1 X-type, Multiple PDZ domain protein, Serine/threonine-protein kinase SIK3, Ribonuclease P protein subunit p21, Serine/threonine-protein kinase MRCK beta, Serine/threonine-protein phosphatase 2A 55 kDa regulatory subunit B alpha isoform, snRNA-activating protein complex subunit 1, Rab proteins geranylgeranyltransferase component A 1, Cystine/glutamate transporter, ER degradation-enhancing alpha-mannosidase-like protein 3, RNA pseudouridylate synthase domain-containing protein 2, DENN domain-containing protein 1B, Trimethylguanosine synthase, Catechol O-methyltransferase, E3 ubiquitin-protein ligase DZIP3, Myotubularin-related protein 13, Epoxide hydrolase 1, RNA-binding motif protein, X-linked-like-2, Tyrosine-protein phosphatase non-receptor type 9, Cell cycle checkpoint control protein RAD9A, UHRF1-binding protein 1-like, Plasma membrane calcium-transporting ATPase 4, Aminoacyl tRNA synthase complex-interacting multifunctional protein 1, Neural Wiskott-Aldrich syndrome protein, Collagen alpha-1(VII) chain, Kelch repeat and BTB domain-containing protein 2, Protein FAM63A, RNA-binding protein with multiple splicing 2, Discoidin domain-containing receptor 2, Actin filament-associated protein 1, Protein Smaug homolog 1, Serum paraoxonase/arylesterase 2, Ankyrin repeat and BTB/POZ domain-containing protein 2, Zinc-binding alcohol dehydrogenase domain-containing protein 2, Serine/threonine-protein kinase 3, Actin-related protein 10, Lipoma-preferred partner, Zinc finger protein RFP, Very-long-chain enoyl-CoA reductase, Elongation protein 4 homolog (S. cerevisiae), isoform CRA_b, Dual specificity protein phosphatase 4, Anoctamin-1, Actin-binding LIM protein 3, Kelch-like protein 9, Cytoplasmic aconitate hydratase, Protein FAM178B, Cell cycle control protein 50A, tRNA wybutosine-synthesizing protein 4, Cholinephosphotransferase 1, Glycogen synthase kinase-3 alpha, Tectonic-3, Paired amphipathic helix protein Sin3b, ATP-binding cassette sub-family D member 3, CCR4-NOT transcription complex subunit 4, Mini-chromosome maintenance complex-binding protein, Integral membrane protein 2C, Protein C-ets-2, Interferon-induced 35 kDa protein, RNA-binding protein NOB1, Selenocysteine insertion sequence-binding protein 2, Enoyl-CoA delta isomerase 2, mitochondrial, Receptor tyrosine-protein kinase erbB-3, Partitioning defective 3 homolog B, F-box only protein 42, Brain-specific angiogenesis inhibitor 1-associated protein 2, Hemoglobin subunit gamma-2, Zinc transporter 6, La-related protein 4, Zinc transporter 7, Ribonuclease P protein subunit p30, Tensin-2, Volume-regulated anion channel subunit LRRC8E, Kinesin-like protein KIF3B, Cytochrome c oxidase assembly protein COX11, mitochondrial, Tripartite motif-containing protein 47, Monocarboxylate transporter 1, DDB1- and CUL4-associated factor 4, Kinesin-like protein KIF1A, Kinesin-like protein KIF13A, ATP synthase F(0) complex subunit B1, mitochondrial, LIM domain-containing protein ajuba, UDP-glucose 6-dehydrogenase, Transcriptional enhancer factor TEF-3, Midi-interacting protein 1, Lipase maturation factor 2, Ganglioside-induced differentiation-associated protein 2, BAG family molecular chaperone regulator 4, InaD-like protein, RNA binding protein fox-1 homolog 2, Protein TANC2, Probable E3 ubiquitin-protein ligase HECTD2, Medium-chain specific acyl-CoA dehydrogenase, mitochondrial, Prenylcysteine oxidase 1, Interferon alpha-inducible protein 27-like protein 2, RNA-binding protein 38, Ephrin-A1, Glycine dehydrogenase (decarboxylating), mitochondrial, Protein FAM50A, ELM2 and SANT domain-containing protein 1, UPF0668 protein C10orf76, Synaptonemal complex protein SC65, 5'-AMP-activated protein kinase catalytic subunit alpha-1, Peroxisome assembly protein 26, Thioredoxin domain-containing protein 5, Cell cycle and apoptosis regulator protein 2, X-box-binding protein 1, Protein YIF1A, PAB-dependent poly(A)-specific ribonuclease subunit PAN2, Methionine-R-sulfoxide reductase B1, Calcineurin-binding protein cabin-1, Protein RTF2 homolog, Endoplasmic reticulum-Golgi intermediate compartment protein 2, General transcription factor 3C polypeptide 3, N-acylneuraminate cytidylyltransferase, Zinc finger protein ZXDC, PRKCA-binding protein, Talin-2, SURP and G-patch domain-containing protein 2, Kinesin-1 heavy chain, Syntaxin-8, Galectin-3-binding protein, Ankyrin repeat and zinc finger domain-containing protein 1, E3 ubiquitin-protein ligase NEURL1B, Transcription and mRNA export factor ENY2, V-type proton ATPase 21 kDa proteolipid subunit, Probable RNA-binding protein 19, Selenoprotein O, Zinc finger protein 622, Origin recognition complex subunit 3, Serine/threonine-protein phosphatase 6 regulatory ankyrin repeat subunit A, 39S ribosomal protein L22, mitochondrial, Chromosome transmission fidelity protein 8 homolog isoform 2, Zinc finger protein 574, Ubiquitin-conjugating enzyme E2 T, Anthrax toxin receptor 2, Cilia- and flagella-associated protein 58, Mitogen-activated protein kinase-binding protein 1, Glucosamine 6-phosphate N-acetyltransferase, UPF0472 protein C16orf72, NAD(P) transhydrogenase, mitochondrial, E3 ubiquitin-protein ligase RNF220, Collagen alpha-1(XII) chain, Serine/threonine-protein kinase OSR1, Inositol-pentakisphosphate 2-kinase, General transcription factor IIH subunit 2, Polycomb group RING finger protein 6, Isocitrate dehydrogenase [NAD] subunit alpha, mitochondrial, Protein MMS22-like, HAUS augmin-like complex subunit 7, PIN2/TERF1-interacting telomerase inhibitor 1, Homeobox protein Hox-A13, Tubby-related protein 4, Golgi apparatus membrane protein TVP23 homolog B, Phosphoribosyl pyrophosphate synthase-associated protein 1, Protein phosphatase methylesterase 1, Uncharacterized aarF domain-containing protein kinase 5, Protein canopy homolog 4, Zinc transporter ZIP3, L-xylulose reductase, Protein S 100-A16, Zinc finger SWIM domain-containing protein 8, Charged multivesicular body protein 3, Aspartyl aminopeptidase, TSC22 domain family protein 4, 5'-AMP-activated protein kinase subunit gamma-1, CD99 antigen-like protein 2, CD81 antigen, Inositol 1,4,5-trisphosphate receptor-interacting protein, Ankyrin-2, Leucine-rich repeat protein SHOC-2, Angiomotin-like protein 2, Zinc finger protein 580, Proteasome subunit beta type-10, Torsin-1A-interacting protein 2, Centrosomal protein of 95 kDa, Securin, 26S protease regulatory subunit 8, Nucleoporin NUP53, Nicotinamide/nicotinic acid mononucleotide adenylyltransferase 1, Mediator of RNA polymerase II transcription subunit 13-like, Protein FAM172A, N-acetyl-D-glucosamine kinase, Hsp70-binding protein 1, Ribosomal RNA-processing protein 7 homolog A, Methylmalonic aciduria and homocystinuria type D protein, mitochondrial, Glycerol-3-phosphate dehydrogenase 1-like protein, 3-ketoacyl-CoA thiolase, mitochondrial, COMM domain-containing protein 6, Replication protein A 14 kDa subunit, Peptidyl-prolyl cis-trans isomerase CWC27 homolog, Uncharacterized protein C16orf45, NF-kappa-B inhibitor-interacting Ras-like protein 1, FRAS1-related extracellular matrix protein 2, Semaphorin-3C, Maturin, U11/U12 small nuclear ribonucleoprotein 48 kDa protein, Inactive tyrosine-protein kinase transmembrane receptor ROR1, Vacuolar protein sorting-associated protein 4B, UPF0469 protein KIAA0907, Melanoma-associated antigen D1, HLA class I histocompatibility antigen, alpha chain F, Zinc finger protein 506, Kinesin-like protein KIF22, Phosphatidylinositol 4-phosphate 3-kinase C2 domain-containing subunit alpha, Sarcosine dehydrogenase, mitochondrial, Glutamine and serine-rich protein 1, Alpha-parvin, Transmembrane protein 97, Importin subunit alpha-7, 60S ribosomal protein L11, TBC1 domain family member 22B, Neuronal calcium sensor 1, Glutamyl-tRNA(Gln) amidotransferase subunit C, mitochondrial, E3 ubiquitin-protein ligase RNF187, von Willebrand factor A domain-containing protein 5A, Class E basic helix-loop-helix protein 41, Box C/D snoRNA protein 1, C-terminal-binding protein 1, Acyl-CoA synthetase family member 4, Fos-related antigen 2, Mitofusin-1, Retinoic acid receptor gamma, Uncharacterized protein C17orf85, Very-long-chain (3R)-3-hydroxyacyl-CoA dehydratase 1, Tripartite motif-containing protein 65, Thioredoxin reductase 1, cytoplasmic, Cdc42 effector protein 3, Regulator of chromosome condensation, Glutamine-rich protein 1, Sphingosine-1-phosphate phosphatase 1, WD repeat-containing protein 92, Unconventional myosin-IXa, Biogenesis of lysosome-related organelles complex 1 subunit 4, Neurobeachin-like protein 1, Phosphomannomutase 1, Probable phospholipid-transporting ATPase IIA, Thioredoxin domain-containing protein 9, Inter-alpha-trypsin inhibitor heavy chain H5, E3 ubiquitin-protein ligase CBL, E3 SUMO-protein ligase PIAS1, Tenascin, NADH dehydrogenase [ubiquinone] iron-sulfur protein 6, mitochondrial, Glutathione synthetase, Ectonucleoside triphosphate diphosphohydrolase 4, V-type proton ATPase subunit B, brain isoform, TBC1 domain family member 14, DNA-directed RNA polymerases I and III subunit RPAC2, X-linked retinitis pigmentosa GTPase regulator, PTB domain-containing engulfment adapter protein 1, Protein Churchill, SUN domain-containing protein 1, E3 ubiquitin-protein ligase pellino homolog 3, Synembryn-A, SAP30-binding protein, Zinc finger and BTB domain-containing protein 7B, Ubinuclein-1, Cysteine-tRNA ligase, cytoplasmic, Protein FAM135A, PERQ amino acid-rich with GYF domain-containing protein 1, Cytochrome cl, heme protein, mitochondrial, FUN14 domain-containing protein 1, Isocitrate dehydrogenase [NAD] subunit gamma, mitochondrial, DNA damage-binding protein 2, Integrin beta-5, Histone-lysine N-methyltransferase 2A, KN motif and ankyrin repeat domain-containing protein 1, Small ubiquitin-related modifier 1, Derlin-3, Replication factor C subunit 3, Beta-crystallin B2, Elongator complex protein 6, Kelch domain-containing protein 2, Focadhesin, 26S proteasome non-ATPase regulatory subunit 7, U4/U6.U5 tri-snRNP-associated protein 2, Calpain-5, Cyclin E variant ex7del, BTB/POZ domain-containing protein 10, Beta-soluble NSF attachment protein, SMC5-SMC6 complex localization factor protein 2, WW domain-binding protein 2, F-box/WD repeat-containing protein 8, Ceramide synthase 2, WD repeat-containing protein WRAP73, Transmembrane protein 165, Zinc finger protein AEBP2, Charged multivesicular body protein 4a, Transcriptional adapter 3, Trafficking kinesin-binding protein 2, [Pyruvate dehydrogenase (acetyl-transferring)] kinase isozyme 4, mitochondrial, Cytochrome b-c1 complex subunit Rieske, mitochondrial, Protein bicaudal D homolog 2, Nibrin, SNW domain-containing protein 1, Sperm-associated antigen 5, TSC22 domain family protein 1, Corepressor interacting with RBPJ 1, Kinesin-like protein, General transcription factor II-I repeat domain-containing protein 1, RNA-binding protein PNO1, Vacuolar protein sorting-associated protein 52 homolog, Actin-related protein 5, Ran-binding protein 17, Intermediate filament family orphan 2, Ubiquitin-conjugating enzyme E2 G2, Myeloid leukemia factor 1, Poly(A) polymerase alpha, Protein IMPACT, Proto-oncogene tyrosine-protein kinase receptor Ret, Heat shock factor protein 1, PDZ domain-containing RING finger protein 4, Mothers against decapentaplegic homolog 4, RING finger protein 113A, Neuron navigator 3, Conserved oligomeric Golgi complex subunit 3, CASP8-associated protein 2, Glutathione S-transferase omega-1, BAH and coiled-coil domain-containing protein 1, Dynactin subunit 4, Transcription elongation factor B polypeptide 1, Tight junction-associated protein 1, Anaphase-promoting complex subunit 5, DNA replication ATP-dependent helicase/nuclease DNA2, Integrin alpha-9, Sarcospan, Catenin delta-1, Ankycorbin, Lamina-associated polypeptide 2, isoforms beta/gamma, Intraflagellar transport protein 74 homolog, Actin-related protein 8, Neuron-specific calcium-binding protein hippocalcin, Pre-mRNA-processing factor 40 homolog B, Tumor protein D54, Mitogen-activated protein kinase kinase kinase kinase 4, Myristoylated alanine-rich C-kinase substrate, Kinetochore protein Spc25, B9 domain-containing protein 1, Zinc finger homeobox protein 3, Membrane metallo-endopeptidase-like 1, Vesicle-associated membrane protein-associated protein B/C, Zinc finger CCCH domain-containing protein 11A, 60S ribosomal protein L39-like, Transcription initiation factor TFIID subunit 7, Transforming growth factor beta-1, Max-like protein X, tRNA pseudouridine synthase A, mitochondrial, Asparagine synthetase domain-containing protein 1, mRNA-capping enzyme, Zinc finger protein SNAI2, ETS translocation variant 1, 5'-AMP-activated protein kinase catalytic subunit alpha-2, Kinesin-like protein KIFC3, Cathepsin L1, Aspartyl/asparaginyl beta-hydroxylase, Leucine-rich repeat-containing protein 61, Zinc finger protein 721, Flavin reductase (NADPH), Voltage-dependent anion-selective channel protein 1, KH domain-containing, RNA-binding, signal transduction-associated protein 3, Probable E3 ubiquitin-protein ligase HERC6, ER membrane protein complex subunit 3, Homeobox protein Hox-B7, Zinc finger C2HC domain-containing protein 1A, T-box transcription factor TBX15, Putative zinc finger protein 724, Zinc finger protein 486, Zinc finger protein 675, Prolyl endopeptidase-like, UBX domain-containing protein 8, Gamma-aminobutyric acid receptor subunit pi, ATP-dependent RNA helicase DDX54, Lysine-specific demethylase 4B, Protocadherin-1, Zinc finger protein 490, NKG2D ligand 3, Uncharacterized protein C18orf63, Peptidyl-prolyl cis-trans isomerase B, Plasma alpha-L-fucosidase, Notchless protein homolog 1, Adenosine 3'-phospho 5'-phosphosulfate transporter 1, Nucleus accumbens-associated protein 1, Biorientation of chromosomes in cell division protein 1-like 1, CDK5 and ABL1 enzyme substrate 2, Putative tRNA (cytidine(32)/guanosine(34)-2'-O)-methyltransferase, tRNA-splicing endonuclease subunit Sen54, Beta-galactosidase-1-like protein 2, Protein archease, Formin-binding protein 1-like, Eukaryotic translation initiation factor 2 subunit 2, Centromere/kinetochore protein zwl 0 homolog, Pyridoxal kinase, Tyrosine-protein phosphatase non-receptor type 14, Phosphatidate cytidylyltransferase 2, M-phase phosphoprotein 8, Ribonuclease P/MRP protein subunit POP5, DENN domain-containing protein 5A, Nuclear receptor coactivator 6, UDP-N-acetylhexosamine pyrophosphorylase, Mediator of RNA polymerase II transcription subunit 22, Transcription factor COE2, Niban-like protein 1, GREB1-like protein, Vesicular integral-membrane protein VIP36, Dynactin subunit 6, Sperm-associated antigen 16 protein, Abelson tyrosine-protein kinase 2, Opioid growth factor receptor, Proteasomal ubiquitin receptor ADRM1, Gamma-aminobutyric acid receptor-associated protein, B-cell CLL/lymphoma 9-like protein, Retroviral-like aspartic protease 1, Procollagen-lysine,2-oxoglutarate 5-dioxygenase 3, Bifunctional arginine demethylase and lysyl-hydroxylase JMJD6, Histone-lysine N-methyltransferase SETD7, Ras-associated and pleckstrin homology domains-containing protein 1, Mortality factor 4-like protein 2, Kinesin-like protein KIF15, Pleckstrin homology-like domain family B member 1, Zinc finger protein ubi-d4, KxDL motif-containing protein 1, Transmembrane protein 160, Very long-chain specific acyl-CoA dehydrogenase, mitochondrial, Signal recognition particle receptor subunit beta, Small G protein signaling modulator 3, Sodium-dependent lysophosphatidylcholine symporter 1, DNA-directed RNA polymerase III subunit RPC5, Protein Tob2, UPF0488 protein C8orf33, DNA-directed RNA polymerase Ill subunit RPC2, Protein spire homolog 1, Spectrin beta chain, non-erythrocytic 2, Phosphatidylinositol transfer protein beta isoform, CCAAT/enhancer-binding protein beta, Ras and Rab interactor 2, Histone-lysine N-methyltransferase 2D, ADP-ribose pyrophosphatase, mitochondrial, Peptidyl-prolyl cis-trans isomerase FKBP14, Transcription factor AP-2 alpha (Activating enhancer binding protein 2 alpha), isoform CRA_c, Putative pituitary tumor-transforming gene 3 protein, WW domain-containing transcription regulator protein 1, AP-5 complex subunit sigma-1, Protein EFR3 homolog A, Tubulin polyglutamylase TTLL7, BolA-like protein 3, MORC family CW-type zinc finger protein 3, Cleavage stimulation factor subunit 2 tau variant, Pleckstrin homology domain-containing family A member 5, Coronin-2B, Arpin, Reticulon-1, Centrosomal protein of 41 kDa, NEDD8-conjugating enzyme Ubc12, Protein S100-A13, ATP synthase subunit a, Fibronectin type-III domain-containing protein 3A, Serine/threonine-protein phosphatase 2A 56 kDa regulatory subunit delta isoform, Lipase maturation factor 1, Pituitary tumor-transforming gene 1 protein-interacting protein, GRAM domain-containing protein 1B, DNA topoisomerase 3-alpha, Uncharacterized protein, Dynamin-1, Cell division cycle protein 23 homolog, Pre-mRNA-splicing factor SYF1, Focal adhesion kinase 1, SH2B adapter protein 1, Breast cancer metastasis-suppressor 1-like protein, Putative protein N-methyltransferase FAM86B1, Dual specificity protein kinase CLK1, Non-structural maintenance of chromosomes element 4 homolog A, Nephrocystin-1, Ectonucleoside triphosphate diphosphohydrolase 6, Protein LSM12 homolog, Tubulin-tyrosine ligase-like protein 12, Leucine-rich repeat-containing protein 57, Nuclear factor 1 C-type, Diphosphoinositol polyphosphate phosphohydrolase 3-alpha, Ras and Rab interactor 1, Acyl-CoA dehydrogenase family member 10, Coiled-coil domain-containing protein 115, Serine/threonine-protein kinase B-raf, Arf-GAP with GTPase, ANK repeat and PH domain-containing protein 3, 28S ribosomal protein S15, mitochondrial, E3 ubiquitin-protein ligase NEDD4, Monofunctional C1-tetrahydrofolate synthase, mitochondrial, 3-hydroxybutyrate dehydrogenase type 2, Cysteine-rich with EGF-like domain protein 1, Zinc finger MYM-type protein 1, Exostosin-like 2, LysM and putative peptidoglycan-binding domain-containing protein 2, SLAIN motif-containing protein 2, SWI/SNF complex subunit SMARCC1, Charged multivesicular body protein 1a, Cytochrome c oxidase assembly protein COX14, Uncharacterized protein KIAA1522, Kinesin-like protein KIF2C, Protein-cysteine N-palmitoyltransferase HHAT, Deoxyguanosine kinase, mitochondrial, Potassium voltage-gated channel subfamily G member 1, Thyroid transcription factor 1-associated protein 26, Centrosomal protein of 89 kDa, Leucine zipper putative tumor suppressor 1, Rap guanine nucleotide exchange factor 6, Histone-lysine N-methyltransferase EHMT2, Fanconi anemia group C protein, COBW domain-containing protein 5, MICAL-like protein 2, Zinc finger protein 217, Protein CASC3, GPI-anchor transamidase, Caspase-8, Centrin-1, Ubiquitin carboxyl-terminal hydrolase 43, Protein deglycase DJ-1, Zinc finger and BTB domain-containing protein 2, Dual specificity mitogen-activated protein kinase kinase 1, Rho-related GTP-binding protein RhoE, Reticulon-3, Sialin, Kit ligand, Nuclear receptor coactivator 3, Calmodulin-regulated spectrin-associated protein 2, Wiskott-Aldrich syndrome protein family member 2, Histone H1x, Mothers against decapentaplegic homolog 6, Activating transcription factor 7-interacting protein 2, Uncharacterized protein C17orf112, Leukocyte tyrosine kinase receptor, PRELI domain containing protein 3A, Sugar phosphate exchanger 3, Type I inositol 3,4-bisphosphate 4-phosphatase, E3 ubiquitin-protein ligase TRIM38, DNA primase small subunit, Pleckstrin homology-like domain family B member 2, GDH/6PGL endoplasmic bifunctional protein, D-beta-hydroxybutyrate dehydrogenase, mitochondrial, Ubiquitin carboxyl-terminal hydrolase isozyme L5, Chloride channel CLIC-like protein 1, Zinc finger SWIM domain-containing protein 7, mRNA-decapping enzyme 1A, Centromere protein J, G protein pathway suppressor 2, Protein CYR61, Rho guanine nucleotide exchange factor 35, Integrin alpha-7, Transcriptional coactivator YAP1, Spermatogenesis-associated serine-rich protein 2, Myotubularin-related protein 14, GATS-like protein 2, Oxidative stress-responsive serine-rich protein 1, Tigger transposable element-derived protein 2, Mediator of RNA polymerase II transcription subunit 20, Guanine nucleotide-binding protein G(I)/G(S)/G(O) subunit gamma-12, Mediator of RNA polymerase II transcription subunit 25, Protein FAM84B, Protein FAN, Nitric oxide synthase-interacting protein, Striatin, Phosducin-like protein, Protein fuzzy homolog, Tubby-related protein 3, SEC14 domain and spectrin repeat-containing protein 1, NHS-like protein 1, Lysine-specific demethylase 3A, TGF-beta-activated kinase 1 and MAP3K7-binding protein 2, LON peptidase N-terminal domain and RING finger protein 1, DNA topoisomerase 2-binding protein 1, MAP7 domain-containing protein 3, BRCA1-associated RING domain protein 1, DNA-directed RNA polymerase, mitochondrial, GAS2-like protein 3, Probable 8-oxo-dGTP diphosphatase NUDT15, Transmembrane and TPR repeat-containing protein 2, Selenoprotein N, Zinc finger protein 383, Tumor necrosis factor receptor superfamily member 3, Transmembrane protein 39A, Tetraspanin-10, Serine/threonine-protein kinase LATS2, BRF1 protein, Apoptosis-inducing factor 2, GLTSCR1-like protein, Calmodulin-binding transcription activator 1, Syndecan-3, Uncharacterized protein C1orf198, Cell division cycle protein 20 homolog, SH3 domain-containing protein 19, Ephrin-A5, Synphilin-1, SWI/SNF-related matrix-associated actin-dependent regulator of chromatin subfamily D member 1, Protein FAM204A, Dual specificity mitogen-activated protein kinase kinase 3, Germinal-center associated nuclear protein, Protein transport protein Sec24B, Putative UDP-GlcNAc:betaGal beta-1,3-N-acetylglucosaminyltransferase LOC100288842, Glycogenin-2, EF-hand calcium-binding domain-containing protein 11, ATP-dependent 6-phosphofructokinase, liver type, Hydroxyacylglutathione hydrolase-like protein, StAR-related lipid transfer protein 13, Dynactin subunit 3, Alpha-internexin, Dehydrogenase/reductase SDR family member on chromosome X, Transcription initiation factor IIA subunit 1, Copine-2, Acyl-CoA:lysophosphatidylglycerol acyltransferase 1, Dolichyl-diphosphooligosaccharide-protein glycosyltransferase subunit 4, Fas-activated serine/threonine kinase, Zinc finger CCCH domain-containing protein 7A, Golgin-45, Oxidoreductase HTATIP2, Neuronal regeneration-related protein, E3 ubiquitin-protein ligase TRIM23, Vacuolar protein sorting-associated protein 45, Sulfate anion transporter 1, Uncharacterized protein C5orf42, Small nuclear ribonucleoprotein Sm D3, Selenoprotein K, Bcl-2 homologous antagonist/killer, Mitochondrial peptide methionine sulfoxide reductase, Latent-transforming growth factor beta-binding protein 3, Uncharacterized protein C11orf80, Integrin alpha-11, A-kinase anchor protein 12, Ras-related protein Rab-1B, Acetyl-CoA carboxylase 2, RNA-binding motif protein, X-linked 2, Tubulin-specific chaperone C, Tensin-3, Uncharacterized protein CXorf57, ER lumen protein-retaining receptor 3, Disabled homolog 2-interacting protein, 7-methylguanosine phosphate-specific 5'-nucleotidase, Ataxin-2, Caveolin-2, Calcium-responsive transactivator, Melanophilin, Coiled-coil domain-containing protein 130, Alpha-actinin-3, Serine/threonine-protein kinase ULK3, Myelin expression factor 2, Multifunctional methyltransferase subunit TRM112-like protein, Protein FAM214A, Potassium voltage-gated channel subfamily KQT member 5, Sialate O-acetylesterase, Protein ELFN1, TATA-box-binding protein, Mitogen-activated protein kinase kinase kinase 12, Aurora kinase A-interacting protein, Tetratricopeptide repeat protein 12, Transcription factor E2F4, CAP-Gly domain-containing linker protein 4, Glutamine synthetase, Signal peptide peptidase-like 2A, Glucoside xylosyltransferase 1, GEM-interacting protein, Zinc finger protein 277, Ubiquitin carboxyl-terminal hydrolase 14, Calcium-binding mitochondrial carrier protein Aralar1, N(G),N(G)-dimethylarginine dimethylaminohydrolase 1, GTP-binding protein Rit1, Matrix Gla protein, Cell surface glycoprotein MUC18, Polypeptide N-acetylgalactosaminyltransferase 5, Calcyphosin, PEST proteolytic signal-containing nuclear protein, Serine/threonine-protein kinase Nek7, Calpain-3, Membrane-associated transporter protein, V-type proton ATPase subunit B, kidney isoform, Sialidase-4, Zinc finger protein 552, Colipase-like protein 2, ATP-binding cassette sub-family G member 1, Fumarate hydratase, mitochondrial, Protein phosphatase inhibitor 2, Tyrosine-protein kinase HCK, 2-oxoglutarate dehydrogenase, mitochondrial, Uncharacterized protein ENSP00000382042, Testicular acid phosphatase, Lysosomal acid phosphatase, Protein FAM195A, Nuclear inhibitor of protein phosphatase 1, Exosome complex component CSL4, Sodium-coupled neutral amino acid transporter 5, Protein arginine N-methyltransferase 5, Peptidase M20 domain-containing protein 2, Drebrin, NAD(P)H-hydrate epimerase, 1-phosphatidylinositol 4,5-bisphosphate phosphodiesterase beta-1, DCN1-like protein 2, DnaJ homolog subfamily B member 9, NACHT, LRR and PYD domains-containing protein 7, Cystatin-B, Fatty aldehyde dehydrogenase, D(2) dopamine receptor, Reticulon-2, COBW domain-containing protein 6, Myosin light chain 1/3, skeletal muscle isoform, Zinc finger Ran-binding domain-containing protein 2, Peptidyl-prolyl cis-trans isomerase FKBP1A, Immunoglobulin superfamily member 10, Olfactomedin-like protein 2B, Proteasome activator complex subunit 1, Putative uncharacterized protein C10orf113, Protein disulfide-isomerase TMX3, Plastin-2, Transmembrane protein 14D, Nck-associated protein 1-like, CXXC-type zinc finger protein 1, Guanine nucleotide-binding protein G(s) subunit alpha isoforms XLas, Integrator complex subunit 10, Protein FAM217A, HAUS augmin-like complex subunit 8, Mesoderm development candidate 1, Zinc finger protein 827, DNA-directed RNA polymerase I subunit RPA49, Symplekin, Protein spinster homolog 3, 28S ribosomal protein S9, mitochondrial, Melanocyte-stimulating hormone receptor, Enteropeptidase, Poly(A) polymerase gamma, Ribosomal RNA processing protein 1 homolog A, Disintegrin and metalloproteinase domain-containing protein 15, Activator of basal transcription 1, Ribonuclease K6, Centromere protein N, Olfactory receptor 5K3, N-acetyllactosaminide beta-1,6-N-acetylglucosaminyl-transferase, isoform A, Serine/threonine-protein phosphatase 6 regulatory subunit 1, Leukocyte-associated immunoglobulin-like receptor 1, 39S ribosomal protein L44, mitochondrial, Ig lambda-2 chain C regions, Sialoadhesin, Transmembrane inner ear expressed protein, Tetraspanin-18, Protein-glutamine gamma-glutamyltransferase 4, Endothelin-1 receptor, Protein FAM127A, Period circadian protein homolog 1, Autism susceptibility gene 2 protein, Voltage-dependent T-type calcium channel subunit alpha-1G, Protein Hook homolog 2, Cyclin-Y-like protein 2, BPI fold-containing family A member 2, Solute carrier family 2, facilitated glucose transporter member 2, Peroxidasin-like protein, Mitochondrial import receptor subunit TOM6 homolog, Phosphorylase b kinase gamma catalytic chain, skeletal muscle/heart isoform, Inosine-5'-monophosphate dehydrogenase 1, Proline and serine-rich protein 3, WD repeat-containing protein 54, Protein FAM117A, Carboxylesterase 3, Bardet-Biedl syndrome 7 protein, Exocyst complex component 5, Probable phospholipid-transporting ATPase VA, Pre-B-cell leukemia transcription factor-interacting protein 1, MICAL C-terminal-like protein, Protein transport protein Sec24C, Epiplakin, Inactive ubiquitin carboxyl-terminal hydrolase 17-like protein 4, Kinesin heavy chain isoform 5A, Hyaluronan and proteoglycan link protein 2, Intraflagellar transport protein 46 homolog, Kinesin-like protein KIF21 B, OTU domain-containing protein 6B, C—X—C motif chemokine 9, Uncharacterized protein CXorf23, Centrosomal protein of 170 kDa protein B, Testis-specific Y-encoded-like protein 2, Oxysterols receptor LXR-beta, Williams-Beuren syndrome chromosomal region 16 protein, Zinc finger protein 559, Glutamate-rich protein 3, GLIPR1-like protein 2, Pleckstrin homology domain-containing family G member 3, Putative vomeronasal receptor-like protein 4, Gamma-glutamyltransferase 6, Serine/threonine-protein kinase pim-3, Ribonuclease H2 subunit C, Neurexin-3, Mucin-16, Non-structural maintenance of chromosomes element 1 homolog, E2F-associated phosphoprotein, Actin-binding LIM protein 1, Non-canonical poly(A) RNA polymerase PAPD7, Nuclear receptor-binding factor 2, Gypsy retrotransposon integrase-like protein 1, Monocarboxylate transporter 4, Coiled-coil domain-containing protein 60, Inactive phospholipase D5, Microtubule cross-linking factor 1, ATP synthase subunit delta, mitochondrial, G patch domain-containing protein 2, Protein disulfide-isomerase A2, ATP-binding cassette sub-family A member 9, Unconventional myosin-Ih, Band 4.1-like protein 1, Gigaxonin, Acyl-CoA-binding domain-containing protein 6, Complement receptor type 2, Eukaryotic elongation factor 2 kinase, Large subunit GTPase 1 homolog, tRNA (uracil(54)-C(5))-methyltransferase homolog, Nectin-1, Zinc finger protein 460, Ras association domain-containing protein 2, SLIT-ROBO Rho GTPase-activating protein 3, ETS domain-containing protein Elk-4, Nucleoporin-like protein 2, U2 small nuclear ribonucleoprotein auxiliary factor 35 kDa subunit-related protein 2, Bestrophin-3, Heparan-alpha-glucosaminide N-acetyltransferase, Protein SGT1 homolog, Choline-phosphate cytidylyltransferase B, Fibrillin-3, GPALPP motifs-containing protein 1, Meiosis arrest female protein 1, ETS domain-containing protein Elk-3, Embigin, Protein TFG, Phosphomannomutase 2, V-type proton ATPase subunit G 1, T-box transcription factor TBX20, Beta-1,3-galactosyltransferase 5, Olfactory receptor 12D2, Laminin subunit alpha-5, Forkhead box protein O3, Tumor necrosis factor receptor superfamily member 18, Leukocyte elastase inhibitor, Solute carrier family 22 member 9, Nuclease EXOG, mitochondrial, Leucine-rich repeat LGI family member 4, Anosmin-1, Centrosomal protein of 152 kDa, Selenocysteine-specific elongation factor, Hairy/enhancer-of-split related with YRPW motif protein 1, Scaffold attachment factor B1, Cytochrome b-c1 complex subunit 2, mitochondrial, Tetratricopeptide repeat protein 8, Ubiquitin carboxyl-terminal hydrolase 1, Phospholipid phosphatase 5, Zinc finger protein 623, Zinc finger protein 791, Zinc finger protein with KRAB and SCAN domains 1, Zinc finger protein 397, O-acetyl-ADP-ribose deacetylase MACROD1, Ig lambda chain V-II region BOH, Ig kappa chain V-I region Walker, MYCBP-associated protein, 60S ribosomal protein L36a, Phospholipase ABHD3, TBC1 domain family member 9, Ras GTPase-activating protein 1, Solute carrier family 35 member E2B, Calcium channel flower homolog, T-cell-specific surface glycoprotein CD28, Sterile alpha motif domain-containing protein 9-like, Hydroxysteroid dehydrogenase-like protein 2, Tripartite motif-containing protein 26, Vitamin D 25-hydroxylase, Pre-mRNA-splicing factor SLU7, WD repeat-containing protein 75, Zinc finger protein 213, Zinc finger protein 845, Ras-related protein Rab-6A, Zinc finger protein 264, Estradiol 17-beta-dehydrogenase 8, Dual specificity protein phosphatase 16, Protein lin-7 homolog C, Major vault protein, Interferon-induced protein 44, Golgi pH regulator A, Ethanolamine kinase 1, Phosphatidylinositol 3-kinase regulatory subunit alpha, Protein phosphatase 1K, mitochondrial, Transmembrane protein 222, DC-STAMP domain-containing protein 2, Basic salivary proline-rich protein 4, Ig kappa chain V-I region WAT, Fibronectin, FERM domain-containing protein 3, Zinc finger protein 507, NADH dehydrogenase [ubiquinone] 1 alpha subcomplex subunit 8, Olfactory receptor 812, Dual adapter for phosphotyrosine and 3-phosphotyrosine and 3-phosphoinositide, Splicing factor 3A subunit 2, Dynein heavy chain 6, axonemal, HLA class I histocompatibility antigen, A-30 alpha chain, Tryptophan 2,3-dioxygenase, MKL/myocardin-like protein 1, Rho guanine nucleotide exchange factor 5, Protein phosphatase 2C-like domain-containing protein 1, Histatin-3, 60S ribosomal protein L36a-like, Cancer/testis antigen 47A, Centrosomal protein of 97 kDa, Thyroid hormone receptor-associated protein 3, Beta-galactoside alpha-2,6-sialyltransferase 2, Transcription factor ETV6, Gamma-glutamyltranspeptidase 1, Suppression of tumorigenicity 18 protein, Calpain-12, Neuropeptide FF receptor 1, AP-1 complex subunit gamma-like 2, Uncharacterized protein C2orf16, Programmed cell death protein 10, TBC1 domain family member 2B, Hematopoietic SH2 domain-containing protein, Thrombospondin type-1 domain-containing protein 7B, Paired box protein Pax-9, Mucin-3A, 5-phosphohydroxy-L-lysine phospho-lyase, Extracellular matrix protein FRAS1, Transmembrane protein 201, Monoacylglycerol lipase ABHD12, Low-density lipoprotein receptor-related protein 1 B, DENN domain-containing protein 1A, Basic helix-loop-helix domain-containing protein KIAA2018, Olfactory receptor 5H15, Leucine-rich repeat-containing protein 16A, Calcium/calmodulin-dependent protein kinase type 1, G-protein coupled receptor 98, Tumor suppressor candidate 2, Stress-associated endoplasmic reticulum protein 1, Annexin A7, Tetraspanin-8, 60S ribosomal protein L12, Probable ATP-dependent RNA helicase DDX52, Ribulose-phosphate 3-epimerase, Eukaryotic translation initiation factor 5B, Ubiquitin carboxyl-terminal hydrolase 40, Trace amine-associated receptor 6, Tetrapeptide repeat homeobox protein 1, Serine/threonine-protein phosphatase 4 regulatory subunit 2, Protein capicua homolog, Sphingomyelin phosphodiesterase 3, Sodium channel protein type 5 subunit alpha, Calcineurin subunit B type 2, Methylcrotonoyl-CoA carboxylase subunit alpha, mitochondrial, Kelch repeat and BTB domain-containing protein 12, Titin, NADH dehydrogenase [ubiquinone] 1 beta subcomplex subunit 1, Pre-mRNA-splicing factor SYF2, Zinc finger protein 215, Collagen alpha-6(VI) chain, Zinc finger protein 491, Phosphoenolpyruvate carboxykinase, cytosolic [GTP], Zinc finger protein 726, PDZ domain-containing protein 8, Zinc finger protein 470, Glucose-6-phosphate translocase, Protein bassoon, Ciliogenesis-associated TTC17-interacting protein, Heparan-sulfate 6-O-sulfotransferase 2, Stabilin-2, Desmoglein-2, Tumor necrosis factor ligand superfamily member 11, Arginase-1, Repetin, Potassium-transporting ATPase alpha chain 1, C1GALT1-specific chaperone 1, UPF0729 protein C18orf32, Cholesterol 24-hydroxylase, Spermidine synthase, TRAF-interacting protein with FHA domain-containing protein A, Protein FAM 173B, Leydig cell tumor 10 kDa protein homolog, Brain-specific angiogenesis inhibitor 1-associated protein 2-like protein 1, General transcription factor 3C polypeptide 4, Synaptojanin-2, Protein KIAA2022, Regulatory factor X-associated protein, Prefoldin subunit 3, Poly(ADP-ribose) glycohydrolase, Sorting nexin-29, 3-hydroxyisobutyryl-CoA hydrolase, mitochondrial, Oxysterol-binding protein 1, F-BAR and double SH3 domains protein 2, Remodeling and spacing factor 1, Zymogen granule protein 16 homolog B, Ubiquitin carboxyl-terminal hydrolase 3, Rap guanine nucleotide exchange factor 2, Dynein heavy chain 1, axonemal, Dedicator of cytokinesis protein 3, Nucleoporin p58/p45, MARCKS-related protein, MARVEL domain-containing protein 2, ADP-ribosylation factor-binding protein GGA2, Cancer-related nucleoside-triphosphatase, Unconventional myosin-Vllb, Cyclin-dependent kinase-like 5, Dol-P-Glc:Glc(2)Man(9)GlcNAc(2)-PP-Dol alpha-1,2-glucosyltransferase, Leucine-rich repeat-containing protein 40, Solute carrier family 7 member 13, Aromatase, Thromboxane-A synthase, Hypoxia up-regulated protein 1, Translin, ADP-ribosylation factor-like protein 11, Peptidylprolyl isomerase domain and WD repeat-containing protein 1, Proto-oncogene vav, Protein mab-21-like 3, Suppressor of tumorigenicity 7 protein-like, Apolipoprotein B receptor, Dystrophin-related protein 2, Orexin receptor type 1, Nucleolar protein 16, 60S ribosomal protein L29, Potassium-transporting ATPase alpha chain 2, Sodium-driven chloride bicarbonate exchanger, Uncharacterized protein C9orf171, Ankyrin repeat and LEM domain-containing protein 1, Vasohibin-2, Putative nuclease HARBI1, Hyaluronidase-4, G-protein coupled receptor family C group 6 member A, Nucleoporin Nup43, Delta(14)-sterol reductase, Phospholipid-transporting ATPase ID, GTP-binding protein 1, G patch domain-containing protein 8, IQ motif and SEC7 domain-containing protein 1, Selenoprotein S, DnaJ homolog subfamily C member 13, Leucine-rich repeat and fibronectin type-III domain-containing protein 4, Dynein heavy chain 9, axonemal, Dynein heavy chain 10, axonemal, Echinoderm microtubule-associated protein-like 4, Melatonin receptor type 1A, CTP synthase 2, Ubiquitin-like modifier-activating enzyme ATG7, Carboxy-terminal domain RNA polymerase II polypeptide A small phosphatase 1, Neutrophil cytosol factor 4, Collagen alpha-2(IV) chain, Protein unc-13 homolog C, TBC1 domain family member 4, Acyl-coenzyme A synthetase ACSM5, mitochondrial, FH1/FH2 domain-containing protein 1, FYVE, RhoGEF and PH domain-containing protein 5, Cilia- and flagella-associated protein 54, Alpha-ketoglutarate-dependent dioxygenase alkB homolog 7, mitochondrial, WD repeat-containing protein 7, Transcription factor SOX-30, Cationic amino acid transporter 3, Mitogen-activated protein kinase kinase kinase 10, Glypican-4, Transmembrane protein with metallophosphoesterase domain, Transcription factor SOX-6, 28S ribosomal protein S14, mitochondrial, Steroid 21-hydroxylase, XK-related protein 5, N-acetylated-alpha-linked acidic dipeptidase 2, Mucin-17, Butyrophilin-like protein 8, Zinc finger protein 28, Major facilitator superfamily domain-containing protein 9, Small nuclear ribonucleoprotein-associated protein N, Coiled-coil domain-containing protein 42A, Frizzled-4, Putative tripartite motif-containing protein 49B, C—C chemokine receptor type 9, Centrosomal protein of 72 kDa, Adenosine receptor A2b, Protein CREG1, P2X purinoceptor 7, F-box only protein 44, BEN domain-containing protein 1, Rho guanine nucleotide exchange factor 11, Lethal(3)malignant brain tumor-like protein 3, Metalloreductase STEAP2, CD97 antigen, Putative uncharacterized protein ENSP00000381562, Ubiquitin carboxyl-terminal hydrolase isozyme L3, Transmembrane protein 114, Leucine-twenty homeobox, Protein Tob1, Deoxyribonuclease-1-like 1, Neuronal acetylcholine receptor subunit alpha-4, Lymphocyte antigen 86, Dentin matrix acidic phosphoprotein 1, Striatin-interacting protein 1, Zinc finger protein 425, Inactive phospholipase C-like protein 1, Tyrosine-protein phosphatase non-receptor type 2, SPARC-related modular calcium-binding protein 1, NACHT, LRR and PYD domains-containing protein 4, Olfactory receptor 4K1, BUB3-interacting and GLEBS motif-containing protein ZNF207, Protein SSX4, Putative uncharacterized protein ENSP00000383407, von Willebrand factor A domain-containing protein 5B2, Cytochrome c oxidase subunit 8C, mitochondrial, Retrotransposon gag domain-containing protein 1, Nuclear receptor coactivator 2, Laminin subunit alpha-2, Toll-like receptor 3, Transmembrane channel-like protein 2, Clathrin coat assembly protein AP180, RING finger protein 148, Zinc finger protein ZFPM2, Cerebral dopamine neurotrophic factor, Testis- and ovary-specific PAZ domain-containing protein 1, Vomeronasal type-1 receptor 3, Receptor expression-enhancing protein 2, Secretogranin-1, Protocadherin-19, Protein RMD5 homolog A, Protein dopey-2, Protein FAM193A, Vesicle transport protein SFT2B, C—X—C chemokine receptor type 4, Sialic acid-binding Ig-like lectin 9, Leucine-rich repeat and calponin homology domain-containing protein 2, Dynein regulatory complex protein 1, Gamma-aminobutyric acid receptor subunit delta, Anaphase-promoting complex subunit CDC26, Nuclear transcription factor Y subunit alpha, Unconventional myosin-XV, Olfactory receptor 5D18, Sodium- and chloride-dependent glycine transporter 2, Peroxiredoxin-4, Leucine-rich repeat-containing protein 26, Dystrophia myotonica WD repeat-containing protein, Zinc finger protein 853, Integrin beta-6, AF4/FMR2 family member 2, RAS guanyl-releasing protein 2, Coiled-coil domain-containing protein 8, Cornulin, Metastasis-associated in colon cancer protein 1, Mitochondrial import inner membrane translocase subunit Tim17-B, Protocadherin Fat 4, Transmembrane protein 205, CX3C chemokine receptor 1, Inositol polyphosphate 5-phosphatase K, Torsin-3A, PAX-interacting protein 1, G protein-regulated inducer of neurite outgrowth 3, Class A basic helix-loop-helix protein 15, Glutathione peroxidase 7, N-terminal EF-hand calcium-binding protein 2, Ig heavy chain V-II region MCE, CDGSH iron-sulfur domain-containing protein 3, mitochondrial, Apolipoprotein L6, Synapsin-2, Chloride transport protein 6, dCTP pyrophosphatase 1, Histamine H1 receptor, Pyruvate dehydrogenase protein X component, mitochondrial, Mismatch repair endonuclease PMS2, CD160 antigen, Solute carrier family 15 member 3, tRNA dimethylallyltransferase, mitochondrial, Voltage-dependent L-type calcium channel subunit alpha-1D, Ras-related protein Rab-30, Colorectal mutant cancer protein, Beta-1,4-galactosyltransferase 6, Exophilin-5, Ribosome biogenesis protein TSR3 homolog, Actin filament-associated protein 1-like 2, Eukaryotic peptide chain release factor GTP-binding subunit ERF3B, Cytochrome c oxidase subunit 5A, mitochondrial, Protein ENL, CD2 antigen cytoplasmic tail-binding protein 2, Neurabin-2, von Willebrand factor A domain-containing protein 9, Ubiquitin carboxyl-terminal hydrolase 47, Mitochondrial carrier homolog 2, Max-binding protein MNT, Nuclear pore complex protein Nup85, N-alpha-acetyltransferase 35, NatC auxiliary subunit, Cyclic GMP-AMP synthase, Myosin light chain kinase 2, skeletal/cardiac muscle, C-type lectin domain family 4 member F, Proteasome assembly chaperone 4, Cytochrome c oxidase assembly protein COX15 homolog, R3H domain-containing protein 2, Protein FAM46A, DnaJ homolog subfamily C member 10, Androglobin, Ankyrin repeat domain-containing protein 13C, Eyes absent homolog 1, Histone-lysine N-methyltransferase EZH2, Bystin, Dipeptidyl peptidase 3, Deleted in malignant brain tumors 1 protein, Pleckstrin homology domain-containing family B member 1, Multidrug resistance-associated protein 4, CapZ-interacting protein, Mucin-20, AFG3-like protein 2, Obscurin, Lipase member J, Protein phosphatase 1 regulatory subunit 14B, Kinesin-like protein KIFC2, Sorting nexin-19, Mucin-7, Putative uncharacterized protein FLJ37218, Protein FAM78A, Cytochrome c oxidase subunit 7B, mitochondrial, 39S ribosomal protein L17, mitochondrial, CLOCK-interacting pacemaker, DNA-binding protein RFX7, Protein EVI2B, Copper-transporting ATPase 2, NADH dehydrogenase [ubiquinone] 1 beta subcomplex subunit 8, mitochondrial, Core-binding factor subunit beta, CWF19-like protein 2, E3 ubiquitin-protein ligase RING1, Ubiquitin-conjugating enzyme E2 A, Deoxyribonuclease-2-alpha, Intraflagellar transport protein 80 homolog, Protein yippee-like 3, Calcium-dependent secretion activator 1, Protein YIPF1, 7-dehydrocholesterol reductase, Gamma-tubulin complex component 6, Intraflagellar transport protein 140 homolog, Nuclear pore membrane glycoprotein 210-like, Ribonuclease 3, Protein S100-A7, Protein AF-17, Fanconi anemia group E protein, NEDD8-activating enzyme E1 catalytic subunit, WD repeat-containing protein 97, Hematological and neurological expressed 1 protein, Uncharacterized protein C20orf195, Putative glycosylation-dependent cell adhesion molecule 1, Nucleolar and coiled-body phosphoprotein 1, Intraflagellar transport protein 88 homolog, Syndecan-1, XK-related protein 9, Uncharacterized protein C9orf78, cTAGE family member 5, Glutaryl-CoA dehydrogenase, mitochondrial, BMP/retinoic acid-inducible neural-specific protein 2, Homeodomain-interacting protein kinase 3, Bone marrow stromal antigen 2, Myocyte-specific enhancer factor 2C, Stromal cell-derived factor 2, Lymphoid-restricted membrane protein, Myosin-binding protein H-like, WD repeat-containing protein 5, Disintegrin and metalloproteinase domain-containing protein 17, Cerebral cavernous malformations 2 protein, DNA dC→dU-editing enzyme APOBEC-3C, Protein FAM185A, Far upstream element-binding protein 2, Vacuolar protein sorting-associated protein VTA1 homolog, TBC1 domain family member 30, Intercellular adhesion molecule 1, Vesicular, overexpressed in cancer, prosurvival protein 1, Translocating chain-associated membrane protein 2, Target of Nesh-SH3, Serine/threonine-protein kinase VRK1, Uncharacterized protein DKFZp434B061, Putative coiled-coil-helix-coiled-coil-helix domain-containing protein CHCHD2P9, mitochondrial, Ataxin-7, Eukaryotic translation initiation factor 3 subunit G, Serine/threonine-protein phosphatase 2A 65 kDa regulatory subunit A beta isoform, Exocyst complex component 3, Cathepsin B, G1/S-specific cyclin-E1, Ubiquitin carboxyl-terminal hydrolase 30, Ubiquitin carboxyl-terminal hydrolase 51, Interleukin-1 receptor accessory protein-like 1, Ankyrin-1, Transmembrane protein 106C, Phosphatidylinositol transfer protein alpha isoform, Transportin-2, Polyhomeotic-like protein 3, Charged multivesicular body protein 2b, Ubiquitin D, RING finger protein unkempt homolog, Protein SMG7, E3 ubiquitin-protein ligase RNF144A, Mediator of RNA polymerase II transcription subunit 15, Cytochrome c oxidase subunit 8A, mitochondrial, NADH dehydrogenase [ubiquinone] flavoprotein 3, mitochondrial, Calcipressin-1, Vesicle-fusing ATPase, Putative ATP-dependent RNA helicase DHX33, Alpha-synuclein, Carbonic anhydrase 2, Complement factor H, RalBP1-associated Eps domain-containing protein 2, Semaphorin-3A, Core histone macro-H2A.2, Melanotransferrin, SKI family transcriptional corepressor 2, Collagen alpha-1 (VI) chain, Dachshund homolog 1, Protein BTG1, Cyclin-dependent kinase 18, T-box transcription factor TBX2, IgGFc-binding protein, Voltage-dependent L-type calcium channel subunit alpha-1C, Zinc finger protein 516, Guanine nucleotide-binding protein G(olf) subunit alpha, Melanoma-associated antigen 9, Protocadherin gamma-B2, RING finger protein 112, Transcription factor SOX-10, Peroxisome assembly protein 12, Collagen alpha-1(XI) chain, Tripartite motif-containing protein 67, H(+)/Cl(−) exchange transporter 5, Probable phospholipid-transporting ATPase VB, Aldose reductase, Receptor-type tyrosine-protein phosphatase zeta, Kinesin-like protein KIF2A, Arginyl-tRNA-protein transferase 1, ATP synthase subunit epsilon, mitochondrial, Alpha-protein kinase 2, Putative hexokinase HKDC1, Metastasis-associated protein MTA1, Seizure 6-like protein 2, Chloride channel protein 2, RNA 3'-terminal phosphate cyclase, Poly(rC)-binding protein 4, Oxidation resistance protein 1, Kinesin light chain 4, E3 ubiquitin-protein ligase TRIM33, Receptor-type tyrosine-protein phosphatase gamma, Chromobox protein homolog 8, Cathepsin F, Integrin beta-8, C-type lectin domain family 11 member A, Keratin, type I cytoskeletal 27, Ankyrin repeat and SAM domain-containing protein 1A, Eukaryotic translation initiation factor 2-alpha kinase 4, Transforming growth factor-beta-induced protein ig-h3, Jerky protein homolog, Fucose-1-phosphate guanylyltransferase, ATP-binding cassette sub-family A member 13, Sodium-dependent phosphate transporter 2, Outer dense fiber protein 2-like, G1/S-specific cyclin-D1, Phosphatidylinositol 3-kinase catalytic subunit type 3, Immunity-related GTPase family Q protein, Transmembrane O-methyltransferase, Sulfate transporter, Protein eva-1 homolog A, Putative tyrosine-protein phosphatase auxilin, Ankyrin repeat and SOCS box protein 11, Protein cordon-bleu, Bestrophin-1, Putative ribosome-binding factor A, mitochondrial, Protocadherin gamma-A2, Formin-1, Nuclear receptor subfamily 1 group D member 2, Interleukin-17 receptor D, Rootletin, Serine incorporator 5, Glutamate receptor ionotropic, kainate 3, Plexin-A2, tRNA (uracil-5-)-methyltransferase homolog A, WD repeat-containing protein 60, Hemicentin-1, E3 ubiquitin-protein ligase MIB2, Lysosome-associated membrane glycoprotein 1, Dynein heavy chain domain-containing protein 1, Uncharacterized protein C17orf51, UPF0669 protein C6orf120, La-related protein 7, DNA-binding protein RFX5, Alpha-1-syntrophin, Nance-Horan syndrome protein, Dickkopf-related protein 3, Voltage-dependent T-type calcium channel subunit alpha-1H, HLA class I histocompatibility antigen, A-69 alpha chain, F-box/LRR-repeat protein 18, Arrestin domain-containing protein 1, Membrane-associated guanylate kinase, WW and PDZ domain-containing protein 2, Receptor-type tyrosine-protein phosphatase mu, Thioredoxin domain-containing protein 12, Adhesion G protein-coupled receptor A3, Proline synthase co-transcribed bacterial homolog protein, Solute carrier family 52, riboflavin transporter, member 2, Cystic fibrosis transmembrane conductance regulator, Kinesin-like protein KIF3C, Endothelin B receptor, Sideroflexin-3, Tubulin alpha-3E chain, SH3 domain-containing RING finger protein 3, GTP-binding protein Di-Ras2, Low-density lipoprotein receptor-related protein 2, Pirin, Trinucleotide repeat-containing gene 6C protein, Fanconi anemia group B protein, Coagulation factor VIII, E3 ubiquitin-protein ligase TRIM13, Lysophosphatidic acid receptor 1, Collagen alpha-1(XXII) chain, Low affinity sodium-glucose cotransporter, Density-regulated protein, Uncharacterized protein C15orf52, Zinc finger SWIM domain-containing protein 6, Protocadherin gamma-A12, Importin subunit alpha-3, Cubilin, Putative segment polarity protein dishevelled homolog DVL1P1, Aggrecan core protein, Prohibitin-2, Rho GTPase-activating protein 33, Myotubularin-related protein 3, Phosphorylase b kinase regulatory subunit alpha, skeletal muscle isoform, Biotin-protein ligase, 1-phosphatidylinositol 4,5-bisphosphate phosphodiesterase beta-4, Protein AHNAK2, Inosine triphosphate pyrophosphatase, Cadherin-2, DNA helicase MCM9, Putative signal peptidase complex catalytic subunit SEC11 B, Maestro heat-like repeat-containing protein family member 6, Prolyl 4-hydroxylase subunit alpha-2, Integral membrane protein DGCR2/IDD, Zinc finger protein 469, Sorbin and SH3 domain-containing protein 1, Multidrug resistance-associated protein 5, Down syndrome critical region protein 3, V-set and immunoglobulin domain-containing protein 10-like, Coronin-6, Kinesin-like protein KIF13B, Tribbles homolog 2, STAM-binding protein, Zinc finger E-box-binding homeobox 2, FERM domain-containing protein 5, Tropomodulin-2, Lymphoid enhancer-binding factor 1, General receptor for phosphoinositides 1-associated scaffold protein, Dedicator of cytokinesis protein 10, Protein ITFG3, Heat shock protein beta-8, Secretory phospholipase A2 receptor, FYVE, RhoGEF and PH domain-containing protein 6, Ankyrin repeat domain-containing protein SOWAHB, Nurim, Integral membrane protein GPR137C, Keratin, type II cytoskeletal ib, Netrin receptor UNC5A, Receptor-type tyrosine-protein phosphatase C, UPF0606 protein KIAA1549, RNA-binding protein Nova-1, Zinc finger protein 317, Lysophosphatidylcholine acyltransferase 2, Aspartate aminotransferase, mitochondrial, Histone-lysine N-methyltransferase SETDB1, Frizzled-1, ATP-binding cassette sub-family C member 11, Arf-GAP with SH3 domain, ANK repeat and PH domain-containing protein 3, Sodium-dependent phosphate transport protein 2C, Dynein light chain 4, axonemal, Cyclin-dependent kinase 3, Vitamin K-dependent gamma-carboxylase, BTB/POZ domain-containing protein KCTD15, Cyclin-related protein FAM58A, Tripartite motif-containing protein 2, Calcium/calmodulin-dependent 3',5'-cyclic nucleotide phosphodiesterase 1C, Guanine nucleotide-binding protein subunit beta-4, Ubiquitin-like-conjugating enzyme ATG10, Protein SMG8, Putative bifunctional UDP-N-acetylglucosamine transferase and deubiquitinase ALG13, Protein naked cuticle homolog 1, Protein S100-A1, Paraneoplastic antigen Ma2, Transmembrane protein 106B, Hephaestin, POU domain, class 2, transcription factor 1, Maltase-glucoamylase, intestinal, Kelch domain-containing protein 8B, VWFA and cache domain-containing protein 1, Adenylate kinase isoenzyme 5, BTB/POZ domain-containing protein KCTD9, Ankyrin-3, TBC1 domain family member 8B, Intraflagellar transport protein 56, G-protein coupled receptor 56, Protocadherin Fat 3, Cortactin-binding protein 2, 5,6-dihydroxyindole-2-carboxylic acid oxidase, Multidrug and toxin extrusion protein 1, Peroxisome biogenesis factor 1, NADH dehydrogenase [ubiquinone] 1 alpha subcomplex subunit 9, mitochondrial, Ropporin-1A, Histone deacetylase 11, Collagen alpha-1(VIII) chain, Zinc finger HIT domain-containing protein 1, Citron Rho-interacting kinase, Uncharacterized protein C20orf194, Sodium/potassium/calcium exchanger 1, Paired box protein Pax-1, Homeobox protein TGIF1, Transmembrane 9 superfamily member 4, CUB and sushi domain-containing protein 1, FRAS1-related extracellular matrix protein 1, Leucine-rich repeat protein 1, Protein FAM127B, 2-hydroxyacylsphingosine 1-beta-galactosyltransferase, Glioma tumor suppressor candidate region gene 1 protein, Tectonic-1, Zinc finger protein 618, Palmitoyl-protein thioesterase 1, Serine/threonine-protein kinase 36, Tetratricopeptide repeat protein 31, Neurobeachin, Adenosylhomocysteinase 3, Sickle tail protein homolog, Fibrocystin, Mastermind-like protein 2, Frizzled-8, Vesicle transport protein SFT2C, Pecanex-like protein 2, Suppression of tumorigenicity 5 protein, Zinc finger and BTB domain-containing protein 10, Matrix metalloproteinase-24, Peroxisomal biogenesis factor 19, Protein piccolo, Prostaglandin reductase 1, Electrogenic sodium bicarbonate cotransporter 4, Neuronal PAS domain-containing protein 3, Homeobox even-skipped homolog protein 2, Keratin, type II cytoskeletal 3, Protein Jumonji, Lipoprotein lipase, Interferon alpha-inducible protein 27, mitochondrial, Zinc finger ZZ-type and EF-hand domain-containing protein 1, Mesoderm induction early response protein 3, Equilibrative nucleoside transporter 1, Prominin-2, Zinc finger and BTB domain-containing protein 39, Heat shock 70 kDa protein 12A, Sodium- and chloride-dependent creatine transporter 1, Rho GTPase-activating protein 23, Ciliary neurotrophic factor, Sodium-dependent multivitamin transporter, Elastin, Bifunctional heparan sulfate N-deacetylase/N-sulfotransferase 3, 28 kDa heat- and acid-stable phosphoprotein, Receptor-type tyrosine-protein phosphatase T, Protein farnesyltransferase subunit beta, Contactin-associated protein-like 3B, DnaJ homolog subfamily B member 11, Actin-like protein 6B, G-protein coupled receptor 143, Purine nucleoside phosphorylase, Testis anion transporter 1, Disco-interacting protein 2 homolog C, Zinc transporter ZIP14, RNA pseudouridylate synthase domain-containing protein 1, E3 ubiquitin-protein ligase HERC2, Lysophosphatidic acid phosphatase type 6, Glucocorticoid modulatory element-binding protein 2, Complement receptor type 1, Fibrillin-2, Tyrosine-protein phosphatase non-receptor type substrate 1, Myosin-Illb, Collagen alpha-2(XI) chain, Collagen alpha-1(Ill) chain, Collagen alpha-3(IV) chain, REST corepressor 2, Collagen alpha-1(V) chain, Tyrosine-protein phosphatase non-receptor type 21, FH2 domain-containing protein 1, CDK-activating kinase assembly factor MAT1, Alpha-1,3-mannosyl-glycoprotein 4-beta-N-acetylglucosaminyltransferase B, Protein-methionine sulfoxide oxidase MICAL1, A-kinase anchor protein 8, Ribosomal protein S6 kinase alpha-6, Keratin, type II cytoskeletal 71, PH-interacting protein, Polyadenylate-binding protein 2, Hemicentin-2, Complement C3, Biotinidase, T-cell immunomodulatory protein, Zinc finger CCCH domain-containing protein 14, Neuronal cell adhesion molecule, Ropporin-1B, Centrosomal protein C10orf90, Growth/differentiation factor 15, Sex comb on midleg-like protein 2, Echinoderm microtubule-associated protein-like 6, Fibrocystin-L, DIS3-like exonuclease 1, Carbonic anhydrase 14, Vesicle-trafficking protein SEC22c, Leucine-rich repeat-containing protein C10orf11, Zinc finger protein 879, UDP-galactose translocator, Alpha/beta hydrolase domain-containing protein 13, Protein EURL homolog, Porphobilinogen deaminase, Microtubule-associated proteins 1A/1B light chain 3B, Melanoma-derived growth regulatory protein, Platelet-derived growth factor D, Probable dimethyladenosine transferase, Ras association domain-containing protein 5, Consortin, Transcription factor Sp1, Derlin-2, Solute carrier family 25 member 35, Inositol 1,4,5-trisphosphate receptor type 2, Mannose-6-phosphate isomerase, RNA-binding Raly-like protein, Syntaxin-7, Exonuclease 3'-5' domain-containing protein 2, Globoside alpha-1,3-N-acetylgalactosaminyltransferase 1, Acyl-CoA synthetase short-chain family member 3, mitochondrial, Pleckstrin homology domain-containing family H member 1, Mitochondrial tRNA-specific 2-thiouridylase 1, UDP-glucose 4-epimerase, Voltage-dependent calcium channel subunit alpha-2/delta-2, Kinesin-like protein KIF1B, Carbonic anhydrase-related protein, Tribbles homolog 1, Lecithin retinol acyltransferase, Tissue-type plasminogen activator, Laminin subunit beta-1, Zinc finger protein basonuclin-1, T-lymphoma invasion and metastasis-inducing protein 1, Adipocyte enhancer-binding protein 1, Estradiol 17-beta-dehydrogenase 11, LINE-1 retrotransposable element ORF2 protein, Zinc finger and SCAN domain-containing protein 25, AP2-associated protein kinase 1, Fibrous sheath-interacting protein 2, Heat shock factor protein 4, Leucine-rich repeat-containing G-protein coupled receptor 6, Interferon-induced transmembrane protein 10, E3 ubiquitin-protein ligase RNF13, Potassium/sodium hyperpolarization-activated cyclic nucleotide-gated channel 4, Protein wntless homolog, Integrin-alpha FG-GAP repeat-containing protein 2, Neprilysin, Leucine-rich repeat-containing protein 34, Armadillo repeat-containing X-linked protein 2, G protein-coupled receptor kinase 4, G protein-coupled receptor kinase 6, T-cell surface glycoprotein CD8 beta chain, Sorting nexin-13, Methylcrotonoyl-CoA carboxylase beta chain, mitochondrial, Elongator complex protein 4, Mitochondrial calcium uniporter regulator 1, Zinc finger protein 382, Ubiquitin-conjugating enzyme E2 N, Diacylglycerol kinase zeta, Protein unc-119 homolog A, Alpha-2-macroglobulin, Sprouty-related, EVH1 domain-containing protein 1, Zinc finger protein castor homolog 1, Protein-methionine sulfoxide oxidase MICAL3, Phosphorylase b kinase regulatory subunit beta, Tubulin alpha-1A chain, Multidrug resistance-associated protein 7, B-cell CLL/lymphoma 9 protein, Collagen alpha-1(IV) chain, Nebulin, Serine/arginine-rich splicing factor 4, Unconventional myosin-Vlla, Calcium-binding mitochondrial carrier protein SCaMC-2, 28S ribosomal protein S2, mitochondrial, Upstream stimulatory factor 2, Sodium/potassium/calcium exchanger 5, Protein sidekick-1, Melanoma-associated antigen 6, Vesicle transport protein USE1, SLIT-ROBO Rho GTPase-activating protein 2C, Plexin-A3, E3 ubiquitin-protein ligase RNF139, Probable ATP-dependent RNA helicase DHX58, Serine/threonine-protein kinase Sgk3, Kin of IRRE-like protein 1, Lactoperoxidase, SH3 domain-binding protein 4, Centromere protein R, Pleckstrin homology domain-containing family M member 2, Atrial natriuretic peptide receptor 2, Laminin subunit beta-2, Zinc finger protein ZIC 1, Puratrophin-1, High affinity cAMP-specific and IBMX-insensitive 3',5'-cyclic phosphodiesterase 8B, Threonine synthase-like 2, Interleukin-24, Phosphatidylinositol 4,5-bisphosphate 3-kinase catalytic subunit beta isoform, Neuron navigator 1, KDEL motif-containing protein 1, Ceramide synthase 1, COX assembly mitochondrial protein homolog, DnaJ homolog subfamily A member 4, Anion exchange protein 3, Adenylate cyclase type 1, Plexin-D1, Procollagen galactosyltransferase 1, Insulin-like growth factor 1 receptor, Transcriptional protein SWT1, Copine-9, Protein HEG homolog 1, Transmembrane protein 98, Zinc finger protein ZIC 2, RAC-gamma serine/threonine-protein kinase, Protein FAM184A, Transcription factor Dp-2, Non-receptor tyrosine-protein kinase TNK1, GPI mannosyltransferase 1, Solute carrier family 41 member 2, RNA-binding motif protein, X chromosome, Alpha-fetoprotein, Membrane progestin receptor alpha, Centrosomal protein of 135 kDa, Melanoma-associated antigen B1, Protein lifeguard 4, Zinc finger protein ZFAT, Zinc finger protein 92, Zinc finger protein 708, Digestive organ expansion factor homolog, Protein shisa-4, Alpha-2-macroglobulin-like protein 1, Collagen alpha-1(XX) chain, Mitochondrial dicarboxylate carrier, Voltage-dependent calcium channel subunit alpha-2/delta-1, Thioredoxin domain-containing protein 15, Calpain-2 catalytic subunit, Protein-glutamine gamma-glutamyltransferase 5, CCR4-NOT transcription complex subunit 3, Putative RNA exonuclease NEF-sp, Torsin-1B, General transcription factor IIH subunit 3, RWD domain-containing protein 1, N-terminal kinase-like protein, Transmembrane and coiled-coil domain-containing protein 3, Contactin-associated protein-like 4, Armadillo repeat protein deleted in velo-cardio-facial syndrome, RNA-binding protein 20, Coiled-coil domain-containing protein 180, Protein Bop, Serine/threonine-protein kinase MRCK gamma, Probable palmitoyltransferase ZDHHC24, Zinc finger X-linked protein ZXDA, Zinc transporter ZIP1, Tastin, Mitochondrial dynamics protein MID49, Transmembrane protein 132B, Ephrin type-B receptor 3, Glypican-6, F-box only protein 46, Probable E3 SUMO-protein ligase RNF212, Matrix metalloproteinase-17, Serine/threonine-protein kinase 32A, Adhesion G-protein coupled receptor F3, Sorting nexin-10, BTB/POZ domain-containing protein 1, Phosphatidylinositol 5-phosphate 4-kinase type-2 beta, Constitutive coactivator of PPAR-gamma-like protein 2, Potassium/sodium hyperpolarization-activated cyclic nucleotide-gated channel 3, AT-hook-containing transcription factor, Legumain, Retinoic acid receptor RXR-beta, Mucin-19, Ubiquitin domain-containing protein UBFD1, Ras-related protein Rab-38, Bromodomain-containing protein 4, Cap-specific mRNA (nucleoside-2'-O-)-methyltransferase 1, Ubiquitin-associated protein 1, Periaxin, Protein O-mannosyl-transferase 1, Metallophosphoesterase MPPED2, NAD-dependent protein deacetylase sirtuin-2, NAD-dependent protein deacetylase sirtuin-3, mitochondrial, Peroxisome proliferator-activated receptor gamma coactivator-related protein 1, Zinc finger homeobox protein 2, Proline-rich transmembrane protein 3, Zinc transporter ZIP12, Phosphorylase b kinase regulatory subunit alpha, liver isoform, Caprin-2, Zinc finger with UFM1-specific peptidase domain protein, Protocadherin-15, POU domain, class 6, transcription factor 2, Insulin-like growth factor-binding protein complex acid labile subunit, Adenomatous polyposis coli protein 2, Thioredoxin reductase 2, mitochondrial, Kelch-like protein 29, DNA-binding protein RFXANK, GPI mannosyltransferase 2, Cleavage and polyadenylation specificity factor subunit 6, Myotubularin-related protein 12, SUN domain-containing ossification factor, Solute carrier family 25 member 34, NTF2-related export protein 2, Protein CLN8, Beta-galactosidase-1-like protein, Mitogen-activated protein kinase 1, EH domain-containing protein 3, 6.8 kDa mitochondrial proteolipid, Death-associated protein kinase 1, RB1-inducible coiled-coil protein 1, Exostosin-like 1, Nuclear factor related to kappa-B-binding protein, Zinc finger protein 512B, Dihydropyrimidinase-related protein 3, Inactive ubiquitin carboxyl-terminal hydrolase 53, Neuronal membrane glycoprotein M6-a, DNA-binding protein SATB1, Forkhead box protein C1, Serine/threonine-protein phosphatase 2A regulatory subunit B" subunit alpha, RNA-binding motif, single-stranded-interacting protein 3, Protocadherin gamma-A9, RNA-binding protein Nova-2, Glyceraldehyde-3-phosphate dehydrogenase, testis-specific, CMP-sialic acid transporter, GPI ethanolamine phosphate transferase 3, Protein EFR3 homolog B, CUB and sushi domain-containing protein 3, Krueppel-like factor 15, Receptor-type tyrosine-protein phosphatase kappa, Sodium-dependent proline transporter, Protein phosphatase Slingshot homolog 1, Beta-Ala-His dipeptidase, Sushi repeat-containing protein SRPX, Calmodulin-regulated spectrin-associated protein 3, Tissue factor pathway inhibitor 2, Phosphoinositide 3-kinase regulatory subunit 5, SH3 and multiple ankyrin repeat domains protein 1, Homeobox protein SIX5, Putative exonuclease GOR, Uncharacterized protein KIAA0556, Transmembrane and TPR repeat-containing protein 1, SH2 domain-containing protein 3A, Shadow of prion protein, Mucin-5B, ATP synthase subunit d, mitochondrial, Transforming acidic coiled-coil-containing protein 2, Transmembrane protein 238, Serine/threonine-protein kinase WNK2, Acrosin, Disintegrin and metalloproteinase domain-containing protein 18, BAll-associated protein 3, Serine/threonine-protein kinase ICK, Doublesex- and mab-3-related transcription factor A2, UPF0609 protein C4orf27, Single-stranded DNA-binding protein 3, Enolase-like protein ENO4, Dedicator of cytokinesis protein 6, Nuclear distribution protein nudE-like 1, Glycogenin-1, Scavenger receptor cysteine-rich type 1 protein M160, Stathmin-3, Mitogen-activated protein kinase kinase kinase kinase 5, Protein transport protein Sec24D, Proprotein convertase subtilisin/kexin type 7, Serine/threonine-protein phosphatase 1 regulatory subunit 10, Dynein heavy chain 8, axonemal, Dehydrogenase/reductase SDR family member 2, mitochondrial, Complement factor I, E3 ubiquitin-protein ligase TRIM63, Liprin-alpha-2, Protein Shroom4, Potassium voltage-gated channel subfamily H member 2, Rho GTPase-activating protein 31, Tetratricopeptide repeat protein 37, Interphotoreceptor matrix proteoglycan 1, Nodal modulator 1, Receptor-type tyrosine-protein phosphatase delta, Ribosome maturation protein SBDS, ATP-binding cassette sub-family A member 2, Zinc finger protein 423, Transcription factor SOX-5, Forkhead box protein D3, Protein NipSnap homolog 2, Uncharacterized protein C11orf96, Collagen alpha-2(V) chain, Alpha-globin transcription factor CP2, Ellis-van Creveld syndrome protein, EMILIN-1, Keratin, type I cytoskeletal 24, Apolipoprotein E, Cysteine and glycine-rich protein 2, Protein fantom, Homeobox protein Hox-B9, Apolipoprotein C-III, Regulator of G-protein signaling 12, WD repeat-containing protein 90, YrdC domain-containing protein, mitochondrial, Zinc finger BED domain-containing protein 6, Desumoylating isopeptidase 1, Protein asteroid homolog 1, Mitochondrial 2-oxoglutarate/malate carrier protein, Glycosylated lysosomal membrane protein, Chondroitin sulfate synthase 2, 6-phosphofructo-2-kinase/fructose-2,6-bisphosphatase 2, VPS10 domain-containing receptor SorCS1, UPF0524 protein C3orf70, Thiosulfate sulfurtransferase/rhodanese-like domain-containing protein 2, Mannosyl-oligosaccharide 1,2-alpha-mannosidase IB, PDZ domain-containing protein 2, Growth arrest-specific protein 6, Homeobox protein Hox-A4, ETS homologous factor, DBIRD complex subunit ZNF326, Cyclin-dependent kinase 5 activator 1, Signal peptidase complex subunit 3, Protein Hook homolog 3, TGF-beta receptor type-1, Phosphatidylserine synthase 1, HLA class II histocompatibility antigen, DM beta chain, Solute carrier family 22 member 6, Mucolipin-1, Rab 1 family-interacting protein 5, Translation initiation factor eIF-2B subunit alpha, Ribosomal RNA-processing protein 8, Nidogen-2, Polycomb group RING finger protein 1, Major centromere autoantigen B, Transmembrane protein 121, F-box/LRR-repeat protein 7, HLA class I histocompatibility antigen, Cw-17 alpha chain, Zinc finger and BTB domain-containing protein 11, Heterogeneous nuclear ribonucleoprotein H2, FTS and Hook-interacting protein, Leucine-rich repeat LGI family member 3, Zinc finger protein 45, Leucine-rich repeat transmembrane neuronal protein 3, Ubiquitin carboxyl-terminal hydrolase 13, Motor neuron and pancreas homeobox protein 1, Transcription factor MafF, PR domain zinc finger protein 8, Armadillo repeat-containing protein 1, Phosphoglucomutase-1, Serine/threonine-protein phosphatase 2A regulatory subunit B" subunit gamma, Microtubule-associated protein 9, Immunoglobulin superfamily member 3, Sal-like protein 1, Homeobox protein Hox-D9, Zinc finger protein 175, ATP-dependent RNA helicase DDX39A, Protein phosphatase 1J, Plasma protease C1 inhibitor, Protein phosphatase 1 regulatory subunit 3F, Transmembrane channel-like protein 4, Adenylate kinase 9, Raftlin-2, Cyclic AMP-dependent transcription factor ATF-6 alpha, Sestrin-2, Growth factor receptor-bound protein 10, Regulator of G-protein signaling 20, Cytokine receptor common subunit beta, Mannosyl-oligosaccharide 1,2-alpha-mannosidase IA, Uracil phosphoribosyltransferase homolog, Caspase-4, Vesicular glutamate transporter 2, Probable phospholipid-transporting ATPase IH, Protein LMBR1L, Metallophosphoesterase 1, Delphilin, Oxysterol-binding protein-related protein 5, Matrix metalloproteinase-14, Ethanolamine kinase 2, Protein phosphatase 1 regulatory subunit 21, Alpha-ketoglutarate-dependent dioxygenase alkB homolog 3, Coiled-coil domain-containing protein 91, Centrosomal protein of 290 kDa, Transcription factor HIVEP3, Transcription factor AP-2-epsilon, Arylsulfatase B, Membrane magnesium transporter 1, Protein YIPF4, Glutaminyl-peptide cyclotransferase, Zinc finger protein 160, Serine palmitoyltransferase 3, Aldehyde dehydrogenase, mitochondrial, Rho guanine nucleotide exchange factor 26, Sodium-dependent neutral amino acid transporter B(0)AT2, Immunoglobulin superfamily member 11, Collagen triple helix repeat-containing protein 1, Delta-like protein 3, RPA-interacting protein, Rho GTPase-activating protein 32, Zinc finger CCHC domain-containing protein 24, Very large A-kinase anchor protein, Ras-associating and dilute domain-containing protein, B-cell lymphoma 6 protein, Vasorin, Alpha-1D adrenergic receptor, Cyclin-dependent kinase-like 3, Neutrophil collagenase, Transducin-like enhancer protein 3, Protein LZIC, CXXC-type zinc finger protein 5, Zinc finger CCHC domain-containing protein 3, Zinc finger protein 518B, GDNF-inducible zinc finger protein 1, Phospholipase B-like 1, Glutathione reductase, mitochondrial, Histone-lysine N-methyltransferase SETD1B, Dimethyladenosine transferase 1, mitochondrial, PR domain zinc finger protein 2, Suppressor of tumorigenicity 7 protein, Semaphorin-3D, Retrotransposon gag domain-containing protein 4, E3 ubiquitin-protein ligase TRIM58, Triokinase/FMN cyclase, Alpha-1,6-mannosylglycoprotein 6-beta-N-acetylglucosaminyltransferase A, Guanine nucleotide exchange factor for Rab-3A, Large neutral amino acids transporter small subunit 1, SH3 domain-binding protein 5, NHL repeat-containing protein 2, Telomeric repeat-binding factor 1, Zinc finger protein 480, Zinc finger protein 98, Histone-lysine N-methyltransferase, H3 lysine-36 and H4 lysine-20 specific, Vascular endothelial growth factor receptor 2, Transmembrane protease serine 9, Ethanolaminephosphotransferase 1, WD repeat-containing protein 73, Calcium-dependent secretion activator 2, RING finger protein 150, Proteinase-activated receptor 1, Peptidyl-tRNA hydrolase 2, mitochondrial, Ethanolamine-phosphate phospholyase, Essential MCU regulator, mitochondrial, Vacuolar protein-sorting-associated protein 25, Histone acetyltransferase KAT2B, Uveal autoantigen with coiled-coil domains and ankyrin repeats, Serine/threonine-protein kinase ULK2, WD repeat-containing protein 5B, Bifunctional lysine-specific demethylase and histidyl-hydroxylase NO66, Ubiquitin-conjugating enzyme E2 G1, Cytoplasmic polyadenylation element-binding protein 2, Gamma-aminobutyric acid receptor subunit beta-2, Zinc finger protein 354B, E3 ubiquitin-protein ligase RNF169, Galactose-3-O-sulfotransferase 4, Myosin-IIIa, Mitogen-activated protein kinase kinase kinase 14, Signal-induced proliferation-associated 1-like protein 3, Runt-related transcription factor 1, Transmembrane protein 9, DNA annealing helicase and endonuclease ZRANB3, Ryanodine receptor 2, Diamine acetyltransferase 1, Transmembrane protein 231, Cartilage acidic protein 1, UPF0415 protein C7orf25, Protein NLRC3, Immunoglobulin superfamily DCC subclass member 4, Multidrug resistance-associated protein 6, Dynein heavy chain 17, axonemal, Protein phosphatase 1 regulatory subunit 12B, Small conductance calcium-activated potassium channel protein 2, Protein FAM13B, Serine/arginine-rich splicing factor 2, Probable tRNA methyltransferase 9-like protein, COP9 signalosome complex subunit 7b, Zinc finger protein 518A, Urocortin-2, Probable cytosolic iron-sulfur protein assembly protein CIAO1, Transmembrane protein 94, Protein-associating with the carboxyl-terminal domain of ezrin, Protein misato homolog 1, Protocadherin beta-8, Slit homolog 3 protein, Slit homolog 2 protein, Xylosyltransferase 1, Nectin-3, Endoglin, Solute carrier family 2, facilitated glucose transporter member 14, COMM domain-containing protein 7, Diacylglycerol O-acyltransferase 1, F-box/WD repeat-containing protein 9, Spectrin beta chain, non-erythrocytic 5, Mitochondrial pyruvate carrier 1, Anion exchange protein, Microtubule-associated protein, Large neutral amino acids transporter small subunit 2, Adhesion G protein-coupled receptor F5, Heat shock transcription factor, X-linked, Solute carrier family 26 member 10, ABCB9 protein, Cancer/testis antigen 55, Calcium-binding mitochondrial carrier protein SCaMC-1, N-acylglucosamine 2-epimerase, UBX domain-containing protein 6, Tripartite motif-containing protein 55, Polycystic kidney disease 2-like 1 protein, Zinc finger protein 529, Polynucleotide 5'-hydroxyl-kinase NOL9, Kidney mitochondrial carrier protein 1, Sprouty-related, EVH1 domain-containing protein 2, Leptin receptor gene-related protein, GDP-fucose protein O-fucosyltransferase 1, Solute carrier family 12 member 2, Coiled-coil domain-containing protein 34, MAGUK p55 subfamily member 5, Protein SSX5, ATP-binding cassette sub-family C member 8, Tyrosine-protein kinase receptor, Inositol-trisphosphate 3-kinase A, Thioredoxin domain-containing protein 16, Electroneutral sodium bicarbonate exchanger 1, E3 ubiquitin-protein ligase TRIM36, Maestro heat-like repeat-containing protein family member 7, Protein dopey-1, Serine/threonine-protein kinase A-Raf, Probable G-protein coupled receptor 158, PHD finger protein 20, Exportin-7, TBC1 domain family member 16, Homeodomain-interacting protein kinase 4, SLIT and NTRK-like protein 2, Bromo adjacent homology domain-containing 1 protein, Protocadherin Fat 2, HLA class I histocompatibility antigen, B-49 alpha chain, CASP8 and FADD-like apoptosis regulator, Neuroligin-3, Katanin p60 ATPase-containing subunit A1, Protein FAM72C, Nuclear receptor coactivator 1, Mediator of RNA polymerase II transcription subunit 8, Paired box protein Pax-2, Glutamyl aminopeptidase, Egl nine homolog 3, Protein-lysine 6-oxidase, Insulin-like growth factor-binding protein 3, Thrombospondin-1, Thrombospondin-2, Matrilysin, Thioredoxin-related transmembrane protein 4, ATP synthase subunit gamma, mitochondrial, Guanylate kinase, Calcium-binding mitochondrial carrier protein Aralar2, Iroquois-class homeodomain protein IRX-2, Bcl-2-binding component 3, Protein Shroom2, LRRN4 C-terminal-like protein, Neuronal pentraxin receptor, UBA-like domain-containing protein 1, Macrophage-capping protein, Malate dehydrogenase, cytoplasmic, Numb-like protein, Vesicle transport through interaction with t-SNAREs homolog 1B, Protein SFI1 homolog, Metalloproteinase inhibitor 2, ALK tyrosine kinase receptor, MAD2L1-binding protein, Ewing's tumor-associated antigen 1, Rho-related GTP-binding protein RhoQ, Serine dehydratase-like, Kv channel-interacting protein 2, Phosphatidylinositol 3-kinase regulatory subunit beta, Tropomodulin-1, Beta-1,4-glucuronyltransferase 1, 17-beta-hydroxysteroid dehydrogenase 14, TATA box-binding protein-like protein 1, Ribonuclease pancreatic, NADPH oxidase 5, Spliceosome-associated protein CWC15 homolog, Serine/threonine-protein kinase PRP4 homolog, Cytoglobin, Homer protein homolog 3, Metastasis suppressor protein 1, 1-acyl-sn-glycerol-3-phosphate acyltransferase gamma, Neuralized-like protein 4, Coiled-coil domain-containing protein 154, HRAS-like suppressor 3, Neuroblastoma breakpoint family member 6, Separin, Fucose mutarotase, Ankyrin repeat domain-containing protein SOWAHC, Protein AAR2 homolog, Atherin, Patatin-like phospholipase domain-containing protein 7, CD276 antigen, Cytoplasmic polyadenylation element-binding protein 1, E3 ubiquitin-protein ligase MSL2, Transient receptor potential cation channel subfamily M member 1, Suppressor of IKBKE 1, Centrosomal protein of 68 kDa, Amino-terminal enhancer of split, SH2B adapter protein 3, Protein argonaute-1, Oxidative stress-induced growth inhibitor 1, Apolipoprotein D, Semaphorin-5A, Nephrocystin-3, F-BAR domain only protein 2, Vacuolar-sorting protein SNF8, Septin-4, Eukaryotic translation initiation factor 3 subunit J, RanBP-type and C3HC4-type zinc finger-containing protein 1, Mitochondrial import inner membrane translocase subunit Tim13, cDNA FLJ78342, Armadillo repeat-containing X-linked protein 5, Adenosine 3'-phospho 5'-phosphosulfate transporter 2, RING finger protein 37, Zinc finger protein 28 homolog, Proline-rich protein 13, Interleukin-1 receptor accessory protein, Glutamate receptor ionotropic, NMDA 2A, Pleckstrin homology domain-containing family A member 1, Hyaluronidase-2, 72 kDa type IV collagenase, Calcineurin subunit B type 1, Protein phosphatase 1 B, Delta-1-pyrroline-5-carboxylate synthase, 28S ribosomal protein S22, mitochondrial, Probable ATP-dependent RNA helicase DDX58, Trimethyllysine dioxygenase, mitochondrial, Pantothenate kinase 2, mitochondrial, R3H and coiled-coil domain-containing protein 1, CUGBP Elav-like family member 5, Probable fibrosin-1, Microtubule-associated serine/threonine-protein kinase 4, Calcium/calmodulin-dependent protein kinase kinase 2, Glycogen [starch] synthase, muscle, EPM2A-interacting protein 1, Coiled-coil domain-containing protein 22, Zinc finger protein 1 homolog, KAT8 regulatory NSL complex subunit 2, GTPase KRas, Cyclin-G1, Regulator of nonsense transcripts 3B, Telomerase-binding protein EST1A, Nuclear factor of activated T-cells, cytoplasmic 3, Nucleolar protein 4-like, Gamma-glutamylaminecyclotransferase, Bcl-2-like protein 12, Methyltransferase-like protein 13, Methylthioribose-1-phosphate isomerase, Apoptogenic protein 1, mitochondrial, UTP-glucose-1-phosphate uridylyltransferase, G-protein coupled receptor 126, Zinc finger CCCH-type with G patch domain-containing protein, C2 domain-containing protein 5, Cytoplasmic polyadenylation element-binding protein 4, UPF0489 protein C5orf22, Intermediate filament family orphan 1, Nuclear receptor subfamily 4 group A member 2, Peptidyl-glycine alpha-amidating monooxygenase, Ethanolamine-phosphate cytidylyltransferase, Zinc finger CCCH domain-containing protein 13, Putative GTP-binding protein 6, WD repeat domain-containing protein 83, DNA excision repair protein ERCC-8, Serine/threonine-protein kinase N3, MOB kinase activator 2, Ankyrin repeat and BTB/POZ domain-containing protein 1, Kaptin, Caveolin-1, Death effector domain-containing protein, Spindle and kinetochore-associated protein 1, Elongation factor G, mitochondrial, Coenzyme Q-binding protein COQ10 homolog B, mitochondrial, Transmembrane protein 168, PRKR-interacting protein 1, RIB43A-like with coiled-coils protein 2, TATA box-binding protein-associated factor RNA polymerase I subunit C, DCN1-like protein 4, Peptidyl-prolyl cis-trans isomerase H, Glypican-1, Cat eye syndrome critical region protein 5, Cystathionine gamma-lyase, Protein GREB1, ATP-dependent DNA helicase Q4, Metal transporter CNNM3, Nucleoside diphosphate kinase, mitochondrial, Small integral membrane protein 8, N-lysine methyltransferase SMYD2, E3 ubiquitin-protein ligase Praja-1, TNF receptor-associated factor 5, LIX1-like protein, Renalase, Trafficking protein particle complex subunit 12, Protein mago nashi homolog 2, Transmembrane protein 150C, NADH dehydrogenase [ubiquinone] 1 alpha subcomplex subunit 11, Alpha- and gamma-adaptin-binding protein p34, Ribosome-releasing factor 2, mitochondrial, Zinc finger protein 322, AF4/FMR2 family member 3, Shugoshin-like 2, NEDD4-binding protein 1, Arf-GAP with Rho-GAP domain, ANK repeat and PH domain-containing protein 2, Peroxisomal NADH pyrophosphatase NUDT12, Mixed lineage kinase domain-like protein, MRG/MORF4L-binding protein, Tyrosine-protein phosphatase non-receptor type 3, Prostacyclin synthase, Protein FAM46D, Transcriptional repressor NF-X1, Oligodendrocyte transcription factor 2, FYVE and coiled-coil domain-containing protein 1, Tripartite motif-containing protein 42, Centrosomal protein of 112 kDa, THO complex subunit 3, Uncharacterized protein C20orf96, LisH domain-containing protein FOPNL, Cyclin-dependent kinase 17, Histone-lysine N-methyltransferase SUV420H1, Serine/threonine-protein kinase Nek2, RNA polymerase II elongation factor ELL2, Serine/threonine-protein kinase TAO3, F-box only protein 34, DNA replication complex GINS protein PSF2, Kinetochore-associated protein DSN1 homolog, Inositol-3-phosphate synthase 1, 15-hydroxyprostaglandin dehydrogenase [NAD(+)], Mitogen-activated protein kinase 8, THO complex subunit 1, Dual specificity protein phosphatase 19, Protein fem-1 homolog B, Prolyl endopeptidase FAP, 28S ribosomal protein S18b, mitochondrial, Serine/threonine-protein kinase Nek3, Cell division cycle-associated protein 7, Dual specificity protein kinase TTK, ER degradation-enhancing alpha-mannosidase-like protein 2, GATA zinc finger domain-containing protein 1, Ceramide synthase 4, Leucine-rich repeat-containing protein 9, Cytochrome b5 domain-containing protein 1, Coiled-coil domain-containing protein 158, Transcriptional enhancer factor TEF-1, OTU domain-containing protein 7B, Exonuclease 1, Lactosylceramide alpha-2,3-sialyltransferase, HLA class I histocompatibility antigen, A-66 alpha chain, YLP motif-containing protein 1, Alpha-1,3-mannosyl-glycoprotein 2-beta-N-acetylglucosaminyltransferase, Exocyst complex component 8, Tudor domain-containing protein 7, Putative pre-mRNA-splicing factor ATP-dependent RNA helicase DHX32, Dephospho-CoA kinase domain-containing protein, Telomeric repeat-binding factor 2, Uncharacterized protein C7orf43, Nucleoside diphosphate kinase homolog 5, Alpha-aminoadipic semialdehyde synthase, mitochondrial, TBC1 domain family member 10A, GRIP and coiled-coil domain-containing protein 1, Mitochondrial Rho GTPase 1, Vacuolar protein-sorting-associated protein 36, Transmembrane protein 260, HAUS augmin-like complex subunit 2, dTDP-D-glucose 4,6-dehydratase, S-phase kinase-associated protein 2, DNA repair protein complementing XP-A cells, Protein LTV1 homolog, UPF0462 protein C4orf33, Alpha-centractin, LIM domain-binding protein 3, Transient receptor potential cation channel subfamily M member 7, ETS-related transcription factor Elf-2, Ribosome-recycling factor, mitochondrial, Carnitine O-acetyltransferase, Serine-tRNA ligase, mitochondrial, E3 ubiquitin-protein ligase RFWD3, Rho GTPase-activating protein 26, Pre-mRNA-splicing regulator WTAP, Uncharacterized protein C1orf112, 28S ribosomal protein S23, mitochondrial, Phosphoprotein associated with glycosphingolipid-enriched microdomains 1, Peroxisome proliferator-activated receptor delta, Trafficking kinesin-binding protein 1, Nuclear receptor 2C2-associated protein, Exocyst complex component 7, C—C motif chemokine 28, Myotonin-protein kinase, Condensin complex subunit 2, Protein phosphatase 1H, 5'-nucleotidase, cDNA FLJ60317, highly similar to Aminoacylase-1 (EC 3.5.1.14), Endophilin-B2, FAST kinase domain-containing protein 5, Zinc finger and SCAN domain-containing protein 30, Coiled-coil domain-containing protein 136, RCC1 and BTB domain-containing protein 2, Phosphatase and actin regulator 1, Aryl hydrocarbon receptor nuclear translocator 2, 2-methoxy-6-polyprenyl-1,4-benzoquinol methylase, mitochondrial, Alpha/beta hydrolase domain-containing protein 17A, SH3 and PX domain-containing protein 2A, Mitochondrial ribonuclease P protein 3, SH3 and PX domain-containing protein 2B, Protein phosphatase 1 regulatory subunit 37, Protein TMEPAI, Mitogen-activated protein kinase kinase kinase 11, Exosome complex component RRP43, Cofilin-2, Protein FRA10AC1, Protein CIP2A, CREB3 regulatory factor, Pseudopodium-enriched atypical kinase 1, ATP-binding cassette sub-family A member 5, Phospholipid scramblase 2, Translation initiation factor eIF-2B subunit gamma, Ras association domain-containing protein 8, Ras-related GTP-binding protein D, Pachytene checkpoint protein 2 homolog, Estradiol 17-beta-dehydrogenase 1, Ubiquitin-associated protein 1-like, MAGEC3 protein, Protein FAM118A, Procollagen C-endopeptidase enhancer 2, mRNA turnover protein 4 homolog, Protein NATD1, Protein FAM135B, Meckel syndrome type 1 protein, Lactadherin, Putative butyrophilin subfamily 2 member A3, Butyrophilin subfamily 2 member A1, Interleukin-1 receptor-associated kinase 4, Protein FAM111 B, NADH-ubiquinone oxidoreductase 75 kDa subunit, mitochondrial, Proton myo-inositol cotransporter, Transcription factor TFIIIB component B" homolog, Xenotropic and polytropic retrovirus receptor 1, Prostaglandin E synthase 2, Ribonucleoprotein PTB-binding 2, Teneurin-4, EH domain-binding protein 1-like protein 1, Formin-binding protein 4, NGFI-A-binding protein 1, Glutamate decarboxylase 1, Putative ATP-dependent RNA helicase TDRD9, DCN1-like protein 5, 3 beta-hydroxysteroid dehydrogenase type 7, Tetratricopeptide repeat protein 5, Diacylglycerol kinase theta, 39S ribosomal protein L21, mitochondrial, Radial spoke head 10 homolog B2, Transcription factor SOX-13, Unconventional myosin-IXb, DDB1- and CUL4-associated factor 7, Tyrosine-protein kinase ABL1, Muscular LMNA-interacting protein, rRNA methyltransferase 2, mitochondrial, Nucleoside diphosphate kinase 7, Kinesin-like protein KIF14, Melanoma-associated antigen C1, Phosphatidylinositol 3,4,5-trisphosphate 3-phosphatase and dual-specificity protein phosphatase PTEN, Apolipoprotein B-100, Probable tRNA (uracil-O(2)-)-methyltransferase, Polyphosphoinositide phosphatase, Protein argonaute-3, Protein FAM102B, Probable guanine nucleotide exchange factor MCF2L2, Tubulin polyglutamylase complex subunit 1, Nephrocystin-4, Cleft lip and palate transmembrane protein 1-like protein, TNF receptor-associated factor 4, FAD-dependent oxidoreductase domain-containing protein 2, Zinc finger and BTB domain-containing protein 7A, WD repeat-containing protein 89, Calcium-transporting ATPase type 2C member 1, Complement factor H-related protein 2, Leucine zipper putative tumor suppressor 2, Probable N-acetyltransferase 16, Ornithine aminotransferase, mitochondrial, Polypeptide N-acetylgalactosaminyltransferase 16, 2'-5'-oligoadenylate synthase-like protein, Solute carrier family 25 member 33, U7 snRNA-associated Sm-like protein LSm10, Autophagy-related protein 2 homolog A, BMP and activin membrane-bound inhibitor homolog, Bifunctional lysine-specific demethylase and histidyl-hydroxylase MINA, Uncharacterized protein KIAA1841, Stromal membrane-associated protein 2, Protein FAM98A, CAP-Gly domain-containing linker protein 3, Protein SCAI, Anoctamin-4, HLA class I histocompatibility antigen, B-50 alpha chain, Phytanoyl-CoA dioxygenase, peroxisomal, Dyslexia-associated protein KIAAO319-like protein, 28S ribosomal protein S16, mitochondrial, Retinol dehydrogenase 8, 39S ribosomal protein L41, mitochondrial, Mitochondrial intermediate peptidase, Protein FAM83D, MpV17 transgene, murine homolog, glomerulosclerosis, isoform CRA_f, Sorcin, Putative germ cell-less protein-like 1-like, Protein-glutamine gamma-glutamyltransferase 6, Transforming growth factor-beta receptor-associated protein 1, Sex comb on midleg-like protein 4, Insulin-like growth factor-binding protein 7, Putative RNA-binding protein Luc7-like 1, Monocarboxylate transporter 5, Cadherin-19, Putative heat shock protein HSP 90-beta-3, G protein-coupled receptor kinase 5, Retinol dehydrogenase 14, UBX domain-containing protein 2A, Histone H3-like centromeric protein A, UPF0536 protein C12orf66, Putative ATP-dependent RNA helicase TDRD12, NADH-ubiquinone oxidoreductase chain 4, Thiamin pyrophosphokinase 1, Sulfotransferase 1 C2, Zinc finger SWIM domain-containing protein 3, Catenin delta-2, Transient receptor potential cation channel subfamily A member 1, Alstrom syndrome protein 1, Tubulin alpha-3C/D chain, 40S ribosomal protein S20, Adenine DNA glycosylase, Protein O-linked-mannose beta-1,2-N-acetylglucosaminyltransferase 1, CD63 antigen, Zinc finger protein DZIP1, Discoidin, CUB and LCCL domain-containing protein 1, Protein pelota homolog, Tubulin polyglutamylase TTLL5, S-methyl-5'-thioadenosine phosphorylase, Serologically defined colon cancer antigen 8, Cytoplasmic protein NCK2, Alpha-1,6-mannosylglycoprotein 6-beta-N-acetylglucosaminyltransferase B, Iroquois-class homeodomain protein IRX-5, Succinate dehydrogenase [ubiquinone] flavoprotein subunit, mitochondrial, Tetratricopeptide repeat protein 38, Aprataxin, Sodium-dependent phosphate transporter 1, Oxidoreductase-like domain-containing protein 1, P protein, Protein bicaudal C homolog 1, Voltage-gated potassium channel subunit beta-1, Regulator of telomere elongation helicase 1, Probable phospholipid-transporting ATPase IIB, Sideroflexin-1, Phosphoribosylformylglycinamidine synthase, Tetratricopeptide repeat protein 39B, Uncharacterized protein KIAA1210, N-acyl-aromatic-L-amino acid amidohydrolase (carboxylate-forming), Transforming growth factor beta receptor type 3, Metalloproteinase inhibitor 4, Beta-adrenergic receptor kinase 2, Dipeptidyl peptidase 4, Protein SMG5, P antigen family member 5, Carbohydrate sulfotransferase 9, Zinc finger and SCAN domain-containing protein 21, Zinc finger protein 7, Zinc finger protein 430, Xaa-Pro dipeptidase, Protein ECT2, Protein FAM161A, NF-kappa-B inhibitor zeta, Zinc finger protein 860, Rho guanine nucleotide exchange factor 40, Ras-related protein Ral-A, Ras-related protein Rab-17, Loss of heterozygosity 12 chromosomal region 1 protein, Ras-related protein Rab-13, Ras-related protein Rab-34, Filamin A-interacting protein 1-like, Nuclear receptor subfamily 4 group A member 3, Armadillo repeat-containing X-linked protein 1, CD302 antigen, Zinc finger protein 141, Tudor domain-containing protein 3, RanBP2-like and GRIP domain-containing protein 3, Creatine kinase S-type, mitochondrial, Dynein heavy chain 5, axonemal, E3 ubiquitin-protein ligase UBR3, WD repeat and HMG-box DNA-binding protein 1, Retinaldehyde-binding protein 1, Ubiquitin-conjugating enzyme E2 Q1, S-adenosylmethionine decarboxylase proenzyme, RUN and FYVE domain-containing protein 2, Bardet-Biedl syndrome 5 protein, Treslin, Gap junction alpha-3 protein, Dual specificity tyrosine-phosphorylation-regulated kinase 3, Transient receptor potential cation channel subfamily M member 2, MICAL-like protein 1, Aryl hydrocarbon receptor nuclear translocator, 5-demethoxyubiquinone hydroxylase, mitochondrial, Round spermatid basic protein 1, Glutathione S-transferase theta-2B, EF-hand calcium-binding domain-containing protein 14, DnaJ homolog subfamily C member 4, Protein Simiate, 60S ribosomal protein L35a, LON peptidase N-terminal domain and RING finger protein 2, Bifunctional UDP-N-acetylglucosamine 2-epimerase/N-acetylmannosamine kinase, Alternative protein MKKS, TBC1 domain family member 15, PHD finger-like domain-containing protein 5A, Tumor necrosis factor receptor superfamily member 14, Protein PRR5-ARHGAP8, Mitochondrial inner membrane protease ATP23 homolog, Huntingtin-interacting protein 1-related protein, Proteasome subunit alpha type-1, Transcription factor IIIA, Poly(A)-specific ribonuclease PARN-like domain-containing protein 1, Myosin regulatory light chain 10, Serine/threonine-protein phosphatase 2A activator, Caspase-2, SLIT-ROBO Rho GTPase-activating protein 1, B-cell CLL/lymphoma 7 protein family member B, Uncharacterized protein C10orf88, 39S ribosomal protein L51, mitochondrial, Zinc finger CCHC-type and RNA-binding motif-containing protein 1, DNA helicase MCM8, Fc receptor-like protein 3, Tripartite motif-containing protein 35, Rho GTPase-activating protein 11B, Ribosomal protein S6 kinase alpha-2, Dual specificity protein phosphatase 3, Transmembrane protein 8A, Serine protease 56, Connector enhancer of kinase suppressor of ras 3, Protein FAM167B, Coiled-coil domain-containing protein 77, Hydrocephalus-inducing protein homolog, Serine beta-lactamase-like protein LACTB, mitochondrial, Solute carrier family 40 member 1, Lysosomal-associated transmembrane protein 4B, Histone deacetylase complex subunit SAP30L, Lipoxygenase homology domain-containing protein 1, Alpha-1-antichymotrypsin, Granulocyte-macrophage colony-stimulating factor receptor subunit alpha, Probable serine carboxypeptidase CPVL, Teashirt homolog 3, Interleukin-13 receptor subunit alpha-2, Sorting nexin-21, Torsin-1A-interacting protein 2, isoform IFRG15, DST protein, Carboxypeptidase N catalytic chain, Aspartate beta-hydroxylase domain-containing protein 1, Protein FAM69B, Ectonucleotide pyrophosphatase/phosphodiesterase family member 1, Coiled-coil domain-containing protein 13, Zinc finger protein 703, Low affinity immunoglobulin gamma Fc region receptor II-b, Putative stereocilin-like protein, EF-hand calcium-binding domain-containing protein 6, Zinc finger and BTB domain-containing protein 34, Glutathione S-transferase theta-1, Amphoterin-induced protein 1, Delta and Notch-like epidermal growth factor-related receptor, Synaptosomal-associated protein 23, Inactive rhomboid protein 2, Thymidine phosphorylase, Olfactory receptor 4M2, Protein mago nashi homolog, Nidogen-1, Prostate tumor-overexpressed gene 1 protein, ADP-ribosylation factor-like protein 5B, TBC1 domain family member 7, SEC14-like protein 2, ATP synthase subunit e, mitochondrial, NGFI-A- binding protein 2, Peptidase inhibitor 15, Small glutamine-rich tetratricopeptide repeat-containing protein alpha, Leucine-rich repeat-containing protein 4C, RNA polymerase-associated protein RTF1 homolog, Transcription initiation factor IIA subunit 2, Pseudouridine-5'-phosphatase, Zinc finger protein 583, Zinc finger protein 280D, DNA-directed RNA polymerase III subunit RPC10, Phenylalanine-tRNA ligase beta subunit, Fructose-bisphosphate aldolase C, Short/branched chain specific acyl-CoA dehydrogenase, mitochondrial, Geranylgeranyl transferase type-2 subunit beta, tRNA (guanine(37)-N1)-methyltransferase, Probable crossover junction endonuclease EME2, Neuronal acetylcholine receptor subunit alpha-3, Carbohydrate sulfotransferase 5, Tyrosine-protein phosphatase non-receptor type 20, Leucine-rich repeat-containing protein 15, Methyltransferase-like protein 25, Histone-lysine N-methyltransferase SUV39H1, PH and SEC7 domain-containing protein 3, Zinc finger and BTB domain-containing protein 37, Chromosome-associated kinesin KIF4A, Voltage-gated potassium channel subunit beta-2, Sodium/myo-inositol cotransporter, Kelch-like protein 42, Putative E3 ubiquitin-protein ligase UNKL, Interleukin-13 receptor subunit alpha-1, Centrosomal protein of 295 kDa, Sec1 family domain-containing protein 2, Xylulose kinase, Uncharacterized protein KIAA0930, Guanine nucleotide exchange factor DBS, ALX homeobox protein 1, Vacuolar protein sorting-associated protein 72 homolog, Beta-citrylglutamate synthase B, 60S ribosomal protein L3-like, Protein orai-2, B-cell lymphoma 3 protein, Serine/threonine-protein kinase Nek9, Protein lin-9 homolog, N-alpha-acetyltransferase 11, Intersectin-2, Ras-responsive element-binding protein 1, Cytoplasmic dynein 1 intermediate chain 1, Dexamethasone-induced Ras-related protein 1, Transmembrane channel-like protein 6, Rab-like protein 3, DNA mismatch repair protein Msh3, POM121 and ZP3 fusion protein, Transmembrane protein 230, Serine/threonine-protein phosphatase 2A regulatory subunit B" subunit beta, Peroxisome biogenesis factor 10, Actin filament-associated protein 1-like 1, Choline kinase alpha, Uncharacterized protein C1orf21, Synaptonemal complex central element protein 1, Ribosomal protein 63, mitochondrial, RNA-binding E3 ubiquitin-protein ligase MEX3C, Ankyrin repeat and SOCS box protein 4, Long-chain fatty acid transport protein 3, Nuclear RNA export factor 1, Potassium voltage-gated channel subfamily G member 3, Coiled-coil domain-containing protein 138, Uncharacterized protein C19orf60, Homeobox protein cut-like 1, Armadillo repeat-containing protein 2, 28S ribosomal protein S5, mitochondrial, Chromatin assembly factor 1 subunit A, Rho guanine nucleotide exchange factor 39, Transcription factor SPT20 homolog, E3 ubiquitin-protein ligase RNF14, Glioma tumor suppressor candidate region gene 2 protein, Dehydrodolichyl diphosphate syntase complex subunit DHDDS, Nuclear receptor-interacting protein 3, Beta-1,3-N-acetylglucosaminyltransferase radical fringe, Transmembrane protein 51, Scavenger receptor class A member 5, Protein FAM167A, Protogenin, EF-hand domain-containing protein D2, Coiled-coil domain-containing protein 144A, Cryptochrome-2, ADP-ribosylation factor-like protein 4D, Partitioning defective 6 homolog beta, HCG2002594, isoform CRA_c, Leucine-rich repeat and WD repeat-containing protein 1, 60S ribosomal protein L39, Meiotic nuclear division protein 1 homolog, cDNA FLJ57726, highly similar to Heterogeneous nuclear ribonucleoprotein H3, Mesencephalic astrocyte-derived neurotrophic factor, Arginine/serine-rich coiled-coil protein 2, Cytochrome P450 2U1, THAP domain-containing protein 1, Hom s 2, Protein CREG2, FLYWCH-type zinc finger-containing protein 1, Rhomboid-like protein, Serine/threonine-protein kinase VRK2, Acyl-coenzyme A thioesterase THEM4, UHRF1-binding protein 1, EWS RNA-binding protein variant 6, Testis-specific Y-encoded protein 1, Butyrophilin subfamily 2 member A2, CDKN2AIP N-terminal-like protein, HIRA-interacting protein 3, Protein FAM199X, Multivesicular body subunit 12B, Spindle and centriole-associated protein 1, COBW domain-containing protein 2, Glycerol kinase, (E3-independent) E2 ubiquitin-conjugating enzyme, Uncharacterized protein KIAA1211, Histone-lysine N-methyltransferase SETMAR, Arginine vasopressin-induced protein 1, Chondroitin sulfate synthase 3, Caspase-9, SHC-transforming protein 3, Tumor protein D53, ENTH domain-containing protein 1, Uncharacterized protein C19orf52, 14-3-3 protein sigma, B-cell CLL/lymphoma 7 protein family member A, ATPase family AAA domain-containing protein 3A, Charged multivesicular body protein 1 b, Platelet-activating factor acetylhydrolase 2, cytoplasmic, ADP-ribosylation factor GTPase-activating protein 1, NADH dehydrogenase [ubiquinone] 1 alpha subcomplex subunit 6, Methyltransferase-like protein 8, Follistatin-related protein 5, ATP-binding cassette sub-family B member 6, mitochondrial, Protein fem-1 homolog C, Ankyrin repeat domain-containing protein 20B, Ventricular zone-expressed PH domain-containing protein homolog 1, Gap junction beta-1 protein, Vitamin K epoxide reductase complex subunit 1, Frataxin, mitochondrial, E3 ubiquitin-protein ligase TRIM32, Protein maestro, Receptor-interacting serine/threonine-protein kinase 1, 2'-5'-oligoadenylate synthase 2, Regulator of nonsense transcripts 2, ATP-sensitive inward rectifier potassium channel 10, Microtubule-associated tumor suppressor 1, Metalloproteinase inhibitor 3, Homeobox protein SEBOX, Nuclear receptor subfamily 4 group A member 1, Carboxypeptidase M, Small glutamine-rich tetratricopeptide repeat-containing protein beta, Alpha-aminoadipic semialdehyde dehydrogenase, Cysteine protease ATG4C, IL6ST nirs variant 1, 60S ribosomal protein L38, Transcription cofactor HES-6, Uncharacterized protein C17orf98, RING finger protein 10, Alpha-crystallin B chain, Probable ATP-dependent RNA helicase DHX40, Transcobalamin-1, Protein argonaute-2, Protein argonaute-4, Pleckstrin homology-like domain family A member 2, Arginine/serine-rich protein 1, Tubulin-specific chaperone E, ELL-associated factor 1, Phosphatase and actin regulator, F-box-like/WD repeat-containing protein TBL1XR1, Osteopontin, Carbohydrate sulfotransferase 11, Olfactory receptor 52E1, HBS1-like protein, Zinc finger protein 43, COMM domain-containing protein 10, Complement component 1 Q subcomponent-binding protein, mitochondrial, Transcription initiation factor TFIID subunit 6, Transcription initiation factor TFIID subunit 7-like, Latent-transforming growth factor beta-binding protein 2, Zinc finger protein 280B, N-acetylglucosamine-1-phosphodiester alpha-N-acetylglucosaminidase, Myb-related protein B, Zinc finger protein 212, Calcium uptake protein 1, mitochondrial, E3 ubiquitin-protein ligase ZNRF1, Phosphomevalonate kinase, Mitochondrial basic amino acids transporter, Protein tweety homolog 2, BMP-2-inducible protein kinase, Histone acetyltransferase KAT7, Ras-related protein Rab-6B, BTB/POZ domain-containing protein 9, Lipid phosphate phosphatase-related protein type 3, Fanconi anemia group A protein, Ran-specific GTPase-activating protein, 39S ribosomal protein L48, mitochondrial, CTP synthase 1, Zinc finger MYM-type protein 6, Protein tweety homolog 3, Interleukin-1 receptor-associated kinase 1, Nuclear distribution protein nudE homolog 1, Krueppel-like factor 5, Bcl-2-related protein A1, CDC42 small effector protein 2, GRAM domain-containing protein 1A, Centrosomal protein of 131 kDa, Inositol hexakisphosphate and diphosphoinositol-pentakisphosphate kinase 2, Presequence protease, mitochondrial, Uncharacterized membrane protein C19orf24, MAM and LDL-receptor class A domain-containing protein 1, NADH-ubiquinone oxidoreductase chain 2, DBH-like monooxygenase protein 1, Biliverdin reductase A, Tetraspanin-14, NADH-ubiquinone oxidoreductase chain 4L, Calcium permeable stress-gated cation channel 1, 60S ribosomal protein L14, WW domain-containing adapter protein with coiled-coil, Poly [ADP-ribose] polymerase 11, KN motif and ankyrin repeat domain-containing protein 4, Methyl-CpG-binding domain protein 6, IQ domain-containing protein G, Glutamate receptor ionotropic, kainate 5, Apoptosis-stimulating of p53 protein 1, Transformer-2 protein homolog beta, Succinyl-CoA ligase [ADP/GDP-forming] subunit alpha, mitochondrial, Neurofilament light polypeptide, Aminoacyl tRNA synthase complex-interacting multifunctional protein 2, Protein FAM73B, Volume-regulated anion channel subunit LRRC8B, Olfactory receptor 51G2, Ubiquitin carboxyl-terminal hydrolase 24, Integrin alpha-2, DnaJ homolog subfamily B member 1, Prostaglandin E2 receptor EP4 subtype, Transmembrane protein 186, RNA-binding protein Musashi homolog 2, Phosphatidylinositol 3,4,5-trisphosphate 5-phosphatase 2, Sodium/iodide cotransporter, Protocadherin-18, Trafficking protein particle complex subunit 8, Protocadherin alpha-1, NF-kappa-B inhibitor epsilon, Peroxisomal trans-2-enoyl-CoA reductase, Protein GPR108, ADP/ATP translocase 1, Uncharacterized protein C4orf36, MAM domain-containing glycosylphosphatidylinositol anchor protein 1, Natriuretic peptides A, PAB-dependent poly(A)-specific ribonuclease subunit PAN3, Zinc finger protein with KRAB and SCAN domains 2, Uncharacterized protein C11orf63, Short-chain-specific acyl-CoA dehydrogenase, mitochondrial, Tyrosine-protein kinase TXK, Lymphocyte antigen 6E, Pappalysin-1, Thiosulfate sulfurtransferase, Threonine-tRNA ligase, mitochondrial, Zinc finger protein 362, Beta-catenin-interacting protein 1, Lysyl oxidase homolog 4, HLA class I histocompatibility antigen, Cw-8 alpha chain, Unconventional myosin-Vb, Unconventional myosin-XIX, GPI inositol-deacylase, Methyl-CpG-binding domain protein 4, PDZ and LIM domain protein 2, Sphingosine-1-phosphate lyase 1, CBP80/20-dependent translation initiation factor, Nuclear receptor ROR-beta, Sulfhydryl oxidase 2, Partner of Y14 and mago, Plexin-A1, Sialomucin core protein 24, Neural cell adhesion molecule L1-like protein, Lysosome membrane protein 2, ATP-binding cassette subfamily A member 1, Signal-regulatory protein delta.

According to preferred embodiments, the at least one antigenic peptide or protein encoded by the at least one coding region of the artificial nucleic acid molecule, preferably RNA, of the invention, may be derived from a mutated tumor antigen selected from ZFHX3 (R1893G), XPO1 (E571K), VHL (S111N; S65*; S68*), VHL (L89H), UBR5 (E2121K), U2AF1 (S34F), TSC2 (splice variant), TRRAP (S722F), TP53 (A159P; A159V; A161 T; C135F; C135Y; C141Y; C176F; C176Y; C229Y; C238F; C238Y; C242A; C242F; C275F; C275Y; C277F; D259Y; D281N; D281Y; E198*; E204*; E221*; E224D; E271K; E285*; E285K; E286K; E294*; E298*; E56*; F134L; G154A; G244C; G244D; G244S; G245C; G245D; G245S; G245V; G262V; G266*; G266E; G266R; G266V; H179L; H179R; H179Y; H193L; H193P; H193R; H193Y; H214R; I195T; I255F; K132E; K132N; K132R; L130F; L194R; M237I; N239*; N239S; P151H; P151S; P152L; P177R; P250L; P278A; P278L; P278R; P278S; P27L; Q104*; Q136*; Q144*; Q167*; Q192*; Q317*; Q331*; R110L; R156P; R158G; R158H; R158L; R175G; R175H; R196*; R196P; R213*; R213Q; R248Q; R248W; R249G; R249M; R249S; R249W; R267P; R273C; R273H; R273L; R273P; R280G; R280I; R280K; R280T; R282W; R306*; R337C; R337L; R342*; S127F; S127Y; S183*; S215I; S215R; S241F; T125T; T155N; T155P; V122D; V157F; V173L; V173M; V216M; V272M; V274A; V73W; W146*; W91*; Y163C; Y205C; Y220C; Y234C; Y236C), STK11 (splice variant), STIP1 (splice variant), STAG2 (splice variant), SPOP (F133L), SPEN (R806T), SOX17 (S403I), SMO (L412F), SMARCA4 (G1232S; R1135W; T910M), SMARCA1 (splice variant), SMAD4 (R361C; R361H; R445*), SF3B1 (G742D; K700E), SETD2 (splice variant), SCAI (Q155H), RUNX1 (R201*), RRAS2 (Q72L), RQCD1 (P131L), RPSAP58 (Q111E), RNF43 (G659V), RHOA (E40Q), RHEB (Y35N), RB1 (R579*), RAC1 (P29S), PTPRB (D1778N), PTPN11 (G503V; T468M), PTEN (A328Q; P248T; Q298*; R130*; R130G; R130L; R130P; R130Q; R233*; R335*; S170N; T319*; Y27D), PPP6C (R301C; S307L), PPP2R1A (P179R; R183W), POLE (splice variant), PIK3R1 (G376R; K567E; N564D), PIK3CA (C420R; C901F; D350G; E110delE; E453K; E542K; E545A; E545G; E545K; E726K; E81K; G1049R; G118D; H1047L; H1047R; K111 E; K111N; M1043I; M1043V; N1044K; N345K; Q546K; Q546P; Q546R; R108H; R38H; R88Q; R93Q; V344G; V344M), PBRM1 (splice variant), PABPC3 (A313R), NRAS (G12C; G12D; G13D; G13R; Q61H; Q61K; Q61L; Q61R), NPM1 (Q289S; W288L), NOTCH1 (E2515V), NFE2L2 (D29H; E79Q; R34G), NF1 (K1661G; R440*), NCOR1 (splice variant), MYD88 (L265P), MYCN (P44L), MUC4 (H4205Q), MLL3 (splice variant), MLL2 (splice variant), MGA (R2435Q), MED12 (L1224F), MAX (H28R; R60Q), MAP2K4 (S184L), MAP2K1 (E203K; P124S), LRPPRC (splice variant), KRAS (A146T; G12A; G12C; G12D; G12F; G12R; G12S; G12V; G13C; G13D; K117N; Q61H; Q61K; Q61L; Q61R), KIT (D816V), KDR (S1100F), KDM6A (Q555*), ING1 (R339*), IDH2 (R140Q; R172K), IDH1 (R132C; R132G; R132H; R132S), HRAS (G12D; G13V; Q61K; Q61R), HIST1H3B (E74K), HERC2 (splice variant), GNAS (R201C), GATA3 (P409A), FRG1 (E176*), FLT3 (D835Y), FGFR3 (S249C), FGFR2 (N550K; S252W), FBXW7 (G423V; R465C; R465H; R479Q; R505C; R505G), FAT1 (splice variant), FANCD2 (splice variant), ERBB4 (R711C), ERBB3 (D297Y; V104L; V104M), ERBB2 (D769Y; L755S; R678Q; S31 OF; V8421), EP300 (D1399N), EIF2AK3 (R911E), EGFR (A289T; A289V; G598V; L858R; L861Q; R108K; R222C), EEF1B2 (S43G), DNMT3A (R882C; R882H), CUL3 (splice variant), CUL1 (E485K), CTNNB1 (D32N; D32Y; G34E; G34R; S33C; S33F; S33Y; S37A; S37C; S37F; S37Y; S45F; T41A; T41I), CTCF (R448*), CSNK2A1 (H236R), CREBBP (R1446C), CR1 (E2220*; R2194*), CNOT3 (E20K), CLOCK (L123*), CLCC1 (P406Q), CLASP2 (M965W), CIC (R215W), CHD8 (splice variant), CHD4 (R 162W; R975H), CEP290 (1556N), CDKN2A (D84N; E120*; E88*; H83Y; P114L; P48L; Q50*; R58*; R80*; W110*), CDH1 (splice variant), CARM1 (A202V), BRAF (G466V; K601E; N581S; V600E; V600K), BAP1 (splice variant), B2M (L15F), ATRX (R1426*), ATM (splice variant), ARID2 (S297F), ARID1A (R1276*; R1335*; R1989*; R2158*; R693*, ARFGAP3 (N299M), APC (E1374*; F1491L; Q1367*; Q1378*; R1114*; R1450*; R213*; R216*; R302*; R564*; R805*; R876*; S1346*; T1556N), ALK (F1174L; R1275Q), AKT1 (E17K), ACVR2A (K437R), Prostate-specific antigen precursor, Kita-kyushu lung cancer antigen 1, Trophoblast glycoprotein, Cyclin-dependent kinase inhibitor 2A, Cyclin-dependent kinase inhibitor 2A, isoforms 1/2/3, multiple tumor suppressor 1/cyclin-dependent kinase 4 inhibitor p16, GTPase NRas or a fragment, variant or derivative of any one of said mutated tumor antigens, or any combination thereof. (Sequence changes at protein level with an asterix are described as amino acid deletion introducing an immediate translation stop codon).

According to preferred embodiments, the artificial nucleic acid molecule according to the invention may encode in its at least one encoding region at least one antigenic peptide or protein comprising or consisting of an amino acid sequence according to any one of SEQ ID NOs: 3719-27945; 76420-76439, 76440-76474 or a fragment, variant or derivative of any one of said sequences, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably at least 90% and most preferably of at least 95% or even 97%, sequence identity to any of these sequences.

According to preferred embodiments, artificial nucleic acid molecule according to the invention may encode in its at least one coding region at least one antigenic pepide or protein comprising or consisting of an amino acid sequence according to SEQ ID NOs: 1-504 in patent application WO2017182634 (as listed in Table 1) or a fragment, variant or derivative of any one of said sequences, preferably comprising or consisting of an amino acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

Accordingly, the coding region of the artificial nucleic acid molecule according to the invention may preferably comprise a nucleic acid sequence according to any one of SEQ ID NOs: 27946-52172; 76495-76514, 52173-76399; 76570-76589, 76515-76549, 76590-76624 or a fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

According to preferred embodiments, the artificial nucleic acid molecule according to the invention may comprise in its at least one coding region at least one nucleic acid sequence according to SEQ ID NOs: 505-4536 in patent application WO2017182634 (as listed in Table 1) or a fragment, variant or derivative of any one of said sequences, preferably comprising or consisting of a nucleic acid sequence having, in increasing order of preference, at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

According to particularly preferred embodiments, the artificial nucleic acid molecule, preferably RNA, of the invention may encode in its at least one coding region an antigenic peptide or protein derived from a tumor antigen selected from BRAF, PIK3CA, KRAS, IDH1, TP53, NRAS, AKTI, SF3B1, CDKN2A, RPSAP58, EGFR, NY-ESO1, MUC-1, 5T4, Her2, MAGE-A3, LY6K, CEACAM6, CEA, MCAK, KK-LC1, Gastrin, VEGFR2, MMP-7, MPHOSPH1, MAGE-A4, MAGE-A1, MAGE-C1, PRAME, Survivin, MAGE-A9, MAGE-C2, FGFR2, WT1, PSA, PSMA, Prostate-specific antigen precursor, Kita-kyushu lung cancer antigen 1, Trophoblast glycoprotein, Cyclin-dependent kinase inhibitor 2A, Cyclin-dependent kinase inhibitor 2A, isoforms 1/2/3, multiple tumor suppressor 1/cyclin-dependent kinase 4 inhibitor p16, GTPase NRas, or a fragment, variant or derivative of any one of said tumor antigens, or any combination thereof.

Bacterial, Viral, Protozoal, Fungal Antigens

According to further preferred embodiments, the artificial nuclei acid molecule, preferably RNA, according to the invention encodes, in its at least one coding region, at least one antigenic peptide or protein derived from a bacterial, viral, protozoal or fungal antigen.

Preferably, said at least one antigenic peptide or protein encoded by the at least one coding region of the artificial nucleic acid molecule, preferably RNA, of the invention, may be derived from a bacterial, viral, protozoal or fungal antigen derived from *Agrobacterium tumefaciens, Ajellomyces dermatitidis* ATCC 60636, Alphapapillomavirus 10, Andes orthohantavirus, Andes virus CHI-7913, *Aspergillus terreus* NIH2624, Avian hepatitis E virus, *Babesia microti, Bacillus anthracis*, Bacteria, Betacoronavirus England 1, *Blattella germanica, Bordetella pertussis*, Borna disease virus Giessen strain He/80, *Borrelia burgdorferi* B31, *Borrelia burgdorferi* CA12, *Borrelia burgdorferi* N40, *Borrelia burgdorferi* ZS7, *Borrelia garinii* IP90, *Borrelia hermsii, Borreliella afzelii, Borreliella burgdorferi, Borreliella garinii, Bos taurus, Brucella melitensis, Brugia malayi, Bundibugyo ebolavirus, Burkholderia pseudomallei, Burkholderia pseudomallei* K96243, *Campylobacter jejuni, Campylobacter upsaliensis, Candida albicans, Cavia porcellus*, Chikungunya virus, Chikungunya virus MY/08/065, Chikungunya virus Singapore/11/2008, Chikungunya virus strain LR2006_OPY1 IMT/Reunion Island/2006, Chikungunya virus strain S27-African prototype, *Chlamydia pneumoniae, Chlamydia trachomatis, Chlamydia trachomatis* Serovar D, Chlamydiae, Clostridioides *difficile, Clostridium difficile* BI/NAP1/027, *Clostridium tetani*, Convict Creek 107 virus, *Corynebacterium diphtheriae*, Cowpox virus (Brighton Red) White-pock, Coxsackievirus A16, Coxsackievirus A9, Coxsackievirus B1, Coxsackievirus B2, Coxsackievirus B3, Coxsackievirus B4, Crimean-Congo hemorrhagic fever orthonairovirus, *Cryptosporidium parvum*, Dengue virus, Dengue virus 1, Dengue virus 1 Nauru/West Pac/1974, Dengue virus 1 PVP159, Dengue virus 1 Singapore/S275/1990, Dengue virus 2, Dengue virus 2 D2/SG/05K4155DK1/2005, Dengue virus 2 Jamaica/i 1409/1983, Dengue virus 2 Puerto Rico/PR159-S1/1969, Dengue virus 2 strain 43, Dengue virus 2 Thailand/16681/84, Dengue virus 2 Thailand/NGS-C/1944, Dengue virus 3, Dengue virus 4, Dengue virus 4 Dominica/814669/1981, Dengue virus 4 Thailand/0348/1991, Dengue virus type 1 Hawaii, Ebola virus—Mayinga, Zaire, 1976, Ebolavirus, *Echinococcus granulosus, Echinococcus multilocularis*, Echovirus E11, Echovirus E9, *Ehrlichia canis* str. Jake, *Ehrlichia chaffeensis, Ehrlichia chaffeensis* str. Arkansas, *Entamoeba histolytica, Entamoeba histolytica* YS-27, *Enterococcus fae-*

*cium*, Enterovirus A, Enterovirus A71, Enterovirus C, *Escherichia coli, Fasciola gigantica, Fasciola hepatica*, Four Corners hantavirus, *Francisella tularensis, Francisella tularensis* subsp. holarctica LVS, *Francisella tularensis* subsp. *tularensis* SCHU S4, Gambierdiscus toxicus, GB virus C, *Glossina morsitans morsitans, Gnathostoma* binucleatum, Gp160, H1N1 subtype, H5N1 subtype, *Haemophilus influenzae* NTHi 1128, *Haemophilus influenzae* Serotype B, *Haemophilus influenzae* Subtype 1H, Hantaan orthohantavirus, Hantaan virus 76-118, HBV genotype D, *Helicobacter pylori, Helicobacter pylori* 26695, Heligmosomoides polygyrus, Hepatitis B virus, Hepatitis B virus adr4, Hepatitis B virus ayw/France/Tiollais/1979, Hepatitis B virus genotype D, Hepatitis B virus subtype adr, Hepatitis B virus subtype adw, Hepatitis B virus subtype adw2, Hepatitis B virus subtype adyw, Hepatitis B virus subtype AYR, Hepatitis B virus subtype ayw, Hepatitis C virus, Hepatitis C virus (isolate 1), Hepatitis C virus (isolate BK), Hepatitis C virus (isolate Conl), Hepatitis C virus (isolate Glasgow), Hepatitis C virus (isolate H), Hepatitis C virus (isolate H77), Hepatitis C virus (isolate HC-G9), Hepatitis C virus (isolate HCV-K3a/650), Hepatitis C virus (isolate Japanese), Hepatitis C virus (isolate JK049), Hepatitis C virus (isolate NZL1), Hepatitis C virus (isolate Taiwan), Hepatitis C virus genotype 1, Hepatitis C virus genotype 2, Hepatitis C virus genotype 3, Hepatitis C virus genotype 4, Hepatitis C virus genotype 5, Hepatitis C virus genotype 6, Hepatitis C virus HCT18, Hepatitis C virus HCV-KF, Hepatitis C virus isolate HC-J1, Hepatitis C virus isolate HC-J6, Hepatitis C virus isolate HC-J8, Hepatitis C virus JFH-1, Hepatitis C virus subtype 1a, Hepatitis C virus subtype 1a Chiron Corp., Hepatitis C virus subtype 1 b, Hepatitis C virus subtype 1b AD78, Hepatitis C virus subtype 1b isolate BE-11, Hepatitis C virus subtype 1b JK1, Hepatitis C virus subtype 2a, Hepatitis C virus subtype 2b, Hepatitis C virus subtype 3a, Hepatitis C virus subtype 5a, Hepatitis C virus subtype 6a, Hepatitis delta virus, Hepatitis delta virus TW2667, Hepatitis E virus, Hepatitis E virus (strain Burma), Hepatitis E virus (strain Mexico), Hepatitis E virus SAR-55, Hepatitis E virus type 3 Kernow-C1, Hepatitis E virus type 4 JAK-Sai, Hepatovirus A, Heron hepatitis B virus, Herpes simplex virus (type 1/strain 17), Herpesviridae, HIV-1 CRF01_AE, HIV-1 group O, HIV-1 M:A, HIV-1 M:B, HIV-1 M:B_89.6, HIV-1 M:B_HXB2R, HIV-1 M:B_MN, HIV-1 M:C, HIV-1 M:CRF01_AE, HIV-1 M:G, HIV-1 O_ANT70, Human adenovirus 11, Human adenovirus 2, Human adenovirus 40, Human adenovirus 5, Human alphaherpesvirus 1, Human alphaherpesvirus 2, Human alphaherpesvirus 3, Human betaherpesvirus 5, Human betaherpesvirus 6B, Human bocavirus 1, Human bocavirus 2, Human bocavirus 3, Human coronavirus 229E, Human coronavirus OC43, Human endogenous retrovirus, Human endogenous retrovirus H, Human endogenous retrovirus K, Human enterovirus 71 Subgenogroup C4, Human gammaherpesvirus 4, Human gammaherpesvirus 8, Human hepatitis A virus Hu/Australia/HM175/1976, Human herpesvirus 1 strain KOS, Human herpesvirus 2 strain 333, Human herpesvirus 2 strain HG52, Human herpesvirus 3H-551, Human herpesvirus 3 strain Oka vaccine, Human herpesvirus 4 strain B95-8, Human herpesvirus 4 type 1, Human herpesvirus 4 type 2, Human herpesvirus 5 strain AD169, Human herpesvirus 5 strain Towne, Human herpesvirus 6 (strain Uganda-1102), Human herpesvirus 7 strain JI, Human immunodeficiency virus 1, Human immunodeficiency virus 2, Human immunodeficiency virus type 1 (isolate YU2), Human immunodeficiency virus type 1 (JRCSF ISOLATE), Human immunodeficiency virus type 1 (NEW YORK-5 ISOLATE), Human immunodeficiency virus type 1 (SF162 ISOLATE), Human immunodeficiency virus type 1 (SF33 ISOLATE), Human immunodeficiency virus type 1 BH10, Human metapneumovirus, Human orthopneumovirus, Human papillomavirus, Human papillomavirus type 11, Human papillomavirus type 16, Human papillomavirus type 18, Human papillomavirus type 29, Human papillomavirus type 31, Human papillomavirus type 33, Human papillomavirus type 35, Human papillomavirus type 39, Human papillomavirus type 44, Human papillomavirus type 45, Human papillomavirus type 51, Human papillomavirus type 52, Human papillomavirus type 58, Human papillomavirus type 59, Human papillomavirus type 6, Human papillomavirus type 68, Human papillomavirus type 6b, Human papillomavirus type 73, Human parainfluenza 3 virus (strain NIH 47885), Human parechovirus 1, Human parvovirus 4, Human parvovirus B19, Human poliovirus 1, Human poliovirus 1 Mahoney, Human poliovirus 3, Human polyomavirus 1, Human respiratory syncytial virus (strain RSB1734), Human respiratory syncytial virus (strain RSB6190), Human respiratory syncytial virus (strain RSB6256), Human respiratory syncytial virus (strain RSB642), Human respiratory syncytial virus (subgroup B/strain 18537), Human respiratory syncytial virus A, Human respiratory syncytial virus A strain Long, Human respiratory syncytial virus A2, Human respiratory syncytial virus S2, Human respirovirus 3, Human rhinovirus A89, Human rotavirus A, Human T-cell lymphotrophic virus type 1 (Caribbean isolate), Human T-cell lymphotrophic virus type 1 (isolate MT-2), Human T-cell lymphotrophic virus type 1 (strain ATK), Human T-cell lymphotropic virus type 1 (african isolate), Human T-lymphotropic virus 1, Human T-lymphotropic virus 2, Influenza A virus, Influenza A virus (A/Anhui/1/2005(H5N1)), Influenza A virus (A/Anhui/PA-1/2013 (H7N9)), Influenza A virus (A/Argentina/3779/94(H3N2)), Influenza A virus (A/Auckland/1/2009(H1N1)), Influenza A virus (A/Bar-headed Goose/Qinghai/61/05(H5N1)), Influenza A virus (A/Brevig Mission/1/1918(H1N1)), Influenza A virus (A/California/04/2009(H1N1)), Influenza A virus (A/California/07/2009(H1N1)), Influenza A virus (A/California/08/2009(H1N1)), Influenza A virus (A/California/10/1978(H1N1)), Influenza A virus (A/Christchurch/2/1988 (H3N2)), Influenza A virus (A/Cordoba/3278/96(H3N2)), Influenza A virus (A/France/75/97(H3N2)), Influenza A virus (A/Fujian/411/2002(H3N2)), Influenza A virus (A/Hong Kong/01/2009(H1N1)), Influenza A virus (A/Hong Kong/1/1968(H3N2)), Influenza A virus (A/Indonesia/CDC699/2006(H5N1)), Influenza A virus (A/lran/1/1957 (H2N2)), Influenza A virus (A/Memphis/13/1978(H1N1)), Influenza A virus (A/Memphis/4/1980(H3N2)), Influenza A virus (A/Nanchang/58/1993(H3N2)), Influenza A virus (A/New York/232/2004(H3N2)), Influenza A virus (A/New_York/15/94(H3N2)), Influenza A virus (A/New_York/17/94(H3N2)), Influenza A virus (A/Ohio/3/95(H3N2)), Influenza A virus (A/Otago/5/2005(H1N1)), Influenza A virus (A/Puerto Rico/8/1934(H1N1)), Influenza A virus (A/Shangdong/5/94(H3N2)), Influenza A virus (A/Solomon Islands/3/2006 (Egg passage)(H1N1)), Influenza A virus (A/South Carolina/1/1918(H1N1)), Influenza A virus (A/swine/Hong Kong/126/1982(H3N2)), Influenza A virus (A/swine/Ilowa/15/1930(H1N1)), Influenza A virus (A/Sydney/05/97-like(H3N2)), Influenza A virus (A/Texas/1/1977 (H3N2)), Influenza A virus (A/Udorn/307/1972(H3N2)), Influenza A virus (A/Uruguay/716/2007(H3N2)), Influenza A virus (A/USSR/26/1985(H3N2)), Influenza A virus (ANiet Nam/1203/2004(H5N1)), Influenza A virus (A/Vietnam/1194/2004(H5N1)), Influenza A virus (A/Wellington/

75/2006(H1N1)), Influenza A virus (A/Wilson-Smith/1933 (H1N1)), Influenza A virus (A/Wuhan/359/1995(H3N2)), Influenza A virus (STRAIN A/EQUINE/NEW MARKET/76), Influenza B virus, Japanese encephalitis virus, Japanese encephalitis virus strain Nakayama, Japanese encephalitis virus Vellore P20778, JC polyomavirus, *Junin mammarenavirus, Klebsiella pneumoniae*, Kumlinge virus, Lake Victoria marburgvirus—Popp, Lassa mammarenavirus, Lassa virus Josiah, *Leishmania, Leishmania aethiopica, Leishmania braziliensis, Leishmania braziliensis* MHOM/BR/75/M2904, *Leishmania chagasi, Leishmania donovani, Leishmania infantum, Leishmania major, Leishmania major* strain Friedlin, *Leishmania panamensis, Leishmania pifanoi, Leptospira interrogans, Leptospira interrogans* serovar *Australis, Leptospira interrogans* serovar Copenhageni, *Leptospira interrogans* serovar Copenhageni str. Fiocruz L1-130, *Leptospira interrogans* serovar Lai, *Leptospira interrogans* serovar Lai str. HY-1, *Leptospira interrogans* serovar Pomona, Little cherry virus 1, Lymphocytic choriomeningitis mammarenavirus, Measles morbillivirus, Measles virus strain Edmonston, Merkel cell polyomavirus, Mobala mammarenavirus, Modified Vaccinia Ankara virus, *Moraxella catarrhalis* 035E, Mupapillomavirus 1, *Mus musculus, Mycobacterium, Mycobacterium abscessus, Mycobacterium avium, Mycobacterium avium* serovar 8, *Mycobacterium avium* subsp. paratuberculosis, *Mycobacterium bovis* AN5, *Mycobacterium bovis* BCG, *Mycobacterium bovis* BCG str. Pasteur 1173P2, *Mycobacterium fortuitum* subsp. *fortuitum, Mycobacterium gilvum, Mycobacterium intracellulare, Mycobacterium kansasii, Mycobacterium leprae, Mycobacterium leprae* TN, *Mycobacterium marinum, Mycobacterium neoaurum, Mycobacterium phlei, Mycobacterium smegmatis, Mycobacterium tuberculosis, Mycobacterium tuberculosis* CDC1551, *Mycobacterium tuberculosis* H37Ra, *Mycobacterium tuberculosis* H37Rv, *Mycobacterium ulcerans, Mycoplasma pneumoniae, Mycoplasma pneumoniae* FH, *Mycoplasma pneumoniae* M129, *Necator americanus, Neisseria gonorrhoeae, Neisseria meningitidis* serogroup B H44/76, Nipah henipavirus, Norovirus genogroup 2 Camberwell 1890, *Onchocerca volvulus, Orientia tsutsugamushi, Oryctolagus cuniculus*, Pan troglodytes, *Paracoccidioides brasiliensis, Paracoccidioides brasiliensis* B339, *Plasmodium falciparum, Plasmodium falciparum* 3D7, *Plasmodium falciparum* 7G8, *Plasmodium falciparum* FC27/Papua New Guinea, *Plasmodium falciparum* FCR-3/Gambia, *Plasmodium falciparum* isolate WELLCOME, *Plasmodium falciparum* K1, *Plasmodium falciparum* LE5, *Plasmodium falciparum* Mad20/Papua New Guinea, *Plasmodium falciparum* NF54, *Plasmodium falciparum* Palo Alto/Uganda, *Plasmodium falciparum* RO-33, *Plasmodium reichenowi, Plasmodium vivax, Plasmodium vivax* NK, *Plasmodium vivax* Sal-1, *Plasmodium vivax* strain Belem, *Plasmodium vivax*-like sp., *Porphyromonas gingivalis, Porphyromonas gingivalis* 381, *Porphyromonas gingivalis* OMZ 409, *Prevotella* sp. oral taxon 472 str. F0295, *Pseudomonas aeruginosa*, Puumala orthohantavirus, Puumala virus (strain Umea/hu), Puumala virus sotkamo/v-2969/81, *Pythium insidiosum*, Ravn virus—Ravn, Kenya, 1987, Respiratory syncytial virus, *Rhodococcus fascians, Rhodococcus hoagii*, Rubella virus, Rubella virus strain M33, Rubella virus strain Therien, Rubella virus vaccine strain RA27/3, *Saccharomyces cerevisiae*, Saimiriine gammaherpesvirus 2, *Salmonella enterica* subsp. *enterica* serovar *Typhi, Salmonella* 'group A', *Salmonella* 'group D', *Salmonella* sp. 'group B', Sapporo rat virus, SARS coronavirus, SARS coronavirus BJ01, SARS coronavirus TJF, SARS coronavirus Tor2, SARS coronavirus Urbani, *Schistosoma, Schistosoma japonicum, Schistosoma mansoni, Schistosoma mansoni* Puerto Rico, Sin Nombre orthohantavirus, Sindbis virus, *Staphylococcus aureus, Staphylococcus aureus* subsp. *aureus* COL, *Staphylococcus aureus* subsp. *aureus* MRSA252, *Streptococcus, Streptococcus mutans, Streptococcus mutans* MT 8148, *Streptococcus oralis, Streptococcus pneumoniae, Streptococcus pyogenes, Streptococcus pyogenes* serotype M24, *Streptococcus pyogenes* serotype M3 D58, *Streptococcus pyogenes* serotype M5, *Streptococcus pyogenes* serotype M6, *Streptococcus* sp. 'group A', *Taenia crassiceps, Taenia saginata, Taenia solium*, Tick-borne encephalitis virus, *Toxocara canis, Toxoplasma gondii, Toxoplasma gondii* ME49, *Toxoplasma gondii* RH, *Toxoplasma gondii* type I, *Toxoplasma gondii* type II, *Toxoplasma gondii* type III, *Toxoplasma gondii* VEG, *Treponema pallidum, Treponema pallidum* subsp. *pallidum* str. Nichols, *Trichomonas vaginalis, Triticum aestivum, Trypanosoma brucei brucei, Trypanosoma brucei* gambiense, *Trypanosoma cruzi, Trypanosoma cruzi* Dm28c, *Trypanosoma cruzi* strain CL Brener, Vaccinia virus, Vesicular stomatitis virus, *Vibrio cholerae*, West Nile virus, West Nile virus NY-99, *Wuchereria bancrofti*, Yellow fever virus 17D/Tiantan, *Yersinia enterocolitica*, Zaire ebolavirus, Zika virus, or a fragment, variant or derivative of any one of said bacterial, viral, protozoal, fungal antigens, or any combination thereof.

Allogeneic Antigens

According to further preferred embodiments, the artificial nuclei acid molecule, preferably RNA, according to the invention encodes, in its at least one coding region, at least one antigenic peptide or protein derived from an allogeneic antigen.

An "allogeneic antigen" or "alloantigen" or "isoantigen" is an antigen existing in alternative (allelic) forms in a species, and can therefore induce alloimmunity (or isoimmunity) in members of the same species, e.g. upon blood transfusion, tissue or organ transplantation, or sometimes pregnancy. Typical allogeneic antigens include histocompatibility antigens and blood group antigens. In the context of the present invention, allogeneic antigens are preferably of human origin. The provision of an artificial nucleic acid, preferably RNA, encoding an antigenic protein or peptide derived from an allogeneic antigen can, for instance, be used to induce immune tolerance towards said allogeneic antigen.

Preferably, the at least one antigenic peptide or protein encoded by the at least one coding region of the artificial nucleic acid molecule, preferably RNA, of the invention, may be derived from an allogeneic antigen derived or selected from UDP-glucuronosyltransferase 2B17 precursor, MHC class I antigen HLA-A2, Coagulation factor VIII precursor, coagulation factor VIII, Thrombopoietin precursor (Megakaryocyte colony-stimulating factor) (Myeloproliferative leukemia virus oncogene ligand) (C-mpl ligand) (ML) (Megakaryocyte growth and development factor) (MGDF), Integrin beta-3, histocompatibility (minor) HA-1, SMCY, thymosin beta-4, Y-chromosomal, Histone demethylase UTY, HLA class II histocompatibility antigen, DP(W2) beta chain, lysine-specific demethylase 5D isoform 1, myosin-lg, Probable ubiquitin carboxyl-terminal hydrolase FAF-Y, Pro-cathepsin H, DRB1, MHC DR beta DRw13 variant, HLA class II histocompatibility antigen, DRB1-15 beta chain, HLA class II histocompatibility antigen, DRB1-1 beta chain precursor, Minor histocompatibility protein HMSD variant form, HLA-DR3, Chain B, Hla-Drl (Dra, Drb10101) Human Class Iii Histocompatibility Protein (Extracellular Domain) Complexed With Endogenous Peptide, MHC classII HLA-DRB1, MHC class I HLA-A, human leukocyte antigen B, RAS protein activator like-3, anoctamin-9, ATP-dependent RNA helicase DDX3Y, Protocadherin-11 Y-linked, KIAA0020, platelet glycoprotein IIIa leucine-33 form-specific antibody light chain variable region, dead box, Y isoform, ATP-dependent RNA helicase DDX3X isoform 2, HLA-DRB1 protein, truncated integrin beta 3, glycoprotein IIIa, platelet membrane glycoprotein IIb, Carbonic anhydrase 1, HLA class I histocompatibility antigen, A-11 alpha chain precursor, HLA-A11 antigen A11.2, HLA class I histocompatibility antigen, A-68 alpha chain, MHC HLA-B51, MHC class I antigen HLA-A30, HLA class I histocompatibility antigen, A-1 alpha chain precursor variant, HLA class I histocompatibility antigen B-57, MHC class I antigen, MHC class II antigen, MHC HLA-DR-beta cell surface glycoprotein, DR7 beta-chain glycoprotein, MHC DR-beta, lymphocyte antigen, collagen type V alpha 1, collagen alpha-2(V) chain preproprotein, sp 10 nuclear body protein isoform d, integrin, alpha 2b (platelet glycoprotein IIb of IIb/IIIa complex, antigen CD41), isoform CRA_c, 40S ribosomal protein S4, Y isoform 1, uncharacterized protein KIAA1551, factor VIII, UDP-glucuronosyltransferase 2B17, HLA class I histocompatibility antigen, A-2 alpha chain, Thrombopoietin, Minor histocompatibility protein HA-1, Lysine-specific demethylase 5D, HLA class II histocompatibility antigen, DP beta 1 chain, Unconventional myosin-lg, HLA class II histocompatibility antigen, DRB1-13 beta chain, HLA class II histocompatibility antigen, DRB1-1 beta chain, HLA class II histocompatibility antigen, DRB1-3 chain, HLA class I histocompatibility antigen, B-46 alpha chain, Pumilio homolog 3, ATP-dependent RNA helicase DDX3X, Integrin alpha-11b, HLA class I histocompatibility antigen, A-11 alpha chain, HLA class I histocompatibility antigen, B-51 alpha chain, HLA class I histocompatibility antigen, A-30 alpha chain, HLA class I histocompatibility antigen, A-1 alpha chain, HLA class I histocompatibility antigen, B-57 alpha chain, HLA class I histocompatibility antigen, B-40 alpha chain, HLA class II histocompatibility antigen, DRB1-7 beta chain, HLA class II histocompatibility antigen, DRB1-12 beta chain, Collagen alpha-1(V) chain, Collagen alpha-2(V) chain, Sp110 nuclear body protein, or a fragment, variant or derivative of any one of said allogeneic antigens, or any combination thereof.

Autoantigens

According to further preferred embodiments, the artificial nuclei acid molecule, preferably RNA, according to the invention encodes, in its at least one coding region, at least one antigenic peptide or protein derived from an autoantigen.

An "autoantigen" an endogenous "self-" antigen that-despite being a normal body constituent-induces an autoimmune reaction in the host. In the context of the present invention, autoantigens are preferably of human origin. The provision of an artificial nucleic acid, preferably RNA, encoding an antigenic protein or peptide derived from an autoantigen can, for instance, be used to induce immune tolerance towards said autoantigen.

Preferably, the at least one antigenic peptide or protein encoded by the at least one coding region of the artificial nucleic acid molecule, preferably RNA, of the invention, may encode an antigenic peptide or protein derived from an autoantigen derived or selected from 60 kDa chaperonin 2, Lipoprotein LpqH, Melanoma antigen recognized by T-cells 1, MHC class I polypeptide-related sequence A, Parent Protein, Structural polyprotein, Tyrosinase, Myelin proteolipid protein, Epstein-Barr nuclear antigen 1, Envelope glycoprotein GP350, Genome polyprotein, Collagen alpha-1(II) chain, Aggrecan core protein, Melanocyte-stimulating hormone receptor, Acetylcholine receptor subunit alpha, 60 kDa heat shock protein, mitochondrial, Histone H4, Myosin-11, Glutamate decarboxylase 2, 60 kDa chaperonin, PqqC-like protein, Thymosin beta-10, Myelin basic protein, Epstein-Barr nuclear antigen 4, Melanocyte protein PMEL, HLA class II histocompatibility antigen, DQ beta 1 chain, Latent membrane protein 2, Integrin beta-3, Nucleoprotein, 60S ribosomal protein L10, Protein BOLF1, 60S acidic ribosomal protein P2, Latent membrane protein 1, Collagen alpha-2(VI) chain, Exodeoxyribonuclease V, Gamma, Trans-activator protein BZLF1, S-arrestin, HLA class I histocompatibility antigen, A-3 alpha chain, Protein CT_579, Matrin-3, Envelope glycoprotein B, ATP-dependent zinc metalloprotease FtsH, U1 small nuclear ribonucleoprotein 70 kDa, CD48 antigen, Tubulin beta chain, Actin, cytoplasmic 1, Epstein-Barr nuclear antigen 3, NEDD4 family-interacting protein 1, 60S ribosomal protein L28, Immediate-early protein 2, Insulin, isoform 2, Keratin, type II cytoskeletal 3, Matrix protein 1, Histone H2A.Z, mRNA export factor ICP27 homolog, Small nuclear ribonucleoprotein-associated proteins B and B', Large cysteine-rich periplasmic protein OmcB, Smoothelin, Small nuclear ribonucleoprotein Sm D1, Acetylcholine receptor subunit epsilon, Invasin repeat family phosphatase, Alpha-crystallin B chain, HLA class II histocompatibility antigen, DRB1-13 beta chain, HLA class II histocompatibility antigen, DRB1-4 beta chain, Dihydrolipoyllysine-residue acetyltransferase component of pyruvate dehydrogenase complex, mitochondrial, Keratin, type I cytoskeletal 18, Epstein-Barr nuclear antigen 6, Protein Tax-1, Vimentin, Keratin, type I cytoskeletal 16, Keratin, type I cytoskeletal 10, HLA class I histocompatibility antigen, B-27 alpha chain, Thyroglobulin, Acetylcholine receptor subunit gamma, Chaperone protein DnaK, Protein U24, Na(+)-translocating NADH-quinone reductase subunit A, 65 kDa phosphoprotein, Probable ATP-dependent Clp protease ATP-binding subunit, Probable outer membrane protein PmpC, Heat shock 70 kDa protein 1B, Hemagglutinin, Tetanus toxin, Enolase, Ras-associated and pleckstrin homology domains-containing protein 1, Keratin, type II cytoskeletal 7, Myosin-9, Histone H1-like protein Hcl, Envelope glycoprotein gp160, Urease subunit beta, Vasoactive intestinal polypeptide receptor 1, Viral interleukin-10 homolog, Histone H3.3, Replication protein A 32 kDa subunit, Probable outer membrane protein PmpD, Insulin-2, L-dopachrome tautomerase, Keratin, type I cytoskeletal 9, Envelope glycoprotein H, DNA polymerase catalytic subunit, Beta-2-glycoprotein 1, Envelope glycoprotein gp62, Serum albumin, Major DNA-binding protein, HLA class I histocompatibility antigen, A-2 alpha chain, Myeloblastin, POTE ankyrin domain family member I, Protein E7, Predicted Efflux Protein, Replication and transcription activator, Gag-Pro-Pol polyprotein, Capsid protein VP26, Major capsid protein, Apoptosis regulator BHRF1, Epstein-Barr nuclear antigen 2, HLA class I histocompatibility antigen, B-7 alpha chain, Calreticulin, Gamma-secretase C-terminal fragment 59, Insulin, Glucose-6-phosphatase 2, Islet amyloid polypeptide, Receptor-type tyrosine-protein phosphatase N2, Receptor-type tyrosine-protein phosphatase-like N, Islet cell autoantigen 1, Bos d 6, Glutamate decarboxylase 1, 60S ribosomal protein L29, 28S ribosomal protein 531, mitochondrial, HLA class II histocompatibility antigen, DRB1-16 beta chain, Collagen alpha-3(IV) chain, Glucose-6-phosphatase, Glucose-6-phosphatase 3, Collagen alpha-5(IV) chain, Protein Nef, Glial fibrillary acidic protein, Fibrillin-1, Tenascin, Stromelysin-1, Interstitial collagenase, Calpain-2 catalytic subunit, Chondroitin sulfate proteoglycan 4, Fibrinogen beta chain, Chaperone protein DnaJ, Chitinase-3-like protein 1, Matrix metalloproteinase-16, DNA topoisomerase 1, Follistatin-related protein 1, Ig gamma-1 chain C region, Ig gamma-3 chain C region, Collagen alpha-2(XI) chain, Desmoglein-3, Fibrinogen alpha chain, Filaggrin, T-cell receptor beta chain V region CTL-L17, T-cell receptor beta-1 chain C region, Ig heavy chain V-I region EU, Collagen alpha-1(IV) chain, HLA class I histocompatibility antigen, Cw-7 alpha chain, HLA class I histocompatibility antigen, B-35 alpha chain, HLA class I histocompatibility antigen, B-38 alpha chain, High mobility group protein B2, Ig heavy chain V-III region ARH-77, HLA class II histocompatibility antigen, DR beta 4 chain, Ig kappa chain C region, Alpha-enolase, Lysosomal-associated transmembrane protein 5, HLA class I histocompatibility antigen, B-52 alpha chain, Heterogeneous nuclear ribonucleoproteins A2/B1, T-cell receptor beta chain V region YT35, Ig gamma-4 chain C region, T-cell receptor beta-2 chain C region, DnaJ homolog subfamily B member 2, DnaJ homolog subfamily A member 1, Ig kappa chain V-IV region Len, Ig heavy chain V-III region OU, Ig kappa chain V-IV region B17, 2',3'-cyclic-nucleotide 3'-phosphodiesterase, Ig heavy chain V-III region MCE, Ig kappa chain V-III region HIC, Ig heavy chain V-III region COR, Myelin-oligodendrocyte glycoprotein, Ig kappa chain V-III region RPMI 6410, Ig kappa chain V-III region GM607, Immunoglobulin lambda-like polypeptide 5, Ig heavy chain V-III region WAH, Biotin-protein ligase, Oligodendrocyte-myelin glycoprotein, Transaldolase, DNA helicase/primase complex-associated protein, Interferon beta, Myelin-associated oligodendrocyte basic protein, Myelin-associated glycoprotein, Fusion glycoprotein F0, Myelin protein P0, Ig lambda chain V-II region MGC, DNA primase, Minor capsid protein L2, Myelin P2 protein, Peripheral myelin protein 22, Retinol-binding protein 3, Butyrophilin subfamily 1 member A1, Alkaline nuclease, Claudin-11, N-acetylmuramoyl-L-alanine amidase CwlH, GTPase Der, Possible transposase, ABC transporter, ATP-binding protein, putative, Collagen alpha-2(IV) chain, Calpastatin, Ig kappa chain V-III region SIE, E3 ubiquitin-protein ligase TRIM68, Glutamate receptor ionotropic, NMDA 2A, Spectrin alpha chain, non-erythrocytic 1, Lupus La protein, Complement C1q subcomponent subunit A, U1 small nuclear ribonucleoprotein A, 60 kDa SS-A/Ro ribonucleoprotein, DNA repair protein XRCC4, Histone H3-like centromeric protein A, Histone H1.4, Putative HTLV-1-related endogenous sequence, HLA class II histocompatibility antigen, DRB1-3 chain, HLA class II histocompatibility antigen, DRB1-1 beta chain, Small nuclear ribonucleoprotein Sm D3, Tumor necrosis factor receptor superfamily member 6, Phosphomannomutase/phosphoglucomutase, Tripartite terminase subunit UL15, Proteasome subunit beta type-3, Proliferating cell nuclear antigen, Inner capsid protein sigma-2, Histone H2B type 1, E3 ubiquitin-protein ligase TRIM21, DNA-directed RNA polymerase II subunit RPB1, X-ray repair cross-complementing protein 6, U1 small nuclear ribonucleoprotein C, Caspase-8, 60S ribosomal protein L7, 5-hydroxytryptamine receptor 4, Small nuclear ribonucleoprotein-associated protein N, Exportin-1, 60S acidic ribosomal protein P0, Neurofilament heavy polypeptide, putative env, T-cell receptor alpha chain C region, T-cell receptor alpha chain V region CTL-L17, RNA polymerase sigma factor SigA, Small nuclear ribonucleoprotein Sm D2, Immunoglobulin iota chain, Ig kappa chain V-III region WOL, Histone H2B type 1-F/J/L, High mobility group protein B1, X-ray repair cross-complementing protein 5, Muscarinic acetylcholine receptor M3, Major viral transcription factor ICP4, Voltage-dependent P/Q-type calcium channel subunit alpha-1A, Heat shock protein HSP 90-beta, DNA topoisomerase 2-beta, Histone H3.1, Tumor necrosis factor ligand superfamily member 6, Phospho-N-acetylmuramoyl-pentapeptide-transferase, Hemoglobin subunit alpha, Apolipoprotein E, CD99 antigen, ATP synthase subunit beta, mitochondrial, Acetylcholine receptor subunit delta, Acyl-CoA dehydrogenase family member 10, KN motif and ankyrin repeat domain-containing protein 3, SAM and SH3 domain-containing protein 1, Elongation factor 1-alpha 1, GTP-binding nuclear protein Ran, Myosin-7, Sal-like protein 1, IgGFc-binding protein, E3 ubiquitin-protein ligase SIAH1, Muscleblind-like protein 2, Annexin A1, Protein PET117 homolog, mitochondrial, Nuclear ubiquitous casein and cyclin-dependent kinase substrate 1, Pleiotropic regulator 1, NADH dehydrogenase [ubiquinone] 1 alpha subcomplex subunit 3, Guanine nucleotide-binding protein G(o) subunit alpha, Microtubule-associated protein 1B, L-serine dehydratase/L-threonine deaminase, Centromere protein J, SH3 and multiple ankyrin repeat domains protein 3, Fumarate hydratase, mitochondrial, Cofilin-1, Rho GTPase-activating protein 9, Phosphatidate cytidylyltransferase 1, Neurofilament light polypeptide, Calsyntenin-1, GPI transamidase component PIG-T, Perilipin-3, Protein unc-13 homolog D, WD40 repeat-containing protein SMU1, Neurofilament medium polypeptide, Protein S100-B, Carboxypeptidase E, Neurexin-2-beta, NAD-dependent protein deacetylase sirtuin-2, Tripartite motif-containing protein 40, Neurexin-1-beta, Annexin A11, Hemoglobin subunit beta, Glyceraldehyde-3-phosphate dehydrogenase, Histidine triad nucleotide-binding protein 3, ATP synthase subunit e, mitochondrial, 10 kDa heat shock protein, mitochondrial, Cellular tumor antigen p53, Leukocyte-associated immunoglobulin-like receptor 1, Tubulin alpha-1B chain, Splicing factor, proline- and glutamine-rich, Olfactory receptor 10A4, Histone H2B type 2-F, Calmodulin, RNA-binding protein Raly, Phosphoinositide-3-kinase-interacting protein 1, Alpha-2-macroglobulin, Glycogen phosphorylase, brain form, THO complex subunit 4, Neuroblast differentiation-associated protein AHNAK, Phosphoserine aminotransferase, Mitochondrial folate transporter/carrier, Sentrin-specific protease 3, Cytosolic Fe—S cluster assembly factor NUBP2, Histone deacetylase 7, Serine/threonine-protein phosphatase 2A 55 kDa regulatory subunit B alpha isoform, Serine/threonine-protein phosphatase 2A regulatory subunit B" subunit alpha, Gelsolin, Insulin-like growth factor II, Tight junction protein ZO-1, Hsc70-interacting protein, FXYD domain-containing ion transport regulator 6, AP-1 complex subunit mu-1, Syntenin-1, NADH dehydrogenase [ubiquinone] iron-sulfur protein 7, mitochondrial, Low-density lipoprotein receptor, LIM domain transcription factor LMO4, Spectrin beta chain, non-erythrocytic 1, ATP-binding cassette sub-family A member 2, NADH dehydrogenase [ubiquinone] 1 subunit C2, SPARC-like protein 1, Electron transfer flavoprotein subunit alpha, mitochondrial, Glutamate dehydrogenase 1, mitochondrial, Complexin-2, Protein-serine O-palmitoleoyltransferase porcupine, Plexin domain-containing protein 2, Threonine synthase-like 2, Testican-2, C—X—C chemokine receptor type 1, Arachidonate 5-lipoxygenase-activating protein, Neuroguidin, Fatty acid 2-hydroxylase, Nuclear factor 1 X-type, LanC-like protein 1, Glutamine synthetase, Lysosome-associated membrane glycoprotein 1, Apolipoprotein A-I, Alpha-adducin, Guanine nucleotide-binding protein G(I)/G(S)/G(T) subunit beta-3, Integral membrane protein GPR137B, Ubiquilin-1, Aldose reductase, Clathrin light chain B, V-type proton ATPase subunit F, Apolipoprotein D, 40S ribosomal protein SA, Bcl-2-associated transcription factor 1, Phosphatidate cytidylyltransferase 2, ATP synthase-coupling factor 6, mitochondrial, Receptor tyrosine-protein kinase erbB-2, Echinoderm microtubule-associated protein-like 5, Phosphatidylethanolamine-binding protein 1, Myc box-dependent-interacting protein 1, Membrane-associated phosphatidylinositol transfer protein 1, 40S ribosomal protein S29, Small acidic protein, Galectin-3-binding protein, Fatty acid synthase, Baculoviral IAP repeat-containing protein 5, Septin-2, cAMP-dependent protein kinase type II-alpha regulatory subunit, Reelin, Apoptosis facilitator Bcl-2-like protein 14, Staphylococcal nuclease domain-containing protein 1, Methyl-CpG-binding domain protein 2, Transformation/transcription domain-associated protein, Transcription factor HES-1, Protein transport protein Sec23B, Paralemmin-2, C—C motif chemokine 15, Sodium/potassium-transporting ATPase subunit alpha-1, Stathmin, Heterogeneous nuclear ribonucleoprotein L-like, Nodal modulator 3, Interferon-induced GTP-binding protein Mx2, Integrin alpha-D, Low-density lipoprotein receptor-related protein 5-like protein, Macrophage migration inhibitory factor, Ferritin light chain, Dihydropyrimidinase-related protein 2, Neuronal membrane glycoprotein M6-b, ATP-binding cassette subfamily A member 5, Synaptosomal-associated protein 25, Insulin-like growth factor I, Ankyrin repeat domain-containing protein 29, Protein spinster homolog 3, Peflin, Contactin-1, Microfibril-associated glycoprotein 3, von Willebrand factor, Small nuclear ribonucleoprotein G, Interleukin-12 receptor subunit beta-1, Epoxide hydrolase 1, Cytochrome b-c1 complex subunit 10, Monoglyceride lipase, Serotransferrin, Alpha-synuclein, Cytosolic non-specific dipeptidase, Transgelin-2, Testisin, Fms-related tyrosine kinase 3 ligand, Noelin-2, Serine/threonine-protein kinase DCLK1, Interferon alpha-2, Acetylcholine receptor subunit beta, Histone H2A type 1, Beta-2 adrenergic receptor, Putrescine aminotransferase, Interferon alpha-1/13, Protein NEDD1, DnaJ homolog subfamily B member 1, Tubulin beta-6 chain, Non-histone chromosomal protein HMG-17, Polyprotein, Exosome component 10, Natural cytotoxicity triggering receptor 3 ligand 1, Gag polyprotein, Band 3 anion transport protein, Protease, Histidine-tRNA ligase, cytoplasmic, Collagen alpha-1(XVII) chain, Envoplakin, Histone H2B type 1-C/E/F/G/I, Diaminopimelate decarboxylase, Histone H2B type 2-E, Cytochrome P450 2D6, Dihydrolipoyllysine-residue succinyltransferase component of 2-oxoglutarate dehydrogenase complex, Histone H2B type 1-H, Thyroid peroxidase, Proline-rich transmembrane protein 2, Periplakin, Integrin alpha-6, Dystonin, Desmoplakin, Histone H2B type 1-J, Histone H2B type 1-B, 6,7-dimethyl-8-ribityllumazine synthase, Thyrotropin receptor, Integrin alpha-11b, Nuclear pore membrane glycoprotein 210, Protein U2, DST protein, Plectin, S110397 protein, Bos d 10, Outer capsid protein VP4, 5,6-dihydroxyindole-2-carboxylic acid oxidase, O-phosphoseryl-tRNA(Sec) selenium transferase, ATP-dependent Clp protease proteolytic subunit, Lymphocyte activation gene 3 protein, Phosphoprotein 85, L1 protein, Actin, alpha skeletal muscle, Dihydrolipoyl dehydrogenase, Dihydrolipoyllysine-residue succinyltransferase component of 2-oxoglutarate dehydrogenase complex, mitochondrial, Liver carboxylesterase 1, Dihydrolipoyllysine-residue acetyltransferase component of pyruvate dehydrogenase complex, Acetyltransferase component of pyruvate dehydrogenase complex, Pyruvate dehydrogenase protein X component, mitochondrial, Dihydrolipoamide acetyltransferase, Protein disulfide-isomerase A3, Flotillin-2, Beta-galactosidase, TSHR protein, Lipoamide acyltransferase component of branched-chain alpha-keto acid dehydrogenase complex, mitochondrial, Nuclear autoantigen Sp-100, Desmoglein-1, Glucagon receptor, Membrane glycoprotein US8, Sodium/iodide cotransporter, ORF2, Capsid protein, Uncharacterized protein LF3, Formimidoyltransferase-cyclodeaminase, Core-capsid bridging protein, Neurovirulence factor ICP34.5, Probable RNA-binding protein, Cholesterol side-chain cleavage enzyme, mitochondrial, Histone H1.0, Non-histone chromosomal protein HMG-14, Histone H5, 60S acidic ribosomal protein P1, Pyruvate dehydrogenase E1 component subunit alpha, somatic form, mitochondrial, Leiomodin-1, Uncharacterized protein RP382, Uncharacterized protein U95, (Type IV) pilus assembly protein PilIB, 2-succinylbenzoate-CoA ligase, TAZ protein, Tafazzin, Putative lactose-specific phosphotransferase system (PTS), IIBC component, Claudin-17, Pericentriolar material 1 protein, Yop proteins translocation protein L, Laminin subunit alpha-1, A disintegrin and metalloproteinase with thrombospondin motifs 13, Keratin, type I cytoskeletal 14, Coagulation factor VIII, Keratin, type I cytoskeletal 17, Neutrophil defensin 1, Ig alpha-1 chain C region, BRCA1-associated RING domain protein 1, Trinucleotide repeat-containing gene 6A protein, Thrombopoietin, Plasminogen-binding protein PgbA, Steroid 17-alpha-hydroxylase/17,20 lyase, Nucleolar RNA helicase 2, Histone H2B type 1-N, Steroid 21-hydroxylase, UreB, Melanin-concentrating hormone receptor 1, Blood group Rh(CE) polypeptide, HLA class II histocompatibility antigen, DP beta 1 chain, Platelet glycoprotein 1b alpha chain, Muscarinic acetylcholine receptor M1, Outer capsid glycoprotein VP7, Fibronectin, HLA class I histocompatibility antigen, B-8 alpha chain, AhpC, Cytoskeleton-associated protein 5, Sucrase-isomaltase, intestinal, Leukotriene B4 receptor 2, Glutathione peroxidase 2, Collagen alpha-1(VII) chain, Nucleosome assembly protein 1-like 4, Alanine-tRNA ligase, cytoplasmic, Extracellular calcium-sensing receptor, Major centromere autoantigen B, Large tegument protein deneddylase, Blood group Rh(D) polypeptide, Kininogen-1, Peroxiredoxin-2, Ezrin, DNA replication and repair protein RecF, Keratin, type II cytoskeletal 6C, Trigger factor, Serpin B5, Heat shock protein beta-1, Protein-arginine deiminase type-4, Potassium-transporting ATPase alpha chain 1, Potassium-transporting ATPase subunit beta, Forkhead box protein E3, Condensin-2 complex subunit D3, Myotonin-protein kinase, Zinc transporter 8, ABC transporter, substrate-binding protein, putative, Aquaporin-4, Cartilage intermediate layer protein 1, HLA class II histocompatibility antigen, DR beta 5 chain, Small nuclear ribonucleoprotein F, Small nuclear ribonucleoprotein E, Ig kappa chain V-V region L7, Ig heavy chain Mem5, Ig heavy chain V-III region J606, Hemoglobin subunit delta, Collagen alpha-1 (XV) chain, 78 kDa glucose-regulated protein, 60S ribosomal protein L22, Alpha-1-acid glycoprotein 1, Malate dehydrogenase, mitochondrial, 60S ribosomal protein L8, Serine protease HTRA2, mitochondrial, 60S ribosomal protein L23a, Complement C3, Collagen alpha-1(XII) chain, Angiotensinogen, Protein S100-A9, Annexin A2, Alpha-actinin-4, HLA class II histocompatibility antigen, DQ alpha 1 chain, Apolipoprotein A-IV, Actin, aortic smooth muscle, HLA class II histocompatibility antigen, DP alpha 1 chain, Creatine kinase B-type, HLA class II histocompatibility antigen, DR beta 3 chain, Histone H1x, Heterogeneous nuclear ribonucleoprotein U-like protein 2, Basement membrane-specific heparan sulfate proteoglycan core protein, Cadherin-5, 40S ribosomal protein S13, Alpha-1-antitrypsin, Multimerin-2, Centromere protein F, 40S ribosomal protein S18, 40S ribosomal protein S25, Na(+)/H(+) exchange regulatory cofactor NHE-RF1, Actin, cytoplasmic 2, Hemoglobin subunit gamma-1, Hemoglobin subunit gamma-2, Protein NipSnap homolog 3A, Cathepsin D, 1-phosphatidylinositol 4,5-bisphosphate phosphodiesterase epsilon-1, 40S ribosomal protein S17, Apolipoprotein B-100, Histone H2B type 1-K, Collagen alpha-1(I) chain, Collagen alpha-2(I) chain, 3-hydroxyacyl-CoA dehydrogenase type-2, 60S ribosomal protein L27, Histone H1.2, Nidogen-2, Cadherin-1, 60S ribosomal protein L27a, HLA class II histocompatibility antigen, DR alpha chain, Dipeptidyl peptidase 1, Ubiquitin-40S ribosomal protein S27a, Citrate synthase, mitochondrial, Taxi-binding protein 1, Myeloperoxidase, Plexin domain-containing protein 1, Glycogen synthase, [Pyruvate dehydrogenase [acetyl-transferring]]-phosphatase 1, mitochondrial, Phorbol-12-myristate-13-acetate-induced protein 1, Peroxiredoxin-5, mitochondrial, 14-3-3 protein zeta/delta, ATP synthase subunit d, mitochondrial, Vitronectin, Lipopolysaccharide-binding protein, Ig heavy chain V-III region GAL, Protein CREG1, 60S ribosomal protein L6, Stabilin-1, Plasma protease C1 inhibitor, Ig kappa chain V-III region VG, Inter-alpha-trypsin inhibitor heavy chain H4, Alpha-1B-glycoprotein, Tartrate-resistant acid phosphatase type 5, Sulfhydryl oxidase 1, Complement component C6, Glycogen phosphorylase, muscle form, SH3 domain-binding glutamic acid-rich-like protein 3, Transforming protein RhoA, Albumin, isoform CRA_k, V-type proton ATPase subunit G 1, Flavin reductase (NADPH), Heat shock cognate 71 kDa protein, Lipoprotein lipase, Plasminogen, Annexin, Syntaxin-7, Transmembrane glycoprotein NMB, Coagulation factor XIII A chain, Apolipoprotein A-II, N-acetylglucosamine-6-sulfatase, Complement C1q subcomponent subunit B, Protein S100-A10, Microfibril-associated glycoprotein 4, 72 kDa type IV collagenase, Collagen alpha-1(XI) chain, Cathepsin B, Palmitoyl-protein thioesterase 1, Macrosialin, Histone H1.1, Histone H1.5, Fibromodulin, Thrombospondin-1, Rho GDP-dissociation inhibitor 2, Alpha-galactosidase A, Superoxide dismutase [Cu—Zn], HLA class I histocompatibility antigen, alpha chain E, Phosphatidylcholine-sterol acyltransferase, Legumain, Low affinity immunoglobulin gamma Fc region receptor II-c, Fructose-bisphosphate aldolase A, Cytochrome c oxidase subunit 8A, mitochondrial, Pyruvate kinase PKM, Endoglin, Target of Nesh-SH3, Cytochrome c oxidase subunit 5A, mitochondrial, EGF-containing fibulin-like extracellular matrix protein 2, Epididymal secretory protein E1, Cathepsin S, Annexin A5, Allograft inflammatory factor 1, Decorin, Complement C1s subcomponent, Low affinity immunoglobulin gamma Fc region receptor II-b, Leucine-rich alpha-2-glycoprotein, Lysosomal alpha-glucosidase, Disintegrin and metalloproteinase domain-containing protein 9, Transthyretin, Malate dehydrogenase, cytoplasmic, Filamin-A, Retinoic acid receptor responder protein 1, T-cell surface glycoprotein CD4, Procollagen-lysine,2-oxoglutarate 5-dioxygenase 1, Fibrinogen gamma chain, Collagen alpha-2(V) chain, Cystatin-B, Lysosomal protective protein, Granulins, Collagen alpha-1(XIV) chain, C-reactive protein, Beta-1,4-galactosyltransferase 1, Prolow-density lipoprotein receptor-related protein 1, Ig heavy chain V-III region 23, Phosphoglycerate kinase 1, Alpha-2-antiplasmin, V-set and immunoglobulin domain-containing protein 4, Probable serine carboxypeptidase CPVL, NEDD8, Ganglioside GM2 activator, Clusterin, Alpha-2-HS-glycoprotein, HLA class I histocompatibility antigen, B-37 alpha chain, Adenosine deaminase CECR1, HLA class II histocompatibility antigen, DRB1-11 beta chain, Monocyte differentiation antigen CD14, Erythrocyte band 7 integral membrane protein, Profilin-1, E3 ubiquitin-protein ligase TRIM9, Tripartite motif-containing protein 67, TNF receptor-associated factor 1, Alpha-crystallin A chain, Mitotic checkpoint serine/threonine-protein kinase BUB1, TATA-binding protein-associated factor 2N, Cyclin-F, Centromere protein C, Apoptosis regulator Bcl-2, 2-oxoisovalerate dehydrogenase subunit beta, mitochondrial, Coilin, Nucleoplasmin-3, Homeobox protein Hox-A1, Serine/threonine-protein kinase Chk1, Mitotic checkpoint protein BUB3, Deoxyribonuclease-1, rRNA 2'-O-methyltransferase fibrillarin, Histone H1.3, DNA-directed RNA polymerase Ill subunit RPC1, DNA-directed RNA polymerase Ill subunit RPC2, Centromere-associated protein E, Kinesin-like protein KIF11, Histone H4-like protein type G, Tyrosine 3-monooxygenase, ABC transporter, permease/ATP-binding protein, Translation initiation factor IF-1, Protein FAN, Reticulon-4 receptor, Myeloid cell nuclear differentiation antigen, Glucose-6-phosphate isomerase, High affinity immunoglobulin gamma Fc receptor I, Tryptophan 5-hydroxylase 1, Tryptophan 5-hydroxylase 2, Secretory phospholipase A2 receptor, Aquaporin TIP4-1, Histone H2B type F-S, Histone H2AX, Histone H2A type 1-C, ATP-sensitive inward rectifier potassium channel 10, pVII, hypothetical protein TTV27_gp4, hypothetical protein TTV25_gp2, Alpha-1D adrenergic receptor, Alpha-1B adrenergic receptor, Packaging protein 3, hypothetical protein TTV14_gp2, KRR1 small subunit processome component homolog, Bestrophin-4, Alpha-2C adrenergic receptor, Uncharacterized ORF3 protein, Retinoic acid receptor beta, Retinoic acid receptor alpha, B-cell lymphoma 3 protein, Carbohydrate sulfotransferase 8, Harmonin, Prolactin-releasing peptide receptor, Sphingosine 1-phosphate receptor 1, Acyl-CoA-binding domain-containing protein 5, ORF1, hypothetical protein TTMV3_gp2, Mitochondrial import inner membrane translocase subunit Tim17-B, hypothetical protein TTV2_gp2, Absent in melanoma 1 protein, hypothetical protein TTV28_gp1, hypothetical protein TTV26_gp2, hypothetical protein TTV4_gp2, hypothetical protein TTV28_gp4, Mesencephalic astrocyte-derived neurotrophic factor, hypothetical protein TTMV7_gp2, hypothetical protein TTV19_gp2, pORF1, Pre-histone-like nucleoprotein, hypothetical protein TTV8_gp4, hypothetical protein TTV16_gp2, hypothetical protein TTV15_gp2, ORF2/4 protein, P2X purinoceptor 2, membrane glycoprotein E3 CR1-beta, D(2) dopamine receptor, Toll-like receptor 9, Phosphatidylcholine transfer protein, Transcription factor HIVEP2, Probable peptidylarginine deiminase, 60S ribosomal protein L9, Integrin beta-4, Keratin, type II cytoskeletal 1, Chromogranin-A, Histone H3.1t, Voltage-dependent L-type calcium channel subunit alpha-1D, Heat shock 70 kDa protein 1-like, ABC transporter related, UDP-N-acetylglucosamine pyrophosphorylase, Protein GREB1, Aldo/keto reductase, Component of the TOM (Translocase of outer membrane) complex, Excinuclease ABC C subunit domain protein, Phosphoenolpyruvate carboxylase, Arylacetamide deacetylase-like 4, Dynein heavy chain 10, axonemal, Putative Uracil-DNA glycosylase, Spore germination protein PE, Teneurin-1, Putative dehydrogenase, Polysaccharide biosynthesis protein, VCBS, Glutamate/aspartate transport system permease protein GltK, Noggin, Sclerostin, HLA class I histocompatibility antigen, A-30 alpha chain, HLA class I histocompatibility antigen, A-69 alpha chain, HLA class I histocompatibility antigen, B-15 alpha chain, Glutamate receptor ionotropic, NMDA 1, NarH, 40S ribosomal protein S21, Ceruloplasmin, 3-hydroxy-3-methylglutaryl-coenzyme A reductase, 60S ribosomal protein L30, HLA class II histocompatibility antigen gamma chain, HLA class I histocompatibility antigen, Cw-6 alpha chain, HLA class I histocompatibility antigen, Cw-16 alpha chain, Lysosomal alpha-mannosidase, Heat shock protein HSP 90-alpha, Histone H3.2, Histone H2A.J, Voltage-dependent T-type calcium channel subunit alpha-1G, Syncytin-1, Cathelicidin antimicrobial peptide, Tubulin beta-3 chain, Stress-70 protein, mitochondrial, Probable 1,4-alpha-glucan branching enzyme Rv3031, Nuclease-sensitive element-binding protein 1, Complement factor H-related protein 1, Glutaredoxin-1, Gamma-enolase, Platelet-derived growth factor receptor alpha, Collagen alpha-1(VIII) chain, Matrix metalloproteinase-25, Interferon regulatory factor 5, Cytochrome c oxidase subunit 7C, mitochondrial, Heat shock-related 70 kDa protein 2, Cysteine-rich protein 1, NADH dehydrogenase [ubiquinone] flavoprotein 2, mitochondrial, Glutathione S-transferase P, HLA class I histocompatibility antigen, A-68 alpha chain, HLA class II histocompatibility antigen, DM beta chain, Fructose-bisphosphate aldolase C, Beta-2-microglobulin, Cytochrome c oxidase subunit 5B, mitochondrial, Heat shock 70 kDa protein 13, ATP synthase protein 8, 60S ribosomal protein L13a, TRNA nucleotidyltransferase family enzyme, Ferredoxin-dependent glutamate synthase 2, Alkaline phosphatase, tissue-nonspecific isozyme, SLAM family member 5, Slit homolog 3 protein, Transforming growth factor-beta-induced protein ig-h3, Mannose-binding protein C, Calpain-1 catalytic subunit, Actin, gamma-enteric smooth muscle, Creatine kinase M-type, Protein THEM6, Histone-lysine N-methyltransferase ASH1 L, C2 calcium-dependent domain-containing protein 4A, Ras association domain-containing protein 10, Hepatocyte cell adhesion molecule, ADAMTS-like protein 5, HLA class II histocompatibility antigen, DRB1-15 beta chain, Anoctamin-2, Phosphoglycerate mutase 1, Por secretion system protein porV (Pg27, IptO), Beta-enolase, Receptor antigen A, 3-oxoacyl-[acyl-carrier-protein] synthase 2, Putative heat shock protein HSP 90-beta 2, Radixin, Tubulin beta-1 chain, Vacuolar protein sorting-associated protein 26A, Serine/threonine-protein phosphatase 5, Catalase, Transketolase, Protein S100-A1, Alpha-centractin, Tubulin beta-4A chain, Beta-centractin, Probable phosphoglycerate mutase 4, Beta-actin-like protein 2, Tubulin beta-4B chain, Phosphoglycerate mutase 2, Alpha-internexin, Tubulin beta-2A chain, Dihydropyrimidinase-related protein 3, Putative heat shock protein HSP 90-beta-3, Fructose-bisphosphate aldolase B, Protein P, Endoplasmin, ATP synthase subunit O, mitochondrial, Heat shock 70 kDa protein 6, Glyceraldehyde-3-phosphate dehydrogenase, testis-specific, Nascent polypeptide-associated complex subunit alpha-2, Carbonic anhydrase 2, Annexin A6, E3 ubiquitin-protein ligase RNF13, Myeloid-derived growth factor, Tyrosine-protein phosphatase non-receptor type substrate 1, Laminin subunit gamma-1, Trichohyalin, Thrombospondin-2, Sialoadhesin, GTPase IMAP family member 1, C4b-binding protein alpha chain, Voltage-dependent anion-selective channel protein 1, Hemopexin, Complement C5, FYVE, RhoGEF and PH domain-containing protein 2, Haptoglobin, Cytochrome P450 1B1, Titin, Myeloma-overexpressed gene 2 protein, Adipocyte enhancer-binding protein 1, Protein-glutamine gamma-glutamyltransferase 2, Protein Trim21, ADAMTS-like protein 3, N-alpha-acetyltransferase 16, NatA auxiliary subunit, Transforming growth factor beta-1, Elastin, Protein disulfide-isomerase A5, Plastin-2, Leukocyte immunoglobulin-like receptor subfamily B member 1, Histamine H2 receptor, Elongation factor 2, Caveolin-1, Ig gamma-2 chain C region, Immunoglobulin superfamily containing leucine-rich repeat protein, 40S ribosomal protein S9, Prolyl 4-hydroxylase subunit alpha-1, Endoplasmic reticulum-Golgi intermediate compartment protein 1, Tetranectin, Serine protease HTRA1, Heterogeneous nuclear ribonucleoprotein A1, Phosducin-like protein 3, Ig lambda chain V-VI region EB4, Fibronectin type III domain-containing protein 1, Keratin, type II cytoskeletal 2 epidermal, Ferritin heavy chain, Y-box-binding protein 3, Complement C4-B, HLA class I histocompatibility antigen, Cw-15 alpha chain, HLA class I histocompatibility antigen, B-42 alpha chain, Collagen alpha-1(V) chain, HLA class I histocompatibility antigen, B-73 alpha chain, Integral membrane protein 2B, Lysosome-associated membrane glycoprotein 3, Proteoglycan 4, Ribosomal protein S6 kinase alpha-6, Metalloproteinase inhibitor 2, HLA class II histocompatibility antigen, DRB1-12 beta chain, ATP-sensitive inward rectifier potassium channel 15, Vitamin D-binding protein, Osteopontin, Deoxynucleotidyltransferase terminal-interacting protein 2, Olfactory receptor 5K4, Myosin light chain kinase 2, skeletal/cardiac muscle, Non-POU domain-containing octamer-binding protein, Ubiquilin-2, HLA class I histocompatibility antigen, B-51 alpha chain, Minor histocompatibility antigen H13, Glycophorin-C, Eosinophil cationic protein, SWI/SNF complex subunit SMARCC2, Macrophage mannose receptor 1, tRNA-splicing ligase RtcB homolog, Reticulocalbin-2, Heterogeneous nuclear ribonucleoprotein L, 40S ribosomal protein S30, Collagen alpha-3(VI) chain, Matrix metalloproteinase-14, Antithrombin-III, 60S ribosomal protein L10a, Retinol-binding protein 4, Heterogeneous nuclear ribonucleoprotein R, Lithostathine-1-alpha, Ret finger protein-like 2, Zinc-alpha-2-glycoprotein, Carboxypeptidase Q, HLA class I histocompatibility antigen, B-56 alpha chain, Chondroadherin, Cysteine-rich protein 2, Prosaposin, Complement component C9, Apolipoprotein C-III, Protocadherin-16, Leukocyte immunoglobulin-like receptor subfamily B member 4, Galactokinase, Complement factor H, Uncharacterized protein YEL014C, Glycerophosphocholine phosphodiesterase GPCPD1, Echinoderm microtubule-associated protein-like 6, or a fragment, variant or derivative of any one of said autoantigens, or any combination thereof.

Allergens

According to further preferred embodiments, the artificial nuclei acid molecule, preferably RNA, according to the invention encodes, in its at least one coding region, at least one antigenic peptide or protein derived from an allergen. An “allergen” is any substance, in particular a protein or peptide, which induces allergy, an abnormal immune reaction of the body to a (previously encountered) foreign substance typically introduced by inhalation, ingestion, injection, or skin contact.

Preferably, the at least one antigenic peptide or protein encoded by the at least one coding region of the artificial nucleic acid molecule, preferably RNA, of the invention, may be derived from an allergen derived or selected from Allergen Pen n 18, Antigen Name, Ara h 2.01 allergen, Melanoma antigen recognized by T-cells 1, Non-specific lipid-transfer protein precursor (LTP) (Allergen Mal d 3), ovalbumin, Parvalbumin beta, Pollen allergen Lol p VA precursor, Pollen allergen Phl p 5b precursor, pru p 1, Pollen allergen Phl p 5a, Der p 1 allergen precursor, Pollen allergen KBG 60 precursor, major allergen Tur c1—Turbo cornutus, Mite group 2 allergen Lep d 2 precursor, Lep D 2 precursor, Major latex allergen Hev b 5, major allergen Cor a 1.0401, Major pollen allergen Art v 1 precursor, Major pollen allergen Bet v 1-A, Beta-lactoglobulin precursor, Alpha-amylase inhibitor 0.28 precursor (CIII) (WMAI-1), group V allergen Phl p 5.0203 precursor, Polygalacturonase precursor, pollen allergen Phl pl, Der f 2 allergen, Probable non-specific lipid-transfer protein 2 precursor, Venom allergen 5 precursor, Pollen allergen Phl p 1 precursor, group V allergen, Chain A, Crystal Structure Of The Calcium-Binding Pollen Allergen Phl P 7 (Polcalcin) At 1.75 Angstroem, Tri r 2 allergen, Pathogenesis-related protein precursor, Globin CTT-III precursor, Major allergen Alt a 1, 13S globulin seed storage protein 3 precursor (Legumin-like protein 3) (Allergen Fag e 1), Lit v 1 tropomyosin, Rubber elongation factor protein, Ovomucoid precursor, Small rubber particle protein, Mag3, Allergen Ara h 1, clone P41B precursor, 13S globulin seed storage protein 1 precursor (Legumin-like protein 1), Pollen allergen Lol p 1 precursor, Major pollen allergen Jun a 1 precursor, Sugi basic protein precursor, profilin, Globin CTT-IV precursor, alkaline serine protease, Glycinin, Conglutin-7 precursor, 2S protein 1, Globin CTT-VI precursor, Ribonuclease mitogillin precursor, Major pollen allergen Cyn d 1, Melanocyte-stimulating hormone receptor, P34 probable thiol protease precursor, Vicilin-like protein, Major allergen Equ c 1 precursor, major allergen Bet v 1, Major allergen Can f 1 precursor, Bd 30K (34 kDa maturing seed protein), Major pollen allergen, Major pollen allergen Hol l 1 precursor, Kappa-casein precursor, major allergen Dau c 1/1, Stress-induced protein SAM22, Major allergen Api g 1, Glycinin G2 precursor, allergen Arah3/Arah4, Der f 1 allergen, Peptidase 1 precursor (Mite group 1 allergen Eur m 1) (Allergen Eur m I), Oryzin precursor, alpha S1 casein, Major pollen allergen Cha o 1 precursor, Non-specific lipid-transfer protein 1, collagen, type I, alpha 2, Der P 1, Peptidase 1 precursor (Major mite fecal allergen Der p 1) (Allergen Der p I), pollen allergen Bet v 1, Phospholipase A2 precursor, Mite group 2 allergen Der p 2, Allergen Mag, Major urinary protein precursor, Major allergen I polypeptide chain 2 precursor, Pen a 1 allergen, Fag e 1, Serum albumin precursor, Pollen allergen Amb a 3, putative alpha-amylase inhibitor 0.28, Albumin seed storage protein, 2S sulfur-rich seed storage protein precursor (Allergen Ber e 1), seed storage protein SSP2, Pro-hevein precursor, pollen allergen, Der p 2 allergen precursor, 2S seed storage protein 1 precursor, prohevein, 2s albumin, major allergen I, polypeptide chain 1, Major allergen I polypeptide chain 1 precursor, Cry j IB precursor, Mite group 2 allergen Der f 2 precursor, beta-casein precursor, Lep D 2 allergen precursor, Allergen Cry j 2 (Pollen allergen), KIAA1224 protein, Hydrophobic seed protein, Allergen Bos d 2 precursor, Allergen II, Mite group 2 allergen Der p 2 precursor, Mite allergen Blo t 5, Peptidase 1 precursor (Major mite fecal allergen Der f 1) (Allergen Der f I), Par j, Can f I, Pollen allergen Lol p 2-A (Lol p II-A), Paramyosin, Alpha-S2-casein precursor, P34 probable thiol protease, beta-lactoglobulin, major allergen Phl p 5, Chain A, Structure Of Erythrocruorin In Different Ligand States Refined At 1.4 Angstroms Resolution, Globin CTT-VIII, Major allergen Asp f 2 precursor, tropomyosin, core protein [Hepatitis B virus], Omega gliadin storage protein, Alpha/beta-gliadin A-V, group 14 allergen protein, Pollen allergen Amb a 1.1 precursor, Glycinin G1 precursor, Pollen allergen Amb a 2 precursor, Cry j 1 precursor, allergen Ziz m 1, Glycine-rich cell wall structural protein 1.8 precursor, Putative pectate lyase 17 precursor, pectate lyase, Pectate lyase precursor, Probable pectate lyase 18 precursor, major allergen beta-lactoglobulin, Major allergen Mal d 1, Alpha-S1-casein precursor, 2S seed storage protein 1, plectrovirus spv1-r8a2b orf 14 transmembrane protein, allergen I/a, Allergen Cr-PI, Probable non-specific lipid-transfer protein 1, Cr-PII allergen, melanoma antigen gp100, Alpha-lactalbumin precursor, Chain A, Anomalous Substructure Of Alpha-Lactalbumin, Pilosulin-1 precursor (Major allergen Myr p 1) (Myr p I), Pollen allergen Lol p 3 (Lol p III), Lipocalin 1 (tear prealbumin), Major pollen allergen Cup a 1, Melanocyte protein Pmel 17 precursor, major house dust allergen, Non-specific lipid-transfer protein 1 (LTP 1) (Major allergen Pru d 3), Non-specific lipid-transfer protein 1 (LTP 1) (Major allergen Pru ar 3), Pollen allergen Lol p 1, alpha-gliadin, Cr-PII, albumin, Alpha-S1-casein, major allergen I, Ribonuclease mitogillin, beta-casein, UA3-recognized allergen, 2S sulfur-rich seed storage protein 1, unnamed protein product, Polygalacturonase, Major allergen Pru av 1, Der p 1 allergen, lyase allergen, Major pollen allergen Bet v 1-F/I, Gamma-gliadin precursor, 5-hydroxytryptamine receptor 2C (5-HT-2C) (Serotonin receptor 2C) (5-HT2C) (5-HTR2C) (5HT-1C), omega-5 gliadin, Enolase 1 (2-phosphoglycerate dehydratase) (2-phospho-D-glycerate hydro-lyase), Probable non-specific lipid-transfer protein, Allergen Sin a 1, Glutenin, low molecular weight subunit precursor, Major Peanut Allergen Ara H 1, mal d 3, Eukaryotic translation initiation factor 3 subunit D, tyrosinase-related protein-2, PC4 and SFRS1-interacting protein, RAD51-like 1 isoform 1, Antimicrobial peptide 2, Proteasome subunit alpha type-3, Neurofilament heavy polypeptide (NF-H) (Neurofilament triplet H protein) (200 kDa neurofilament protein), Superoxide dismutase, Major pollen allergen Cor a 1 isoforms 5, 6, 11 and 16, cherry-allergen PRUA1, Allergen Asp f 4 precursor, Chain A, Tertiary Structure Of The Major House Dust Mite Allergen Der P 2, Nmr, 10 Structures, RNA-binding protein NOB1, Dermatan-sulfate epimerase precursor, Squamous cell carcinoma antigen recognized by T-cells 3, Peptidyl-prolyl cis-trans isomerase B precursor, Probable glycosidase crf1, Chain A, Birch Pollen Profilin, Profilin-1, avenin precursor (clone pAv122)—oat, gamma 3 avenin, coeliac immunoreactive protein 2, CIP-2, prolamin 2 {N-terminal}, avenin gamma-3-small naked oat (fragment), major pollen allergen Ole e 1, Cytochrome P450 3A1, Ole e 1 protein, Ole e 1.0102 protein, Der f 2, GroEL-like chaperonin, major allergen Arahi, manganese superoxide dismutase, beta-1,3-glucanase-like protein, Ara h 1 allergen, Major allergen Alt a 1 precursor, Bla g 4 allergen, Per a 4 allergen variant 1, Lyc e 2.0101, pectate lyase 2, allergen, hypothetical protein, Probable pectate lyase P59, Pollen allergen Amb a 1.4, Patatin-2-Kuras 1, calcium-binding protein, vicilin seed storage protein, major allergenic protein Mal f4, pel protein, ripening-related pectate lyase, pectate lyase/Amb allergen, Bet v 4, Polcalcin Bet v 4, Mite allergen Der f 6, Allergen Alt a 2, Extracellular elastinolytic metalloproteinase, pectate lyase-like protein, Pectate lyase E, Profilin-2, Venom allergen 5, Cucumisin, Putative peroxiredoxin, putative pectate lyase precursor, Serum albumin, pollen allergen Phl p 11, serine (or cysteine) proteinase inhibitor, clade B (ovalbumin), member 3, Allergen Bla g 4 precursor (Bla g IV), Allergen Pen n 13, Hyaluronidase A, pectate lyase homolog, putative allergen Cup a 1, Major pollen allergen Jun v 1, putative allergen jun o 1, Pollen allergen Amb a 1.2, Probable pectate lyase 13, P8 protein, Cytochrome c, Glucan endo-1,3-beta-glucosidase, basic vacuolar isoform, 13S globulin, beta-1,3-glucanase, beta-1,3-glucananse, Glutenin, high molecular weight subunit DX5 precursor, X-type HMW glutenin, Glutenin, high molecular weight subunit DX5, high-molecular-weight glutenin subunit 1 Dx2.1, high molecular weight glutenin subunit, 11S globulin-like protein, seed storage protein, alpha-L-Fucp-(1→3)-[alpha-D-Manp-(1→6)-[beta-D-Xylp-(1→2)]-beta-D-Manp-(1→4)-beta-D-GlcpNAc-(1→4)]-D-GlcpNAc, beta casein B, type 1 non-specific lipid transfer protein precursor, Fas AMA, Caspase-8 precursor, H antigen glycoprotein, H antigen gl, Heat shock protein HSP 90-beta, dihydrolipoamide S-acetyltransferase (E2 component of pyruvate dehydrogenase complex), isoform CRA_a, Group V allergen Phl p 5.0103 precursor, Phl p6 allergen precursor, Group V allergen Phl p 5, Major pollen allergen Phl p 4 precursor, Pollen allergen Phl p V, Phl p 3 allergen, Pollen allergen Phl pl precursor, Chain A, Crystal Structure Of Phl P 1, A Major Timothy Grass Pollen Allergen, Pollen allergen Phl p 4, Profilin-3, Profilin-2/4, Pollen allergen Phl p 2, Phl p6 IgE binding fragment, Phlp5, Chain N, Crystal Structure Of Phl P 6, A Major Timothy Grass Pollen Allergen Co-Crystallized With Zinc, group V allergen Phl p 5.0206 precursor, allergenic protein, Major allergen Ani s 1, allergen Ana o 2, ENSP-like protein, BW 16 kDa allergen, alpha2(1) collagen, collagen a2(I), type 1 collagen alpha 2, Cyn d 1, Major pollen allergen Aln g 1 (Allergen Aln g I), allergen Len c 1.0101, galactomannan, Aspartic protease Bla g 2, alcohol dehydrogenase, lipid transfer protein precursor, alpha/beta gliadin precursor, Der f 7 allergen, Der p 7 allergen polypeptide, non-specific lipid transfer protein, Major allergen I polypeptide chain 1, prunin 1 precursor, prunin 2 precursor, 11S legumin protein, Ara h 7 allergen precursor, vicilin-like protein precursor, allergen Arah6, parvalbumin like 2, parvalbumin like 1, casein kappa, Ribosomal biogenesis protein LAS1 L, Pen c 1, SchS21 protein, Inactive hyaluronidase B, Mup1 protein, Macrophage migration inhibitory factor, Eukaryotic translation initiation factor 2 subunit 3, CR2/CD21/C3d/Epstein-Barr virus receptor precursor, DNA topoisomerase 2-alpha, pollen allergen Cyn d 23, major allergen Bla g 1.02, pectin methylesterase allergenic protein, major allergen Pha a 5 isoform, 2S albumin seed storage protein, aldehyde dehydrogenase (NAD+), pollen allergen Poa p 5, Bla g 1.02 variant allergen, partial, Major pollen allergen Lol p 5b, allergen Bla g 6.0301, protein disulfide isomerase, putative mannitol dehydrogenase, pollen allergen Lol p 4, Aspartic protease pep1, enolase, IgE-binding protein, Minor allergen Alt a 5, HDM allergen, Chain A, Crystal Structure Of An Mbp-Der P 7 Fusion Protein, allergen Bla g 6.0201, major allergen Bla g 1.0101, alpha-amylase, minor allergen, ribosomal protein P2, metalloprotease (MEP), autophagic serine protease Alp2, allergenic isoflavone reductase-like protein Bet v 6.0102, Chain A, Crystal Structure Of The Complex Of Antibody And The Allergen Bla G 2, minor allergen, thioredoxin TrxA, enolase, allergen Cla h 6, glutathione-S-transferase, molecular chaperone and allergen Mod-E/Hsp90/Hspl, major allergen Asp F2, Mite allergen Der p 3, Chain B, Crystal Structure Of *Aspergillus Fumigatus* Mnsod, Glutathione S-transferase (GST class-sigma) (Major allergen Bla g 5), Minor allergen Cla h 7, unknown protein, allergenic cerato-platanin Asp F13, art v 2 allergen, Polcalcin Aln g 4, major allergen and cytotoxin AspF1, pollen allergen Que a 1 isoform, trypsin-like serine protease, Mite group 6 allergen Der p 6, allergen Asp F7, cell wall protein PhiA, 60 kDa allergen Der f 18p, hsp70, Sal k 3 pollen allergen, acidic ribosomal protein P2, Chain B, Crystal Structure Of The Nadp-Dependent Mannitol Dehydrogenase From *Cladosporium Herbarum*., Art v 3.0301 allergen precursor, 60S ribosomal protein L3, Der p 20 allergen, Pollen allergen Sal k 1, Per a 6 allergen, gelsolin-like allergen Der f 16, Chain A, Structural Characterization Of The Tetrameric Form Of The Major Cat Allergen Fel D 1, Glutathione S-transferase, Fel d 4 allergen, Major pollen allergen Dac g 4, Group I allergen Ant o I (Form 1), pollen, allergen Bla g 6.0101, cystatin, Mite allergen Der p 5, allergen Fra e 1, allergen Asp F4, major antigen-like protein, PR5 allergen Cup s 3.1 precursor, heat shock protein, allergene precursor, arginine esterase precursor, Sal k 4 pollen allergen, 60S acidic ribosomal protein P1, pollen allergen Jun o 4, Polcalcin Cyn d 7, group I pollen allergen, peptidyl-prolyl cis-trans isomerase/cyclophilin, putative, profilin 2, pollen allergen Cyn d 15, Der f 13 allergen, Can f 2, peroxisomal-like protein, peptidylprolyl isomerase (cyclophilin), MHC class II antigen, BETV4 protein, Major pollen allergen Pla I 1, peptidase, MPA3 allergen, plantain pollen major allergen, Pla I 1.0103, major allergen Bla g 1.0101, partial, Pollen allergen Amb p 5a, Der f 16 allergen, Pollen allergen Dac g 2, IgE-binding protein C-terminal fragment (148 AA), Pollen allergen Dac g 3, PPlase, rAsp f 9, Mite allergen Der p 7, thioredoxin, hydrolase, Major pollen allergen Pha a 1, Der p 13 allergen, Chain B, X-Ray Structure Of Der P 2, The Major House Dust Mite Allergen, oleosin 3, Peptidyl-prolyl cis-trans isomerase, Chain A, Crystal Structure Of A Major House Dust Mite Allergen, Derf 2, Chain A, Crystal Structure Of Major Allergens, Bla G 4 From Cockroaches, Amb a 1-like protein, D-type LMW glutenin subunit, Glutathione S-transferase 2, acidic Cyn d 1 isoallergen isoform 4 precursor, albumin seed storage protein precursor, tyrosine 3-monooxygenase isoform b, N-glycoprotein, FAD-linked oxidoreductase BG60, Blot 21 allergen, Ubiquitin D, Nucleoporin Nup37, Non-POU domain-containing octamer-binding protein, Transcription elongation factor SPT5, Major allergen Mal d 1 (Yprl0 protein), Serpin-Z2B, Pas n 1 allergen precursor, arginine kinase, Lit v 3 allergen myosin light chain, sarcoplasmic calcium-binding protein, alpha subunit of beta conglycinin, prunin, allergen Cry j 2, Plexin-A4, Non-specific lipid-transfer protein, Low molecular weight glutenin subunit precursor, gamma-gliadin, friend of GATA-1, Wilms tumor protein, Ubiquitin-conjugating enzyme E2 C, Fatty acid synthase, Histone H4, Fructose-bisphosphate aldolase A, oxidoreductase, lactoglobulin beta, immunoglobulin gamma 3 heavy chain constant region, Phlp5 precursor, dust mite allergen precursor, heat shock protein 70, Major allergen I polypeptide chain 2, alpha-lactalbumin precursor protein, 30 kDa pollen allergen, group 5 allergen precursor, group 1 allergen Dac g 1.01 precursor, uncharacterized protein, unknown Timothy grass protein, kappa-casein, alpha-S1 casein, SXP/RAL-2 family protein, Lipocalin-1 precursor, alpha purothionin, major allergen Bet v 1.01A, P2 protein, Osmotin, Major Peanut Allergen Ara H 2, Der f 3 allergen, Conglutin, Ara h 6 allergen, Cathelicidin antimicrobial peptide, cholinesterase, Per a 2 allergen, Submaxillary gland androgen-regulated protein 3B, chitinase, partial, allergen Can f 4 precursor, Can f 4 variant allergen precursor, nascent polypeptide-associated complex subunit alpha-2, Polcalcin Phl p 7 (Calcium-binding pollen allergen Phl p 7) (P7), Der p II allergen, main allergen Ara hi, allergen Ara h 2.02, fatty acid binding protein, glutamate receptor, glycinin A3B4 subunit, profilin isoallergen 2, Pollen allergen Amb p 5b, calcium-binding protein isoallergen 2, calcium-binding protein isoallergen 1, cysteine protease, profilin isoallergen 1, ragweed homologue of Art v 1 precursor, Amb p 5, ragweed homologue of Art v 1 (isoform 1), partial, antigen E, putative pectate lyase precursor, partial, Pollen allergen Amb a 5, Amb p V allergen, hemocyanin subunit 6, major pollen allergen Cha o 2, trichohyalin, aspartyl endopeptidase, NCRA10, allergen bla g 8, vitellogenin, NCRA3, NCRA4, allergen Bla g 3 isoform 2 precursor, partial, NCRA2, NCRA13, NCRA8, NCRA1, Bla g 11, receptor for activated protein kinase C-like, NCRA5, NCRA14, triosephosphate isomerase, NCRA12, NCRA7, NCRA11, trypsin, triosephosphate isomerase, partial, NCRA6, structural protein, NCRA15, NCRA9, NCRA16, Der f 4 allergen, Der f 5 allergen, Phl p6 allergen, Der f Gal d 2 allergen, Derp_19830, glucosylceramidase, carboxypeptidase, Der f 8 allergen, partial, fructose bisphosphate aldolase, ATP synthase, Der f Alt a 10 allergen, glutamine synthetase, Derp_c23425, myosin, Der f 8 allergen, LytFM, Der f 11 allergen, serine protease, glutathione transferase mu, triose-phosphate isomerase, ubiquinol-cytochrome c reductase binding protein-like protein, ferritin, isomerase, filamin C, Der p 5, Mag44, partial, venom, muscle specific protein, Der f 5.02 allergen, Mag44, Derp_c21462, group 18 allergen protein, Derf_c9409, napin-type 2S albumin 1 precursor, napin-type 2S albumin 3, isoflavone reductase-like protein CJP-6, Pectate lyase 1, allergen Cry j 2, partial, Major allergen Dau c 1, Filamin-C, putative, Pis v 5.0101 allergen 11S globulin precusor, Pis v 5, 48-kDa glycoprotein precursor, vicilin, or a variant, fragment or derivative of any of said allergens, or any combination thereof.

Signal Peptide (SIG)

According to preferred embodiments, the artificial nucleic acid molecule, preferably RNA, of the invention further encodes, in its at least one coding region, at least one signal peptide.

A "signal peptide" (sometimes referred to as signal sequence, targeting signal, localization signal, localization sequence, transit peptide, leader sequence or leader peptide) is typically a short (5-30 amino acids long) N-terminal peptide.

According to preferred embodiments, the nucleic acid sequence encoding said at least one signal peptide may be fused (in frame) to a nucleic acid sequence encoding the at least one $IRST_{epm}$-derived amino acid sequence or the at least one antigenic peptide or protein. Therefore, expression of the artificial nucleic acid molecule, preferably RNA, of the invention may preferably result in a fusion protein comprising the at least one signal peptide joined to (optionally via appropriate peptide linkers) said $IRST_{epm}$-derived amino acid sequence and/or said antigenic protein or peptide. Said additional amino acid sequence preferably directs the antigenic peptide or protein to the plasma membrane, where antigenic peptides or proteins are preferably anchored via the TM domain and recycled to MHC class I and more preferably MHC class II processing compartments, resulting in both enhanced MHC class I and preferably MHC class II presentation. The signal peptide is envisaged to preferably mediate or support the transport of the antigenic construct (in) to a defined cellular compartment, in particular the external side of the plasma membrane.

Generally, the present invention envisages the combination of any of the signal peptides described herein with any of the antigenic peptides or proteins, any of the $IRST_{epm}$-derived additional amino acid sequences, any of the linkers, in any suitable order, in the antigenic fusion proteins encoded by the artificial nucleic acid molecules, preferably RNAs, of the invention.

According to preferred embodiments, the artificial nucleic acid molecule, preferably RNA, of the invention may encode in its at least one coding region at least one signal peptide selected from the signal peptides indicated in Table 4 below, or a (preferably functional) fragment, variant or derivative of any of said signal peptides.

TABLE 4

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 76 | P14207 | FOLR2 | Folate receptor beta (FR-beta) (Folate receptor 2) (Folate receptor, fetal/placental) (Placental folate-binding protein) (FBP) | 1-16 | 1 | 255 | FOLR2 | 209, 417, 625, 833, 1041, 1249, 1457, 1665, 1873, 2081, 2289, 2497, 2705 |
| 77 | O75787 | RENR | Renin receptor (ATPase H(+)-transporting lysosomal accessory protein 2) (ATPase H(+)-transporting lysosomal-interacting protein 2) (ER-localized type I transmembrane adaptor) (Embryonic liver differentiation factor 10) (N14F) (Renin/prorenin receptor) (Vacuolar ATP synthase membrane sector-associated protein M8-9) (ATP6M8-9) (V-ATPase M8.9 subunit) | 1-16 | 2 | 350 | ATP6AP2 ATP6IP2 CAPER ELDF10 HT028 MSTP009 PSEC0072 | 210, 418, 626, 834, 1042, 1250, 1458, 1666, 1874, 2082, 2290, 2498, 2706 |
| 78 | P07359 | GP1BA | Platelet glycoprotein lb alpha chain (GP-lb alpha) (GPlb-alpha) (GPlbA) (Glycoprotein lbalpha) (Antigen CD42b-alpha) (CD antigen CD42b) [Cleaved into: Glycocalicin] | 1-16 | 3 | 652 | GP1BA | 211, 419, 627, 835, 1043, 1251, 1459, 1667, 1875, 2083, 2291, 2499, 2707 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 79 | P08637 | FCG3A | Low affinity immunoglobulin gamma Fc region receptor III-A (CD16a antigen) (Fc-gamma RIII-alpha) (Fc-gamma RIII) (Fc-gamma RIIIa) (FcRIII) (FcRIIIa) (FcR-10) (IgG Fc receptor III-2) (CD antigen CD16a) | 1-16 | 4 | 254 | FCGR3A CD16A FCG3 FCGR3 IGFR3 | 212, 420, 628, 836, 1044, 1252, 1460, 1668, 1876, 2084, 2292, 2500, 2708 |
| 8081 | P07237 | PDIA1 | Protein disulfide-isomerase (PDI) (EC 5.3.4.1) (Cellular thyroid hormone-binding protein) (Prolyl 4-hydroxylase subunit beta) (p55) | 1-17 | 5 | 508 | P4HB ERBA2L PDI PDIA1 PO4DB | 213, 421, 629, 837, 1045, 1253, 1461, 1669, 1877, 2085, 2293, 2501, 2709 |
| 82 | O60911 | CATL2 | Cathepsin L2 (EC 3.4.22.43) (Cathepsin U) (Cathepsin V) | 1-17 | 6 | 334 | CTSV CATL2 CTSL2 CTSU UNQ268/PRO305 | 214, 422, 630, 838, 1046, 1254, 1462, 1670, 1878, 2086, 2294, 2502, 2710 |
| 83 | P20138 | CD33 | Myeloid cell surface antigen CD33 (Sialic acid-binding Ig-like lectin 3) (Siglec-3) (gp67) (CD antigen CD33) | 1-17 | 7 | 364 | CD33 SIGLEC3 | 215, 423, 631, 839, 1047, 1255, 1463, 1671, 1879, 2087, 2295, 2503, 2711 |
| 8485 | P27797 | CALR | Calreticulin (CRP55) (Calregulin) (Endoplasmic reticulum resident protein 60) (ERp60) (HACBP) (grp60) | 1-17 | 8 | 417 | CALR CRTC | 216, 424, 632, 840, 1048, 1256, 1464, 1672, 1880, 2088, 2296, 2504, 2712 |
| 86 | P10747 | CD28 | T-cell-specific surface glycoprotein CD28 (TP44) (CD antigen CD28) | 1-18 | 9 | 220 | CD28 | 217, 425, 633, 841, 1049, 1257, 1465, 1673, 1881, 2089, 2297, 2505, 2713 |
| 87 | O75487 | GPC4 | Glypican-4 (K-glypican) [Cleaved into: Secreted glypican-4] | 1-18 | 10 | 556 | GPC4 UNQ474/PRO937 | 218, 426, 634, 842, 1050, 1258, 1466, 1674, 1882, 20920, 2298, 2506, 2714 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 8889 | P07996 | TSP1 | Thrombospondin-1 | 1-18 | 11 | 1170 | THBS1 TSP TSP1 | 219, 427, 635, 843, 1051, 1259, 1467, 1675, 1883, 2091, 2299, 2507, 2715 |
| 90 | P22748 | CAH4 | Carbonic anhydrase 4 (EC 4.2.1.1) (Carbonate dehydratase IV) (Carbonic anhydrase IV) (CA-IV) | 1-18 | 12 | 312 | CA4 | 220, 428, 636, 844, 1052, 1260, 1468, 1676, 1884, 2092, 2300, 2508, 2716 |
| 91 | Q15762 | CD226 | CD226 antigen (DNAX accessory molecule 1) (DNAM-1) (CD antigen CD226) | 1-18 | 13 | 336 | CD226 DNAM1 | 221, 429, 637, 845, 1053, 1261, 1469, 1677, 1885, 2093, 2301, 2509, 2717 |
| 9293 | P30273 | FCERG | High affinity immunoglobulin epsilon receptor subunit gamma (Fc receptor gamma-chain) (FcRgamma) (Fc-epsilon RI-gamma) (IgE Fc receptor subunit gamma) (FceRI gamma) | 1-18 | 14 | 86 | FCER1G | 222, 430, 638, 846, 1054, 1262, 1470, 1678, 1886, 2094, 2302, 2510, 2718 |
| 94 | P38570 | ITAE | Integrin alpha-E (HML-1 antigen) (Integrin alpha-IEL) (Mucosal lymphocyte 1 antigen) (CD antigen CD103) [Cleaved into: Integrin alpha-E light chain; Integrin alpha-E heavy chain] | 1-18 | 15 | 1179 | ITGAE | 223, 431, 639, 847, 1055, 1263, 1471, 1679, 1887, 2095, 2303, 2511, 2719 |
| 95 | Q01638 | ILRL1 | Interleukin-1 receptor-like 1 (Protein ST2) | 1-18 | 16 | 556 | IL1RL1 DER4 ST2 T1 | 224, 432, 640, 848, 1056, 1264, 1472, 1680, 1888, 2096, 2304, 2512, 2720 |
| 96 | Q9NZQ7 | PD1L1 | Programmed cell death 1 ligand 1 (PD-L1) (PDCD1 ligand 1) (Programmed death ligand 1) (B7 homolog 1) (B7-H1) (CD antigen CD274) | 1-18 | 17 | 290 | CD274 B7H1 PDCD1L1 PDCD1LG1 PDL1 | 225, 433, 641, 849, 1057, 1265, 1473, 1681, 1889, 2097, 2305, 2513, 2712 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 97 | P30443 | HLA-A | HLA class I histocompatibility antigen, A-1 alpha chain (MHC class Iantigen A*1) | 1-18 | 76948 | 365 | HLA-A HLAA | 76952, 76956, 76960, 76964, 76968, 76972, 76976, 76980, 76984, 76988, 76992, 76996, 77000 |
| 98 | Q6GPI1 | CTRB2 | Chymotrypsinogen B2 | 1-18 | 76949 | 263 | CTRB2 | 76953, 76957, 76961, 76965, 76969, 76973, 76977, 76981, 76985, 76989, 76993, 76997, 77001 |
| 99 | P02768 | ALB | Serum albumin (ALB) (ALBU) (humanes serum albumin) | 1-18 | 76950 | 609 | ALB ALBU HSA | 76954, 76958, 76962, 76966, 76970, 76974, 76978, 76982, 76986, 76990, 76994, 76998, 77002 |
| 100 | AAB59424.1 | IGHE | Ig heavy chain epsilon-1 (V-D-J region) | 1-18 | 76951 | 574 | IgE, IgHE | 76955, 76959, 76963, 76967, 76971, 76975, 76979, 76983, 76987, 76991, 76995, 76999, 77003 |
| 101 | P13591 | NCAM1 | Neural cell adhesion molecule 1 (N-CAM-1) (NCAM-1) (CD antigen CD56) | 1-19 | 18 | 858 | NCAM1 NCAM | 226, 434, 642, 850, 1058, 1266, 1474, 1682, 1890, 2098, 2306, 2514, 2722 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 102 | P26842 | CD27 | CD27 antigen (CD27L receptor) (T-cell activation antigen CD27) (T14) (Tumor necrosis factor receptor superfamily member 7) (CD antigen CD27) | 1-19 | 19 | 260 | CD27 TNFRSF7 | 227, 435, 643, 851, 1059, 1267, 1475, 1683, 1891, 2099, 2307, 2515, 2723 |
| 103 | P15391 | CD19 | B-lymphocyte antigen CD19 (B-lymphocyte surface antigen B4) (Differentiation antigen CD19) (T-cell surface antigen Leu-12) (CD antigen CD19) | 1-19 | 20 | 556 | CD19 | 228, 436, 644, 852, 1060, 1268, 1476, 1684, 1892, 2100, 2308, 2516, 2724 |
| 104 | Q8NI17 | IL31R | Interleukin-31 receptor subunit alpha (IL-31 receptor subunit alpha) (IL-31R subunit alpha) (IL-31R-alpha) (IL-31RA) (Cytokine receptor-like 3) (GLM-R) (hGLM-R) (Gp130-like monocyte receptor) (Gp130-like receptor) (ZcytoR17) | 1-19 | 21 | 732 | IL31RA CRL3 GPL UNQ6368/PRO21073/PRO21384 | 229, 437, 645, 853, 1061, 1269, 1477, 1685, 1893, 2101, 2309, 2517, 2725 |
| 105 | P08571 | CD14 | Monocyte differentiation antigen CD14 (Myeloid cell-specific leucine-rich glycoprotein) (CD antigen CD14) [Cleaved into: Monocyte differentiation antigen CD14, urinary form; Monocyte differentiation antigen CD14, membrane-bound form] | 1-19 | 22 | 375 | CD14 | 230, 438, 646, 854, 1062, 1270, 1478, 1686, 1894, 2102, 2310, 2518, 2726 |
| 106 | P05154 | IPSP | Plasma serine protease inhibitor (Acrosomal serine protease inhibitor) (Plasminogen activator inhibitor 3) (PAI-3) (PAI3) (Protein C inhibitor) (PCI) (Serpin A5) | 1-19 | 23 | 406 | SERPINA5 PCI PLANH3 PROCI | 231, 439, 647, 855, 1063, 1271, 1479, 1687, 1895, 2103, 2311, 2519, 2727 |
| 107 | P02787 | TRFE | Serotransferrin (Transferrin) (Beta-1 metal-binding globulin) (Siderophilin) | 1-19 | 24 | 698 | TF PRO1400 | 232, 440, 648, 856, 1064, 1272, 1480, 1688, 1896, 2104, 2312, 2520, 2728 |
| 108 | P02671 | FIBA | Fibrinogen alpha chain [Cleaved into: Fibrinopeptide A; Fibrinogen alpha chain] | 1-19 | 25 | 866 | FGA | 233, 441, 649, 857, 1065, 1273, 1481, 1689, 1897, 2105, 2313, 2521, 2729 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 109 | P04216 | THY1 | Thy-1 membrane glycoprotein (CDw90) (Thy-1 antigen) (CD antigen CD90) | 1-19 | 26 | 161 | THY1 | 234, 442, 650, 858, 1066, 1274, 1482, 1690, 1898, 2106, 2314, 2522, 2730 |
| 110 | P00747 | PLMN | Plasminogen (EC 3.4.21.7) [Cleaved into: Plasmin heavy chain A; Activation peptide; Angiostatin; Plasmin heavy chain A, short form; Plasmin light chain B] | 1-19 | 27 | 810 | PLG | 235, 443, 651, 859, 1067, 1275, 1483, 1691, 1899, 2107, 2315, 2523, 2731 |
| 111 | P01764 | HV323 | Immunoglobulin heavy variable 3-23 (Ig heavy chain V-III region LAY) (Ig heavy chain V-III region POM) (Ig heavy chain V-III region TEI) (Ig heavy chain V-III region TIL) (Ig heavy chain V-III region TUR) (Ig heavy chain V-III region VH26) (Ig heavy chain V-III region WAS) (Ig heavy chain V-III region ZAP) | 1-19 | 28 | 117 | IGHV3-23 | 236, 444, 652, 860, 1068, 1276, 1484, 1692, 1900, 2108, 2316, 2524, 2732 |
| 112 | P16150 | LEUK | Leukosialin (Galactoglycoprotein) (GALGP) (Leukocyte sialoglycoprotein) (Sialophorin) (CD antigen CD43) | 1-19 | 29 | 400 | SPN CD43 | 237, 445, 653, 861, 1069, 1277, 1485, 1693, 1901, 2109, 2317, 2525, 2733 |
| 113 | Q6DN72 | FCRL6 | Fc receptor-like protein 6 (FcR-like protein 6) (FcRL6) (Fc receptor homolog 6) (FcRH6) (IFGP6) | 1-19 | 30 | 434 | FCRL6 FCRH6 | 238, 446, 654, 862, 1070, 1278, 1486, 1694, 1902, 2110, 2318, 2526, 2734 |
| 114 | Q01151 | CD83 | CD83 antigen (hCD83) (B-cell activation protein) (Cell surface protein HB15) (CD antigen CD83) | 1-19 | 31 | 205 | CD83 | 239, 447, 655, 863, 1071, 1279, 1487, 1695, 1903, 2111, 2319, 2527, 2735 |
| 115 | P07093 | GDN | Glia-derived nexin (GDN) (Peptidase inhibitor 7) (PI-7) (Protease nexin 1) (PN-1) (Protease nexin I) (Serpin E2) | 1-19 | 32 | 398 | SERPINE2 PI7 PN1 | 240, 448, 656, 864, 1072, 1280, 1488, 1696, 1904, 2112, 2320, 2528, 2736 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 116 | Q8WWQ8 | STAB2 | Stabilin-2 (FAS1 EGF-like and X-link domain-containing adhesion molecule 2) (Fasciclin, EGF-like, laminin-type EGF-like and link domain-containing scavenger receptor 2) (FEEL-2) (Hyaluronan receptor for endocytosis) [Cleaved into: 190 kDa form stabilin-2 (190 kDa hyaluronan receptor for endocytosis)] | 1-19 | 33 | 2551 | STAB2 FEEL2 FELL FEX2 HARE | 241, 449, 657, 865, 1073, 1281, 1489, 1697, 1905, 2113, 2321, 2529, 2737 |
| 117 | Q13291 | SLAF1 | Signaling lymphocytic activation molecule (CDw150) (IPO-3) (SLAM family member 1) (CD antigen CD150) | 1-20 | 34 | 335 | SLAMF1 SLAM | 242, 450, 658, 866, 1074, 1282, 1490, 1698, 1906, 2114, 2322, 2530, 2738 |
| 118 | P35225 | IL13 | Interleukin-13 (IL-13) | 1-20 | 35 | 146 | IL13 NC30 | 243, 451, 659, 867, 1075, 1283, 1491, 1699, 1907, 2115, 2323, 2531, 2739 |
| 119 | P25942 | TNR5 | Tumor necrosis factor receptor superfamily member 5 (B-cell surface antigen CD40) (Bp50) (CD40L receptor) (CDw40) (CD antigen CD40) | 1-20 | 36 | 277 | CD40 TNFRSF5 | 244, 452, 660, 868, 1076, 1284, 1492, 1700, 1908, 2116, 2324, 2532, 2740 |
| 120 | P52803 | EFNA5 | Ephrin-A5 (AL-1) (EPH-related receptor tyrosine kinase ligand 7) (LERK-7) | 1-20 | 37 | 228 | EFNA5 EPLG7 LERK7 | 245, 453, 661, 869, 1077, 1285, 1493, 1701, 1909, 2117, 2325, 2533, 2741 |
| 121 | Q15116 | PDCD1 | Programmed cell death protein 1 (Protein PD-1) (hPD-1) (CD antigen CD279) | 1-20 | 38 | 288 | PDCD1 PD1 | 246, 454, 662, 870, 1078, 1286, 1494, 1702, 1910, 2118, 2326, 2534, 2742 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 122 | P05556 | ITB1 | Integrin beta-1 (Fibronectin receptor subunit beta) (Glycoprotein IIa) (GPIIA) (VLA-4 subunit beta) (CD antigen CD29) | 1-20 | 39 | 798 | ITGB1 FNRB MDF2 MSK12 | 247, 455, 663, 871, 1079, 1287, 1495, 1703, 1911, 2119, 2327, 2535, 2743 |
| 123 | Q12891 | HYAL2 | Hyaluronidase-2 (Hyal-2) (EC 3.2.1.35) (Hyaluronoglucosaminidase-2) (Lung carcinoma protein 2) (LuCa-2) | 1-20 | 40 | 473 | HYAL2 LUCA2 | 248, 456, 664, 872, 1080, 1288, 1496, 1704, 1912, 2120, 2328, 2536, 2744 |
| 124 | Q8IV16 | HDBP1 | Glycosylphosphatidylinositol-anchored high density lipoprotein-binding protein 1 (GPI-HBP1) (GPI-anchored HDL-binding protein 1) (High density lipoprotein-binding protein 1) | 1-20 | 41 | 184 | GPIHBP1 HBP1 | 249, 457, 665, 873, 1081, 1289, 1497, 1705, 1913, 2121, 2329, 2537, 2745 |
| 125 | Q03167 | TGBR3 | Transforming growth factor beta receptor type 3 (TGF-beta receptor type 3) (TGFR-3) (Betaglycan) (Transforming growth factor beta receptor III) (TGF-beta receptor type III) | 1-20 | 42 | 851 | TGFBR3 | 250, 458, 666, 874, 1082, 1290, 1498, 1706, 1914, 2122, 2330, 2538, 2746 |
| 126 | Q14246 | AGRE1 | Adhesion G protein-coupled receptor E1 (EGF-like module receptor 1) (EGF-like module-containing mucin-like hormone receptor-like 1) (EMR1 hormone receptor) | 1-20 | 43 | 886 | ADGRE1 EMR1 TM7LN3 | 251, 459, 667, 875, 1083, 1291, 1499, 1707, 1915, 2123, 2331, 2539, 2747 |
| 127 | P16871 | IL7RA | Interleukin-7 receptor subunit alpha (IL-7 receptor subunit alpha) (IL-7R subunit alpha) (IL-7R-alpha) (IL-7RA) (CDw127) (CD antigen CD127) | 1-20 | 44 | 459 | IL7R | 252, 460, 668, 876, 1084, 1292, 1500, 1708, 1916, 2124, 2332, 2540, 2748 |
| 128 | P61769 | B2MG | Beta-2-microglobulin [Cleaved into: Beta-2-microglobulin form pI 5.3] | 1-20 | 45 | 119 | B2M CDABP0092 HDCMA22P | 253, 461, 669, 877, 1085, 1293, 1501, 1709, 1917, 2125, 2333, 2541, 2749 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 129 | Q9Y6W8 | ICOS | Inducible T-cell costimulator (Activation-inducible lymphocyte immunomediatory molecule) (CD antigen CD278) | 1-20 | 46 | 199 | ICOS AILIM | 254, 462, 670, 878, 1086, 1294, 1502, 1710, 1918, 2126, 2334, 2542, 2750 |
| 130 | P10966 | CD86 | T-cell surface glycoprotein CD8 beta chain (CD antigen CD8b) | 1-21 | 47 | 210 | CD86 CD8B1 | 255, 463, 671, 879, 1087, 1295, 1503, 1711, 1919, 2127, 2335, 2543, 2751 |
| 131 | Q9BZW8 | CD244 | Natural killer cell receptor 2B4 (NK cell activation-inducing ligand) (NAIL) (NK cell type I receptor protein 2B4) (NKR2B4) (h2B4) (SLAM family member 4) (SLAMF4) (Signaling lymphocytic activation molecule 4) (CD antigen CD244) | 1-21 | 48 | 370 | CD244 2B4 | 256, 464, 672, 880, 1088, 1296, 1504, 1712, 1920, 2128, 2336, 2544, 2752 |
| 132 | P02778 | CXL10 | C-X-C motif chemokine 10 (10 kDa interferon gamma-induced protein) (Gamma- IP10) (IP-10) (Small-inducible cytokine B10) [Cleaved into: CXCL10(1-73)] | 1-21 | 49 | 98 | CXCL10 INP10 SCYB10 | 257, 465, 673, 881, 1089, 1297, 1505, 1713, 1921, 2129, 2337, 2545, 2753 |
| 133 | P18564 | ITB6 | Integrin beta-6 | 1-21 | 50 | 788 | ITGB6 | 258, 466, 674, 882, 1090, 1298, 1506, 1714, 1922, 2130, 2338, 2546, 2754 |
| 134 | O14525 | ASTN1 | Astrotactin-1 | 1-21 | 51 | 1302 | ASTN1 ASTN KIAA0289 | 259, 467, 675, 883, 1091, 1299, 1507, 1715, 1923, 2131, 2339, 2547, 2755 |
| 135 | P01130 | LDLR | Low-density lipoprotein receptor (LDL receptor) | 1-21 | 52 | 860 | LDLR | 260, 468, 676, 884, 1092, 1300, 1508, 1716, 1924, 2132, 2340, 2548, 2756 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 136 | P01732 | CD8A | T-cell surface glycoprotein CD8 alpha chain (T-lymphocyte differentiation antigen T8/Leu-2) (CD antigen CD8a) | 1-21 | 53 | 235 | CD8A MAL | 261, 469, 677, 885, 1093, 1301, 1509, 1717, 1925, 2133, 2341, 2549, 2757 |
| 137 | P48061 | SDF1 | Stromal cell-derived factor 1 (SDF-1) (hSDF-1) (C-X-C motif chemokine 12) (Intercrine reduced in hepatomas) (IRH) (hIRH) (Pre-B cell growth-stimulating factor) (PBSF) [Cleaved into: SDF-1-beta(3-72); SDF-1-alpha(3-67)] | 1-21 | 54 | 93 | CXCL12 SDF1 SDF1A SDF1B | 262, 470, 678, 886, 1094, 1302, 1510, 1718, 1926, 2134, 2342, 2550, 2758 |
| 138 | P01589 | IL2RA | Interleukin-2 receptor subunit alpha (IL-2 receptor subunit alpha) (IL-2-RA) (IL-2R subunit alpha) (1L2-RA) (TAC antigen) (p55) (CD antigen CD25) | 1-21 | 55 | 272 | IL2RA | 263, 471, 679, 887, 1095, 1303, 1511, 1719, 1927, 2135, 2343, 2551, 2759 |
| 139 | Q86113 | CLC14 | C-type lectin domain family 14 member A (Epidermal growth factor receptor 5) (EGFR-5) | 1-21 | 56 | 490 | CLEC14A C14orf27 EGFR5 UNQ236/PRO269 | 264, 472, 680, 888, 1096, 1304, 1512, 1720, 1928, 2136, 2344, 2552, 2760 |
| 140 | Q5DID0 | UROL1 | Uromodulin-like 1 (Olfactorin) | 1-21 | 57 | 1318 | UMODL1 | 265, 473, 681, 889, 1097, 1305, 1513, 1721, 1929, 2137, 2345, 2553, 2761 |
| 141 | P40189 | IL6RB | Interleukin-6 receptor subunit beta (IL-6 receptor subunit beta) (IL-6R subunit beta) (IL-6R-beta) (IL-6RB) (CDw130) (Interleukin-6 signal transducer) (Membrane glycoprotein 130) (gp130) (Oncostatin-M receptor subunit alpha) (CD antigen CD130) | 1-22 | 58 | 918 | IL6ST | 266, 474, 682, 890, 1098, 1306, 1514, 1722, 1930, 2138, 2346, 2554, 2762 |
| 142 | Q86YL7 | PDPN | Podoplanin (Aggrus) (Glycoprotein 36) (Gp36) (PA2.26 antigen) (T1-alpha) (T1A) | 1-22 | 59 | 162 | PDPN GP36 PSEC0003 PSEC0025 | 267, 475, 683, 891, 1099, 1307, 1515, 1723, 1931, 2139, 2347, 2555, 2763 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 143 | P55075 | FGF8 | Fibroblast growth factor 8 (FGF-8) (Androgen-induced growth factor) (AIGF) (Heparin-binding growth factor 8) (HBGF-8) | 1-22 | 60 | 233 | FGF8 AIGF | 268, 476, 684, 892, 1100, 1308, 1516, 1724, 1932, 2140, 2348, 2556, 2764 |
| 144 | Q30201 | HFE | Hereditary hemochromatosis protein (HLA-H) | 1-22 | 61 | 348 | HFE HLAH | 269, 477, 685, 893, 1101, 1309, 1517, 1725, 1933, 2141, 2349, 2557, 2765 |
| 145 | P07766 | CD3E | T-cell surface glycoprotein CD3 epsilon chain (T-cell surface antigen T3/Leu-4 epsilon chain) (CD antigen CD3e) | 1-22 | 62 | 207 | CD3E T3E | 270, 478, 686, 894, 1102, 1310, 1518, 1726, 1934, 2142, 2350, 2558, 2766 |
| 146 | P18827 | SDC1 | Syndecan-1 (SYND1) (CD antigen CD138) | 1-22 | 63 | 310 | SDC1 SDC | 271, 479, 687, 895, 1103, 1311, 1519, 1727, 1935, 2143, 2351, 2559, 2767 |
| 147 | P55290 | CAD13 | Cadherin-13 (Heart cadherin) (H-cadherin) (P105) (Truncated cadherin) (T-cad) (T-cadherin) | 1-22 | 64 | 713 | CDH13 CDHH | 272, 480, 688, 896, 1104, 1312, 1520, 1728, 1936, 2144, 2352, 2560, 2768 |
| 148 | P37173 | TGFR2 | TGF-beta receptor type-2 (TGFR-2) (EC 2.7.11.30) (TGF-beta type II receptor) (Transforming growth factor-beta receptor type II) (TGF-beta receptor type II) (TbetaR-II) | 1-22 | 65 | 567 | TGFBR2 | 273, 481, 689, 897, 1105, 1313, 1521, 1729, 1937, 2145, 2353, 2561, 2769 |
| 149 | Q07325 | CXCL9 | C-X-C motif chemokine 9 (Gamma-interferon-induced monokine) (Monokine induced by interferon-gamma) (HuMIG) (MIG) (Small-inducible cytokine B9) | 1-22 | 66 | 125 | CXCL9 CMK MIG SCYB9 | 274, 482, 690, 898, 1106, 1314, 1522, 1730, 1938, 2146, 2354, 2562, 2770 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 150 | P04156 | PRIO | Major prion protein (PrP) (ASCR) (PrP27-30) (PrP33-35C) (CD antigen CD230) | 1-22 | 67 | 253 | PRNP ALTPRP PRIP PRP | 275, 483, 691, 899, 1107, 1315, 1523, 1731, 1939, 2147, 2355, 2563, 2771 |
| 151 | P31785 | IL2RG | Cytokine receptor common subunit gamma (Interleukin-2 receptor subunit gamma) (IL-2 receptor subunit gamma) (IL-2R subunit gamma) (IL-2RG) (gammaC) (p64) (CD antigen CD132) | 1-22 | 68 | 369 | IL2RG | 276, 484, 692, 900, 1108, 1316, 1524, 1732, 1940, 2148, 2356, 2564, 2772 |
| 152 | P01579 | IFNG | Interferon gamma (IFN-gamma) (Immune interferon) | 1-23 | 69 | 166 | IFNG | 277, 485, 693, 901, 1109, 1317, 1525, 1733, 1941, 2149, 2357, 2565, 2773 |
| 153 | P23229 | ITA6 | Integrin alpha-6 (CD49 antigen-like family member F) (VLA-6) (CD antigen CD49f) [Cleaved into: Integrin alpha-6 heavy chain; Integrin alpha-6 light chain; Processed integrin alpha-6 (Alpha6p)] | 1-23 | 70 | 1130 | ITGA6 | 278, 486, 694, 902, 1110, 1318, 1526, 1734, 1942, 2150, 2358, 2566, 2774 |
| 154 | O60494 | CUBN | Cubilin (460 kDa receptor) (Intestinal intrinsic factor receptor) (Intrinsic factor-cobalamin receptor) (Intrinsic factor-vitamin B12 receptor) | 1-23 | 71 | 3623 | CUBN IFCR | 279, 487, 695, 903, 1111, 1319, 1527, 1735, 1943, 2151, 2359, 2567, 2775 |
| 155 | P08575 | PTPRC | Receptor-type tyrosine-protein phosphatase C (EC 3.1.3.48) (Leukocyte common antigen) (L-CA) (1200) (CD antigen CD45) | 1-23 | 72 | 1304 | PTPRC CD45 | 280, 488, 696, 904, 1112, 1320, 1528, 1736, 1944, 2152, 2360, 2568, 2776 |
| 156 | Q8IWY4 | SCUB1 | Signal peptide, CUB and EGF-like domain-containing protein 1 | 1-23 | 73 | 988 | SCUBE1 | 281, 489, 697, 905, 1113, 1321, 1529, 1737, 1945, 2153, 2361, 2569, 2777 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 157 | Q08431 | MFGM | Lactadherin (Breast epithelial antigen BA46) (HMFG) (MFGM) (Milk fat globule-EGF factor 8) (MFG-E8) (SED1) [Cleaved into: Lactadherin short form; Medin] | 1-23 | 74 | 387 | MFGE8 | 282, 490, 698, 906, 1114, 1322, 1530, 1738, 1946, 2154, 2362, 2570, 2778 |
| 158 | Q99665 | I12R2 | Interleukin-12 receptor subunit beta-2 (IL-12 receptor subunit beta-2) (IL-12R subunit beta-2) (IL-12R-beta-2) (IL-12RB2) | 1-23 | 75 | 862 | IL12RB2 | 283, 491, 699, 907, 1115, 1323, 1531, 1739, 1947, 2155, 2363, 2571, 2779 |
| 159 | Q6Q8B3 | MO2R2 | Cell surface glycoprotein CD200 receptor 2 (CD200 cell surface glycoprotein receptor-like 2) (CD200 receptor-like 2) (HuCD200R2) (CD200 cell surface glycoprotein receptor-like a) (CD200RLa) (Cell surface glycoprotein CD200 receptor 1-like) (Cell surface glycoprotein OX2 receptor 2) | 1-23 | 76 | 271 | CD200R1L CD200R2 | 284, 492, 700, 908, 1116, 1324, 1532, 1740, 1948, 2156, 2364, 2572, 2780 |
| 160 | Q07011 | TNR9 | Tumor necrosis factor receptor superfamily member 9 (4-1BB ligand receptor) (CDw137) (T-cell antigen 4-1BB homolog) (T-cell antigen ILA) (CD antigen CD137) | 1-23 | 77 | 255 | TNFRSF9 CD137 ILA | 285, 493, 701, 909, 1117, 1325, 1533, 1741, 1949, 2157, 2365, 2573, 2781 |
| 161 | Q8NHL6 | LIRB1 | Leukocyte immunoglobulin-like receptor subfamily B member 1 (LIR-1) (Leukocyte immunoglobulin-like receptor 1) (CD85 antigen-like family member J) (Immunoglobulin-like transcript 2) (ILT-2) (Monocyte/macrophage immunoglobulin-like receptor 7) (MIR-7) (CD antigen CD85j) | 1-23 | 78 | 650 | LILRB1 ILT2 LIR1 MIR7 | 286, 494, 702, 910, 1118, 1326, 1534, 1742, 1950, 2158, 2366, 2574, 2782 |
| 162 | P36894 | BMR1A | Bone morphogenetic protein receptor type-1A (BMP type-1A receptor) (BMPR-1A) (EC 2.7.11.30) (Activin receptor-like kinase 3) (ALK-3) (Serine/threonine-protein kinase receptor R5) (SKR5) (CD antigen CD292) | 1-23 | 79 | 532 | BMPR1A ACVRLK3 ALK3 | 287, 495, 703, 911, 1119, 1327, 1535, 1743, 1951, 2159, 2367, 2575, 2783 |
| 163 | Q16552 | IL17 | Interleukin-17A (IL-17) (IL-17A) (Cytotoxic T-lymphocyte-associated antigen 8) (CTLA-8) | 1-23 | 80 | 155 | IL17A CTLA8 IL17 | 288, 496, 704, 912, 1120, 1328, 1536, 1744, 1952, 2160, 2368, 2576, 2784 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 164 | P42081 | CD86 | T-lymphocyte activation antigen CD86 (Activation B7-2 antigen) (B70) (BU63) (CTLA-4 counter-receptor B7.2) (FUN-1) (CD antigen CD86) | 1-23 | 8 | 329 | CD86 CD28LG2 | 289, 497, 705, 913, 1121, 1329, 1537, 1745, 1953, 2161, 2369, 2577, 2785 |
| 165 | P43121 | MUC18 | Cell surface glycoprotein MUC18 (Cell surface glycoprotein P1H12) (Melanoma cell adhesion molecule) (Melanoma-associated antigen A32) (Melanoma-associated antigen MUC18) (S-endo 1 endothelial-associated antigen) (CD antigen CD146) | 1-23 | 82 | 646 | MCAM MUC18 | 290, 498, 706, 914, 1122, 1330, 1538, 1746, 1954, 2162, 2370, 2578, 2786 |
| 166 | O00206 | TLR4 | Toll-like receptor 4 (hToll) (CD antigen CD284) | 1-23 | 83 | 839 | TLR4 | 291, 499, 707, 915, 1123, 1331, 1539, 1747, 1955, 2163, 2371, 2579, 2787 |
| 167 | P42701 | I12R1 | Interleukin-12 receptor subunit beta-1 (IL-12 receptor subunit beta-1) (IL-12R subunit beta-1) (IL-12R-beta-1) (IL-12RB1) (IL-12 receptor beta component) (CD antigen CD212) | 1-23 | 84 | 662 | IL12RB1 IL12R IL12RB | 292, 500, 708, 916, 1124, 1332, 1540, 1748, 1956, 2164, 2372, 2580, 2788 |
| 168 | P06729 | CD2 | T-cell surface antigen CD2 (Erythrocyte receptor) (LFA-2) (LFA-3 receptor) (Rosette receptor) (T-cell surface antigen T11/Leu-5) (CD antigen CD2) | 1-24 | 85 | 351 | CD2 SRBC | 293, 501, 709, 917, 1125, 1333, 1541, 1749, 1957, 2165, 2373, 2581, 2789 |
| 169 | P15328 | FOLR1 | Folate receptor alpha (FR-alpha) (Adult folate-binding protein) (FBP) (Folate receptor 1) (Folate receptor, adult) (KB cells FBP) (Ovarian tumor-associated antigen MOv18) | 1-24 | 86 | 257 | FOLR1 FOLR | 294, 502, 710, 918, 1126, 1334, 1542, 1750, 1958, 2166, 2374, 2582, 2790 |
| 170 | P05112 | IL4 | Interleukin-4 (1L-4) (B-cell stimulatory factor 1) (BSF-1) (Binetrakin) (Lymphocyte stimulatory factor 1) (Pitrakinra) | 1-24 | 87 | 153 | IL4 | 295, 503, 711, 919, 1127, 1335, 1543, 1751, 1959, 2167, 2375, 2583, 2791 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 171 | P06127 | CD5 | T-cell surface glycoprotein CD5 (Lymphocyte antigen T1/Leu-1) (CD antigen CD5) | 1-24 | 88 | 495 | CD5 LEU1 | 296, 504, 712, 920, 1128, 1336, 1544, 1752, 1960, 2168, 2376, 2584, 2792 |
| 172 | P32248 | CCR7 | C-C chemokine receptor type 7 (C-C CKR-7) (CC-CKR-7) (CCR-7) (BLR2) (CDw197) (Epstein-Barr virus-induced G-protein coupled receptor 1) (EBI1) (EBV-induced G-protein coupled receptor 1) (MIP-3 beta receptor) (CD antigen CD197) | 1-24 | 89 | 378 | CCR7 CMKBR7 EBI1 EVI1 | 297, 505, 713, 921, 1129, 1337, 1545, 1753, 1961, 2169, 2377, 2585, 2793 |
| 173 | Q7Z7D3 | VTCN1 | V-set domain-containing T-cell activation inhibitor 1 (B7 homolog 4) (B7-H4) (B7h.5) (Immune costimulatory protein B7-H4) (Protein B7S1) (T-cell costimulatory molecule B7x) | 1-24 | 90 | 282 | VTCN1 B7H4 UNQ659/PRO1291 | 298, 506, 714, 922, 1130, 1338, 1546, 1754, 1962, 2170, 2378, 2586, 2794 |
| 174 | P54756 | EPHA5 | Ephrin type-A receptors (EC 2.7.10.1) (Brain-specific kinase) (EPH homology kinase 1) (EHK-1) (EPH-like kinase 7) (EK7) (hEK7) | 1-24 | 91 | 1037 | EPHA5 BSK EHK1 HEK7 TYRO4 | 299, 507, 715, 923, 1131, 1339, 1547, 1755, 1963, 2171, 2379, 2587, 2795 |
| 175 | Q92823 | NRCAM | Neuronal cell adhesion molecule (Nr-CAM) (Neuronal surface protein Bravo) (hBravo) (NgCAM-related cell adhesion molecule) (Ng-CAM-related) | 1-24 | 92 | 1304 | NRCAM KIAA0343 | 300, 508, 716, 924, 1132, 1340, 1548, 1756, 1964, 2172, 2380, 2588, 2796 |
| 176 | P19320 | VCAM1 | Vascular cell adhesion protein 1 (V-CAM 1) (VCAM-1) (INCAM-100) (CD antigen CD106) | 1-24 | 93 | 739 | VCAM1 | 301, 509, 717, 925, 1133, 1341, 1549, 1757, 1965, 2173, 2381, 2589, 2797 |
| 177 | Q86UN2 | R4RL1 | Reticulon-4 receptor-like 1 (Nogo receptor-like 2) (Nogo-66 receptor homolog 2) (Nogo-66 receptor-related protein 3) (NgR3) | 1-24 | 94 | 441 | RTN4RL1 NGRH2 NGRL2 | 302, 510, 718, 926, 1134, 1342, 1550, 1758, 1966, 2174, 2382, 2590, 2798 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 178 | P33151 | CADH5 | Cadherin-5 (764 antigen) (Vascular endothelial cadherin) (VE-cadherin) (CD antigen CD144) | 1-25 | 95 | 784 | CDH5 | 303, 511, 719, 927, 1135, 1343, 1551, 1759, 1967, 2175, 2383, 2591, 2799 |
| 179 | P17813 | EGLN | Endoglin (CD antigen CD105) | 1-25 | 96 | 658 | ENG END | 304, 512, 720, 928, 1136, 1344, 1552, 1760, 1968, 2176, 2384, 2592, 2800 |
| 180 | P25445 | TNR6 | Tumor necrosis factor receptor superfamily member 6 (Apo-1 antigen) (Apoptosis-mediating surface antigen FAS) (FASLG receptor) (CD antigen CD95) | 1-25 | 97 | 335 | FAS APT1 FAS1 TNFRSF6 | 305, 513, 721, 929, 1137, 1345, 1553, 1761, 1969, 2177, 2385, 2593, 2801 |
| 181 | P01730 | CD4 | T-cell surface glycoprotein CD4 (T-cell surface antigen T4/Leu-3) (CD antigen CD4) | 1-25 | 98 | 458 | CD4 | 306, 514, 722, 930, 1138, 1346, 1554, 1762, 1970, 2178, 2386, 2594, 2802 |
| 182 | Q685J3 | MUC17 | Mucin-17 (MUC-17) (Small intestinal mucin-3) (MUC-3) | 1-25 | 99 | 4493 | MUC17 MUC3 | 307, 515, 723, 931, 1139, 1347, 1555, 1763, 1971, 2179, 2387, 2595, 2803 |
| 183 | P17787 | ACHB2 | Neuronal acetylcholine receptor subunit beta-2 | 1-25 | 100 | 502 | CHRNB2 | 308, 516, 724, 932, 1140, 1348, 1556, 1764, 1972, 2180, 2388, 2596, 2804 |
| 184 | Q6UQ28 | PLET1 | Placenta-expressed transcript 1 protein | 1-25 | 101 | 207 | PLET1 C11orf34 | 309, 517, 725, 933, 1141, 1349, 1557, 1765, 1973, 2181, 2389, 2597, 2805 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 185 | P13987 | CD59 | CD59 glycoprotein (1F5 antigen) (20 kDa homologous restriction factor) (HRF-20) (HRF20) (MAC-inhibitory protein) (MAC-IP) (MEM43 antigen) (Membrane attack complex inhibition factor) (MACIF) (Membrane inhibitor of reactive lysis) (MIRL) (Protectin) (CD antigen CD59) | 1-25 | 102 | 128 | CD59 MIC11 MIN1 MIN2 MIN3 MSK21 | 310, 518, 726, 934, 1142, 1350, 1558, 1766, 1974, 2182, 2390, 2598, 2806 |
| 186 | P10721 | KIT | Mast/stem cell growth factor receptor Kit (SCFR) (EC 2.7.10.1) (Piebald trait protein) (PBT) (Proto-oncogene c-Kit) (Tyrosine-protein kinase Kit) (p145 c-kit) (v-kit Hardy-Zuckerman 4 feline sarcoma viral oncogene homolog) (CD antigen CD117) | 1-25 | 103 | 976 | KIT SCFR | 311, 519, 727, 935, 1143, 1351, 1559, 1767, 1975, 2183, 2391, 2599, 2807 |
| 187 | P12319 | FCERA | High affinity immunoglobulin epsilon receptor subunit alpha (Fc-epsilon RI-alpha) (FcERI) (IgE Fc receptor subunit alpha) | 1-25 | 104 | 257 | FCER1A FCE1A | 312, 520, 728, 936, 1144, 1352, 1560, 1768, 1976, 2184, 2392, 2600, 2808 |
| 188 | Q9BZR6 | RTN4R | Reticulon-4 receptor (Nogo receptor) (NgR) (Nogo-66 receptor) | 1-26 | 105 | 473 | RTN4R NOGOR UNQ330/PRO526 | 313, 521, 729, 937, 1145, 1353, 1561, 1769, 1977, 2185, 2393, 2601, 2809 |
| 189 | P25063 | CD24 | Signal transducer CD24 (Small cell lung carcinoma cluster 4 antigen) (CD antigen CD24) | 1-26 | 106 | 80 | CD24 CD24A | 314, 522, 730, 938, 1146, 1354, 1562, 1770, 1978, 2186, 2394, 2602, 2810 |
| 190 | Q9NR97 | TLR8 | Toll-like receptor 8 (CD antigen CD288) | 1-26 | 107 | 1041 | TLR8 UNQ249/PRO286 | 315, 523, 731, 939, 1147, 1355, 1563, 1771, 1979, 2187, 2395, 2603, 2811 |
| 191 | Q8N131 | PORIM | Porimin (Keratinocytes-associated transmembrane protein 3) (KCT-3) (Pro-oncosis receptor inducing membrane injury) (Transmembrane protein 123) | 1-26 | 108 | 208 | TMEM123 KCT3 PSEC0111 UNQ641/PRO1271 | 316, 524, 732, 940, 1148, 1356, 1564, 1772, 1980, 2188, 2396, 2604, 2812 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 192 | P49771 | FLT3L | Fms-related tyrosine kinase 3 ligand (Flt3 ligand) (Flt3L) (SL cytokine) | 1-26 | 109 | 235 | FLT3LG | 317, 525, 733, 941, 1149, 1357, 1565, 1773, 1981, 2189, 2397, 2605, 2813 |
| 193 | P02679 | FIBG | Fibrinogen gamma chain | 1-26 | 110 | 453 | FGG PRO2061 | 318, 526, 734, 942, 1150, 1358, 1566, 1774, 1982, 2190, 2398, 2606, 2814 |
| 194 | P14784 | IL2RB | Interleukin-2 receptor subunit beta (IL-2 receptor subunit beta) (IL-2R subunit beta) (IL-2RB) (High affinity IL-2 receptor subunit beta) (p70-75) (p75) (CD antigen CD122) | 1-26 | 111 | 551 | IL2RB | 319, 527, 735, 943, 1151, 1359, 1567, 1775, 1983, 2191, 2399, 2607, 2815 |
| 195 | P05362 | ICAM1 | Intercellular adhesion molecule 1 (ICAM-1) (Major group rhinovirus receptor) (CD antigen CD54) | 1-27 | 112 | 532 | ICAM1 | 320, 528, 736, 944, 1152, 1360, 1568, 1776, 1984, 2192, 2400, 2608, 2816 |
| 196 | Q13740 | CD166 | CD166 antigen (Activated leukocyte cell adhesion molecule) (CD antigen CD166) | 1-27 | 113 | 583 | ALCAM MEMD | 321, 529, 737, 945, 1153, 1361, 1569, 1777, 1985, 2193, 2401, 2609, 2817 |
| 197 | Q13443 | ADAM9 | Disintegrin and metalloproteinase domain-containing protein 9 (ADAM 9) (EC 3.4.24.-) (Cellular disintegrin-related protein) (Meltrin-gamma) (Metalloprotease/disintegrin/cysteine-rich protein 9) (Myeloma cell metalloproteinase) | 1-28 | 114 | 819 | ADAM9 KIAA0021 MCMP MDC9 MLTNG | 322, 530, 738, 946, 1154, 1362, 1570, 1778, 1986, 2194, 2402, 2610, 2818 |
| 198 | P14151 | LYAM1 | L-selectin (CD62 antigen-like family member L) (Leukocyte adhesion molecule 1) (LAM-1) (Leukocyte surface antigen Leu-8) (Leukocyte-endothelial cell adhesion molecule 1) (LECAM1) (Lymph node homing receptor) (TQ1) (gp90-MEL) (CD antigen CD62L) | 1-28 | 115 | 372 | SELL LNHR LYAM1 | 323, 531, 739, 947, 1155, 1363, 1571, 1779, 1987, 2195, 2403, 2611, 2819 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 199 | P56199 | ITA1 | Integrin alpha-1 (CD49 antigen-like family member A) (Laminin and collagen receptor) (VLA-1) (CD antigen CD49a) | 1-28 | 116 | 1179 | ITGA1 | 324, 532, 740, 948, 1156, 1364, 1572, 1780, 1988, 2196, 2404, 2612, 2820 |
| 200 | P11279 | LAMP1 | Lysosome-associated membrane glycoprotein 1 (LAMP-1) (Lysosome-associated membrane protein 1) (CD107 antigen-like family member A) (CD antigen CD107a) | 1-28 | 117 | 417 | LAMP1 | 325, 533, 741, 949, 1157, 1365, 1573, 1781, 1989, 2197, 2405, 2613, 2821 |
| 201 | P40259 | CD79B | B-cell antigen receptor complex-associated protein beta chain (B-cell-specific glycoprotein B29) (Ig-beta) (Immunoglobulin-associated B29 protein) (CD antigen CD79b) | 1-28 | 118 | 229 | CD79B B29 IGB | 326, 534, 742, 950, 1158, 1366, 1574, 1782, 1990, 2198, 2406, 2614, 2822 |
| 202 | P43681 | ACHA4 | Neuronal acetylcholine receptor subunit alpha-4 | 1-28 | 119 | 627 | CHRNA4 NACRA4 | 327, 535, 743, 951, 1159, 1367, 1575, 1783, 1991, 2199, 2407, 2615, 2823 |
| 203 | P18627 | LAG3 | Lymphocyte activation gene 3 protein (LAG-3) (Protein FDC) (CD antigen CD223) | 1-28 | 120 | 525 | LAG3 FDC | 328, 536, 744, 952, 1160, 1368, 1576, 1784, 1992, 2200, 2408, 2616, 2824 |
| 204 | Q5ZPR3 | CD276 | CD276 antigen (4Ig-B7-H3) (B7 homolog 3) (B7-H3) (Costimulatory molecule) (CD antigen CD276) | 1-28 | 121 | 534 | CD276 B7H3 PSEC0249 UNQ309/PRO352 | 329, 537, 745, 953, 1161, 1369, 1577, 1785, 1993, 2201, 2409, 2617, 2825 |
| 205 | P23415 | GLRA1 | Glycine receptor subunit alpha-1 (Glycine receptor 48 kDa subunit) (Glycine receptor strychnine-binding subunit) | 1-28 | 122 | 457 | GLRA1 | 330, 538, 746, 954, 1162, 1370, 1578, 1786, 1994, 2202, 2410, 2618, 2826 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 206 | Q8TD46 | MO2R1 | Cell surface glycoprotein CD200 receptor 1 (CD200 cell surface glycoprotein receptor) (Cell surface glycoprotein OX2 receptor 1) | 1-28 | 123 | 325 | CD200R1 CD200R CRTR2 MOX2R OX2R UNQ2522/PRO6015 | 331, 539, 747, 955, 1163, 1371, 1579, 1787, 1995, 2203, 2411, 2619, 2827 |
| 207 | P17301 | ITA2 | Integrin alpha-2 (CD49 antigen-like family member B) (Collagen receptor) (Platelet membrane glycoprotein Ia) (GPIa) (VLA-2 subunit alpha) (CD antigen CD49b) | 1-29 | 124 | 1181 | ITGA2 CD49B | 332, 540, 748, 956, 1164, 1372, 1580, 1788, 1996, 2204, 2412, 2620, 2828 |
| 208 | P12821 | ACE | Angiotensin-converting enzyme (ACE) (EC 3.2.1.-) (EC 3.4.15.1) (Dipeptidyl carboxypeptidase 1) (Kininase II) (CD antigen CD143) [Cleaved into: Angiotensin-converting enzyme, soluble form] | 1-29 | 125 | 1306 | ACE DCP DCP1 | 333, 541, 749, 957, 1165, 1373, 1581, 1789, 1997, 2205, 2413, 2621, 2829 |
| 209 | Q14118 | DAG1 | Dystroglycan (Dystrophin-associated glycoprotein 1) [Cleaved into: Alpha-dystroglycan (Alpha-DG); Beta-dystroglycan (Beta-DG)] | 1-29 | 126 | 895 | DAG1 | 334, 542, 750, 958, 1166, 1374, 1582, 1790, 1998, 2206, 2414, 2622, 2830 |
| 210 | P05231 | IL6 | Interleukin-6 (IL-6) (B-cell stimulatory factor 2) (BSF-2) (CTL differentiation factor) (CDF) (Hybridoma growth factor) (Interferon beta-2) (IFN-beta-2) | 1-29 | 127 | 212 | IL6 IFNB2 | 335, 543, 751, 959, 1167, 1375, 1583, 1791, 1999, 2207, 2415, 2623, 2831 |
| 211 | O00602 | FCN1 | Ficolin-1 (Collagen/fibrinogen domain-containing protein 1) (Ficolin-A) (Ficolin-alpha) (M-ficolin) | 1-29 | 128 | 326 | FCN1 FCNM | 336, 544, 752, 960, 1168, 1376, 1584, 1792, 2000, 2208, 2416, 2624, 2832 |
| 212 | Q9Y6Q6 | TNR11 | Tumor necrosis factor receptor superfamily member 11A (Osteoclast differentiation factor receptor) (ODFR) (Receptor activator of NF-KB) (CD antigen CD265) | 1-29 | 129 | 616 | TNFRSF11A RANK | 337, 545, 753, 961, 1169, 1377, 1585, 1793, 2001, 2209, 2417, 2625, 2833 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 213 | Q9ULI3 | HEG1 | Protein HEG homolog 1 | 1-29 | 130 | 1381 | HEG1 KIAA1237 | 338, 546, 754, 962, 1170, 1378, 1586, 1794, 2002, 2210, 2418, 2626, 2834 |
| 214 | Q8NBP7 | PCSK9 | Proprotein convertase subtilisin/kexin type 9 (EC 3.4.21.-) (Neural apoptosis-regulated convertase 1) (NARC-1) (Proprotein convertase 9) (PC9) (Subtilisin/kexin-like protease PC9) | 1-30 | 131 | 692 | PCSK9 NARC1 PSEC0052 | 339, 547, 755, 963, 1171, 1379, 1587, 1795, 2003, 2211, 2419, 2627, 2835 |
| 215 | P02675 | FIBB | Fibrinogen beta chain [Cleaved into: Fibrinopeptide B; Fibrinogen beta chain] | 1-30 | 132 | 491 | FGB | 340, 548, 756, 964, 1172, 1380, 1588, 1796, 2004, 2212, 2420, 2628, 2836 |
| 216 | P06756 | ITAV | Integrin alpha-V (Vitronectin receptor subunit alpha) (CD antigen CD51) [Cleaved into: Integrin alpha-V heavy chain; Integrin alpha-V light chain] | 1-30 | 133 | 1048 | ITGAV MSK8 VNRA | 341, 549, 757, 965, 1173, 1381, 1589, 1797, 2005, 2213, 2421, 2629, 2837 |
| 217 | O60609 | GFRA3 | GDNF family receptor alpha-3 (GDNF receptor alpha-3) (GDNFR-alpha-3) (GFR-alpha-3) | 1-31 | 134 | 400 | GFRA3 UNQ339/PRO538/PRO3664 | 342, 550, 758, 966, 1174, 1382, 1590, 1798, 2006, 2214, 2422, 2630, 2838 |
| 218 | P50895 | BCAM | Basal cell adhesion molecule (Auberger B antigen) (B-CAM cell surface glycoprotein) (F8/G253 antigen) (Lutheran antigen) (Lutheran blood group glycoprotein) (CD antigen CD239) | 1-31 | 135 | 628 | BCAM LU MSK19 | 343, 551, 759, 967, 1175, 1383, 1591, 1799, 2007, 2215, 2423, 2631, 2839 |
| 219 | P28906 | CD34 | Hematopoietic progenitor cell antigen CD34 (CD antigen CD34) | 1-31 | 136 | 385 | CD34 | 344, 552, 760, 968, 1176, 1384, 1592, 1800, 2008, 2216, 2424, 2632, 2840 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 220 | P08514 | ITA2B | Integrin alpha-IIb (GPalpha IIb) (GPIIb) (Platelet membrane glycoprotein IIb) (CD antigen CD41) [Cleaved into: Integrin alpha-IIb heavy chain; Integrin alpha-IIb light chain, form 1; Integrin alpha-IIb light chain, form 2] | 1-31 | 137 | 1039 | ITGA2B GP2B ITGAB | 345, 553, 761, 969, 1177, 1385, 1593, 1801, 2009, 2217, 2425, 2633, 2841 |
| 221 | P00742 | FA10 | Coagulation factor X (EC 3.4.21.6) (Stuart factor) (Stuart-Prower factor) [Cleaved into: Factor X light chain; Factor X heavy chain; Activated factor Xa heavy chain] | 1-31 | 138 | 488 | F10 | 346, 554, 762, 970, 1178, 1386, 1594, 1802, 2010, 2218, 2426, 2634, 2842 |
| 222 | P26006 | ITA3 | Integrin alpha-3 (CD49 antigen-like family member C) (FRP-2) (Galactoprotein B3) (GAPB3) (VLA-3 subunit alpha) (CD antigen CD49c) [Cleaved into: Integrin alpha-3 heavy chain; Integrin alpha-3 light chain] | 1-32 | 139 | 1051 | ITGA3 MSK18 | 347, 555, 763, 971, 1179, 1387, 1595, 1803, 2011, 2219, 2427, 2635, 2843 |
| 223 | P13726 | TF | Tissue factor (TF) (Coagulation factor III) (Thromboplastin) (CD antigen CD142) | 1-32 | 140 | 295 | F3 | 348, 556, 764, 972, 1180, 1388, 1596, 1804, 2012, 2220, 2428, 2636, 2844 |
| 224 | P11912 | CD79A | B-cell antigen receptor complex-associated protein alpha chain (Ig-alpha) (MB-1 membrane glycoprotein) (Membrane-bound immunoglobulin-associated protein) (Surface IgM-associated protein) (CD antigen CD79a) | 1-32 | 141 | 226 | CD79A IGA MB1 | 349, 557, 765, 973, 1181, 1389, 1597, 1805, 2013, 2221, 2429, 2637, 2845 |
| 225 | Q9H6X2 | ANTR1 | Anthrax toxin receptor 1 (Tumor endothelial marker 8) | 1-32 | 142 | 564 | ANTXR1 ATR TEM8 | 350, 558, 766, 974, 1182, 1390, 1598, 1806, 2014, 2222, 2430, 2638, 2846 |
| 226 | Q8IWK6 | AGRA3 | Adhesion G protein-coupled receptor A3 (G-protein coupled receptor 125) | 1-33 | 143 | 1321 | ADGRA3 GPR125 UNQ556/PRO1113 | 351, 559, 767, 975, 1183, 1391, 1599, 1807, 2015, 2223, 2431, 2639, 2847 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 227 | P58335 | ANTR2 | Anthrax toxin receptor 2 (Capillary morphogenesis gene 2 protein) (CMG-2) | 1-33 | 144 | 489 | ANTXR2 CMG2 | 352, 560, 768, 976, 1184, 1392, 1600, 1808, 2016, 2224, 2432, 2640, 2848 |
| 228 | P06731 | CEAM5 | Carcinoembryonic antigen-related cell adhesion molecule 5 (Carcinoembryonic antigen) (CEA) (Meconium antigen 100) (CD antigen CD66e) | 1-34 | 145 | 702 | CEACAM5 CEA | 353, 561, 769, 977, 1185, 1393, 1601, 1809, 2017, 2225, 2433, 2641, 2849 |
| 229 | P33681 | CD80 | T-lymphocyte activation antigen CD80 (Activation B7-1 antigen) (BB1) (CTLA-4 counter-receptor B7.1) (B7) (CD antigen CD80) | 1-34 | 146 | 288 | CD80 CD28LG CD28LG1 LAB7 | 354, 562, 770, 978, 1186, 1394, 1602, 1810, 2018, 2226, 2434, 2642, 2850 |
| 230 | P38567 | HYALP | Hyaluronidase PH-20 (Hyal-PH20) (EC 3.2.1.35) (Hyaluronoglucosaminidase PH-20) (Sperm adhesion molecule 1) (Sperm surface protein PH-20) | 1-35 | 147 | 509 | SPAM1 HYAL3 PH20 | 355, 563, 771, 979, 1187, 1395, 1603, 1811, 2019, 2227, 2435, 2643, 2851 |
| 231 | P16410 | CTLA4 | Cytotoxic T-lymphocyte protein 4 (Cytotoxic T-lymphocyte-associated antigen 4) (CTLA-4) (CD antigen CD152) | 1-35 | 148 | 223 | CTLA4 CD152 | 356, 564, 772, 980, 1188, 1396, 1604, 1812, 2020, 2228, 2436, 2644, 2852 |
| 232 | P15814 | IGLL1 | Immunoglobulin lambda-like polypeptide 1 (CD179 antigen-like family member B) (Ig lambda-5) (Immunoglobulin omega polypeptide) (Immunoglobulin-related protein 14.1) (CD antigen CD179b) | 1-37 | 149 | 213 | IGLL1 IGL1 | 357, 565, 773, 981, 1189, 1397, 1605, 1813, 2021, 2229, 2437, 2645, 2853 |
| 233 | Q92956 | TNR14 | Tumor necrosis factor receptor superfamily member 14 (Herpes virus entry mediator A) (Herpesvirus entry mediator A) (HveA) (Tumor necrosis factor receptor-like 2) (1R2) (CD antigen CD270) | 1-38 | 150 | 283 | TNFRSF14 HVEA HVEM UNQ329/PRO509 | 358, 566, 774, 982, 1190, 1398, 1606, 1814, 2022, 2230, 2438, 2646, 2854 |

TABLE 4-continued

Signal peptides

| # | UniProt Identifier | Short Name | Protein names | Amino Acid position | SEQ ID NO (AA) | Full length | Gene names | SEQ ID NO: wt and optimized nucleic acid sequence |
|---|---|---|---|---|---|---|---|---|
| 234 | Q86VB7 | C163A | Scavenger receptor cysteine-rich type 1 protein M130 (Hemoglobin scavenger receptor) (CD antigen CD163) [Cleaved into: Soluble CD163 (sCD163)] | 1-41 | 151 | 1156 | CD163 M130 | 359, 567, 775, 983, 1191, 1399, 1607, 1815, 2023, 2231, 2439, 2647, 2855 |
| 235 | P08648 | ITA5 | Integrin alpha-5 (CD49 antigen-like family member E) (Fibronectin receptor subunit alpha) (Integrin alpha-F) (VLA-5) (CD antigen CD49e) [Cleaved into: Integrin alpha-5 heavy chain; Integrin alpha-5 light chain] | 1-41 | 152 | 1049 | ITGA5 FNRA | 360, 568, 776, 984, 1192, 1400, 1608, 1816, 2024, 2232, 2440, 2648, 2856 |
| 236 | P16109 | LYAM3 | P-selectin (CD62 antigen-like family member P) (Granule membrane protein 140) (GMP-140) (Leukocyte-endothelial cell adhesion molecule 3) (LECAM3) (Platelet activation dependent granule-external membrane protein) (PADGEM) (CD antigen CD62P) | 1-41 | 153 | 830 | SELP GMRP GRMP | 361, 569, 777, 985, 1193, 1401, 1609, 1817, 2025, 2233, 2441, 2649, 2857 |
| 237 | O75326 | SEM7A | Semaphorin-7A (CDw108) (JMH blood group antigen) (John-Milton-Hargen human blood group Ag) (Semaphorin-K1) (Sema K1) (Semaphorin-L) (Sema L) (CD antigen CD108) | 1-44 | 154 | 666 | SEMA7A CD108 SEMAL | 362, 570, 778, 986, 1194, 1402, 1610, 1818, 2026, 2234, 2442, 2650, 2858 |
| 238 | Q8N2Q7 | NLGN1 | Neuroligin-1 | 1-45 | 155 | 840 | NLGN1 KIAA1070 | 363, 571, 779, 987, 1195, 1403, 1611, 1819, 2027, 2235, 2443, 2651, 2859 |
| 239 | Q86UN3 | R4RL2 | Reticulon-4 receptor-like 2 (Nogo receptor-like 3) (Nogo-66 receptor homolog 1) (Nogo-66 receptor-related protein 2) (NgR2) | 1-46 | 156 | 420 | RTN4RL2 NGRH1 NGRL3 | 364, 572, 780, 988, 1196, 1404, 1612, 1820, 2028, 2236, 2444, 2652, 2860 |

Accordingly, in preferred embodiments, the artificial nucleic acid molecule, preferably RNA, of the invention may encode in its at least one coding region an amino acid sequence comprising or consisting of an amino acid sequence as defined by any one of SEQ ID NOs: 1-156, 76948-76951, or a (preferably functional) fragment, variant or derivative of any one of said sequences, preferably comprising or consisting of an amino acid sequence having at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

Accordingly, in preferred embodiments, the artificial nucleic acid molecule, preferably RNA, of the invention may comprise, in its at least one coding region, a nucleic acid sequence comprising or consisting of a nucleic acid sequence as defined by any one of SEQ ID NOs: 209-364, 417-572, 625-780, 833-988, 1041-1196, 1249-1404, 1457-1612, 1665-1820, 1873-2028, 2081-2236, 2289-2444, 2497-2652, 2705-2860, 76952-77003 or a (preferably functional) fragment, variant or derivative of any one of said sequences, preferably comprising or consisting of a nucleic acid sequence having at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any of these sequences.

Linker (L)

According to preferred embodiments, the at least one coding region of the artificial nucleic acid molecule according to the invention further encodes e. at least one linker.

The term "linker" preferably refers to peptide linkers, i.e. typically short (i.e. comprising 1-150 amino acids, preferably 1-50 amino acids, more preferably 1 to 20 amino acids), linear amino acid sequences connecting or linking two polypeptide sequences. Linkers according to the invention may be derived from any protein of human, animal, plant, bacterial or viral origin. Linkers according to the invention may be naturally occurring or artificial (i.e. synthetic or non-naturally occurring) linkers. Preferably, the linker(s) is/are non-immunogenic, i.e. do not trigger an immune response. Linkers may be employed to connect or link at least two components of the antigenic fusion protein encoded by the artificial nucleic acid molecule, preferably RNA, of the invention. The coding region of the artificial nucleic acid molecule according to the invention may encode at least one linker, or a plurality of at least 2, 3, 4, 5, 6, 7, 8, 9 or 10 identical or different linkers, as described herein. In case a plurality of linkers is encoded by the artificial nucleic acid molecule it is particularly preferred that the linkers differ in their amino acid sequence and/or nucleic acid sequence encoding the respective linkers.

Peptide linkers of interest are generally known in the art and may be classified into three types: flexible linkers, rigid linkers, and cleavable linkers. Flexible linkers are usually applied when the joined polypeptide sequences require a certain degree of movement or interaction. They are generally rich in small, non-polar (e.g. Gly) or polar (e.g. Ser or Thr) amino acids to provide good flexibility and solubility, and support the mobility of the connected polypeptide sequences. Exemplary flexible linker arm sequences typically contain about 4 to about 10 glycine residues. The incorporation of Ser or Thr may maintain the stability of the linker in aqueous solutions by forming hydrogen bonds with water molecules, and therefore reduces unfavorable interactions between the linker and the protein moieties.

The most commonly used flexible linkers have sequences consisting primarily of stretches of Gly and Ser residues ("GS" linker). An example of the most widely used flexible linker has the sequence of (Gly-Gly-Gly-Gly-Ser)$_n$. By adjusting the copy number "n", the length of this GS linker can be optimized to achieve appropriate separation of the protein domains, or to maintain necessary inter-domain interactions. Aside from GS linkers, many other flexible linkers are known in the art. These flexible linkers are also rich in small or polar amino acids such as Gly and Ser, but may contain additional amino acids such as Thr and Ala to maintain flexibility, as well as polar amino acids such as Lys and Glu to improve solubility. Rigid linkers may be employed to ensure separation of the joined polypeptide sequences and reduce interference or sterical hindrance. Cleavable linkers, on the other hand, can be introduced to release free functional domains in vivo. For instance, the cleavable linkers may be Arg-Arg or Lys-Lys that is sensitive to cleavage with an enzyme such as cathepsin or trypsin. Chen et al. Adv Drug Deliv Rev. 2013 Oct. 15; 65(10): 1357-1369 reviews the most commonly used peptide linkers and their applications, and is incorporated herein by reference in its entirety. Linkers of interest in the context of the present invention are inter alia disclosed in WO 2002/014478, WO 2001/008636, WO 2013/171505, WO 2008/017517 and WO 1997/047648, which are incorporated by reference in their entirety as well.

According to preferred embodiments, the artificial nucleic acid molecule, preferably RNA, of the invention encodes, in its at least one coding region, at least one linker, which is preferably a non-immunogenic linker, optionally comprising or consisting of an amino acid sequence selected from: SGGSGGSGG, RR, LL, GGGGSGGGGT, GGGGSGGGG, GPSL, GSTVAAPS, TVAAPSGS, GSTVAAPSGS, GGGGS, TVAAPS, GS, PAS, PAVPPP, TVSDVP, TGLDSP, HYGAEALERAG, AAY, AAAA, G, SG, GGS, GSG, SGG, GGG, GGGS, SGGG, GGGGSGS, GGGGSGGS, GGGGSGGGS, GGGGSGGGGSGGGGS, AKTTPKLEEGEFSEAR, AKTTPKLEEGEFSEARV, AKTTPKLGG, SAKTTPKLGG, AKTTPKLEEGEFSEARV, SAKTTP, SAKTTPKLGG, RADAAP, RADAAPTVS, RADAAAAGGPGS, RADAAAAGGGGS, SAKTTP, SAKTTPKLGG, SAKTTPKLEEGEFSEARV, ADAAP, ADAAPTVSIFPP, TVAAP, TVAAPSVFIFPP, QPKAAP, QPKAAPSVTLFPP, AKTTPP, AKTTPPSVTPLAP, AKTTAP, AKTTAPSVYPLAP, ASTKGP, ASTKGPSVFPLAP, GENKVEYAPALMALS, GPAKELTPLKEAKVS and GHEAAAVMQVQYPAS.

According to preferred embodiments, the artificial nucleic acid molecule, preferably RNA, of the invention encodes, in its at least one coding region, at least one linker, which is preferably a non-immunogenic linker, optionally comprising or consisting of an amino acid sequence according to any one of SEQ ID NOs: 2937, 76400-76418, 77018-77058. Accordingly, the artificial nucleic acid molecule, preferably RNA, of the invention preferably comprises, in its at least one coding region, a nucleic acid sequence comprising or consisting of a nucleic acid sequence according to any one of SEQ ID NOs: 2936, 76494, 76569, 76475-76493, 76550-76568, 77059-77061 or a (preferably functional) fragment, variant or derivative thereof, preferably comprising or consisting of a nucleic acid sequence having at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

T Helper Epitopes (TH)

The at least one coding region of the artificial nucleic acid molecule, preferably RNA, of the invention may preferably further encode f. at least one T helper epitope.

According to preferred embodiments, the nucleic acid sequence encoding said at least one T helper epitope may be fused (in frame) to a nucleic acid sequence encoding the at least one $IRST_{epm}$-derived amino acid sequence or the at least one antigenic peptide or protein. Therefore, expression of the artificial nucleic acid molecule, preferably RNA, of the invention may preferably result in a fusion protein comprising the at least one T helper epitope joined to (optionally via appropriate peptide linkers) said $IRST_{epm}$-derived amino acid sequence and/or said antigenic protein or peptide. The expressed antigenic fusion protein is processed and its fragments (including the T helper epitopes) are loaded onto MHC molecules, where they are presented to and recognized by antigen-specific T cells.

The artificial nucleic acid molecule according to the invention may encode in its at least one coding region one or a plurality of two or more T helper epitopes. Generally, the present invention envisages the combination of any of the T helper epitopes described herein with any of the antigenic peptides or proteins, any of the $IRST_{epm}$-derived additional amino acid sequences, any of the linkers, and any of the signal peptides, in any suitable order, in the antigenic fusion proteins encoded by the artificial nucleic acid molecules, preferably RNAs, of the invention.

The term "T helper epitope" refers to an antigenic determinant capable of binding to MHC moelcules, preferably MHC Class II molecules, thereby being recognized by $CD4^+$ T helper (Th) cells. Preferably, such T helper epitopes induce or enhance $CD4^+$ Th cell activation, differentiation, and/or proliferation (commonly referred to as "$CD4^+$ Th cell responses"). Activated $CD4^+$ Th cells are may preferably (1) (directly or indirectly) induce or enhance cytotoxic T lymphocyte (CTL) differentiation, and/or proliferation ("CTL responses"), and/or (2) (directly or indirectly) induce or enhance antibody-producing plasma cell differentiation, and/or proliferation ("B cell responses"). In this respect, "directly or indirectly" means that activated $CD4^+$ Th cells may induce or enhance the respective immune responses either via direct interaction with target cells or precursors thereof (e.g. B cells) or indirectly via interacting with other cells (e.g. dendritic cells) that in turn directly interact with target cells or precursors thereof (e.g. nafve $CD8^+$ T cells).

Thus, T helper epitopes may advantageously be used to induce or enhance $CD4^+$ Th cell responses, CTL responses (preferably including increased cell-mediated immunity and enhanced, e.g., anti-tumor or anti-viral immune responses) and/or to induce or enhance B cell responses (preferably including increased antibody production and enhanced, e.g., anti-bacterial immune responses) to the antigenic peptide or protein encoded by the artificial nucleic acid molecule, preferably RNA, of the invention.

T helper epitopes according to the invention may be derived from any protein of human, animal, plant, bacterial or viral origin. T helper epitopes according to the invention may be naturally occurring or artificial (i.e. synthetic or non-naturally occurring) epitopes. It may be preferred to employ generic T helper cell epitopes, i.e. promiscuous or permissive (generic) T helper epitopes, which are capable of interacting with a majority of MHC class II haplotypes, and thus preferably induce or enhance $T_h$ cell responses, CTL responses or B cell responses in the majority of the human or other mammalian populations.

In the context of the present invention, preferred T helper epitopes include the T helper epitopes disclosed in WO 2001/062284, WO 2010/023247, WO 2004/058297, WO 2004/000873 and WO 2006/113792.

Particularly preferred T helper cell epitopes in the context of the present invention include naturally occurring or artificial T helper epitopes derived from PADRE; Hepatitis C virus (Core); Hepatitis C virus (E1); Hepatitis C virus (E2); Hepatitis C virus (NS2); Hepatitis C virus (NS3); Hepatitis C virus (NS4); Hepatitis C virus (NS4a); Hepatitis C virus (NS4b); Hepatitis C virus (NS5a); Hepatitis C virus (NS5b); Influenza A; Measles virus (F protein); Canine distemper virus (Fusion protein); Mucin-1; foot-and-mouth disease virus (VP3); foot-and-mouth disease virus; *Clostridium tetani*); Human immunodeficiency virus 1 (gp120 protein); Human immunodeficiency virus 1 (gag protein); Human immunodeficiency virus 1 (envelope glycoprotein); Tetanus Toxid; Human papilloma virus 16 (E17); Diphtheria toxoid; *P. falciparum* (CS) or a functional fragment, variant or derivative thereof.

"PADRE" (pan DR epitope peptides") as described in WO 95/07707 and in Alexander J et al., 1994, Immunity 1: 751-761, with or without carrying D-amino acids in the C- and N-termini, are preferred T helper epitopes in the context of the present invention.

According to preferred embodiments, the artificial nucleic acid molecule, preferably RNA, of the invention encodes, in its at least one coding region, at least one T helper epitope comprising or consisting of an amino acid sequence according to any one of SEQ ID NOs: 3083-3294, or a (preferably functional) fragment, variant or derivative of any one of said sequences, preferably comprising or consisting of an amino acid sequence having at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

Accordingly, the artificial nucleic acid molecule, preferably RNA, of the invention preferably comprises, in its at least one coding region, a nucleic acid sequence comprising or consisting of a nucleic acid sequence according to any one of SEQ ID Nos: 3295-3506, 3507-3718, or a (preferably functional) fragment, variant or derivative of any one of said sequences, preferably comprising or consisting of a nucleic acid sequence having at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

Antiqenic Fusion Proteins

As indicated above, the artificial nucleic acid molecules, preferably RNAs, of the invention may encode, in their at least one encoding region, at least one antigenic fusion protein as defined herein. Said antigenic fusion protein may preferably be expressed (in particular translated) in the cytoplasm of recipient host cells, processed into fragments and loaded onto MHC class I and preferably also MHC class II molecules. The different components of the antigenic fusion protein each preferably fulfil a different functional role. Presentation of antigens/epitopes typically requires degradation of the antigenic fusion protein in the endosomal lysosomal compartment. The $IRST_{epm}$-derived additional amino acid sequence (in particular TM and optionally CD domains) preferably direct trafficking of the fused antigenic peptides or proteins to the plasma membrane, and via recycling to desired MHC processing compartments, where they are degraded and loaded onto MHC class I and in particular also MHC class II molecules for presentation to antigen-specific T cells. T helper epitopes preferably enhance the T helper cell response. Without wishing to be bound by specific theory, it is thought that $CD4^+$ T cell help is critical for effective induction of CTL responses and anti-tumor immunity. Preferably, the unique design of the inventive artificial nucleic acid molecules, preferably RNAs, provide for simultaneous MHC I and MHC II presentation, and achieves both $CD4'$ and $CD8^+$ T cell responses, resulting in increased overall immune responses and an enhanced therapeutic/prophylactic effect.

According to preferred embodiments, the artificial nucleic acid molecule, preferably RNA, of the invention comprises at least one coding region of the following Formula (I), preferably in 5'-3' direction:

$$-(SIG)_a-(L)_b-[(AN)_c-(L)_d]_e-[(TH)_m-(L)_n]_o-(TMD/TMCD)_p- \quad (I)$$

wherein

"SIG" encodes a signal peptide, preferably as defined elsewhere herein,

"L" encodes a linker sequence, preferably as defined elsewhere herein,

"AN" encodes each independently an antigenic peptide or protein, preferably as defined elsewhere herein, "TH" encodes a T helper epitope, preferably as defined elsewhere herein, "TMD/TMCD" encodes an amino acid sequence derived from an immune response signal transduction protein located in the external plasma membrane, preferably a transmembrane domain, preferably as defined elsewhere herein, and optionally a cytoplasmic domain, b, d, m, n, o is each independently an integer selected from 0, 1, 2, 3, 4, 5, 6, 7, 8, 9, and 10, a, c, e, p is each independently an integer selected from 1, 2, 3, 4, 5, 6, 7, 8, 9 and 10.

Preferably, a, e, and p may be 1—i.e., the artificial nucleic acid molecule, preferably RNA, of the invention encodes in its at least one coding region a signal peptide, as defined elsewhere herein, connected (optionally via a suitable peptide linker as defined elsewhere) herein to an antigenic peptide or protein as defined elsewhere herein, which is (optionally via a suitable peptide linker as defined elsewhere herein) connected to an $IRST_{epm}$-derived transmembrane domain (optionally connected to cytoplasmic domain) as defined elsewhere herein. More preferably, a b, c, d, e, m, n, o and p may each be 1, i.e. the coding region of the artificial nucleic acid molecule, preferably RNA, of the invention encodes one of each of the components described herein. The individual components of the antigenic fusion protein (SIG, L, AN, TH, TMD/TMCD) may be arranged (and thus encoded) in any suitable order.

RNAs

The inventive artificial nucleic acid molecule may preferably be an RNA. It will be understood that the term "RNA" refers to ribonucleic acid molecules characterized by the specific succession of their nucleotides joined to form said molecules (i.e. their RNA sequence). The term "RNA" may thus be used to refer to RNA molecules or RNA sequences as will be readily understood by the skilled person in the respective context. For instance, the term "RNA" as used in the context of the invention preferably refers to an RNA molecule (said molecule being characterized, inter alia, by its particular RNA sequence). The term "RNA" in the context of sequence modifications will be understood to relate to modified RNA sequences, but typically also includes the resulting RNA molecules (which are modified with regard to their RNA sequence).

In preferred embodiments, the RNA may be an mRNA, a viral RNA or a replicon RNA, preferably an mRNA.

In embodiments, the artificial RNA is a circular RNA. As used herein, "circular RNA" or "circRNA" has to be understood as a circular polynucleotide that can encode at least one antigenic peptide or protein as defined herein. E.g., said circular RNA may comprise at least one coding sequence encoding at least one antigenic peptide or protein derived from LASV or a fragment or variant thereof. Further, said circRNA may comprise at least one 3'-UTR and/or 5'-UTR as defined herein. The production of circRNAs can be performed using various methods provided in the art. E.g., U.S. Pat. No. 6,210,931 teaches a method of synthesizing circRNAs by inserting DNA fragments into a plasmid containing sequences having the capability of spontaneous cleavage and self-circularization. U.S. Pat. No. 5,773,244 teaches producing circRNAs by making a DNA construct encoding an RNA cyclase ribozyme, expressing the DNA construct as RNA, and then allowing the RNA to self-splice, which produces a circRNA free from intron in vitro. WO1992/001813 teaches a process of making single strand circular nucleic acids by synthesizing a linear polynucleotide, combining the linear nucleotide with a complementary linking oligonucleotide under hybridization conditions, and ligating the linear polynucleotide. The person skilled in the art may also use methods provided in WO2015/034925 or WO2016/011222 to produce circular RNA. Accordingly, methods for producing circular RNA as provided in U.S. Pat. Nos. 6,210,931, 5,773,244, WO1992/001813, WO2015/034925 and WO2016/011222 may suitably be used to generate the artificial RNA, i.e. the circRNA of the invention.

In embodiments, the artificial RNA is a replicon RNA. The term "replicon RNA" will be recognized and understood by the person of ordinary skill in the art, and is e.g. intended to be an optimized self-replicating artificial RNA. Such constructs may include replication elements (replicase) derived from e.g. alphaviruses and the substitution of the structural virus proteins with the artificial nucleic acid of interest. Alternatively, the replicase may be provided on an independent nucleic acid construct comprising a replicase sequence derived from e.g. Semliki forest virus (SFV), Sindbis virus (SIN), Venezuelan equine Encephalitis virus (VEE), Ross-River virus (RRV), or other viruses belonging to the alphavirus family. Downstream of the replicase may be a sub-genomic promoter that controls replication of the artificial RNA of the first aspect.

In particularly preferred embodiments the artificial nucleic acid of the present invention is an RNA, more preferably an mRNA.

The term "mRNA" (abbreviation of "messenger RNA") will be recognized and understood by the person of ordinary skill in the art, and is e.g. intended to be a ribonucleic acid molecule, i.e. a polymer consisting of nucleotides. These nucleotides are usually connected to each other along a so-called backbone. The backbone is formed by phosphodiester bonds between the sugar, i.e. ribose, of a first and a phosphate moiety of a second, adjacent monomer.

The specific succession of the monomers is called the RNA-sequence. The mRNA usually provides the coding sequence that is translated into an amino-acid sequence of a particular peptide or protein. Typically, an mRNA comprises a 5' cap structure, UTR elements, and a 3' poly(A)sequence.

The artificial RNA, preferably the mRNA of the invention may be prepared using any method known in the art, including chemical synthesis such as e.g. solid phase RNA synthesis, as well as in vitro methods, such as RNA in vitro transcription reactions.

In a preferred embodiment, the artificial RNA, preferably the mRNA is obtained by RNA in vitro transcription.

Accordingly, the RNA of the invention is an in vitro transcribed RNA, preferably an in vitro-transcribed mRNA.

Mono-, Bi- or Multicistronic RNAs

The artificial nucleic acid molecule, preferably RNA, may be mono-, bi-, or multicistronic, preferably as defined herein. "Bi- or multicistronic" RNAs typically comprise two (bicistronic) or more (multicistronic) open reading frames (ORF). An "open reading frame" is a sequence of codons that is translatable into a peptide or protein.

The ORFs in a bi- or multicistronic artificial nucleic acid molecule, may be identical or different from each other. "Identical" ORFs share a % sequence identity of 100%, and encode identical antigenic fusion proteins, whereas "different" ORFs share a % sequence identity of less than 100%, such as 99% or less, 90% or less, 80% or less, 70% or less, 60% or less, 50% or less, 40% or less, 30% or less, 20% or less, 10% or less, 5% or less, or 2% or less, and encode identical (due to the degeneracy of the genetic code) or different antigenic fusion proteins.

It may be preferred that "bi- or multicistronic" artificial nucleic acid molecules, preferably RNAs, encode different antigenic fusion proteins. For example, bi- or even multicistronic artificial nucleic acid molecules, preferably RNAs, may each encode, for example, at least two, three, four, five, six or more (preferably different) antigenic fusion proteins as defined herein.

The ORFs in a bi- or multicistronic artificial nucleic acid molecule, preferably RNA, encoding two or more (identical or different) antigenic fusion proteins as defined herein, may be separated by at least one IRES (internal ribosomal entry site) sequence. The term "IRES" (internal ribosomal entry site) refers to an RNA sequence that allows for translation initiation. An IRES can function as a sole ribosome binding site, but it can also serve to provide a bi- or even multicistronic artificial nucleic acid molecule, preferably RNA as defined above, which encodes several (identical or different) antigenic fusion proteins, which are to be translated by the ribosomes independently of one another.

Examples of IRES sequences, which can be used according to the invention, are those derived from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

Preferably, the artificial nucleic acid molecule, preferably RNA, comprises a length of about 50 to about 20000, or 100 to about 20000 nucleotides, preferably of about 250 to about 20000 nucleotides, more preferably of about 500 to about 10000, even more preferably of about 500 to about 5000.

The artificial nucleic acid molecule, preferably RNA, of the invention may further be single stranded or double stranded. When provided as a double stranded RNA, the artificial nucleic acid molecule preferably comprises a sense and a corresponding antisense strand.

Nucleic Acid Modifications

Artificial nucleic acid molecules, preferably RNAs, of the invention, may be provided in the form of modified nucleic acids. Suitable nucleic acid modifications envisaged in the context of the present invention are described below.

Preferably, the at least one artificial nucleic acid molecule, preferably RNA (sequence) of the invention, is modified as defined herein. A "modification" as defined herein preferably leads to a stabilization of said artificial nucleic acid molecule, preferably RNA. More preferably, the invention thus provides a "stabilized" artificial nucleic acid molecule, preferably RNA.

Preferably, the artificial nucleic acid molecule, preferably RNA, of the invention may thus be provided as a "stabilized" artificial nucleic acid molecule, preferably RNA, in particular mRNA, i.e. which is essentially resistant to in vivo degradation (e.g. by an exo- or endo-nuclease).

Such stabilization can be achieved, for example, by a modified phosphate backbone of the artificial nucleic acid molecule, preferably RNA. A backbone modification in connection with the present invention is a modification in which phosphates of the backbone of the nucleotides contained in said artificial nucleic acid molecule, preferably RNA, are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized artificial nucleic acid molecule, preferably RNAs, may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-O-(1-thiophosphate)).

In the following, specific modifications are described, which are preferably capable of "stabilizing" the artificial nucleic acid molecule, preferably RNA, of the invention.

Chemical Modifications

The term "modification" as used herein may refer to chemical modifications comprising backbone modifications as well as sugar modifications or base modifications.

In this context, a "modified" artificial nucleic acid molecule, preferably RNA, may contain nucleotide analogues/modifications (modified nucleotides or nucleosides), e.g. backbone modifications, sugar modifications or base modifications.

A backbone modification in connection with the present invention is a modification, in which phosphates of the backbone of the nucleotides contained in said artificial nucleic acid molecule, preferably RNA herein are chemically modified. A sugar modification in connection with the present invention is a chemical modification of the sugar of the nucleotides of the artificial nucleic acid molecule, preferably RNA. Furthermore, a base modification in connection with the present invention is a chemical modification of the base moiety of the nucleotides of the artificial nucleic acid molecule, preferably RNA. In this context, nucleotide analogues or modifications are preferably selected from nucleotide analogues, which are applicable for transcription and/or translation.

Sugar Modifications:

(Chemically) modified nucleic acids, in particular artificial nucleic acid molecules according to the invention, may comprise sugar modifications, i.e., nucleosides/nucleotides that are modified in their sugar moiety.

For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O($CH_2CH_2O$)n$CH_2CH_2OR$; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. $NH_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified artificial nucleic acid molecule, preferably RNA can include nucleotides containing, for instance, arabinose as the sugar.

Backbone Modifications:

(Chemically) modified nucleic acids, in particular artificial nucleic acid molecules according to the invention, may comprise backbone modifications, i.e., nucleosides/nucleotides that are modified in their phosphate backbone.

The phosphate groups of the backbone can be modified by replacing one or more of the oxygen atoms with a different substituent. Further, the modified nucleosides and nucleotides can include the full replacement of an unmodified phosphate moiety with a modified phosphate as described herein.

Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

(Chemically) modified nucleic acids, in particular artificial nucleic acid molecules according to the invention, may comprise (nucleo-)base modifications, i.e., nucleosides/ nucleotides that are modified in their nucleobase moiety.

Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

The artificial nucleic acid molecule, preferably RNA, of the invention may comprise modified nucleosides selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate, or combinations thereof.

The artificial nucleic acid molecule, preferably RNA, of the invention may comprise modified nucleosides selected from pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, or combinations thereof.

The artificial nucleic acid molecule, preferably RNA, of the invention may comprise modified nucleosides selected from 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine, or combinations thereof.

The artificial nucleic acid molecule, preferably RNA, of the invention may comprise modified nucleosides selected from 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, or combinations thereof.

The artificial nucleic acid molecule, preferably RNA, of the invention may comprise modified nucleosides selected from inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, or combinations thereof.

The artificial nucleic acid molecule, preferably RNA, of the invention may comprise nucleotides modified on the major groove face, e.g. by replacing hydrogen on C-5 of uracil with a methyl group or a halo group, optionally selected from 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

The artificial nucleic acid molecule, preferably RNA, of the invention may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Alternatively, a "modified" artificial nucleic acid molecule, preferably RNA, may comprise none of the chemical modifications (or any other of chemical modification) described herein. Such modified artificial nucleic acids, may nevertheless comprise a lipid modification or a sequence modification as described below.

Lipid Modifications

Artificial nucleic acid molecules, preferably RNAs, of the invention may preferably contain at least one lipid modification. Such a lipid-modified artificial nucleic acid molecule, preferably RNA of the invention typically comprises (i) an artificial nucleic acid molecule, preferably RNA as defined herein, (ii) at least one linker covalently linked with said artificial nucleic acid molecule, preferably RNA, and (iii) at least one lipid covalently linked with the respective linker.

Alternatively, the lipid-modified artificial nucleic acid molecule, preferably RNA comprises at least one artificial nucleic acid molecule, preferably RNA and at least one (bifunctional) lipid covalently linked (without a linker) with said artificial nucleic acid molecule, preferably RNA.

Alternatively, the lipid-modified artificial nucleic acid molecule, preferably RNA, comprises (i) an artificial nucleic acid molecule, preferably RNA, (ii) at least one linker covalently linked with said artificial nucleic acid molecule, preferably RNA, and (iii) at least one lipid covalently linked with the respective linker, and also (iv) at least one (bifunctional) lipid covalently linked (without a linker) with said artificial nucleic acid molecule, preferably RNA.

In this context, it is particularly preferred that the lipid modification is present at the terminal ends of a linear artificial nucleic acid molecule, preferably RNA.

Sequence Modifications

According to preferred embodiments, the artificial nucleic acid molecule, preferably RNA, of the invention may be "sequence-modified", i.e. may comprise at least one sequence modification as described below. Without wishing to be bound by specific theory, such sequence modifications may increase stability and/or enhance expression of the inventive artificial nucleic acid molecules, preferably RNAs.

G/C Content Modification

According to preferred embodiments, the artificial nucleic acid molecule, preferably RNA, more preferably mRNA, of the invention, may be modified, and thus stabilized, by modifying its guanosine/cytosine (G/C) content, preferably by modifying the G/C content of the at least one coding sequence. In other words, the artificial nucleic acid molecule, preferably RNA, of the invention and preferably its sequence may be G/C modified.

A "G/C-modified" nucleic acid (preferably RNA) sequence typically refers to a nucleic acid (preferably RNA) comprising a nucleic acid (preferably RNA) sequence that is based on a modified wild-type nucleic acid (preferably RNA) sequence and comprises an altered number of guanosine and/or cytosine nucleotides as compared to said wild-type nucleic acid (preferably RNA) sequence. Such an altered number of G/C nucleotides may be generated by substituting codons containing adenosine or thymidine nucleotides by "synonymous" codons containing guanosine or cytosine nucleotides. Accordingly, the codon substitutions preferably do not alter the encoded amino acid residues, but exclusively alter the G/C content of the nucleic acid (preferably RNA).

In preferred embodiments, the G/C content of the coding sequence of the artificial nucleic acid molecule, preferably RNA, of the invention is modified, particularly increased, compared to the G/C content of the coding sequence of the respective wild-type, i.e. unmodified nucleic acid. The amino acid sequence encoded by the inventive artificial nucleic acid molecule, preferably RNA is preferably not modified as compared to the amino acid sequence encoded by the respective wild-type nucleic acid, preferably RNA.

Such modification of the inventive artificial nucleic acid molecule, preferably RNA is based on the fact that the sequence of any RNA region to be translated is important for efficient translation of said RNA. Thus, the composition of the RNA and the sequence of various nucleotides are important. In particular, sequences having an increased G (guanosine)/C (cytosine) content are more stable than sequences having an increased A (adenosine)/U (uracil) content.

According to the invention, the codons of the inventive artificial nucleic acid molecule, preferably RNA, may therefore preferably be varied compared to the respective wild-type nucleic acid, preferably RNA, while retaining the translated amino acid sequence, such that they include an increased amount of G/C nucleotides.

In respect to the fact that several codons code for one and the same amino acid (so-called degeneration of the genetic code), the most favourable codons for the stability can be determined (so-called alternative codon usage). Depending on the amino acid to be encoded by the inventive artificial nucleic acid molecule, preferably RNA, there are various possibilities for modification its nucleic acid sequence, compared to its wild-type sequence. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons, which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gin can be modified from CAA to CAG; the codons for lie can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in all possible combinations to increase the G/C content of the inventive artificial nucleic acid sequence, preferably RNA sequence (or any other nucleic acid sequence as defined herein) compared to its particular wild-type nucleic acid sequence (i.e. the original sequence). Thus, for example, all codons for Thr occurring in the wild-type sequence can be modified to ACC (or ACG). Preferably, however, for example, combinations of the above substitution possibilities are used:

substitution of all codons coding for Thr in the original sequence (wild-type RNA) to ACC (or ACG) and substitution of all codons originally coding for Ser to UCC (or UCG or AGC); substitution of all codons coding for Ile in the original sequence to AUC and substitution of all codons originally coding for Lys to AAG and substitution of all codons originally coding for Tyr to UAC; substitution of all codons coding for Val in the original sequence to GUC (or GUG) and substitution of all codons originally coding for Glu to GAG and substitution of all codons originally coding for Ala to GCC (or GCG) and substitution of all codons originally coding for Arg to CGC (or CGG); substitution of all codons coding for Val in the original sequence to GUC (or GUG) and substitution of all codons originally coding for Glu to GAG and substitution of all codons originally coding for Ala to GCC (or GCG) and substitution of all codons originally coding for Gly to GGC (or GGG) and substitution of all codons originally coding for Asn to AAC; substitution of all codons coding for Val in the original sequence to GUC (or GUG) and substitution of all codons originally coding for Phe to UUC and substitution of all codons originally coding for Cys to UGC and substitution of all codons originally coding for Leu to CUG (or CUC) and substitution of all codons originally coding for Gin to CAG and substitution of all codons originally coding for Pro to CCC (or CCG); etc.

Preferably, the G/C content of the coding sequence of the artificial nucleic acid molecule, preferably RNA, of the invention is increased by at least 7%, more preferably by at least 15%, particularly preferably by at least 20%, compared to the G/C content of the coding sequence of the respective wild-type nucleic acid, preferably RNA.

According to preferred embodiments, at least 5%, 10%, 20%, 30%, 40%, 50%, 60%, more preferably at least 70%, even more preferably at least 80% and most preferably at least 90%, 95% or even 100% of the substitutable codons in the coding region or the whole sequence of the wild type RNA sequence are substituted, thereby increasing the G/C content of said sequence.

In this context, it is particularly preferable to increase the G/C content of the artificial nucleic acid molecule, preferably RNA, of the invention, preferably of its at least one coding sequence, to the maximum (i.e. 100% of the substitutable codons) as compared to respective the wild-type nucleic acid, preferably RNA, sequence.

According to a preferred embodiment, the present invention provides a nucleic acid sequence, preferably RNA, comprising at least one coding sequence comprising or consisting of any one of the RNA sequences according to SEQ ID NOs: 417-624, 2915, 2916, 2932, 2935, 76671-76693, 76956-76959, 1249-1456, 76763-76785, 76972-76975, 1457-1664, 76786-76808, 76976-76979, 1665-1872, 76809-76831, 76980-76983, 1873-2080, 76832-76854, 76984-76987, 2081-2288, 76855-76877, 76988-76991, 2289-2496, 76878-76900, 76992-76995, 2497-2704, 76901-76923, 76996-76999, 2705-2912, 76924-76946, 77000-77003, 76947, 77004-77017, 77059-77061, 77066 or of a fragment or variant of any one of these sequences.

Substitution of Rare Codons

A further preferred modification of the artificial nucleic acid molecule, preferably RNA, of the invention is based on the finding that the translation efficiency is also determined by a different frequency in the occurrence of tRNAs in cells. Thus, if so-called "rare codons" are present in the artificial nucleic acid molecule, preferably RNA, of the invention to an increased extent, the corresponding modified RNA sequence is translated to a significantly poorer degree than in the case where codons coding for relatively "frequent" tRNAs are present.

In some preferred embodiments, in modified artificial nucleic acid molecule, preferably RNAs defined herein, the region which codes for a protein is modified compared to the corresponding region of the wild-type nucleic acid, preferably RNA, such that at least one codon of the wild-type sequence, which codes for a tRNA which is relatively rare in the cell, is exchanged for a codon, which codes for a tRNA which is relatively frequent in the cell and carries the same amino acid as the relatively rare tRNA.

Thereby, the sequences of the artificial nucleic acid molecule, preferably RNA, of the invention is modified such that codons for which frequently occurring tRNAs are available are inserted. In other words, according to the invention, by this modification all codons of the wild-type sequence, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons, which use for the particular amino acid the tRNA which occurs the most frequently, e.g. the Gly codon, which uses the tRNA, which occurs the most frequently in the (human) cell, are particularly preferred.

According to the invention, it is particularly preferable to link the sequential G/C content which is increased, in particular maximized, in the modified artificial nucleic acid molecule, preferably RNA, of the invention with the "frequent" codons without modifying the encoded amino acid sequence encoded by the coding sequence of said artificial nucleic acid molecule, preferably RNA. Such preferred embodiments allow the provision of a particularly efficiently translated and stabilized (modified) artificial nucleic acid molecule, preferably RNA (or any other nucleic acid as defined herein).

The determination of a modified artificial nucleic acid molecule, preferably RNA as described above (increased G/C content; exchange of tRNAs) can be carried out using the computer program explained in WO 02/098443, the disclosure content of which is included in its full scope in the present invention. Using this computer program, the nucleotide sequence of any desired nucleic acid, in particular RNA, can be modified with the aid of the genetic code or the degenerative nature thereof such that a maximum G/C content results, in combination with the use of codons which code for tRNAs occurring as frequently as possible in the cell, the amino acid sequence coded by the modified nucleic acid, in particular RNA, preferably not being modified compared to the non-modified sequence.

Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443.

A/U Content Modification

Preferably, the A/U content in the environment of the ribosome binding site of the artificial nucleic acid molecule, preferably RNA, of the invention is increased compared to the A/U content in the environment of the ribosome binding site of its respective wild-type nucleic acid, preferably RNA.

This modification (an increased A/U content around the ribosome binding site) increases the efficiency of ribosome binding to said artificial nucleic acid molecule, preferably RNA. An effective binding of the ribosomes to the ribosome binding site (Kozak sequence, SEQ ID NO: 3081) in turn has the effect of an efficient translation of the artificial nucleic acid molecule, preferably RNA.

DSE Modifications

Preferably, the artificial nucleic acid molecule, preferably RNA, of the invention may be modified with respect to potentially destabilizing sequence elements. Particularly, the coding sequence and/or the 5' and/or 3' untranslated region of said artificial nucleic acid molecule, preferably RNA may be modified compared to the respective wild-type nucleic acid, preferably RNA (or said other wild-type nucleic acid) such that it contains no destabilizing sequence elements, the encoded amino acid sequence of the modified artificial nucleic acid molecule, preferably RNA preferably not being modified compared to its respective wild-type nucleic acid, preferably RNA (or said other wild-type nucleic acid).

It is known that, for example in sequences of eukaryotic RNAs, destabilizing sequence elements (DSE) occur, to which signal proteins bind and regulate enzymatic degradation of RNA in vivo. For further stabilization of the modified artificial nucleic acid molecule, preferably RNA, optionally in its at least one coding region, one or more such modifications compared to the corresponding region of the wild-type nucleic acid, preferably RNA, can therefore be carried out, so that no or substantially no destabilizing sequence elements are contained there.

According to the invention, DSE present in the untranslated regions (3'- and/or 5'-UTR) can also be eliminated from the artificial nucleic acid molecule, preferably RNA by such modifications. Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The artificial nucleic acid molecule, preferably RNA, of the invention is therefore preferably modified compared to the respective wild-type nucleic acid, preferably RNA (or said respective other wild-type nucleic acid) such that said artificial nucleic acid molecule, preferably RNA, contains no such destabilizing sequences. This also applies to those sequence motifs, which are recognized by possible endonucleases, e.g. the sequence GAACAAG, which is contained in the 3'-UTR segment of the gene encoding the transferrin receptor (Binder et al., EMBO J. 1994, 13: 1969 to 1980). These sequence motifs are also preferably removed from said artificial nucleic acid molecule, preferably RNA.

Sequences Adapted to Human Codon Usage:

A further preferred modification of the artificial nucleic acid molecule, preferably RNA, of the invention is based on the finding that codons encoding the same amino acid typically occur at different frequencies. According to further preferred embodiments, in the modified artificial nucleic acid molecule, preferably RNA, the coding sequence is modified compared to the corresponding region of the respective wild-type nucleic acid, preferably RNA such that the frequency of the codons encoding the same amino acid corresponds to the naturally occurring frequency of that codon according to the human codon usage as e.g. shown in Table 5.

For example, in the case of the amino acid alanine (Ala) present in an amino acid sequence encoded by the at least one coding sequence of the artificial nucleic acid molecule, preferably RNA, of the invention, the wild type coding sequence is preferably adapted in a way that the codon "GCC" is used with a frequency of 0.40, the codon "GCT" is used with a frequency of 0.28, the codon "GCA" is used with a frequency of 0.22 and the codon "GCG" is used with a frequency of 0.10 etc. (see Table 5).

TABLE 5

Human codon usage table

| Amino acid | codon | fraction | /1000 |
| --- | --- | --- | --- |
| Ala | GCG | 0.10 | 7.4 |
| Ala | GCA | 0.22 | 15.8 |
| Ala | GCT | 0.28 | 18.5 |
| Ala | GCC* | 0.40 | 27.7 |
| Cys | TGT | 0.42 | 10.6 |
| Cys | TGC* | 0.58 | 12.6 |

TABLE 5-continued

Human codon usage table

| Amino acid | codon | fraction | /1000 |
|---|---|---|---|
| Asp | GAT | 0.44 | 21.8 |
| Asp | GAC* | 0.56 | 25.1 |
| Glu | GAG* | 0.59 | 39.6 |
| Glu | GAA | 0.41 | 29.0 |
| Phe | ITT | 0.43 | 17.6 |
| Phe | TTC* | 0.57 | 20.3 |
| Gly | GGG | 0.23 | 16.5 |
| Gly | GGA | 0.26 | 16.5 |
| Gly | GGT | 0.18 | 10.8 |
| Gly | GGC* | 0.33 | 22.2 |
| His | CAT | 0.41 | 10.9 |
| His | CAC* | 0.59 | 15.1 |
| Ile | ATA | 0.14 | 7.5 |
| Ile | ATT | 0.35 | 16.0 |
| Ile | ATC* | 0.52 | 20.8 |
| Lys | AAG* | 0.60 | 31.9 |
| Lys | AAA | 0.40 | 24.4 |
| Leu | TTG | 0.12 | 12.9 |
| Leu | TTA | 0.06 | 7.7 |
| Leu | CTG* | 0.43 | 39.6 |
| Leu | CTA | 0.07 | 7.2 |
| Leu | CTT | 0.12 | 13.2 |
| Leu | CTC | 0.20 | 19.6 |
| Met | ATG* | 1 | 22.0 |
| Asn | AAT | 0.44 | 17.0 |
| Asn | AAC* | 0.56 | 19.1 |
| Pro | CCG | 0.11 | 6.9 |
| Pro | CCA | 0.27 | 16.9 |
| Pro | CCT | 0.29 | 17.5 |
| Pro | CCC* | 0.33 | 19.8 |
| Gln | CAG* | 0.73 | 34.2 |
| Gln | CAA | 0.27 | 12.3 |
| Arg | AGG | 0.22 | 12.0 |
| Arg | AGA* | 0.21 | 12.1 |
| Arg | CGG | 0.19 | 11.4 |
| Arg | CGA | 0.10 | 6.2 |
| Arg | CGT | 0.09 | 4.5 |
| Arg | CGC | 0.19 | 10.4 |
| Ser | AGT | 0.14 | 12.1 |
| Ser | AGC* | 0.25 | 19.5 |
| Ser | TCG | 0.06 | 4.4 |
| Ser | TCA | 0.15 | 12.2 |
| Ser | TCT | 0.18 | 15.2 |
| Ser | TCC | 0.23 | 17.7 |
| Thr | ACG | 0.12 | 6.1 |
| Thr | ACA | 0.27 | 15.1 |
| Thr | ACT | 0.23 | 13.1 |
| Thr | ACC* | 0.38 | 18.9 |
| Val | GTG* | 0.48 | 28.1 |
| Val | GTA | 0.10 | 7.1 |
| Val | GTT | 0.17 | 11.0 |
| Val | GTC | 0.25 | 14.5 |
| Trp | TGG* | 1 | 13.2 |
| Tyr | TAT | 0.42 | 12.2 |
| Tyr | TAC* | 0.58 | 15.3 |
| Stop | TGA* | 0.61 | 1.6 |
| Stop | TAG | 0.17 | 0.8 |
| Stop | TAA | 0.22 | 1.0 |

*most frequent codon

According to a preferred embodiment, the present invention provides a nucleic acid sequence, preferably RNA, most preferably mRNA, comprising at least one coding sequence comprising or consisting of any one of the RNA sequences according to SEQ ID NOs: 833-1040, 76717-76739, 76964-76967, or of a fragment or variant of any one of these sequences.

Codon-Optimized Sequences:

As described above, preferably all codons of the wild-type sequence which code for a tRNA, which is relatively rare in the cell, may be exchanged for a codon which codes for a tRNA, which is relatively frequent in the cell and which, in each case, carries the same amino acid as the relatively rare tRNA.

Therefore, it is particularly preferred that the most frequent codons are used for each encoded amino acid (see Table 5, most frequent codons are marked with asterisks). Such an optimization procedure increases the codon adaptation index (CAI) and ultimately maximises the CAI. In the context of the invention, sequences with increased or maximized CAI are typically referred to as "codon-optimized" sequences and/or "CAI increased" and/or "maximized" sequences.

Preferably, the artificial nucleic acid molecule, preferably RNA, of the invention may comprise at least one coding sequence, wherein the coding sequence is codon-optimized as described herein. More preferably, the codon adaptation index (CAI) of the at least one coding sequence is at least 0.5, at least 0.8, at least 0.9 or at least 0.95. Most preferably, the codon adaptation index (CAI) of the at least one coding sequence may be 1.

For example, in the case of the amino acid alanine (Ala) present in the amino acid sequence encoded by the at least one coding sequence of the artificial nucleic acid molecule, preferably RNA, of the invention, the wild type coding sequence is adapted in a way that the most frequent human codon "GCC" is always used for said amino acid, or for the amino acid Cysteine (Cys), the wild type sequence is adapted in a way that the most frequent human codon "TGC" is always used for said amino acid etc.

According to a preferred embodiment, the present invention provides a nucleic acid sequence, preferably RNA, most preferably mRNA, comprising at least one coding sequence comprising or consisting of any one of the RNA sequences according to SEQ ID NOs: 834-1248, 76740-76762, 76968-76971, or of a fragment or variant of any one of these sequences.

C-Optimized Sequences:

Preferably, the artificial nucleic acid molecule, preferably RNA, of the invention may be modified by modifying, preferably increasing, the cytosine (C) content of said artificial nucleic acid molecule, preferably RNA, in particular in its at least one coding sequence.

Preferably, the C content of the coding sequence of the artificial nucleic acid molecule, preferably RNA, of the invention is modified, preferably increased, compared to the C content of the coding sequence of the respective wild-type (unmodified) nucleic acid. The amino acid sequence encoded by the at least one coding sequence of the artificial nucleic acid molecule, preferably RNA, of the invention is preferably not modified as compared to the amino acid sequence encoded by the respective wild-type nucleic acid, preferably RNA (or the respective other wild type nucleic acid).

Preferably, said modified artificial nucleic acid molecule, preferably RNA is modified such that at least 10%, 20%, 30%, 40%, 50%, 60%, 70% or 80%, or at least 90% of the theoretically possible maximum cytosine-content or even a maximum cytosine-content is achieved.

Preferably, at least 10%, 20%, 30%, 40%, 50%, 60%, 70%, 80%, 90% or even 100% of the codons of the wild-type nucleic acid, preferably RNA, sequence, which are "cytosine content optimizable" are replaced by codons having a higher cytosine-content than the ones present in the wild type sequence.

It may further be preferred that some of the codons of the wild type coding sequence may additionally be modified such that a codon for a relatively rare tRNA in the cell is exchanged by a codon for a relatively frequent tRNA in the cell, provided that the substituted codon for a relatively frequent tRNA carries the same amino acid as the relatively rare tRNA of the original wild type codon. Preferably, all of the codons for a relatively rare tRNA are replaced by a codon for a relatively frequent tRNA in the cell, except codons encoding amino acids, which are exclusively encoded by codons not containing any cytosine, or except for glutamine (Gln), which is encoded by two codons each containing the same number of cytosines.

It may be further preferred that the modified artificial nucleic acid molecule, preferably RNA is modified such that at least 80%, or at least 90% of the theoretically possible maximum cytosine-content or even a maximum cytosine-content is achieved by means of codons, which code for relatively frequent tRNAs in the cell, wherein the amino acid sequence remains unchanged.

Due to the naturally occurring degeneracy of the genetic code, more than one codon may encode a particular amino acid. Accordingly, 18 out of 20 naturally occurring amino acids are encoded by more than one codon (with Tryp and Met being an exception), e.g. by 2 codons (e.g. Cys, Asp, Glu), by three codons (e.g. Ile), by 4 codons (e.g. Al, Gly, Pro) or by 6 codons (e.g. Leu, Arg, Ser). However, not all codons encoding the same amino acid are utilized with the same frequency under in vivo conditions. Depending on each single organism, a typical codon usage profile is established.

The term "cytosine content-optimizable codon" as used within the context of the present invention refers to codons, which exhibit a lower content of cytosines than other codons encoding the same amino acid. Accordingly, any wild type codon, which may be replaced by another codon encoding the same amino acid and exhibiting a higher number of cytosines within that codon, is considered to be cytosine-optimizable (C-optimizable). Any such substitution of a C-optimizable wild type codon by the specific C-optimized codon within a wild type coding sequence increases its overall C-content and reflects a C-enriched modified RNA sequence.

Preferably, the artificial nucleic acid molecule, preferably RNA, of the invention, and in particular its at least one coding sequence, may comprise or consist of a C-maximized sequence containing C-optimized codons for all potentially C-optimizable codons. Accordingly, 100% or all of the theoretically replaceable C-optimizable codons are preferably replaced by C-optimized codons over the entire length of the coding sequence.

In this context, cytosine-content optimizable codons are codons, which contain a lower number of cytosines than other codons coding for the same amino acid.

Any of the codons GCG, GCA, GCU codes for the amino acid Ala, which may be exchanged by the codon GCC encoding the same amino acid, and/or the codon UGU that codes for Cys may be exchanged by the codon UGC encoding the same amino acid, and/or the codon GAU which codes for Asp may be exchanged by the codon GAC encoding the same amino acid, and/or the codon that UUU that codes for Phe may be exchanged for the codon UUC encoding the same amino acid, and/or any of the codons GGG, GGA, GGU that code Gly may be exchanged by the codon GGC encoding the same amino acid, and/or the codon CAU that codes for His may be exchanged by the codon CAC encoding the same amino acid, and/or any of the codons AUA, AUU that code for Iie may be exchanged by the codon AUC, and/or any of the codons UUG, UUA, CUG, CUA, CUU coding for Leu may be exchanged by the codon CUC encoding the same amino acid, and/or the codon AAU that codes for Asn may be exchanged by the codon AAC encoding the same amino acid, and/or any of the codons CCG, CCA, CCU coding for Pro may be exchanged by the codon CCC encoding the same amino acid, and/or any of the codons AGG, AGA, CGG, CGA, CGU coding for Arg may be exchanged by the codon CGC encoding the same amino acid, and/or any of the codons AGU, AGC, UCG, UCA, UCU coding for Ser may be exchanged by the codon UCC encoding the same amino acid, and/or any of the codons ACG, ACA, ACU coding for Thr may be exchanged by the codon ACC encoding the same amino acid, and/or any of the codons GUG, GUA, GUU coding for Val may be exchanged by the codon GUC encoding the same amino acid, and/or the codon UAU coding for Tyr may be exchanged by the codon UAC encoding the same amino acid.

In any of the above instances, the number of cytosines is increased by 1 per exchanged codon. Exchange of all non C-optimized codons (corresponding to C-optimizable codons) of the coding sequence results in a C-maximized coding sequence. In the context of the invention, at least 70%, preferably at least 80%, more preferably at least 90%, of the non C-optimized codons within the at least one coding sequence of the artificial nucleic acid molecule, preferably RNA, of the invention are replaced by C-optimized codons.

It may be preferred that for some amino acids the percentage of C-optimizable codons replaced by C-optimized codons is less than 70%, while for other amino acids the percentage of replaced codons is higher than 70% to meet the overall percentage of C-optimization of at least 70% of all C-optimizable wild type codons of the coding sequence.

Preferably, in a C-optimized artificial nucleic acid molecule, preferably RNA, at least 50% of the C-optimizable wild type codons for any given amino acid are replaced by C-optimized codons, e.g. any modified C-enriched RNA (or other nucleic acid, in particular RNA) preferably contains at least 50% C-optimized codons at C-optimizable wild type codon positions encoding any one of the above mentioned amino acids Ala, Cys, Asp, Phe, Gly, His, Iie, Leu, Asn, Pro, Arg, Ser, Thr, Val and Tyr, preferably at least 60%.

In this context codons encoding amino acids, which are not cytosine content-optimizable and which are, however, encoded by at least two codons, may be used without any further selection process. However, the codon of the wild type sequence that codes for a relatively rare tRNA in the cell, e.g. a human cell, may be exchanged for a codon that codes for a relatively frequent tRNA in the cell, wherein both code for the same amino acid.

Accordingly, the relatively rare codon GAA coding for Glu may be exchanged by the relative frequent codon GAG coding for the same amino acid, and/or the relatively rare codon AAA coding for Lys may be exchanged by the relative frequent codon AAG coding for the same amino acid, and/or the relatively rare codon CAA coding for Gin may be exchanged for the relative frequent codon CAG encoding the same amino acid.

In this context, the amino acids Met (AUG) and Trp (UGG), which are encoded by only one codon each, remain unchanged. Stop codons are not cytosine-content optimized, however, the relatively rare stop codons amber, ochre (UAA, UAG) may be exchanged by the relatively frequent stop codon opal (UGA).

The single substitutions listed above may be used individually as well as in all possible combinations in order to optimize the cytosine-content of the modified artificial nucleic acid molecule, preferably RNA, compared to the wild type sequence.

Accordingly, the at least one coding sequence as defined herein may be changed compared to the coding sequence of the respective wild type nucleic acid, preferably RNA, in such a way that an amino acid encoded by at least two or more codons, of which one comprises one additional cytosine, such a codon may be exchanged by the C-optimized codon comprising one additional cytosine, wherein the amino acid is preferably unaltered compared to the wild type sequence.

According to a preferred embodiment, the present invention provides a nucleic acid sequence, preferably RNA, most preferably mRNA, comprising at least one coding sequence comprising or consisting of any one of the RNA sequences according to SEQ ID NOs: 625-832, 76694-76716, 76960-76963, or of a fragment or variant of any one of these sequences.

Combined Modifications

The sequence modifications described herein are particularly envisaged to be applied to the coding sequences of the artificial nucleic acid molecules, preferably RNAs, as described herein. The modifications (including chemical modifications, lipid modifications and sequence modifications) may, if suitable or necessary, be combined with each other in any combination, provided that the combined modifications do not interfere with each other, and preferably provided that the encoded antigenic fusion proteins preferably retain their desired functionality or property, as described herein above.

Preferably, artificial nucleic acids, preferably RNAs, according to the invention comprise at least one coding sequence as defined herein, wherein said coding sequence has been modified as described above, and encodes an antigenic fusion protein as defined herein.

According to preferred embodiments, the inventive artificial nucleic acid molecule, preferably RNA, comprises at least one coding sequence as defined herein, wherein (a) the G/C content of the at least one coding sequence of said artificial nucleic acid molecule, preferably RNA, is increased compared to the G/C content of the corresponding coding sequence of the corresponding wild-type nucleic acid (preferably RNA), and/or (b) wherein the C content of the at least one coding sequence of said artificial nucleic acid molecule, preferably RNA, is increased compared to the C content of the corresponding coding sequence of the corresponding wild-type nucleic acid (preferably RNA), and/or (c) wherein the codons in the at least one coding sequence of said artificial nucleic acid molecule, preferably RNA, are adapted to human codon usage, wherein the codon adaptation index (CAI) is preferably increased or maximized in the at least one coding sequence of said artificial nucleic acid molecule, preferably RNA, and wherein the amino acid sequence encoded by said artificial nucleic acid molecule, preferably RNA, is preferably not being modified compared to the amino acid sequence encoded by the corresponding wild-type nucleic acid (preferably RNA).

Preferably, the artificial nucleic acid molecule, preferably RNA, of the invention may comprise at least one coding region comprising or consisting of a nucleic acid sequence according to any one of SEQ ID NOs: 625-832, 76694-76716, 76960-76963, 833-1040, 76717-76739, 76964-76967, 417-624, 2915, 2916, 2932, 2935, 76671-76693, 76956-76959, 1249-1456, 76763-76785, 76972-76975, 1457-1664, 76786-76808, 76976-76979, 1665-1872, 76809-76831, 76980-76983, 1873-2080, 76832-76854, 76984-76987, 2081-2288, 76855-76877, 76988-76991, 2289-2496, 76878-76900, 76992-76995, 2497-2704, 76901-76923, 76996-76999, 2705-2912, 76924-76946, 77000-77003, 76947, 834-1248, 76740-76762, 76968-76971, 77004-77017, 77066, 76569, 76550-76568, 2936, 76494, 76475-76493, 77059-77061, 3295-3506, 3507-3718, 27946-52172, 76495-76514, 52173-76399; 76570-76589, or a (preferably functional) fragment, variant or derivative of any one of said sequences, preferably comprising or consisting of a nucleic acid sequence having at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, sequence identity to any one of said sequences.

5' Cap

According to preferred embodiments, artificial nucleic acid molecules, preferably RNAs as defined herein, may be modified by the addition of a so-called "5' cap" structure, which preferably stabilizes said artificial nucleic acid molecule, preferably RNA, as described herein.

Accordingly, in preferred embodiments, the artificial nucleic acid, preferably RNA, of the invention may comprise a 5'-cap structure, preferably m7G (m7G(5')ppp(5')G), cap0, cap1, cap2, a modified cap0 or a modified cap1 structure (generated using a cap analogue as defined below).

A "5'-cap" is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an mRNA. m7GpppN is the 5'-cap structure, which naturally occurs in mRNA transcribed by polymerase II and is therefore preferably not considered as modification comprised in a "modified" mRNA in this context. Accordingly, a "modified" artificial nucleic acid molecule, preferably RNA may comprise a m7GpppN as 5'-cap, but additionally said modified artificial nucleic acid molecule, preferably RNA, typically comprises at least one further modification as defined herein. Preferably, the 5'-cap is added using a 5'-5'-triphosphate linkage (also named m7GpppN). Further examples of 5' cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety. These modified 5'-cap structures are regarded as at least one modification in this context.

Particularly preferred "modified" 5'-cap structures are cap1 (methylation of the ribose of the adjacent nucleotide of m7G), cap2 (additional methylation of the ribose of the 2nd nucleotide downstream of the m7G), cap3 (additional methylation of the ribose of the 3rd nucleotide downstream of the m7G), cap4 (methylation of the ribose of the 4th nucleotide downstream of the m7G), ARCA (anti-reverse cap analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

According to preferred embodiments of the present invention, the artificial nucleic acid molecule, in particular RNA, comprises a 5'-Cap structure selected from m7GpppN or cap1.

A 5'-cap (cap0 or cap1) structure may be formed in chemical RNA synthesis or RNA in vitro transcription (co-transcriptional capping) using cap analogues.

The term "cap analogue" as used herein will be recognized and understood by the person of ordinary skill in the art, and is e.g. intended to refer to a non-polymerizable di-nucleotide that has cap functionality in that it facilitates translation or localization, and/or prevents degradation of a nucleic acid molecule, particularly of an RNA molecule, when incorporated at the 5'-end of the nucleic acid molecule. Non-polymerizable means that the cap analogue will be incorporated only at the 5'-terminus because it does not have a 5' triphosphate and therefore cannot be extended in the 3'-direction by a template-dependent polymerase, particularly, by template-dependent RNA polymerase. Examples of cap analogues include, but are not limited to, a chemical structure selected from the group consisting of m7GpppG, m7GpppA, m7GpppC; unmethylated cap analogues (e.g. GpppG); dimethylated cap analogue (e.g. m2,7GpppG), trimethylated cap analogue (e.g. m2,2,7GpppG), dimethylated symmetrical cap analogues (e.g. m7Gpppm7G), or anti reverse cap analogues (e.g. ARCA; m7,2'OmeGpppG, m7,2'dGpppG, m7,3'OmeGpppG, m7,3'dGpppG and their tetraphosphate derivatives). Further cap analogues have been described previously (WO2008/016473, WO2008/157688, WO2009/149253, WO2011/015347, and WO2013/059475). Further suitable cap analogues in that context are described in WO2017/066793, WO2017/066781, WO2017/066791, WO2017/066789, WO2017/053297, WO2017/066782, WO2018075827 and WO2017/066797 wherein the disclosures referring to cap analogues are incorporated herewith by reference.

In embodiments, a modified cap1 structure is generated using a cap analogue as disclosed in WO2017/053297, WO2017/066793, WO2017/066781, WO2017/066791, WO2017/066789, WO2017/066782, WO2018075827 and WO2017/066797. In particular, any cap structures derivable from the structure disclosed in claim 1-5 of WO2017/053297 may be suitably used to co-transcriptionally generate a modified cap1 structure. Further, any cap structures derivable from the structure defined in claim 1 or claim 21 of WO2018075827 may be suitably used to co-transcriptionally generate a modified cap1 structure.

In preferred embodiments, the 5'-cap structure may suitably be added co-transcriptionally using cap-analogues as defined herein in an RNA in vitro transcription reaction as defined herein. Preferred cap-analogues in the context of the invention are m7G(5')ppp(5')G (m7G) or 3'-O-Me-m7G(5')ppp(5')G. Further preferred cap-analogues in the context of the invention are m7G(5')ppp(5')(2'OMeA)pG or m7G(5')ppp(5')(2'OMeG)pG to co-transcriptionally generate cap1 structures.

In other embodiments, the 5'-cap structure is added via enzymatic capping using capping enzymes (e.g. vaccinia virus capping enzymes and/or cap-dependent 2'-O methyltransferases) to generate cap0 or cap1 or cap2 structures. The 5'-cap structure (cap0 or cap1) may be added using immobilized capping enzymes and/or cap-dependent 2'-O methyltransferases using methods and means disclosed in WO2016/193226.

Accordingly, the RNA of the first aspect may comprise a 5'-cap structure, preferably m7G (m7G(5')), m7G(5')ppp(5')(2'OMeA), or m7G(5')ppp(5')(2'OMeG).

Poly(A)

According to further preferred embodiments, the artificial nucleic acid molecule, preferably RNA, of the invention may contain a poly(A) sequence.

A "poly(A) sequence", also called "poly(A) tail" or "3'-poly(A) tail", is typically understood to be a sequence of adenosine nucleotides, e.g., of up to about 400 adenosine nucleotides, e.g. from about 20 to about 400, preferably from about 50 to about 400, more preferably from about 50 to about 300, even more preferably from about 50 to about 250, most preferably from about 60 to about 250 adenosine nucleotides. As used herein, a poly(A) sequence may also comprise about 10 to 200 adenosine nucleotides, preferably about 10 to 100 adenosine nucleotides, more preferably about 40 to 80 adenosine nucleotides or even more preferably about 50 to 70 adenosine nucleotides. A poly(A) sequence is typically located at the 3'-end of an RNA, in particular a mRNA.

Preferably, the artificial nucleic acid molecule, preferably RNA, of the invention may contain at its 3' terminus a poly(A) tail of typically about 10 to 200 adenosine nucleotides, preferably about 10 to 100 adenosine nucleotides, more preferably about 40 to 80 adenosine nucleotides or even more preferably about 50 to 70 adenosine nucleotides.

Preferably, the poly(A) sequence in the artificial nucleic acid molecule, preferably RNA, of the invention may be derived from a DNA template by RNA in vitro transcription.

Alternatively, the poly(A) sequence may also be obtained in vitro by common methods of chemical-synthesis without being necessarily transcribed from a DNA-progenitor.

Moreover, poly(A) sequences, or poly(A) tails may be generated by enzymatic polyadenylation of the artificial nucleic acid molecule, preferably RNA, of the invention using commercially available polyadenylation kits and corresponding protocols known in the art. "Polyadenylation" is typically understood to be the addition of a poly(A) sequence to a nucleic acid molecule, such as an RNA molecule, e.g. to a premature mRNA. Polyadenylation may be induced by a so-called polyadenylation signal. This signal is preferably located within a stretch of nucleotides at the 3'-end of the mRNA to be polyadenylated.

A polyadenylation signal typically comprises a hexamer consisting of adenine and uracil/thymine nucleotides, preferably the hexamer sequence AAUAAA. Other sequences, preferably hexamer sequences, are also conceivable.

Polyadenylation typically occurs during processing of a pre-mRNA (also called premature-mRNA). Typically, RNA maturation (from pre-mRNA to mature mRNA) comprises a step of polyadenylation.

Accordingly, the artificial nucleic acid molecule, preferably RNA, of the invention may comprise a polyadenylation signal which conveys polyadenylation to a (transcribed) RNA by specific protein factors (e.g. cleavage and polyadenylation specificity factor (CPSF), cleavage stimulation factor (CstF), cleavage factors I and II (CF I and CF II), poly(A) polymerase (PAP)). In this context, a consensus polyadenylation signal is preferred comprising the NN(U/T)ANA consensus sequence. In a particularly preferred aspect, the polyadenylation signal comprises one of the following sequences: AA(U/T)AAA or A(U/T)(U/T)AAA (wherein uridine is usually present in RNA and thymidine is usually present in DNA).

Poly(C)

According to preferred embodiments, the artificial nucleic acid molecule, preferably RNA, of the invention may contain a poly(C) tail on the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

UTRs

According to preferred embodiments, the artificial nucleic acid molecule, preferably RNA, of the invention may comprise at least one 5'- and/or 3'-UTR element. A "UTR element" comprises or consists of a nucleic acid sequence, which is derived from the 5'- or 3'-UTR of any naturally occurring gene or which is derived from a fragment, a homolog or a variant of the 5'- or 3'-UTR of a gene. Preferably, 5'- or 3'-UTR elements may be heterologous to the at least one coding sequence of said artificial nucleic acid molecule, preferably RNA. Even though 5'- or 3'-UTR elements derived from naturally occurring genes may be preferred, synthetically engineered UTR elements may also be used in the context of the present invention.

3' UTR

The term "3'UTR element" typically refers to a nucleic acid sequence, which comprises or consists of a nucleic acid sequence that is derived from a 3'UTR or from a variant of a 3'UTR. Generally, the term "3'-UTR" refers to a part of a nucleic acid molecule, which is located 3' (i.e. "downstream") of an open reading frame and which is not translated into protein. In the context of the present invention, a 3'-UTR corresponds to a sequence which is located between the stop codon of the protein coding sequence, preferably immediately 3' to the stop codon of the protein coding sequence, and optionally the poly(A) sequence of the artificial nucleic acid molecule, preferably RNA, of the invention.

The term "corresponds to" means that the 3'-UTR sequence may be an RNA sequence, such as in the mRNA sequence used for defining the 3'-UTR sequence, or a DNA sequence, which corresponds to such RNA sequence. In the context of the present invention, the term "a 3'-UTR of a gene", such as "a 3'-UTR of a ribosomal protein gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence (both sense and antisense strand and both mature and immature) of the 3'-UTR.

A 3'UTR element in the sense of the present invention may represent the 3'UTR of an RNA, preferably an mRNA. Thus, in the sense of the present invention, preferably, a 3'UTR element may be the 3'UTR of an RNA, preferably of an mRNA, or it may be the transcription template for a 3'UTR of an RNA. Thus, a 3'UTR element preferably is a nucleic acid sequence which corresponds to the 3'UTR of an RNA, preferably to the 3'UTR of an mRNA, such as an mRNA obtained by transcription of a genetically engineered vector construct. Preferably, the 3'UTR element fulfils the function of a 3'UTR or encodes a sequence which fulfils the function of a 3'UTR.

Preferably, the at least one 3'UTR element comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

Preferably, the artificial nucleic acid molecule, preferably RNA, of the invention comprises a 3'UTR element, which may be derivable from a gene that relates to an mRNA with an enhanced half-life (that provides a stable mRNA), for example a 3'UTR element as defined and described below. Preferably, the 3'-UTR element is a nucleic acid sequence derived from a 3'-UTR of a gene, which preferably encodes a stable mRNA, or from a homolog, a fragment or a variant of said gene It may be particularly preferred that the 3'UTR element comprises or consists of a nucleic acid sequence, which is derived from a 3'UTR of a gene selected from the group consisting of an albumin gene, an alpha-globin gene, a beta-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an alpha-globin gene, a beta-globin gene, a tyrosine hydroxylase gene, a lipoxygenase gene, and a collagen alpha gene, such as a collagen alpha 1(I) gene according to SEQ ID NO: 1369-1390 of the patent application WO2013/143700, whose disclosure is incorporated herein by reference, or from a homolog, a fragment or a variant thereof.

The term "a nucleic acid sequence which is derived from the 3'UTR of a [ . . . ] gene" preferably refers to a nucleic acid sequence which is based on the 3'UTR sequence of a [ . . . ] gene or on a part thereof, such as on the 3'UTR of an albumin gene, an alpha-globin gene, a beta-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

Albumin-Derived 3' UTRs

Preferably, the 3'UTR element may comprise or consist of a nucleic acid sequence which is derived from a 3'UTR of an albumin gene, preferably a vertebrate albumin gene, more preferably a mammalian albumin gene, most preferably a human albumin gene according to SEQ ID NO: 3073 or the corresponding RNA sequence (SEQ ID NO: 3074).

Human albumin 3'UTR SEQ ID NO: 3073: CATCACATTT AAAAGCATCT CAGCCTACCA TGAGAATAAG AGAAAGAAAA TGAAGATCAA AAGCTTATTC ATCTGTTTTT CTTTTTCGTT GGTGTAAAGC CAACACCCTG TCTAAAAAAC ATAAATTTCT TTAATCATTT TGCCTCTTTT CTCTGTGCTT CAATTAATAA AAAATGGAAA GAATCT (corresponding to SEQ ID No: 1369 of the patent application PCT/EP2013/000938 published under WO2013/143700).

The artificial nucleic acid molecule, preferably RNA, of the invention may comprise a 3'-UTR element comprising a corresponding RNA sequence derived from the nucleic acids according to SEQ ID NOs: 1369-1390 of the patent application WO2013/143700 or a fragment, homolog or variant thereof.

Preferably, the 3'-UTR element may comprise the nucleic acid sequence derived from a fragment of the human albumin gene according to SEQ ID NO: 3075 or 3077: albumin7 3'UTR CATCACATTTAAAAGCATCTCAGCCTACCAT-GAGAATAAGAGAAAGAAAATGAAGATCAATAGCT-TATTCATCTCT TTTTCTTTTTCGTTGGTGTAAAGC-CAACACCCTGTCTAAAAAACATAAATTTCTTTAAT-CATTTTGCCTCTTTTCTCT GTGCTTCAAT-TAATAAAAAATGGAAAGAACCT (SEQ ID NO: 3075 corresponding to SEQ ID No: 1376 of the patent application WO2013/143700)

The 3'-UTR element of the artificial nucleic acid molecule, preferably RNA, of the invention may preferably comprise or consist of a corresponding RNA sequence of the nucleic acid sequence according to SEQ ID NO: 3076 or 3078.

Globin-Derived 3'UTRs

In another particularly preferred embodiment, the 3'UTR element comprises or consists of a nucleic acid sequence which is derived from a 3'UTR of an alpha-globin gene, preferably a vertebrate alpha- or beta-globin gene, more preferably a mammalian alpha- or beta-globin gene, most preferably a human alpha- or beta-globin gene according to SEQ ID NO: 3065, 3067 or 3069 or the corresponding RNA sequences:

3'-UTR of *Homo sapiens* hemoglobin, alpha 1 (HBA1)
GCTGGAGCCTCGGTGGC-
CATGCTTCTTGCCCCTTGGGCCTCCCCCCAGCCC-
CTCCTCCCCTTCCTGCACCCGT
ACCCCCGTGGTCTTTGAATAAAGTCT-
GAGTGGGCGGC (SEQ ID NO: 3065 corresponding to SEQ ID NO: 1370 of the patent application WO2013/143700)

3'-UTR of *Homo sapiens* hemoglobin, alpha 2 (HBA2)
GCTG-
GAGCCTCGGTAGCCGTTCCTCCTGCCCGCTGG-
GCCTCC-
CAACGGGCCCTCCTCCCCTCCTTGCACCGGC
CCTTCCTGGTCTTTGAATAAAGTCTGAGTGGGCAG (SEQ ID NO: 3067 corresponding to SEQ ID NO: 1371 of the patent application WO2013/143700)

3'-UTR of *Homo sapiens* hemoglobin, beta (HBB)
GCTCGCTTTCTTGCTGTCCAATTTCTAT-
TAAAGGTTCCTTTGTTCCCTAAGTCCAAC-
TACTAAACTGGGGGATATT ATGAAGGGCCTTGAG-
CATCTGGATTCTGCCTAATAAAAAACATTTATTTT-
CATTGC (SEQ ID NO: 3069 corresponding to SEQ ID NO: 1372 of the patent application WO2013/143700)

For example, the 3'UTR element may comprise or consist of the center, alpha-complex-binding portion of the 3'UTR of an alpha-globin gene, such as of a human alpha-globin gene, or a homolog, a fragment, or a variant of an alpha-globin gene, preferably according to SEQ ID NO: 3071:

Center, alpha-complex-binding portion of the 3'UTR of an alpha-globin gene ("muag"):
GCCCGATGGGCCTCC-
CAACGGGCCCTCCTCCCCTCCTTGCACCG (SEQ ID NO: 3071 corresponding to SEQ ID NO: 1393 of the patent application WO2013/143700).

5' UTR

A "5'-UTR" is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites. The 5'-UTR may be post-transcriptionally modified, for example by addition of a 5'-Cap. In the context of the present invention, a 5'-UTR corresponds to the sequence of a mature mRNA, which is located between the 5'-Cap and the start codon. Preferably, the 5'-UTR corresponds to the sequence, which extends from a nucleotide located 3' to the 5'-Cap, preferably from the nucleotide located immediately 3' to the 5'-Cap, to a nucleotide located 5' to the start codon of the protein coding sequence, preferably to the nucleotide located immediately 5' to the start codon of the protein coding sequence. The nucleotide located immediately 3' to the 5'-Cap of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence, which corresponds to such RNA sequence. In the context of the present invention, the term "a 5'-UTR of a gene" is the sequence, which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR. By the inventive embodiments such a 5'-UTR may be provided 5'-terminal to the coding sequence. Its length is typically less than 500, 400, 300, 250 or less than 200 nucleotides. In other embodiments its length may be in the range of at least 10, 20, 30 or 40, preferably up to 100 or 150, nucleotides.

In the context of the present invention, 5' UTRs comprising or consisting of a nucleic acid sequence, which is derived from the 5'UTR of a TOP gene or which is derived from a fragment, homolog or variant of the 5'UTR of a TOP gene, may be particularly preferred.

The 5' terminal oligopyrimidine tract (TOP) is typically a stretch of pyrimidine nucleotides located in the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. An mRNA that contains a 5' terminal oligopyrimidine tract is often referred to as "TOP mRNA". Accordingly, genes that provide such messenger RNAs are referred to as "TOP genes".

TOP sequences have, for example, been found in genes and mRNAs encoding peptide elongation factors and ribosomal proteins.

TOP genes are typically characterized by the presence of a 5' terminal oligopyrimidine tract (TOP). Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID NOs: 1-1363 of the patent application WO2013/143700, whose disclosure is incorporated herewith by reference. In this context, a particularly preferred fragment of a 5'UTR of a TOP gene is a 5'UTR of a TOP gene lacking the 5'TOP motif. The terms "5'UTR of a TOP gene" or "5'-TOP UTR" preferably refer to the 5'UTR of a naturally occurring TOP gene.

In the context of the present invention, a "TOP motif" is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5' end with a cytosine nucleotide. In TOP genes and TOP mRNAs, the TOP-motif preferably starts at its 5' end with the transcriptional start site and ends one nucleotide 5' to the first purin residue in said gene or mRNA. A TOP motif in the sense of the present invention is preferably located at the 5' end of a sequence, which represents a 5'UTR, or at the 5' end of a sequence, which codes for a 5'UTR. Thus, preferably, a stretch of 3 or more pyrimidine nucleotides is called "TOP motif" in the sense of the present invention if this stretch is located at the 5' end of a respective sequence, such as the artificial nucleic acid molecule, the 5'UTR element of the artificial nucleic acid molecule, or the nucleic acid sequence which is derived from the 5'UTR of a TOP gene as described herein. In other words, a stretch of 3 or more pyrimidine nucleotides, which is not located at the 5'-end of a 5'UTR or a 5'UTR element but anywhere within a 5'UTR or a 5'UTR element, is preferably not referred to as "TOP motif".

Preferably, the 5'UTR element of the artificial nucleic acid molecule, preferably RNA, of the invention may not comprise a TOP-motif or a 5'TOP, as defined above.

The nucleic acid sequence of the 5'UTR element, which is derived from a 5'UTR of a TOP gene, may preferably terminate at its 3'-end with a nucleotide located at position 1, 2, 3, 4, 5, 6, 7, 8, 9 or 10 upstream of the start codon (e.g. A(U/T)G) of the gene or mRNA it is derived from. Accordingly, the 5'UTR element may preferably not comprise any part of the protein coding sequence.

Therefore, preferably, the only amino acid coding part of the at least one artificial nucleic acid molecule, preferably RNA, of the invention may be provided by its coding region.

The nucleic acid sequence derived from the 5'UTR of a TOP gene may preferably be derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element may preferably be selected from 5'-UTR elements comprising or consisting of a nucleic acid sequence, which is derived from a nucleic acid sequence selected from the group consisting of SEQ ID Nos: 1-1363, SEQ ID NO: 1395, SEQ ID NO: 1421 and SEQ ID NO: 1422 of the patent application WO2013/143700, whose disclosure is incorporated herein by reference, from the homologs of SEQ ID NOs: 1-1363, SEQ ID NO: 1395, SEQ ID NO: 1421 and SEQ ID NO: 1422 of the patent application WO2013/143700, from a variant thereof, or preferably from a corresponding RNA sequence. The term "homologs of SEQ ID NOs: 1-1363, SEQ ID NO: 1395, SEQ ID NO: 1421 and SEQ ID NO: 1422 of the patent application WO2013/143700" refers to sequences of other species than *Homo sapiens*, which are homologous to the sequences according to SEQ ID NOs: 1-1363, SEQ ID NO: 1395, SEQ ID NO: 1421 and SEQ ID NO: 1422 of the patent application WO2013/143700.

Preferably, the 5'UTR element of the artificial nucleic acid molecule, preferably RNA, of the invention may comprise or consist of a nucleic acid sequence, which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs: 1-1363, SEQ ID NO: 1395, SEQ ID NO: 1421 and SEQ ID NO: 1422 of the patent application WO2013/143700, from the homologs of SEQ ID NOs: 1-1363, SEQ ID NO: 1395, SEQ ID NO: 1421 and SEQ ID NO: 1422 of the patent application WO2013/143700 from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs: 1-1363, SEQ ID NO: 1395, SEQ ID NO: 1421 and SEQ ID NO: 1422 of the patent application WO2013/143700, from the homologs of SEQ ID NOs: 1-1363, SEQ ID Nos: 1395, SEQ ID No: 1421 and SEQ ID NO: 1422 of the patent application WO2013/143700, from a variant thereof, or a corresponding RNA sequence.

It may be particularly preferred that the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element may preferably comprise or consist of a nucleic acid sequence, which is derived from a 5'UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3' end of the sequences) corresponds to the 5'UTR of said sequences.

The artificial nucleic acid molecule, preferably RNA, of the invention may thus comprise a 5'UTR element, which comprises or consists of a nucleic acid sequence, which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5' terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

Preferably, the 5'UTR element may comprise or consist of a nucleic acid sequence, which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH 1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine amidohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

ATP5A1 Derived 5' UTR

Preferably, the artificial nucleic acid molecule, preferably RNA, of the invention may comprise a 5'UTR element which comprises or consists of a nucleic acid sequence, which is derived from a 5'UTR of a TOP gene encoding a mitochondrial ATP synthase subunit alpha or from a homolog or variant of a 5'UTR of a TOP gene encoding a mitochondrial ATP synthase subunit alpha, preferably lacking the 5'TOP motif.

In this context, the 5'UTR element preferably comprises or consists of a nucleic acid sequence which is derived from the 5'UTR of a mitochondrial ATP synthase subunit alpha gene, preferably from a vertebrate mitochondrial ATP synthase subunit alpha (ATP5A1) gene, more preferably from a mammalian mitochondrial ATP synthase subunit alpha (ATP5A1) gene, most preferably from a human mitochondrial ATP synthase subunit alpha (ATP5A1) gene, or from a variant of the 5'UTR of a mitochondrial ATP synthase subunit alpha gene, preferably from a vertebrate mitochondrial ATP synthase subunit alpha (ATP5A1) gene, more preferably from a mammalian mitochondrial ATP synthase subunit alpha (ATP5A1) gene, most preferably from a human mitochondrial ATP synthase subunit alpha (ATP5A1) gene, wherein preferably the 5'UTR element does not comprise the 5'TOP of said gene.

Accordingly, in a particularly preferred embodiment, the 5'UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 3063 (5'-UTR of ATP5A1 lacking the 5' terminal oligopyrimidine tract: GCGGCTCGGCCAT-TTTGTCCCAGTCAGTCCG-GAGGCTGCGGCTGCAGAAGTACCGCCTGCG-GAGTAACTGCAA AG; corresponding to SEQ ID NO: 1414 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 3063 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

L32 Derived 5' UTR

Preferably, the artificial nucleic acid molecule, preferably RNA, of the invention may comprise a 5'UTR element which comprises or consists of a nucleic acid sequence, which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence, which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In this context, the 5'UTR element may preferably comprise or consist of a nucleic acid sequence which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, the 5'UTR element may preferably comprise or consist of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 3061 (5'-UTR of human ribosomal protein Large 32 lacking the 5' terminal oligopyrimidine tract: GGCGCTGCCTACG-GAGGTGGCAGCCATCTCCTTCTCGGCATC; corresponding to SEQ ID NO: 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 3061 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Histone Stem-Loop

According to preferred embodiments, the artificial nucleic acid molecule, preferably RNA, of the invention comprises a histone stem-loop sequence/structure.

Such histone stem-loop sequences are preferably selected from histone stem-loop sequences as disclosed in WO 2012/019780, the disclosure of which is incorporated herewith by reference.

A histone stem-loop sequence, suitable to be used within the present invention, is preferably selected from at least one of the following formulae (II) or (III):

Formula (II) (Stem-Loop Sequence without Stem Bordering Elements):

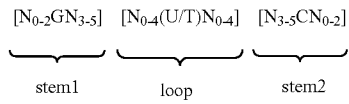

Formula (III) (Stem-Loop Sequence with Stem Bordering Elements):
wherein:

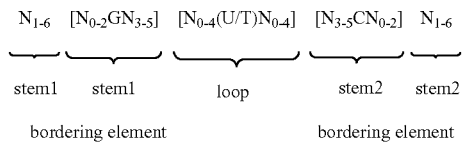

| | |
|---|---|
| stem1 or stem2 bordering elements $N_{1-6}$ | is a consecutive sequence of 1 to 6, preferably of 2 to 6, more preferably of 2 to 5, even more preferably of 3 to 5, most preferably of 4 to 5 or 5N, wherein each N is independently from another selected from a nucleotide selected from A, U, T, G and C, or a nucleotide analogue thereof; |
| stem1 $[N_{0-2}GN_{3-5}]$ | is reverse complementary or partially reverse complementary with element stem2, and is a consecutive sequence between of 5 to 7 nucleotides; wherein $N_{0-2}$ is a consecutive sequence of 0 to 2, preferably of 0 to 1, more preferably of 1N, wherein each N is independently from another selected from a nucleotide selected from A, U, T, G and C or a nucleotide analogue thereof; wherein $N_{3-5}$ is a consecutive sequence of 3 to 5, preferably of 4 to 5, more preferably of 4N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine; |
| loop sequence $[N_{0-4}(U/T)N_{0-4}]$ | is located between elements stem1 and stem2, and is a consecutive sequence of 3 to 5 nucleotides, more preferably of 4 nucleotides; wherein each $N_{0-4}$ is independent from another a consecutive sequence of 0 to 4, preferably of 1 to 3, more preferably of 1 to 2N, wherein each N is independently from another selected from a nucleotide selected from A, U, T, G and C or a nucleotide analogue thereof; and wherein U/T represents uridine, or optionally thymidine; |
| stem2 $[N_{3-5}CN_{0-2}]$ | is reverse complementary or partially reverse complementary with element stem1, and is a consecutive sequence between of 5 to 7 nucleotides; wherein $N_{3-5}$ is a consecutive sequence of 3 to 5, preferably of 4 to 5, more preferably of 4N, wherein each N is independently from another selected from a nucleotide selected from A, U, T, G and C or a nucleotide analogue thereof; wherein $N_{0-2}$ is a consecutive sequence of 0 to 2, preferably of 0 to 1, more preferably of 1N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine; | wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment, the artificial nucleic acid molecule, preferably RNA, of the invention may comprise at least one histone stem-loop sequence according to at least one of the following specific formulae (IIa) or (IIIa):

Formula (IIa) (Stem-Loop Sequence without Stem Bordering Elements):

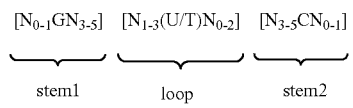

Formula (IIIa) (Stem-Loop Sequence with Stem Bordering Elements):

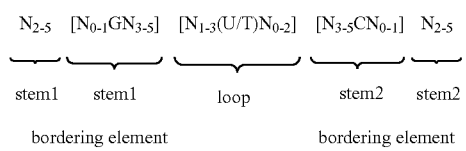

wherein:
N, C, G, T and U are as defined above.

According to a further more particularly preferred embodiment, the artificial nucleic acid molecule, preferably RNA, of the invention may comprise at least one histone stem-loop sequence according to at least one of the following specific formulae (IIb) or (IIIb):

Formula (IIb) (Stem-Loop Sequence without Stem Bordering Elements):

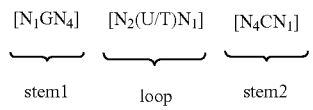

Formula (IIIb) (Stem-Loop Sequence with Stem Bordering Elements):

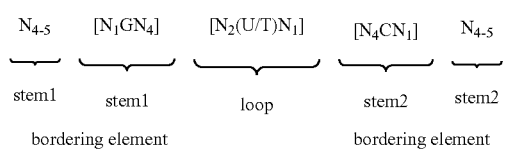

wherein:
N, C, G, T and U are as defined above.

A particularly preferred histone stem-loop sequence is the sequence CAAAGGCTCTTTTCAGAGCCACCA (SEQ ID NO: 3079) or more preferably the corresponding RNA sequence CAAAGGCUCUUUUCAGAGCCACCA (SEQ ID NO: 3080).

Constructs

The artificial nucleic acid molecule, preferably RNA, of the invention, which comprises at least one coding sequence as defined herein preferably comprises at least one 5' UTR and/or at least one 3' UTR as described herein, and optionally at least one histone stem-loop.

The 3' UTR of the artificial nucleic acid molecule, preferably RNA, of the invention (or any other nucleic acid, in particular RNA, as defined herein) may further comprise a poly(A) and/or a poly(C) sequence as defined herein. The single elements of the 3' UTR may occur therein in any order from 5' to 3' along the sequence of the artificial nucleic acid molecule, preferably RNA, of the invention.

In addition, further elements as described herein, may also be contained, such as a stabilizing sequence as defined herein (e.g. derived from the UTR of a globin gene), IRES sequences, etc. Each of the elements may also be repeated in the artificial nucleic acid molecule, preferably RNA, of the invention at least once (particularly in di- or multicistronic constructs), e.g. twice or more. As an example, the single elements may be present in the artificial nucleic acid molecule, preferably RNA, of the invention in the following order:

5'-coding sequence-histone stem-loop-poly(A)/(C) sequence-3'; or

5'-coding sequence-poly(A)/(C) sequence-histone stem-loop-3'; or

5'-coding sequence-histone stem-loop-polyadenylation signal-3'; or

5'-coding sequence-polyadenylation signal-histone stem-loop-3'; or

5'-coding sequence-histone stem-loop-histone stem-loop-poly(A)/(C) sequence-3'; or 5'-coding sequence-histone stem-loop-histone stem-loop-polyadenylation signal-3'; or 5'-coding sequence-stabilizing sequence-poly(A)/(C) sequence-histone stem-loop-3'; or 5'-coding sequence-stabilizing sequence-poly(A)/(C) sequence-poly(A)/(C) sequence-histone stem-loop-3'; etc.

According to further embodiments, the artificial nucleic acid molecule, preferably RNA, preferably further comprises at least one of the following structural elements: a histone-stem-loop structure, preferably a histone-stem-loop in its 3' untranslated region; a 5'-cap structure; a poly-A tail; or a poly(C) sequence.

According to some embodiments, in addition to the (poly-)peptides or proteins described herein, a further peptide or protein is encoded by the at least one coding sequence as defined herein, wherein the further peptide or protein is preferably no histone protein, no reporter protein (e.g. Luciferase, GFP and its variants (such as eGFP, RFP or BFP), and/or no marker or selection protein, including alpha-globin, galactokinase and Xanthine:Guanine phosphoribosyl transferase (GPT), hypoxanthine-guanine phosphoribosyltransferase (HGPRT), beta-galactosidase, galactokinase, alkaline phosphatase, secreted embryonic alkaline phosphatase (SEAP) or a resistance gene (such as a resistance gene against neomycin, puromycin, hygromycin and zeocin). In preferred embodiments, the artificial nucleic acid molecule, preferably RNA, does not encode a reporter gene or a marker gene. In preferred embodiments, the artificial nucleic acid molecule, preferably RNA, does not encode luciferase. In other embodiments, the artificial nucleic acid molecule, preferably RNA, does not encode GFP or a variant thereof.

Specifically, artificial nucleic acid molecules, in particular RNAs, according to the invention may comprise preferably in 5' to 3' direction, the following elements:
a) a 5'-CAP structure, preferably m7GpppN or Cap1
b) a 5'-UTR element, which comprises or consists of a nucleic acid sequence, which is derived from a 5'-UTR as defined herein, preferably comprising a nucleic acid sequence corresponding to the nucleic acid sequence according to SEQ ID NO: 3061, 3063, or a homolog, fragment or variant thereof;
c) at least one coding sequence as defined herein;
d) a 3'-UTR element, which comprises or consists of a nucleic acid sequence, which is derived from a 3'-UTR as defined herein, preferably comprising a nucleic acid sequence corresponding to the nucleic acid sequence according to SEQ ID NO: 3065, 3067, 3069, 3071, 3073, 3075, 3077, or a homolog, a fragment or a variant thereof,
e) optionally a poly(A) tail, preferably consisting of 10 to 1000, 10 to 500, 10 to 300 10 to 200, 10 to 100, 40 to 80 or 50 to 70 adenosine nucleotides,
f) optionally a poly(C) tail, preferably consisting of 10 to 200, 10 to 100, 20 to 70, 20 to 60 or 10 to 40 cytosine nucleotides, and
g) optionally a histone stem-loop.

Complexation

According to some embodiments of the present invention, the artificial nucleic acid molecule, preferably RNA, of the invention, and/or any other nucleic acid disclosed herein (e.g. immunostimulatory nucleic acids) may be provided in a "naked" form, i.e. without being associated with any further vehicle, transfection or complexation agent for increasing the transfection efficiency and/or the immunostimulatory properties of said artificial nucleic acid molecule, preferably RNA, or of any other nucleic acid.

According to other preferred embodiments, the artificial nucleic acid molecule, preferably RNA, of the invention, and/or any other nucleic acid disclosed herein (e.g. immunostimulatory nucleic acids) is/are provided in a complexed form. Therein, the at least artificial nucleic acid molecule, preferably RNA, or any other nucleic acid disclosed herein may be associated with a suitable vehicle, transfection or complexation agent for increasing the transfection efficiency and/or the immunostimulatory properties of said artificial nucleic acid molecule, preferably RNA, or said other nucleic acid.

According to preferred embodiments, said artificial nucleic acid molecule, preferably RNA, and/or said other nucleic acid(s)) is/are complexed or associated with one or more (poly-)cationic compounds, preferably with (poly-)cationic polymers, (poly-)cationic peptides or proteins, e.g. protamine, (poly-)cationic polysaccharides and/or [(poly-)cationic]lipids. In this context, the terms "complexed" or "associated" refer to the essentially stable combination of said artificial nucleic acid molecule, preferably RNA, or said other nucleic acid, with one or more of the aforementioned compounds into larger complexes or assemblies without covalent binding.

Lipids

According to preferred embodiments, the artificial nucleic acid molecule, preferably RNA, or any other nucleic acid disclosed herein, is complexed with one or more lipids, thereby forming lipid nanoparticles, lipoplexes and/or preferably liposomes.

Therefore, the artificial nucleic acid molecule, preferably RNA, of the invention and/or any other nucleic acid disclosed herein may be provided in the form of a lipid-based formulation, in particular in the form of liposomes, lipoplexes, and/or lipid nanoparticles comprising said artificial nucleic acid molecule, preferably RNA, and/or said other nucleic acid disclosed herein.

The term "lipid nanoparticle", also referred to as "LNP", is not restricted to any particular morphology, and include any morphology generated when a cationic lipid and optionally one or more further lipids are combined, e.g. in an aqueous environment and/or in the presence of RNA. For example, a liposome, a lipid complex, a lipoplex and the like are within the scope of a lipid nanoparticle (LNP).

Lipid Nanoparticles

The artificial nucleic acid molecule, preferably RNA, of the invention, or any other nucleic acid disclosed herein, may be complexed or associated with lipids (in particular cationic and/or neutral lipids) to form one or more lipid nanoparticles.

Preferably, lipid nanoparticles (LNPs) comprise: (a) at least one artificial nucleic acid molecule, preferably RNA, of the invention or any other nucleic acid disclosed herein, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol. In particular, LNPs may comprise, in addition to the at least one artificial nucleic acid molecule, preferably RNA, of the invention, and/or any other nucleic acid disclosed herein (i) at least one cationic lipid; (ii) a neutral lipid; (iii) a sterol, e.g., cholesterol; and (iv) a PEG-lipid, in a molar ratio of about 20-60% cationic lipid: 5-25% neutral lipid:25-55% sterol; 0.5-15% PEG-lipid.

The artificial nucleic acid molecule, preferably RNA, of the invention and/or any other nucleic acid disclosed herein, may be formulated in an aminoalcohol lipidoid. Aminoalcohol lipidoids which may be used in the present invention may be prepared by the methods described in U.S. Pat. No. 8,450,298, herein incorporated by reference in its entirety.

LNPs typically comprise a cationic lipid and one or more excipient selected from neutral lipids, charged lipids, steroids and polymer conjugated lipids (e.g. PEGylated lipid). The RNA may be encapsulated in the lipid portion of the LNP or an aqueous space enveloped by some or the entire lipid portion of the LNP. The RNA or a portion thereof may also be associated and complexed with the LNP. An LNP may comprise any lipid capable of forming a particle to which the nucleic acids are attached, or in which the one or more nucleic acids are encapsulated. Preferably, the LNP comprising nucleic acids comprises one or more cationic lipids, and one or more stabilizing lipids. Stabilizing lipids include neutral lipids and PEGylated lipids.

The cationic lipid of an LNP may be cationisable, i.e. it becomes protonated as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

(i) Cationic Lipids

LNPs may include any cationic lipid suitable for forming a lipid nanoparticle. Preferably, the cationic lipid carries a net positive charge at about physiological pH.

The cationic lipid may be an amino lipid. As used herein, the term "amino lipid" is meant to include those lipids having one or two fatty acid or fatty alkyl chains and an amino head group (including an alkylamino or dialkylamino group) that may be protonated to form a cationic lipid at physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethyl ammonium propane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-ylinolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta-[d][1,3]dioxol-5-amine, (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)-didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28,31-tetraen-19-yl 4-(di-methylamino)butanoate (DLin-M-C3-DMA), 3-((6Z,9Z,28Z,31 Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethyl-butan-1-amine (MC4 Ether), or any combination of any of the foregoing.

Other cationic lipids include, but are not limited to, N,N-distearyl-N,N-dimethylammonium bromide (DDAB), 3P—(N—(N',N'-dimethylaminoethane)-carbamoyl)cholesterol (DC-Chol), N-(1-(2,3-dioleyloxy)propyl)-N-2-(spermine-carboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al, PNAS, 107(5), 1864-69, 2010.

In some embodiments, the lipid is selected from the group consisting of 98N12-5, C12-200, and ckk-E12.

In another embodiment, ionizable lipids can also be the compounds as disclosed in WO2015/074085A1 (i.e. ATX-001 to ATX-032 or the compounds as specified in claims 1-26), U.S. Appl. Nos. 61/905,724 and 15/614,499 or U.S. Pat. Nos. 9,593,077 and 9,567,296 hereby incorporated by reference in their entirety.

In that context, any lipid derived from generic Formula (LNP-I)

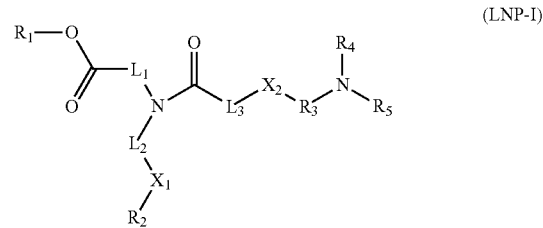

(LNP-I)

wherein, $R_1$ and $R_2$ are the same or different, each a linear or branched alkyl consisting of 1 to 9 carbons, an alkenyl or alkynyl consisting of 2 to 11 carbons, $L_1$ and $L_2$ are the same or different, each a linear alkylene or alkenylene consisting of 5 to 18 carbons, or forming a heterocycle with N, $X_1$ is a bond, or is —CO—O— whereby -$L_2$-CO—O—$R_2$ is formed, $X_2$ is S or O, $L_3$ is a bond or a linear or branched alkylene consisting of 1 to 6 carbons, or forming a heterocycle with N, $R_3$ is a linear or branched alkylene consisting of 1 to 6 carbons, and $R_4$ and $R_5$ are the same or different, each hydrogen or a linear or branched alkyl consisting of 1 to 6 carbons; or a pharmaceutically acceptable salt thereof may be suitably used.

In other embodiments, suitable cationic lipids can also be the compounds as disclosed in WO2017/117530A1 (i.e. lipids 13, 14, 15, 16, 17, 18, 19, 20, or the compounds as specified in the claims), hereby incorporated by reference in its entirety.

In that context, any lipid derived from generic Formula (LNP-II)

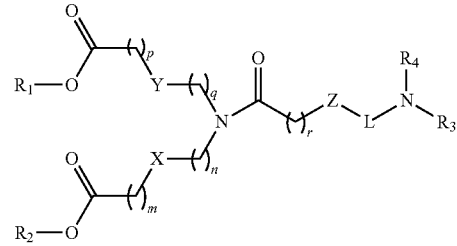

wherein
X is a linear or branched alkylene or alkenylene, monocyclic, bicyclic, or tricyclic arene or heteroarene;
Y is a bond, an ethene, or an unsubstituted or substituted aromatic or heteroaromatic ring; Z is S or O;
L is a linear or branched alkylene of 1 to 6 carbons;
$R_3$ and $R_4$ are independently a linear or branched alkyl of 1 to 6 carbons;
$R_1$ and $R_2$ are independently a linear or branched alkyl or alkenyl of 1 to 20 carbons; r is 0 to 6; and
m, n, p, and q are independently 1 to 18;

wherein when n=q, m=p, and R$_1$=R$_2$, then X and Y differ;
wherein when X=Y, n=q, m=p, then R$_1$ and R$_2$ differ;
wherein when X=Y, n=q, and R$_1$=R$_2$, then m and p differ; and
wherein when X=Y, m=p, and R$_1$=R$_2$, then n and q differ;
or a pharmaceutically acceptable salt thereof.

In preferred embodiments, a lipid may be used derived from Formula (LNP-II), wherein, X is a bond, linear or branched alkylene, alkenylene, or monocyclic, bicyclic, or tricyclic arene or heteroarene; Y is a monocyclic, bicyclic, or tricyclic arene or heteroarene; Z is S or O; L is a linear or branched alkylene of 1 to 6 carbons; R$_3$ and R$_4$ are independently a linear or branched alkyl of 1 to 6 carbons; R$_1$ and R$_2$ are independently a linear or branched alkyl or alkenyl of 1 to 20 carbons; r is 0 to 6; and m, n, p, and q are independently 1 to 18; or a pharmaceutically acceptable salt thereof may be suitably used.

In preferred embodiments, ionizable lipids may also be selected from the lipid compounds disclosed in PCT application PCT/EP2017/077517 (i.e. lipid compounds derived form Formula I, II, and III of PCT/EP2017/077517, or lipid compounds as specified in Claims 1 to 12 of PCT/EP2017/077517), the disclosure of PCT/EP2017/077517 hereby incorporated by reference in its entirety. In that context, lipid compounds disclosed in Table 7 of PCT/EP2017/077517 (e.g. lipid compounds derived from Formula I-1 to 1-41) and lipid compounds disclosed in Table 8 of PCT/EP2017/077517 (e.g. lipid compounds derived from Formula II-1 to 11-36) may be suitably used in the context of the invention. Accordingly, Formula I-1 to Formula I-41 and Formula II-1 to Formula II-36 of PCT/EP2017/077517, and the specific disclosure relating thereto, are herewith incorporated by reference.

In particularly preferred embodiments of the second aspect, a suitable lipid may be a cationic lipid according to Formula (LNP-III)

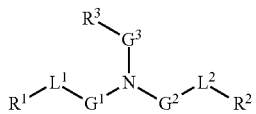

or a pharmaceutically acceptable salt, tautomer, prodrug or stereoisomer thereof, wherein, R$^1$, R$^2$, R$^3$, L$^1$, L$^2$, G$^1$, G$^2$, and G$^3$ are as below.

Formula (LNP-III) is further defined in that: one of L$^1$ or L$^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, —NR$^a$C(=O)NR$^a$—, —OC(=O)NR$^a$— or —NR$^a$C(=O)O—, and the other of L$^1$ or L$^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, —NR$^a$C(=O)NR$^a$—, —OC(=O)NR$^a$— or —NR$^a$C(=O)O— or a direct bond;

G$^1$ and G$^2$ are each independently unsubstituted C$_1$-C$_{12}$ alkylene or C$_1$-C$_{12}$ alkenylene;

G$^3$ is C$_1$-C$_{24}$ alkylene, C$_1$-C$_{24}$ alkenylene, C$_3$-C$_8$ cycloalkylene, C$_3$-C$_8$ cycloalkenylene;

R$^a$ is H or C$_1$-C$_{12}$ alkyl;

R$^1$ and R$^2$ are each independently C$_6$-C$_{24}$ alkyl or C$_6$-C$_{24}$ alkenyl;

R$^3$ is H, OR$^5$, CN, —C(=O)OR$^4$, —OC(=O)R$^4$ or —NR$^5$C(=O)R$^4$;

R$^4$ is C$_1$-C$_{12}$ alkyl;

R$^5$ is H or C$_1$-C$_6$ alkyl; and x is 0, 1 or 2.

In some of the foregoing embodiments of Formula (LNP-III), the lipid has one of the following structures (LNP-IIIA) or (LNP-IIIB):

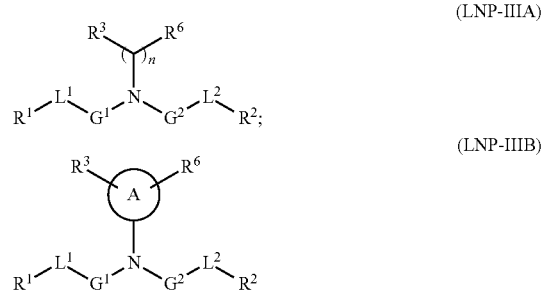

wherein:

A is a 3 to 8-membered cycloalkyl or cycloalkylene ring;

R$^6$ is, at each occurrence, independently H, OH or C$_1$-C$_{24}$ alkyl;

n is an integer ranging from 1 to 15.

In some of the foregoing embodiments of Formula (LNP-III), the lipid has structure (LNP-IIIA), and in other embodiments, the lipid has structure (LNP-IIIB).

In other embodiments of Formula (LNP-III), the lipid has one of the following structures (LNP-IIIC) or (LNP-IIID):

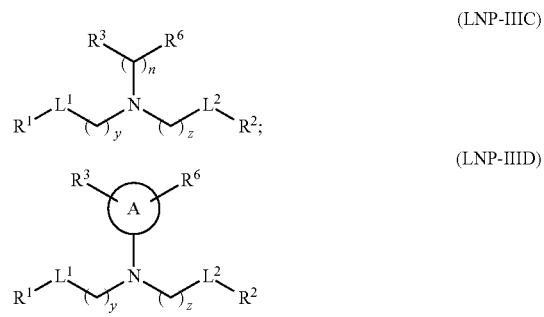

wherein y and z are each independently integers ranging from 1 to 12.

In any of the foregoing embodiments of Formula (LNP-III), one of L$^1$ or L$^2$ is —O(C=O)—. For example, in some embodiments each of L$^1$ and L$^2$ are —O(C=O)—. In some different embodiments of any of the foregoing, L$^1$ and L$^2$ are each independently —(C=O)O— or —O(C=O)—. For example, in some embodiments each of L$^1$ and L$^2$ is —(C=O)O—.

In preferred embodiments, the cationic lipid of the LNP is a compound of Formula (LNP-III), wherein:

L$^1$ and L$^2$ are each independently —O(C=O)— or (C=O)—O—;

G$^3$ is C$_1$-C$_{24}$ alkylene or C$_1$-C$_{24}$ alkenylene; and

R$^3$ is H or OR$^5$.

In some different embodiments of Formula (LNP-III), the lipid has one of the following structures (LNP-IIIE) or (LNP-IIIF):

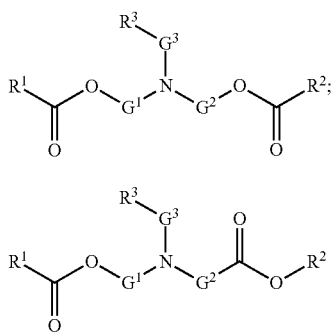

(LNP-IIIE)

(LNP-IIIF)

In some of the foregoing embodiments of Formula (LNP-III), the lipid has one of the following structures (LNP-IIIG), (LNP-IIIH), (LNP-IIII), or (LNP-IIIJ):

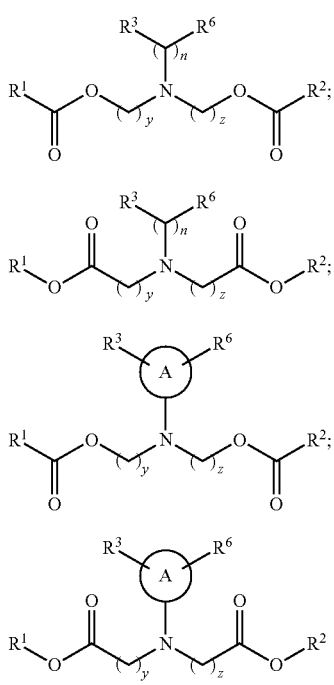

(LNP-IIIG)

(LNP-IIIH)

(LNP-IIII)

(LNP-IIIJ)

In some of the foregoing embodiments of Formula (LNP-III), n is an integer ranging from 2 to 12, for example from 2 to 8 or from 2 to 4. In some embodiments, n is 3, 4, 5 or 6. In some embodiments, n is 3. In some embodiments, n is 4.

In some embodiments, n is 5. In some embodiments, n is 6. In some other of the foregoing embodiments of Formula (LNP-III), y and z are each independently an integer ranging from 2 to 10. For example, in some embodiments, y and z are each independently an integer ranging from 4 to 9 or from 4 to 6. In some of the foregoing embodiments of Formula (LNP-III), $R^6$ is H. In other of the foregoing embodiments, $R^6$ is $C_1$-$C_{24}$ alkyl. In other embodiments, $R^6$ is OH. In some embodiments of Formula (LNP-III), $G^3$ is unsubstituted. In other embodiments, $G^3$ is substituted. In various different embodiments, $G^3$ is linear $C_1$-$C_{24}$ alkylene or linear $C_1$-$C_{24}$ alkenylene. In some other foregoing embodiments of Formula (LNP-III), $R^1$ or $R^2$, or both, is $C_6$-$C_{24}$ alkenyl. For example, in some embodiments, $R^1$ and $R^2$ each, independently have the following structure:

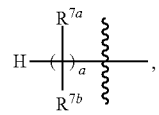

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12. In some of the foregoing embodiments of Formula (LNP-III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (LNP-III), $R^1$ or $R^2$, or both, has one of the following structures:

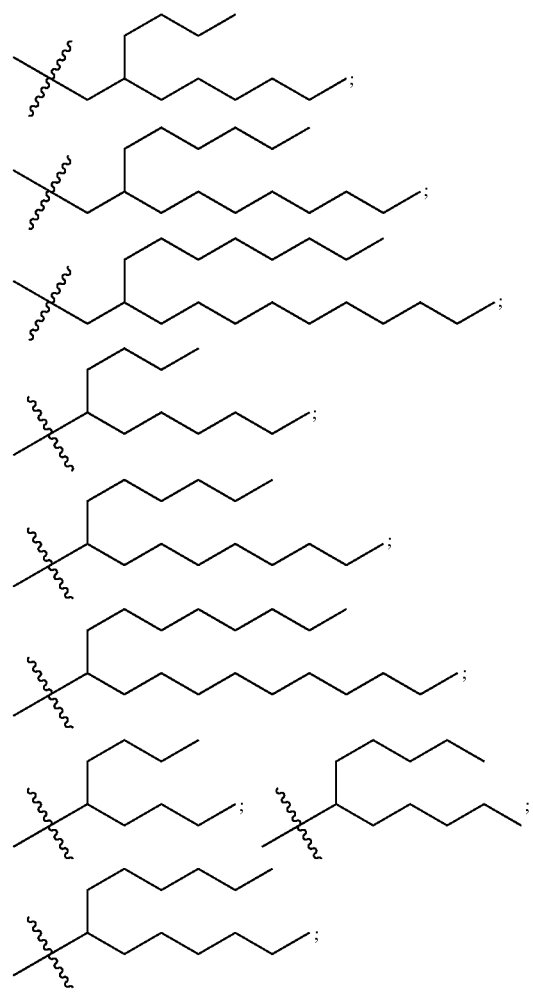

221

-continued

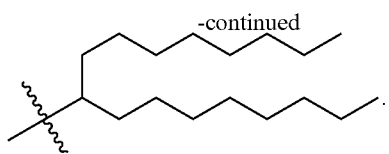

In preferred embodiments, the cationic lipid of the LNP is a compound of formula (LNP-III), wherein:
L$^1$ and L$^2$ are each independently —O(C=O)— or (C=O)—O—; and
R$^1$ and R$^2$ each independently have one of the following structures:

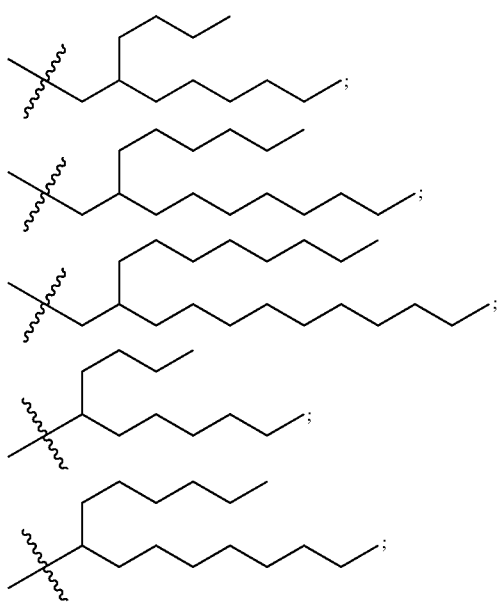

222

-continued

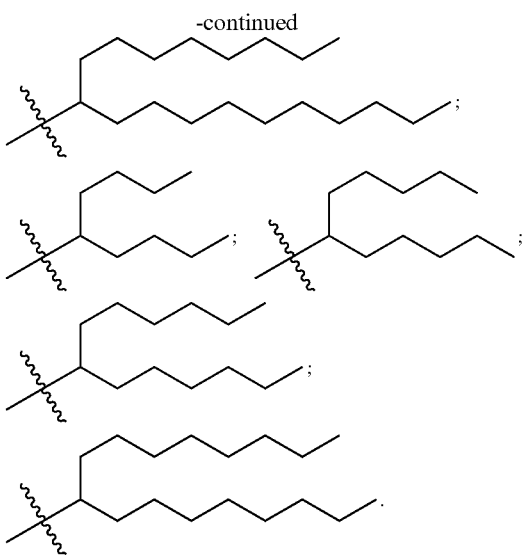

In some of the foregoing embodiments of Formula (LNP-III), R$^3$ is OH, CN, —C(=O)OR$^4$, —OC(=O)R$^4$ or —NHC(=O)R$^4$. In some embodiments, R$^4$ is methyl or ethyl.

In preferred embodiments of the second aspect, the cationic lipid of the LNP is a compound of Formula (LNP-III), wherein R$^3$ is OH.

In particularly preferred embodiment, the artificial nucleic acid, preferably RNA of the first aspect is complexed with one or more lipids thereby forming lipid nanoparticles (LNP), wherein the LNP is selected from structures (LNP-III-1) to (LNP-III-36) (see Table 6).

TABLE 6

Representative lipid compounds derived from Formula (LNP-III)

| No. | Structure |
|---|---|
| LNP-III-1 | 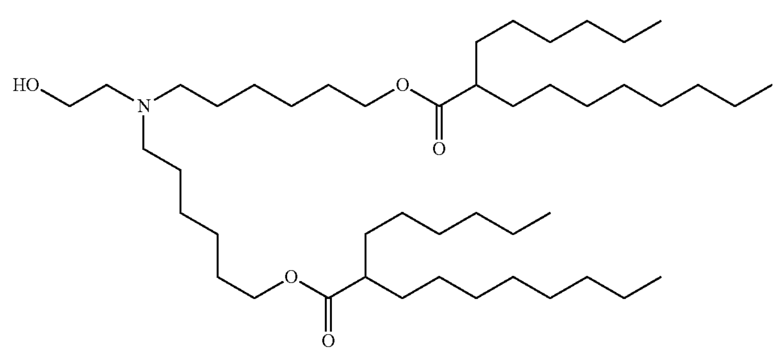 [SMILES: CCCCCCCCC(CCCCCC)C(=O)OCCCCCCN(CCO)CCCCCCOC(=O)C(CCCCCC)CCCCCCCC] |

TABLE 6-continued

Representative lipid compounds derived from Formula (LNP-III)

| No. | Structure |
|---|---|
| LNP-III-2 | 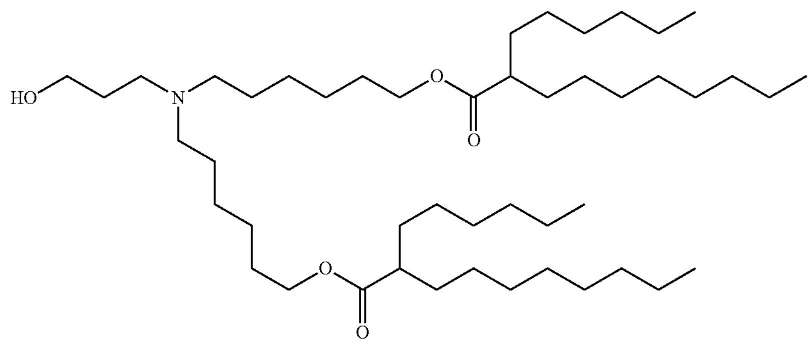 [SMILES: CCCCCCCCC(CCCCCC)C(=O)OCCCCCCN(CCCO)CCCCCCOC(=O)C(CCCCCC)CCCCCCCC] |
| LNP-III-3 | 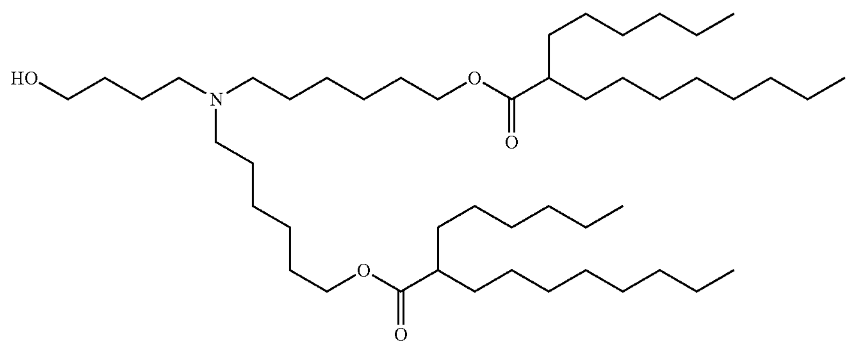 [SMILES: CCCCCCCCC(CCCCCC)C(=O)OCCCCCCN(CCCCO)CCCCCCOC(=O)C(CCCCCC)CCCCCCCC] |
| LNP-III-4 | 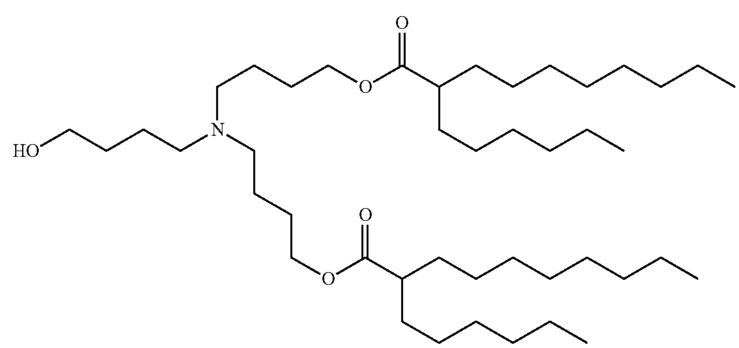 [SMILES: CCCCCCCCC(CCCCCC)C(=O)OCCCCN(CCCCO)CCCCOC(=O)C(CCCCCC)CCCCCCCC] |
| LNP-III-5 | 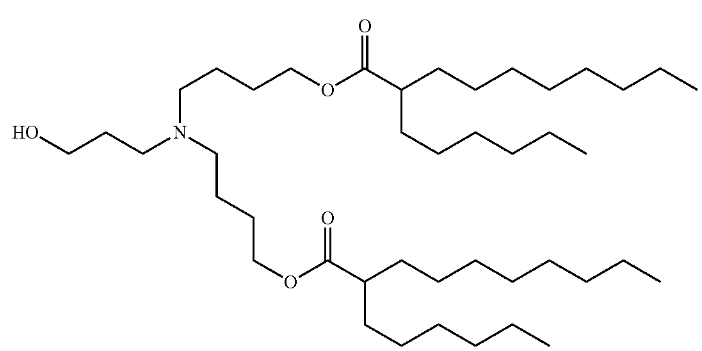 [SMILES: CCCCCCCCC(CCCCCC)C(=O)OCCCCN(CCCO)CCCCOC(=O)C(CCCCCC)CCCCCCCC] |

TABLE 6-continued

Representative lipid compounds derived from Formula (LNP-III)

| No. | Structure |
|---|---|
| LNP-III-6 | 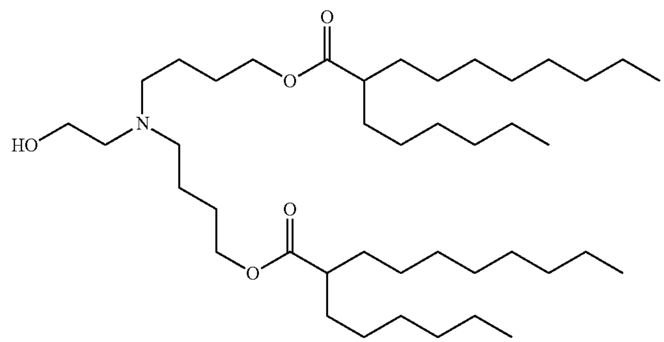 [SMILES: CCCCCCCCC(CCCCCC)C(=O)OCCCCN(CCO)CCCCOC(=O)C(CCCCCC)CCCCCCCC] |
| LNP-III-7 | 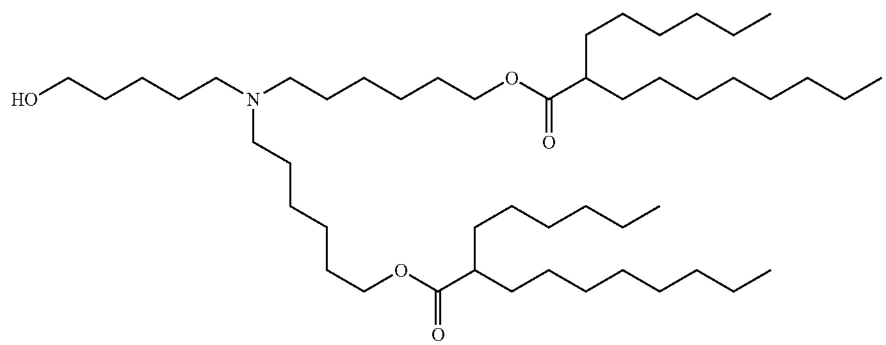 [SMILES: CCCCCCCCC(CCCCCC)C(=O)OCCCCCCN(CCCCCO)CCCCCCOC(=O)C(CCCCCC)CCCCCCCC] |
| LNP-III-8 | 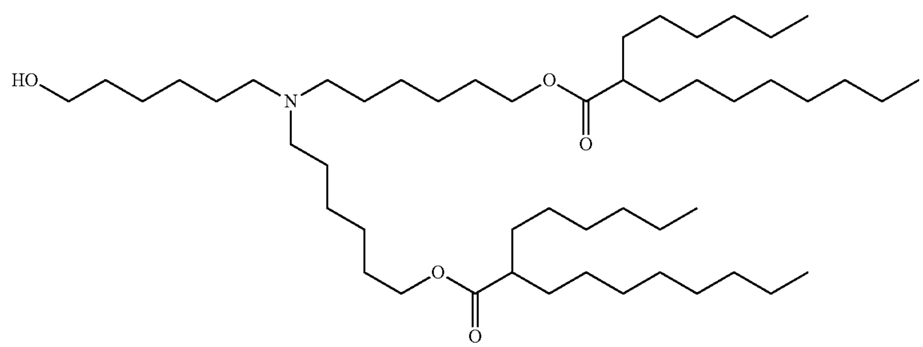 [SMILES: CCCCCCCCC(CCCCCC)C(=O)OCCCCCCN(CCCCCCO)CCCCCCOC(=O)C(CCCCCC)CCCCCCCC] |
| LNP-III-9 | 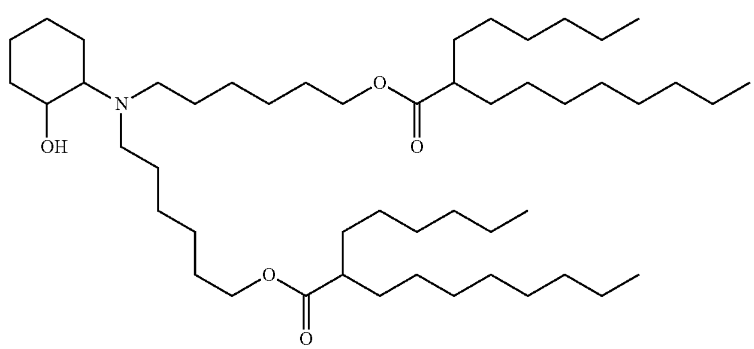 [SMILES: CCCCCCCCC(CCCCCC)C(=O)OCCCCCCN(CCCCCCOC(=O)C(CCCCCC)CCCCCCCC)C1CCCCC1O] |

TABLE 6-continued
Representative lipid compounds derived from Formula (LNP-III)
| No. | Structure |
|---|---|
| LNP-III-10 | 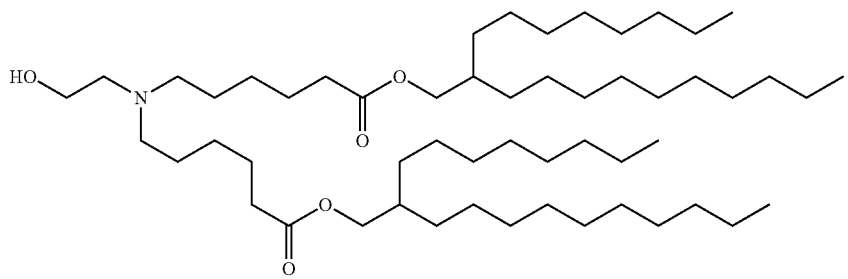 [SMILES: CCCCCCCCCCC(CCCCCCCC)COC(=O)CCCCCN(CCO)CCCCCC(=O)OCC(CCCCCCCC)CCCCCCCCCC] |
| LNP-III-11 | 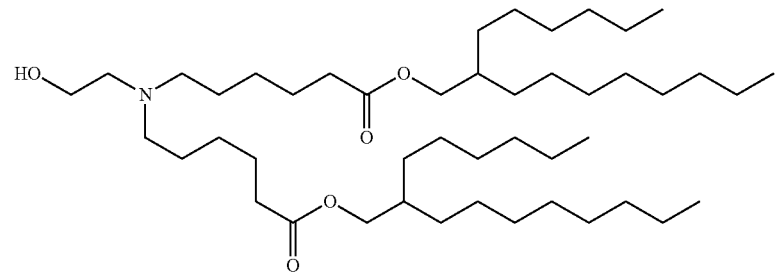 [SMILES: CCCCCCCCC(CCCCCC)COC(=O)CCCCCN(CCO)CCCCCC(=O)OCC(CCCCCC)CCCCCCCC] |
| LNP-III-12 | 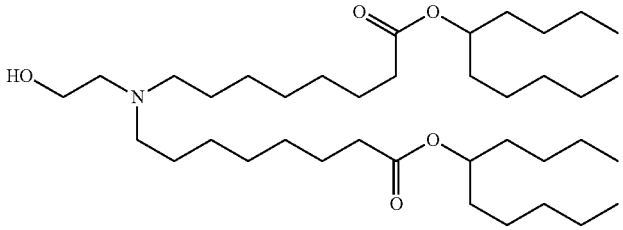 [SMILES: CCCCCC(CCCC)OC(=O)CCCCCCCN(CCO)CCCCCCCC(=O)OC(CCCC)CCCCC] |
| LNP-III-13 | 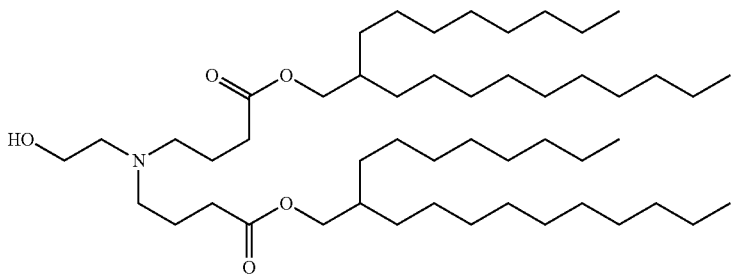 [SMILES: CCCCCCCCCCC(CCCCCCCC)COC(=O)CCCN(CCO)CCCC(=O)OCC(CCCCCCCC)CCCCCCCCCC] |
| LNP-III-14 | 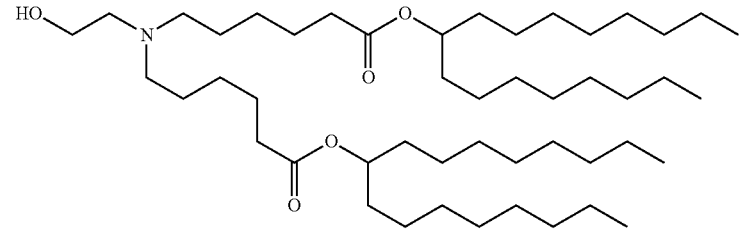 [SMILES: CCCCCCCCC(CCCCCCCC)OC(=O)CCCCCN(CCO)CCCCCC(=O)OC(CCCCCCCC)CCCCCCCC] |

TABLE 6-continued

Representative lipid compounds derived from Formula (LNP-III)

| No. | Structure |
|---|---|
| LNP-III-15 | 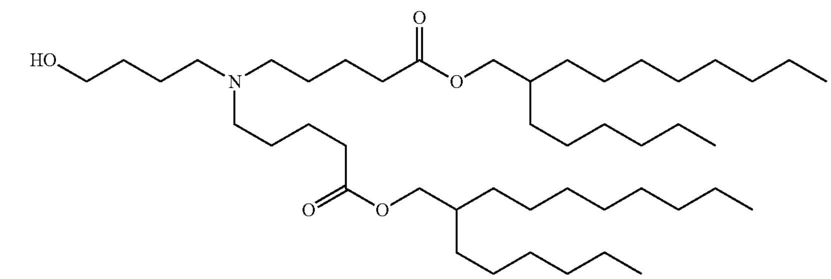 [SMILES: CCCCCCCCC(CCCCCC)COC(=O)CCCCN(CCCCO)CCCCC(=O)OCC(CCCCCC)CCCCCCCC] |
| LNP-III-16 | 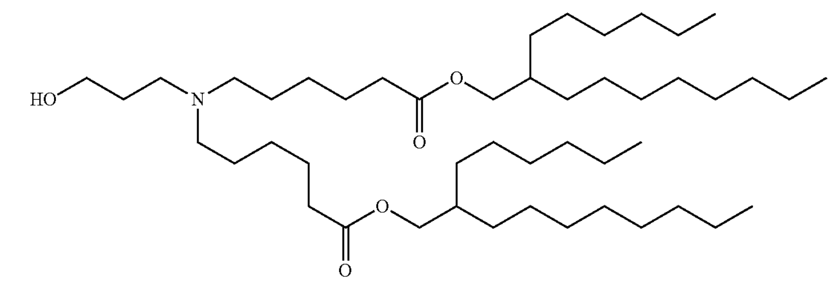 [SMILES: CCCCCCCCC(CCCCCC)COC(=O)CCCCCN(CCCO)CCCCCC(=O)OCC(CCCCCC)CCCCCCCC] |
| LNP-III-17 | 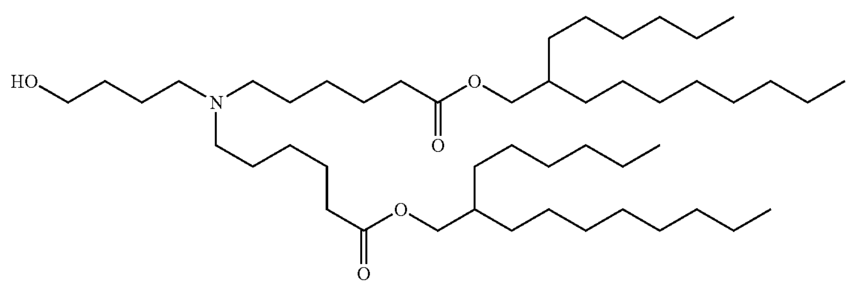 [SMILES: CCCCCCCCC(CCCCCC)COC(=O)CCCCCN(CCCCO)CCCCCC(=O)OCC(CCCCCC)CCCCCCCC] |
| LNP-III-18 | 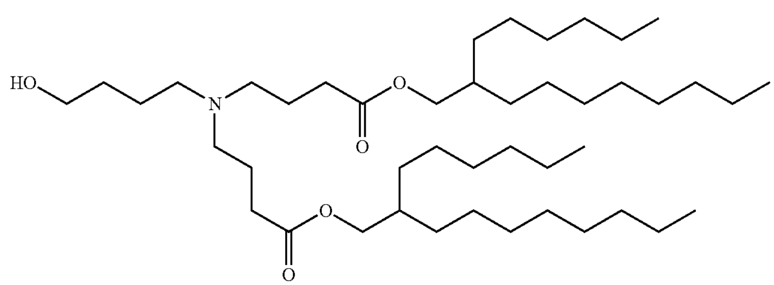 [SMILES: CCCCCCCCC(CCCCCC)COC(=O)CCCN(CCCCO)CCCC(=O)OCC(CCCCCC)CCCCCCCC] |
| LNP-III-19 | 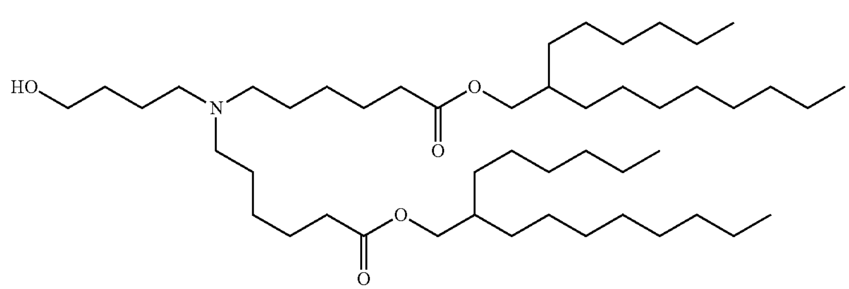 [SMILES: CCCCCCCCC(CCCCCC)COC(=O)CCCCCN(CCCCO)CCCCCC(=O)OCC(CCCCCC)CCCCCCCC] |

TABLE 6-continued

Representative lipid compounds derived from Formula (LNP-III)

| No. | Structure |
|---|---|
| LNP-III-20 | 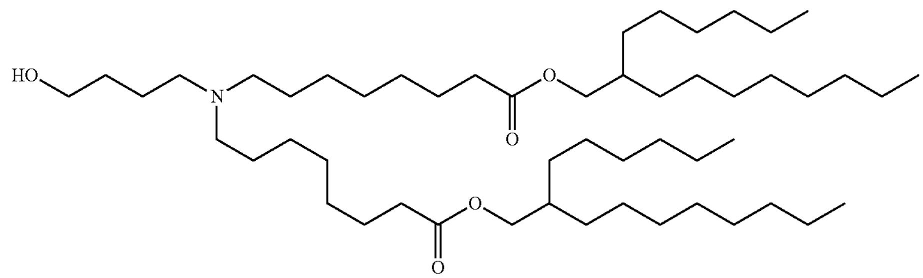 [SMILES: CCCCCCCCC(CCCCCC)COC(=O)CCCCCCCN(CCCCO)CCCCCCCC(=O)OCC(CCCCCC)CCCCCCCC] |
| LNP-III-21 | 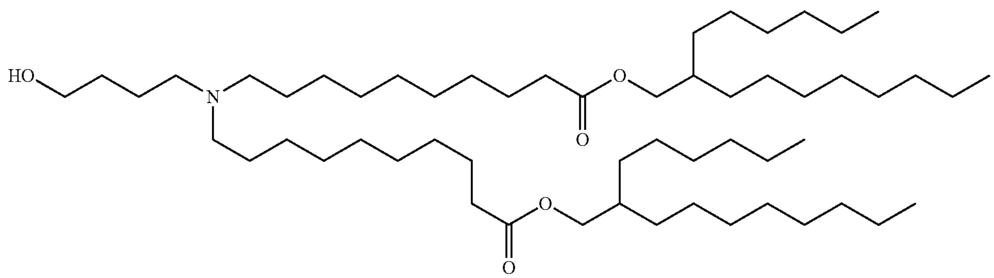 [SMILES: CCCCCCCCC(CCCCCC)COC(=O)CCCCCCCCCN(CCCCO)CCCCCCCCCC(=O)OCC(CCCCCC)CCCCCCCC] |
| LNP-III-22 | 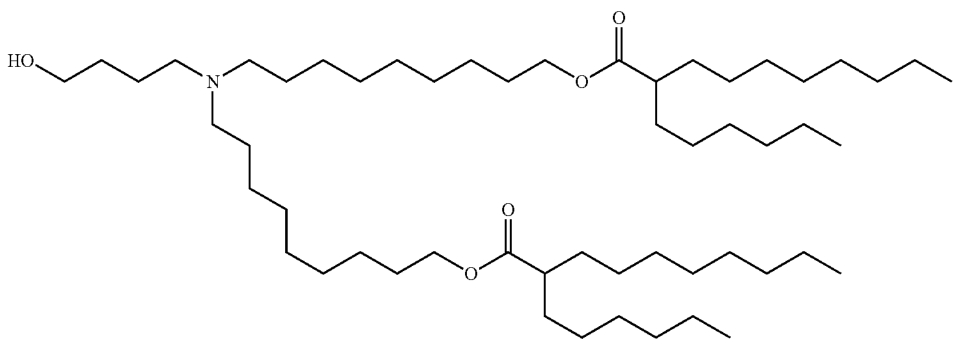 [SMILES: CCCCCCCCC(CCCCCC)C(=O)OCCCCCCCCCN(CCCCO)CCCCCCCCCOC(=O)C(CCCCCC)CCCCCCCC] |
| LNP-III-23 | 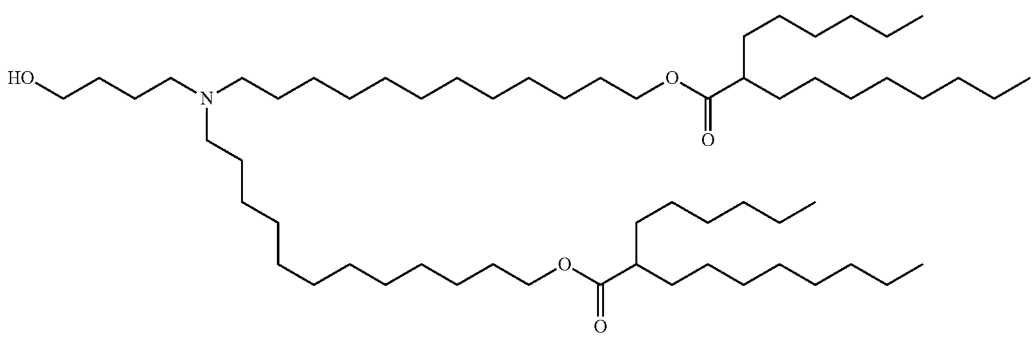 [SMILES: CCCCCCCCC(CCCCCC)C(=O)OCCCCCCCCCCCCN(CCCCO)CCCCCCCCCCCCOC(=O)C(CCCCCC)CCCCCCCC] |
| LNP-III-24 | 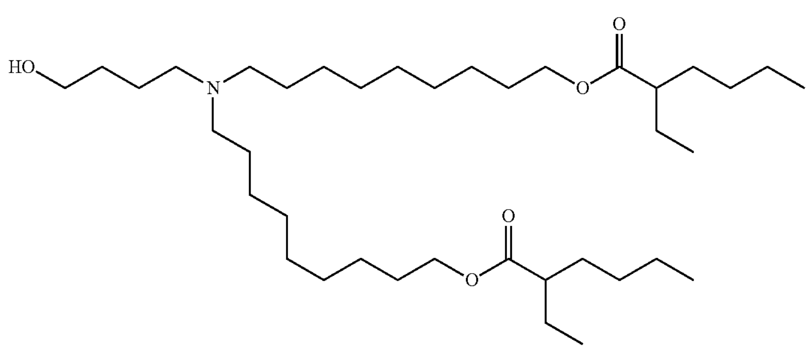 [SMILES: CCCCC(CC)C(=O)OCCCCCCCCCN(CCCCO)CCCCCCCCCOC(=O)C(CC)CCCC] |

TABLE 6-continued

Representative lipid compounds derived from Formula (LNP-III)

| No. | Structure |
|---|---|
| LNP-III-25 | 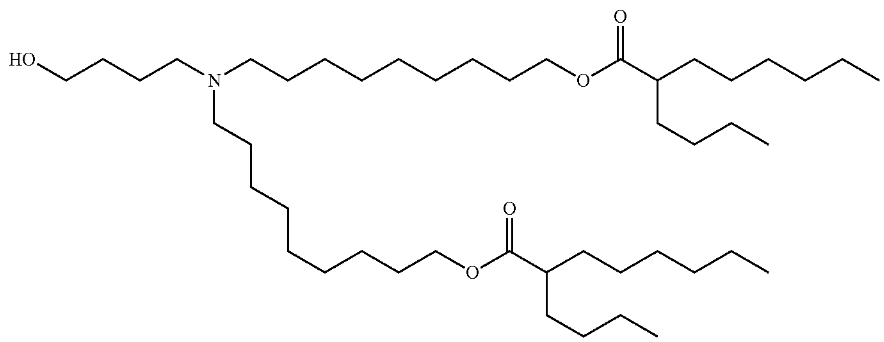 [SMILES: CCCCCCC(CCCC)C(=O)OCCCCCCCCCN(CCCCO)CCCCCCCCCOC(=O)C(CCCC)CCCCCC] |
| LNP-III-26 | 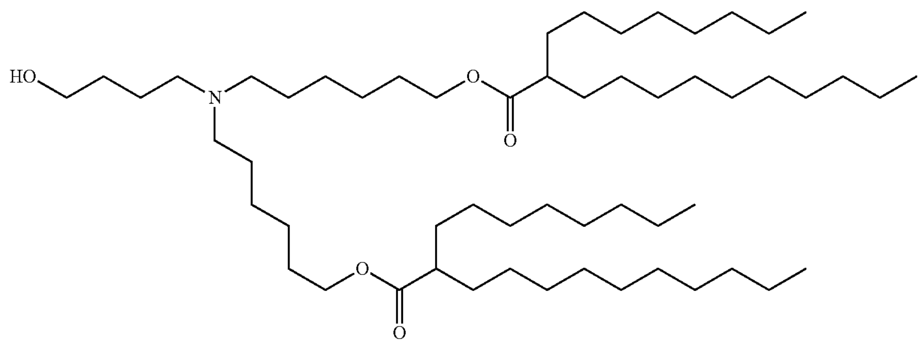 [SMILES: CCCCCCCCCCC(CCCCCCCC)C(=O)OCCCCCCN(CCCCO)CCCCCCOC(=O)C(CCCCCCCC)CCCCCCCCCC] |
| LNP-III-27 | 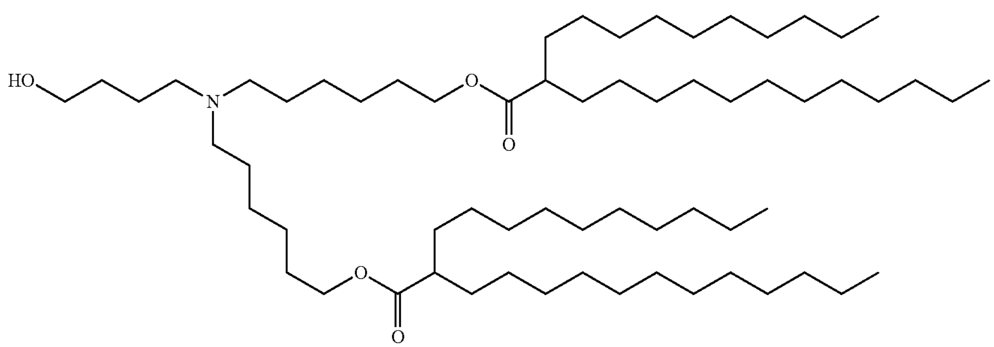 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| LNP-III-28 | 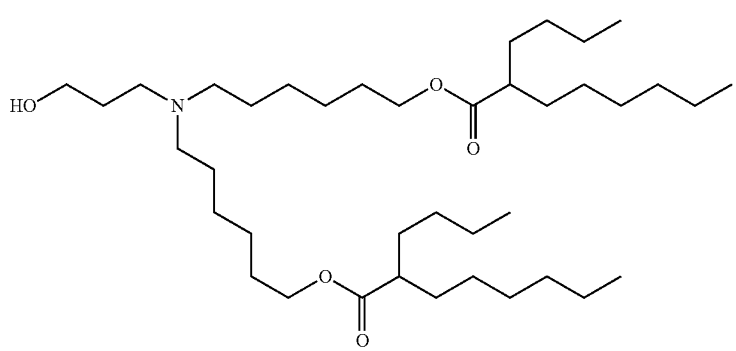 [SMILES: CCCCCCC(CCCC)C(=O)OCCCCCCN(CCCO)CCCCCCOC(=O)C(CCCC)CCCCCC] |

TABLE 6-continued

Representative lipid compounds derived from Formula (LNP-III)

| No. | Structure |
|---|---|
| LNP-III-29 | 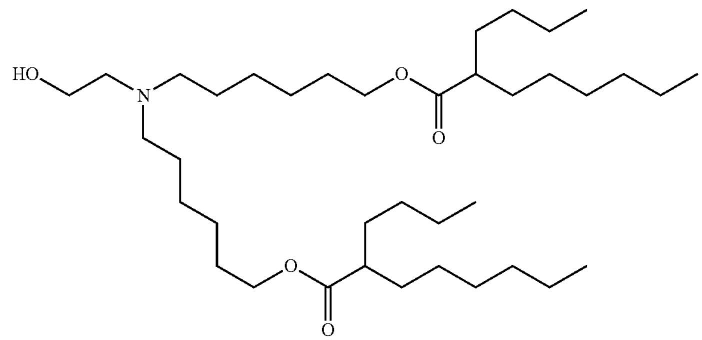 [SMILES: CCCCCCC(CCCC)C(=O)OCCCCCCN(CCO)CCCCCCOC(=O)C(CCCC)CCCCCC] |
| LNP-III-30 | 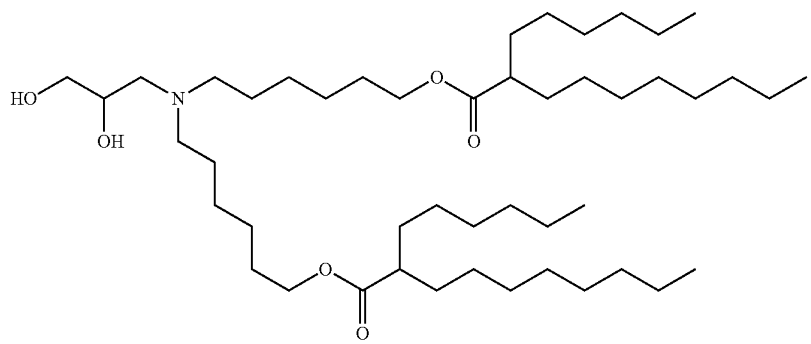 [SMILES: CCCCCCCCC(CCCCCC)C(=O)OCCCCCCN(CCCCCCOC(=O)C(CCCCCC)CCCCCCCC)CC(O)CO] |
| LNP-III-31 | 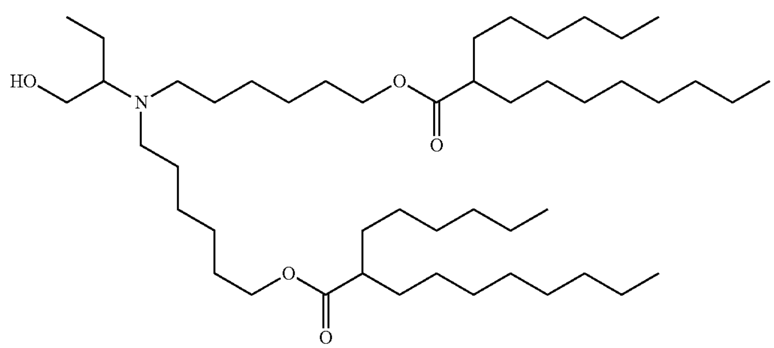 [SMILES: CCCCCCCCC(CCCCCC)C(=O)OCCCCCCN(CCCCCCOC(=O)C(CCCCCC)CCCCCCCC)C(CC)CO] |
| LNP-III-32 | 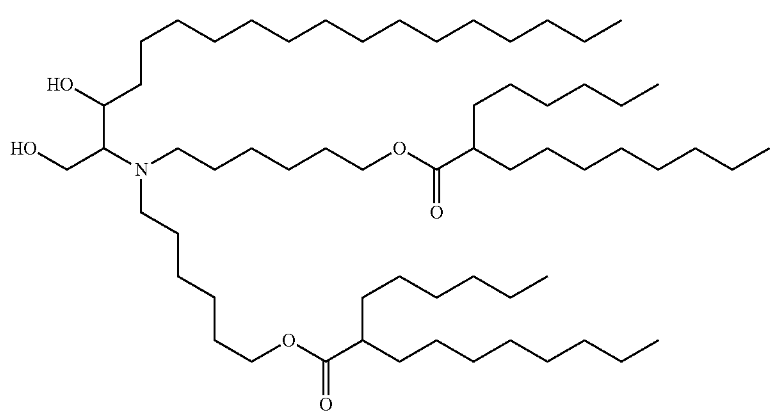 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |

TABLE 6-continued

Representative lipid compounds derived from Formula (LNP-III)

| No. | Structure |
| --- | --- |
| LNP-III-33 | 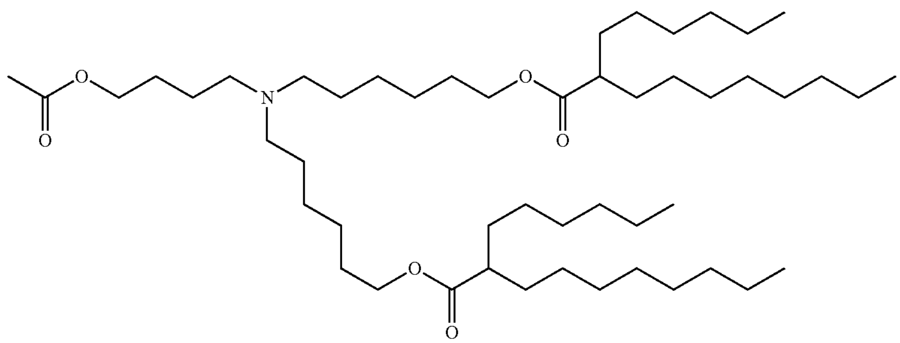 [SMILES: CCCCCCCCC(CCCCCC)C(=O)OCCCCCCN(CCCCCCOC(=O)C(CCCCCC)CCCCCCCC)CCCCOC(C)=O] |
| LNP-III-34 | 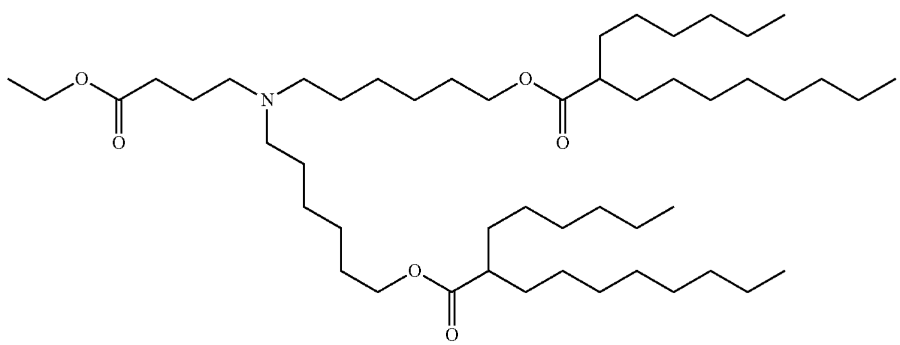 [SMILES: CCCCCCCCC(CCCCCC)C(=O)OCCCCCCN(CCCCCCOC(=O)C(CCCCCC)CCCCCCCC)CCCC(=O)OCC] |
| LNP-III-35 | 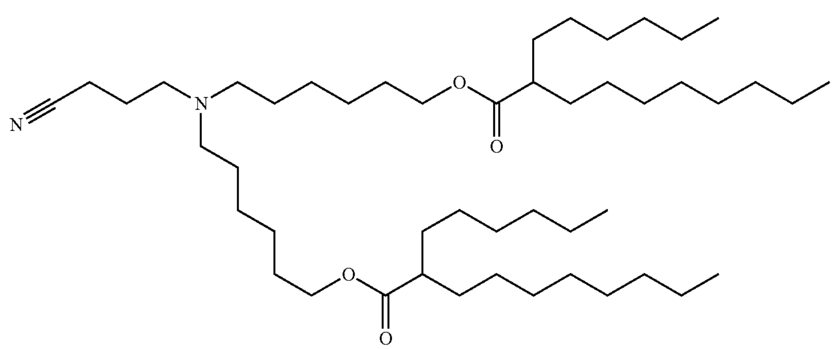 [SMILES: CCCCCCCCC(CCCCCC)C(=O)OCCCCCCN(CCCC#N)CCCCCCOC(=O)C(CCCCCC)CCCCCCCC] |
| LNP-III-36 | 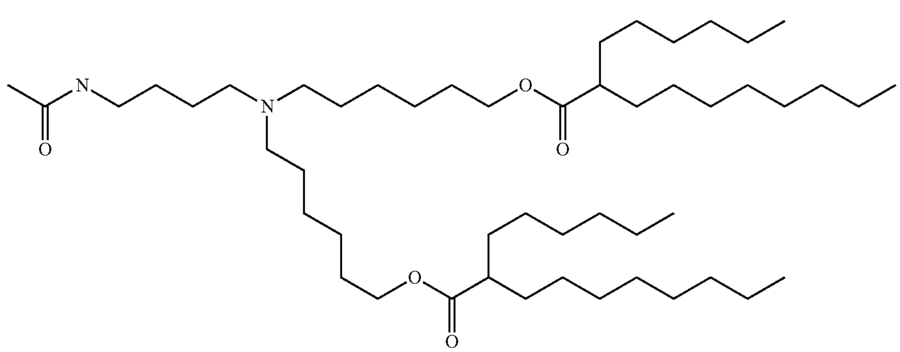 |

In some embodiments, the LNPs comprise a lipid of Formula (LNP-III), an artificial nucleic acid, preferably RNA of the first aspect, and one or more excipient selected from neutral lipids, steroids and PEGylated lipids. In some embodiments the lipid of Formula (LNP-III) is compound (LNP-III-3). In some embodiments the lipid of Formula (LNP-III) is compound (LNP-III-7).

In preferred embodiments, the LNP comprises a cationic lipid selected from:

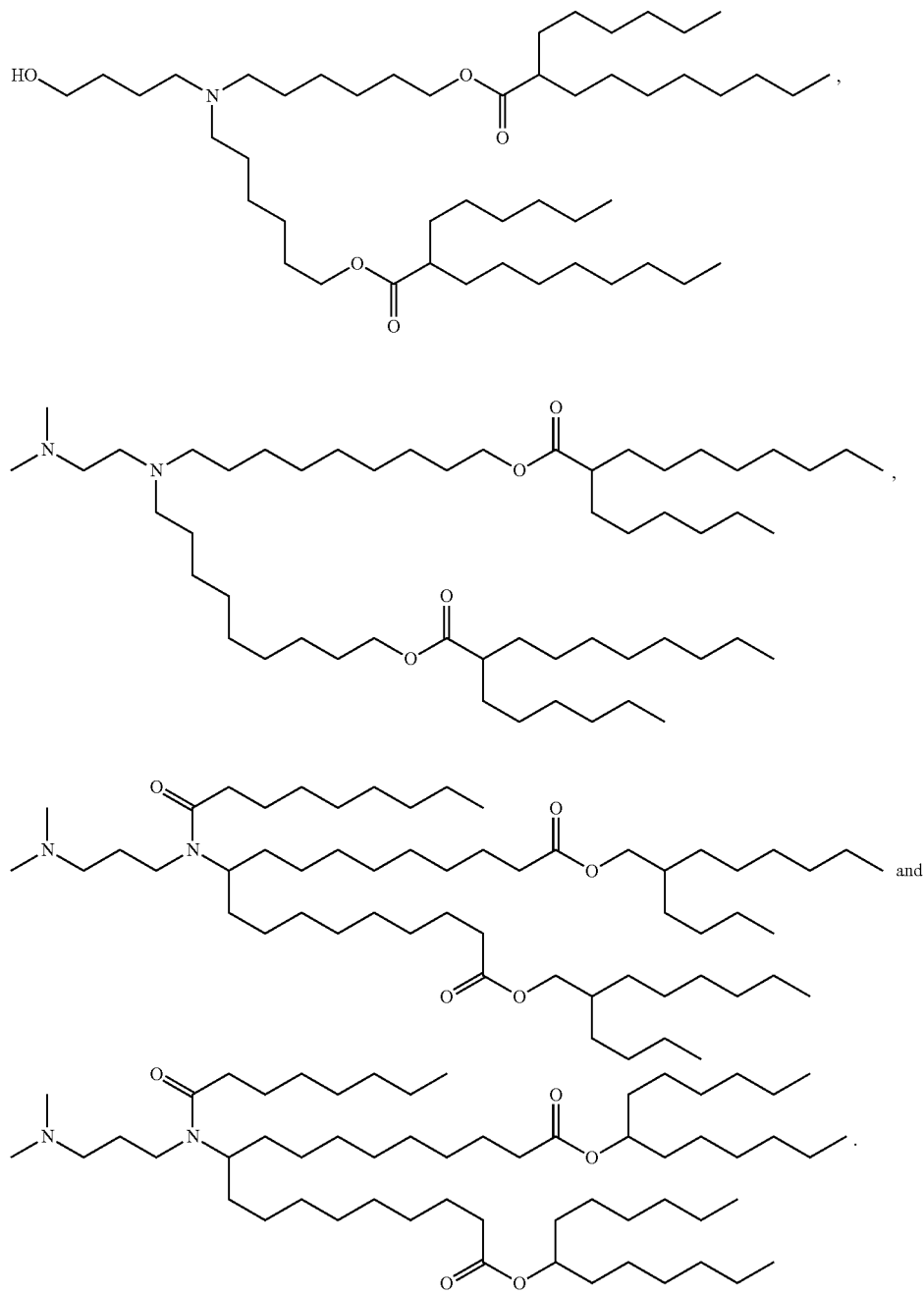

In particularly preferred embodiment, the artificial nucleic acid, preferably RNA of the first aspect is complexed with one or more lipids thereby forming lipid nanoparticles (LNP), wherein the LNP comprises the following cationic lipid (lipid according to Formula LNP-III-3 of Table 6):

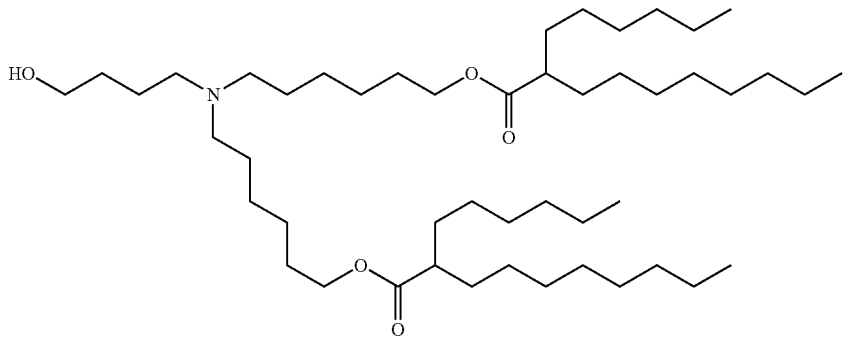 [SMILES: CCCCCCCCC(CCCCCC)C(=O)OCCCCCCN(CCCCO)CCCCCCOC(=O)C(CCCCCC)CCCCCCCC]

In certain embodiments, the cationic lipid as defined herein, preferably as disclosed in Table 6, more preferably cationic lipid compound LNP-III-3, is present in the LNP in an amount from about 30 to about 95 mole percent, relative to the total lipid content of the LNP. If more than one cationic lipid is incorporated within the LNP, such percentages apply to the combined cationic lipids.

In one embodiment, the cationic lipid is present in the LNP in an amount from about 30 to about 70 mole percent. In one embodiment, the cationic lipid is present in the LNP in an amount from about 40 to about 60 mole percent, such as about 40, 41, 42, 43, 44, 45, 46, 47, 48, 49, 50, 51, 52, 53, 54, 55, 56, 57, 58, 59 or 60 mole percent, respectively. In embodiments, the cationic lipid is present in the LNP in an amount from about 47 to about 48 mole percent, such as about 47.0, 47.1, 47.2, 47.3, 47.4, 47.5, 47.6, 47.7, 47.8, 47.9, 50.0 mole percent, respectively, wherein 47.7 mole percent are particularly preferred.

In some embodiments, the cationic lipid is present in a ratio of from about 20 mol % to about 70 or 75 mol % or from about 45 to about 65 mol % or about 20, 25, 30, 35, 40, 45, 50, 55, 60, 65, or about 70 mol % of the total lipid present in the LNP. In further embodiments, the LNPs comprise from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle). In some embodiments, the ratio of cationic lipid to nucleic acid, preferably to the artificial RNA of the first aspect, is from about 3 to about 15, such as from about 5 to about 13 or from about 7 to about 11.

In some embodiments of the invention the LNP comprises a combination or mixture of any the lipids described above. Other suitable (cationic) lipids are disclosed in WO2009/086558, WO2009/127060, WO2010/048536, WO2010/054406, WO2010/088537, WO2010/129709, WO2011/153493, US2011/0256175, US2012/0128760, US2012/0027803, U.S. Pat. No. 8,158,601, WO2016118724, WO2016118725, WO2017070613, WO2017070620, WO2017099823, and WO2017112865. In that context, the disclosures of WO2009/086558, WO2009/127060, WO2010/048536, WO2010/054406, WO2010/088537, WO2010/129709, WO2011/153493, US2011/0256175, US2012/0128760, US2012/0027803, U.S. Pat. No. 8,158,601, WO2016118724, WO2016118725, WO2017070613, WO2017070620, WO2017099823, and WO2017112865 specifically relating to (cationic) lipids suitable for LNPs are incorporated herewith by reference.

In some embodiments, amino or cationic lipids as defined herein have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of lipids have to be present in the charged or neutral form. Lipids having more than one protonatable or deprotonatable group, or which are zwitterionic, are not excluded and may likewise suitable in the context of the present invention.

In some embodiments, the protonatable lipids have a pKa of the protonatable group in the range of about 4 to about 11, e.g., a pKa of about 5 to about 7.

LNPs can comprise two or more (different) cationic lipids. The cationic lipids may be selected to contribute different advantageous properties. For example, cationic lipids that differ in properties such as amine pKa, chemical stability, half-life in circulation, half-life in tissue, net accumulation in tissue, or toxicity can be used in the LNP. In particular, the cationic lipids can be chosen so that the properties of the mixed-LNP are more desirable than the properties of a single-LNP of individual lipids.

The amount of the permanently cationic lipid or lipidoid may be selected taking the amount of the nucleic acid cargo into account. In one embodiment, these amounts are selected such as to result in an N/P ratio of the nanoparticle(s) or of the composition in the range from about 0.1 to about 20. In this context, the N/P ratio is defined as the mole ratio of the nitrogen atoms ("N") of the basic nitrogen-containing groups of the lipid or lipidoid to the phosphate groups ("P") of the RNA which is used as cargo. The N/P ratio may be calculated on the basis that, for example, 1 μg RNA typically contains about 3 nmol phosphate residues, provided that the RNA exhibits a statistical distribution of bases. The "N"-value of the lipid or lipidoid may be calculated on the basis of its molecular weight and the relative content of permanently cationic and—if present—cationisable groups.

LNP in vivo characteristics and behavior can be modified by addition of a hydrophilic polymer coating, e.g. polyethylene glycol (PEG), to the LNP surface to confer steric stabilization. Furthermore, LNPs can be used for specific targeting by attaching ligands (e.g. antibodies, peptides, and carbohydrates) to its surface or to the terminal end of the attached PEG chains (e.g. via PEGylated lipids).

In some embodiments, the LNPs comprise a polymer conjugated lipid. The term "polymer conjugated lipid" refers to a molecule comprising both a lipid portion and a polymer portion. An example of a polymer conjugated lipid is a PEGylated lipid. The term "PEGylated lipid" refers to a molecule comprising both a lipid portion and a polyethylene glycol portion. PEGylated lipids are known in the art and include 1-(monomethoxy-polyethyleneglycol)-2,3-dimyristoylglycerol (PEG-s-DMG) and the like.

Other suitable amino lipids include those having alternative fatty acid groups and other dialkylamino groups, including those in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ may be used. Other scaffolds can also be used to separate the amino group and the fatty acid or fatty alkyl portion of the amino lipid.

Amino or cationic lipids may have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention.

The protonatable lipids may have a pKa of the protonatable group in the range of about 4 to about 11, e.g., a pKa of about 5 to about 7.

LNPs may include two or more cationic lipids. The cationic lipids may be selected to contribute different advantageous properties. For example, cationic lipids that differ in properties such as amine pKa, chemical stability, half-life in circulation, half-life in tissue, net accumulation in tissue, or toxicity may be used in the LNP. In particular, the cationic lipids may be chosen so that the properties of the mixed-LNP are more desirable than the properties of a single-LNP of individual lipids.

The cationic lipid may be present in a ratio of from about 20 mol % to about 70 or 75 mol % or from about 45 to about 65 mol % or about 20, 25, 30, 35, 40, 45, 50, 55, 60, 65, or about 70 mol % of the total lipid present in the LNP. LNPs may comprise from about 25% to about 75% on a molar basis of cationic lipid, e.g., from about 20 to about 70%, from about 35 to about 65%, from about 45 to about 65%, about 60%, about 50% or about 40% on a molar basis (based upon 100% total moles of lipid in the lipid nanoparticle). The ratio of cationic lipid to nucleic acid may be from about 3 to about 15, such as from about 5 to about 13 or from about 7 to about 11. Specifically, the liposome may have a molar ratio of nitrogen atoms in the cationic lipid to the phosphates in the RNA (N:P ratio) of between 1:1 and 20:1 as described in International Publication No. WO 2013/006825 A1, herein incorporated by reference in its entirety. Alternatively, the liposome may have a N:P ratio of greater than 20:1 or less than 1:1.

(ii) Neutral and Non-Cationic Lipids

The non-cationic lipid may be a neutral lipid, an anionic lipid, or an amphipathic lipid. Neutral lipids, when present, may be selected any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., LNP size and stability of the LNP in the bloodstream. Preferably, the neutral lipid is a lipid having two acyl groups (e.g., diacylphosphatidylcholine and diacylphosphatidylethanolamine).

Neutral lipids may contain saturated fatty acids with carbon chain lengths in the range of $C_{10}$ to $C_{20}$. In other embodiments, neutral lipids with mono or diunsaturated fatty acids with carbon chain lengths in the range of $C_{10}$ to $C_{20}$ are used. Additionally or alternatively, neutral lipids having mixtures of saturated and unsaturated fatty acid chains may be used.

Suitable neutral lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), dimyristoyl phosphatidylcholine (DMPC), distearoyl-phosphatidyl-ethanolamine (DSPE), SM, 16-O-monomethyl PE, 16-O-dimethyl PE, 18-1-trans PE, 1-stearoyl-2-oleoyl-phosphatidyethanolamine (SOPE), cholesterol, or a mixture thereof. Anionic lipids suitable for use in LNPs include, but are not limited to, phosphatidylglycerol, cardiolipin, diacyl-phosphatidylserine, diacylphosphatidic acid, N-dodecanoyl phosphatidylethanoloamine, N-succinyl phosphatidyl-ethanolamine, N-glutaryl phosphatidylethanolamine, lysylphosphatidylglycerol, and other anionic modifying groups joined to neutral lipids.

Amphipathic lipids refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and beta-acyloxyacids, can also be used.

In some embodiments, the LNPs comprise a neutral lipid selected from DSPC, DPPC, DMPC, DOPC, POPC, DOPE and SM. In various embodiments, the molar ratio of the cationic lipid to the neutral lipid ranges from about 2:1 to about 8:1.

In preferred embodiments the neutral lipid is 1,2-distearoyl-sn-glycero-3-phosphocholine (DSPC). The molar ratio of the cationic lipid to DSPC may be in the range from about 2:1 to 8:1.

The non-cationic lipid may be present in a ratio of from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the LNP.

LNPs may comprise from about 0% to about 15 or 45% on a molar basis of neutral lipid, e.g., from about 3 to about 12% or from about 5 to about 10%. For instance, LNPs may include about 15%, about 10%, about 7.5%, or about 7.1% of neutral lipid on a molar basis (based upon 100% total moles of lipid in the LNP).

(iii) Sterols

The sterol may preferably be cholesterol.

The sterol may be present in a ratio of about 10 mol % to about 60 mol % or about 25 mol % to about 40 mol % of the LNP. The sterol may be present in a ratio of about 10, 15, 20, 25, 30, 35, 40, 45, 50, 55, or about 60 mol % of the total lipid present in the LNP. LNPs may comprise from about 5% to about 50% on a molar basis of the sterol, e.g., about 15% to about 45%, about 20% to about 40%, about 48%, about 40%, about 38.5%, about 35%, about 34.4%, about 31.5% or about 31% on a molar basis (based upon 100% total moles of lipid in the LNP).

(iv) Aggregation Reducing Agents

The aggregation reducing agent may be a lipid capable of reducing aggregation.

Examples of such lipids include, but are not limited to, polyethylene glycol (PEG)-modified lipids, monosialoganglioside Gml, and polyamide oligomers (PAO) such as those described in U.S. Pat. No. 6,320,017, which is incorporated by reference in its entirety. Other compounds with uncharged, hydrophilic, steric-barrier moieties, which prevent aggregation during formulation, like PEG, Gml or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613, each of which is incorporated by reference in its entirety.

The aggregation reducing agent may be, for example, selected from a polyethyleneglycol (PEG)-lipid including, without limitation, a PEG-diacylglycerol (DAG), a PEG-dialkylglycerol, a PEG-dialkyloxypropyl (DAA), a PEG-phospholipid, a PEG-ceramide (Cer), or a mixture thereof (such as PEG-Cer$_{14}$ or PEG-Cer$_{20}$). The PEG-DAA conjugate may be, for example, a PEG-dilauryloxypropyl (C$_{12}$), a PEG-dimyristyloxypropyl (C$_{14}$), a PEG-dipalmityloxypropyl (C$_{16}$), or a PEG-distearyloxypropyl (C$_{18}$). Other pegylated-lipids include, but are not limited to, polyethylene glycol-didimyristoyl glycerol (C$_{14}$-PEG or PEG-C$_{14}$, where PEG has an average molecular weight of 2000 Da) (PEG-DMG); (R)-2,3-bis(octadecyloxy)propyl-1-(methoxy poly(ethyleneglycol)2000)propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy)propyl-1-(methoxy poly(ethylene glycol)2000)propylcarbamate)) (GalNAc-PEG-DSG); mPEG (mw2000)-diastearoylphosphatidyl-ethanolamine (PEG-DSPE); and polyethylene glycol-dipalmitoylglycerol (PEG-DPG).

Preferably, the aggregation reducing agent may be selected from PEG-DMG or PEG-c-DMA.

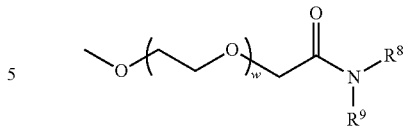
(LNP-IV)

or a pharmaceutically acceptable salt, tautomer or stereoisomer thereof, wherein $R^8$ and $R^9$ are each independently a straight or branched, saturated or unsaturated alkyl chain containing from 10 to 30 carbon atoms, wherein the alkyl chain is optionally interrupted by one or more ester bonds; and w has mean value ranging from 30 to 60.

In some of the foregoing embodiments of the PEGylated lipid according to Formula (LNP-IV), $R^8$ and $R^9$ are not both n-octadecyl when w is 42. In some other embodiments, $R^8$ and $R^9$ are each independently a straight or branched, saturated or unsaturated alkyl chain containing from 10 to 18 carbon atoms. In some embodiments, $R^8$ and $R^9$ are each independently a straight or branched, saturated or unsaturated alkyl chain containing from 12 to 16 carbon atoms. In some embodiments, $R^8$ and $R^9$ are each independently a straight or branched, saturated or unsaturated alkyl chain containing 12 carbon atoms. In some embodiments, $R^8$ and $R^9$ are each independently a straight or branched, saturated or unsaturated alkyl chain containing 14 carbon atoms. In other embodiments, $R^8$ and $R^9$ are each independently a straight or branched, saturated or unsaturated alkyl chain containing 16 carbon atoms. In still more embodiments, $R^8$ and $R^9$ are each independently a straight or branched, saturated or unsaturated alkyl chain containing 18 carbon atoms. In still other embodiments, $R^8$ is a straight or branched, saturated or unsaturated alkyl chain containing 12 carbon atoms and $R^9$ is a straight or branched, saturated or unsaturated alkyl chain containing 14 carbon atoms.

In various embodiments, w spans a range that is selected such that the PEG portion of the PEGylated lipid according to Formula (LNP-IV) has an average molecular weight of about 400 to about 6000 g/mol. In some embodiments, the average w is about 50.

In preferred embodiments of the second aspect, $R^8$ and $R^9$ of the PEGylated lipid according to Formula (LNP-IV) are saturated alkyl chains.

In a particularly preferred embodiment of the second aspect, the artificial RNA of the first aspect is complexed with one or more lipids thereby forming lipid nanoparticles (LNP), wherein the LNP additionally comprises a PEGylated lipid, wherein the PEG lipid is of Formula (LNP-IVa)

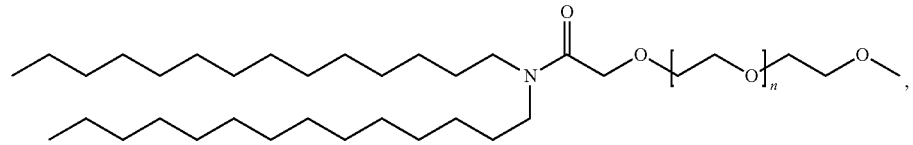
(LNP-IVa)

In preferred embodiments the artificial nucleic acid, preferably RNA of the first aspect is complexed with one or more lipids thereby forming lipid nanoparticles (LNP), wherein the LNP additionally comprises a PEGylated lipid with the Formula (LNP-IV):

wherein n has a mean value ranging from 30 to 60, such as about 28 to about 32, about 30 to about 34, 32 to about 36, about 34 to about 38, 36 to about 40, about 38 to about 42, 40 to about 44, about 42 to about 46, 44 to about 48, about 46 to about 50, 48 to about 52, about 50 to about 54, 52 to about 56, about 54 to about 58, 56 to about 60, about 58 to about 62. In preferred embodiments, n is about 45, 46, 47, 48, 49, 50, 51, 52, 53, 54. In a most preferred embodiment n has a mean value of 49.

In other embodiments, the PEGylated lipid has one of the following structures:

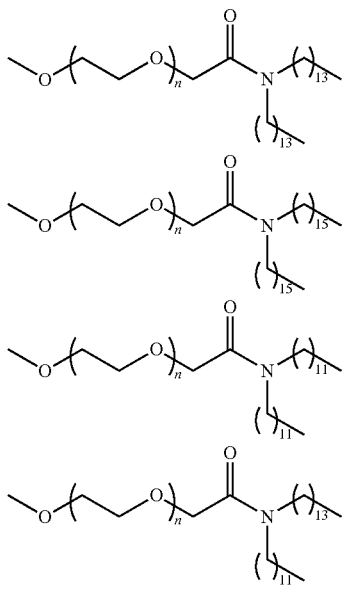

wherein n is an integer selected such that the average molecular weight of the PEGylated lipid is about 2500 g/mol, most preferably n is about 49.

Further examples of PEG-lipids suitable in that context are provided in US20150376115A1 and WO2015199952, each of which is incorporated by reference in its entirety.

In some embodiments, LNPs include less than about 3, 2, or 1 mole percent of PEG or PEG-modified lipid, based on the total moles of lipid in the LNP. In further embodiments, LNPs comprise from about 0.1% to about 20% of the PEG-modified lipid on a molar basis, e.g., about 0.5 to about 10%, about 0.5 to about 5%, about 10%, about 5%, about 3.5%, about 3%, about 2,5%, about 2%, about 1.5%, about 1%, about 0.5%, or about 0.3% on a molar basis (based on 100% total moles of lipids in the LNP). In preferred embodiments, LNPs comprise from about 1.0% to about 2.0% of the PEG-modified lipid on a molar basis, e.g., about 1.2 to about 1.9%, about 1.2 to about 1.8%, about 1.3 to about 1.8%, about 1.4 to about 1.8%, about 1.5 to about 1.8%, about 1.6 to about 1.8%, in particular about 1.4%, about 1.5%, about 1.6%, about 1.7%, about 1.8%, about 1.9%, most preferably 1.7% (based on 100% total moles of lipids in the LNP).

In various embodiments, the molar ratio of the cationic lipid to the PEGylated lipid ranges from about 100:1 to about 25:1.

LNP Composition

The composition of LNPs may be influenced by, inter alia, the selection of the cationic lipid component, the degree of cationic lipid saturation, the nature of the PEGylation, the ratio of all components and biophysical parameters such as its size. In one example by Semple et al. (Semple et al. Nature Biotech. 2010 28: 172-176; herein incorporated by reference in its entirety), the LNP composition was composed of 57.1% cationic lipid, 7.1% dipalmitoylphosphatidylcholine, 34.3% cholesterol, and 1.4% PEG-c-DMA (Basha et al. Mol Ther. 2011 19:2186-2200; herein incorporated by reference in its entirety).

LNPs may comprise from about 35 to about 45% cationic lipid, from about 40% to about 50% cationic lipid, from about 50% to about 60% cationic lipid and/or from about 55% to about 65% cationic lipid. The ratio of lipid to nucleic acid may range from about 5:1 to about 20: 1, from about 10:1 to about 25: 1, from about 15:1 to about 30: 1 and/or at least 30: 1.

The average molecular weight of the PEG moiety in the PEG-modified lipids can range from about 500 to about 8,000 Daltons (e.g., from about 1,000 to about 4,000 Daltons). In one preferred embodiment, the average molecular weight of the PEG moiety is about 2,000 Daltons.

The concentration of the aggregation reducing agent may range from about 0.1 to about 15 mol %, per 100% total moles of lipid in the LNP. In some embodiments, LNPs include less than about 3, 2, or 1 mole percent of PEG or PEG-modified lipid, based on the total moles of lipid in the LNP. In further embodiments, LNPs comprise from about 0.1% to about 20% of the PEG-modified lipid on a molar basis, e.g., about 0.5 to about 10%, about 0.5 to about 5%, about 10%, about 5%, about 3.5%, about 1.5%, about 0.5%, or about 0.3% on a molar basis (based on 100% total moles of lipids in the LNP).

Different LNPs having varying molar ratios of cationic lipid, non-cationic (or neutral) lipid, sterol (e.g., cholesterol), and aggregation reducing agent (such as a PEG-modified lipid) on a molar basis (based upon the total moles of lipid in the lipid nanoparticles) as depicted in Table 7 below. In preferred embodiments, the lipid nanoparticle formulation of the invention consists essentially of a lipid mixture in molar ratios of about 20-70% cationic lipid: 5-45% neutral lipid: 20-55% cholesterol, 0.5-15% PEG-modified lipid, more preferably in molar ratios of about 20-60% cationic lipid: 5-25% neutral lipid: 25-55% cholesterol: 0.5-15% PEG-modified lipid.

TABLE 7

Lipid-based formulations

Molar ratio of Lipids
(based upon 100% total moles of lipid in the lipid nanoparticle)

| # | Cationic Lipid | Non-Cationic (or Neutral) Lipid | Sterol | Aggregation Reducing Agent (e.g., PEG-lipid) |
|---|---|---|---|---|
| 1 | from about 35% to about 65% | from about 3% to about 12% or 15% | from about 15% to about 45% | from about 0.1% to about 10% (preferably from about 0.5% to about 2% or 3% |
| 2 | from about 20% to about 70% | from about 5% to about 45% | from about 20% to about 55% | from about 0.1% to about 10% (preferably from about 0.5% to about 2% or 3% |
| 3 | from about 45% to about 65% | from about 5% to about 10% | from about 5% to about 45% | from about 0.1% to about 3% |
| 4 | from about 20% to about 60% | from about 5% to about 25% | from about 25% to about 40% | from about 0.1% to about 5% (preferably from about 0.1% to about 3%) |
| 5 | about 40% | about 10% | from about 25% to about 55% | about 10% |

TABLE 7-continued

Lipid-based formulations

Molar ratio of Lipids
(based upon 100% total moles of lipid in the lipid nanoparticle)

| # | Cationic Lipid | Non-Cationic (or Neutral) Lipid | Sterol | Aggregation Reducing Agent (e.g., PEG-lipid) |
|---|---|---|---|---|
| 6 | about 35% | about 15% | | about 10% |
| 7 | about 52% | about 13% | | about 5% |
| 8 | about 50% | about 10% | | about 1.5% |

LNPs may occur as liposomes or lipoplexes as described in further detail below.

Preferably, lipid nanoparticles (LNPs) comprise: (a) at least one artificial nucleic acid, preferably RNA, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol.

In some embodiments, the LNPs comprise a lipid of Formula (LNP-III), an artificial nucleic acid, preferably RNA as defined above, a neutral lipid, a steroid and a PEGylated lipid. In preferred embodiments, the lipid of Formula (LNP-III) is lipid compound (LNP-III-3), the neutral lipid is DSPC, the steroid is cholesterol, and the PEGylated lipid is the compound of Formula (LNP-IVa).

In a preferred embodiment the LNP consists essentially of (i) at least one cationic lipid; (ii) a neutral lipid; (iii) a sterol, e.g., cholesterol; and (iv) a PEG-lipid, e.g. PEG-DMG or PEG-cDMA, in a molar ratio of about 20-60% cationic lipid:5-25% neutral lipid:25-55% sterol; 0.5-15% PEG-lipid.

In particularly preferred embodiments of the second aspect, the artificial nucleic acid, preferably RNA of the first aspect is complexed with one or more lipids thereby forming lipid nanoparticles (LNP), wherein the LNP essentially consists of
  (i) at least one cationic lipid as defined herein, preferably a lipid of Formula (LNP-III), more preferably lipid (LNP-III-3);
  (ii) a neutral lipid as defined herein, preferably 1,2-distearoyl-sn-glycero-3-phosphocholine (DSPC);
  (iii) a steroid or steroid analogue as defined herein, preferably cholesterol; and
  (iv) a PEG-lipid as defined herein, e.g. PEG-DMG or PEG-cDMA, preferably a PEGylated lipid of Formula (LNP-IVa),
  wherein (i) to (iv) are in a molar ratio of about 20-60% cationic lipid:5-25% neutral lipid:25-55% sterol; 0.5-15% PEG-lipid.

In one preferred embodiment, the lipid nanoparticle comprises: a cationic lipid with Formula (LNP-III) and/or PEG lipid with Formula (LNP-IV), optionally a neutral lipid, preferably 1,2-distearoyl-sn-glycero-3-phosphocholine (DSPC) and optionally a steroid, preferably cholesterol, wherein the molar ratio of the cationic lipid to DSPC is optionally in the range from about 2:1 to 8:1, wherein the molar ratio of the cationic lipid to cholesterol is optionally in the range from about 2:1 to 1:1.

In a particular preferred embodiment, the lipid nanoparticles (LNPs), have a molar ratio of approximately 50:10:38.5:1.5, preferably 47.5:10:40.8:1.7 or more preferably 47.4:10:40.9:1.7 (i.e. proportion (mol %) of cationic lipid (preferably lipid LNP-III-3), DSPC, cholesterol and PEG-lipid ((preferably PEG-lipid of Formula (LNP-IVa) with n=49); solubilized in ethanol).

The total amount of nucleic acid, preferably RNA in the lipid nanoparticles may vary and is defined depending on the e.g. RNA to total lipid w/w ratio. In one embodiment of the invention the artificial nucleic acid, preferably RNA to total lipid ratio is less than 0.06 w/w, preferably between 0.03 w/w and 0.04 w/w.

LNP Size

According to some embodiments, LNPs have a median diameter size of from about 50 nm to about 300 nm, such as from about 50 nm to about 250 nm, for example, from about 50 nm to about 200 nm.

According to some embodiments, smaller LNPs may be used. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um. In another embodiment, nucleic acids may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

According to some embodiments, the LNP may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

According to other embodiments, LNPs have a single mode particle size distribution (i.e., they are not bi- or poly-modal).

Other Components

LNPs may further comprise one or more lipids and/or other components in addition to those mentioned above.

Other lipids may be included in the liposome compositions for a variety of purposes, such as to prevent lipid oxidation or to attach ligands onto the liposome surface. Any of a number of lipids may be present in LNPs, including amphipathic, neutral, cationic, and anionic lipids. Such lipids can be used alone or in combination.

Additional components that may be present in a LNP include bilayer stabilizing components such as polyamide oligomers (see, e.g., U.S. Pat. No. 6,320,017, which is incorporated by reference in its entirety), peptides, proteins, and detergents.

Liposomes

In some embodiments, artificial nucleic acid molecules, preferably RNAs, or any other nucleic acid disclosed herein, are formulated/provided as liposomes.

Cationic lipid-based liposomes are able to complex with negatively charged nucleic acids (e.g. RNAs) via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the nucleic acid is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Liposomes typically consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposomes may have one or more lipid membranes. Liposomes can be single-layered, referred to as unilamellar, or multi-layered, referred to as multilamellar.

Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are typically present as spherical vesicles and can range in size from 20 nm to a few microns.

Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety. The artificial nucleic acid molecule, preferably RNA, of the invention, and/or any other nucleic acid disclosed herein, may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In some embodiments, the artificial nucleic acid molecule, preferably RNA, of the invention or any other nucleic acid disclosed herein herein, may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

Lipoplexes

According to some embodiments, artificial nucleic acid molecule, preferably RNAs, and/or any other nucleic acid disclosed herein, are provided/formulated as lipoplexes, i.e. cationic lipid bilayers sandwiched between nucleic acid layers.

Cationic lipids, such as DOTAP, (1,2-dioleoyl-3-trimethylammonium-propane) and DOTMA (N-[1-(2,3-dioleoyloxy)propyl]-N,N,N-trimethyl-ammonium methyl sulfate) can form complexes or lipoplexes with negatively charged nucleic acids to form nanoparticles by electrostatic interaction, providing high in vitro transfection efficiency.

Nanoliposomes

According to some embodiments, artificial nucleic acid molecule, preferably RNAs, or any other nucleic acid disclosed herein, are provided/formulated as neutral lipid-based nanoliposomes such as 1,2-dioleoyl-sn-glycero-3-phosphatidylcholine (DOPC)-based nanoliposomes (Adv Drug Deliv Rev. 2014 February; 66: 110-116.).

Emulsions

According to some embodiments, artificial nucleic acid molecule, preferably RNAs, and/or any other nucleic acid disclosed herein, are provided/formulated as emulsions. In another embodiment, said artificial nucleic acid molecule, preferably RNAs, or any other nucleic acid disclosed herein, are formulated in a cationic oil-in-water emulsion where the emulsion particle comprises an oil core and a cationic lipid which can interact with the nucleic acid(s) anchoring the molecule to the emulsion particle (see International Pub. No. WO2012006380; herein incorporated by reference in its entirety). In some embodiments, said artificial nucleic acid molecule, preferably RNA, or any other nucleic acid disclosed herein, is formulated in a water-in-oil emulsion comprising a continuous hydrophobic phase in which the hydrophilic phase is dispersed. As a non-limiting example, the emulsion may be made by the methods described in International Publication No. WO201087791, the contents of which are herein incorporated by reference in its entirety.

(Poly-)Cationic Compounds and Polymeric Carriers

According to preferred embodiments, the artificial nucleic acid molecule, preferably RNA, of the invention, and/or any other nucleic acid disclosed herein, is complexed or associated with a cationic or polycationic compound ("(poly-)cationic compound") and/or a polymeric carrier.

The term "(poly-)cationic compound" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4.

Accordingly, a "(poly-)cationic compound" may be any positively charged compound or polymer, preferably a cationic peptide or protein, which is positively charged under physiological conditions, particularly under physiological conditions in vivo. A "(poly-)cationic peptide or protein" may contain at least one positively charged amino acid, or more than one positively charged amino acid, e.g. selected from Arg, His, Lys or Orn, as described below.

(Poly-)Cationic Amino Acids, Peptides and Proteins (Poly-)cationic compounds being particularly preferred agents for complexation or association of the artificial nucleic acid molecule, preferably RNA, of the invention, or any other nucleic acid disclosed herein, include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, or histones. More preferably, the artificial nucleic acid molecule, preferably RNA, of the invention, or any other nucleic acid disclosed herein, is complexed with protamine or oligofectamine, most preferably with protamine. Alternatively or additionally, such cationic or polycationic peptides or proteins may be selected from proteins or peptides of the following general formula (CAT-I):

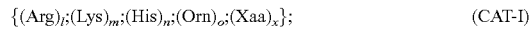

{(Arg)$_l$;(Lys)$_m$;(His)$_n$;(Orn)$_o$;(Xaa)$_x$}; (CAT-I)

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. Arg$_7$, Arg$_8$, Arg$_9$, H$_3$R$_9$, R$_9$H$_3$, H$_3$R$_9$H$_3$, YSSR$_9$SSY, (RKH)$_4$, Y(RKH)$_2$R, etc.

In this context the disclosure of WO 2009/030481 is incorporated herewith by reference.

(Poly-)Cationic Polysaccharides

Further preferred (poly-)cationic compounds for complexation of or association with the artificial nucleic acid molecule, preferably RNA, of the invention or any other nucleic acid disclosed herein include (poly-)cationic polysaccharides, e.g. chitosan, polybrene, cationic polymers, e.g. polyethyleneimine (PEI).

(Poly-)Cationic Lipids

Further preferred (poly-)cationic compounds for complexation of or association with the artificial nucleic acid molecule, preferably RNA, of the invention or any other nucleic acid disclosed herein include (poly-)cationic lipids, e.g. DOTMA: [1-(2,3-sioleyloxy)propyl)]-N,N,N-trimethyl-ammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(alpha-trimethylammonio-acetyl)-diethanolamine chloride, CLIP1: rac-[(2,3-dioctadecyloxypropyl)(2-hydroxyethyl)]-dimethylammonium chloride, CLIP6: rac-[2(2,3-dihexadecyloxy-propyl-oxymethyloxy)ethyl]trimethylammonium, CLIP9: rac-[2(2,3-dihexadecyl-oxypropyl-oxysuccinyloxy)ethyl]-trimethylammonium, or oligofectamine.

(Poly-)Cationic Polymers

Further preferred (poly-)cationic compounds for complexation of or association with the artificial nucleic acid molecule, preferably RNA, of the invention or any other nucleic acid disclosed herein, include (poly-)cationic polymers, e.g. modified polyaminoacids, such as beta-amino acid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., or block polymers consisting of a combination of one or more cationic blocks (e.g. selected from a cationic polymer as mentioned above) and of one or more hydrophilic or hydrophobic blocks (e.g. polyethyleneglycole).

Polymeric Carriers

According to preferred embodiments, artificial nucleic acid molecule, preferably RNA, of the invention or any other nucleic acid disclosed herein, may be complexed or associated with a polymeric carrier.

A "polymeric carrier" used according to the invention might be a polymeric carrier formed by disulfide-crosslinked cationic components. The disulfide-crosslinked cationic components may be the same or different from each other. The polymeric carrier may also contain further components.

It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO 2012/013326 is incorporated herewith by reference.

In this context, the cationic components, which form basis for the polymeric carrier by disulfide-crosslinkage, are typically selected from any suitable (poly-)cationic peptide, protein or polymer suitable for this purpose, particular any (poly-)cationic peptide, protein or polymer capable of complexing, and thereby preferably condensing, the artificial nucleic acid molecule, preferably RNA, of the invention, or any other nucleic acid as disclosed herein. The (poly-)cationic peptide, protein or polymer, is preferably a linear molecule, however, branched (poly-)cationic peptides, proteins or polymers may also be used.

Every disulfide-crosslinking (poly-)cationic protein, peptide or polymer of the polymeric carrier, which may be used to complex the artificial nucleic acid molecule, preferably RNA, or any other nucleic acid disclosed herein, preferably contains at least one —SH moiety, most preferably at least one cysteine residue or any further chemical group exhibiting an —SH moiety, capable of forming a disulfide linkage upon condensation with at least one further (poly-)cationic protein, peptide or polymer as cationic component of the polymeric carrier as mentioned herein. The polymeric carrier, which may be used to complex the artificial nucleic acid molecule, preferably RNA, of the invention, or any other nucleic acid disclosed herein, may thus preferably be formed by disulfide-crosslinked (poly-)cationic components Polymeric Carriers Comprising (Poly-)Cationic Peptides or Proteins According to one first alternative, at least one (poly-)cationic component of the polymeric carrier, which may be used to complex the artificial nucleic acid molecule, preferably RNA, or any other nucleic acid disclosed herein, may be selected from (poly-)cationic peptides or proteins. Such (poly-)cationic peptides or proteins preferably exhibit a length of about 3 to 100 amino acids, preferably a length of about 3 to 50 amino acids, more preferably a length of about 3 to 25 amino acids, e.g. a length of about 3 to 10, 5 to 15, 10 to 20 or 15 to 25 amino acids. Alternatively or additionally, such (poly-)cationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier comprises a (poly-)cationic peptide or protein, the cationic properties of the (poly-)cationic peptide or protein or of the entire polymeric carrier, if the polymeric carrier is entirely composed of (poly-)cationic peptides or proteins, may be determined upon its content of cationic amino acids. Preferably, the content of cationic amino acids in the (poly-)cationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the aforementioned values, provided, that the content of all amino acids, e.g. cationic, lipophilic, hydrophilic, aromatic and further amino acids, in the (poly-)cationic peptide or protein, or in the entire polymeric carrier, if the polymeric carrier is entirely composed of cationic or polycationic peptides or proteins, is 100%.

According to a preferred embodiment, the (poly-)cationic peptide or protein of the polymeric carrier, when defined according to formula $\{(Arg)_l; (Lys)_m; (His)_n; (Orn)_o; (Xaa)_x\}$ (formula (CAT-I)) as shown above and which comprise or are additionally modified to comprise at least one —SH moeity, may be, without being restricted thereto, selected from subformula (CAT-Ia):

$$\{(Arg)_l;(Lys)_m;(His)_n;(Orn)_o;(Xaa')_x(Cys)_y\} \quad \text{(CAT-Ia)}$$

wherein $(Arg)_l$; $(Lys)_m$; $(His)_n$; $(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the (poly-)cationic peptide or protein of the polymeric carrier, e.g. when defined according to empirical formula $(Arg)_l$; $(Lys)_m$; $(His)_n$; $(Orn)_o$; $(Xaa)_x$ (formula (CAT-I)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

Examples may comprise any of the following sequences: Cys($Arg_7$) (SEQ ID NO: 3048), Cys($Arg_8$) (SEQ ID NO: 3049), Cys($Arg_9$) (SEQ ID NO: 3050), Cys($Arg_{10}$) (SEQ ID NO: 3051), Cys($Arg_{11}$) (SEQ ID NO: 3052), Cys($Arg_{12}$) (SEQ ID NO: 3047), Cys($Arg_{13}$) (SEQ ID NO: 3053), Cys($Arg_{14}$) (SEQ ID NO: 3054), Cys($Arg_{15}$) (SEQ ID NO: 3055), Cys($Arg_{16}$) (SEQ ID NO: 3056), Cys($Arg_{17}$) (SEQ ID NO: 3057), Cys($Arg_{18}$) (SEQ ID NO: 3058), Cys($Arg_{19}$) (SEQ ID NO: 3059), Cys($Arg_{20}$) (SEQ ID NO: 3060).

According to another particularly preferred embodiment, the (poly-)cationic peptide or protein of the polymeric carrier, when defined according to formula $\{(Arg)_l; (Lys)_m; (His)_n; (Orn)_o; (Xaa)_x\}$ (formula (CAT-I)) as shown above, may be, without being restricted thereto, selected from subformula (CAT-Ib):

$$\text{Cys1}\{(Arg)_l;(Lys)_m;(His)_n;(Orn)_o;(Xaa)_x\}\text{Cys2} \quad \text{(CAT-Ib)}$$

wherein empirical formula $\{(Arg)_l; (Lys)_m; (His)_n; (Orn)_o; (Xaa)_x\}$ (formula (CAT-I) is as defined herein and forms a core of an amino acid sequence according to (semiempirical) formula (CAT-II) and wherein Cys1 and Cys2 are cysteines proximal to, or terminal to $(Arg)_l$; $(Lys)_m$; $(His)_n$; $(Orn)_o$; $(Xaa)_x$. Examples may comprise any of the above sequences flanked by two Cys and following sequences:

Cys($Arg_7$)Cys (SEQ ID NO: 3033), Cys($Arg_8$)Cys (SEQ ID NO: 3034), Cys($Arg_9$)Cys (SEQ ID NO: 3035), Cys($Arg_{10}$)Cys (SEQ ID NO: 3036), Cys($Arg_{11}$)Cys (SEQ ID NO: 3037), Cys($Arg_{12}$)Cys (SEQ ID NO: 3046), Cys($Arg_{13}$)Cys (SEQ ID NO: 3038), Cys($Arg_{14}$)Cys (SEQ ID NO: 3039), Cys($Arg_{15}$)Cys (SEQ ID NO: 3040), Cys($Arg_{16}$)Cys (SEQ ID NO: 3041), Cys($Arg_{17}$)Cys (SEQ ID NO: 3042), Cys($Arg_{18}$)Cys (SEQ ID NO: 3043), Cys($Arg_{19}$)Cys (SEQ ID NO: 3044), Cys($Arg_{20}$)Cys (SEQ ID NO: 3045).

This embodiment may apply to situations, wherein the (poly-)cationic peptide or protein of the polymeric carrier, e.g. when defined according to empirical formula $(Arg)_l$; $(Lys)_m$; $(His)_n$; $(Orn)_o$; $(Xaa)_x$ (CAT-I) as shown above, has been modified with at least two cysteines as —SH moieties in the above meaning such that the cationic or polycationic peptide of the polymeric carrier cargo complex as cationic component carries at least two (terminal) cysteines, which are capable to form a disulfide bond with other components of the polymeric carrier.

In a preferred embodiment, the polymeric carrier is formed by, comprises or consists of the peptide CysArg$_{12}$Cys (CRRRRRRRRRRRRC) (SEQ ID NO: 3046) or CysArg$_{12}$ (CRRRRRRRRRRRR) (SEQ ID NO: 3047).

Polymeric Carriers Comprising Non-Peptidic Polymers

According to a second alternative, at least one (poly-)cationic component of the polymeric carrier may be selected from e.g. any (non-peptidic) (poly-)cationic polymer suitable in this context, provided that this (non-peptidic) (poly-)cationic polymer exhibits or is modified to exhibit at least one —SH-moiety, which provides for a disulfide bond linking the (poly-)cationic polymer with another component of the polymeric carrier as defined herein. Thus, likewise as defined herein, the polymeric carrier may comprise the same or different (poly-)cationic polymers.

In the specific case that the cationic component of the polymeric carrier comprises a (non-peptidic) (poly-)cationic polymer the cationic properties of the (non-peptidic) (poly-)cationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a (poly-)cationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) (poly-)cationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO 2012/013326 is incorporated herewith by reference.

In this context, the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex the artificial nucleic acid molecule, preferably RNA, of the invention and/or any other nucleic acid disclosed herein for use as described herein, and thereby preferably condensing said artificial nucleic acid, and/or said other nucleic acid. The cationic or polycationic peptide, protein or polymer, is preferably a linear molecule. However, branched cationic or polycationic peptides, proteins or polymers may also be used.

Every disulfide-crosslinking cationic or polycationic protein, peptide or polymer of the polymeric carrier, which may be used to complex the artificial nucleic acid molecule, preferably RNA, of the invention and/or any other nucleic acid disclosed herein for use as described herein contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the artificial nucleic acid molecule, preferably RNA, of the invention and/or any other nucleic acid disclosed herein for use as described herein may be formed by disulfide-crosslinked cationic (or polycationic) components.

A complex of a nucleic acid, such as the artificial nucleic acid, preferably RNA, of the invention and/or any other nucleic acid disclosed herein for use as described herein, complexed with such polymeric carriers are also referred to herein as "polymeric carrier cargo complexes". According to preferred embodiments, the artificial nucleic acid molecule, preferably RNA, of the invention or any other nucleic acid disclosed herein (preferably an isRNA, preferably comprising or consisting of an RNA sequence corresponding to SEQ ID NO: 2938-3032), may be provided in the form of a polymeric carrier cargo complex, formed by a polymeric carrier, preferably comprising disulfide-crosslinked cationic peptides, preferably Cys-Arg$_{12}$, and/or Cys-Arg$_{12}$-Cys, and said artificial nucleic acid molecule, preferably RNA, or said other nucleic acid.

According to further embodiments, the polymeric carrier may be selected from a polymeric carrier molecule according to generic formula (CAT-II):

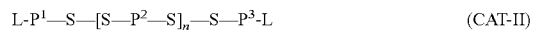
$$L\text{-}P^1\text{---}S\text{---}[S\text{---}P^2\text{---}S]_n\text{---}S\text{---}P^3\text{-}L \qquad (\text{CAT-II})$$

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), (AA)$_x$, or [(AA)$_x$]z if such components are used as a linker between $P^1$ and $P^2$ or $P^3$ and $P^2$) and/or with further components (e.g. (AA), (AA)$_x$, [(AA)$_x$]$_z$ or L), the linear or branched hydrophilic polymer chain selected independent from each other from polyethylene glycol (PEG), poly-N-(2-hydroxypropyl) methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a (poly-)cationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a (poly-)cationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context, the disclosure of WO 2011/026641 is incorporated herewith by reference. Each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (CAT-II) above (the brackets are omitted for better readability), wherein any of S, $P^1$ and $P^3$ are as defined herein, typically represent a situation, wherein one-SH-moiety of hydrophilic polymers $P^1$ and $P^3$ was condensed with one —SH-moiety of component $P^2$ of generic formula (CAT-II) above, wherein both sulphurs of these —SH-moieties form a disulfide bond —S—S— as defined herein in formula (CAT-II). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (CAT-II) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g. maleinimide moieties, α,β-unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

Weight Ratio and N/P Ratio

In some embodiments of the invention, the artificial nucleic acid molecule, preferably RNA (or said other nucleic acid) is associated with or complexed with a (poly-)cationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of nucleic acid to (poly-)cationic compound and/or polymeric carrier; or optionally in a nitrogen/phosphate (N/P) ratio of nucleic acid to (poly-)cationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9. More preferably, the N/P ratio of the at least one artificial nucleic acid molecule, preferably RNA, to the one or more polycations is in the range of about 0.1 to 10, including a range of about 0.3 to 4, of about 0.5 to 2, of about 0.7 to 2 and of about 0.7 to 1.5.

The artificial nucleic acid molecule, preferably RNA, of the invention can also be associated with a vehicle, transfection or complexation agent for increasing the transfection efficiency of said artificial nucleic acid molecule, preferably RNA. In this context, it is particularly preferred that the inventive (pharmaceutical) composition comprises the artificial nucleic acid molecule, preferably RNA that is complexed at least partially with a (poly-)cationic compound and/or a polymeric carrier, preferably cationic proteins or peptides. In this context, the disclosure of WO 2010/037539 and WO 2012/113513 is incorporated herewith by reference. "Partially" means that only a part of said artificial nucleic acid molecule, preferably RNA is complexed with a (poly-)cationic compound and/or polymeric carrier, while the rest of said artificial nucleic acid molecule, preferably RNA is present in uncomplexed form ("free").

Preferably, the molar ratio of the complexed artificial nucleic acid molecule, preferably RNA to the free artificial nucleic acid molecule, preferably RNA is selected from a molar ratio of about 0.001:1 to about 1:0.001, including a ratio of about 1:1. More preferably the ratio of complexed artificial nucleic acid molecule, preferably RNA to free artificial nucleic acid molecule, preferably RNA is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed artificial nucleic acid molecule, preferably RNA to free artificial nucleic acid molecule, preferably RNA is selected from a ratio of about 1:1 (w/w).

The complexed artificial nucleic acid molecule, preferably RNA, of the invention is preferably prepared according to a first step by complexing the artificial nucleic acid molecule, preferably RNA with a (poly-)cationic compound and/or with a polymeric carrier, preferably as defined herein, in a specific ratio to form a stable complex. In this context, it is highly preferable, that no free (poly-)cationic compound or polymeric carrier or only a negligibly small amount thereof remains in the fraction of the complexed artificial nucleic acid molecule, preferably RNA after complexing said artificial nucleic acid molecule, preferably RNA. Accordingly, the ratio of the artificial nucleic acid molecule, preferably RNA and the (poly-)cationic compound and/or the polymeric carrier in the fraction of the complexed RNA is typically selected in a range so that the artificial nucleic acid molecule, preferably RNA is entirely complexed and no free (poly-)cationic compound or polymeric carrier or only a negligibly small amount thereof remains in said fraction.

Preferably, the ratio of the artificial nucleic acid molecule, preferably RNA, to the (poly-)cationic compound and/or the polymeric carrier, preferably as defined herein, is selected from a range of about 6:1 (w/w) to about 0,25:1 (w/w), more preferably from about 5:1 (w/w) to about 0,5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

Alternatively, the ratio of the artificial nucleic acid molecule, preferably RNA, to the (poly-)cationic compound and/or the polymeric carrier may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of artificial nucleic acid molecule, preferably RNA, to (poly-)cationic compound and/or polymeric carrier, preferably as defined herein, in the complex, and most preferably in a range of about 0.7-1,5, 0.5-1 or 0.7-1, and even most preferably in a range of about 0.3-0.9 or 0.5-0.9, preferably provided that the (poly-)cationic compound in the complex is a (poly-)cationic protein or peptide and/or the polymeric carrier as defined above.

In other embodiments, artificial nucleic acid molecule, preferably RNA, may be provided and used in free or naked form without being associated with any further vehicle, transfection or complexation agent.

(Pharmaceutical) Composition

In a further aspect, the present invention provides a composition comprising the artificial nucleic acid molecule, preferably RNA, according to the invention, and at least one pharmaceutically acceptable carrier and/or excipient. The composition according to the invention is preferably provided as a pharmaceutical composition or as a vaccine.

A "vaccine" is typically understood to be a prophylactic or therapeutic material providing at least one antigen, preferably an antigenic peptide or protein. "Providing at least on antigen" means, for example, that the vaccine comprises the antigen or that the vaccine comprises a molecule that, e.g., codes for the antigen.

The (pharmaceutical) composition or vaccine according to the invention comprises at least one artificial nucleic acid molecule, preferably RNA, comprising at least one coding sequence encoding an antigenic peptide or protein. Said antigenic peptide or protein may preferably be derived from a tumor antigen, a bacterial, viral, fungal or protozoal antigen, an autoantigen, an allergen, or an allogenic antigen. Its expression and presentation to the immune system may preferably induce an immune response towards the tumor antigen, or the bacterial, viral, fungal or protozoal antigen, or may induce immune tolerance towards the autoantigen, allergen or allogenic antigen.

The (pharmaceutical) composition or vaccines of the invention preferably comprises at least one, preferably a plurality of at least two artificial nucleic acid molecules, preferably RNAs, as described herein. Said plurality of at least two artificial nucleic acid molecules, preferably RNAs, may be monocistronic, bicistronic or multicistronic as described herein.

Each of the artificial nucleic acid molecules, preferably RNAs, of the (pharmaceutical) composition or vaccine of the invention may encode at least one, or a plurality of at least two (identical or different) antigenic fusion proteins as defined herein. "Different" artificial nucleic acid species in a pharmaceutical composition may encode "different" $IRST_{epm}$-derived amino acid sequences, "different" signal peptides, "different" T helper epitopes, "different" linkers, or preferably "different" antigenic peptides or proteins"

Accordingly, in some embodiments of the invention, the (pharmaceutical) composition or vaccine of the invention comprises a plurality of at least two artificial nucleic acid molecules, preferably RNAs, as described herein, wherein preferably at least two of said plurality of artificial nucleic acid molecules encode a different antigenic peptide or protein, preferably as described herein, or fragment, variant or derivative thereof.

The (pharmaceutical) composition or vaccine of the invention may further comprise at least one pharmaceutically acceptable excipient, carrier, adjuvant or further component (e.g. additional active agents, and the like), as described herein.

Pharmaceutically Acceptable Excipients and Carriers

Preferably, the (pharmaceutical) composition according to the invention comprises at least one pharmaceutically acceptable carrier and/or excipient. The term "pharmaceutically acceptable" refers to a compound or agent that is compatible with the one or more active agent(s) (here: artificial nucleic acid molecule, preferably RNA) and does not interfere with and/or substantially reduce their pharmaceutical activities. Pharmaceutically acceptable carriers and/or excipient preferably have sufficiently high purity and sufficiently low toxicity to make them suitable for administration to a subject to be treated.

Excipients

Pharmaceutically acceptable excipients can exhibit different functional roles and include, without limitation, diluents, fillers, bulking agents, carriers, disintegrants, binders, lubricants, glidants, coatings, solvents and co-solvents, buffering agents, preservatives, adjuvants, anti-oxidants, wetting agents, anti-foaming agents, thickening agents, sweetening agents, flavouring agents and humectants.

For (pharmaceutical) compositions in liquid form, useful pharmaceutically acceptable excipients in general include solvents, diluents or carriers such as (pyrogen-free) water, (isotonic) saline solutions such phosphate or citrate buffered saline, fixed oils, vegetable oils, such as, for example, groundnut oil, cottonseed oil, sesame oil, olive oil, corn oil, ethanol, polyols (for example, glycerol, propylene glycol, polyetheylene glycol, and the like); lecithin; surfactants; preservatives such as benzyl alcohol, parabens, chlorobutanol, phenol, ascorbic acid, thimerosal, and the like; isotonic agents such as sugars, polyalcohols such as manitol, sorbitol, or sodium chloride; aluminum monostearate or gelatin; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. Buffers may be hypertonic, isotonic or hypotonic with reference to the specific reference medium, i.e. the buffer may have a higher, identical or lower salt content with reference to the specific reference medium, wherein preferably such concentrations of the aforementioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

For (pharmaceutical) compositions in (semi-)solid form, useful pharmaceutically acceptable excipients include binders such as microcrystalline cellulose, gum tragacanth or gelatin; starch or lactose; sugars, such as, for example, lactose, glucose and sucrose; starches, such as, for example, corn starch or potato starch; cellulose and its derivatives, such as, for example, sodium carboxymethylcellulose, ethylcellulose, cellulose acetate; disintegrants such as alginic acid; lubricants such as magnesium stearate; glidants such as stearic acid, magnesium stearate; calcium sulphate, colloidal silicon dioxide and the like; sweetening agents such as sucrose or saccharin; and/or flavoring agents such as peppermint, methyl salicylate, or orange flavoring.

Carriers

Suitable pharmaceutically acceptable carriers are typically chosen based on the formulation of the (pharmaceutical) composition.

Liquid (pharmaceutical) compositions administered via injection and in particular via i.v. injection should be sterile and stable under the conditions of manufacture and storage. Such compositions are typically formulated as parenterally acceptable aqueous solutions that are pyrogen-free, have suitable pH, are isotonic and maintain stability of the active ingredient(s).

Particularly useful pharmaceutically acceptable carriers for liquid (pharmaceutical) compositions according to the invention include water, typically pyrogen-free water; isotonic saline or buffered (aqueous) solutions, e.g phosphate, citrate etc. buffered solutions. Particularly for injection of the inventive (pharmaceutical) compositions, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt.

According to preferred embodiments, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, K2CO3, $KHCO_3$, $K_2SO_4$, and examples of calcium salts include e.g. $CaCl_2$, $CaI_2$, $CaBr_2$, $CaCO_3$, CaSO4, $Ca(OH)_2$. Furthermore, organic anions of the aforementioned cations may be contained in the buffer.

According to more preferred embodiments, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride (CaCl$_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

Complexation

The artificial nucleic acid molecule, preferably RNA, of the invention, and/or optionally any other nucleic acid, forming part of the inventive (pharmaceutical) composition or vaccine may be provided in "complexed" or "naked" form as described elsewhere herein, or a mixture thereof.

According to preferred embodiments, the artificial nucleic acid molecule(s), preferably RNA(s), of the (pharmaceutical) composition or vaccine of the invention, or any other nucleic acid disclosed herein, is/are complexed with one or more cationic or polycationic compounds, preferably with cationic or polycationic polymers, cationic or polycationic peptides or proteins, e.g. protamine, cationic or polycationic polysaccharides and/or cationic or polycationic lipids.

Means and methods for providing "complexed" artificial nucleic acid molecules, preferably RNAs, are described in the section headed "Complexation" and are equally applicable to the (pharmaceutical) compositions and vaccines of the invention, mutatis mutandis. Specifically, artificial nucleic acid molecule(s), preferably RNA(s), and/or optionally any other nucleic acid, forming part of the inventive (pharmaceutical) composition or vaccine may be complexed with lipids, (poly-)cationic compounds and carriers, preferably selected from (poly-)cationic amino acids, peptides and proteins, (poly-)cationic polysaccharides, (poly-)cationic lipids, (poly-)cationic polymers, or polymeric carriers as described above.

According to preferred embodiments, the artificial nucleic acid molecule(s), preferably RNA(s), and/or optionally any other nucleic acid, forming part of the inventive (pharmaceutical) composition or vaccine may be complexed with a polymeric carrier formed by disulfide-crosslinked cationic components, preferably disulfide-crosslinked cationic peptides, preferably comprising peptides according to formula (CAT-I), (CAT-Ia) and/or (CAT-Ib) and/or a compound according to formula (Cat-II) (L-P$^1$—S—[S—P$^2$—S]n-S—P$^3$-L) as described above.

Formulation

Generally, (pharmaceutical) compositions for topical administration can be formulated as creams, ointments, gels, pastes or powders. (Pharmaceutical) compositions for oral administration can be formulated as tablets, capsules, liquids, powders or in a sustained release format. However, according to preferred embodiments, the inventive (pharmaceutical) composition is administered parenterally, in particular via intradermal or intramuscular injection, and is accordingly formulated in liquid or lyophilized form for parenteral administration as discussed elsewhere herein. Parenteral formulations are typically stored in vials, IV bags, ampoules, cartridges, or prefilled syringes and can be administered as injections, inhalants, or aerosols, with injections being preferred.

Lyophilized Formulations

In further preferred embodiments, the (pharmaceutical) composition or vaccine is provided in lyophilized form. Preferably, the lyophilized (pharmaceutical) composition or vaccine is reconstituted in a suitable buffer, advantageously based on an aqueous carrier, prior to administration, e.g. Ringer-Lactate solution, which is preferred, Ringer solution, a phosphate buffer solution. In some embodiments, the (pharmaceutical) composition according to the invention contains at least two, three, four, five, six or more artificial nucleic acid molecules, preferably RNAs, which are provided separately in lyophilized form (optionally together with at least one further additive) and which are preferably reconstituted separately in a suitable buffer (such as Ringer-Lactate solution) prior to their use so as to allow individual administration of each of said artificial nucleic acid molecule, preferably RNAs.

Liquid Formulations

In further preferred embodiments, the (pharmaceutical) composition is provided in the form of a saline or a lipid-based formulation. Lipid-based formulations may comprise liposomes, lipoplexes, nanoliposomes and lipid nanoparticles which are described above in the section headed "Complexation".

Adjuvants

According to further embodiments, the (pharmaceutical) composition or vaccine of the invention may further comprise at least one adjuvant.

An "adjuvant" or "adjuvant component" in the broadest sense is typically a pharmacological and/or immunological agent that may modify, e.g. enhance, the effect of other active agents, e.g. therapeutic agents or vaccines. In this context, an "adjuvant" may be understood as any compound, which is suitable to support administration and delivery of the composition according to the invention. Specifically, an adjuvant may preferably enhance the immunostimulatory properties of the (pharmaceutical) composition or vaccine to which it is added. Furthermore, such adjuvants may, without being bound thereto, initiate or increase an immune response of the innate immune system, i.e. a non-specific immune response.

"Adjuvants" typically do not elicit an adaptive immune response. Insofar, "adjuvants" do not qualify as antigens. In other words, when administered, the inventive (pharmaceutical) composition or vaccine typically initiates an adaptive immune response due to an antigenic peptide or protein, which is encoded by the at least one coding sequence of the artificial nucleic acid molecule, preferably RNA, contained in said (pharmaceutical) composition or vaccine. Additionally, an adjuvant present in the (pharmaceutical) composition or vaccine may generate an (supportive) innate immune response.

Suitable adjuvants may be selected from any adjuvant known to a skilled person and suitable for the present case, i.e. supporting the induction of an immune response in a mammal, and include, without limitation, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i)N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXOR-IBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA720™ (metabolisable oil adjuvant); MPL™ (3-Q-desacyl-4"-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Suitable adjuvants may also be selected from (poly-)cationic compounds as described herein as complexation agents (cf. section headed "complexation"), in particular the (poly-)cationic peptides or proteins, (poly-)cationic polysaccharides, (poly-)cationic lipids, or polymeric carriers described herein. Associating or complexing the artificial nucleic acid molecule of the (pharmaceutical) composition or vaccine with (poly-)cationic compounds as defined may preferably provide adjuvant properties and confer a stabilizing effect.

The ratio of the artificial nucleic acid molecule, preferably RNA, to the (poly-)cationic compound in the adjuvant component may be calculated on the basis of the nitrogen/phosphate ratio (N/P-ratio) of the entire complex, i.e. the ratio of positively charged (nitrogen) atoms of the (poly-)cationic compound to the negatively charged phosphate atoms of the artificial nucleic acid molecule, preferably RNA.

In the following, when referring to "RNA", it will be understood that the respective disclosure is applicable to other artificial nucleic acid molecules as well, mutatis mutandis.

For example, 1 μg of RNA may contain about 3 nmol phosphate residues, provided said RNA exhibits a statistical distribution of bases. Additionally, 1 μg of peptide typically contains about x nmol nitrogen residues, dependent on the molecular weight and the number of basic amino acids. When exemplarily calculated for $(Arg)_9$ (molecular weight 1424 g/mol, 9 nitrogen atoms), 1 μg $(Arg)_9$ contains about 700 pmol $(Arg)_9$ and thus 700×9=6300 pmol basic amino acids=6.3 nmol nitrogen atoms. For a mass ratio of about 1:1 RNA/(Arg)9 an N/P ratio of about 2 can be calculated. When exemplarily calculated for protamine (molecular weight about 4250 g/mol, 21 nitrogen atoms, when protamine from salmon is used) with a mass ratio of about 2:1 with 2 μg of RNA, 6 nmol phosphate are to be calculated for the RNA; 1 μg protamine contains about 235 pmol protamine molecules and thus 235×21=4935 pmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.1-10, preferably in a range of about 0.3-4 and most preferably in a range of about 0.5-2 or 0.7-2 regarding the ratio of RNA:peptide in the complex, and most preferably in the range of about 0.7-1.5.

The (pharmaceutical) composition or vaccine of the present invention may be obtained in two separate steps in order to obtain both, an efficient immunostimulatory effect and efficient translation of the artificial nucleic acid molecule, preferably RNA, comprised in said (pharmaceutical) composition or vaccine.

In a first step, an RNA is complexed with a (poly-)cationic compound in a specific ratio to form a stable complex ("complexed (RNA)"). In this context, it is important, that no free (poly-)cationic compound or only a negligibly small amount remains in the fraction of the complexed RNA. Accordingly, the ratio of the RNA and the (poly-)cationic compound is typically selected in a range that the RNA is entirely complexed and no free (poly-)cationic compound or only a neglectably small amount remains in the composition. Preferably the ratio of the RNA to the (poly-)cationic compound is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

In a second step, an RNA is added to the complexed RNA in order to obtain the (pharmaceutical) composition or vaccine of the invention. Therein, said added RNA is present as free RNA, preferably as free mRNA, which is not complexed by other compounds. Prior to addition, the free RNA is not complexed and will preferably not undergo any detectable or significant complexation reaction upon the addition to the complexed RNA. This is due to the strong binding of the (poly-)cationic compound to the complexed RNA. In other words, when the free RNA is added to the complexed RNA, preferably no free or substantially no free (poly-)cationic compound is present, which could form a complex with said free RNA. Accordingly, the free RNA of the inventive (pharmaceutical) composition or vaccine can efficiently be transcribed in vivo.

It may be preferred that the free RNA may be identical or different to the complexed RNA, depending on the specific requirements of therapy. Even more preferably, the free RNA, which is comprised in the inventive combination, (pharmaceutical) composition or vaccine, is identical to the complexed RNA, in other words, the combination, (pharmaceutical) composition or vaccine comprises an otherwise identical RNA in both free and complexed form.

In particularly preferred embodiments, the inventive (pharmaceutical) composition or vaccine thus comprises the RNA as defined herein, wherein said RNA is present in said (pharmaceutical) composition or vaccine partially as free RNA and partially as complexed RNA. Preferably, the RNA as defined herein, preferably an mRNA, is complexed as described above and the same (m)RNA is then added in the form of free RNA, wherein preferably the compound, which is used for complexing the epitope-encoding RNA is not present in free form in the composition at the moment of addition of the free RNA.

The ratio of the complexed RNA and the free RNA may be selected depending on the specific requirements of a particular therapy. Typically, the ratio of the complexed RNA and the free RNA is selected such that a significant stimulation of the innate immune system is elicited due to the presence of the complexed RNA. In parallel, the ratio is selected such that a significant amount of the free RNA can be provided in vivo leading to an efficient translation and concentration of the expressed antigenic fusion protein in vivo. Preferably the ratio of the complexed RNA to free RNA in the inventive (pharmaceutical) composition or vaccine is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably about 1:1 (w/w).

Additionally or alternatively, the ratio of the complexed RNA and the free RNA may be calculated on the basis of the nitrogen/phosphate ratio (N/P-ratio) of the entire RNA complex. In the context of the present invention, an N/P-ratio is preferably in the range of about 0.1-10, preferably in a range of about 0.3-4 and most preferably in a range of about 0.5-2 or 0.7-2 regarding the ratio of RNA:peptide in the complex, and most preferably in the range of about 0.7-1.5.

Additionally or alternatively, the ratio of the complexed RNA and the free RNA may also be selected on the basis of the molar ratio of both RNAs to each other. Typically, the molar ratio of the complexed RNA to the free RNA may be selected such, that the molar ratio suffices the above (w/w) and/or N/P-definitions. More preferably, the molar ratio of the complexed RNA to the free RNA may be selected e.g. from a molar ratio of about 0.001:1, 0.01:1, 0.1:1, 0.2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4, 1:0.3, 1:0.2, 1:0.1, 1:0.01, 1:0.001, etc. or from any range formed by any two of the above values, e.g. a range selected from about 0.001:1 to 1:0.001, including a range of about 0.01:1 to 1:0.001, 0.1:1 to 1:0.001, 0.2:1 to 1:0.001, 0.3:1 to 1:0.001, 0.4:1 to 1:0.001, 0.5:1 to 1:0.001, 0.6:1 to 1:0.001, 0.7:1 to 1:0.001, 0.8:1 to 1:0.001, 0.9:1 to 1:0.001, 1:1 to 1:0.001, 1:0.9 to 1:0.001, 1:0.8 to 1:0.001, 1:0.7 to 1:0.001, 1:0.6 to 1:0.001, 1:0.5 to 1:0.001, 1:0.4 to 1:0.001, 1:0.3 to 1:0.001, 1:0.2 to 1:0.001, 1:0.1 to 1:0.001, 1:0.01 to 1:0.001, or a range of about 0.01:1 to 1:0.01, 0.1:1 to 1:0.01, 0.2:1 to 1:0.01, 0.3:1 to 1:0.01, 0.4:1 to 1:0.01, 0.5:1 to 1:0.01, 0.6:1 to 1:0.01, 0.7:1 to 1:0.01, 0.8:1 to 1:0.01, 0.9:1 to 1:0.01, 1:1 to 1:0.01, 1:0.9 to 1:0.01, 1:0.8 to 1:0.01, 1:0.7 to 1:0.01, 1:0.6 to 1:0.01, 1:0.5 to 1:0.01, 1:0.4 to 1:0.01, 1:0.3 to 1:0.01, 1:0.2 to 1:0.01, 1:0.1 to 1:0.01, 1:0.01 to 1:0.01, or including a range of about 0.001:1 to 1:0.01, 0.001:1 to 1:0.1, 0.001:1 to 1:0.2, 0.001:1 to 1:0.3, 0.001:1 to 1:0.4, 0.001:1 to 1:0.5, 0.001:1 to 1:0.6, 0.001:1 to 1:0.7, 0.001:1 to 1:0.8, 0.001:1 to 1:0.9, 0.001:1 to 1:1, 0.001 to 0.9:1, 0.001 to 0.8:1, 0.001 to 0.7:1, 0.001 to 0.6:1, 0.001 to 0.5:1, 0.001 to 0.4:1, 0.001 to 0.3:1, 0.001 to 0.2:1, 0.001 to 0.1:1, or a range of about 0.01:1 to 1:0.01, 0.01:1 to 1:0.1, 0.01:1 to 1:0.2, 0.01:1 to 1:0.3, 0.01:1 to 1:0.4, 0.01:1 to 1:0.5, 0.01:1 to 1:0.6, 0.01:1 to 1:0.7, 0.01:1 to 1:0.8, 0.01:1 to 1:0.9, 0.01:1 to 1:1, 0.001 to 0.9:1, 0.001 to 0.8:1, 0.001 to 0.7:1, 0.001 to 0.6:1, 0.001 to 0.5:1, 0.001 to 0.4:1, 0.001 to 0.3:1, 0.001 to 0.2:1, 0.001 to 0.1:1, etc.

Even more preferably, the molar ratio of the complexed RNA to the free RNA may be selected e.g. from a range of about 0.01:1 to 1:0.01. Most preferably, the molar ratio of the complexed RNA to the free RNA may be selected e.g. from a molar ratio of about 1:1. Any of the above definitions with regard to (w/w) and/or N/P ratio may also apply.

According to preferred embodiments, the (pharmaceutical) composition or vaccine comprises another nucleic acid, preferably as an adjuvant.

Accordingly, the (pharmaceutical) composition or vaccine of the invention further comprises a non-coding nucleic acid, preferably RNA, selected from the group consisting of small interfering RNA (siRNA), antisense RNA (asRNA), circular RNA (circRNA), ribozymes, aptamers, riboswitches, immunostimulating RNA (isRNA), transfer RNA (tRNA), ribosomal RNA (rRNA), small nuclear RNA (snRNA), small nucleolar RNA (snoRNA), microRNA (miRNA), and Piwi-interacting RNA (piRNA).

In the context of the present invention, non-coding nucleic acids, preferably RNAs, of particular interest include "immune-stimulatory" or "is" nucleic acids, preferably RNAs. "Immune-stimulatory" or "is" nucleic acids or RNAs are typically employed as adjuvants in the (pharmaceutical) composition or vaccine according to the invention.

According to a particularly preferred embodiment, the adjuvant nucleic acid comprises a nucleic acid of the following formula (IS-I) or (IS-II):

$$G_l X_m G_n \qquad \text{(IS-I)}$$

wherein:
G is a nucleotide comprising guanine, uracil or an analogue of guanine or uracil;
X is a nucleotide comprising guanine, uracil, adenine, thymine, cytosine or an analogue thereof;
l is an integer from 1 to 40,
  wherein
  when l=1 G is a nucleotide comprising guanine or an analogue thereof,
  when l>1 at least 50% of the nucleotides comprise guanine or an analogue thereof;
m is an integer and is at least 3;
  wherein
  when m=3, X is a nucleotide comprising uracil or an analogue thereof,
  when m>3, at least 3 successive nucleotides comprising uracils or analogues of uracil occur;
n is an integer from 1 to 40,
  wherein
  when n=1, G is a nucleotide comprising guanine or an analogue thereof,
  when n>1, at least 50% of the nucleotides comprise guanine or an analogue thereof;

$$C_l X_m C_n \qquad \text{(IS-II)}$$

wherein:
C is a nucleotide comprising cytosine, uracil or an analogue of cytosine or uracil;
X is a nucleotide comprising guanine, uracil, adenine, thymine, cytosine or an analogue thereof;
l is an integer from 1 to 40,
  wherein
  when l=1, C is a nucleotide comprising cytosine or an analogue thereof,
  when l>1, at least 50% of the nucleotides comprise cytosine or an analogue thereof;
m is an integer and is at least 3;
  wherein
  when m=3, X comprises uracil or an analogue thereof,
  when m>3, at least 3 successive nucleotides comprise uracils or analogues of uracil occur;
n is an integer from 1 to 40,
  wherein
  when n=1, C is a nucleotide comprising cytosine or an analogue thereof,
  when n>1, at least 50% of the nucleotides comprise cytosine or an analogue thereof.

The nucleic acids of formula (IS-I) or (IS-III), which may be used as isRNA may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the isRNA has a maximum length of, for example, 100 nucleotides, m will typically be ≤98.

The number of nucleotides "G" in the nucleic acid of (IS-I) is determined by l or n. l and n, independently of one another, are each an integer from 1 to 40, wherein when l or n=1 G is a nucleotide comprising guanine or an analogue thereof, and when l or n>1 at least 50% of the nucleotides comprise guanine, or an analogue thereof.

For example, without implying any limitation, when l or n=4 Gl or Gn can be, for example, a GUGU, GGUU, UGUG, UUGG, GUUG, GGGU, GGUG, GUGG, UGGG or GGGG, etc.; when l or n=5 Gl or Gn can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc.

A nucleotide adjacent to $X_m$ in the nucleic acid of formula (IS-I) preferably does not comprise uracil. Similarly, the number of nucleotides "C" in the nucleic acid of formula (IS-III) is determined by l or n. l and n, independently of one another, are each an integer from 1 to 40, wherein when l or n=1 C is a nucleotide comprising cytosine or an analogue thereof, and when l or n>1 at least 50% of the nucleotides comprise cytosine or an analogue thereof.

For example, without implying any limitation, when l or n=4, Cl or $C_n$ can be, for example, a CUCU, CCUU, UCUC, UUCC, CUUC, CCCU, CCUC, CUCC, UCCC or CCCC, etc.; when l or n=5 Cl or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.

A nucleotide adjacent to $X_m$ in the nucleic acid of formula (IS-III) preferably does not comprise uracil. Preferably, for formula (IS-I), when l or n>1, at least 60%, 70%, 80%, 90% or even 100% of the nucleotides comprise guanine or an analogue thereof, as defined above.

The remaining nucleotides to 100% (when nucleotides comprising guanine constitutes less than 100% of the nucleotides) in the flanking sequences G1 and/or $G_n$ are uridine or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (IS-III).

According to a further preferred embodiment, the isRNA as described herein consists of or comprises a nucleic acid of formula (IS-III) or (IS-IV):

$$(N_u G_l X_m G_n N_v)_a \qquad \text{(IS-III)}$$

wherein:
G is a nucleotide comprising guanine, uracil or an analogue of guanine or uracil, preferably comprising guanine or an analogue thereof;
X is a nucleotide comprising guanine, uracil, adenine, thymine, cytosine, or an analogue thereof, preferably comprising uracil or an analogue thereof;
N is a nucleic acid sequence having a length of about 4 to 50, preferably of about 4 to 40, more preferably of about 4 to 30 or 4 to 20 nucleic acids, each N independently being selected from a nucleotide comprising guanine, uracil, adenine, thymine, cytosine or an analogue thereof;
a is an integer from 1 to 20, preferably from 1 to 15, most preferably from 1 to 10;
l is an integer from 1 to 40,
  wherein when l=1, G is a nucleotide comprising guanine or an analogue thereof, when l>1, at least 50% of these nucleotides comprise guanine or an analogue thereof;
m is an integer and is at least 3;
  wherein when m=3, X is a nucleotide comprising uracil or an analogue thereof, and
  when m>3, at least 3 successive nucleotides comprising uracils or analogues of uracils occur;

n is an integer from 1 to 40,
  wherein when n=1, G is a nucleotide comprising guanine or an analogue thereof,
  when n>1, at least 50% of these nucleotides comprise guanine or an analogue thereof;
u,v may be independently from each other an integer from 0 to 50, preferably wherein when u=0, v≥1, or when v=0, u≥1; wherein the nucleic acid molecule of (IS-III) has a length of at least 50 nucleotides, preferably of at least 100 nucleotides, more preferably of at least 150 nucleotides, even more preferably of at least 200 nucleotides and most preferably of at least 250 nucleotides.

  (IS-IV)

wherein:
C is a nucleotide comprising cytosine, uracil or an analogue of cytosine or uracil, preferably cytosine or an analogue thereof;
X is a nucleotide comprising guanine, uracil, adenine, thymine, cytosine or an analogue thereof, preferably comprising uracil or an analogue thereof;
N is each a nucleic acid sequence having independent from each other a length of about 4 to 50, preferably of about 4 to 40, more preferably of about 4 to 30 or 4 to 20 nucleic acids, each N independently being selected from a nucleotide comprising guanine, uracil, adenine, thymine, cytosine or an analogue thereof;
a is an integer from 1 to 20, preferably from 1 to 15, most preferably from 1 to 10;
l is an integer from 1 to 40,
  wherein when l=1, C is a nucleotide comprising cytosine or an analogue thereof,
  when l>1, at least 50% of these nucleotides comprise cytosine or an analogue thereof;
m is an integer and is at least 3;
  wherein when m=3, X is a nucleotide comprising uracil or an analogue thereof,
  when m>3, at least 3 successive nucleotides comprising uracils or analogues of uracil occur;
n is an integer from 1 to 40,
  wherein when n=1, C is a nucleotide comprising cytosine or an analogue thereof,
  when n>1, at least 50% of these nucleotides comprise cytosine or an analogue thereof.
u, v may be independently from each other an integer from 0 to 50,
  preferably wherein when u=0, v≥1, or when v=0, u≥1;
wherein the nucleic acid molecule of (IS-IV) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (IS-IV), any of the definitions given above for elements N (i.e. $N_u$ and $N_v$) and X ($X_m$), particularly the core structure as defined above, as well as for integers a, l, m, n, u and v, similarly apply to elements of formula (CAT-II) correspondingly, wherein in formula (IS-IV) the core structure is defined by $C_lX_mC_n$. The definition of bordering elements $N_u$ and $N_v$ is identical to the definitions given above for $N_u$ and $N_v$.

In particular in the context of formulas (IS-I)-(IS-IV) above, a "nucleotide" is understood as a molecule comprising or preferably consisting of a nitrogenous base (preferably selected from adenine (A), cytosine (C), guanine (G), thymine (T), or uracil (U), a pentose sugar (ribose or deoxyribose), and at least one phosphate group. "Nucleosides" consist of a nucleobase and a pentose sugar (i.e. could be referred to as "nucleotides without phosphate groups"). Thus, a "nucleotide" comprising a specific base (A, C, G, T or U) preferably also comprises the respective nucleoside (adenosine, cytidine, guanosine, thymidine or uridine, respectively) in addition to one (two, three or more) phosphate groups That is, the term "nucleotides" includes nucleoside monophosphates (AMP, CMP, GMP, TMP and UMP), nucleoside diphosphates (ADP, CDP, GDP, TDP and UDP), nucleoside triphosphates (ATP, CTP, GTP, TTP and UTP). In the context of formulas (IS-I)-(IS-IV) above, nucleoside monophosphates are particularly preferred. The expression "a nucleotide comprising ( . . . ) or an analogue thereof" refers to modified nucleotides comprising a modified (phosphate) backbone, pentose sugar(s), or nucleobases. In this context, modifications of the nucleobases are particularly preferred. By way of example, when referring "to a nucleotide comprising guanine, uracil, adenine, thymine, cytosine or an analogue thereof", the term "analogue thereof" refers to both the nucleotide and the recited nucleobases, preferably to the recited nucleobases.

In preferred embodiments, the (pharmaceutical) composition or vaccine of the invention comprises at least one immunostimulating RNA comprising or consisting of a nucleic acid sequence according to formula (IS-I) (GiXmGn), formula (IS-III) ($C_lX_mC_n$), formula (IS-III) ($N_uG_lX_mG_nN_v)_a$, and/or formula (IS-IV) ($N_uC_lX_mC_nN_v)_a$. In particularly preferred embodiments, the (pharmaceutical) composition or vaccine of the invention comprises at least one immunostimulating RNA comprising or consisting of a nucleic acid sequence according to any one of SEQ ID NOs: 2938-3032.

In particularly preferred embodiments, the (pharmaceutical) composition or vaccine of the invention comprises a polymeric carrier cargo complex, formed by a polymeric carrier, preferably comprising disulfide-crosslinked cationic peptides, preferably Cys-Arg$_{12}$, and/or Cys-Arg$_{12}$-Cys, and at least one isRNA, preferably comprising or consisting of a nucleic acid sequence according to any one of SEQ ID NO: 2938-3032.

The (pharmaceutical) composition or vaccine of the invention may additionally contain one or more auxiliary substances in order to increase its immunogenicity or immunostimulatory capacity, if desired. A synergistic action of the inventive polymeric carrier cargo complex as defined herein and of an auxiliary substance, which may be optionally contained in the (pharmaceutical) composition or vaccine of the invention as defined herein, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner.

Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

The (pharmaceutical) composition or vaccine of the invention may additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The (pharmaceutical) composition or vaccine of the invention may additionally contain CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

Kit

In a further aspect, the present invention relates to a kit or kit-of-parts comprising the artificial nucleic acid molecule, preferably RNA, and/or the (pharmaceutical) composition or vaccine of the invention, and optionally a liquid vehicle and/or optionally technical instructions with information on the administration and dosage of the artificial nucleic acid molecule or the composition.

Optionally, the kit-of-parts may comprise at least one further agent as defined herein in the context of the pharmaceutical composition, antimicrobial agents, RNAse inhibitors, solubilizing agents, buffers, or the like. In preferred embodiments, the kit may contain as a part Ringer-Lactate solution.

The kit or kit-of-parts may be a kit of two or more parts and typically comprises each of the components described herein in suitable containers. For example, each container may be in the form of vials, bottles, squeeze bottles, jars, sealed sleeves, envelopes or pouches, tubes or blister packages or any other suitable form provided the container is configured so as to prevent premature mixing of components. Each of the different components may be provided separately, or some of the different components may be provided together (i.e. in the same container). A container may also be a compartment or a chamber within a vial, a tube, a jar, or an envelope, or a sleeve, or a blister package or a bottle, provided that the contents of one compartment are not able to associate physically with the contents of another compartment prior to their deliberate mixing by a pharmacist or physician.

The kit may furthermore contain technical instructions with information on the administration and dosage of any of its components.

Medical Use and Treatment

In a further aspect, the present invention provides the artificial nucleic acid molecule, preferably RNA, the (pharmaceutical) composition or vaccine, or the kit of the invention for human and also for veterinary medical purposes, preferably for human medical purposes.

According to a further aspect, the invention thus relates to the artificial nucleic acid molecule, preferably RNA, or the (pharmaceutical) composition or vaccine, or kit-of-parts for use as a medicament.

The artificial nucleic acid molecule, preferably RNA, or the (pharmaceutical) composition or kit-of-parts are inter alia provided for use in treatment and/or prophylaxis of cancer, infectious diseases including viral, bacterial, fungal or protozoal infections, autoimmune diseases, Graft-versus-host disease (GvHD) or allergies.

The term "treatment" or "treating" of a disease includes preventing or protecting against the disease (that is, causing the clinical symptoms not to develop); inhibiting the disease (i.e., arresting or suppressing the development of clinical symptoms; and/or relieving the disease (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "treatment" thus includes "prophylaxis".

The term "subject", "patient" or "individual" as used herein generally includes humans and non-human animals and preferably mammals (e.g., non-human primates, including marmosets, tamarins, spider monkeys, owl monkeys, vervet monkeys, squirrel monkeys, and baboons, macaques, chimpanzees, orangutans, gorillas; cows; horses; sheep; pigs; chicken; cats; dogs; mice; rat; rabbits; guinea pigs; etc.), including chimeric and transgenic animals and disease models. In the context of the present invention, the term "subject" preferably refers a non-human primate or a human, most preferably a human.

According to preferred embodiments, treatment of cancer, infectious diseases including viral, bacterial, fungal or protozoal infections, autoimmune diseases, Graft-versus-host disease (GvHD) or allergies is accomplished by administering, to a subject in need thereof, at least one artificial nucleic acid molecule, preferably RNA, (pharmaceutical) composition or vaccine, or kit according to the invention. Preferably, administration is accomplished parenterally, preferably intradermally, intramuscularly, intranodally, transdermally, subcutaneous or intratumorally. Preferably, injection is carried out by injection, e.g. using conventional needle injection or (needle-free) jet injection, preferably by using (needle-free) jet injection. Prior to administration, treatment may include an optional step of preparing said artificial nucleic acid molecule, preferably RNA, or the (pharmaceutical) composition or vaccine or kit. The invention further relates to a method of treating cancer, infectious diseases including viral, bacterial, fungal or protozoal infections, autoimmune diseases, Graft-versus-host disease (GvHD) or allergies comprising the steps of (a) optionally preparing the artificial nucleic acid molecule, preferably RNA, or the (pharmaceutical) composition or vaccine or kit of the invention and (b) administering, to a subject in need thereof, at least one artificial nucleic acid molecule, preferably RNA, (pharmaceutical) composition or vaccine, or kit according to the invention.

The invention further relates to the use of the inventive artificial nucleic acid molecule, preferably RNA, or the (pharmaceutical) composition or kit, preferably for manufacturing a medicament for treating cancer, infectious diseases including viral, bacterial, fungal or protozoal infections, autoimmune diseases, Graft-versus-host disease (GvHD) or allergies.

Administration Routes

The inventive artificial nucleic acid molecule, preferably RNA, or the (pharmaceutical) composition or vaccine or kit can be administered, for example, systemically or locally.

Routes for systemic administration in general include, for example, transdermal, oral, parenteral routes, including subcutaneous, intravenous, intramuscular, intraarterial, intradermal and intraperitoneal injections and/or intranasal administration routes.

Routes for local administration in general include, for example, topical administration routes but also intradermal, transdermal, subcutaneous, or intramuscular injections or intralesional, intratumoral, peritumoral, imaging guided loco-regional administration, intracranial, intrapulmonal, intracardial, intranodular and sublingual injections.

It is further conceivable to use different administration routes for different artificial nucleic acid molecules, preferably RNAs, of the invention, and/or different parts of the kit.

According to preferred embodiments, the artificial nucleic acid molecule, preferably RNA, or the (pharmaceutical) composition or vaccine or kit is administered parenterally, preferably intradermally, intramuscularly, intranodally, transdermally, imaging guided loco-regional administration or intratumorally. Preferably, said artificial nucleic acid molecule, preferably RNA, or the (pharmaceutical) composition or vaccine or kit is administered by injection, e.g. subcutaneous, intramuscular, intradermal or intratumoral injection, which may be needle-free and/or needle injection. Accordingly, in preferred embodiments, the medical use and/or method of treatment according to the present invention involves administration of said artificial nucleic acid molecule, preferably RNA, or the (pharmaceutical) composition or vaccine or kit by subcutaneous, intramuscular, intradermal or intratumoral injection. Such injection may be carried out by using conventional needle injection or (needle-free) jet injection, preferably by using (needle-free) jet injection.

Administration Regimen

The artificial nucleic acid molecule, preferably RNA, (pharmaceutical) composition or vaccine or kit of the invention (or their components or parts) may be administered to a subject in need thereof several times a day, daily, every other day, weekly, or monthly; and may be administered sequentially or simultaneously, optionally via different administration routes as defined above.

According to some preferred embodiments, the artificial nucleic acid molecule, preferably RNA, (pharmaceutical) composition or vaccine or kit of the invention (or their components or parts) are administered simultaneously (i.e. at the same time via the same or different administrations routes).

According to other preferred embodiments, the artificial nucleic acid molecule, preferably RNA, (pharmaceutical) composition or vaccine or kit of the invention (or their components or parts) are administered separately (i.e. sequentially at different time points and/or via different administrations routes). Such a sequential administration scheme is also referred to as "time-staggered" administration.

Dose

The artificial nucleic acid molecule, preferably RNA, (pharmaceutical) composition or vaccine or kit of the invention (or their components or parts) is/are preferably administered in a safe and therapeutically effective amount.

As used herein, "safe and therapeutically effective amount" means an amount of the active agent(s) that is sufficient to elicit a desired biological or medicinal response in a tissue, system, animal or human that is being sought. A "safe and therapeutically effective amount" is preferably sufficient for the inducing a positive modification of the disease to be treated, i.e. for alleviation of the symptoms of the disease being treated, reduction of disease progression, or prophylaxis of the symptoms of the disease being prevented. At the same time, however, a "safe and therapeutically effective amount" is small enough to avoid serious side-effects, that is to say to permit a sensible relationship between advantage and risk.

A "safe and therapeutically effective amount" will furthermore vary in connection with the particular condition to be treated and also with the age, physical condition, body weight, sex and diet of the patient to be treated, the severity of the condition, the duration of the treatment, the nature of the accompanying therapy, of the particular pharmaceutically acceptable carrier or excipient used, the treatment regimen and similar factors. It may further vary depending on whether the employed artificial nucleic acid molecule, preferably RNA, is monocistronic, bi- or even multicistronic.

Therapeutic efficacy and toxicity of active agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Active agents which exhibit large therapeutic indices are generally preferred. The data obtained from the cell culture assays and animal studies can be used in formulating a range of dosage for use in humans. The dosage of such compounds lies preferably within a range of circulating concentrations that include the ED50 with little or no toxicity.

For instance, therapeutically effective doses of the inventive artificial nucleic acid molecule, preferably RNA, (pharmaceutical) composition or vaccine or kit described herein may range from about 0.001 mg to 10 mg, preferably from about 0.01 mg to 5 mg, more preferably from about 0.1 mg to 2 mg per dosage unit or from about 0.01 nmol to 1 mmol per dosage unit, in particular from 1 nmol to 1 mmol per dosage unit, preferably from 1 pmol to 1 mmol per dosage unit. It is also envisaged that the therapeutically effective dose of the inventive artificial nucleic acid molecule, preferably RNA, (pharmaceutical) composition or vaccine or kit may range (per kg body weight) from about 0.01 mg/kg to 10 g/kg, preferably from about 0.05 mg/kg to 5 g/kg, more preferably from about 0.1 mg/kg to 2.5 g/kg. Safe and therapeutically effective amounts of the inventive artificial nucleic acid molecule, preferably RNA, (pharmaceutical) composition or vaccine or kit to be administered can be determined by routine experiments, e.g. by using animal models. Such models include, without implying any limitation, rabbit, sheep, mouse, rat, dog and non-human primate models.

Diseases

Cancer

In preferred embodiments, the artificial nucleic acid, preferably RNA, (pharmaceutical) composition or kit is used for treatment or prophylaxis of cancer.

In some embodiments, the artificial nucleic acid, preferably RNA, (pharmaceutical) composition or kit according to the invention may be used as a medicament, in particular for treatment of tumor or cancer diseases. In this context, treatment preferably involves intratumoral application, especially by intratumoral injection. Accordingly, the artificial nucleic acid, preferably RNA, (pharmaceutical) composition or kit according to the invention may be used for preparation of a medicament for treatment of tumor or cancer diseases, said medicament being particularly suitable for intratumoral application (administration) for treatment of tumor or cancer diseases.

Preferably, tumor and cancer diseases as mentioned herein are selected from tumor or cancer diseases which preferably include e.g. Acute lymphoblastic leukemia, Acute myeloid leukemia, Adrenocortical carcinoma, AIDS-related cancers, AIDS-related lymphoma, Anal cancer, Appendix cancer, Astrocytoma, Basal cell carcinoma, Bile duct cancer, Bladder cancer, Bone cancer, Osteosarcoma/Malignant fibrous histiocytoma, Brainstem glioma, Brain tumor, cerebellar astrocytoma, cerebral astrocytoma/malignant glioma, ependymoma, medulloblastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, acute lymphoblastic Leukemia, acute myeloid Leukemia, chronic lymphocytic Leukemia, chronic myelogenous Leukemia, hairy cell Leukemia, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, cutaneous T-Cell Lymphoma, Hodgkin Lymphoma, Non-Hodgkin Lymphomas, Primary Central Nervous System Lymphoma, Waldenström Macroglobulinemia, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Metastatic Squamous Neck Cancer with Occult Primary, Mouth Cancer, Childhood Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Chronic Myelogenous Leukemia, Adult Acute Myeloid Leukemia, Childhood Acute Myeloid Leukemia, Multiple Myeloma (Cancer of the Bone-Marrow), Chronic Myeloproliferative Disorders, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, childhood Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdomyosarcoma, Salivary gland cancer, Sarcoma of the Ewing family of tumors, Kaposi Sarcoma, soft tissue Sarcoma, uterine Sarcoma, Sezary syndrome, Skin cancer (non-melanoma), Skin cancer (melanoma), Merkel cell Skin carcinoma, Small intestine cancer, Squamous cell carcinoma, metastatic Squamous neck cancer with occult primary, childhood Supratentorial primitive neuroectodermal tumor, Testicular cancer, Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, Waldenström macroglobulinemia, and childhood Wilms tumor (kidney cancer).

Especially preferred examples of tumors or cancers that are suitable for intratumoral administration are prostate cancer, lung cancer, breast cancer, brain cancer, head and neck cancer, thyroid cancer, colon cancer, stomach cancer, liver cancer, pancreas cancer, ovary cancer, skin cancer, urinary bladder, uterus and cervix.

Infectious Diseases

The inventive combination, pharmaceutical composition or kit may be used for treating infectious diseases. The term "infection" or "infectious disease" relates to the invasion and multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic system to become systemic. Infectious diseases in this context, preferably include viral, bacterial, fungal or protozoological infectious diseases.

Combination Therapy

According to some preferred embodiments, the medical uses and treatment methods of the invention may include subjecting the patient to a combination therapy. Any therapy amenable for treating or preventing the diseases, disorders and conditions described herein (in particular cancer, infectious diseases, autoimmune diseases, graft-versus-host disease and allergies) may be combined with/employed in addition to the administration of the inventive artificial nucleic acid molecules, preferably RNAs, (pharmaceutical) composition or kit. Combination therapy may generally be effected prior to, simultaneously with, or subsequently to the administration of said artificial nucleic acid molecule, (pharmaceutical) composition or vaccine, or kit of the invention, and inter alia depends on the type and severity of the disease, disorder, or condition to be treated.

Cancer

Treatment of cancer may, in addition to administration of the artificial nucleic acid molecule, (pharmaceutical) composition or vaccine, or kit of the invention, comprise one or more of the following: chemotherapy (e.g. first-line or second-line chemotherapy), radiotherapy, chemoradiation (combination of chemotherapy and radiotherapy), kinase inhibitors, antibody therapy and/or checkpoint modulators (e.g. CTLA4 inhibitors, PD1 pathway inhibitors) or inhibitors inducing expression of T cell epitopes associated with impaired peptide processing (TEIPPs) as disclosed in WO2012/089225. Accordingly, in some embodiments the subject receiving the inventive artificial nucleic acid molecule, (pharmaceutical) composition or vaccine may be a patient with cancer or tumor, who received or receives chemotherapy (e.g. first-line or second-line chemotherapy), radiotherapy, chemoradiation (combination of chemotherapy and radiotherapy), kinase inhibitors, antibody therapy and/or checkpoint modulators (e.g. CTLA4 inhibitors, PD1 pathway inhibitors) or inhibitors inducing expression of T cell epitopes associated with impaired peptide processing (TEIPPs) as disclosed in WO2012/089225, or a patient, who has achieved partial response or stable disease after having received one or more of the treatments specified above.

For instance, the subject receiving the inventive artificial nucleic acid molecule, preferably RNA, (pharmaceutical) composition or kit-of-parts may be a patient with cancer, preferably as defined herein, or a related condition, receiving chemotherapy (e.g. first-line or second-line chemotherapy), radiotherapy, chemoradiation (combination of chemotherapy and radiotherapy), tyrosine kinase inhibitors (e.g. EGFR tyrosine kinase inhibitors), antibody therapy and/or inhibitory and/or stimulatory checkpoint molecules (e.g. PD1, PD-L1 or CTLA4 inhibitors), or a patient, who has achieved partial response or stable disease after having received one or more of the treatments specified above. Or, the subject receiving the inventive artificial nucleic acid molecule, preferably RNA, (pharmaceutical) composition or kit-of-parts may be a patient with an infectious disease, preferably as defined herein, receiving antibiotic, antifungal or antiviral therapy.

In a further aspect, the present invention thus also relates to the use of the inventive artificial nucleic acid molecule, preferably RNA, (pharmaceutical) composition or kit-of-parts for supporting another therapy of cancer, an infectious disease, or any other disease amenable by treatment with said artificial nucleic acid molecule, (pharmaceutical) composition or kit.

"Support" of the treatment or prophylaxis of cancer may be any combination of a conventional cancer therapy method of such as surgery, radiation therapy, chemotherapy (e.g. first-line or second-line chemotherapy), chemoradiation, treatment with tyrosine kinase inhibitors, treatment with inhibitory and/or stimulatory checkpoint molecules, preferably PD1, PD-L1 or CTLA4 inhibitors, antibody therapy or any combination of these, and a therapy using the inventive inventive artificial nucleic acid molecule, preferably RNA, (pharmaceutical) composition or kit-of-parts as defined herein. Administration of the inventive artificial nucleic acid molecule, preferably RNA, (pharmaceutical) composition or kit-of-parts may be accomplished prior to, simultaneously and/or subsequently to administering another therapeutic or subjecting the patient to another therapy that is useful for treatment of the particular disease or condition to be treated.

In Vitro Methods

In a further aspect, the invention relates to an in vitro cell culture or cell treatment method comprising (a) providing cells in vitro, (b) contacting said cells with the artificial nucleic acid molecule, preferably RNA, the (pharmaceutical) composition or vaccine, or the kit of the invention.

Without wishing to be bound by specific theory, said cell culture/treatment method is envisaged to be particularly useful for preparing antigen-presenting cells (APCs), such as dendritic cells (DCs), for subsequent T cell expansion in vitro or in vivo. The cells are preferably contacted with said artificial nucleic acid molecule, preferably RNA, (pharmaceutical) composition or vaccine or kit in a suitable cell culture medium. Step (b) may in particular include a step of transfecting the cells with the artificial nucleic acid molecules, preferably RNAs, optionally comprised by said (pharmaceutical) composition or vaccine, or kit. Transfection, i.e. the act of deliberately introducing the artificial nucleic acid molecules, preferably RNAs, into living cells, may for instance involve microinjection or electroporation. Upon introduction into the recipient cells, the artificial nucleic acid molecules, preferably RNAs, are preferably translated, yielding the antigenic fusion proteins of the invention, which are subsequently presented via the MHC complex.

EXAMPLES

Example 1

C57BL/6 mice were injected intradermally (i.d.) at 4 sites with RNA constructs encoding an Trp2 epitope connected to a T cell helper epitope (PADRE) (64 µg RNA in 50 µl PBS). The Trp2 peptide SVYDFFVWL is a confirmed CD8+ T cell epitope.

Figure 1:
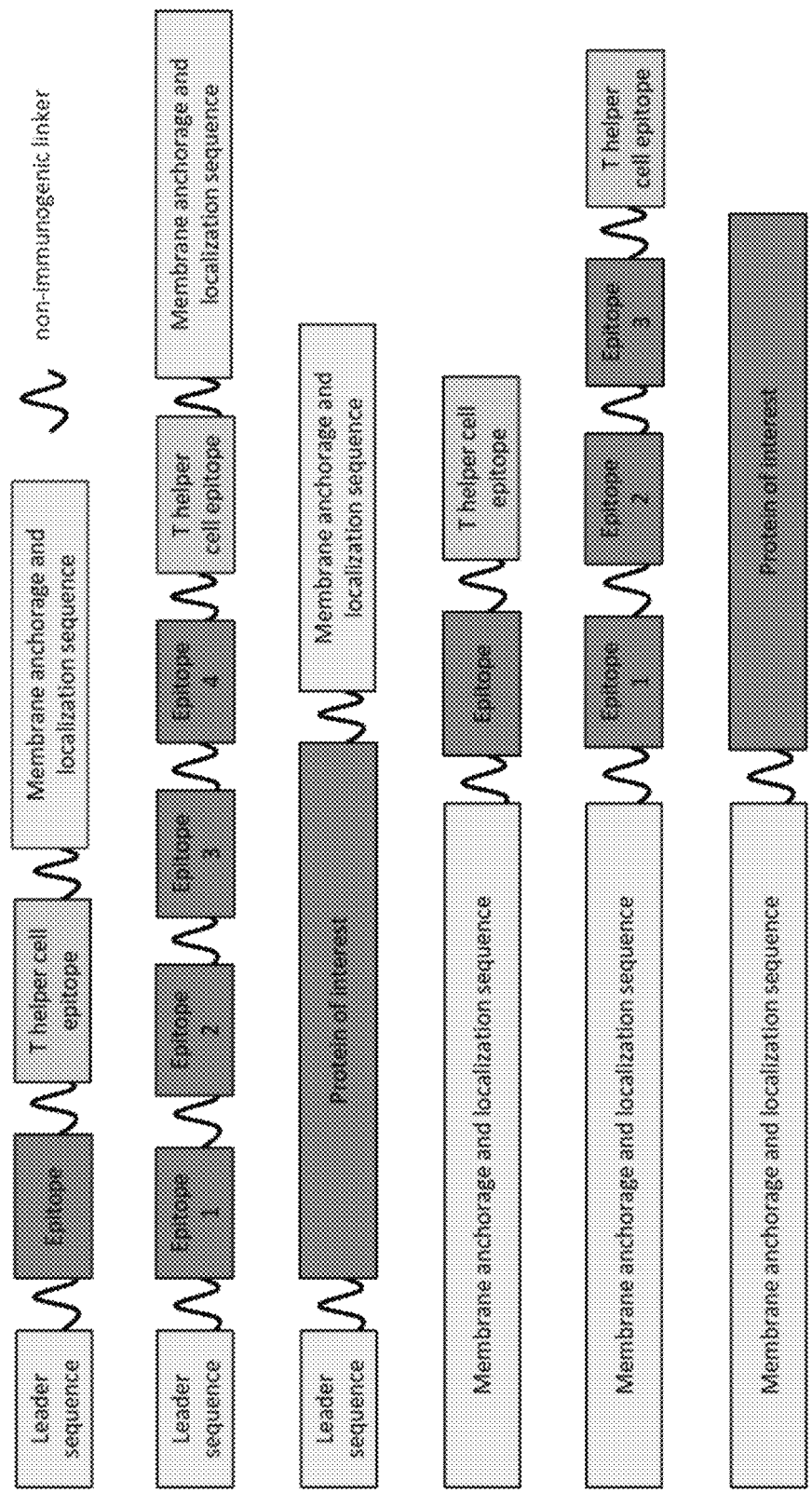
FIG. 1: General design of RNA constructs enabling the targeting of epitopes or antigens to MHC class I and II-containing cellular compartments.
Figure 2:
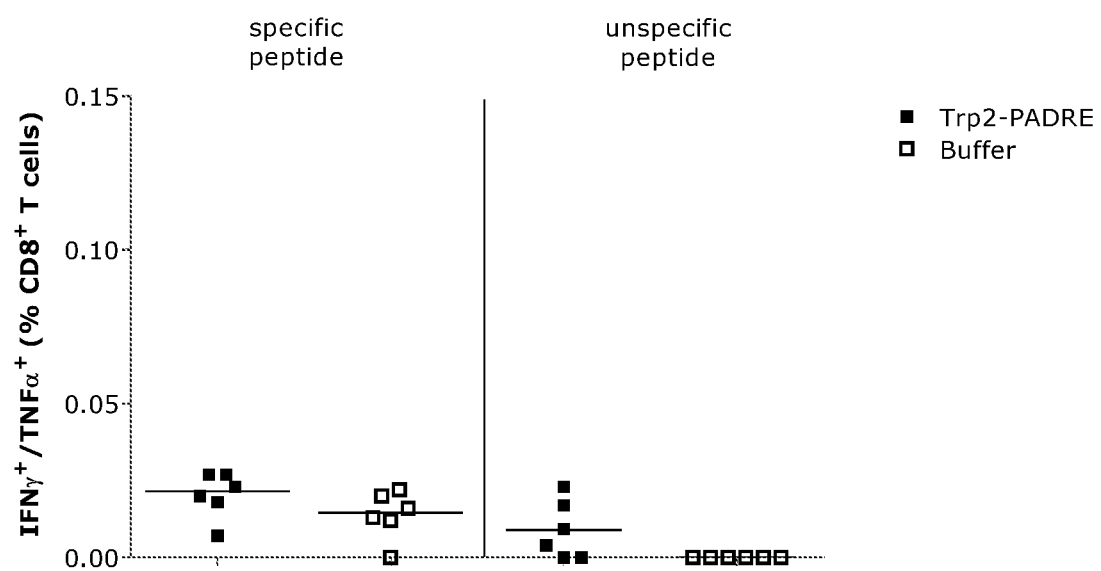
FIG. 2: Induction of epitope-specific CD8+ T cells after vaccination with RNA encoding a murine Trp2 epitope with PADRE.

On days 0, 3, 7, 10 and 14 of the experiment mice were injected i.d. with mRNA solved in Ringer Lactate buffer according to the Table 8 below. The total volume for intradermal vaccination was 80 µl and was distributed to 4 sites of injection. 6 days after the last vaccination an ICS was performed to evaluate epitope-specific CD8+ T cell responses. Therefore CD8+ T cells were stimulated with the corresponding peptide and as a control with an irrelevant peptide. In none of the groups epitope-specific CD8+ T cell responses were observed (FIG. 2).

TABLE 8

| Groups, treatment and RNA dilution | | | |
|---|---|---|---|
| Groups | Constructs (amount of RNA) | No. of mice | SEQ ID NOs: |
| A | Trp2-PADRE (64 µg) | 6 | 2931 |
| B | Buffer | 6 | — |

Example 2

C57BL/6 mice were injected intradermally (i.d.) at 4 sites with RNA constructs encoding an ovalbumin or Trp2 epitope connected to a T cell helper epitope (PADRE) with the CTLA4 targeting approach (64 µg RNA in 50 µl PBS). Peptides of ovalbumin (LESIINFEKLTE) and Trp2 (SVYDFFVWL) are known CD8+ T cell epitopes.

Figure 3:
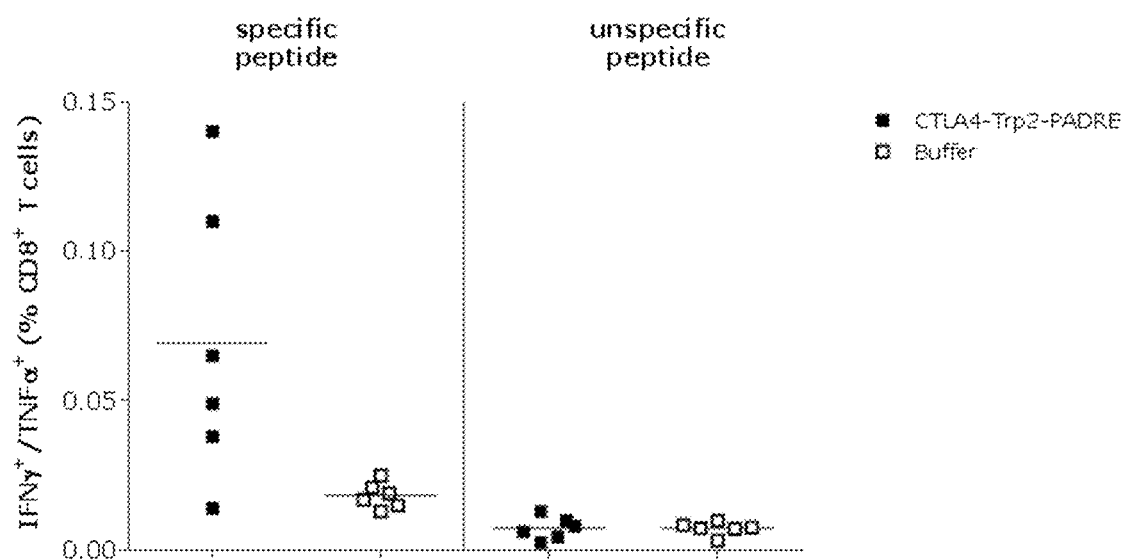
FIG. 3: Induction of epitope-specific CD8+ T cells after vaccination with RNA encoding a murine Trp2 epitope with $IRST_{epm}$-(CTLA4) derived targeting sequence.
Figure 4:
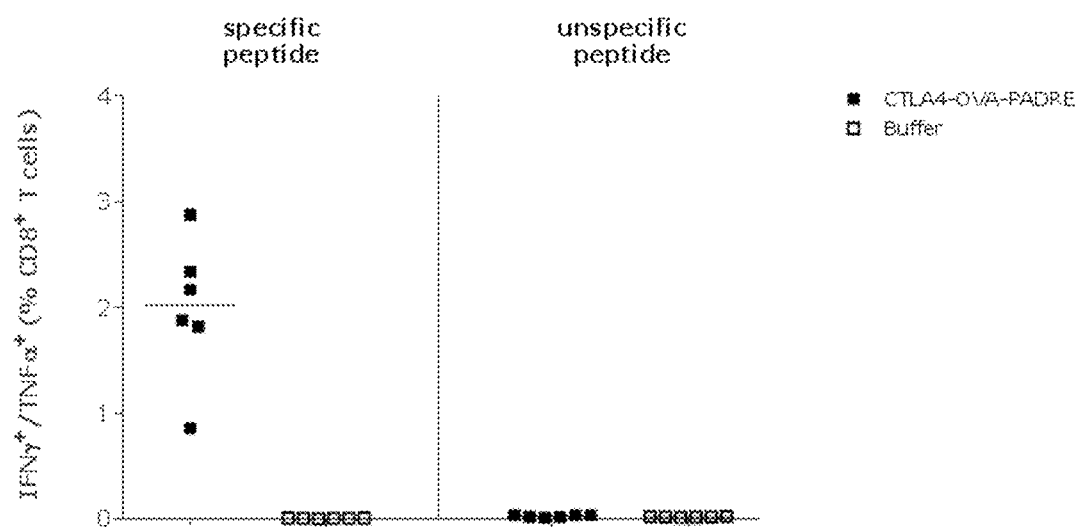
FIG. 4: Induction of epitope-specific CD8+ T cells after vaccination with RNA encoding an ovalbumin epitope with $IRST_{epm}$-(CTLA4) derived targeting sequence.

On days 0, 3, 7, 10 and 14 of the experiment mice were injected i.d. with RNA solved in Ringer Lactate buffer according to the Table 9 below. The total volume for intradermal vaccination was 80 µl and was distributed to 4 sites of injection. 6 days after the last vaccination an ICS was performed to evaluate epitope-specific CD8+ T cell responses. Therefore CD8+ T cells were stimulated with the corresponding peptide and as a control with an irrelevant peptide. In both groups epitope-specific CD8+ T cell responses were observed (FIGS. 3 and 4).

TABLE 9

| Groups, treatment and RNA dilution | | | |
|---|---|---|---|
| Groups | Constructs (amount of RNA) | No. of mice | SEQ ID NOs: |
| A* | CTLA4-OVA-PADRE (64 µg) | 6 | 2913 |
| B | CTLA4-Trp2-PADRE (64 µg) | 6 | 2914 |
| C | Buffer | 6 | |

More specifically, constructs according to A preferably have the following structure: HsCTLA4(1-35)_Linker_GgOva(249-273)_Linker_PADRE_Linker_HsCTLA4(162-223)

Example 3

C57BL/6 mice were injected subcutaneously (s.c.) with 3×10⁵ E.G7-OVA cells per mouse (in a volume of 100 µl PBS) on the right flank on day 0 of the experiment. At day 4 after tumor inoculation C57BL/6 mice were injected i.d. at 4 sites with RNA constructs encoding an epitope of ovalbumin (LESIINFEKLTE) and a T cell helper epitope (PADRE) with the CTLA4 targeting approach (64 µg RNA in 80 µl Ringer Lactate buffer). Two additional groups were vaccinated i.d. with ovalbumin full length protein encoded by mRNA (RNActive) (FIG. 5) or ovalbumin peptide in combination with RNAdjuvant (FIG. 6).

On days 0, 3, 7, 10 and 14 of the experiment mice were injected i.d. with RNA or peptide according to the Table 10 and 11 below.

Tumor growth was monitored by measuring the tumor size in three dimensions using a caliper. Tumor volume was calculated according to the following formula:

$$\text{volume (mm}^3\text{)} = \frac{\text{length (mm)} \times \pi \times \text{width}^2 \text{ (mm}^2\text{)}}{6}$$

Figure 5:
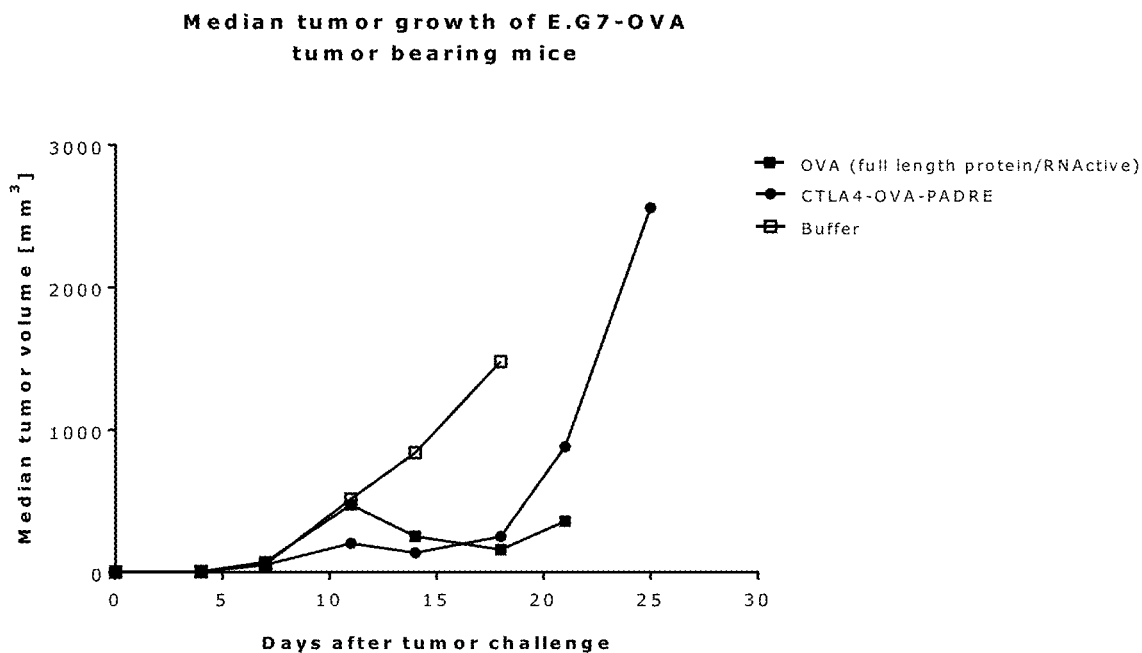
FIG. 5: Vaccination with RNA encoding an OVA epitope with IRSTepm (CTLA4)-derived targeting sequence induces a significant anti-tumor response in E.G7-OVA-tumor-bearing mice.
Figure 6:
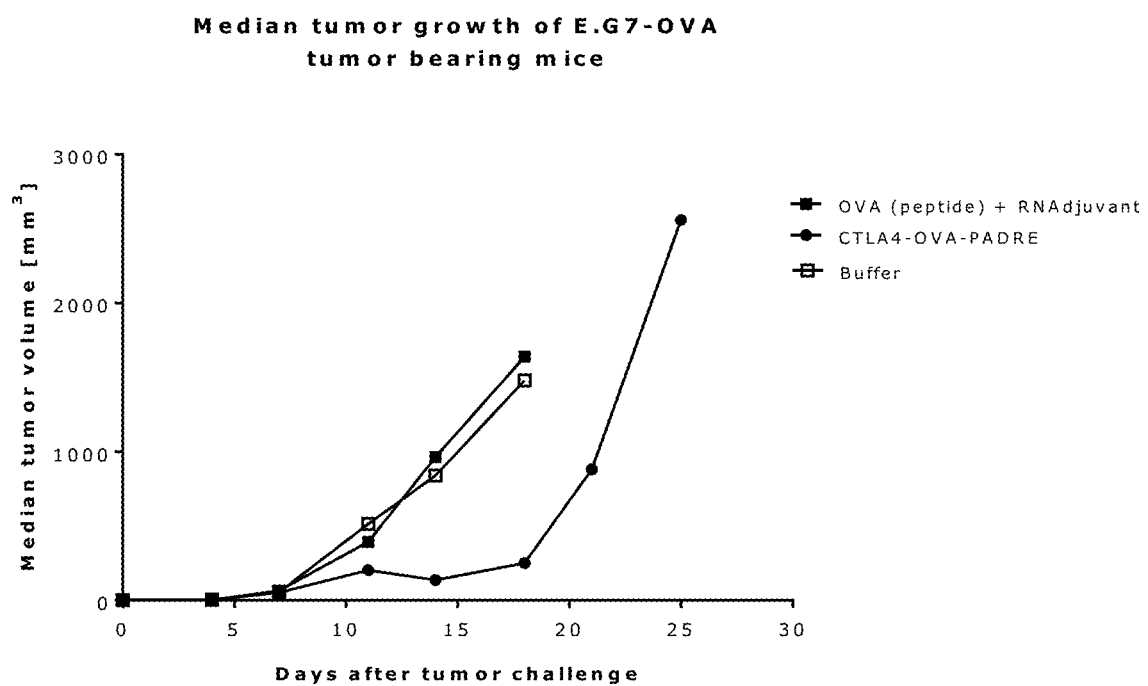
FIG. 6: Anti-tumor response induced by RNA encoding an OVA epitope with $IRST_{epm}$-(CTLA4-) derived targeting sequence is superior in comparison to vaccination with the corresponding peptide plus adjuvant.

Result:

Vaccination with RNA encoding an OVA epitope with the CTLA4 targeting approach induces a significant anti-tumor response in E.G7-OVA-tumor-bearing mice (FIGS. 5 and 6). Anti-tumor response induced by RNA encoding an OVA epitope with the targeting approach is superior in comparison to vaccination with the corresponding peptide plus an RNA-based adjuvant (RNAdjuvant) (FIG. 6).

TABLE 10

| Groups, treatment and RNA dilution | | | |
|---|---|---|---|
| Groups | Constructs (amount of RNA) | No. of mice | SEQ ID NOs: |
| A | OVA RNActive (full length protein) (32 µg) | 8 | 2935 |
| B | CTLA4-OVA-PADRE (64 µg) | 8 | 2913 |
| C | Buffer | 8 | |
| A | OVA (peptide, 50 µg) + RNAdjuvant (50 µg) | 8 | 2927 + 3029 |
| B | CTLA4-OVA-PADRE (64 µg) | 8 | 2913 |
| C | Buffer | 8 | |

Example 4

C57BL/6 mice were injected intradermally (i.d.) at 4 sites with mRNA constructs encoding different ovalbumin epitopes connected to a T cell helper epitope (PADRE) with the CTLA4 targeting approach (32 µg mRNA in 50 µl PBS). Short peptide of ovalbumin (LESIINFEKLTE) and long epitope of ovalbumin (EVSGLEQLESIINFEKLTEWTSSNV) covering the known CD8+ T cell epitope of ovalbumin.

Figure 7:
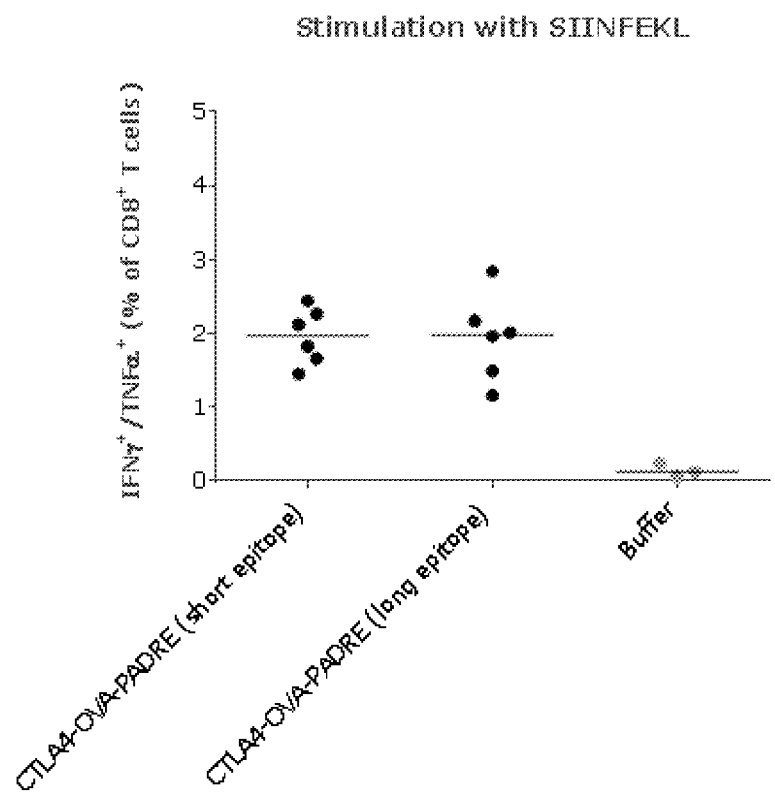
FIG. 7: Induction of epitope-specific CD8+ T cells after vaccination with mRNA encoding different ovalbumin epitopes with the CTLA4 targeting approach.

On days 0, 7 and 14 of the experiment mice were injected i.d. with mRNA solved in Ringer Lactate buffer according to the Table 11 below. The total volume for intradermal vaccination was 80 µl and was distributed to 4 sites of injection. 6 days after the last vaccination an ICS was performed to evaluate epitope-specific CD8+ T cell responses. Therefore CD8+ T cells were stimulated with the corresponding peptide and as a control with media. In both groups epitope-specific CD8+ T cell responses were observed (FIG. 7).

TABLE 11

| Groups, treatment and RNA dilution | | | |
|---|---|---|---|
| Groups | Constructs (amount of RNA) | No. of mice | SEQ ID NOs: |
| A | CTLA4-OVA-PADRE (long peptide) | 6 | 77062 |
| B | CTLA4-OVA-PADRE (short peptide) | 6 | 2913 |
| C | Buffer | 3 | — |

Items

The present invention may be characterized by the following items:
1. An artificial nucleic acid molecule comprising at least one coding region encoding
   a. at least one antigenic peptide or protein,
   and at least one additional amino acid sequence derived from at least one immune response activating signal transduction protein located in the external plasma membrane.
2. The artificial nucleic acid molecule according to item 1, wherein said immune response activating signal transduction protein located in the external plasma membrane (IRST$_{epm}$) is selected from CTLA4 (Cytotoxic T-lymphocyte protein 4), CD36 (Platelet glycoprotein 4), TRBC2 (T-cell receptor beta-2 chain C region), TRDC (T-cell receptor delta chain C region), TLR4 (Toll-like receptor 4), CD4 (T-cell surface glycoprotein CD4), TRBC1 (T-cell receptor beta-1 chain C region), CD3E (T-cell surface glycoprotein CD3 epsilon chain), PTPRC (Receptor-type tyrosine-protein phosphatase C), FCG3A (Low affinity immunoglobulin gamma Fc region receptor LNP-III-A), CD28 (T-cell-specific surface glycoprotein CD28), CD79A (B-cell antigen receptor complex-associated protein alpha chain), CD19 (B-lymphocyte antigen CD19), NKG2D (NKG2-D type II integral membrane protein), FCERG (High affinity immunoglobulin epsilon receptor subunit gamma), CD79B (B-cell antigen receptor complex-associated protein beta chain), CD86 (T-lymphocyte activation antigen CD86), CD226 (CD226 antigen), MUC17 (Mucin-17), CD209 (CD209 antigen), TLR8 (Toll-like receptor 8), or a variant, fragment or derivative of any of these proteins.
3. The artificial nucleic acid molecule according to item 1 or 2, wherein said at least one additional amino acid sequence comprises or consists of:
   b. at least one transmembrane domain and optionally
   c. at least one cytoplasmic domain.
4. The artificial nucleic acid molecule according to any one of the preceding items, wherein said at least one coding region further encodes
   d. at least one signal peptide.
5. The artificial nucleic acid molecule according to any one of the preceding items, wherein said at least one antigenic peptide or protein is selected from or derived from tumor antigens, viral, bacterial, protozoal, fungal or allogenic antigens.
6. The artificial nucleic acid molecule according to item 5, wherein said at least one antigenic peptide or protein comprises or consists of an amino acid sequence corresponding to any one of SEQ ID NOs: 3719-27945; 76420-76439, 76440-76474, or a fragment, variant or derivative thereof, and is optionally encoded by a nucleic acid sequence according to any one of SEQ ID NOs: 27946-52172; 76495-76514, 52173-76399; 76570-76589, 76515-76549, 76590-76624 or a fragment, variant or derivative of any one of said sequences.
7. The artificial nucleic acid molecule according to item 5 or 6, wherein said tumor antigen is selected from BRAF, PIK3CA, KRAS, IDH1, TP53, NRAS, AKT1, SF3B1, CDKN2A, RPSAP58, EGFR, NY-ESO1, MUC-1, 5T4, Her2, MAGE-A3, LY6K, CEACAM6, CEA, MCAK, KK-LC1, Gastrin, VEGFR2, MMP-7, MPHOSPH1, MAGE-A4, MAGE-A1, MAGE-C1, PRAME, Survivin, MAGE-A9, MAGE-C2, FGFR2, WT1, PSA, PSMA, Prostate-specific antigen precursor, Kita-kyushu lung cancer antigen 1, Trophoblast glycoprotein, Cyclin-dependent kinase inhibitor 2A, Cyclin-dependent kinase inhibitor 2A, isoforms 1/2/3, multiple tumor suppressor 1/cyclin-dependent kinase 4 inhibitor p16, GTPase NRas or a fragment, variant or derivative of any of said tumor antigens, or any combination thereof.
8. The artificial nucleic acid molecule according to any one of the preceding items wherein said IRST$_{epm}$ comprises or consists of an amino acid sequence corresponding to any one of SEQ ID NOs: 157-179, or a fragment, variant or derivative thereof, and is optionally encoded by a nucleic acid sequence corresponding to any one of SEQ ID NOs: 365-387, 573-595, 781-803, 989-1011, 1197-1219, 1405-1427, 1613-1635, 1821-1843, 2029-2051, 2237-2259, 2445-2467, 2653-2675, 2861-2883, or a fragment, variant or derivative of any one of said sequences.
9. The artificial nucleic acid molecule according to any one of items 3 to 8, wherein the at least one additional amino acid sequence comprises or consists of at least one transmembrane domain and at least one cytoplasmic domain comprising or consisting of an amino acid sequence corresponding to any one of SEQ ID NOs: 76625-76647, or a fragment, variant or derivative thereof and is optionally encoded by a nucleic acid sequence corresponding to any one of SEQ ID NOs: 76648-76947, 77004-77017, 77066 or a fragment, variant or derivative of any one of said sequences.
10. The artificial nucleic acid molecule according to any one of items 3 to 8, wherein the transmembrane domain comprises or consists of an amino acid sequence corresponding to any one of SEQ ID NOs: 180-208, or a fragment, variant or derivative thereof and is optionally encoded by a nucleic acid sequence corresponding to any one of SEQ ID NOs: 388-416, 596-624, 804-832, 1012-1040, 1220-1248, 1428-1456, 1636-1664, 1844-1872, 2052-2080, 2260-2288, 2468-2496, 2676-2704, 2884-2912, or a fragment, variant or derivative of any one of said sequences.
11. The artificial nucleic acid molecule according to any one of items 4 to 10, wherein the signal peptide comprises or consists of an amino acid sequence corresponding to any one of SEQ ID NOs: 1-156, 76948-76951, or a fragment, variant or derivative thereof, and is optionally encoded by a nucleic acid sequence according to any one of SEQ ID NOs: 209-364, 76952-76955, 625-780, 76960-76963, 833-988, 76964-76967, 417-572, 76956-76959, 1249-1404, 76972-76975, 1457-1612, 76976-76979, 1665-1820, 76980-76983, 1873-2028, 76984-76987, 2081-2236, 76988-76991, 2289-2444, 76992-76995, 2497-2652, 76996-76999, 2705-2860, 77000-77003, 1041-1196, or 76968-76971 or a fragment, variant or derivative thereof.
12. The artificial nucleic acid molecule according to any one of the preceding items, further encoding in its at least one coding region
    e. at least one linker.
13. The artificial nucleic acid molecule according to item 12, wherein said linker is a non-immunogenic linker, optionally comprising or consisting of an amino acid sequence according to any one of SEQ ID NOs: 2937, 76400-76418, 77018-77058 optionally encoded by a nucleic acid sequence according to any one of SEQ ID NOs: 2936, 76494, 76569, 76475-76493, 76550-76568, 77059-77061 or a fragment, variant or derivative of any one of said sequences.
14. The artificial nucleic acid molecule according to any one of the preceding items, wherein said at least one coding region further encodes
    f. at least one T helper epitope.
15. The artificial nucleic acid molecule according to item 14, wherein said helper epitope sequence comprises or consists of an amino acid sequence corresponding to any one of SEQ ID NOs: 3083-3294, or a fragment, variant or derivative thereof, and is optionally encoded by a nucleic acid sequence according to any one of SEQ ID NOs: 3295-3506, 3507-3718, or a fragment, variant or derivative of any one of said sequences.

16. The artificial nucleic acid molecule according to any one of the preceding items, comprising at least one coding region of the following Formula (I), preferably in 5'-3' direction:

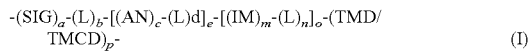

wherein
"SIG" encodes a signal peptide, preferably as defined in item 11,
"L" encodes a linker sequence, preferably as defined in item 13,
each "AN" encodes an identical or different antigenic peptide or protein, preferably as defined in item 5, 6 or 7,
"IM" encodes a helper epitope, preferably as defined in item 14 or 15,
"TMD/TMCD" encodes an amino acid sequence derived from an immune response signal transduction protein located in the external plasma membrane, preferably a transmembrane domain, preferably as defined in item 10, and optionally a cytoplasmic domain, preferably as defined in item 9
b, d, m, n, o is each independently an integer selected from 0, 1, 2, 3, 4, 5, 6, 7, 8, 9, and 10,
a, c, e, p is each independently an integer selected from 1, 2, 3, 4, 5, 6, 7, 8, 9 and 10.

17. The artificial nucleic acid molecule according to any one of the preceding items, encoding in its at least one coding region at least one, or a plurality of at least two, three, four, five, six, seven, eight, nine or ten antigenic peptides or proteins, optionally selected from at least one antigenic peptide or protein according to item 5 or 6, or fragment, variant or derivative thereof, or a combination of said antigenic peptides or proteins, or their fragments, variants or derivatives.

18. The artificial nucleic acid molecule according to any one of items 1 to 17, wherein said artificial nucleic acid molecule is an RNA.

19. The artificial nucleic acid molecule according to item 18, wherein the RNA is an mRNA, a viral RNA, a replicon RNA, or a circular RNA.

20. The artificial nucleic acid molecule, preferably RNA, according to any one of the preceding items, wherein the artificial nucleic acid molecule is mono-, bi-, or multicistronic.

21. The artificial nucleic acid molecule, preferably RNA, according to any one of the preceding items, wherein said artificial nucleic acid molecule is modified, preferably stabilized.

22. The artificial nucleic acid molecule, preferably RNA, according to any one of the preceding items, wherein the G/C content of the at least one coding region is increased compared to the G/C content of the corresponding coding sequence of the corresponding wild-type artificial nucleic acid, and/or wherein
the C content of the at least one coding region is increased compared to the C content of the corresponding coding sequence of the corresponding wild-type artificial nucleic acid, and/or wherein
the codons in the at least one coding region are adapted to human codon usage, wherein the codon adaptation index (CAI) is preferably increased or maximised in the at least one coding sequence of the artificial nucleic acid,
wherein the amino acid sequence encoded by the artificial nucleic acid is preferably not being modified compared to the amino acid sequence encoded by the corresponding wild-type artificial nucleic acid.

23. The artificial nucleic acid molecule, preferably RNA, according to item 22, wherein said at least one coding region comprises or consists of a nucleic acid sequence corresponding to any one of SEQ ID NOs: 417-2912, 76671-76947, 77004-77017, 77066.

24. The artificial nucleic acid molecule, preferably RNA, according to any one of the preceding items, which comprises a 5'-CAP structure, preferably m7GpppN or Cap1.

25. The artificial nucleic acid molecule, preferably RNA, according to any one of the preceding items, which comprises at least one histone stem-loop.

26. The artificial nucleic acid molecule, preferably RNA, according to item 25, wherein the at least one histone stem-loop comprises a nucleic acid sequence according to the following formulae (II) or (III):

formula (II) (stem-loop sequence without stem bordering elements):

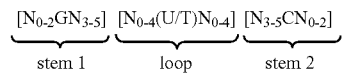

formula (III) (stem-loop sequence with stem bordering elements):

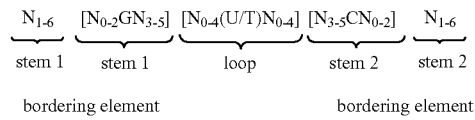

wherein:

| | |
|---|---|
| stem1 or stem2 bordering elements $N_{1-6}$ | is a consecutive sequence of 1 to 6, preferably of 2 to 6, more preferably of 2 to 5, even more preferably of 3 to 5, most preferably of 4 to 5 or 5N, wherein each N is independently from another selected from a nucleotide selected from A, U, T, G and C, or a nucleotide analogue thereof; |
| stem1 $[N_{0-2}GN_{3-5}]$ | is reverse complementary or partially reverse complementary with element stem2, and is a consecutive sequence between of 5 to 7 nucleotides; wherein $N_{0-2}$ is a consecutive sequence of 0 to 2, preferably of 0 to 1, more preferably of 1N, wherein each N is independently from another selected from a nucleotide selected from A, U, T, G and C or a nucleotide analogue thereof; wherein $N_{3-5}$ is a consecutive sequence of 3 to 5, preferably of 4 to 5, more preferably of 4N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine; |

| | |
|---|---|
| loop sequence [N$_{0-4}$(U/T)N$_{0-4}$] | is located between elements stem1 and stem2, and is a consecutive sequence of 3 to 5 nucleotides, more preferably of 4 nucleotides; wherein each N$_{0-4}$ is independent from another a consecutive sequence of 0 to 4, preferably of 1 to 3, more preferably of 1 to 2N, wherein each N is independently from another selected from a nucleotide selected from A, U, T, G and C or a nucleotide analogue thereof; and wherein U/T represents uridine, or optionally thymidine; |
| stem2 [N$_{3-5}$CN$_{0-2}$] | is reverse complementary or partially reverse complementary with element stem1, and is a consecutive sequence between of 5 to 7 nucleotides; wherein N$_{3-5}$ is a consecutive sequence of 3 to 5, preferably of 4 to 5, more preferably of 4N, wherein each N is independently from another selected from a nucleotide selected from A, U, T, G and C or a nucleotide analogue thereof; wherein N$_{0-2}$ is a consecutive sequence of 0 to 2, preferably of 0 to 1, more preferably of 1N, wherein each N is independently from another selected from a nucleotide selected from A, U, T, G and C or a nucleotide analogue thereof; and wherein C is cytidine or an analogue thereof, and may be optionally replaced by a guanosine or an analogue thereof provided that its complementary nucleotide guanosine in stem1 is replaced by cytidine; | wherein
stem1 and stem2 are capable of base pairing with each other forming a reverse complementary sequence, wherein base pairing may occur between stem1 and stem2, or forming a partially reverse complementary sequence, wherein an incomplete base pairing may occur between stem1 and stem2.

27. The artificial nucleic acid molecule, preferably RNA, according to item 25 or 26, wherein the at least one histone stem-loop comprises a nucleic acid sequence according to the following formulae (IIa) or (IIIa):
formula (IIa) (stem-loop sequence without stem bordering elements):

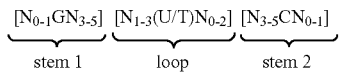

formula (IIIa) (stem-loop sequence with stem bordering elements):

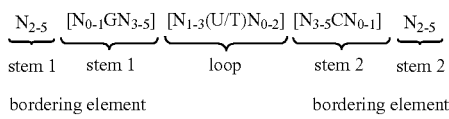

28. The artificial nucleic acid molecule, preferably RNA, according to any one of the preceding items, optionally comprising a poly(A) sequence, preferably comprising 10 to 200, 10 to 100, 40 to 80 or 50 to 70 adenosine nucleotides.

29. The artificial nucleic acid molecule, preferably RNA, according to any one of the preceding items, optionally comprising a poly(C) sequence, preferably comprising 10 to 200, 10 to 100, 20 to 70, 20 to 60 or 10 to 40 cytosine nucleotides.

30. The artificial nucleic acid molecule, preferably RNA, according to any one of the preceding items, which comprises, preferably in 5' to 3' direction, the following elements:
a) a 5'-CAP structure, preferably m7GpppN, an ARCA Cap or Cap1
b) optionally a 5'-UTR element, preferably comprising or consisting of a nucleic acid sequence, corresponding to the nucleic acid sequence according to SEQ ID NOs: 3061 or 3063 or a fragment, variant or corresponding RNA sequence thereof,
c) at least one coding sequence as defined in any one of the preceding items,
d) optionally a 3'-UTR element, preferably comprising or consisting of a nucleic acid sequence corresponding to the nucleic acid sequence according to SEQ ID NOs: 3065; 3067; 3069; 3071; 3073; 3075 or 3077, or a fragment, variant or corresponding RNA sequence thereof,
e) optionally a poly(A) tail, preferably consisting of 10 to 1000, 10 to 500, 10 to 300 10 to 200, 10 to 100, 40 to 80 or 50 to 70 adenosine nucleotides,
f) optionally a poly(C) tail, preferably consisting of 10 to 200, 10 to 100, 20 to 70, 20 to 60 or 10 to 40 cytosine nucleotides, and
g) optionally a histone stem-loop, optionally comprising or consisting of a nucleic acid sequence corresponding to SEQ ID NO: 3079 or 3080.

31. Composition comprising at least one artificial nucleic acid molecule, preferably RNA, according to any one of items 1 to 30 and a pharmaceutically acceptable carrier and/or excipient.

32. Composition according to item 31 comprising a plurality of at least two artificial nucleic acid molecules according to any one of items 1 to 30, wherein preferably at least two of said plurality of artificial nucleic acid molecules encode a different antigenic peptide or protein, optionally selected from an antigenic peptide or protein as defined in item 5, 6 or 7, or a fragment, variant or derivative thereof.

33. Composition according to item 31 or 32, wherein said composition is a pharmaceutical composition, optionally a vaccine.

34. The (pharmaceutical) composition or vaccine according to item 33, wherein the artificial nucleic acid molecule, preferably RNA, is complexed with one or more cationic or polycationic compounds, preferably with cationic or polycationic polymers, cationic or polycationic peptides or proteins, e.g. protamine, cationic or polycationic polysaccharides and/or cationic or polycationic lipids.

35. The (pharmaceutical) composition or vaccine according to item 34, wherein the cationic or polycationic compound is a polymeric carrier.

36. The (pharmaceutical) composition or vaccine according to item 34, wherein the N/P ratio of the artificial nucleic acid molecule, preferably RNA, to the one or more cationic or polycationic compounds is in the range of about 0.1 to 10, including a range of about 0.3 to 4, of about 0.5 to 2, of about 0.7 to 2 and of about 0.7 to 1.5.

37. The (pharmaceutical) composition or vaccine according to any one of items 31 to 36, wherein the artificial nucleic acid molecule, preferably RNA, is complexed with one or more lipids, thereby forming lipid nanoparticles, lipoplexes and/or preferably liposomes.

38. The (pharmaceutical) composition or vaccine according to any one of items 31 to 37, said composition further comprising a non-coding RNA selected from the group consisting of small interfering RNA (siRNA), antisense RNA (asRNA), circular RNA (circRNA), ribozymes, aptamers, riboswitches, immunostimulating RNA (isRNA), transfer RNA (tRNA), ribosomal RNA (rRNA), small nuclear RNA (snRNA), small nucleolar RNA (snoRNA), microRNA (miRNA), and Piwi-interacting RNA (piRNA).

39. The (pharmaceutical) composition or vaccine according to item 38, wherein the immunostimulating RNA comprises at least one RNA sequence according to formula (IS-I) $(GiX_mG_n)$, formula (IS-II) $(C_lX_mC_n)$, formula (IS-IIII) $(N_uG_lX_mG_nN_v)_a$, and/or formula (IS-IV) $(N_uC_lX_mC_nN_v)_a$.

40. The (pharmaceutical) composition or vaccine according to item 39, wherein the immunostimulating RNA comprises at least one RNA sequence corresponding to any one of SEQ ID NOs: 2938-3032.

41. The (pharmaceutical) composition or vaccine of any one of items 31 to 40, wherein the composition comprises a polymeric carrier cargo complex, formed by a polymeric carrier, preferably comprising disulfide-crosslinked cationic peptides, preferably $Cys-Arg_{12}$, and/or $Cys-Arg_{12}-Cys$, and an isRNA, preferably comprising or consisting of an RNA sequence corresponding to SEQ ID NOs: 2938-3032.

42. Kit, preferably kit of parts, comprising the artificial nucleic acid molecule, preferably RNA, according to any one of items 1 to 30 or the (pharmaceutical) composition or vaccine according to any one of items 31 to 41, and optionally a liquid vehicle and/or optionally technical instructions with information on the administration and dosage of the artificial nucleic acid molecule or the composition.

43. The kit according to item 42, wherein the kit contains as a part Ringer-Lactate solution.

44. The artificial nucleic acid molecule, preferably RNA, according to any one of items 1 to 30, the (pharmaceutical) composition or vaccine according to any one of items 31 to 41, or the kit according to item 42 to 43 for use as a medicament.

45. The artificial nucleic acid molecule, preferably RNA, according to any one of items 1 to 30, the (pharmaceutical) composition or vaccine according to any one of items 31 to 41, or the kit according to item 42 to 44 for use in a method of treatment or prophylaxis of cancer, infectious diseases including viral, bacterial, fungal or protozoal infections, autoimmune diseases, Graft-versus-host disease (GvHD) or allergies.

46. The artificial nucleic acid molecule, preferably RNA, for the use according to item 45, wherein said use comprises (a) administering, to a subject in need thereof, said artificial nucleic acid molecule, preferably RNA, said (pharmaceutical) composition or vaccine, or said kit.

47. The artificial nucleic acid molecule, preferably RNA, for the use according to item 46, wherein administration is accomplished parenterally, preferably intradermally, subcutaneously, intravenously, intramuscularly, intranodally, transdermally, or intratumorally.

48. A method of treating or preventing cancer, autoimmune diseases, or infectious diseases including viral, bacterial, fungal or protozoal infections, wherein the method comprises administering, to a patient in need thereof, an effective amount of the artificial nucleic acid molecule, preferably RNA, according to any one of items 1 to 30, the (pharmaceutical) composition or vaccine according to any one of items 31 to 41, or the kit according to item 42 to 43.

49. The use according to any one of items 44 to 47, or the method according to item 48, further comprising subjecting the patient to at least one or more of the following additional therapies: chemotherapy (e.g. first-line or second-line chemotherapy), radiotherapy, chemoradiation (combination of chemotherapy and radiotherapy), kinase inhibitors, antibody therapy and/or checkpoint modulators (e.g. CTLA4 inhibitors, PD1 pathway inhibitors) or inhibitors inducing expression of T cell epitopes associated with impaired peptide processing (TEIPPs).

50. The use according to item 49, wherein said additional therapy is effected prior, simultaneously, or subsequently to the administration of said artificial nucleic acid molecule, (pharmaceutical) composition or vaccine, or kit.

51. An in vitro cell culture or cell treatment method comprising (a) providing cells in vitro, (b) contacting said cells with the artificial nucleic acid molecule, preferably RNA, according to any one of items 1 to 30, the (pharmaceutical) composition or vaccine according to any one of items 31 to 41, or the kit according to item 42 to 43.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10988754B2). An electronic copy of the "Sequence Listing" will also be available from the USPTO upon request and payment of the fee set forth in 37 CFR 1.19(b)(3).

The invention claimed is:

1. A method of treating or preventing cancer, autoimmune diseases, or infectious diseases, wherein the method comprises administering, to a patient in need thereof, an effective amount of an artificial nucleic acid molecule comprising at least one coding region encoding:

(a) at least one antigenic peptide or protein; and (b) at least one additional amino acid sequence derived from at least one immune response activing signal transduction protein located in the external plasma membrane ($IRST_{epm}$), wherein said at least one additional amino acid sequence derived from at least one IRST$_{epm}$ comprises at least one transmembrane domain from CTLA4 (Cytotoxic T-lymphocyte protein 4) and localizes the antigenic peptide or protein to the plasma membrane.

2. The method of claim 1, wherein said at least one additional amino acid sequence further comprises at least one cytoplasmic domain of CTLA4.

3. The method of claim 2, wherein the at least one antigenic peptide or protein is from KRAS.

4. The method of claim 2, wherein the at least one antigenic peptide or protein is from a viral antigen.

5. The method of claim 1, wherein said at least one coding region further encodes at least one signal peptide.

6. The method of claim 5, wherein the at least one signal peptide comprises or consists of an amino acid sequence corresponding to any one of SEQ ID NOs: 1-156, 76948-76951, or a fragment, variant or derivative thereof, and is optionally encoded by a nucleic acid sequence according to any one of SEQ ID NOs: 209-364, 76952-76955, 625-780, 76960-76963, 833-988, 76964-76967, 417-572, 76956-76959, 1249-1404, 76972-76975, 1457-1612, 76976-76979, 1665-1820, 76980-76983, 1873-2028, 76984-76987, 2081-2236, 76988-76991, 2289-2444, 76992-76995, 2497-2652, 76996-76999, 2705-2860, 77000-77003, 1041-1196, or 76968-76971.

7. The method of claim 1, wherein said at least one antigenic peptide or protein is selected from or derived from tumor antigens, viral, bacterial, protozoal, fungal or allogenic antigens.

8. The method of claim 7, wherein said at least one antigenic peptide or protein comprises or consists of an amino acid sequence corresponding to any one of SEQ ID NOs: 3719-27945; 76420-76439, 76440-76474, and is optionally encoded by a nucleic acid sequence according to any one of SEQ ID NOs: 27946-52172; 76495-76514, 52173-76399; 76570-76589, 76515-76549, 76590-76624.

9. The method of claim 1, wherein said antigenic peptide or protein is from a tumor antigen is selected from BRAF, PIK3CA, KRAS, IDH1, TP53, NRAS, AKTI, SF3B1, CDKN2A, RPSAP58, EGFR, NY-ESO1, MUC-1, 5T4, Her2, MAGE-A3, LY6K, CEACAM6, CEA, MCAK, KK-LC1, Gastrin, VEGFR2, MMP-7, MPHOSPH1, MAGE-A4, MAGE-A1, MAGE-C1, PRAME, Survivin, MAGE-A9, MAGE-C2, FGFR2, WT1, PSA, PSMA, Prostate-specific antigen precursor, Kita-kyushu lung cancer antigen 1, Trophoblast glycoprotein, Cyclin-dependent kinase inhibitor 2A, Cyclin-dependent kinase inhibitor 2A, isoforms 1/2/3, multiple tumor suppressor 1/cyclin-dependent kinase 4 inhibitor p16, GTPase NRas or any combination thereof.

10. The method of claim 1, wherein said at least one IRST$_{epm}$ comprises or consists of an amino acid sequence corresponding to SEQ ID NO: 169, optionally encoded by a nucleic acid sequence corresponding to any one of SEQ ID NOs: 585, 793, 1001, 1209, 1417, 1625, 1833, 2041, 2249, 2457, 2665 or 2873.

11. The method of claim 1, further encoding in its at least one coding region at least one linker.

12. The method of claim 11, wherein said linker is a non-immunogenic linker, optionally comprising or consisting of an amino acid sequence according to any one of SEQ ID NOs: 2937, 76400-76418, 77018-77058 optionally encoded by a nucleic acid sequence according to any one of SEQ ID NOs: 2936, 76494, 76569, 76475-76493, 76550-76568, or 77059-77061.

13. The method of claim 1, wherein said at least one coding region further encodes at least one T helper epitope.

14. The method of claim 13, wherein said at least one helper epitope sequence comprises or consists of an amino acid sequence corresponding to any one of SEQ ID NOs: 3083-3294, optionally encoded by a nucleic acid sequence according to any one of SEQ ID NOs: 3295-3506, or 3507-3718.

15. The method of claim 1, wherein said artificial nucleic acid molecule is an RNA.

16. The method of claim 15, which comprises, preferably in 5' to 3' direction, the following elements:
   a) a 5'-CAP structure,
   b) optionally a 5'-UTR element,
   c) said at least one coding region sequence,
   d) optionally a 3'-UTR element,
   e) optionally a poly(A) tail,
   f) optionally a poly(C) tail, and
   g) optionally a histone stem-loop.

17. The method of claim 1, wherein the method is a method of treating or preventing cancer.

18. The method of claim 17, wherein the at least one antigenic peptide or protein is a KRAS epitope having a mutation selected from the group consisting of A146T; G12A; G12C; G12D; G12F; G12R; G12S; G12V; G13C; G13D; K117N; Q61H; Q61K; Q61L; and Q61R.

19. The method of claim 18, wherein the wherein the method is a method of treating or preventing cancer and wherein the artificial nucleic acid molecule is a mRNA.

20. The method of claim 19, wherein the patient has a pancreatic cancer.

21. The method of claim 1, wherein the method is a method of treating or preventing infectious diseases selected from the group consisting of viral, bacterial, fungal and protozoal infections.

* * * * *